US009771595B2

(12) United States Patent
Flasinski

(10) Patent No.: US 9,771,595 B2
(45) Date of Patent: *Sep. 26, 2017

(54) PLANT REGULATORY ELEMENTS AND USES THEREOF

(71) Applicant: Monsanto Technology LLC, St. Louis, MO (US)

(72) Inventor: Stanislaw Flasinski, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 242 days.

This patent is subject to a terminal disclaimer.

(21) Appl. No.: 14/625,566

(22) Filed: Feb. 18, 2015

(65) Prior Publication Data

US 2015/0167012 A1   Jun. 18, 2015

Related U.S. Application Data

(63) Continuation of application No. 13/428,994, filed on Mar. 23, 2012, now Pat. No. 9,062,316.

(60) Provisional application No. 61/467,875, filed on Mar. 25, 2011.

(51) Int. Cl.
  *C12N 15/82* (2006.01)
  *C12N 15/113* (2010.01)
  *C12N 15/11* (2006.01)
  *C07K 14/415* (2006.01)

(52) U.S. Cl.
  CPC ........ *C12N 15/8216* (2013.01); *C07K 14/415* (2013.01); *C12N 15/11* (2013.01); *C12N 15/113* (2013.01); *C12N 15/8201* (2013.01); *C12N 15/8225* (2013.01); *C12N 15/8227* (2013.01); *C12N 15/8231* (2013.01); *C12N 15/8234* (2013.01); *C12N 15/8241* (2013.01); *C12N 15/8274* (2013.01); *C12N 15/8279* (2013.01)

(58) Field of Classification Search
  None
  See application file for complete search history.

(56) References Cited

U.S. PATENT DOCUMENTS

| | | | |
|---|---|---|---|
| 6,054,574 A | 4/2000 | Quail et al. | |
| 6,596,925 B1 | 7/2003 | Perera et al. | |
| 6,878,818 B1 | 4/2005 | Goldsbrough et al. | |
| 7,211,711 B2 | 5/2007 | Perera et al. | |
| 7,518,034 B2 | 4/2009 | Perera et al. | |
| 7,932,374 B2 | 4/2011 | Perera et al. | |
| 9,062,316 B2 * | 6/2015 | Flasinski | C07K 14/415 |
| 2010/0058495 A1 | 3/2010 | Abbitt | |
| 2011/0023183 A1 | 1/2011 | Stewart et al. | |
| 2015/0232866 A1 | 8/2015 | Flasinski | |
| 2016/0289693 A1 | 10/2016 | Flasinski | |

FOREIGN PATENT DOCUMENTS

| | | |
|---|---|---|
| CL | 1646-04 | 6/2004 |
| EP | 1953232 | 8/2008 |
| WO | WO 99/58659 A2 | 11/1999 |
| WO | WO 01/94394 A2 | 12/2001 |
| WO | WO 2006/101938 A1 | 9/2006 |
| WO | WO 2008/064289 A2 | 5/2008 |
| WO | WO 2009/149304 A2 | 12/2009 |
| WO | WO 2010/144385 A1 | 12/2010 |

OTHER PUBLICATIONS

Christensen et al. Maize polyubiquitin genes: structure, thermalperturbation of expression and transcript splicing, and promoter activity following transfer to protoplasts by electroporation. Plant Molecular Biology. 1992. 18: 675-689.*
U.S. Appl. No. 15/179,635, filed Jun. 10, 2016, Flasinski.
Christensen et al., "Maize polyubiquitin genes: structure, thermal perturbation of expression and transcript splicing, and promoter activity following transfer to protoplasts by electroporation," *Plant Molec Biol* 18(4):675-689, 1992.
EMBL Accession No. CW082733, dated May 19, 2010.
EMBL Accession No. CW0938, XP002685119, dated May 19, 2010.
Frank et al., "Drought and rust effects on gene expression in the dominant plant species of tallgrass prairie, Andropogon gerardii," abstract 16, <http://www.k-state.edu/ecogen/PosterAbstracts-2006.pdf>, 2006.
Frank, "Rust and drought effects on the gene expression and phytohormone concentration in Big Bluestem," thesis, Kansas State University, p. 24, <http://hdl.handle.net/2097/393>, 2007.
GenBank Accession No. X04753, "Potato light-inducible tissue-specific ST-LS1 gene," <http://www.ncbi.nlm.nih.gov/nuccore/X04753>, accessed on Nov. 1, 2012.
International Search Report and Written Opinion issued in PCT/US2012/029990, dated Oct. 29, 2012.
Kim et al., "A 20 nucleotide upstream element is essential for the nopaline synthase (nos) promoter activity," *Plant Molecular Biology* 24:105-117, 1994.
Vettore et al., "The molecular and functional characterization of an Opaque2 homologue gene from *Coix* and a new classification of plant bZIP proteins," *Plant Molecular Biology* 36(2):249-263, 1998.
Wang et al., "Rice ubiquitin promoters: deletion analysis and potential usefulness in plant transformation systems," *Plant Cell Reproduction* 22:129-134, 2003.
Kosugi et al., "Two of three promoter elements identified in a rice gene for proliferating cell nuclear antigen are essential for meristematic tissue-specific expression," *The Plant Journal* 7(6):877-886, 1995.

(Continued)

*Primary Examiner* — Ashley K Buran
(74) *Attorney, Agent, or Firm* — Dentons US LLP; Carine M. Doyle, Esq.

(57) ABSTRACT

The present invention provides novel DNA molecules and constructs, including their nucleotide sequences, useful for modulating gene expression in plants and plant cells. The invention also provides transgenic plants, plant cells, plant parts, seeds, and commodity products comprising the DNA molecules operably linked to heterologous transcribable polynucleotides, along with methods of their use.

15 Claims, 31 Drawing Sheets

(56) References Cited

OTHER PUBLICATIONS

U.S. Appl. No. 14/686,602, filed Apr. 14, 2015, Flasinski.
Chilean Office Action regarding 2707-13, dated Feb. 16, 2015.
Dolferus, et al. Differential interactions of promoter elements in stress response of the *Arabidopsis adh* gene, *Plant Physiol.*, 105:1075-1087, 1994.
Donald et al., Mutation of either G box or I box sequences profoundly affects expression from the *Arabidopsis rbcS-1A* promoter, *The EMBO Journal*, 9(6):1717-1726, 1990.
Response to Non-Final Office Action regarding U.S. Appl. No. 14/686,602, dated Jul. 25, 2017.

* cited by examiner

```
P-ANDge.Ubq1-1:1:9       ------------------------------------------------------------
P-ANDge.Ubq1-1:1:8       ------------------------------------------------------------
P-ANDge.Ubq1-1:1:11      AGCAGACTCGCATTATCGATGGAGGGGTGGGTTTAGAACCCTGAAAACTGGTACTGTTTC
P-ANDge.Ubq1-1:1:12      ------------------------------------------------------------
P-ANDge.Ubq1-1:1:13      ------------------------------------------------------------
P-ANDge.Ubq1-1:1:14      ------------------------------------------------------------
P-ANDge.Ubq1-1:1:10      ------------------------------------------------------------

P-ANDge.Ubq1-1:1:9       ------------------------------------------------------------
P-ANDge.Ubq1-1:1:8       ------------------------------------------------------------
P-ANDge.Ubq1-1:1:11      GAACTGAAAAACACTGTAGCACTTTTCGTTTGTTTGTGGTAAATATTATCTTACTATGGT
P-ANDge.Ubq1-1:1:12      ------------------------------------------------------------
P-ANDge.Ubq1-1:1:13      ------------------------------------------------------------
P-ANDge.Ubq1-1:1:14      ------------------------------------------------------------
P-ANDge.Ubq1-1:1:10      ------------------------------------------------------------

P-ANDge.Ubq1-1:1:9       ------------------------------------------------------------
P-ANDge.Ubq1-1:1:8       ------------------------------------------------------------
P-ANDge.Ubq1-1:1:11      CTAACTAGGCTCAAAAGAATCGTCTCGCAATGTACATCTAAATTATGCAATTAGTTATTT
P-ANDge.Ubq1-1:1:12      ------------------------------------------------------------
P-ANDge.Ubq1-1:1:13      ------------------------------------------------------------
P-ANDge.Ubq1-1:1:14      ------------------------------------------------------------
P-ANDge.Ubq1-1:1:10      ------------------------------------------------------------

P-ANDge.Ubq1-1:1:9       ------------------------------------------------------------
P-ANDge.Ubq1-1:1:8       ------------------------------------------------------------
P-ANDge.Ubq1-1:1:11      TGTTTACCTGCATTTCATACTCCGAGCATGCGTCTTTTGGTACATTTAATGCTTCGATGT
P-ANDge.Ubq1-1:1:12      ------------------------------------------------------------
P-ANDge.Ubq1-1:1:13      ------------------------------------------------------------
P-ANDge.Ubq1-1:1:14      ------------------------------------------------------------
P-ANDge.Ubq1-1:1:10      ------------------------------------------------------------

P-ANDge.Ubq1-1:1:9       ------------------------------------------------------------
P-ANDge.Ubq1-1:1:8       ------------------------------------------------------------
P-ANDge.Ubq1-1:1:11      GATGGGAATTTTAAAAATTTTGGAGAAAAGTTGGTTTCTAAACACCCCCGAGGACGAAAT
P-ANDge.Ubq1-1:1:12      ------------------------------------------------------------
P-ANDge.Ubq1-1:1:13      ------------------------------------------------------------
P-ANDge.Ubq1-1:1:14      ------------------------------------------------------------
P-ANDge.Ubq1-1:1:10      ------------------------------------------------------------

P-ANDge.Ubq1-1:1:9       ------------------------------------------------------------
P-ANDge.Ubq1-1:1:8       ------------------------------------------------------------
P-ANDge.Ubq1-1:1:11      TGGATTCGGTCTTTGACGCGGATGCAGCAACTGCAGTGCGCAGGATACCATCTTAGCCGT
P-ANDge.Ubq1-1:1:12      ------------------------------------------------------------
P-ANDge.Ubq1-1:1:13      ------------------------------------------------------------
P-ANDge.Ubq1-1:1:14      ------------------------------------------------------------
P-ANDge.Ubq1-1:1:10      ------------------------------------------------------------
```

FIG. 1a

```
P-ANDge.Ubq1-1:1:9    ------------------------------------------------------------
P-ANDge.Ubq1-1:1:8    ------------------------------------------------------------
P-ANDge.Ubq1-1:1:11   TGCGTCGAAGTTCGCTTTGCTAACGTTTTGAGAAAATTAAACCAGCTTTGACCAACGTGA
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    ------------------------------------------------------------
P-ANDge.Ubq1-1:1:8    ------------------------------------------------------------
P-ANDge.Ubq1-1:1:11   GACGAGCGCCTTACGTGGCAGTGTAATGGAACCGGGCACGGCAAGTTTGACGCTGTAGTG
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    ---------CTCGTTACGTTTGGCACAACTTAGTTGAATCCGGCTTCCGGCAAACTATAT
P-ANDge.Ubq1-1:1:8    ------------------------------------------------------------
P-ANDge.Ubq1-1:1:11   TTAGCCGGTCTCGTTACGTTTGGCACAACTTAGTTGAATCCGGCTTCCGGCAAACTATAT
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    GGCAAGTTAGACCCAAGTGTGAGCCGGCCACCGCAAGTTATTGGGACATTATACGTAGGA
P-ANDge.Ubq1-1:1:8    ------------------------------------------------------------
P-ANDge.Ubq1-1:1:11   GGCAAGTTAGACCCAAGTGTGAGCCGGCCACCGCAAGTTATTGGGACATTATACGTAGGA
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    AGCAAGTGTATAATAAGAATATGAGATAATGTAAGCAGCTATATGAATCATCACGTCATA
P-ANDge.Ubq1-1:1:8    ------------------------------------------------------------
P-ANDge.Ubq1-1:1:11   AGCAAGTGTATAATAAGAATATGAGATAATGTAAGCAGCTATATGAATCATCACGTCATA
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    TTTATGTTAAGATGAAGAGGATAGAATAAACGGTATGTAAATTTATAGCGAGTGATAGAC
P-ANDge.Ubq1-1:1:8    ------------------------------------------------------------
P-ANDge.Ubq1-1:1:11   TTTATGTTAAGATGAAGAGGATAGAATAAACGGTATGTAAATTTATAGCGAGTGATAGAC
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------
```

FIG. 1b

```
P-ANDge.Ubq1-1:1:9    GGGCACAAGGCCTCCTAGCTATTTCCATAAATCGGATTTTGTAAGAACAAAAAAGAGGAC
P-ANDge.Ubq1-1:1:8    ------------------------------------------------------------
P-ANDge.Ubq1-1:1:11   GGGCACAAGGCCTCCTAGCTATTTCCATAAATCGGATTTTGTAAGAACAAAAAAGAGGAC
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    TTATTATAAGAGAATGTGGTAAGTAAGTATACTCTCTCCGTTTCAAATTATAAGTTGTTT
P-ANDge.Ubq1-1:1:8    ------------------------------------------------------------
P-ANDge.Ubq1-1:1:11   TTATTATAAGAGAATGTGGTAAGTAAGTATACTCTCTCCGTTTCAAATTATAAGTTGTTT
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    TGATTTTTTTGGTACATCTATTTTACTATGCATTAGATATAATAATGTGTCTAGATACAT
P-ANDge.Ubq1-1:1:8    ------------------------------------------------------------
P-ANDge.Ubq1-1:1:11   TGATTTTTTTGGTACATCTATTTTACTATGCATTAGATATAATAATGTGTCTAGATACAT
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   ------------------------------------------------------------

P-ANDge.Ubq1-1:1:9    AACAAAATGGATGAATCAAAAAAGTCAAAGTGATTTACAATTTGGAACGGAGAGAGTAAG
P-ANDge.Ubq1-1:1:8    ------------------------------------------------------------
P-ANDge.Ubq1-1:1:11   AACAAAATGGATGAATCAAAAAAGTCAAAGTGATTTACAATTTGGAACGGAGAGAGTAAG
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   -----------------------------------------------------------G

P-ANDge.Ubq1-1:1:9    TTCAAGCCGTCAAGGCACTTCTATGCAACCACAGTCAACTTGAATGCCGCTTGAGTGCCT
P-ANDge.Ubq1-1:1:8    ------------------------------------------------------------
P-ANDge.Ubq1-1:1:11   TTCAAGCCGTCAAGGCACTTCTATGCAACCACAGTCAACTTGAATGCCGCTTGAGTGCCT
P-ANDge.Ubq1-1:1:12   ------------------------------------------------------------
P-ANDge.Ubq1-1:1:13   ------------------------------------------------------------
P-ANDge.Ubq1-1:1:14   ------------------------------------------------------------
P-ANDge.Ubq1-1:1:10   TTCAAGCCGTCAAGGCACTTCTATGCAACCACAGTCAACTTGAATGCCGCTTGAGTGCCT

P-ANDge.Ubq1-1:1:9    TCTCAAGTTTTTTTTCTTGCAAAAATCATTTCTTTTTTTAAAAAAAGTATAATTTGGA
P-ANDge.Ubq1-1:1:8    ----------------------------------------------------------
P-ANDge.Ubq1-1:1:11   TCTCAAGTTTTTTTTCTTGCAAAAATCATTTCTTTTTTTAAAAAAAGTATAATTTGGA
P-ANDge.Ubq1-1:1:12   ----------------------------------------------------------
P-ANDge.Ubq1-1:1:13   ----------------------------------------------------------
P-ANDge.Ubq1-1:1:14   ----------------------------------------------------------
P-ANDge.Ubq1-1:1:10   TCTCAAGTTTTTTTTCTTGCAAAAATCATTTCTTTTTTTAAAAAAAGTATAATTTGGA
```

FIG. 1c

```
P-ANDge.Ubq1-1:1:9     TCGTGCAAATTTCTCTCTAGGTGTGTGTGTGACTGTGTGAGTAACAATTTCTCTAGTTGT
P-ANDge.Ubq1-1:1:8     ------------------------------------------------------------
P-ANDge.Ubq1-1:1:11    TCGTGCAAATTTCTCTCTAGGTGTGTGTGTGACTGTGTGAGTAACAATTTCTCTAGTTGT
P-ANDge.Ubq1-1:1:12    ---------------------------------------------------TCTAGTTGT
P-ANDge.Ubq1-1:1:13    ------------------------------------------------------------
P-ANDge.Ubq1-1:1:14    ------------------------------------------------------------
P-ANDge.Ubq1-1:1:10    TCGTGCAAATTTCTCTCTAGGTGTGTGTGTGACTGTGTGAGTAACAATTTCTCTAGTTGT

P-ANDge.Ubq1-1:1:9     GCGCGACTGCTGCTTACTTTGGAGATTACAATATCTTTCTAAAATGCTTCGATTACTTAT
P-ANDge.Ubq1-1:1:8     ------------------------------------------------------------
P-ANDge.Ubq1-1:1:11    GCGCGACTGCTGCTTACTTTGGAGATTACAATATCTTTCTAAAATGCTTCGATTACTTAT
P-ANDge.Ubq1-1:1:12    GCGCGACTGCTGCTTACTTTGGAGATTACAATATCTTTCTAAAATGCTTCGATTACTTAT
P-ANDge.Ubq1-1:1:13    ------------------------------------------------------------
P-ANDge.Ubq1-1:1:14    ------------------------------------------------------------
P-ANDge.Ubq1-1:1:10    GCGCGACTGCTGCTTACTTTGGAGATTACAATATCTTTCTAAAATGCTTCGATTACTTAT

P-ANDge.Ubq1-1:1:9     TTATAAACCGTCTCTAAGGCCAATTGCTCAAGATTCATTCAACAATTGAAACGTCTCACA
P-ANDge.Ubq1-1:1:8     ------------------------------------------------------------
P-ANDge.Ubq1-1:1:11    TTATAAACCGTCTCTAAGGCCAATTGCTCAAGATTCATTCAACAATTGAAACGTCTCACA
P-ANDge.Ubq1-1:1:12    TTATAAACCGTCTCTAAGGCCAATTGCTCAAGATTCATTCAACAATTGAAACGTCTCACA
P-ANDge.Ubq1-1:1:13    ------------------------------------------------------------
P-ANDge.Ubq1-1:1:14    ------------------------------------------------------------
P-ANDge.Ubq1-1:1:10    TTATAAACCGTCTCTAAGGCCAATTGCTCAAGATTCATTCAACAATTGAAACGTCTCACA

P-ANDge.Ubq1-1:1:9     TGATTAAATCATATAAAGTTTCTAAGTCTTGTTTGACAAGATTTTTTAGATTTTCATCT
P-ANDge.Ubq1-1:1:8     ------------------------------------------------------------
P-ANDge.Ubq1-1:1:11    TGATTAAATCATATAAAGTTTCTAAGTCTTGTTTGACAAGATTTTTTAGATTTTCATCT
P-ANDge.Ubq1-1:1:12    TGATTAAATCATATAAAGTTTCTAAGTCTTGTTTGACAAGATTTTTTAGATTTTCATCT
P-ANDge.Ubq1-1:1:13    ------------------------------------------------------------
P-ANDge.Ubq1-1:1:14    ------------------------------------------------------------
P-ANDge.Ubq1-1:1:10    TGATTAAATCATATAAAGTTTCTAAGTCTTGTTTGACAAGATTTTTTAGATTTTCATCT

P-ANDge.Ubq1-1:1:9     AAATTGGATGAAACTATCAAACACTAATTTTAAAAAATATAAGAGAAGCTCCGGAGATAA
P-ANDge.Ubq1-1:1:8     ------------------------------------------------------------
P-ANDge.Ubq1-1:1:11    AAATTGGATGAAACTATCAAACACTAATTTTAAAAAATATAAGAGAAGCTCCGGAGATAA
P-ANDge.Ubq1-1:1:12    AAATTGGATGAAACTATCAAACACTAATTTTAAAAAATATAAGAGAAGCTCCGGAGATAA
P-ANDge.Ubq1-1:1:13    ------------------------------------------------------------
P-ANDge.Ubq1-1:1:14    ------------------------------------------------------------
P-ANDge.Ubq1-1:1:10    AAATTGGATGAAACTATCAAACACTAATTTTAAAAAATATAAGAGAAGCTCCGGAGATAA

P-ANDge.Ubq1-1:1:9     AAGGTCGTCTATGTTATTATAAGAGTAAAGTCGTCTATTCTCTTCGTCCCAACATATATA
P-ANDge.Ubq1-1:1:8     ------------------------------------------------------------
P-ANDge.Ubq1-1:1:11    AAGGTCGTCTATGTTATTATAAGAGTAAAGTCGTCTATTCTCTTCGTCCCAACATATATA
P-ANDge.Ubq1-1:1:12    AAGGTCGTCTATGTTATTATAAGAGTAAAGTCGTCTATTCTCTTCGTCCCAACATATATA
P-ANDge.Ubq1-1:1:13    ------------------------------------------------------------
P-ANDge.Ubq1-1:1:14    ------------------------------------------------------------
P-ANDge.Ubq1-1:1:10    AAGGTCGTCTATGTTATTATAAGAGTAAAGTCGTCTATTCTCTTCGTCCCAACATATATA
```

FIG. 1d

```
P-ANDge.Ubq1-1:1:9     ATTCTAAGCATGAATTGCTTTCTTTTTGGACAAAAGGAGCATGCCACAACACAAGAATGA
P-ANDge.Ubq1-1:1:8     --------------------------------------------------CACAAGAATGA
P-ANDge.Ubq1-1:1:11    ATTCTAAGCATGAATTGCTTTCTTTTTGGACAAAAGGAGCATGCCACAACACAAGAATGA
P-ANDge.Ubq1-1:1:12    ATTCTAAGCATGAATTGCTTTCTTTTTGGACAAAAGGAGCATGCCACAACACAAGAATGA
P-ANDge.Ubq1-1:1:13    ------------------------------------------------------------
P-ANDge.Ubq1-1:1:14    ------------------------------------------------------------
P-ANDge.Ubq1-1:1:10    ATTCTAAGCATGAATTGCTTTCTTTTTGGACAAAAGGAGCATGCCACAACACAAGAATGA

P-ANDge.Ubq1-1:1:9     TGTCACCGTCATGCTTGGATCCTTTTATGGTAAAGCTTCACCTTCTATAATCTAACAATA
P-ANDge.Ubq1-1:1:8     TGTCACCGTCATGCTTGGATCCTTTTATGGTAAAGCTTCACCTTCTATAATCTAACAATA
P-ANDge.Ubq1-1:1:11    TGTCACCGTCATGCTTGGATCCTTTTATGGTAAAGCTTCACCTTCTATAATCTAACAATA
P-ANDge.Ubq1-1:1:12    TGTCACCGTCATGCTTGGATCCTTTTATGGTAAAGCTTCACCTTCTATAATCTAACAATA
P-ANDge.Ubq1-1:1:13    ------------------------------------------------------------
P-ANDge.Ubq1-1:1:14    ------------------------------------------------------------
P-ANDge.Ubq1-1:1:10    TGTCACCGTCATGCTTGGATCCTTTTATGGTAAAGCTTCACCTTCTATAATCTAACAATA

P-ANDge.Ubq1-1:1:9     GAGAAATCAGGGAAAAATCATGTTTTGGTTGTTTTTATTTCTAACCTCCACAATAACTTT
P-ANDge.Ubq1-1:1:8     GAGAAATCAGGGAAAAATCATGTTTTGGTTGTTTTTATTTCTAACCTCCACAATAACTTT
P-ANDge.Ubq1-1:1:11    GAGAAATCAGGGAAAAATCATGTTTTGGTTGTTTTTATTTCTAACCTCCACAATAACTTT
P-ANDge.Ubq1-1:1:12    GAGAAATCAGGGAAAAATCATGTTTTGGTTGTTTTTATTTCTAACCTCCACAATAACTTT
P-ANDge.Ubq1-1:1:13    ------------------------------------------------------------
P-ANDge.Ubq1-1:1:14    ------------------------------------------------------------
P-ANDge.Ubq1-1:1:10    GAGAAATCAGGGAAAAATCATGTTTTGGTTGTTTTTATTTCTAACCTCCACAATAACTTT

P-ANDge.Ubq1-1:1:9     GGTTTACCATTTTTTGTTTGATTTTAGTTTTAGAGAAGCGTTTATAACAGGACCTAAAAT
P-ANDge.Ubq1-1:1:8     GGTTTACCATTTTTTGTTTGATTTTAGTTTTAGAGAAGCGTTTATAACAGGACCTAAAAT
P-ANDge.Ubq1-1:1:11    GGTTTACCATTTTTTGTTTGATTTTAGTTTTAGAGAAGCGTTTATAACAGGACCTAAAAT
P-ANDge.Ubq1-1:1:12    GGTTTACCATTTTTTGTTTGATTTTAGTTTTAGAGAAGCGTTTATAACAGGACCTAAAAT
P-ANDge.Ubq1-1:1:13    ------------------------------------------------------------
P-ANDge.Ubq1-1:1:14    ------------------------------------------------------------
P-ANDge.Ubq1-1:1:10    GGTTTACCATTTTTTGTTTGATTTTAGTTTTAGAGAAGCGTTTATAACAGGACCTAAAAT

P-ANDge.Ubq1-1:1:9     CTTTTTTCAGTACACAGTACAACGCAGACGCTCATACACGCACGCACACTCACCTCTATG
P-ANDge.Ubq1-1:1:8     CTTTTTTCAGTACACAGTACAACGCAGACGCTCATACACGCACGCACACTCACCTCTATG
P-ANDge.Ubq1-1:1:11    CTTTTTTCAGTACACAGTACAACGCAGACGCTCATACACGCACGCACACTCACCTCTATG
P-ANDge.Ubq1-1:1:12    CTTTTTTCAGTACACAGTACAACGCAGACGCTCATACACGCACGCACACTCACCTCTATG
P-ANDge.Ubq1-1:1:13    ------------------------------------------------------------
P-ANDge.Ubq1-1:1:14    ------------------------------------------------------------
P-ANDge.Ubq1-1:1:10    CTTTTTTCAGTACACAGTACAACGCAGACGCTCATACACGCACGCACACTCACCTCTATG

P-ANDge.Ubq1-1:1:9     AACACACGTAAGAAAACCCTACACCTTGAGCACCTTCGAAGGACTGAGCCGGTAAATATA
P-ANDge.Ubq1-1:1:8     AACACACGTAAGAAAACCCTACACCTTGAGCACCTTCGAAGGACTGAGCCGGTAAATATA
P-ANDge.Ubq1-1:1:11    AACACACGTAAGAAAACCCTACACCTTGAGCACCTTCGAAGGACTGAGCCGGTAAATATA
P-ANDge.Ubq1-1:1:12    AACACACGTAAGAAAACCCTACACCTTGAGCACCTTCGAAGGACTGAGCCGGTAAATATA
P-ANDge.Ubq1-1:1:13    ------------------------------------------------------------
P-ANDge.Ubq1-1:1:14    ------------------------------------------------------------
P-ANDge.Ubq1-1:1:10    AACACACGTAAGAAAACCCTACACCTTGAGCACCTTCGAAGGACTGAGCCGGTAAATATA
```

FIG. 1e

| | |
|---|---|
| P-ANDge.Ubq1-1:1:9 | GAGATTCTCGAAGTCACTATTAGCGCCTCGTTGTCAACGGGAATGTCGCTTACCACTTAA |
| P-ANDge.Ubq1-1:1:8 | GAGATTCTCGAAGTCACTATTAGCGCCTCGTTGTCAACGGGAATGTCGCTTACCACTTAA |
| P-ANDge.Ubq1-1:1:11 | GAGATTCTCGAAGTCACTATTAGCGCCTCGTTGTCAACGGGAATGTCGCTTACCACTTAA |
| P-ANDge.Ubq1-1:1:12 | GAGATTCTCGAAGTCACTATTAGCGCCTCGTTGTCAACGGGAATGTCGCTTACCACTTAA |
| P-ANDge.Ubq1-1:1:13 | --------------------------------GTCAACGGGAATGTCGCTTACCACTTAA |
| P-ANDge.Ubq1-1:1:14 | ------------------------------------------------------------ |
| P-ANDge.Ubq1-1:1:10 | GAGATTCTCGAAGTCACTATTAGCGCCTCGTTGTCAACGGGAATGTCGCTTACCACTTAA |
| | |
| P-ANDge.Ubq1-1:1:9 | AGCATAACGCCGAGAAATCCCGTAATAAATCCAGTAAAATACGAGCACCCGTGCCAAGTT |
| P-ANDge.Ubq1-1:1:8 | AGCATAACGCCGAGAAATCCCGTAATAAATCCAGTAAAATACGAGCACCCGTGCCAAGTT |
| P-ANDge.Ubq1-1:1:11 | AGCATAACGCCGAGAAATCCCGTAATAAATCCAGTAAAATACGAGCACCCGTGCCAAGTT |
| P-ANDge.Ubq1-1:1:12 | AGCATAACGCCGAGAAATCCCGTAATAAATCCAGTAAAATACGAGCACCCGTGCCAAGTT |
| P-ANDge.Ubq1-1:1:13 | AGCATAACGCCGAGAAATCCCGTAATAAATCCAGTAAAATACGAGCACCCGTGCCAAGTT |
| P-ANDge.Ubq1-1:1:14 | ------------------------------------------------------------ |
| P-ANDge.Ubq1-1:1:10 | AGCATAACGCCGAGAAATCCCGTAATAAATCCAGTAAAATACGAGCACCCGTGCCAAGTT |
| | |
| P-ANDge.Ubq1-1:1:9 | GAATATTTGAACCCGAGTGGGTAGATTCCACCGCAAAGGACCTAACCAGATCATTTCGCA |
| P-ANDge.Ubq1-1:1:8 | GAATATTTGAACCCGAGTGGGTAGATTCCACCGCAAAGGACCTAACCAGATCATTTCGCA |
| P-ANDge.Ubq1-1:1:11 | GAATATTTGAACCCGAGTGGGTAGATTCCACCGCAAAGGACCTAACCAGATCATTTCGCA |
| P-ANDge.Ubq1-1:1:12 | GAATATTTGAACCCGAGTGGGTAGATTCCACCGCAAAGGACCTAACCAGATCATTTCGCA |
| P-ANDge.Ubq1-1:1:13 | GAATATTTGAACCCGAGTGGGTAGATTCCACCGCAAAGGACCTAACCAGATCATTTCGCA |
| P-ANDge.Ubq1-1:1:14 | ------------------------------------------------------------ |
| P-ANDge.Ubq1-1:1:10 | GAATATTTGAACCCGAGTGGGTAGATTCCACCGCAAAGGACCTAACCAGATCATTTCGCA |
| | |
| P-ANDge.Ubq1-1:1:9 | AACAGGAACTAAAATCGGTAGAGAGCCCAGACAAAAGCCTTTCCTAAGAGCCACTCCAGT |
| P-ANDge.Ubq1-1:1:8 | AACAGGAACTAAAATCGGTAGAGAGCCCAGACAAAAGCCTTTCCTAAGAGCCACTCCAGT |
| P-ANDge.Ubq1-1:1:11 | AACAGGAACTAAAATCGGTAGAGAGCCCAGACAAAAGCCTTTCCTAAGAGCCACTCCAGT |
| P-ANDge.Ubq1-1:1:12 | AACAGGAACTAAAATCGGTAGAGAGCCCAGACAAAAGCCTTTCCTAAGAGCCACTCCAGT |
| P-ANDge.Ubq1-1:1:13 | AACAGGAACTAAAATCGGTAGAGAGCCCAGACAAAAGCCTTTCCTAAGAGCCACTCCAGT |
| P-ANDge.Ubq1-1:1:14 | ------------------------------------------------------------ |
| P-ANDge.Ubq1-1:1:10 | AACAGGAACTAAAATCGGTAGAGAGCCCAGACAAAAGCCTTTCCTAAGAGCCACTCCAGT |
| | |
| P-ANDge.Ubq1-1:1:9 | GGAAGCCCCTACTTTAGGTATAAAATGCAATACTAGTGGGGCTCCTAAATAAACTTCTAT |
| P-ANDge.Ubq1-1:1:8 | GGAAGCCCCTACTTTAGGTATAAAATGCAATACTAGTGGGGCTCCTAAATAAACTTCTAT |
| P-ANDge.Ubq1-1:1:11 | GGAAGCCCCTACTTTAGGTATAAAATGCAATACTAGTGGGGCTCCTAAATAAACTTCTAT |
| P-ANDge.Ubq1-1:1:12 | GGAAGCCCCTACTTTAGGTATAAAATGCAATACTAGTGGGGCTCCTAAATAAACTTCTAT |
| P-ANDge.Ubq1-1:1:13 | GGAAGCCCCTACTTTAGGTATAAAATGCAATACTAGTGGGGCTCCTAAATAAACTTCTAT |
| P-ANDge.Ubq1-1:1:14 | ------------------------------------------------------------ |
| P-ANDge.Ubq1-1:1:10 | GGAAGCCCCTACTTTAGGTATAAAATGCAATACTAGTGGGGCTCCTAAATAAACTTCTAT |
| | |
| P-ANDge.Ubq1-1:1:9 | TTTTCATGGCCTTCTAAAATTCACTCCCAAACCCCTAGCTATAGAAGTCTCTTATCCATC |
| P-ANDge.Ubq1-1:1:8 | TTTTCATGGCCTTCTAAAATTCACTCCCAAACCCCTAGCTATAGAAGTCTCTTATCCATC |
| P-ANDge.Ubq1-1:1:11 | TTTTCATGGCCTTCTAAAATTCACTCCCAAACCCCTAGCTATAGAAGTCTCTTATCCATC |
| P-ANDge.Ubq1-1:1:12 | TTTTCATGGCCTTCTAAAATTCACTCCCAAACCCCTAGCTATAGAAGTCTCTTATCCATC |
| P-ANDge.Ubq1-1:1:13 | TTTTCATGGCCTTCTAAAATTCACTCCCAAACCCCTAGCTATAGAAGTCTCTTATCCATC |
| P-ANDge.Ubq1-1:1:14 | ---------------------CACTCCCAAACCCCTAGCTATAGAAGTCTCTTATCCATC |
| P-ANDge.Ubq1-1:1:10 | TTTTCATGGCCTTCTAAAATTCACTCCCAAACCCCTAGCTATAGAAGTCTCTTATCCATC |
| |                      \*\*\*\*\*\*\*\*\*\*\*\*\*\*\*\*\*\*\*\*\*\*\*\*\*\*\*\*\*\*\*\*\*\*\*\*\*\*\*\* |

FIG. 1f

```
P-ANDge.Ubq1-1:1:9     CTCTAAATAAAAATGGGAGTCTATTTTATTTCACCAGAGTTGATCGTAAATTTAGTCTCT
P-ANDge.Ubq1-1:1:8     CTCTAAATAAAAATGGGAGTCTATTTTATTTCACCAGAGTTGATCGTAAATTTAGTCTCT
P-ANDge.Ubq1-1:1:11    CTCTAAATAAAAATGGGAGTCTATTTTATTTCACCAGAGTTGATCGTAAATTTAGTCTCT
P-ANDge.Ubq1-1:1:12    CTCTAAATAAAAATGGGAGTCTATTTTATTTCACCAGAGTTGATCGTAAATTTAGTCTCT
P-ANDge.Ubq1-1:1:13    CTCTAAATAAAAATGGGAGTCTATTTTATTTCACCAGAGTTGATCGTAAATTTAGTCTCT
P-ANDge.Ubq1-1:1:14    CTCTAAATAAAAATGGGAGTCTATTTTATTTCACCAGAGTTGATCGTAAATTTAGTCTCT
P-ANDge.Ubq1-1:1:10    CTCTAAATAAAAATGGGAGTCTATTTTATTTCACCAGAGTTGATCGTAAATTTAGTCTCT
                       ************************************************************

P-ANDge.Ubq1-1:1:9     CAAATTTTATAAGTTGAGGGTAGAGGATGACTGGAGTTGCTCTAAACGGACCTATCTTCA
P-ANDge.Ubq1-1:1:8     CAAATTTTATAAGTTGAGGGTAGAGGATGACTGGAGTTGCTCTAAACGGACCTATCTTCA
P-ANDge.Ubq1-1:1:11    CAAATTTTATAAGTTGAGGGTAGAGGATGACTGGAGTTGCTCTAAACGGACCTATCTTCA
P-ANDge.Ubq1-1:1:12    CAAATTTTATAAGTTGAGGGTAGAGGATGACTGGAGTTGCTCTAAACGGACCTATCTTCA
P-ANDge.Ubq1-1:1:13    CAAATTTTATAAGTTGAGGGTAGAGGATGACTGGAGTTGCTCTAAACGGACCTATCTTCA
P-ANDge.Ubq1-1:1:14    CAAATTTTATAAGTTGAGGGTAGAGGATGACTGGAGTTGCTCTAAACGGACCTATCTTCA
P-ANDge.Ubq1-1:1:10    CAAATTTTATAAGTTGAGGGTAGAGGATGACTGGAGTTGCTCTAAACGGACCTATCTTCA
                       ************************************************************

P-ANDge.Ubq1-1:1:9     AGTGACCTCAGTGAGCCCGTTTAACGGCGTCGACAAGTTTAATCTAACGGACACCAACCA
P-ANDge.Ubq1-1:1:8     AGTGACCTCAGTGAGCCCGTTTAACGGCGTCGACAAGTTTAATCTAACGGACACCAACCA
P-ANDge.Ubq1-1:1:11    AGTGACCTCAGTGAGCCCGTTTAACGGCGTCGACAAGTTTAATCTAACGGACACCAACCA
P-ANDge.Ubq1-1:1:12    AGTGACCTCAGTGAGCCCGTTTAACGGCGTCGACAAGTTTAATCTAACGGACACCAACCA
P-ANDge.Ubq1-1:1:13    AGTGACCTCAGTGAGCCCGTTTAACGGCGTCGACAAGTTTAATCTAACGGACACCAACCA
P-ANDge.Ubq1-1:1:14    AGTGACCTCAGTGAGCCCGTTTAACGGCGTCGACAAGTTTAATCTAACGGACACCAACCA
P-ANDge.Ubq1-1:1:10    AGTGACCTCAGTGAGCCCGTTTAACGGCGTCGACAAGTTTAATCTAACGGACACCAACCA
                       ************************************************************

P-ANDge.Ubq1-1:1:9     GAGAAGAGAACCACCGCCAGCGCCGAGCCAAGCGACGTTGACATCTTGGCGCGGCACGGC
P-ANDge.Ubq1-1:1:8     GAGAAGAGAACCACCGCCAGCGCCGAGCCAAGCGACGTTGACATCTTGGCGCGGCACGGC
P-ANDge.Ubq1-1:1:11    GAGAAGAGAACCACCGCCAGCGCCGAGCCAAGCGACGTTGACATCTTGGCGCGGCACGGC
P-ANDge.Ubq1-1:1:12    GAGAAGAGAACCACCGCCAGCGCCGAGCCAAGCGACGTTGACATCTTGGCGCGGCACGGC
P-ANDge.Ubq1-1:1:13    GAGAAGAGAACCACCGCCAGCGCCGAGCCAAGCGACGTTGACATCTTGGCGCGGCACGGC
P-ANDge.Ubq1-1:1:14    GAGAAGAGAACCACCGCCAGCGCCGAGCCAAGCGACGTTGACATCTTGGCGCGGCACGGC
P-ANDge.Ubq1-1:1:10    GAGAAGAGAACCACCGCCAGCGCCGAGCCAAGCGACGTTGACATCTTGGCGCGGCACGGC
                       ************************************************************

P-ANDge.Ubq1-1:1:9     ATCTCCCTGGCGTCTGGCCCCCTCTCGAGACTTCCGCTCCACCTCCCACCGGTGGCGGTT
P-ANDge.Ubq1-1:1:8     ATCTCCCTGGCGTCTGGCCCCCTCTCGAGACTTCCGCTCCACCTCCCACCGGTGGCGGTT
P-ANDge.Ubq1-1:1:11    ATCTCCCTGGCGTCTGGCCCCCTCTCGAGACTTCCGCTCCACCTCCCACCGGTGGCGGTT
P-ANDge.Ubq1-1:1:12    ATCTCCCTGGCGTCTGGCCCCCTCTCGAGACTTCCGCTCCACCTCCCACCGGTGGCGGTT
P-ANDge.Ubq1-1:1:13    ATCTCCCTGGCGTCTGGCCCCCTCTCGAGACTTCCGCTCCACCTCCCACCGGTGGCGGTT
P-ANDge.Ubq1-1:1:14    ATCTCCCTGGCGTCTGGCCCCCTCTCGAGACTTCCGCTCCACCTCCCACCGGTGGCGGTT
P-ANDge.Ubq1-1:1:10    ATCTCCCTGGCGTCTGGCCCCCTCTCGAGACTTCCGCTCCACCTCCCACCGGTGGCGGTT
                       ************************************************************
```

FIG. 1g

```
P-ANDge.Ubq1-1:1:9     TCCAAGTCCGTTCCGCCTCCTCTCACACGGCACGAAACCGTGACGGGCACCGGCAGCACG
P-ANDge.Ubq1-1:1:8     TCCAAGTCCGTTCCGCCTCCTCTCACACGGCACGAAACCGTGACGGGCACCGGCAGCACG
P-ANDge.Ubq1-1:1:11    TCCAAGTCCGTTCCGCCTCCTCTCACACGGCACGAAACCGTGACGGGCACCGGCAGCACG
P-ANDge.Ubq1-1:1:12    TCCAAGTCCGTTCCGCCTCCTCTCACACGGCACGAAACCGTGACGGGCACCGGCAGCACG
P-ANDge.Ubq1-1:1:13    TCCAAGTCCGTTCCGCCTCCTCTCACACGGCACGAAACCGTGACGGGCACCGGCAGCACG
P-ANDge.Ubq1-1:1:14    TCCAAGTCCGTTCCGCCTCCTCTCACACGGCACGAAACCGTGACGGGCACCGGCAGCACG
P-ANDge.Ubq1-1:1:10    TCCAAGTCCGTTCCGCCTCCTCTCACACGGCACGAAACCGTGACGGGCACCGGCAGCACG
                       ************************************************************

P-ANDge.Ubq1-1:1:9     GGGGGATTCCTTTCCCACCGCTCCTTCCCTTTCCCTTCCTCTCCCGCCGCTATAAATAGC
P-ANDge.Ubq1-1:1:8     GGGGGATTCCTTTCCCACCGCTCCTTCCCTTTCCCTTCCTCTCCCGCCGCTATAAATAGC
P-ANDge.Ubq1-1:1:11    GGGGGATTCCTTTCCCACCGCTCCTTCCCTTTCCCTTCCTCTCCCGCCGCTATAAATAGC
P-ANDge.Ubq1-1:1:12    GGGGGATTCCTTTCCCACCGCTCCTTCCCTTTCCCTTCCTCTCCCGCCGCTATAAATAGC
P-ANDge.Ubq1-1:1:13    GGGGGATTCCTTTCCCACCGCTCCTTCCCTTTCCCTTCCTCTCCCGCCGCTATAAATAGC
P-ANDge.Ubq1-1:1:14    GGGGGATTCCTTTCCCACCGCTCCTTCCCTTTCCCTTCCTCTCCCGCCGCTATAAATAGC
P-ANDge.Ubq1-1:1:10    GGGGGATTCCTTTCCCACCGCTCCTTCCCTTTCCCTTCCTCTCCCGCCGCTATAAATAGC
                       ************************************************************

P-ANDge.Ubq1-1:1:9     CAGCCCCATCCCCAGCTTCTTTC
P-ANDge.Ubq1-1:1:8     CAGCCCCATCCCCAGCTTCTTTC
P-ANDge.Ubq1-1:1:11    CAGCCCCATCCCCAGCTTCTTTC
P-ANDge.Ubq1-1:1:12    CAGCCCCATCCCCAGCTTCTTTC
P-ANDge.Ubq1-1:1:13    CAGCCCCATCCCCAGCTTCTTTC
P-ANDge.Ubq1-1:1:14    CAGCCCCATCCCCAGCTTCTTTC
P-ANDge.Ubq1-1:1:10    CAGCCCCATCCCCAGCTTCTTTC
                       ***********************
```

FIG. 1h

```
P-ERIra.Ubq1-1:1:9     ------------------------------------------------------------
P-ERIra.Ubq1-1:1:10    GTGGCCAGCTTTTGTTCTAGTTCAACGGCCCCGGCCTTCCGGGCACCTAATACCCTAATT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    AATCTATTGCAGCTAACCTCAAAAGAAATGCATTTGCAGTTGTCTGTCCCAATCAATCTA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    CTAGCAGACTTACATTATAGATGGAGGAAATTAAATTCAGCCTTTGACGTGGATGCAACA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    ACTGCACTGCACAGGATACCATCTTAGCCGTTGTGTCAAAGTTTGCTTTGCTAAACGTTT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    TGAGAAAACCAGCTTTGACCAACGCGAGATGAGCGCCTTACGTTTGGCACAATGTAATGT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     ------------------------------------------------------------
P-ERIra.Ubq1-1:1:10    AATCCGGCACGGCAAGTTAGACTCTGTAGTGTTAGCCGGCCTCTTTACGTTTGGCATAGT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------
```

FIG. 2a

```
P-ERIra.Ubq1-1:1:9     ------------------------------------------------------------
P-ERIra.Ubq1-1:1:10    TTAATTGAATCCGGCATGGCAAGTTAGACCGTAGTGTGAGCCGGCCAACGCAAGTTATTA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     --------GTATAAGAGCAAGTGTATTGTCACGTGATATTTATGTTGAGATGAAGAAGAG
P-ERIra.Ubq1-1:1:10    TGACATATGTATAAGAGCAAGTGTATTGTCACGTGATATTTATGTTGAGATGAAGAAGAG
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     AAAATAAACAGCCTGCAAATTTATAGCGAGTGATAGATGGGCACAAGGCTTCCTATTTCT
P-ERIra.Ubq1-1:1:10    AAAATAAACAGCCTGCAAATTTATAGCGAGTGATAGATGGGCACAAGGCTTCCTATTTCT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     TAAATCAGACTTTGTAAGAACAAAAAAAGGACTTATAAGAGAATGGGATAAACCATATAT
P-ERIra.Ubq1-1:1:10    TAAATCAGACTTTGTAAGAACAAAAAAAGGACTTATAAGAGAATGGGATAAACCATATAT
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     CAATGGTGTAGTATGTTAGTATGCATTAAGATCTGACTATTATATGAGTGAGTTGTTAAA
P-ERIra.Ubq1-1:1:10    CAATGGTGTAGTATGTTAGTATGCATTAAGATCTGACTATTATATGAGTGAGTTGTTAAA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------

P-ERIra.Ubq1-1:1:9     TTCATTTTAGGTGACATGGCCCGGTTAAATTATTAGCCATACCCTAACAGCTCTAAAAAA
P-ERIra.Ubq1-1:1:10    TTCATTTTAGGTGACATGGCCCGGTTAAATTATTAGCCATACCCTAACAGCTCTAAAAAA
P-ERIra.Ubq1-1:1:8     ------------------------------------------------------------
P-ERIra.Ubq1-1:1:11    ------------------------------------------------------------
P-ERIra.Ubq1-1:1:12    ------------------------------------------------------------
P-ERIra.Ubq1-1:1:13    ------------------------------------------------------------
```

FIG. 2b

```
P-ERIra.Ubq1-1:1:9      GATATATTCGTTGAGGCACTTTTATGCAACCACATAGTCAACTTGAATGCCGCTTGAGTG
P-ERIra.Ubq1-1:1:10     GATATATTCGTTGAGGCACTTTTATGCAACCACATAGTCAACTTGAATGCCGCTTGAGTG
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      CGTTCTCAAGTTTTTTTCTTGCAAATTACGCTTTTTAAGAAAGTATAATTTGGATCGT
P-ERIra.Ubq1-1:1:10     CGTTCTCAAGTTTTTTTCTTGCAAATTACGCTTTTTAAGAAAGTATAATTTGGATCGT
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      GCGATTTTTTTCTCTAGGTGTGCGTGACTGTGTGAGTAACAATTTTGGATCTCAGAAAG
P-ERIra.Ubq1-1:1:10     GCGATTTTTTTCTCTAGGTGTGCGTGACTGTGTGAGTAACAATTTTGGATCTCAGAAAG
P-ERIra.Ubq1-1:1:8      ------------------------------------------------------------
P-ERIra.Ubq1-1:1:11     ------------------------------------------------------------
P-ERIra.Ubq1-1:1:12     ------------------------------------------------------------
P-ERIra.Ubq1-1:1:13     ------------------------------------------------------------

P-ERIra.Ubq1-1:1:9      GTAATAAAAGAATAATACTGCTGCCTACTTTGAGGATTACAATATCTTTCTCTAAAATGT
P-ERIra.Ubq1-1:1:10     GTAATAAAAGAATAATACTGCTGCCTACTTTGAGGATTACAATATCTTTCTCTAAAATGT
P-ERIra.Ubq1-1:1:8      ------------------------------------------------------------
P-ERIra.Ubq1-1:1:11     ------------------CTGCTGCCTACTTTGAGGATTACAATATCTTTCTCTAAAATGT
P-ERIra.Ubq1-1:1:12     ------------------------------------------------------------
P-ERIra.Ubq1-1:1:13     ------------------------------------------------------------

P-ERIra.Ubq1-1:1:9      TTTGGTTTGTTATTTAAACCGTCTTTAAGGCCAATTGCTCAAGATTCATTCAACAATTGA
P-ERIra.Ubq1-1:1:10     TTTGGTTTGTTATTTAAACCGTCTTTAAGGCCAATTGCTCAAGATTCATTCAACAATTGA
P-ERIra.Ubq1-1:1:8      ------------------------------------------------------------
P-ERIra.Ubq1-1:1:11     TTTGGTTTGTTATTTAAACCGTCTTTAAGGCCAATTGCTCAAGATTCATTCAACAATTGA
P-ERIra.Ubq1-1:1:12     ------------------------------------------------------------
P-ERIra.Ubq1-1:1:13     ------------------------------------------------------------

P-ERIra.Ubq1-1:1:9      AACGTCTCACATGATTAAATCATATAAGGTTGCTAAGGTCTTGTTTGACAAGGTTTTTTT
P-ERIra.Ubq1-1:1:10     AACGTCTCACATGATTAAATCATATAAGGTTGCTAAGGTCTTGTTTGACAAGGTTTTTTT
P-ERIra.Ubq1-1:1:8      ------------------------------------------------------------
P-ERIra.Ubq1-1:1:11     AACGTCTCACATGATTAAATCATATAAGGTTGCTAAGGTCTTGTTTGACAAGGTTTTTTT
P-ERIra.Ubq1-1:1:12     ------------------------------------------------------------
P-ERIra.Ubq1-1:1:13     ------------------------------------------------------------
```

FIG. 2c

```
P-ERIra.Ubq1-1:1:9      TGTGGAAATTTCATCTAAATTTTTGAGTGAAACTATCAAATACTAATTTAAAAAAGGCAA
P-ERIra.Ubq1-1:1:10     TGTGGAAATTTCATCTAAATTTTTGAGTGAAACTATCAAATACTAATTTAAAAAAGGCAA
P-ERIra.Ubq1-1:1:8      ------------------------------------------------------------
P-ERIra.Ubq1-1:1:11     TGTGGAAATTTCATCTAAATTTTTGAGTGAAACTATCAAATACTAATTTAAAAAAGGCAA
P-ERIra.Ubq1-1:1:12     ------------------------------------------------------------
P-ERIra.Ubq1-1:1:13     ------------------------------------------------------------

P-ERIra.Ubq1-1:1:9      ATTTTGCTGGAGGACACTGCAGAAACGTGTAATTGGCCGGCACAAACCGCCAAACGGAGA
P-ERIra.Ubq1-1:1:10     ATTTTGCTGGAGGACACTGCAGAAACGTGTAATTGGCCGGCACAAACCGCCAAACGGAGA
P-ERIra.Ubq1-1:1:8      ------------------------------------------------------------
P-ERIra.Ubq1-1:1:11     ATTTTGCTGGAGGACACTGCAGAAACGTGTAATTGGCCGGCACAAACCGCCAAACGGAGA
P-ERIra.Ubq1-1:1:12     ------------------------------------------------------------
P-ERIra.Ubq1-1:1:13     ------------------------------------------------------------

P-ERIra.Ubq1-1:1:9      ATTTGCCCAGTACCATTATAAATTCATGATAAATTCATGGTTGTTTGCCAGTGGGGCTAG
P-ERIra.Ubq1-1:1:10     ATTTGCCCAGTACCATTATAAATTCATGATAAATTCATGGTTGTTTGCCAGTGGGGCTAG
P-ERIra.Ubq1-1:1:8      ------------------------------------------------------------
P-ERIra.Ubq1-1:1:11     ATTTGCCCAGTACCATTATAAATTCATGATAAATTCATGGTTGTTTGCCAGTGGGGCTAG
P-ERIra.Ubq1-1:1:12     ------------------------------------------------------------
P-ERIra.Ubq1-1:1:13     ------------------------------------------------------------

P-ERIra.Ubq1-1:1:9      GGTTCCTCGCGTATGGTGCGGAATGTGGTTTGGTTCGACCAACTCGAACTCAATCCGATC
P-ERIra.Ubq1-1:1:10     GGTTCCTCGCGTATGGTGCGGAATGTGGTTTGGTTCGACCAACTCGAACTCAATCCGATC
P-ERIra.Ubq1-1:1:8      ------------------------------------------------------------
P-ERIra.Ubq1-1:1:11     GGTTCCTCGCGTATGGTGCGGAATGTGGTTTGGTTCGACCAACTCGAACTCAATCCGATC
P-ERIra.Ubq1-1:1:12     ------------------------------------------------------------
P-ERIra.Ubq1-1:1:13     ------------------------------------------------------------

P-ERIra.Ubq1-1:1:9      CAAAGGGGCATCAATAGTCATTTTAGAAAGTTTCTCTCTCCCGAGCAGTGGAAATGATTA
P-ERIra.Ubq1-1:1:10     CAAAGGGGCATCAATAGTCATTTTAGAAAGTTTCTCTCTCCCGAGCAGTGGAAATGATTA
P-ERIra.Ubq1-1:1:8      ------------------------------------------------------------
P-ERIra.Ubq1-1:1:11     CAAAGGGGCATCAATAGTCATTTTAGAAAGTTTCTCTCTCCCGAGCAGTGGAAATGATTA
P-ERIra.Ubq1-1:1:12     ------------------------------------------------------------
P-ERIra.Ubq1-1:1:13     ------------------------------------------------------------

P-ERIra.Ubq1-1:1:9      TTCTATTTGGCGCGATGTCCACCGGCAAACAACCACGAATTTGTAATGGTACTAGGCAAA
P-ERIra.Ubq1-1:1:10     TTCTATTTGGCGCGATGTCCACCGGCAAACAACCACGAATTTGTAATGGTACTAGGCAAA
P-ERIra.Ubq1-1:1:8      ------------------CCACCGGCAAACAACCACGAATTTGTAATGGTACTAGGCAAA
P-ERIra.Ubq1-1:1:11     TTCTATTTGGCGCGATGTCCACCGGCAAACAACCACGAATTTGTAATGGTACTAGGCAAA
P-ERIra.Ubq1-1:1:12     ------------------------------------------------------------
P-ERIra.Ubq1-1:1:13     ------------------------------------------------------------
```

FIG. 2d

```
P-ERIra.Ubq1-1:1:9     TTCTCCGTTTGGCGGTGTGTGCCGGCCAATTACACGTTTTTGCGGTGTCCTCCGACAAAA
P-ERIra.Ubq1-1:1:10    TTCTCCGTTTGGCGGTGTGTGCCGGCCAATTACACGTTTTTGCGGTGTCCTCCGACAAAA
P-ERIra.Ubq1-1:1:8     TTCTCCGTTTGGCGGTGTGTGCCGGCCAATTACACGTTTTTGCGGTGTCCTCCGACAAAA
P-ERIra.Ubq1-1:1:11    TTCTCCGTTTGGCGGTGTGTGCCGGCCAATTACACGTTTTTGCGGTGTCCTCCGACAAAA
P-ERIra.Ubq1-1:1:12    ------------------------------------------------------------
P-ERIra.Ubq1-1:1:13    ------------------------------------------------------------

P-ERIra.Ubq1-1:1:9     TTTGCCTTTTAAAAACAATTTTATAAGAGAAGCTCCGGAGATAAAAGGCCGTCAATGTTA
P-ERIra.Ubq1-1:1:10    TTTGCCTTTTAAAAACAATTTTATAAGAGAAGCTCCGGAGATAAAAGGCCGTCAATGTTA
P-ERIra.Ubq1-1:1:8     TTTGCCTTTTAAAAACAATTTTATAAGAGAAGCTCCGGAGATAAAAGGCCGTCAATGTTA
P-ERIra.Ubq1-1:1:11    TTTGCCTTTTAAAAACAATTTTATAAGAGAAGCTCCGGAGATAAAAGGCCGTCAATGTTA
P-ERIra.Ubq1-1:1:12    ------------------------------------------------------------
P-ERIra.Ubq1-1:1:13    ------------------------------------------------------------

P-ERIra.Ubq1-1:1:9     CAAGAGTGAAGTCGTCTACTCCCTCCATCCCAAAAAATGTAATTCTAAGTATGAGTTGTA
P-ERIra.Ubq1-1:1:10    CAAGAGTGAAGTCGTCTACTCCCTCCATCCCAAAAAATGTAATTCTAAGTATGAGTTGTA
P-ERIra.Ubq1-1:1:8     CAAGAGTGAAGTCGTCTACTCCCTCCATCCCAAAAAATGTAATTCTAAGTATGAGTTGTA
P-ERIra.Ubq1-1:1:11    CAAGAGTGAAGTCGTCTACTCCCTCCATCCCAAAAAATGTAATTCTAAGTATGAGTTGTA
P-ERIra.Ubq1-1:1:12    ------------------------------------------------------------
P-ERIra.Ubq1-1:1:13    ------------------------------------------------------------

P-ERIra.Ubq1-1:1:9     TTATTATTTTTGGACAAAAGGAGTATACCACAAGAATGATATCATCGTCATGCTTAGATC
P-ERIra.Ubq1-1:1:10    TTATTATTTTTGGACAAAAGGAGTATACCACAAGAATGATATCATCGTCATGCTTAGATC
P-ERIra.Ubq1-1:1:8     TTATTATTTTTGGACAAAAGGAGTATACCACAAGAATGATATCATCGTCATGCTTAGATC
P-ERIra.Ubq1-1:1:11    TTATTATTTTTGGACAAAAGGAGTATACCACAAGAATGATATCATCGTCATGCTTAGATC
P-ERIra.Ubq1-1:1:12    --------------------------ACCACAAGAATGATATCATCGTCATGCTTAGATC
P-ERIra.Ubq1-1:1:13    ------------------------------------------------------------

P-ERIra.Ubq1-1:1:9     CTTTTTAGTAAAGCTTGAGCTTCTCTAAAAGTAGAGAAATTAGAAAAAAATCACGTTTTT
P-ERIra.Ubq1-1:1:10    CTTTTTAGTAAAGCTTGAGCTTCTCTAAAAGTAGAGAAATTAGAAAAAAATCACGTTTTT
P-ERIra.Ubq1-1:1:8     CTTTTTAGTAAAGCTTGAGCTTCTCTAAAAGTAGAGAAATTAGAAAAAAATCACGTTTTT
P-ERIra.Ubq1-1:1:11    CTTTTTAGTAAAGCTTGAGCTTCTCTAAAAGTAGAGAAATTAGAAAAAAATCACGTTTTT
P-ERIra.Ubq1-1:1:12    CTTTTTAGTAAAGCTTGAGCTTCTCTAAAAGTAGAGAAATTAGAAAAAAATCACGTTTTT
P-ERIra.Ubq1-1:1:13    ------------------------------------------------------------

P-ERIra.Ubq1-1:1:9     GTGGTCTTGATTTCTAGCCTCCACAAAATCTTTGGTTTTACATTTTTTGTTTGATTTTGG
P-ERIra.Ubq1-1:1:10    GTGGTCTTGATTTCTAGCCTCCACAAAATCTTTGGTTTTACATTTTTTGTTTGATTTTGG
P-ERIra.Ubq1-1:1:8     GTGGTCTTGATTTCTAGCCTCCACAAAATCTTTGGTTTTACATTTTTTGTTTGATTTTGG
P-ERIra.Ubq1-1:1:11    GTGGTCTTGATTTCTAGCCTCCACAAAATCTTTGGTTTTACATTTTTTGTTTGATTTTGG
P-ERIra.Ubq1-1:1:12    GTGGTCTTGATTTCTAGCCTCCACAAAATCTTTGGTTTTACATTTTTTGTTTGATTTTGG
P-ERIra.Ubq1-1:1:13    ------------------------------------------------------------
```

FIG. 2e

```
P-ERIra.Ubq1-1:1:9   TTTCAGAAGTCCTTATTTATATGTGCTAGTTTGGCAGCACTTAAAATCGTTAGAGAGAGC
P-ERIra.Ubq1-1:1:10  TTTCAGAAGTCCTTATTTATATGTGCTAGTTTGGCAGCACTTAAAATCGTTAGAGAGAGC
P-ERIra.Ubq1-1:1:8   TTTCAGAAGTCCTTATTTATATGTGCTAGTTTGGCAGCACTTAAAATCGTTAGAGAGAGC
P-ERIra.Ubq1-1:1:11  TTTCAGAAGTCCTTATTTATATGTGCTAGTTTGGCAGCACTTAAAATCGTTAGAGAGAGC
P-ERIra.Ubq1-1:1:12  TTTCAGAAGTCCTTATTTATATGTGCTAGTTTGGCAGCACTTAAAATCGTTAGAGAGAGC
P-ERIra.Ubq1-1:1:13  ------------------------------------------------------------

P-ERIra.Ubq1-1:1:9   CTAAACAAAAGCCTTTTCAAAACGACCTTGAGCCAGATTGGTTGATGGCCAAAATTTGAT
P-ERIra.Ubq1-1:1:10  CTAAACAAAAGCCTTTTCAAAACGACCTTGAGCCAGATTGGTTGATGGCCAAAATTTGAT
P-ERIra.Ubq1-1:1:8   CTAAACAAAAGCCTTTTCAAAACGACCTTGAGCCAGATTGGTTGATGGCCAAAATTTGAT
P-ERIra.Ubq1-1:1:11  CTAAACAAAAGCCTTTTCAAAACGACCTTGAGCCAGATTGGTTGATGGCCAAAATTTGAT
P-ERIra.Ubq1-1:1:12  CTAAACAAAAGCCTTTTCAAAACGACCTTGAGCCAGATTGGTTGATGGCCAAAATTTGAT
P-ERIra.Ubq1-1:1:13  ------------------------------------------------------------

P-ERIra.Ubq1-1:1:9   TGTCAAAACTTAGGCAAGCCAAGATTTTAGCAGCTATTTGGTTTGGTACCAAAATTTGCC
P-ERIra.Ubq1-1:1:10  TGTCAAAACTTAGGCAAGCCAAGATTTTAGCAGCTATTTGGTTTGGTACCAAAATTTGCC
P-ERIra.Ubq1-1:1:8   TGTCAAAACTTAGGCAAGCCAAGATTTTAGCAGCTATTTGGTTTGGTACCAAAATTTGCC
P-ERIra.Ubq1-1:1:11  TGTCAAAACTTAGGCAAGCCAAGATTTTAGCAGCTATTTGGTTTGGTACCAAAATTTGCC
P-ERIra.Ubq1-1:1:12  TGTCAAAACTTAGGCAAGCCAAGATTTTAGCAGCTATTTGGTTTGGTACCAAAATTTGCC
P-ERIra.Ubq1-1:1:13  -----------AGGCAAGCCAAGATTTTAGCAGCTATTTGGTTTGGTACCAAAATTTGCC
                                ************************************************

P-ERIra.Ubq1-1:1:9   AATGATCTGTTCTTTTGCCTTTTCAACCGGTTTATCAGCCGTACTTCAGCTTATTCTCTC
P-ERIra.Ubq1-1:1:10  AATGATCTGTTCTTTTGCCTTTTCAACCGGTTTATCAGCCGTACTTCAGCTTATTCTCTC
P-ERIra.Ubq1-1:1:8   AATGATCTGTTCTTTTGCCTTTTCAACCGGTTTATCAGCCGTACTTCAGCTTATTCTCTC
P-ERIra.Ubq1-1:1:11  AATGATCTGTTCTTTTGCCTTTTCAACCGGTTTATCAGCCGTACTTCAGCTTATTCTCTC
P-ERIra.Ubq1-1:1:12  AATGATCTGTTCTTTTGCCTTTTCAACCGGTTTATCAGCCGTACTTCAGCTTATTCTCTC
P-ERIra.Ubq1-1:1:13  AATGATCTGTTCTTTTGCCTTTTCAACCGGTTTATCAGCCGTACTTCAGCTTATTCTCTC
                     ************************************************************

P-ERIra.Ubq1-1:1:9   TCACAGAACACTATTGAATCAGCCGAAAAGCCACCGCAGAACAGGACCAGTATCTCACAA
P-ERIra.Ubq1-1:1:10  TCACAGAACACTATTGAATCAGCCGAAAAGCCACCGCAGAACAGGACCAGTATCTCACAA
P-ERIra.Ubq1-1:1:8   TCACAGAACACTATTGAATCAGCCGAAAAGCCACCGCAGAACAGGACCAGTATCTCACAA
P-ERIra.Ubq1-1:1:11  TCACAGAACACTATTGAATCAGCCGAAAAGCCACCGCAGAACAGGACCAGTATCTCACAA
P-ERIra.Ubq1-1:1:12  TCACAGAACACTATTGAATCAGCCGAAAAGCCACCGCAGAACAGGACCAGTATCTCACAA
P-ERIra.Ubq1-1:1:13  TCACAGAACACTATTGAATCAGCCGAAAAGCCACCGCAGAACAGGACCAGTATCTCACAA
                     ************************************************************

P-ERIra.Ubq1-1:1:9   ATGGCATGCCAAATATACTCACCGTCAGTGAGCCCGTTTAACGGCGTCGACAAGTCTAAC
P-ERIra.Ubq1-1:1:10  ATGGCATGCCAAATATACTCACCGTCAGTGAGCCCGTTTAACGGCGTCGACAAGTCTAAC
P-ERIra.Ubq1-1:1:8   ATGGCATGCCAAATATACTCACCGTCAGTGAGCCCGTTTAACGGCGTCGACAAGTCTAAC
P-ERIra.Ubq1-1:1:11  ATGGCATGCCAAATATACTCACCGTCAGTGAGCCCGTTTAACGGCGTCGACAAGTCTAAC
P-ERIra.Ubq1-1:1:12  ATGGCATGCCAAATATACTCACCGTCAGTGAGCCCGTTTAACGGCGTCGACAAGTCTAAC
P-ERIra.Ubq1-1:1:13  ATGGCATGCCAAATATACTCACCGTCAGTGAGCCCGTTTAACGGCGTCGACAAGTCTAAC
                     ************************************************************
```

FIG. 2f

```
P-ERIra.Ubq1-1:1:9     GGCCACCAACCAGCGAACCACCAGCGTCAAGCTAGCCAAGCGAAGCAGACGGCCGAGACG
P-ERIra.Ubq1-1:1:10    GGCCACCAACCAGCGAACCACCAGCGTCAAGCTAGCCAAGCGAAGCAGACGGCCGAGACG
P-ERIra.Ubq1-1:1:8     GGCCACCAACCAGCGAACCACCAGCGTCAAGCTAGCCAAGCGAAGCAGACGGCCGAGACG
P-ERIra.Ubq1-1:1:11    GGCCACCAACCAGCGAACCACCAGCGTCAAGCTAGCCAAGCGAAGCAGACGGCCGAGACG
P-ERIra.Ubq1-1:1:12    GGCCACCAACCAGCGAACCACCAGCGTCAAGCTAGCCAAGCGAAGCAGACGGCCGAGACG
P-ERIra.Ubq1-1:1:13    GGCCACCAACCAGCGAACCACCAGCGTCAAGCTAGCCAAGCGAAGCAGACGGCCGAGACG
                       ************************************************************

P-ERIra.Ubq1-1:1:9     TTGACACCTTGGCGCGGGCATCTCTCTGGCCCCCTCTCGAGAGTTCCGCTCCACCTCCAC
P-ERIra.Ubq1-1:1:10    TTGACACCTTGGCGCGGGCATCTCTCTGGCCCCCTCTCGAGAGTTCCGCTCCACCTCCAC
P-ERIra.Ubq1-1:1:8     TTGACACCTTGGCGCGGGCATCTCTCTGGCCCCCTCTCGAGAGTTCCGCTCCACCTCCAC
P-ERIra.Ubq1-1:1:11    TTGACACCTTGGCGCGGGCATCTCTCTGGCCCCCTCTCGAGAGTTCCGCTCCACCTCCAC
P-ERIra.Ubq1-1:1:12    TTGACACCTTGGCGCGGGCATCTCTCTGGCCCCCTCTCGAGAGTTCCGCTCCACCTCCAC
P-ERIra.Ubq1-1:1:13    TTGACACCTTGGCGCGGGCATCTCTCTGGCCCCCTCTCGAGAGTTCCGCTCCACCTCCAC
                       ************************************************************

P-ERIra.Ubq1-1:1:9     TGGTGGCGGTTTCCAAGTCCGTTCCGCCTCCTGCTCCTCCTCACACGGCACGAAACCGTC
P-ERIra.Ubq1-1:1:10    TGGTGGCGGTTTCCAAGTCCGTTCCGCCTCCTGCTCCTCCTCACACGGCACGAAACCGTC
P-ERIra.Ubq1-1:1:8     TGGTGGCGGTTTCCAAGTCCGTTCCGCCTCCTGCTCCTCCTCACACGGCACGAAACCGTC
P-ERIra.Ubq1-1:1:11    TGGTGGCGGTTTCCAAGTCCGTTCCGCCTCCTGCTCCTCCTCACACGGCACGAAACCGTC
P-ERIra.Ubq1-1:1:12    TGGTGGCGGTTTCCAAGTCCGTTCCGCCTCCTGCTCCTCCTCACACGGCACGAAACCGTC
P-ERIra.Ubq1-1:1:13    TGGTGGCGGTTTCCAAGTCCGTTCCGCCTCCTGCTCCTCCTCACACGGCACGAAACCGTC
                       ************************************************************

P-ERIra.Ubq1-1:1:9     ACGGCACCGGCAGCACGGGGGATTCCTTTCCCACCGCTCCTTCCCTTTCCCTTCCTCGCC
P-ERIra.Ubq1-1:1:10    ACGGCACCGGCAGCACGGGGGATTCCTTTCCCACCGCTCCTTCCCTTTCCCTTCCTCGCC
P-ERIra.Ubq1-1:1:8     ACGGCACCGGCAGCACGGGGGATTCCTTTCCCACCGCTCCTTCCCTTTCCCTTCCTCGCC
P-ERIra.Ubq1-1:1:11    ACGGCACCGGCAGCACGGGGGATTCCTTTCCCACCGCTCCTTCCCTTTCCCTTCCTCGCC
P-ERIra.Ubq1-1:1:12    ACGGCACCGGCAGCACGGGGGATTCCTTTCCCACCGCTCCTTCCCTTTCCCTTCCTCGCC
P-ERIra.Ubq1-1:1:13    ACGGCACCGGCAGCACGGGGGATTCCTTTCCCACCGCTCCTTCCCTTTCCCTTCCTCGCC
                       ************************************************************

P-ERIra.Ubq1-1:1:9     CGCCGTTTTAAATAGCCAGCCCCATCCCCAGCTTCTCTCCCC
P-ERIra.Ubq1-1:1:10    CGCCGTTTTAAATAGCCAGCCCCATCCCCAGCTTCTCTCCCC
P-ERIra.Ubq1-1:1:8     CGCCGTTTTAAATAGCCAGCCCCATCCCCAGCTTCTCTCCCC
P-ERIra.Ubq1-1:1:11    CGCCGTTTTAAATAGCCAGCCCCATCCCCAGCTTCTCTCCCC
P-ERIra.Ubq1-1:1:12    CGCCGTTTTAAATAGCCAGCCCCATCCCCAGCTTCTCTCCCC
P-ERIra.Ubq1-1:1:13    CGCCGTTTTAAATAGCCAGCCCCATCCCCAGCTTCTCTCCCC
                       ******************************************
```

FIG. 2g

```
P-Sv.Ubq1-1:1:2     ------------------------------------------------------------
P-Sv.Ubq1-1:1:1     ACTGCCGCGACACGCCTCACTGGCGGGAGGGCTCCGAGCGCTCTCTCCCCGGCGGCCGGC
P-Sv.Ubq1-1:1:3     ------------------------------------------------------------

P-Sv.Ubq1-1:1:2     ------------------------------------------------------------
P-Sv.Ubq1-1:1:1     GGAGCAGCGATCTGGATTGGAGAGAATAGAGGAAAGAGAGGGAAAAGGAGAGAGATAGCG
P-Sv.Ubq1-1:1:3     ------------------------------------------------------------

P-Sv.Ubq1-1:1:2     ------------------------------------------------------------
P-Sv.Ubq1-1:1:1     CAAAGAGCTGAAAAGATAAGGTTGTGCGGGCTGTGGTGATTAGAGGACCACTAATCCCTC
P-Sv.Ubq1-1:1:3     ------------------------------------------------------------

P-Sv.Ubq1-1:1:2     ------------------------------------------------------------
P-Sv.Ubq1-1:1:1     CATCTCCTAATGACGCGGTGCCCAAGACCAGTGCCGCGGCACACCAGCGTCTAAGTGAAC
P-Sv.Ubq1-1:1:3     ------------------------------------------------------------

P-Sv.Ubq1-1:1:2     ------------------------------------------------------------
P-Sv.Ubq1-1:1:1     TTCCGCTAACCTTCCGGTCATTGCGCCTGAAAGATGTCATGTGGCGAGGCCCCCCTCTCA
P-Sv.Ubq1-1:1:3     ------------------------------------------------------------

P-Sv.Ubq1-1:1:2     ------------------------------------------------------------
P-Sv.Ubq1-1:1:1     GTAGATTGCCAACTGCCTACCGTGCCACTCTTCCATGCATGATTGCTCCCGTCTATCCCG
P-Sv.Ubq1-1:1:3     ------------------------------------------------------------

P-Sv.Ubq1-1:1:2     ------------------------------------------------------------
P-Sv.Ubq1-1:1:1     TTTCTCACAACAGATAGACAACAGTAAGCATCACTAAAGCAAGCATGTGTAGAACCTTAA
P-Sv.Ubq1-1:1:3     ------------------------------------------------------------

P-Sv.Ubq1-1:1:2     ----------------------------------------GCCGTTTTTGAAGTATCCAGGA
P-Sv.Ubq1-1:1:1     AAAAAGGCTTATACTACCAGTATACTATCAACCAGCATGCCGTTTTTGAAGTATCCAGGA
P-Sv.Ubq1-1:1:3     ------------------------------------------------------------

P-Sv.Ubq1-1:1:2     TTAGAAGCTTCTACTGCGCTTTTATATTATAGCTGTGGACCTGTGGTAACCTTTCTCTTT
P-Sv.Ubq1-1:1:1     TTAGAAGCTTCTACTGCGCTTTTATATTATAGCTGTGGACCTGTGGTAACCTTTCTCTTT
P-Sv.Ubq1-1:1:3     ------------------------------------------------------------

P-Sv.Ubq1-1:1:2     TGGCGCTTGCTTAATCTCGGCCGTGCTGGTCCATGCTTAGGCACTAGGCAGAGATAGAGC
P-Sv.Ubq1-1:1:1     TGGCGCTTGCTTAATCTCGGCCGTGCTGGTCCATGCTTAGGCACTAGGCAGAGATAGAGC
P-Sv.Ubq1-1:1:3     ------------------------------------------------------------

P-Sv.Ubq1-1:1:2     CGGGGGTGAATGGGGCTAAAGCTCAGCTGCTCGAGGGGCCGTGGGCTGGTTTCCACTAGC
P-Sv.Ubq1-1:1:1     CGGGGGTGAATGGGGCTAAAGCTCAGCTGCTCGAGGGGCCGTGGGCTGGTTTCCACTAGC
P-Sv.Ubq1-1:1:3     ------------------------------------------------------------

P-Sv.Ubq1-1:1:2     CTACAGCTGTGCCACGTGCGGCCGCGCAAGCCGAAGCAAGCACGCTGAGCCGTTGGACAG
P-Sv.Ubq1-1:1:1     CTACAGCTGTGCCACGTGCGGCCGCGCAAGCCGAAGCAAGCACGCTGAGCCGTTGGACAG
P-Sv.Ubq1-1:1:3     ------------------------------------------------------------
```

FIG. 3a

```
P-Sv.Ubq1-1:1:2    CTTGTCATAATGCCATTACGTGGATTACAGGTAACTGGCCCTGTAACTACTCGTTCGGCC
P-Sv.Ubq1-1:1:1    CTTGTCATAATGCCATTACGTGGATTACAGGTAACTGGCCCTGTAACTACTCGTTCGGCC
P-Sv.Ubq1-1:1:3    ------------------------------------------------------------

P-Sv.Ubq1-1:1:2    ATCATCAAACGACGACGTCCGCTAGGCGACGACACGGGTAATGCACGCAGCCACCCAGGC
P-Sv.Ubq1-1:1:1    ATCATCAAACGACGACGTCCGCTAGGCGACGACACGGGTAATGCACGCAGCCACCCAGGC
P-Sv.Ubq1-1:1:3    --------------------------------CACGGGTAATGCACGCAGCCACCCAGGC
                                                   ****************************

P-Sv.Ubq1-1:1:2    GCGCGCGCTAGCGGAGCACGGTCAGGTGACACGGGCGTCGTGACGCTTCCGAGTTGAAGG
P-Sv.Ubq1-1:1:1    GCGCGCGCTAGCGGAGCACGGTCAGGTGACACGGGCGTCGTGACGCTTCCGAGTTGAAGG
P-Sv.Ubq1-1:1:3    GCGCGCGCTAGCGGAGCACGGTCAGGTGACACGGGCGTCGTGACGCTTCCGAGTTGAAGG
                   ************************************************************

P-Sv.Ubq1-1:1:2    GGTTAACGCCAGAAACAGTGTTTGGCCAGGGTATGAACATAACAAAAAATATTCACACGA
P-Sv.Ubq1-1:1:1    GGTTAACGCCAGAAACAGTGTTTGGCCAGGGTATGAACATAACAAAAAATATTCACACGA
P-Sv.Ubq1-1:1:3    GGTTAACGCCAGAAACAGTGTTTGGCCAGGGTATGAACATAACAAAAAATATTCACACGA
                   ************************************************************

P-Sv.Ubq1-1:1:2    AAGAATGGAAGTATGGAGCTGCTACTGTGTAAATGCCAAGCAGGAAACTCACGCCCGCTA
P-Sv.Ubq1-1:1:1    AAGAATGGAAGTATGGAGCTGCTACTGTGTAAATGCCAAGCAGGAAACTCACGCCCGCTA
P-Sv.Ubq1-1:1:3    AAGAATGGAAGTATGGAGCTGCTACTGTGTAAATGCCAAGCAGGAAACTCACGCCCGCTA
                   ************************************************************

P-Sv.Ubq1-1:1:2    ACATCCAACGGCCAACAGCTCGACGTGCCGGTCAGCAGAGACATCGGAACACTGGTGATT
P-Sv.Ubq1-1:1:1    ACATCCAACGGCCAACAGCTCGACGTGCCGGTCAGCAGAGACATCGGAACACTGGTGATT
P-Sv.Ubq1-1:1:3    ACATCCAACGGCCAACAGCTCGACGTGCCGGTCAGCAGAGACATCGGAACACTGGTGATT
                   ************************************************************

P-Sv.Ubq1-1:1:2    GGTGGAGCCGGCAGTATGCGCCCCAGCACGGCCGAGGTGGTGGTGGCCCGTGGCCCTGCT
P-Sv.Ubq1-1:1:1    GGTGGAGCCGGCAGTATGCGCCCCAGCACGGCCGAGGTGGTGGTGGCCCGTGGCCCTGCT
P-Sv.Ubq1-1:1:3    GGTGGAGCCGGCAGTATGCGCCCCAGCACGGCCGAGGTGGTGGTGGCCCGTGGCCCTGCT
                   ************************************************************

P-Sv.Ubq1-1:1:2    GTCTGCGCGGCTCGGGACAACTTGAAACTGGGCCACCGCCTCGTCGCAACTCGCAACCCG
P-Sv.Ubq1-1:1:1    GTCTGCGCGGCTCGGGACAACTTGAAACTGGGCCACCGCCTCGTCGCAACTCGCAACCCG
P-Sv.Ubq1-1:1:3    GTCTGCGCGGCTCGGGACAACTTGAAACTGGGCCACCGCCTCGTCGCAACTCGCAACCCG
                   ************************************************************

P-Sv.Ubq1-1:1:2    TTGGCGGAAGAAAGGAATGGCTCGTAGGGGCCCGGGTAGAATCCAAGAATGTTGCGCTGG
P-Sv.Ubq1-1:1:1    TTGGCGGAAGAAAGGAATGGCTCGTAGGGGCCCGGGTAGAATCCAAGAATGTTGCGCTGG
P-Sv.Ubq1-1:1:3    TTGGCGGAAGAAAGGAATGGCTCGTAGGGGCCCGGGTAGAATCCAAGAATGTTGCGCTGG
                   ************************************************************

P-Sv.Ubq1-1:1:2    GCTTCGATTCACATAACATGGGCCTGAAGCTCTAAAACGACGGCCCGGTCACCGGGCGAT
P-Sv.Ubq1-1:1:1    GCTTCGATTCACATAACATGGGCCTGAAGCTCTAAAACGACGGCCCGGTCACCGGGCGAT
P-Sv.Ubq1-1:1:3    GCTTCGATTCACATAACATGGGCCTGAAGCTCTAAAACGACGGCCCGGTCACCGGGCGAT
                   ************************************************************
```

FIG. 3b

```
P-Sv.Ubq1-1:1:2    GGAAAGAGACCGGATCCTCCTCGTGAATTCTGGAAGGCCACACGAGAGCGACCCACCACC
P-Sv.Ubq1-1:1:1    GGAAAGAGACCGGATCCTCCTCGTGAATTCTGGAAGGCCACACGAGAGCGACCCACCACC
P-Sv.Ubq1-1:1:3    GGAAAGAGACCGGATCCTCCTTGTGAATTCTGGAAGGCCACACGAGAGCGACCCACCACC
                   *********************  *************************************

P-Sv.Ubq1-1:1:2    GACGCGGAGGAGTCGTGCGTGGTCCAACACGGCCGGCGGGCTGGGCTGCGACCTTAACCA
P-Sv.Ubq1-1:1:1    GACGCGGAGGAGTCGTGCGTGGTCCAACACGGCCGGCGGGCTGGGCTGCGACCTTAACCA
P-Sv.Ubq1-1:1:3    GACGCGGAGGAGTCGTGCGTGGTCCAACACGGCCGGCGGGCTGGGCTGCGACCTTAACCA
                   ************************************************************

P-Sv.Ubq1-1:1:2    GCAAGGCACGCCACGACCCGCCTCGCCCTCGAGGCATAAATACCCTCCCATCC
P-Sv.Ubq1-1:1:1    GCAAGGCACGCCACGACCCGCCTCGCCCTCGAGGCATAAATACCCTCCCATCC
P-Sv.Ubq1-1:1:3    GCAAGGCACGCCACGACCCGCCTCGCCCTCGAGGCATAAATACCCTCCCATCC
                   *****************************************************
```

FIG. 3c

```
EXP-Zm.UbqM1:1:2    GTCGTGCCCCTCTCTAGAGATAAAGAGCATTGCATGTCTAAAGTATAAAAAATTACCACA
EXP-Zm.UbqM1:1:5    GTCGTGCCCCTCTCTAGAGATAAAGAGCATTGCATGTCTAAAGTATAAAAAATTACCACA
EXP-Zm.UbqM1:1:1    GTCGTGCCCCTCTCTAGAGATAATGAGCATTGCATGTCTAAGTTATAAAAAATTACCACA
EXP-Zm.UbqM1:1:4    GTCGTGCCCCTCTCTAGAGATAAAGAGCATTGCATGTCTAAGTTATAAAAAATTACCACA
                    ************************ ****************   ****************

EXP-Zm.UbqM1:1:2    TA--TTTTTTTGTCACACT--TATTTGAAGTGTAGTTTATCTATCTCTATACATATATTT
EXP-Zm.UbqM1:1:5    TA--TTTTTTTGTCACACT--TATTTGAAGTGTAGTTTATCTATCTCTATACATATATTT
EXP-Zm.UbqM1:1:1    TATTTTTTTTTGTCACACTTGTGTTTGAAGTGCAGTTTATCTATCTCTATACATATATTT
EXP-Zm.UbqM1:1:4    TA-TTTTTTTTGTCACACT--TGTTTGAAGTGCAGTTTATCTATCTTTATACATATATTT
                    ** **************  * ********* ************* ************

EXP-Zm.UbqM1:1:2    AAACTTCACTCTACAAATAATATAGTCTATAATACTAAAATAATATTAGTGTTTTAGAGG
EXP-Zm.UbqM1:1:5    AAACTTCACTCTACAAATAATATAGTCTATAATACTAAAATAATATTAGTGTTTTAGAGG
EXP-Zm.UbqM1:1:1    AAACTTCACTATATGAATAATATAGTCTATAGTATTAAAATAATATCAATGTTTTAGATG
EXP-Zm.UbqM1:1:4    AAACTTTACTCTACGAATAATATAATCTATAGTACTACAATAATATCAGTGTTTTAGAGA
                    ****** *** **  ********* ****** ** ** ******** * *********

EXP-Zm.UbqM1:1:2    ATCATATAAATAAACTGCTAGACATGGTCTAAAGGATAATTGAATATTTTGACAA-----
EXP-Zm.UbqM1:1:5    ATCATATAAATAAACTGCTAGACATGGTCTAAAGGATAATTGAATATTTTGACAA-----
EXP-Zm.UbqM1:1:1    ATTATATAACTGAACTGCTAGACATGGTCTAAAGGACAACCGAGTATTTTGACAACATGA
EXP-Zm.UbqM1:1:4    ATCATATAAATGAACAGTTAGACATGGTCTAAAGGACAATTGAGTATTTTGACAACAGGA
                    ** ******  ** *   ****************  **  ** ***********

EXP-Zm.UbqM1:1:2    -TCTACAGTTTTATCTTTTTAGTGTGCATGTGATCTCTCTGTTTTTTTTGCAAATAGCTT
EXP-Zm.UbqM1:1:5    -TCTACAGTTTTATCTTTTTAGTGTGCATGTGATCTCTCTGTTTTTTTTGCAAATAGCTT
EXP-Zm.UbqM1:1:1    CTCTACAGTTTTATCTTTTTAGTGTGCATGTGTTCTTT---TTACTTTTGCAAATAGCTT
EXP-Zm.UbqM1:1:4    CTCTACAGTTTTATCTTTTTAGTGTGCATGTGTTCTCCTT-TTTTTTTTGCAAATAGCTT
                    ****************************** ***      **   **************

EXP-Zm.UbqM1:1:2    GACCTATATAATACTTCATCCATTTTATTAGTACATCCATTTAGGATTTAGGGTTGATGG
EXP-Zm.UbqM1:1:5    GACCTATATAATACTTCATCCATTTTATTAGTACATCCATTTAGGATTTAGGGTTGATGG
EXP-Zm.UbqM1:1:1    CACCTATATAATACTTCATCCATTTTATTAGTACATCCATTT------------------
EXP-Zm.UbqM1:1:4    CACCTATATAATACTTCATCCATTTTATTAGTACATCCATTTAGGGTTTAGGGTTAATGG
                     *****************************************

EXP-Zm.UbqM1:1:2    TTTCTATAGACTAA--TTTTTAGTACATCCATTTTATTCT-TTTTAGTCTCTAAATTTTT
EXP-Zm.UbqM1:1:5    TTTCTATAGACTAA--TTTTTAGTACATCCATTTTATTCT-TTTTAGTCTCTAAATTTTT
EXP-Zm.UbqM1:1:1    ---------ACTAAA-TTTTTAGTACATCTATTTTATTCTATTTTAGCCTCTAAA-TTAA
EXP-Zm.UbqM1:1:4    TTTTTATAGACTAATTTTTTTAGTACATCTATTTTATTCTATTTTAGCCTCTAAA-TTAA
                             *****  ************* ********** ****** ******* **

EXP-Zm.UbqM1:1:2    TAAAACTAAAACTCTATTTTAG-TTTTTTATTTAATAATTTAGATATAAAATGAAATAAA
EXP-Zm.UbqM1:1:5    TAAAACTAAAACTCTATTTTAG-TTTTTTATTTAATAATTTAGATATAAAATGAAATAAA
EXP-Zm.UbqM1:1:1    GAAAACTAAAACTCTATTTTAG-TTTTTTATTTAATAATTTAGATATAAAATAGAATAAA
EXP-Zm.UbqM1:1:4    GAAAACTAAAACTCTATTTTAGTTTTTTTTATTTAATAATTTAGATATAAAATAGAATAAA
                     ***** ******************** ********************* ******
```

FIG. 4a

```
EXP-Zm.UbqM1:1:2    ATAAATTGACTACAAATAAAACAAATACCCTTTAAGAAA-TAAAAAAACTAAGCAAACAT
EXP-Zm.UbqM1:1:5    ATAAATTGACTACAAATAAAACAAATACCCTTTAAGAAA-TAAAAAAACTAAGCAAACAT
EXP-Zm.UbqM1:1:1    ATAAAGTGACTAAAAAATAACTAAATACCTTTTAAGAAA-TAAAAAAACTAAGGAACCAT
EXP-Zm.UbqM1:1:4    ATAAAGTGACTAAAAATTAAACAAATACCCTTTAAGAAATTAAAAAAACTAAGGAAACAT
                    *****  ****** ***   ** ******* ********  ************* ** ***

EXP-Zm.UbqM1:1:2    TTTTCTTGTTTCGAGTAGATAATGACAGGCTGTTCAACGCCGTCGACGAGTCTAACGGAC
EXP-Zm.UbqM1:1:5    TTTTCTTGTTTCGAGTAGATAATGACAGGCTGTTCAACGCCGTCGACGAGTCTAACGGAC
EXP-Zm.UbqM1:1:1    TTTTCTTGTTCCGAGTAGATAATGACAGCCTGTTCAACGCCGTCGACGAGTCTAACGGAC
EXP-Zm.UbqM1:1:4    TTTTCTTGTTTCGAGTAGATAATGCCAGCCTGTTAAACGCCGTCGACGAGTCTAACGGAC
                    **********  ************ *** *****  *************************

EXP-Zm.UbqM1:1:2    ACCAACCAGCGAACCAGCAGCGTCGCGTCGGGCCAAGCGAAGCAGACGGCACGGCATCTC
EXP-Zm.UbqM1:1:5    ACCAACCAGCGAACCAGCAGCGTCGCGTCGGGCCAAGCGAAGCAGACGGCACGGCATCTC
EXP-Zm.UbqM1:1:1    ACCAACCAGCGAACCAGCAGCGTCGCGTCGGGCCAAGCGAAGCAGACGGCACGGCATCTC
EXP-Zm.UbqM1:1:4    ACCAACCAGCGAACCAGCAGCGTCGCGTCGGGCCAAGCGAAGCAGACGGCACGGCATCTC
                    ************************************************************

EXP-Zm.UbqM1:1:2    TGTAGCTGCCTCTGGACCCCTCTCGAGAGTTCCGCTCCACCGTTGGACTTGCTCCGCTGT
EXP-Zm.UbqM1:1:5    TGTAGCTGCCTCTGGACCCCTCTCGAGAGTTCCGCTCCACCGTTGGACTTGCTCCGCTGT
EXP-Zm.UbqM1:1:1    TGTAGCTGCCTCTGGACCCCTCTCGAGAGTTCCGCTCCACCGTTGGACTTGCTCCGCTGT
EXP-Zm.UbqM1:1:4    TGTCGCTGCCTCTGGACCCCTCTCGAGAGTTCCGCTCCACCGTTGGACTTGCTCCGCTGT
                    *** ********************************************************

EXP-Zm.UbqM1:1:2    CGGCATCCAGAAATTGCGTGGCGGAGCGGCAGACGTGAGGCGGCACGGCAGGCGGCCTCT
EXP-Zm.UbqM1:1:5    CGGCATCCAGAAATTGCGTGGCGGAGCGGCAGACGTGAGGCGGCACGGCAGGCGGCCTCT
EXP-Zm.UbqM1:1:1    CGGCATCCAGAAATTGCGTGGCGGAGCGGCAGACGTGAGCCGGCACGGCAGGCGG-----
EXP-Zm.UbqM1:1:4    CGGCATCCAGAAATTGCGTGGCGGAGCGGCAGACGTGAGCCGGCACGGCAGGCGGCCTCC
                    ******************************************************      ***************

EXP-Zm.UbqM1:1:2    TCCTCCTCTCACGGCACCGGCAGCTACGGGGGATTCCTTTCCCACCGCTCCTTCGCTTTC
EXP-Zm.UbqM1:1:5    TCCTCCTCTCACGGCACCGGCAGCTACGGGGGATTCCTTTCCCACCGCTCCTTCGCTTTC
EXP-Zm.UbqM1:1:1    -CCTCCTCTCACGGCACCGGCAGCTACGGGGGATTCCTTTCCCACCGCTCCTTCGCTTTC
EXP-Zm.UbqM1:1:4    TCCTCCTCTCACGGCACCGGCAGCTACGGGGGATTCCTTTCCCACCGCTCCTTCGCTTTC
                     ***********************************************************

EXP-Zm.UbqM1:1:2    CCTTCCTCGCCCGCCGTAATAAATAGACACCCCCTCCACACCCTCTTTCCCCAACCTCGT
EXP-Zm.UbqM1:1:5    CCTTCCTCGCCCGCCGTAATAAATAGACACCCCCTCCACACCCTCTTTCCCCAACCTCGT
EXP-Zm.UbqM1:1:1    CCTTCCTCGCCCGCCGTAATAAATAG--ACCCCCTCCACACCCTCTTTCCCCAACCTCGT
EXP-Zm.UbqM1:1:4    CCTTCCTCGCCCGCCGTAATAAATAGACACCCCCTCCACACCTTCTTTCCCCAACCTCGT
                    **************************  ************** ****************

EXP-Zm.UbqM1:1:2    GTTCGTTCGGAGCGCACACACACGCAACCAGATCTCCCCCAAATCCAGCCGTCGGCACCT
EXP-Zm.UbqM1:1:5    GTTCGTTCGGAGCGCACACACACGCAACCAGATCTCCCCCAAATCCAGCCGTCGGCACCT
EXP-Zm.UbqM1:1:1    GTTCGTTCGGAGCGCGCACACACAACCAGATCTCCCCCAAATCCACCCGTCGGCACCT
EXP-Zm.UbqM1:1:4    GTT-GTTCGGAGCGCACACACACACAACCAGATCTCCCCCAAATCCACCCGTCGGCACCT
                    *** ********** ****** ************************* ***********
```

FIG. 4b

```
EXP-Zm.UbqM1:1:2    CCGCTTCAAGGTACGCCGCTCATCCTCCCCCCCCCCCTCTCTCTACCTTCTCTAGATCGG
EXP-Zm.UbqM1:1:5    CCGCTTCAAGGTACGCCGCTCATCCTCCCCCCCCCCCTCTCTCTACCTTCTCTAGATCGG
EXP-Zm.UbqM1:1:1    CCGCTTCAAGGTACGCCGCTCATCCTCCTCCCCCCCCTCTCTCTACCTTCTCTAGATCGG
EXP-Zm.UbqM1:1:4    CCGCTTCAAGGTACGCCGCTCATCCTCCCCCCCCC---CTCTCTACCTTCTCTAGATCGG
                    ***************************** ******   ********************

EXP-Zm.UbqM1:1:2    CGATCCGGTCCATGGTTAGGGCCCGGTAGTTCTACTTCTGTTCATGTTTGTGTTAGAGCA
EXP-Zm.UbqM1:1:5    CGATCCGGTCCATGGTTAGGGCCCGGTAGTTCTACTTCTGTTCATGTTTGTGTTAGAGCA
EXP-Zm.UbqM1:1:1    CGTTTCGGTCCATGGTTAGGGCCCGGTAGTTCTACTTCTGTTCATGTTTGTGTTAGATC-
EXP-Zm.UbqM1:1:4    CGTTCCGGTCCATGGTTAGGGCCCGGTAGTTCTACTTCTGTTCATGTTTGTGTTAGATC-
                    **  * ******************************************************  *

EXP-Zm.UbqM1:1:2    AACATGTTCATGTT-------------------------CATGTTTGTGAT----------
EXP-Zm.UbqM1:1:5    AACATGTTCATGTT-------------------------CATGTTTGTGAT----------
EXP-Zm.UbqM1:1:1    --CGTGTTTGTGTTAGATCCGTGCTGCTAGATTTCGTACACGGATGCGACCTGTACATCA
EXP-Zm.UbqM1:1:4    --CGTGTTTGTGTTAGATCCGTGCTGCTAGCGTTCGTACACGGATGCGACCTGTACGTCA
                      * ****  ****                          ** *  ** **

EXP-Zm.UbqM1:1:2    GATGTGGTCTGGTTG-------GGCGGTCGTTCTAGATCGGAG----TAGGATACTGTTT
EXP-Zm.UbqM1:1:5    GATGTGGTCTGGTTG-------GGCGGTCGTTCTAGATCGGAG----TAGGATACTGTTT
EXP-Zm.UbqM1:1:1    GACATGTTCTGATTGCTAACTTGCCAGTGTTTCTCTTTGGGGAATCCTGGGA---TGGCT
EXP-Zm.UbqM1:1:4    GACACGTTCTGATTGCTAACTTGCCAGTGTTTCTCTTTGGGGAATCCTGGGA---TGGCT
                    **    * **** ***        *  ** ****    * **      *  ***---** *

EXP-Zm.UbqM1:1:2    CAAGCT---------ACCTGGTGGATTT-----ATTAATTTTGTATCTGTATGT------
EXP-Zm.UbqM1:1:5    CAAGCT---------ACCTGGTGGATTT-----ATTAATTTTGTATCTGTATGT------
EXP-Zm.UbqM1:1:1    CTAGCCGTTCCGCAGACGGGATCGATTTCATGAATTTTTTTGTTTCGTTGCATAGGGTT
EXP-Zm.UbqM1:1:4    CTAGCCGTTCCGCAGACGGGATCGATTTCATG-ATTTTTTTGTTTCGTTGCATAGGGTT
                    *  ***         **   * * *****   ***  ****** **   *       *

EXP-Zm.UbqM1:1:2    --GTGTGCCATACATCTTCATAGTTACGAGTTTAAGATGATGGATGGAAATATCGATCTA
EXP-Zm.UbqM1:1:5    --GTGTGCCATACATCTTCATAGTTACGAGTTTAAGATGATGGATGGAAATATCGATCTA
EXP-Zm.UbqM1:1:1    TGGTTTGCCCTTTTCCTTTAT---------TTCAATAT-----------ATGCC------
EXP-Zm.UbqM1:1:4    TGGTTTGCCCTTTTCCTTTAT---------TTCAATAT-----------ATGCC------
                       ** **** *   *** **          ** ** **            ** *

EXP-Zm.UbqM1:1:2    GGATAGGTATACATGTTGATGCGGGT--TTTACTGATGCATATACAGAGATGCTTTTTTT
EXP-Zm.UbqM1:1:5    GGATAGGTATACATGTTGATGCGGGT--TTTACTGATGCATATACAGAGATGCTTTTTTT
EXP-Zm.UbqM1:1:1    ------GTGCACTTGTTTGT-CGGGTCATCTTTTCATG----------------TTTTTT
EXP-Zm.UbqM1:1:4    ------GTGCACTTGTTTGT-CGGGTCATCTTTTCATGC---------------TTTTTT
                          **  ** **** *  *****    *    * * * ***                 ******

EXP-Zm.UbqM1:1:2    CTCGCTTGGTTGTGATGATATGGTCTGGTTGGGCGGTCGTTCTAGATCGGAGTAGAATAC
EXP-Zm.UbqM1:1:5    CTCGCTTGGTTGTGATGATATGGTCTGGTTGGGCGGTCGTTCTAGATCGGAGTAGAATAC
EXP-Zm.UbqM1:1:1    TTGGCTTGGTTGTGATGATGTGGTCTGGTTGGGCGGTCGTTCTAGATCGGAGTAGAATAC
EXP-Zm.UbqM1:1:4    TTGTCTTGGTTGTGATGATGTGGTCTGGTTGGGCGGTCGTTCTAGATCGGAGAAGAATTC
                      *  ************** *********************************** ***** *
```

FIG. 4c

```
EXP-Zm.UbqM1:1:2    TGTTTCAAACTACCTGGTGGATTTATTAAAGGATAAAGGGTCGTTCTAGATCGGAGTAGA
EXP-Zm.UbqM1:1:5    TGTTTCAAACTACCTGGTGGATTTATTAAAGGATAAAGGGTCGTTCTAGATCGGAGTAGA
EXP-Zm.UbqM1:1:1    TGTTTCAAACTACCTGGTGGATTTATTAA-------------------------------
EXP-Zm.UbqM1:1:4    TGTTTCAAACTACCTGGTGGATTTATTAA-------------------------------
                    *****************************

EXP-Zm.UbqM1:1:2    ATACTGTTTCAAACTACCTGGTGGATTTATTAAAGGATCTGTATGTATGTGCC-TACATC
EXP-Zm.UbqM1:1:5    ATACTGTTTCAAACTACCTGGTGGATTTATTAAAGGATCTGTATGTATGTGCC-TACATC
EXP-Zm.UbqM1:1:1    -----------------------------------AGGATCTGTATGTATGTGCCATACATC
EXP-Zm.UbqM1:1:4    -------------------------------TTTTGGATCTGTATGTGTGTGCCATACATA
                                                        *********** ****** *****

EXP-Zm.UbqM1:1:2    TTCATAGTTACGAGTTTAAGATGATGGATGGAAATATCGATCTAGGATAGGTATACATGT
EXP-Zm.UbqM1:1:5    TTCATAGTTACGAGTTTAAGATGATGGATGGAAATATCGATCTAGGATAGGTATACATGT
EXP-Zm.UbqM1:1:1    TTCATAGTTACGAGTTTAAGATGATGGATGGAAATATCGATCTAGGATAGGTATACATGT
EXP-Zm.UbqM1:1:4    TTCATAGTTACGAATTGAAGATGATGGATGGAAATATCGATCTAGGATAGGTATACATGT
                    ************* ** *******************************************

EXP-Zm.UbqM1:1:2    TGATGCGGGTTTTACTGATGCATATACAGAGATGCTTTTT-TTCGCTTGGTTGTGATGAT
EXP-Zm.UbqM1:1:5    TGATGCGGGTTTTACTGATGCATATACAGAGATGCTTTTT-TTCGCTTGGTTGTGATGAT
EXP-Zm.UbqM1:1:1    TGATGCGGGTTTTACTGATGCATATACAGAGATGCTTTTTTTTCGCTTGGTTGTGATGAT
EXP-Zm.UbqM1:1:4    TGATGCGGGTTTTACTGATGCATATACAGAGATGCTTTTTGTTCGCTTGGTTGTGATGAT
                    **************************************** ******************

EXP-Zm.UbqM1:1:2    GTGGTCTGGTTGGGCGG--------TCGTTCTAGATCGGAGTAGAATACTGTTTCAAACT
EXP-Zm.UbqM1:1:5    GTGGTCTGGTTGGGCGG--------TCGTTCTAGATCGGAGTAGAATACTGTTTCAAACT
EXP-Zm.UbqM1:1:1    GTGGTCTGGTCGGGCGG--------TCGTTCTAGATCGGAGTAGAATACTGTTTCAAACT
EXP-Zm.UbqM1:1:4    GTGGTCTGGTTGGGCGGTCGTTCATTCGTTCTAGATCGGAGTAGAATACTGTTTCAAACT
                    ********** ******        **********************************

EXP-Zm.UbqM1:1:2    ACCTGGTGGATTTATTAATTTTGTATCTTTATGTGTGTGCCATACATCTTCATAGTTACG
EXP-Zm.UbqM1:1:5    ACCTGGTGGATTTATTAATTTTGTATCTTTATGTGTGTGCCATACATCTTCATAGTTACG
EXP-Zm.UbqM1:1:1    ACCTGGTGGATTTATTAATTTTGGATCTGTATGTGTGT--CATACATCTTCATAGTTACG
EXP-Zm.UbqM1:1:4    ACCTGGTGTATTTATTAATTTTGGAACTGTATGTGTGTGTCATACATCTTCATAGTTACG
                    ******** ************** * ** ********   *******************

EXP-Zm.UbqM1:1:2    AGTTTAAGATGATGGATGGAAATATTGATCTAGGATAGGTATACATGTTGATGTGGGTTT
EXP-Zm.UbqM1:1:5    AGTTTAAGATGATGGATGGAAATATTGATCTAGGATAGGTATACATGTTGATGTGGGTTT
EXP-Zm.UbqM1:1:1    AGTTTAA---GATCGATGGAAATATCGATCTAGGATAGGTATACATGTTGATGTGGGTTT
EXP-Zm.UbqM1:1:4    AGTTTAA---GATGGATGGAAATATCGATCTAGGATAGGTATACATGTTGATGTGGGTTT
                    *******   *** *********** **********************************

EXP-Zm.UbqM1:1:2    TACTGATGCATATACATGATGGCATATGCGGCATCTATTCATATGCTCTAACCTTGAGTA
EXP-Zm.UbqM1:1:5    TACTGATGCATATACATGATGGCATATGCGGCATCTATTCATATGCTCTAACCTTGAGTA
EXP-Zm.UbqM1:1:1    TACTGATGCATATAC---ATGGCATATGCAGCATCTATTCATATGCTCTAACCTTGAGTA
EXP-Zm.UbqM1:1:4    TACTGATGCATATACATGATGGCATATGCAGCATCTATTCATATGCTCTAACCTTGAGTA
                    ***************   ********** ******************************
```

FIG. 4d

```
EXP-Zm.UbqM1:1:2    CCTATCTATTATAATAAACAAGTATGTTTTATAATTATTTTGATCTTGATATACTTGGAT
EXP-Zm.UbqM1:1:5    CCTATCTATTATAATAAACAAGTATGTTTTATAATTATTTTGATCTTGATATACTTGGAT
EXP-Zm.UbqM1:1:1    CCTATCTATTATAATAAACAAGTATGTTTTATAATTATTTTGATCTTGATATACTTGGAT
EXP-Zm.UbqM1:1:4    CCTATCTATTATAATAAACAAGTATGTTTTATAATTATTTTGATCTTGATATACTTGGAT
                    ************************************************************

EXP-Zm.UbqM1:1:2    GATGGCATATGCAGCAGCTATATGTGGA-TTTTTTAGCCCTGCCTTCATACGCTATTTAT
EXP-Zm.UbqM1:1:5    GATGGCATATGCAGCAGCTATATGTGGA-TTTTTTAGCCCTGCCTTCATACGCTATTTAT
EXP-Zm.UbqM1:1:1    GATGGCATATGCAGCAGCTATATGTGGATTTTTTTAGCCCTGCCTTCATACGCTATTTAT
EXP-Zm.UbqM1:1:4    GATGGCATATGCAGCAGCTATATGTGGATTTTTTTAGCCCTGCCTTCATACGCTATTTAT
                    ****************************  ******************************

EXP-Zm.UbqM1:1:2    TTGCTTGGTACTGTTTCTTTTGTCCGATGCTCACCCTGTTGTTGGGTGATACTTCTGCAG
EXP-Zm.UbqM1:1:5    TTGCTTGGTACTGTTTCTTTTGTCCGATGCTCACCCTGTTGTTTGGTGATACTTCTGCAG
EXP-Zm.UbqM1:1:1    TTGCTTGGTACTGTTTCTTTTGT-CGATGCTCACCCTGTTGTTGGGTGATACTTCTGCAG
EXP-Zm.UbqM1:1:4    TTGCTTGGTACTGTTTCTTTTGT-CGATGCTCACCCTGTTGTTTGGTGATACTTCTGCAG
                    *********************** ****************** ***************
```

FIG. 4e

```
P-Sb.Ubq6-1:1:2    ------------------------------------------------------------
P-Sb.Ubq6-1:1:1    CATTAAAAGTCATTATGTGCATGCGTCGTAACTAACATGGATATGTTGCTGCACTATCTC

P-Sb.Ubq6-1:1:2    ----CACTAGCTGCGCATGATAAAGCCACAAGCCAAAATTAATTATTATGGGTGAGAATA
P-Sb.Ubq6-1:1:1    CTCGCACTAGCTGCGCATGATAAAGCCACAAGCCAAAATTAATTATTATGGGTGAGAATA
                       ********************************************************

P-Sb.Ubq6-1:1:2    AATACGTACCAGCACCGGCCATAGAAAAAGTACATTATTAAAGGTCTAATTTGGAAACAG
P-Sb.Ubq6-1:1:1    AATACGTACCAGCACCGGCCATAGAAAAAGTACATTATTAAAGGTCTAATTTGGAAACAG
                   ************************************************************

P-Sb.Ubq6-1:1:2    TCTGAAAACGACGTGCGCTGCAGAGGTAAATGTAATTTTCGGCACTAAAACCATTATCAA
P-Sb.Ubq6-1:1:1    TCTGAAAACGACGTGCGCTGCAGAGGTAAATGTAATTTTCGGCACTAAAACCATTATCAA
                   ************************************************************

P-Sb.Ubq6-1:1:2    CTAATTCATTCAATAACAGTTATTTAGAAAATGTATAGCTCGCTCTAAAAAAACAGTTTA
P-Sb.Ubq6-1:1:1    CTAATTCATTCAATAACAGTTATTTAGAAAATGTATAGCTCGCTCTAAAAAAACAGTTTA
                   ************************************************************

P-Sb.Ubq6-1:1:2    GAAAAACAGTCAAAATAATTCGACCAACAAACAGTTAATAAGGTTCATTAAATATATAAT
P-Sb.Ubq6-1:1:1    GAAAAACAGTCAAAATAATTCGACCAACAAACAGTTAATAAGGTTCATTAAATATATAAT
                   ************************************************************

P-Sb.Ubq6-1:1:2    GCACGGTGCTATTTGATCTTTTAAAGGAAAAAGAGGAATAGTCGTGGGCGCCAGGCGGGA
P-Sb.Ubq6-1:1:1    GCACGGTGCTATTTGATCTTTTAAAGGAAAAAGAGGAATAGTCGTGGGCGCCAGGCGGGA
                   ************************************************************

P-Sb.Ubq6-1:1:2    ATTGGGGCGCGGGAGTCTGCCGGACGACGCGTTCCGTCCGAACGGCCGGACCCGACGAGG
P-Sb.Ubq6-1:1:1    ATTGGGGCGCGGGAGTCTGCCGGACGACGCGTTCCGTCCGAACGGCCGGACCCGACGAGG
                   ************************************************************

P-Sb.Ubq6-1:1:2    CCCCCCCGCCGCCCCACGTCGCAGAACCGTCCGTGGGTGGTAATCTGGCCGGGTACACCA
P-Sb.Ubq6-1:1:1    CCCCCCCGCCGCCCCACGTCGCAGAACCGTCCGTGGGTGGTAATCTGGCCGGGTACACCA
                   ************************************************************

P-Sb.Ubq6-1:1:2    GCCGTCCCCTTGGGCGGCCTCACAGCACTGGGCTCACACGTGAGTTTTGTTCTGGGCTTC
P-Sb.Ubq6-1:1:1    GCCGTCCCCTTGGGCGGCCTCACAGCACTGGGCTCACACGTGAGTTTTGTTCTGGGCTTC
                   ************************************************************

P-Sb.Ubq6-1:1:2    GGATCGCACCATATGGGCCTCGGCATCAGAAAGACGGGGCCCGTCTGGGATAGAAGAGAC
P-Sb.Ubq6-1:1:1    GGATCGCACCATATGGGCCTCGGCATCAGAAAGACGGGGCCCGTCTGGGATAGAAGAGAC
                   ************************************************************
```

FIG. 5a

```
P-Sb.Ubq6-1:1:2    AGGAACCTCCTCGTGGATTCCAGAAGCCAGCCACGAGCGACCACCGACGCGGAGGATACT
P-Sb.Ubq6-1:1:1    AGGAACCTCCTCGTGGATTCCAGAAGCCAGCCACGAGCGACCACCGACGCGGAGGATACT
                   ************************************************************

P-Sb.Ubq6-1:1:2    CGTCGTCCAAGTCCAACACGGCGGGCGGGCGGGCGGACGCGTGGGCTGGGCTAACTGCCT
P-Sb.Ubq6-1:1:1    CGTCGTCCAAGTCCAACACGGCGGGCGGGCGGGCGGACGCGTGGGCTGGGCTAACTGCCT
                   ************************************************************

P-Sb.Ubq6-1:1:2    AACCTTAACCTCCAAGGCACGCCAAGGCCCGCTTCTCCCACCCGACATAAATATCCCCCC
P-Sb.Ubq6-1:1:1    AACCTTAACCTCCAAGGCACGCCAAGGCCCGCTTCTCCCACCCGACATAAATATCCCCCC
                   ************************************************************

P-Sb.Ubq6-1:1:2    ATCCAGGCAAGGCGC
P-Sb.Ubq6-1:1:1    ATCCAGGCAAGGCGC
                   ***************
```

FIG. 5b

```
P-SETit.Ubq1-1:1:4    ACTGCCGCGACACGCCTCACTGGCGGGAGGGCTCCGAGCGCTCTCTCCCCGGCGGCCGGC
P-SETit.Ubq1-1:1:3    ------------------------------------------------------------
P-SETit.Ubq1-1:1:1    ACTGCCGCGACACGCCTCACTGGCGGGAGGGCTCCGAGCGCTCTCTCCCCGGCGGCCGGC
P-SETit.Ubq1-1:1:2    ------------------------------------------------------------

P-SETit.Ubq1-1:1:4    GGAGCAGCGATCTGGATTGGAGAGAATAGAGGAAAGAGAGGGAAAAGGAGAGAGATAGCG
P-SETit.Ubq1-1:1:3    ------------------------------------------------------------
P-SETit.Ubq1-1:1:1    GGAGCAGCGATCTGGATTGGAGAGAATAGAGGAAAGAGAGGGAAAAGGAGAGAGATAGCG
P-SETit.Ubq1-1:1:2    ------------------------------------------------------------

P-SETit.Ubq1-1:1:4    CAAAGAGCTGAAAAGATAAGGTTGTGCGGGCTGTGGTGATTAGAGGACCACTAATCCCTC
P-SETit.Ubq1-1:1:3    ------------------------------------------------------------
P-SETit.Ubq1-1:1:1    CAAAGAGCTGAAAAGATAAGGTTGTGCGGGCTGTGGTGATTAGAGGACCACTAATCCCTC
P-SETit.Ubq1-1:1:2    ------------------------------------------------------------

P-SETit.Ubq1-1:1:4    CATCTCCTAATGACGCGGTGCCCAAGACCAGTGCCGCGGCACACCAGCGTCTAAGTGAAC
P-SETit.Ubq1-1:1:3    ------------------------------------------------------------
P-SETit.Ubq1-1:1:1    CATCTCCTAATGACGCGGTGCCCAAGACCAGTGCCGCGGCACACCAGCGTCTAAGTGAAC
P-SETit.Ubq1-1:1:2    ------------------------------------------------------------

P-SETit.Ubq1-1:1:4    TTCCGCTAACCTTCCGGTCATTGCGCCTGAAAGATGTCATGTGGCGAGGCCCCCCTCTCA
P-SETit.Ubq1-1:1:3    ------------------------------------------------------------
P-SETit.Ubq1-1:1:1    TTCCGCTAACCTTCCGGTCATTGCGCCTGAAAGATGTCATGTGGCGAGGCCCCCCTCTCA
P-SETit.Ubq1-1:1:2    ------------------------------------------------------------

P-SETit.Ubq1-1:1:4    GTAGATTGCCAACTGCCTACCGTGCCACTCTTCCATGCATGATTGCTCCCGTCTATCCCG
P-SETit.Ubq1-1:1:3    ------------------------------------------------------------
P-SETit.Ubq1-1:1:1    GTAGATTGCCAACTGCCTACCGTGCCACTCTTCCATGCATGATTGCTCCCGTCTATCCCG
P-SETit.Ubq1-1:1:2    ------------------------------------------------------------

P-SETit.Ubq1-1:1:4    TTTCTCACAACAGATAGACAACAGTAAGCATCACTAAAGCAAGCATGTGTAGAACCTTAA
P-SETit.Ubq1-1:1:3    ------------------------------------------------------------
P-SETit.Ubq1-1:1:1    TTTCTCACAACAGATAGACAACAGTAAGCATCACTAAAGCAAGCATGTGTAGAACCTTAA
P-SETit.Ubq1-1:1:2    ------------------------------------------------------------

P-SETit.Ubq1-1:1:4    AAAAAGGCTTATACTACCAGTATACTATCAACCAGCATGCCGTTTTTGAAGTATCCAGGA
P-SETit.Ubq1-1:1:3    ------------------------------------------------------------
P-SETit.Ubq1-1:1:1    AAAAAGGCTTATACTACCAGTATACTATCAACCAGCATGCCGTTTTTGAAGTATCCAGGA
P-SETit.Ubq1-1:1:2    ---------------------------------------GCCGTTTTTGAAGTATCCAGGA

P-SETit.Ubq1-1:1:4    TTAGAAGCTTCTACTGCGCTTTTATATTATAGCTGTGGACCCGTGGTAACCTTTCTCTTT
P-SETit.Ubq1-1:1:3    ------------------------------------------------------------
P-SETit.Ubq1-1:1:1    TTAGAAGCTTCTACTGCGCTTTTATATTATAGCTGTGGACCTGTGGTAACCTTTCTCTTT
P-SETit.Ubq1-1:1:2    TTAGAAGCTTCTACTGCGCTTTTATATTATAGCTGTGGACCTGTGGTAACCTTTCTCTTT

P-SETit.Ubq1-1:1:4    TGGCGCTTGCTTAATCTCGGCCGTGCTGGTCCATGCTTAGGCACTAGGCAGAGATAGAGC
P-SETit.Ubq1-1:1:3    ------------------------------------------------------------
P-SETit.Ubq1-1:1:1    TGGCGCTTGCTTAATCTCGGCCGTGCTGGTCCATGCTTAGGCACTAGGCAGAGATAGAGC
P-SETit.Ubq1-1:1:2    TGGCGCTTGCTTAATCTCGGCCGTGCTGGTCCATGCTTAGGCACTAGGCAGAGATAGAGC
```

FIG. 6a

```
P-SETit.Ubq1-1:1:4    CGGGGGTGAATGGGGCTAAAGCTCAGCTGCTCGAGGGGCCGTGGGCTGGTTTCCACTAGC
P-SETit.Ubq1-1:1:3    ------------------------------------------------------------
P-SETit.Ubq1-1:1:1    CGGGGGTGAATGGGGCTAAAGCTCAGCTGCTCGAGGGGCCGTGGGCTGGTTTCCACTAGC
P-SETit.Ubq1-1:1:2    CGGGGGTGAATGGGGCTAAAGCTCAGCTGCTCGAGGGGCCGTGGGCTGGTTTCCACTAGC

P-SETit.Ubq1-1:1:4    CTACAGCTGTGCCACGTGCGGCCGCGCAAGCCGAAGCAAGCACGCTGAGCCGTTGGACAG
P-SETit.Ubq1-1:1:3    ------------------------------------------------------------
P-SETit.Ubq1-1:1:1    CTACAGCTGTGCCACGTGCGGCCGCGCAAGCCGAAGCAAGCACGCTGAGCCGTTGGACAG
P-SETit.Ubq1-1:1:2    CTACAGCTGTGCCACGTGCGGCCGCGCAAGCCGAAGCAAGCACGCTGAGCCGTTGGACAG

P-SETit.Ubq1-1:1:4    CTTGTCATAATGCCATTACGTGGATTACACGTAACTGGCCCTGTAACTACTCGTTCGGCC
P-SETit.Ubq1-1:1:3    ------------------------------------------------------------
P-SETit.Ubq1-1:1:1    CTTGTCATAATGCCATTACGTGGATTACACGTAACTGGCCCTGTAACTACTCGTTCGGCC
P-SETit.Ubq1-1:1:2    CTTGTCATAATGCCATTACGTGGATTACACGTAACTGGCCCTGTAACTACTCGTTCGGCC

P-SETit.Ubq1-1:1:4    ATCATCAAACGACGACGTCCGCTAGGCGACGACACGGGTAATGCACGCAGCCACCCAGGC
P-SETit.Ubq1-1:1:3    ------------------------------CACGGGTAATGCACGCAGCCACCCAGGC
P-SETit.Ubq1-1:1:1    ATCATCAAACGACGACGTCCGCTAGGCGACGACACGGGTAATGCACGCAGCCACCCAGGC
P-SETit.Ubq1-1:1:2    ATCATCAAACGACGACGTCCGCTAGGCGACGACACGGGTAATGCACGCAGCCACCCAGGC
                                                    ****************************

P-SETit.Ubq1-1:1:4    GCGCGCGCTAGCGGAGCACGGTCAGGTGACACGGGCGTCGTGACGCTTCCGAGTTGAAGG
P-SETit.Ubq1-1:1:3    GCGCGCGCTAGCGGAGCACGGTCAGGTGACACGGGCGTCGTGACGCTTCCGAGTTGAAGG
P-SETit.Ubq1-1:1:1    GCGCGCGCTAGCGGAGCACGGTCAGGTGACACGGGCGTCGTGACGCTTCCGAGTTGAAGG
P-SETit.Ubq1-1:1:2    GCGCGCGCTAGCGGAGCACGGTCAGGTGACACGGGCGTCGTGACGCTTCCGAGTTGAAGG
                      ************************************************************

P-SETit.Ubq1-1:1:4    GGTTAACGCCAGAAACAGTGTTTGGCCAGGGTATGAACATAACAAAAAATATTCACACGA
P-SETit.Ubq1-1:1:3    GGTTAACGCCAGAAACAGTGTTTGGCCAGGGTATGAACATAACAAAAAATATTCACACGA
P-SETit.Ubq1-1:1:1    GGTTAACGCCAGAAACAGTGTTTGGCCAGGGTATGAACATAACAAAAAATATTCACACGA
P-SETit.Ubq1-1:1:2    GGTTAACGCCAGAAACAGTGTTTGGCCAGGGTATGAACATAACAAAAAATATTCACACGA
                      ************************************************************

P-SETit.Ubq1-1:1:4    AAGAATGGAAGTATGGAGCTGCTACTGTGTAAATGCCAAGCAGGAAACTCACGCCCGCTA
P-SETit.Ubq1-1:1:3    AAGAATGGAAGTATGGAGCTGCTACTGTGTAAATGCCAAGCAGGAAACTCACGCCCGCTA
P-SETit.Ubq1-1:1:1    AAGAATGGAAGTATGGAGCTGCTACTGTGTAAATGCCAAGCAGGAAACTCACGCCCGCTA
P-SETit.Ubq1-1:1:2    AAGAATGGAAGTATGGAGCTGCTACTGTGTAAATGCCAAGCAGGAAACTCACGCCCGCTA
                      ************************************************************

P-SETit.Ubq1-1:1:4    ACATCCAACGGCCAACAGCTCGACGTGCCGGTCAGCAGAGCATCGGAACACTGGTGATTG
P-SETit.Ubq1-1:1:3    ACATCCAACGGCCAACAGCTCGACGTGCCGGTCAGCAGAGCATCGGAACACTGGTGATTG
P-SETit.Ubq1-1:1:1    ACATCCAACGGCCAACAGCTCGACGTGCCGGTCAGCAGAGCATCGGAACACTGGTGATTG
P-SETit.Ubq1-1:1:2    ACATCCAACGGCCAACAGCTCGACGTGCCGGTCAGCAGAGCATCGGAACACTGGTGATTG
                      ************************************************************

P-SETit.Ubq1-1:1:4    GTGGAGCCGGCAGTATGCGCCCCAGCACGGCCGAGGTGGTGGTGGCCCGTGGCCCTGCTG
P-SETit.Ubq1-1:1:3    GTGGAGCCGGCAGTATGCGCCCCAGCACGGCCGAGGTGGTGGTGGCCCGTGGCCCTGCTG
P-SETit.Ubq1-1:1:1    GTGGAGCCGGCAGTATGCGCCCCAGCACGGCCGAGGTGGTGGTGGCCCGTGGCCCTGCTG
P-SETit.Ubq1-1:1:2    GTGGAGCCGGCAGTATGCGCCCCAGCACGGCCGAGGTGGTGGTGGCCCGTGGCCCTGCTG
                      ************************************************************
```

FIG. 6b

```
P-SETit.Ubq1-1:1:4    TCTGCGCGGCTCGGGACAACTTGAAACTGGGCCACCGCCTCGTCGCAACTCGCAACCCGT
P-SETit.Ubq1-1:1:3    TCTGCGCGGCTCGGGACAACTTGAAACTGGGCCACCGCCTCGTCGCAACTCGCAACCCGT
P-SETit.Ubq1-1:1:1    TCTGCGCGGCTCGGGACAACTTGAAACTGGGCCACCGCCTCGTCGCAACTCGCAACCCGT
P-SETit.Ubq1-1:1:2    TCTGCGCGGCTCGGGACAACTTGAAACTGGGCCACCGCCTCGTCGCAACTCGCAACCCGT
                      ************************************************************

P-SETit.Ubq1-1:1:4    TGGCGGAAGAAAGGAATGGCTCGTAGGGGCCCGGGTAGAATCGAAGAATGTTGCGCTGGG
P-SETit.Ubq1-1:1:3    TGGCGGAAGAAAGGAATGGCTCGTAGGGGCCCGGGTAGAATCGAAGAATGTTGCGCTGGG
P-SETit.Ubq1-1:1:1    TGGCGGAAGAAAGGAATGGCTCGTAGGGGCCCGGGTAGAATCGAAGAATGTTGCGCTGGG
P-SETit.Ubq1-1:1:2    TGGCGGAAGAAAGGAATGGCTCGTAGGGGCCCGGGTAGAATCGAAGAATGTTGCGCTGGG
                      ************************************************************

P-SETit.Ubq1-1:1:4    CTTCGATTCACATAACATGGGCCTGAAGCTCTAAAACGACGGCCCGGTCGCCGCGCGATG
P-SETit.Ubq1-1:1:3    CTTCGATTCACATAACATGGGCCTGAAGCTCTAAAACGACGGCCCGGTCGCCGCGCGATG
P-SETit.Ubq1-1:1:1    CTTCGATTCACATAACATGGGCCTGAAGCTCTAAAACGACGGCCCGGTCGCCGCGCGATG
P-SETit.Ubq1-1:1:2    CTTCGATTCACATAACATGGGCCTGAAGCTCTAAAACGACGGCCCGGTCGCCGCGCGATG
                      ************************************************************

P-SETit.Ubq1-1:1:4    GAAAGAGACCGGATCCTCCTCGTGAATTCTGGAAGGCCACACGAGAGCGACCCACCACCG
P-SETit.Ubq1-1:1:3    GAAAGAGACCGGATCCTCCTCGTGAATTCTGGAAGGCCACACGAGAGCGACCCACCACCG
P-SETit.Ubq1-1:1:1    GAAAGAGACCGGATCCTCCTCGTGAATTCTGGAAGGCCACACGAGAGCGACCCACCACCG
P-SETit.Ubq1-1:1:2    GAAAGAGACCGGATCCTCCTCGTGAATTCTGGAAGGCCACACGAGAGCGACCCACCACCG
                      ************************************************************

P-SETit.Ubq1-1:1:4    ACGCGGAGGAGTCGTGCGTGGTCCAACACGGCCGGCGGGCTGGGCTGCGACCTTAACCAG
P-SETit.Ubq1-1:1:3    ACGCGGAGGAGTCGTGCGTGGTCCAACACGGCCGGCGGGCTGGGCTGCGACCTTAACCAG
P-SETit.Ubq1-1:1:1    ACGCGGAGGAGTCGTGCGTGGTCCAACACGGCCGGCGGGCTGGGCTGCGACCTTAACCAG
P-SETit.Ubq1-1:1:2    ACGCGGAGGAGTCGTGCGTGGTCCAACACGGCCGGCGGGCTGGGCTGCGACCTTAACCAG
                      ************************************************************

P-SETit.Ubq1-1:1:4    CAAGGCACGCCACGACCCGCCCCGCCCTCGAGGCATAAATACCCTCCCATCC
P-SETit.Ubq1-1:1:3    CAAGGCACGCCACGACCCGCCCCGCCCTCGAGGCATAAATACCCTCCCATCC
P-SETit.Ubq1-1:1:1    CAAGGCACGCCACGACCCGCCCCGCCCTCGAGGCATAAATACCCTCCCATCC
P-SETit.Ubq1-1:1:2    CAAGGCACGCCACGACCCGCCCCGCCCTCGAGGCATAAATACCCTCCCATCC
                      ****************************************************
```

FIG. 6c

```
E-Cl.Ubq1-1:1:1    AGCAGACTCGCATTATCGATGGAGCTCTACCAAACTGGCCCTAGGCATTAACCTACCATG
P-Cl.Ubq1-1:1:1    AGCAGACTCGCATTATCGATGGAGCTCTACCAAACTGGCCCTAGGCATTAACCTACCATG
P-Cl.Ubq1-1:1:3    ------------------------------------------------------------
P-Cl.Ubq1-1:1:4    ------------------------------------------------------------
P-Cl.Ubq1-1:1:5    ------------------------------------------------------------

E-Cl.Ubq1-1:1:1    GATCACATCGTAAAAAAAAAACCCTACCATGGATCCTATCTGTTTTCTTTTTGCCCTGAA
P-Cl.Ubq1-1:1:1    GATCACATCGTAAAAAAAAAACCCTACCATGGATCCTATCTGTTTTCTTTTTGCCCTGAA
P-Cl.Ubq1-1:1:3    ------------------------------------------------------------
P-Cl.Ubq1-1:1:4    ----------------------------------CTATCTGTTTTCTTTTTGCCCTGAA
P-Cl.Ubq1-1:1:5    ------------------------------------------------------------

E-Cl.Ubq1-1:1:1    AGAGTGAAGTCATCATCATATTTACCATGGCGCGCGTAGGAGCGCTTCGTCGAAGACCCA
P-Cl.Ubq1-1:1:1    AGAGTGAAGTCATCATCATATTTACCATGGCGCGCGTAGGAGCGCTTCGTCGAAGACCCA
P-Cl.Ubq1-1:1:3    ------------------------------------------------------------
P-Cl.Ubq1-1:1:4    AGAGTGAAGTCATCATCATATTTACCATGGCGCGCGTAGGAGCGCTTCGTCGAAGACCCA
P-Cl.Ubq1-1:1:5    ------------------------------------------------------------

E-Cl.Ubq1-1:1:1    TAGGGGGGCGGTACTCGCACCGTGGTTGTTTCCTGTTATGTAATATCGGATGGGGGAGCA
P-Cl.Ubq1-1:1:1    TAGGGGGGCGGTACTCGCACCGTGGTTGTTTCCTGTTATGTAATATCGGATGGGGGAGCA
P-Cl.Ubq1-1:1:3    ------------------------------------------------------------
P-Cl.Ubq1-1:1:4    TAGGGGGGCGGTACTCGCACCGTGGTTGTTTCCTGTTATGTAATATCGGATGGGGGAGCA
P-Cl.Ubq1-1:1:5    ------------------------------------------------------------

E-Cl.Ubq1-1:1:1    GTCGGCTAGGTTGGTCCCATCGGTACTGGTCGTCCCCTAGTGCGCTAGATGCGCGATGTT
P-Cl.Ubq1-1:1:1    GTCGGCTAGGTTGGTCCCATCGGTACTGGTCGTCCCCTAGTGCGCTAGATGCGCGATGTT
P-Cl.Ubq1-1:1:3    ------------------------------------------------------------
P-Cl.Ubq1-1:1:4    GTCGGCTAGGTTGGTCCCATCGGTACTGGTCGTCCCCTAGTGCGCTAGATGCGCGATGTT
P-Cl.Ubq1-1:1:5    ------------------------------------------------------------

E-Cl.Ubq1-1:1:1    TGTCCTCAAAAACTCTTTTCTTCTTAATAACAATCATACGCAAATTTTTTGCGTATTCGA
P-Cl.Ubq1-1:1:1    TGTCCTCAAAAACTCTTTTCTTCTTAATAACAATCATACGCAAATTTTTTGCGTATTCGA
P-Cl.Ubq1-1:1:3    ------------------------------------------------------------
P-Cl.Ubq1-1:1:4    TGTCCTCAAAAACTCTTTTCTTCTTAATAACAATCATACGCAAATTTTTTGCGTATTCGA
P-Cl.Ubq1-1:1:5    ------------------------------------------------------------

E-Cl.Ubq1-1:1:1    GAAAAAAAGAAGATTCTATCTGTTTTTTTTTTGAAATGGCTCCAATTTATAGGAGGAGCC
P-Cl.Ubq1-1:1:1    GAAAAAAAGAAGATTCTATCTGTTTTTTTTTTGAAATGGCTCCAATTTATAGGAGGAGCC
P-Cl.Ubq1-1:1:3    ------------------------------------------------------------
P-Cl.Ubq1-1:1:4    GAAAAAAAGAAGATTCTATCTGTTTTTTTTTTGAAATGGCTCCAATTTATAGGAGGAGCC
P-Cl.Ubq1-1:1:5    ------------------------------------------------------------

E-Cl.Ubq1-1:1:1    CGTTTAACGGCGTCGACAAATCTAACGGACACCAACCAGCGAATGAGCGAACCCACCAGC
P-Cl.Ubq1-1:1:1    CGTTTAACGGCGTCGACAAATCTAACGGACACCAACCAGCGAATGAGCGAACCCACCAGC
P-Cl.Ubq1-1:1:3    ----------------CAAATCTAACGGACACCAACCAGCGAATGAGCGAACCCACCAGC
P-Cl.Ubq1-1:1:4    CGTTTAACGGCGTCGACAAATCTAACGGACACCAACCAGCGAATGAGCGAACCCACCAGC
P-Cl.Ubq1-1:1:5    ------------------------------------------------------------
```

FIG. 7a

```
E-Cl.Ubq1-1:1:1    GCCAAGCTAGCCAAGCGAAGCAGACGGCCGAGACGCTGACACCCTTGCCTTGGCGCGGCA
P-Cl.Ubq1-1:1:1    GCCAAGCTAGCCAAGCGAAGCAGACGGCCGAGACGCTGACACCCTTGCCTTGGCGCGGCA
P-Cl.Ubq1-1:1:3    GCCAAGCTAGCCAAGCGAAGCAGACGGCCGAGACGCTGACACCCTTGCCTTGGCGCGGCA
P-Cl.Ubq1-1:1:4    GCCAAGCTAGCCAAGCGAAGCAGACGGCCGAGACGCTGACACCCTTGCCTTGGCGCGGCA
P-Cl.Ubq1-1:1:5    ------------------------------------------------------------

E-Cl.Ubq1-1:1:1    TCTCCGTCGCTGGCTCGCTGGCTCTGGCCCCTTCGCGAGAGTTCCGGTCCACCTCCACCT
P-Cl.Ubq1-1:1:1    TCTCCGTCGCTGGCTCGCTGGCTCTGGCCCCTTCGCGAGAGTTCCGGTCCACCTCCACCT
P-Cl.Ubq1-1:1:3    TCTCCGTCGCTGGCTCGCTGGCTCTGGCCCCTTCGCGAGAGTTCCGGTCCACCTCCACCT
P-Cl.Ubq1-1:1:4    TCTCCGTCGCTGGCTCGCTGGCTCTGGCCCCTTCGCGAGAGTTCCGGTCCACCTCCACCT
P-Cl.Ubq1-1:1:5    ------------------------------------------------------------

E-Cl.Ubq1-1:1:1    GTGTCGGTTTCCAACTCCGTTCCGCCTTCGCGTGGGACTTGTTCCGTTCATCCGTTGGCG
P-Cl.Ubq1-1:1:1    GTGTCGGTTTCCAACTCCGTTCCGCCTTCGCGTGGGACTTGTTCCGTTCATCCGTTGGCG
P-Cl.Ubq1-1:1:3    GTGTCGGTTTCCAACTCCGTTCCGCCTTCGCGTGGGACTTGTTCCGTTCATCCGTTGGCG
P-Cl.Ubq1-1:1:4    GTGTCGGTTTCCAACTCCGTTCCGCCTTCGCGTGGGACTTGTTCCGTTCATCCGTTGGCG
P-Cl.Ubq1-1:1:5    ------------------------------------------------------------

E-Cl.Ubq1-1:1:1    GCATCCGGAAATTGCGTGGCGTAGAGCACGGGGCCCTCCTCTCACACGGCACGGAACCGT
P-Cl.Ubq1-1:1:1    GCATCCGGAAATTGCGTGGCGTAGAGCACGGGGCCCTCCTCTCACACGGCACGGAACCGT
P-Cl.Ubq1-1:1:3    GCATCCGGAAATTGCGTGGCGTAGAGCACGGGGCCCTCCTCTCACACGGCACGGAACCGT
P-Cl.Ubq1-1:1:4    GCATCCGGAAATTGCGTGGCGTAGAGCACGGGGCCCTCCTCTCACACGGCACGGAACCGT
P-Cl.Ubq1-1:1:5    ------------------------------------------------------------

E-Cl.Ubq1-1:1:1    CACGAGCTCACGGCACCGGCAGCACGGCGGGGATTCCTTCCCCACCACCGCTCCTTCCCT
P-Cl.Ubq1-1:1:1    CACGAGCTCACGGCACCGGCAGCACGGCGGGGATTCCTTCCCCACCACCGCTCCTTCCCT
P-Cl.Ubq1-1:1:3    CACGAGCTCACGGCACCGGCAGCACGGCGGGGATTCCTTCCCCACCACCGCTCCTTCCCT
P-Cl.Ubq1-1:1:4    CACGAGCTCACGGCACCGGCAGCACGGCGGGGATTCCTTCCCCACCACCGCTCCTTCCCT
P-Cl.Ubq1-1:1:5    ------------------------------------------------------------

E-Cl.Ubq1-1:1:1    TTCCCTTCCTCGCCCGCC------------------------------------------
P-Cl.Ubq1-1:1:1    TTCCCTTCCTCGCCCGCCATCATAAATAGCCACCCCTCCCAGCTTCCTTCGCCACAT
P-Cl.Ubq1-1:1:3    TTCCCTTCCTCGCCCGCCATCATAAATAGCCACCCCTCCCAGCTTCCTTCGCCACAT
P-Cl.Ubq1-1:1:4    TTCCCTTCCTCGCCCGCCATCATAAATAGCCACCCCTCCCAGCTTCCTTCGCCACAT
P-Cl.Ubq1-1:1:5    ---CCTTCCTCGCCCGCCATCATAAATAGCCACCCCTCCCAGCTTCCTTCGCCACAT
                      ***************
```

FIG. 7b

Transgene Cassette Configuration 1
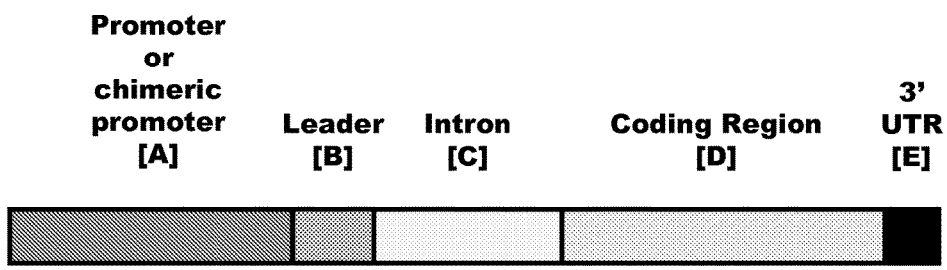
Transgene Cassette Configuration 2
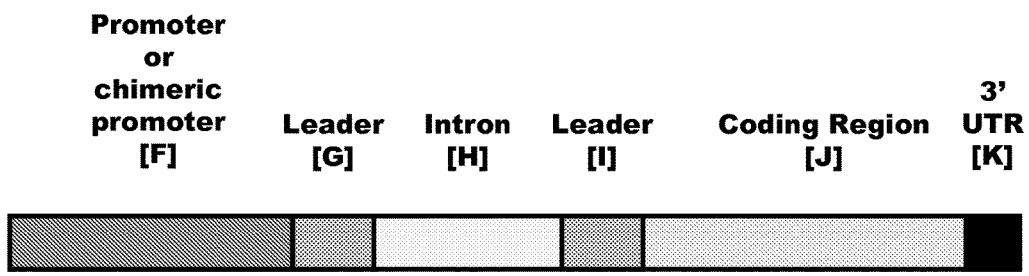
Transgene Cassette Configuration 3
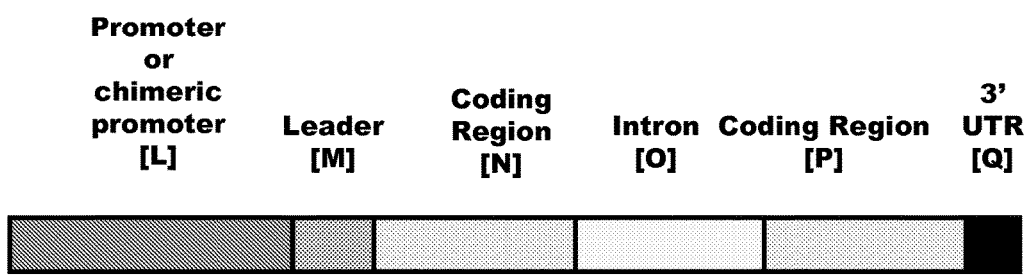
FIG. 8

SEQUENCE LISTING

```
<160> NUMBER OF SEQ ID NOS: 183

<210> SEQ ID NO 1
<211> LENGTH: 3741
<212> TYPE: DNA
<213> ORGANISM: Andropogon gerardii

<400> SEQUENCE: 1
agcagactcg cattatcgat ggaggggtgg gtttagaacc ctgaaaactg gtactgtttc      60
gaactgaaaa acactgtagc acttttcgtt tgtttgtggt aaatattatc ttactatggt     120
```

```
ctaactaggc tcaaaagaat cgtctcgcaa tgtacatcta aattatgcaa ttagttattt      180
tgtttacctg catttcatac tccgagcatg cgtcttttgg tacatttaat gcttcgatgt      240
gatgggaatt ttaaaaattt tggagaaaag ttggtttcta acaccccg aggacgaaat        300 tggattcggt ctttgacgcg gatgcagcaa ctgcagtgcg caggatacca tcttagccgt      360
tgcgtcgaag ttcgctttgc taacgttttg agaaaattaa accagctttg accaacgtga      420
gacgagcgcc ttacgtggca gtgtaatgga accgggcacg gcaagtttga cgctgtagtg      480
ttagccggtc tcgttacgtt tggcacaact tagttgaatc cggcttccgg caaactatat      540
ggcaagttag acccaagtgt gagccggcca ccgcaagtta ttgggacatt atacgtagga     600
agcaagtgta taataagaat atgagataat gtaagcagct atatgaatca tcacgtcata     660
tttatgttaa gatgaagagg atagaataaa cggtatgtaa atttatagcg agtgatagac     720
gggcacaagg cctcctagct atttccataa atcggatttt gtaagaacaa aaaagaggac    780
ttattataag agaatgtggt aagtaagtat actctctccg tttcaaatta taagttgttt     840
tgattttttt ggtacatcta ttttactatg cattagatat aataatgtgt ctagatacat    900
aacaaaatgg atgaatcaaa aaagtcaaag tgatttacaa tttggaacgg agagagtaag    960
ttcaagccgt caaggcactt ctatgcaacc acagtcaact tgaatgccgc ttgagtgcct    1020
tctcaagttt ttttttcttg caaaaatcat ttctttttt taaaaaagt ataatttgga      1080 tcgtgcaaat ttctctctag gtgtgtgtgt gactgtgtga gtaacaattt ctctagttgt    1140
gcgcgactgc tgcttacttt ggagattaca atatctttct aaaatgcttc gattacttat    1200
ttataaaccg tctctaaggc caattgctca agattcattc aacaattgaa acgtctcaca    1260
tgattaaatc atataaagtt tctaagtctt gtttgacaag attttttag attttcatct     1320 aaattggatg aaactatcaa acactaattt taaaaaatat aagagaagct ccggagataa    1380
aaggtcgtct atgttattat aagagtaaag tcgtctattc tcttcgtccc aacatatata    1440
attctaagca tgaattgctt tcttttggga caaaaggagc atgccacaac acaagaatga    1500
tgtcaccgtc atgcttggat ccttttatgg taaagcttca ccttctataa tctaacaata    1560
gagaaatcag ggaaaaatca tgttttggtt gttttattt ctaacctcca caataacttt     1620
ggtttaccat ttttttgtttg attttagttt tagagaagcg tttataacag gacctaaaat   1680
cttttttcag tacacagtac aacgcagacg ctcatacacg cacgcacact cacctctatg    1740
aacacacgta agaaaaccct acaccttgag caccttcgaa ggactgagcc ggtaaatata    1800
gagattctcg aagtcactat tagcgcctcg ttgtcaacgg gaatgtcgct taccacttaa    1860
agcataacgc cgagaaatcc cgtaataaat ccagtaaaat acgagcaccc gtgccaagtt    1920
gaatatttga acccgagtgg gtagattcca ccgcaaagga cctaaccaga tcatttcgca    1980
aacaggaact aaaatcggta gagagcccag acaaaagcct ttcctaagag ccactccagt    2040
ggaagcccct actttaggta taaaatgcaa tactagtggg gctcctaaat aaacttctat    2100
ttttcatggc cttctaaaat tcactcccaa accctagct atagaagtct cttatccatc      2160
ctctaaataa aaatgggagt ctattttatt tcaccagagt tgatcgtaaa tttagtctct    2220
caaattttat aagttgaggg tagaggatga ctggagttgc tctaaacgga cctatcttca    2280
agtgacctca gtgagcccgt ttaacggcgt cgacaagttt aatctaacgg acaccaacca    2340
gagaagagaa ccaccgccag cgccgagcca agcgacgttg acatcttggc gcggcacggc    2400
atctccctgg cgtctggccc cctctcgaga cttccgctcc acctcccacc ggtggcggtt    2460
```

```
tccaagtccg ttccgcctcc tctcacacgg cacgaaaccg tgacgggcac cggcagcacg   2520
gggggattcc tttcccaccg ctccttccct ttcccttcct ctcccgccgc tataaatagc   2580
cagccccatc cccagcttct ttccccaacc tcatcttctc tcgtgttgtt cggcacaacc   2640
cgatcgatcc ccaactccct cgtcgtctct cctcgcgagc ctcgtcgatc ccccgcttca   2700
aggtacggcg atcgattatc ttccctctct ctaccttctc tctcttatag ggcctgctag   2760
ctctgttcct gttttttccat ggctgcgagg tacaatagat cggcgatcca tggttagggc   2820
ctgctagttg tgttcctgtt tttccatggc tgcgaggcac aatagatctg atggcgttat   2880
gatggttaac ttgtcatact cttgcgatct atggtccctt taggagttta ggacatctat   2940
ttaatttcgg atagttcgag atctgtgatc catggttagt accctaggca gtggggttag   3000
atccgtgctg ttatggttcg tagatggatt ctgattgctc agtaactggg aatcctggga   3060
tggttctagc tggttcgcag ataagatcga tttcatgata tgctatatct tgtttggttg   3120
ccgtggttcc gttaaatctg tctgttatga tcttagtctt tgataaggtt cggtcgtgct   3180
agctacgtcc tgtgcagcac ttaattgtca ggtcataatt tttagcatgc cttttttta   3240 ttggtttggt tttgtctgac tgggctgtag atagtttcaa tctttgtctg actgggctgt   3300
agatagtttc aatctacctg tcggtttatt ttattaaatt tggatctgta tgtgtgtcat   3360
atatcttcat cttttagata tatcgatagg tttatatgtt gctgtcggtt ttttactgtt   3420
cctttatgag atatattcat gcttagatac atgaaacaac gtgctgttac agtttaatag   3480
ttcttgttta tctaataaac aaataaggat aggtatatgc tgcagttagt tttactggta   3540
ctttttttga catgaaccta cggcttaata attagtcttc atcaaataaa agcatattt   3600 tttaattatt tcgatatact tgaatgatgt catatgcagc atctgtgtga attttttggcc   3660 ctgtcttcat atgctgttta tttgtttggg actgtttctt tggttgataa ctcatcctgt   3720
tgtttggtga tccttttgca g                                             3741

<210> SEQ ID NO 2
<211> LENGTH: 2603
<212> TYPE: DNA
<213> ORGANISM: Andropogon gerardii

<400> SEQUENCE: 2
agcagactcg cattatcgat ggaggggtgg gtttagaacc ctgaaaactg gtactgtttc     60
gaactgaaaa acactgtagc acttttcgtt tgtttgtggt aaatattatc ttactatggt    120
ctaactaggc tcaaaagaat cgtctcgcaa tgtacatcta aattatgcaa ttagttattt    180
tgtttacctg catttcatac tccgagcatg cgtcttttgg tacatttaat gcttcgatgt    240
gatgggaatt ttaaaaattt tggagaaaag ttggtttcta acaccccccg aggacgaaat    300
tggattcggt ctttgacgcg gatgcagcaa ctgcagtgcg caggatacca tcttagccgt    360
tgcgtcgaag ttcgctttgc taacgttttg agaaaattaa accagctttg accaacgtga    420
gacgagcgcc ttacgtggca gtgtaatgga accgggcacg gcaagtttga cgctgtagtg    480
ttagccggtc tcgttacgtt tggcacaact tagttgaatc cggcttccgg caaactatat    540
ggcaagttag acccaagtgt gagccggcca ccgcaagtta ttgggacatt atacgtagga    600
agcaagtgta taataagaat atgagataat gtaagcagct atatgaatca tcacgtcata    660
tttatgttaa gatgaagagg atagaataaa cggtatgtaa atttatagcg agtgatagac    720
gggcacaagg cctcctagct atttccataa atcggatttt gtaagaacaa aaaagaggac    780
ttattataag agaatgtggt aagtaagtat actctctccg tttcaaatta taagttgttt    840
```

-continued

```
tgattttttt ggtacatcta ttttactatg cattagatat aataatgtgt ctagatacat      900
aacaaaatgg atgaatcaaa aaagtcaaag tgatttacaa tttggaacgg agagagtaag      960
ttcaagccgt caaggcactt ctatgcaacc acagtcaact tgaatgccgc ttgagtgcct     1020
tctcaagttt ttttttcttg caaaaatcat ttctttttt taaaaaagt ataatttgga      1080
tcgtgcaaat ttctctctag gtgtgtgtgt gactgtgtga gtaacaattt ctctagttgt     1140
gcgcgactgc tgcttacttt ggagattaca atatctttct aaaatgcttc gattacttat     1200
ttataaaccg tctctaaggc caattgctca agattcattc aacaattgaa acgtctcaca     1260
tgattaaatc atataaagtt tctaagtctt gtttgacaag atttttttag attttcatct     1320
aaattggatg aaactatcaa acactaattt taaaaaatat aagagaagct ccggagataa     1380
aaggtcgtct atgttattat aagagtaaag tcgtctattc cttcgtccc aacatatata      1440
attctaagca tgaattgctt tcttttggga caaaaggagc atgccacaac acaagaatga     1500
tgtcaccgtc atgcttggat cctttttatgg taaagcttca ccttctataa tctaacaata     1560
gagaaatcag ggaaaaatca tgttttggtt gtttttattt ctaacctcca caataacttt     1620
ggtttaccat ttttttgtttg attttagttt tagagaagcg tttataacag gacctaaaat    1680
cttttttcag tacacagtac aacgcagacg ctcatacacg cacgcacact cacctctatg     1740
aacacacgta agaaaaccct acaccttgag caccttcgaa ggactgagcc ggtaaatata     1800
gagattctcg aagtcactat tagcgcctcg ttgtcaacgg gaatgtcgct taccacttaa     1860
agcataacgc cgagaaatcc cgtaataaat ccagtaaaat acgagcaccc gtgccaagtt     1920
gaatatttga acccgagtgg gtagattcca ccgcaaagga cctaaccaga tcatttcgca     1980
aacaggaact aaaatcggta gagagcccag acaaaagcct ttcctaagag ccactccagt     2040
ggaagcccct actttaggta taaaatgcaa tactagtggg gctcctaaat aaacttctat     2100
ttttcatggc cttctaaaat tcactcccaa accctagct atagaagtct cttatccatc      2160
ctctaaataa aaatgggagt ctattttatt tcaccagagt tgatcgtaaa tttagtctct     2220
caaatttta aagttgaggg tagaggatga ctggagttgc tctaaacgga cctatcttca     2280
agtgacctca gtgagcccgt ttaacggcgt cgacaagttt aatctaacgg acaccaacca     2340
gagaagagaa ccaccgccag cgccgagcca agcgacgttg acatcttggc gcggcacggc     2400
atctccctgg cgtctggccc cctctcgaga cttccgctcc acctcccacc ggtggcggtt     2460
tccaagtccg ttccgcctcc tctcacacgg cacgaaaccg tgacgggcac cggcagcacg     2520
gggggattcc tttcccaccg ctccttccct ttcccttcct ctcccgccgc tataaatagc     2580
cagccccatc cccagcttct ttc                                             2603
```

<210> SEQ ID NO 3
<211> LENGTH: 99
<212> TYPE: DNA
<213> ORGANISM: Andropogon gerardii
<400> SEQUENCE: 3

```
cccaacctca tcttctctcg tgttgttcgg cacaacccga tcgatcccca actccctcgt       60
cgtctctcct cgcgagcctc gtcgatcccc cgcttcaag                              99
```

<210> SEQ ID NO 4
<211> LENGTH: 1039
<212> TYPE: DNA
<213> ORGANISM: Andropogon gerardii

```
<400> SEQUENCE: 4
gtacggcgat cgattatctt ccctctctct accttctctc tcttataggg cctgctagct      60
ctgttcctgt ttttccatgg ctgcgaggta caatagatcg gcgatccatg gttagggcct     120
gctagttgtg ttcctgtttt tccatggctg cgaggcacaa tagatctgat ggcgttatga     180
tggttaactt gtcatactct tgcgatctat ggtcccttta ggagtttagg acatctattt     240
aatttcggat agttcgagat ctgtgatcca tggttagtac cctaggcagt ggggttagat     300
ccgtgctgtt atggttcgta gatggattct gattgctcag taactgggaa tcctgggatg     360
gttctagctg gttcgcagat aagatcgatt tcatgatatg ctatatcttg tttggttgcc     420
gtggttccgt taaatctgtc tgttatgatc ttagtctttg ataaggttcg gtcgtgctag     480
ctacgtcctg tgcagcactt aattgtcagg tcataatttt tagcatgcct tttttttatt     540
ggtttggttt tgtctgactg ggctgtagat agtttcaatc tttgtctgac tgggctgtag     600
atagtttcaa tctacctgtc ggtttatttt attaaatttg gatctgtatg tgtgtcatat     660
atcttcatct tttagatata tcgataggtt tatatgttgc tgtcggtttt ttactgttcc     720
tttatgagat atattcatgc ttagatacat gaaacaacgt gctgttacag tttaatagtt     780
cttgtttatc taataaacaa ataaggatag gtatatgctg cagttagttt tactggtact     840
ttttttgaca tgaacctacg gcttaataat tagtcttcat caaataaaaa gcatattttt     900
taattatttc gatatacttg aatgatgtca tatgcagcat ctgtgtgaat ttttggccct     960
gtcttcatat gctgtttatt tgtttgggac tgtttctttg gttgataact catcctgttg    1020
tttggtgatc cttttgcag                                                 1039

<210> SEQ ID NO 5
<211> LENGTH: 3255
<212> TYPE: DNA
<213> ORGANISM: Andropogon gerardii

<400> SEQUENCE: 5
ctcgttacgt ttggcacaac ttagttgaat ccggcttccg gcaaactata tggcaagtta      60
gacccaagtg tgagccggcc accgcaagtt attgggacat tatacgtagg aagcaagtgt     120
ataataagaa tatgagataa tgtaagcagc tatatgaatc atcacgtcat atttatgtta     180
agatgaagag gatagaataa acggtatgta aatttatagc gagtgataga cgggcacaag     240
gcctcctagc tatttccata aatcggattt tgtaagaaca aaaagagga cttattataa     300 gagaatgtgg taagtaagta tactctctcc gtttcaaatt ataagttgtt ttgatttttt     360
tggtacatct attttactat gcattagata taataatgtg tctagataca taacaaaatg     420
gatgaatcaa aaaagtcaaa gtgatttaca atttggaacg gagagagtaa gttcaagccg     480
tcaaggcact tctatgcaac cacagtcaac ttgaatgccg cttgagtgcc ttctcaagtt     540
tttttttctt gcaaaaatca tttctttttt ttaaaaaaag tataatttgg atcgtgcaaa     600
tttctctcta ggtgtgtgtg tgactgtgtg agtaacaatt tctctagttg tgcgcgactg     660
ctgcttactt tggagattac aatatctttc taaaatgctt cgattactta tttataaacc     720
gtctctaagg ccaattgctc aagattcatt caacaattga aacgtctcac atgattaaat     780
catataaagt ttctaagtct tgtttgacaa gatttttta gattttcatc taaattggat     840
gaaactatca aacactaatt ttaaaaaata taagagaagc tccggagata aaggtcgtc     900 tatgttatta taagagtaaa gtcgtctatt ctcttcgtcc caacatatat aattctaagc     960
atgaattgct ttcttttggg acaaaaggag catgccacaa cacaagaatg atgtcaccgt    1020
```

```
catgcttgga tccttttatg gtaaagcttc accttctata atctaacaat agagaaatca      1080
gggaaaaatc atgttttggt tgtttttatt tctaacctcc acaataactt tggtttacca      1140
ttttttgttt gattttagtt ttagagaagc gtttataaca ggacctaaaa tcttttttca      1200
gtacacagta caacgcagac gctcatacac gcacgcacac tcacctctat gaacacacgt      1260
aagaaaaccc tacaccttga gcaccttcga aggactgagc cggtaaatat agagattctc      1320
gaagtcacta ttagcgcctc gttgtcaacg ggaatgtcgc ttaccactta agcataacg       1380 ccgagaaatc ccgtaataaa tccagtaaaa tacgagcacc cgtgccaagt tgaatatttg      1440
aacccgagtg ggtagattcc accgcaaagg acctaaccag atcatttcgc aaacaggaac      1500
taaaatcggt agagagccca gacaaaagcc tttcctaaga gccactccag tggaagcccc      1560
tactttaggt ataaaatgca atactagtgg ggctcctaaa taaacttcta tttttcatgg      1620
ccttctaaaa ttcactccca aaccctagc tatagaagtc tcttatccat cctctaaata       1680
aaaatgggag tctattttat ttcaccagag ttgatcgtaa atttagtctc tcaaatttta      1740
taagttgagg gtagaggatg actggagttg ctctaaacgg acctatcttc aagtgacctc      1800
agtgagcccg tttaacggcg tcgacaagtt taatctaacg acaccaacc agagaagaga       1860 accaccgcca gcgccgagcc aagcgacgtt gacatcttgg cgcggcacgg catctccctg      1920
gcgtctggcc ccctctcgag acttccgctc cacctcccac cggtggcggt ttccaagtcc      1980
gttccgcctc ctctcacacg gcacgaaacc gtgacgggca ccggcagcac gggggattc      2040 cttttcccacc gctccttccc tttcccttcc tctcccgccg ctataaatag ccagccccat      2100
ccccagcttc tttccccaac ctcatcttct ctcgtgttgt tcggcacaac ccgatcgatc      2160
cccaactccc tcgtcgtctc tcctcgcgag cctcgtcgat cccccgcttc aaggtacggc      2220
gatcgattat cttccctctc tctaccttct ctctcttata gggcctgcta gctctgttcc      2280 tgttttttcca tggctgcgag gtacaataga tcggcgatcc atggttaggg cctgctagtt      2340
gtgttcctgt ttttccatgg ctgcgaggca aatagatct gatggcgtta tgatggttaa       2400
cttgtcatac tcttgcgatc tatggtccct ttaggagttt aggacatcta tttaatttcg      2460
gatagttcga gatctgtgat ccatggttag taccctaggc agtggggtta gatccgtgct      2520
gttatggttc gtagatggat tctgattgct cagtaactgg gaatcctggg atggttctag      2580
ctggttcgca gataagatcg atttcatgat atgctatatc ttgtttggtt gccgtggttc      2640
cgttaaatct gtctgttatg atcttagtct ttgataaggt tcggtcgtgc tagctacgtc      2700
ctgtgcagca cttaattgtc aggtcataat ttttagcatg cctttttttt attggtttgg      2760
ttttgtctga ctgggctgta gatagtttca atctttgtct gactgggctg tagatagttt      2820
caatctacct gtcggtttat tttattaaat ttggatctgt atgtgtgtca tatatcttca      2880
tcttttagat atatcgatag gtttatatgt tgctgtcggt ttttttactgt tcctttatga     2940 gatatattca tgcttagata catgaaacaa cgtgctgtta cagtttaata gttcttgttt      3000
atctaataaa caaataagga taggtatatg ctgcagttag ttttactggt acttttttg       3060 acatgaacct acggcttaat aattagtctt catcaaataa aaagcatatt ttttaattat      3120
ttcgatatac ttgaatgatg tcatatgcag catctgtgtg aatttttggc cctgtcttca     3180
tatgctgttt attgtttgg gactgttttct ttggttgata actcatcctg ttgtttggtg      3240
atccttttgc aggtg                                                       3255
```

<210> SEQ ID NO 6

<211> LENGTH: 2114
<212> TYPE: DNA
<213> ORGANISM: Andropogon gerardii

<400> SEQUENCE: 6

```
ctcgttacgt ttggcacaac ttagttgaat ccggcttccg gcaaactata tggcaagtta      60
gacccaagtg tgagccggcc accgcaagtt attgggacat tatacgtagg aagcaagtgt     120
ataataagaa tatgagataa tgtaagcagc tatatgaatc atcacgtcat atttatgtta     180
agatgaagag gatagaataa acggtatgta aatttatagc gagtgataga cgggcacaag     240
gcctcctagc tatttccata aatcggattt tgtaagaaca aaaagagga cttattataa     300
gagaatgtgg taagtaagta tactctctcc gtttcaaatt ataagttgtt ttgatttttt     360
tggtacatct attttactat gcattagata taataatgtg tctagataca taacaaaatg     420
gatgaatcaa aaaagtcaaa gtgatttaca atttggaacg gagagagtaa gttcaagccg     480
tcaaggcact tctatgcaac cacagtcaac ttgaatgccg cttgagtgcc ttctcaagtt     540
tttttttctt gcaaaaatca tttcttttt ttaaaaaaag tataatttgg atcgtgcaaa     600
tttctctcta ggtgtgtgtg tgactgtgtg agtaacaatt tctctagttg tgcgcgactg     660
ctgcttactt tggagattac aatatctttc taaaatgctt cgattactta tttataaacc     720
gtctctaagg ccaattgctc aagattcatt caacaattga aacgtctcac atgattaaat     780
catataaagt ttctaagtct tgtttgacaa gattttttta gattttcatc taaattggat     840
gaaactatca aacactaatt ttaaaaaata taagagaagc tccggagata aaaggtcgtc     900
tatgttatta taagagtaaa gtcgtctatt ctcttcgtcc caacatatat aattctaagc     960
atgaattgct ttcttttttgg acaaaaggag catgccacaa cacaagaatg atgtcaccgt    1020
catgcttgga tccttttatg gtaaagcttc accttctata atctaacaat agagaaatca    1080
gggaaaaatc atgttttggt tgtttttatt tctaacctcc acaataactt tggtttacca    1140
tttttttgttt gattttagtt ttagagaagc gtttataaca ggacctaaaa tcttttttca    1200
gtacacagta caacgcagac gctcatacac gcacgcacac tcacctctat gaacacacgt    1260
aagaaaaccc tacaccttga gcaccttcga aggactgagc cggtaaatat agagattctc    1320
gaagtcacta ttagcgcctc gttgtcaacg ggaatgtcgc ttaccactta aagcataacg    1380
ccgagaaatc ccgtaataaa tccagtaaaa tacgagcacc cgtgccaagt tgaatatttg    1440
aacccgagtg ggtagattcc accgcaaagg acctaaccag atcatttcgc aaacaggaac    1500
taaaatcggt agagagccca gacaaaagcc tttcctaaga gccactccag tggaagcccc    1560
tactttaggt ataaaatgca atactagtgg ggctcctaaa taaacttcta tttttcatgg    1620
ccttctaaaa ttcactccca aaccctagc tatagaagtc tcttatccat cctctaaata    1680
aaaatgggag tctattttat ttcaccagag ttgatcgtaa atttagtctc tcaaatttta    1740
taagttgagg gtagaggatg actggagttg ctctaaacgg acctatcttc aagtgacctc    1800
agtgagcccg tttaacggcg tcgacaagtt taatctaacg gacaccaacc agagaagaga    1860
accaccgcca gcgccgagcc aagcgacgtt gacatcttgg cgcggcacgg catctccctg    1920
gcgtctggcc ccctctcgag acttccgctc cacctcccac cggtggcggt ttccaagtcc    1980
gttccgcctc ctctcacacg gcacgaaacc gtgacgggca ccggcagcac gggggggattc    2040
cctttcccacc gctccttccc tttccccttcc tctcccgccg ctataaatag ccagccccat    2100
ccccagcttc tttc                                                       2114
```

```
<210> SEQ ID NO 7
<211> LENGTH: 1042
<212> TYPE: DNA
<213> ORGANISM: Andropogon gerardii

<400> SEQUENCE: 7
gtacggcgat cgattatctt ccctctctct accttctctc tcttataggg cctgctagct      60
ctgttcctgt ttttccatgg ctgcgaggta caatagatcg gcgatccatg gttagggcct     120
gctagttgtg ttcctgtttt tccatggctg cgaggcacaa tagatctgat ggcgttatga     180
tggttaactt gtcatactct tgcgatctat ggtcccttta ggagtttagg acatctattt     240
aatttcggat agttcgagat ctgtgatcca tggttagtac cctaggcagt ggggttagat     300
ccgtgctgtt atggttcgta gatggattct gattgctcag taactgggaa tcctgggatg     360
gttctagctg gttcgcagat aagatcgatt catgatatg ctatatcttg tttggttgcc      420
gtggttccgt taaatctgtc tgttatgatc ttagtctttg ataaggttcg gtcgtgctag     480
ctacgtcctg tgcagcactt aattgtcagg tcataaattt tagcatgcct tttttttatt     540
ggtttggttt tgtctgactg ggctgtagat agtttcaatc tttgtctgac tgggctgtag     600
atagtttcaa tctacctgtc ggtttatttt attaaatttg gatctgtatg tgtgtcatat     660
atcttcatct tttagatata tcgataggtt tatatgttgc tgtcggtttt ttactgttcc     720
tttatgagat atattcatgc ttagatacat gaaacaacgt gctgttacag tttaatagtt     780
cttgtttatc taataaacaa ataaggatag gtatatgctg cagttagttt tactggtact     840
tttttttgaca tgaacctacg gcttaataat tagtcttcat caaataaaaa gcatattttt     900
taattatttc gatatacttg aatgatgtca tatgcagcat ctgtgtgaat ttttggccct     960
gtcttcatat gctgtttatt tgtttgggac tgtttctttg gttgataact catcctgttg    1020
tttggtgatc cttttgcagg tg                                             1042

<210> SEQ ID NO 8
<211> LENGTH: 2785
<212> TYPE: DNA
<213> ORGANISM: Andropogon gerardii

<400> SEQUENCE: 8
gttcaagccg tcaaggcact tctatgcaac cacagtcaac ttgaatgccg cttgagtgcc      60
ttctcaagtt ttttttcctt gcaaaaatca tttcttttt ttaaaaaaag tataatttgg      120
atcgtgcaaa ttctctctcta ggtgtgtgtg tgactgtgtg agtaacaatt tctctagttg     180
tgcgcgactg ctgcttactt tggagattac aatatcttc taaaatgctt cgattactta     240
tttataaacc gtctctaagg ccaattgctc aagattcatt caacaattga aacgtctcac     300
atgattaaat catataaagt ttctaagtct tgtttgacaa gatttttta gattttcatc     360
taaattggat gaaactatca aacactaatt ttaaaaaata taagagaagc tccggagata     420
aaaggtcgtc tatgttatta taagagtaaa gtcgtctatt ctcttcgtcc caacatatat     480
aattctaagc atgaattgct ttcttttggg acaaaaggag catgccacaa cacaagaatg     540
atgtcaccgt catgcttgga tccttttatg gtaaagcttc accttctata atctaacaat     600
agagaaatca gggaaaaatc atgttttggt tgtttttatt tctaacctcc acaataactt     660
tggtttacca tttttttgttt gattttagtt ttagagaagc gtttataaca ggacctaaaa     720
tcttttttca gtacacagta caacgcagac gctcatacac gcacgcacac tcacctctat     780
gaacacacgt aagaaaaccc tacaccttga gcaccttcga aggactgagc cggtaaatat     840
```

| | |
|---|---:|
| agagattctc gaagtcacta ttagcgcctc gttgtcaacg ggaatgtcgc ttaccactta | 900 |
| aagcataacg ccgagaaatc ccgtaataaa tccagtaaaa tacgagcacc cgtgccaagt | 960 |
| tgaatatttg aacccgagtg ggtagattcc accgcaaagg acctaaccag atcatttcgc | 1020 |
| aaacaggaac taaaatcggt agagagccca gacaaaagcc tttcctaaga gccactccag | 1080 |
| tggaagcccc tactttaggt ataaaatgca atactagtgg ggctcctaaa taaacttcta | 1140 |
| tttttcatgg ccttctaaaa ttcactccca aaccccctagc tatagaagtc tcttatccat | 1200 |
| cctctaaata aaaatgggag tctattttat ttcaccagag ttgatcgtaa atttagtctc | 1260 |
| tcaaatttta taagttgagg gtagaggatg actggagttg ctctaaacgg acctatcttc | 1320 |
| aagtgacctc agtgagcccg tttaacggcg tcgacaagtt taatctaacg gacaccaacc | 1380 |
| agagaagaga accaccgcca gcgccgagcc aagcgacgtt gacatcttgg cgcggcacgg | 1440 |
| catctccctg gcgtctggcc ccctctcgag acttccgctc cacctcccac cggtggcggt | 1500 |
| ttccaagtcc gttccgcctc ctctcacacg gcacgaaacc gtgacgggca ccggcagcac | 1560 |
| ggggggattc ctttcccacc gctccttccc tttcccttcc tctcccgccg ctataaatag | 1620 |
| ccagccccat cccagcttc ttttcccaac ctcatcttct ctcgtgttgt tcggcacaac | 1680 |
| ccgatcgatc cccaactccc tcgtcgtctc tcctcgcgag cctcgtcgat cccccgcttc | 1740 |
| aaggtacggc gatcgattat cttccctctc tctaccttct ctctcttata gggcctgcta | 1800 |
| gctctgttcc tgttttttcca tggctgcgag gtacaataga tcggcgatcc atggttaggg | 1860 |
| cctgctagtt gtgttcctgt ttttccatgg ctgcgaggca caatagatct gatggcgtta | 1920 |
| tgatggttaa cttgtcatac tcttgcgatc tatggtccct ttaggagttt aggacatcta | 1980 |
| tttaatttcg gatagttcga gatctgtgat ccatggttag taccctaggc agtggggtta | 2040 |
| gatccgtgct gttatggttc gtagatggat tctgattgct cagtaactgg gaatcctggg | 2100 |
| atggttctag ctggttcgca gataagatcg atttcatgat atgctatatc ttgtttggtt | 2160 |
| gccgtggttc cgttaaatct gtctgttatg atcttagtct ttgataaggt tcggtcgtgc | 2220 |
| tagctacgtc ctgtgcagca cttaattgtc aggtcataat ttttagcatg cctttttttt | 2280 |
| attggtttgg ttttgtctga ctgggctgta gatagtttca atctttgtct gactgggctg | 2340 |
| tagatagttt caatctacct gtcggtttat tttattaaat ttggatctgt atgtgtgtca | 2400 |
| tatatcttca tcttttagat atatcgatag gtttatatgt tgctgtcggt tttttactgt | 2460 |
| tcctttatga gatatattca tgcttagata catgaaacaa cgtgctgtta cagtttaata | 2520 |
| gttcttgttt atctaataaa caaataagga taggtatatg ctgcagttag ttttactggt | 2580 |
| acttttttg acatgaacct acggcttaat aattagtctt catcaaataa aaagcatatt | 2640 |
| ttttaattat ttcgatatac ttgaatgatg tcatatgcag catctgtgtg aattttttggc | 2700 |
| cctgtcttca tatgctgttt atttgtttgg gactgtttct ttggttgata actcatcctg | 2760 |
| ttgtttggtg atccttttgc aggtg | 2785 |

```
<210> SEQ ID NO 9
<211> LENGTH: 1644
<212> TYPE: DNA
<213> ORGANISM: Andropogon gerardii

<400> SEQUENCE: 9
```

| | |
|---|---:|
| gttcaagccg tcaaggcact tctatgcaac cacagtcaac ttgaatgccg cttgagtgcc | 60 |
| ttctcaagtt ttttttctt gcaaaaatca tttctttttt ttaaaaaaag tataaatttgg | 120 |
| atcgtgcaaa tttctctcta ggtgtgtgtg tgactgtgtg agtaacaatt tctctagttg | 180 |

```
tgcgcgactg ctgcttactt tggagattac aatatctttc taaaatgctt cgattactta    240
tttataaacc gtctctaagg ccaattgctc aagattcatt caacaattga aacgtctcac    300
atgattaaat catataaagt ttctaagtct tgtttgacaa gattttttta gattttcatc    360
taaattggat gaaactatca aacactaatt ttaaaaaata taagagaagc tccggagata    420
aaaggtcgtc tatgttatta taagagtaaa gtcgtctatt ctcttcgtcc caacatatat    480
aattctaagc atgaattgct ttcttttgg acaaaaggag catgccacaa cacaagaatg    540
atgtcaccgt catgcttgga tccttttatg gtaaagcttc accttctata atctaacaat    600
agagaaatca gggaaaaatc atgttttggt tgtttttatt tctaacctcc acaataactt    660
tggtttacca ttttttgttt gattttagtt ttagagaagc gtttataaca ggacctaaaa    720
tcttttttca gtacacagta caacgcagac gctcatacac gcacgcacac tcacctctat    780
gaacacacgt aagaaaaccc tacaccttga gcaccttcga aggactgagc cggtaaatat    840
agagattctc gaagtcacta ttagcgcctc gttgtcaacg ggaatgtcgc ttaccactta    900
aagcataacg ccgagaaatc ccgtaataaa tccagtaaaa tacgagcacc cgtgccaagt    960
tgaatatttg aacccgagtg ggtagattcc accgcaaagg acctaaccag atcatttcgc   1020
aaacaggaac taaaatcggt agagagccca gacaaaagcc tttcctaaga gccactccag   1080
tggaagcccc tactttaggt ataaaatgca atactagtgg ggctcctaaa taaacttcta   1140
tttttcatgg ccttctaaaa ttcactccca aaccctagc tatagaagtc tcttatccat    1200
cctctaaata aaaatgggag tctatttat ttcaccagag ttgatcgtaa atttagtctc   1260
tcaaatttta aagttgagg gtagaggatg actggagttg ctctaaacgg acctatcttc   1320
aagtgacctc agtgagcccg tttaacggcg tcgacaagtt taatctaacg gacaccaacc   1380
agagaagaga accaccgcca gcgccgagcc aagcgacgtt gacatcttgg cgcggcacgg   1440
catctccctg gcgtctggcc ccctctcgag acttccgctc cacctcccac cggtggcggt   1500
ttccaagtcc gttccgcctc ctctcacacg gcacgaaacc gtgacgggca ccggcagcac   1560 gggggggattc cttttcccacc gctccttccc tttcccttcc tctcccgccg ctataaatag   1620 ccagcccat cccccagcttc tttc                                          1644

<210> SEQ ID NO 10
<211> LENGTH: 2613
<212> TYPE: DNA
<213> ORGANISM: Andropogon gerardii

<400> SEQUENCE: 10
tctagttgtg cgcgactgct gcttactttg gagattacaa tatctttcta aaatgcttcg     60
attacttatt tataaaccgt ctctaaggcc aattgctcaa gattcattca acaattgaaa    120
cgtctcacat gattaaatca tataaagttt ctaagtcttg tttgacaaga ttttttttaga    180 ttttcatcta aattggatga aactatcaaa cactaatttt aaaaaatata agagaagctc    240
cggagataaa aggtcgtcta tgttattata agagtaaagt cgtctattct cttcgtccca    300
acatatataa ttctaagcat gaattgcttt cttttttggac aaaaggagca tgccacaaca    360
caagaatgat gtcaccgtca tgcttggatc cttttatggt aaagcttcac cttctataat    420
ctaacaatag agaaatcagg gaaaaatcat gttttggttg ttttttatttc taacctccac    480 aataactttg gtttaccatt ttttgtttga ttttagtttt agagaagcgt ttataacagg    540
acctaaaatc ttttttcagt acacagtaca acgcagacgc tcatacacgc acgcacactc    600
```

```
acctctatga acacacgtaa gaaaacccta caccttgagc accttcgaag gactgagccg    660
gtaaatatag agattctcga agtcactatt agcgcctcgt tgtcaacggg aatgtcgctt    720
accacttaaa gcataacgcc gagaaatccc gtaataaatc cagtaaaata cgagcacccg    780
tgccaagttg aatatttgaa cccgagtggg tagattccac cgcaaaggac ctaaccagat    840
catttcgcaa acaggaacta aaatcggtag agagcccaga caaaagcctt tcctaagagc    900
cactccagtg gaagcccta ctttaggtat aaaatgcaat actagtgggg ctcctaaata    960
aacttctatt tttcatggcc ttctaaaatt cactcccaaa ccctagcta tagaagtctc   1020 ttatccatcc tctaaataaa aatgggagtc tattttattt caccagagtt gatcgtaaat   1080
ttagtctctc aaattttata agttgagggt agaggatgac tggagttgct ctaaacggac   1140
ctatcttcaa gtgacctcag tgagcccgtt taacggcgtc gacaagttta atctaacgga   1200
caccaaccag agaagagaac caccgccagc gccgagccaa gcgacgttga catcttggcg   1260
cggcacggca tctccctggc gtctggcccc ctctcgagac ttccgctcca cctcccaccg   1320
gtggcggttt ccaagtccgt tccgcctcct ctcacacggc acgaaaccgt gacgggcacc   1380
ggcagcacgg ggggattcct ttcccaccgc tccttccctt tccctcctc tccgccgct   1440 ataaatagcc agccccatcc ccagcttctt tccccaacct catcttctct cgtgttgttc   1500
ggcacaaccc gatcgatccc caactccctc gtcgtctctc ctcgcgagcc tcgtcgatcc   1560
cccgcttcaa ggtacggcga tcgattatct tccctctctc taccttctct ctcttatagg   1620
gcctgctagc tctgttcctg ttttttcatg gctgcgaggt acaatagatc ggcgatccat   1680
ggttagggcc tgctagttgt gttcctgttt tccatggct gcgaggcaca atagatctga   1740
tggcgttatg atggttaact tgtcatactc ttgcgatcta tggtcccttt aggagtttag   1800
gacatctatt taatttcgga tagttcgaga tctgtgatcc atggttagta ccctaggcag   1860
tggggttaga tccgtgctgt tatggttcgt agatggattc tgattgctca gtaactggga   1920
atcctgggat ggttctagct ggttcgcaga taagatcgat ttcatgatat gctatatctt   1980
gtttggttgc cgtggttccg ttaaatctgt ctgttatgat cttagtcttt gataaggttc   2040
ggtcgtgcta gctacgtcct gtgcagcact taattgtcag gtcataattt ttagcatgcc   2100
ttttttttat tggtttggtt ttgtctgact gggctgtaga tagtttcaat cttgtctga   2160 ctgggctgta gatagtttca atctacctgt cggtttattt tattaaattt ggatctgtat   2220
gtgtgtcata tatcttcatc ttttagatat atcgataggt ttatatgttg ctgtcggttt   2280
tttactgttc ctttatgaga tatattcatg cttagataca tgaaacaacg tgctgttaca   2340
gtttaatagt tcttgtttat ctaataaaca aataaggata ggtatatgct gcagttagtt   2400
ttactggtac ttttttttgac atgaacctac ggcttaataa ttagtcttca tcaaataaaa   2460
agcatatttt ttaattattt cgatatactt gaatgatgtc atatgcagca tctgtgtgaa   2520
tttttggccc tgtcttcata tgctgtttat ttgtttggga ctgtttcttt ggttgataac   2580
tcatcctgtt gtttggtgat cctttttgcag gtg                               2613

<210> SEQ ID NO 11
<211> LENGTH: 1472
<212> TYPE: DNA
<213> ORGANISM: Andropogon gerardii

<400> SEQUENCE: 11
tctagttgtg cgcgactgct gcttactttg gagattacaa tatctttcta aaatgcttcg     60
attacttatt tataaaccgt ctctaaggcc aattgctcaa gattcattca acaattgaaa    120
```

```
cgtctcacat gattaaatca tataaagttt ctaagtcttg tttgacaaga ttttttttaga        180 ttttcatcta aattggatga aactatcaaa cactaattt aaaaaatata agagaagctc         240
cggagataaa aggtcgtcta tgttattata agagtaaagt cgtctattct cttcgtccca        300
acatatataa ttctaagcat gaattgcttt cttttttggac aaaaggagca tgccacaaca       360
caagaatgat gtcaccgtca tgcttggatc cttttatggt aaagcttcac cttctataat       420
ctaacaatag agaaatcagg gaaaaatcat gttttggttg ttttttatttc taacctccac      480 aataactttg gtttaccatt ttttgtttga tttttagtttt agagaagcgt ttataacagg       540
acctaaaatc ttttttcagt acacagtaca acgcagacgc tcatacacgc acgcacactc       600
acctctatga acacacgtaa gaaaaccta caccttgagc accttcgaag gactgagccg        660
gtaaatatag agattctcga agtcactatt agcgcctcgt tgtcaacggg aatgtcgctt       720
accacttaaa gcataacgcc gagaaatccc gtaataaatc cagtaaaata cgagcacccg       780
tgccaagttg aatatttgaa cccgagtggg tagattccac cgcaaaggac ctaaccagat       840
catttcgcaa acaggaacta aaatcggtag agagcccaga caaaagcctt tcctaagagc      900
cactccagtg gaagccccta ctttaggtat aaaatgcaat actagtgggg ctcctaaata       960
aacttctatt tttcatggcc ttctaaaatt cactcccaaa cccctagcta tagaagtctc      1020
ttatccatcc tctaaataaa aatgggagtc tattttatt caccagagtt gatcgtaaat       1080
ttagtctctc aaattttata agttgagggt agaggatgac tggagttgct ctaaacggac      1140
ctatcttcaa gtgacctcag tgagcccgtt taacggcgtc gacaagtta atctaacgga       1200 caccaaccag agaagagaac caccgccagc gccgagccaa gcgacgttga catcttggcg      1260
cggcacggca tctccctggc gtctggcccc ctctcgagac ttccgctcca cctcccaccg      1320
gtggcggttt ccaagtccgt tccgcctcct ctcacacggc acgaaaccgt gacgggcacc      1380
ggcagcacgg ggggattcct ttcccaccgc tccttccctt tccctttcct tccccgccgct    1440 ataaatagcc agccccatcc ccagcttctt tc                                    1472

<210> SEQ ID NO 12
<211> LENGTH: 2255
<212> TYPE: DNA
<213> ORGANISM: Andropogon gerardii

<400> SEQUENCE: 12
cacaagaatg atgtcaccgt catgcttgga tccttttatg gtaaagcttc accttctata       60
atctaacaat agagaaatca gggaaaaatc atgttttggt tgttttttatt tctaacctcc    120 acaataactt tggtttacca ttttttgttt gatttttagtt ttagagaagc gtttataaca    180
ggacctaaaa tctttttttca gtacacagta caacgcagac gctcatacac gcacgcacac    240
tcacctctat gaacacacgt aagaaaaccc tacaccttga gcaccttcga aggactgagc     300
cggtaaatat agagattctc gaagtcacta ttagcgcctc gttgtcaacg gaatgtcgc      360 ttaccactta aagcataacg ccgagaaatc ccgtaataaa tccagtaaaa tacgagcacc     420
cgtgccaagt tgaatatttg aacccgagtg ggtagattcc accgcaaagg acctaaccag     480
atcatttcgc aaacaggaac taaatcggt agagagccca gacaaaagcc tttcctaaga     540
gccactccag tggaagcccc tactttaggt ataaaatgca atactagtgg ggctcctaaa     600
taaacttcta ttttcatgg ccttctaaaa ttcactccca acccctagc tatagaagtc      660 tcttatccat cctctaaata aaaatgggag tctatttat ttcaccagag ttgatcgtaa     720
```

```
atttagtctc tcaaatttta taagttgagg gtagaggatg actggagttg ctctaaacgg    780
acctatcttc aagtgacctc agtgagcccg tttaacggcg tcgacaagtt taatctaacg    840
gacaccaacc agagaagaga accaccgcca gcgccgagcc aagcgacgtt gacatcttgg    900
cgcggcacgg catctccctg gcgtctggcc ccctctcgag acttccgctc cacctcccac    960
cggtggcggt ttccaagtcc gttccgcctc ctctcacacg gcacgaaacc gtgacgggca   1020
ccggcagcac ggggggattc ctttcccacc gctccttccc tttcccttcc tctcccgccg   1080
ctataaatag ccagccccat ccccagcttc tttccccaac ctcatcttct ctcgtgttgt   1140
tcggcacaac ccgatcgatc cccaactccc tcgtcgtctc tcctcgcgag cctcgtcgat   1200
cccccgcttc aaggtacggc gatcgattat cttccctctc tctaccttct ctctcttata   1260
gggcctgcta gctctgttcc tgttttttcca tggctgcgag gtacaataga tcggcgatcc   1320
atggttaggg cctgctagtt gtgttcctgt ttttccatgg ctgcgaggca caatagatct   1380
gatggcgtta tgatggttaa cttgtcatac tcttgcgatc tatggtccct ttaggagttt   1440
aggacatcta tttaatttcg gatagttcga gatctgtgat ccatggttag taccctaggc   1500
agtggggtta gatccgtgct gttatggttc gtagatggat tctgattgct cagtaactgg   1560
gaatcctggg atggttctag ctggttcgca gataagatcg atttcatgat atgctatatc   1620
ttgtttggtt gccgtggttc cgttaaatct gtctgttatg atcttagtct ttgataaggt   1680
tcggtcgtgc tagctacgtc ctgtgcagca cttaattgtc aggtcataat ttttagcatg   1740
cctttttttt attggtttgg ttttgtctga ctgggctgta gatagtttca atctttgtct   1800
gactgggctg tagatagttt caatctacct gtcggtttat tttattaaat ttggatctgt   1860
atgtgtgtca tatatcttca tcttttagat atatcgatag gtttatatgt tgctgtcggt   1920 ttttactgt  tcctttatga gatatattca tgcttagata catgaaacaa cgtgctgtta   1980
cagtttaata gttcttgttt atctaataaa caaataagga taggtatatg ctgcagttag   2040
ttttactggt acttttttg acatgaacct acggcttaat aattagtctt catcaaataa   2100
aaagcatatt ttttaattat ttcgatatac ttgaatgatg tcatatgcag catctgtgtg   2160 aattttggc cctgtcttca tatgctgttt atttgtttgg gactgtttct ttggttgata   2220
actcatcctg ttgtttggtg atccttttgc aggtg                             2255
```

<210> SEQ ID NO 13
<211> LENGTH: 1114
<212> TYPE: DNA
<213> ORGANISM: Andropogon gerardii

<400> SEQUENCE: 13

```
cacaagaatg atgtcaccgt catgcttgga tccttttatg gtaaagcttc accttctata     60
atctaacaat agagaaatca gggaaaaatc atgttttggt tgttttttatt tctaacctcc    120 acaataactt tggtttacca ttttttgttt gatttttagtt ttagagaagc gtttataaca    180
ggacctaaaa tcttttttca gtacacagta caacgcagac gctcatacac gcacgcacac    240
tcacctctat gaacacacgt aagaaaaccc tacaccttga gcaccttcga aggactgagc    300
cggtaaatat agagattctc gaagtcacta ttagcgcctc gttgtcaacg ggaatgtcgc    360
ttaccactta aagcataacg ccgagaaatc ccgtaataaa tccagtaaaa tacgagcacc    420
cgtgccaagt tgaatatttg aacccgagtg ggtagattcc accgcaaagg acctaaccag    480
atcatttcgc aaacaggaac taaaatcggt agagagccca gacaaaagcc tttcctaaga    540
gccactccag tggaagcccc tactttaggt ataaaatgca atactagtgg ggctcctaaa    600
```

| | |
|---|---|
| taaacttcta tttttcatgg ccttctaaaa ttcactccca aaccoctagc tatagaagtc | 660 |
| tcttatccat cctctaaata aaatgggag tctattttat ttcaccagag ttgatcgtaa | 720 |
| atttagtctc tcaaatttta taagttgagg gtagaggatg actggagttg ctctaaacgg | 780 |
| acctatcttc aagtgacctc agtgagcccg tttaacggcg tcgacaagtt taatctaacg | 840 |
| gacaccaacc agagaagaga accaccgcca gcgccgagcc aagcgacgtt gacatcttgg | 900 |
| cgcggcacgg catctccctg gcgtctggcc ccctctcgag acttccgctc cacctcccac | 960 |
| cggtggcggt ttccaagtcc gttccgcctc ctctcacacg gcacgaaacc gtgacgggca | 1020 |
| ccggcagcac gggggattc ctttcccacc gctccttccc tttcccttcc tctcccgccg | 1080 |
| ctataaatag ccagccccat ccccagcttc tttc | 1114 |

<210> SEQ ID NO 14
<211> LENGTH: 1912
<212> TYPE: DNA
<213> ORGANISM: Andropogon gerardii

<400> SEQUENCE: 14

| | |
|---|---|
| gtcaacggga atgtcgctta ccacttaaag cataacgccg agaaatcccg taataaatcc | 60 |
| agtaaaatac gagcacccgt gccaagttga atatttgaac ccgagtgggt agattccacc | 120 |
| gcaaaggacc taaccagatc atttcgcaaa caggaactaa atcggtaga gagcccagac | 180 |
| aaaagccttt cctaagagcc actccagtgg aagcccctac tttaggtata aaatgcaata | 240 |
| ctagtggggc tcctaaataa acttctattt ttcatggcct tctaaaattc actcccaaac | 300 |
| ccctagctat agaagtctct tatccatcct ctaaataaaa atgggagtct attttatttc | 360 |
| accagagttg atcgtaaatt tagtctctca aattttataa gttgagggta gaggatgact | 420 |
| ggagttgctc taaacggacc tatcttcaag tgacctcagt gagcccgttt aacggcgtcg | 480 |
| acaagtttaa tctaacggac accaaccaga agagaacc accgccagcg ccgagccaag | 540 |
| cgacgttgac atcttggcgc ggcacggcat ctccctggcg tctggccccc tctcgagact | 600 |
| tccgctccac ctcccaccgg tggcggtttc aagtccgtt ccgcctcctc tcacacggca | 660 |
| cgaaaccgtg acgggcaccg gcagcacggg gggattcctt tcccaccgct ccttcccttt | 720 |
| cccttcctct cccgccgcta taaatagcca gccccatccc cagcttcttt ccccaacctc | 780 |
| atcttctctc gtgttgttcg gcacaacccg atcgatcccc aactccctcg tcgtctctcc | 840 |
| tcgcgagcct cgtcgatccc ccgcttcaag gtacggcgat cgattatctt ccctctctct | 900 |
| accttctctc tcttataggg cctgctagct ctgttcctgt ttttccatgg ctgcgaggta | 960 |
| caatagatcg gcgatccatg gttagggcct gctagttgtg ttcctgtttt tccatggctg | 1020 |
| cgaggcacaa tagatctgat ggcgttatga tggttaactt gtcatactct tgcgatctat | 1080 |
| ggtcccttta ggagtttagg acatctattt aatttcggat agttcgagat ctgtgatcca | 1140 |
| tggttagtac cctaggcagt ggggttagat ccgtgctgtt atggttcgta gatgattct | 1200 |
| gattgctcag taactgggaa tcctgggatg ttctagctg gttcgcagat aagatcgatt | 1260 |
| tcatgatatg ctatatcttg tttggttgcc gtggttccgt taaatctgtc tgttatgatc | 1320 |
| ttagtctttg ataaggttcg gtcgtgctag ctacgtcctg tgcagcactt aattgtcagg | 1380 |
| tcataatttt tagcatgcct ttttttatt ggtttggttt tgtctgactg ggctgtagat | 1440 |
| agttcaatc tttgtctgac tgggctgtag atagttccaa tctacctgtc ggtttatttt | 1500 |
| attaaatttg gatctgtatg tgtgtcatat atcttcatct tttagatata tcgataggtt | 1560 |

```
tatatgttgc tgtcggtttt ttactgttcc tttatgagat atattcatgc ttagatacat    1620
gaaacaacgt gctgttacag tttaatagtt cttgtttatc taataaacaa ataaggatag    1680
gtatatgctg cagttagttt tactggtact tttttgaca tgaacctacg gcttaataat    1740
tagtcttcat caaataaaaa gcatattttt taattatttc gatatacttg aatgatgtca    1800
tatgcagcat ctgtgtgaat ttttggccct gtcttcatat gctgtttatt tgtttgggac    1860
tgtttctttg gttgataact catcctgttg tttggtgatc cttttgcagg tg            1912
```

<210> SEQ ID NO 15
<211> LENGTH: 771
<212> TYPE: DNA
<213> ORGANISM: Andropogon gerardii

<400> SEQUENCE: 15

```
gtcaacggga atgtcgctta ccacttaaag cataacgccg agaaatcccg taataaatcc      60
agtaaaatac gagcacccgt gccaagttga atatttgaac ccgagtgggt agattccacc     120
gcaaaggacc taaccagatc atttcgcaaa caggaactaa aatcggtaga gagcccagac     180
aaaagccttt cctaagagcc actccagtgg aagcccctac tttaggtata aaatgcaata     240
ctagtggggc tcctaaataa acttctattt ttcatggcct tctaaaattc actcccaaac     300
ccctagctat agaagtctct tatccatcct ctaaataaaa atgggagtct attttatttc     360
accagagttg atcgtaaatt tagtctctca aattttataa gttgagggta gaggatgact     420
ggagttgctc taaacggacc tatcttcaag tgacctcagt gagcccgttt aacggcgtcg     480
acaagtttaa tctaacggac accaaccaga gaagagaacc accgccagcg ccgagccaag     540
cgacgttgac atcttggcgc ggcacggcat ctccctggcg tctggccccc tctcgagact     600
tccgctccac ctcccaccgg tggcggtttc caagtccgtt ccgcctcctc tcacacggca     660
cgaaaccgtg acgggcaccg gcagcacggg gggattcctt tcccaccgct ccttcccttt     720
cccttcctct cccgccgcta taaatagcca gccccatccc cagcttcttt c              771
```

<210> SEQ ID NO 16
<211> LENGTH: 1623
<212> TYPE: DNA
<213> ORGANISM: Andropogon gerardii

<400> SEQUENCE: 16

```
cactcccaaa cccctagcta tagaagtctc ttatccatcc tctaaataaa aatgggagtc      60
tattttattt caccagagtt gatcgtaaat ttagtctctc aaattttata agttgagggt     120
agaggatgac tggagttgct ctaaacggac ctatcttcaa gtgacctcag tgagcccgtt     180
taacggcgtc gacaagttta atctaacgga caccaaccag agaagagaac caccgccagc     240
gccgagccaa gcgacgttga catcttggcg cggcacggca tctccctggc gtctggcccc     300
ctctcgagac ttccgctcca cctcccaccg gtggcggttt ccaagtccgt tccgcctcct     360
ctcacacggc acgaaaccgt gacgggcacc ggcagcacgg gggattcctt tcccaccgc     420 tccttccctt tcccttcctc tcccgccgct ataaatagcc agccccatcc ccagcttctt     480
tccccaacct catcttctct cgtgttgttc ggcacaaccc gatcgatccc caactccctc     540
gtcgtctctc ctcgcgagcc tcgtcgatcc cccgcttcaa ggtacggcga tcgattatct     600
tccctctctc taccttctct ctcttatagg gcctgctagc tctgttcctg tttttccatg     660
gctgcgaggt acaatagatc ggcgatccat ggttagggcc tgctagttgt gttcctgttt     720
ttccatggct gcgaggcaca atagatctga tggcgttatg atggttaact tgtcatactc     780
```

```
ttgcgatcta tggtcccttt aggagtttag gacatctatt taatttcgga tagttcgaga      840
tctgtgatcc atggttagta ccctaggcag tggggttaga tccgtgctgt tatggttcgt      900
agatggattc tgattgctca gtaactggga atcctgggat ggttctagct ggttcgcaga      960
taagatcgat ttcatgatat gctatatctt gtttggttgc cgtggttccg ttaaatctgt     1020
ctgttatgat cttagtcttt gataaggttc ggtcgtgcta gctacgtcct gtgcagcact     1080
taattgtcag gtcataattt ttagcatgcc tttttttat tggtttggtt ttgtctgact      1140
gggctgtaga tagtttcaat ctttgtctga ctgggctgta gatagtttca atctacctgt     1200
cggtttattt tattaaattt ggatctgtat gtgtgtcata tcttccatc tttagatat       1260 atcgataggt ttatatgttg ctgtcggttt tttactgttc ctttatgaga tatattcatg     1320
cttagataca tgaaacaacg tgctgttaca gtttaatagt tcttgtttat ctaataaaca     1380
aataaggata ggtatatgct gcagttagtt ttactggtac tttttttgac atgaacctac     1440
ggcttaataa ttagtcttca tcaaataaaa agcatatttt ttaattattt cgatatactt     1500
gaatgatgtc atatgcagca tctgtgtgaa ttttttggccc tgtcttcata tgctgtttat    1560
ttgtttggga ctgtttcttt ggttgataac tcatcctgtt gtttggtgat ccttttgcag     1620
gtg                                                                  1623

<210> SEQ ID NO 17
<211> LENGTH: 482
<212> TYPE: DNA
<213> ORGANISM: Andropogon gerardii

<400> SEQUENCE: 17
cactcccaaa cccctagcta tagaagtctc ttatccatcc tctaaataaa aatgggagtc       60 tattttatt caccagagtt gatcgtaaat ttagtctctc aaattttata agttgagggt       120
agaggatgac tggagttgct ctaaacggac ctatcttcaa gtgacctcag tgagcccgtt      180
taacggcgtc gacaagttta atctaacgga caccaaccag agaagagaac caccgccagc      240
gccgagccaa gcgacgttga catcttggcg cggcacggca tctccctggc gtctggcccc      300
ctctcgagac ttccgctcca cctcccaccg gtggcggttt ccaagtccgt tccgcctcct     360
ctcacacggc acgaaaccgt gacgggcacc ggcagcacgg ggggattcct ttcccaccgc     420 tccttcccctt tccttcctc tcccgccgct ataaatagcc agcccatcc ccagcttctt     480 tc                                                                    482

<210> SEQ ID NO 18
<211> LENGTH: 3483
<212> TYPE: DNA
<213> ORGANISM: Saccharum ravennae

<400> SEQUENCE: 18
gtggccagct tttgttctag ttcaacggcc ccggccttcc gggcacctaa tacccctaatt      60 aatctattgc agctaacctc aaaagaaatg catttgcagt tgtctgtccc aatcaatcta     120
ctagcagact tacattatag atggaggaaa ttaaattcag cctttgacgt ggatgcaaca     180
actgcactgc acaggatacc atcttagccg ttgtgtcaaa gtttgctttg ctaaacgttt     240
tgagaaaacc agctttgacc aacgcgagat gagcgcctta cgtttggcac aatgtaatgt     300
aatccggcac ggcaagttag actctgtagt gttagccggc ctcttacgt ttggcatagt      360 ttaattgaat ccggcatggc aagttagacc gtagtgtgag ccggccaacg caagttatta     420
```

```
tgacatatgt ataagagcaa gtgtattgtc acgtgatatt tatgttgaga tgaagaagag    480
aaaataaaca gcctgcaaat ttatagcgag tgatagatgg gcacaaggct tcctatttct    540
taaatcagac tttgtaagaa caaaaaaagg acttataaga gaatgggata aaccatatat    600
caatggtgta gtatgttagt atgcattaag atctgactat tatatgagtg agttgttaaa    660
ttcattttag gtgacatggc ccggttaaat tattagccat accctaacag ctctaaaaaa    720
gatatattcg ttgaggcact tttatgcaac cacatagtca acttgaatgc cgcttgagtg    780
cgttctcaag ttttttttct tgcaaattac gcttttttaa gaaagtataa tttggatcgt    840 gcgattttt ttctctaggt gtgcgtgact gtgtgagtaa cattttttgga tctcagaaag    900 gtaataaaag aataatactg ctgcctactt tgaggattac aatatctttc tctaaaatgt    960
tttggtttgt tatttaaacc gtctttaagg ccaattgctc aagattcatt caacaattga   1020
aacgtctcac atgattaaat catataaggt tgctaaggtc ttgtttgaca aggtttttttt   1080 tgtggaaatt tcatctaaat ttttgagtga actatcaaa tactaattta aaaaaggcaa   1140
attttgctgg aggacactgc agaaacgtgt aattggccgg cacaaaccgc caaacggaga   1200
atttgcccag taccattata aattcatgat aaattcatgg ttgtttgcca gtggggctag   1260
ggttcctcgc gtatggtgcg gaatgtggtt tggttcgacc aactcgaact caatccgatc   1320
caaaggggca tcaatagtca ttttagaaag tttctctctc ccgagcagtg gaaatgatta   1380
ttctatttgg cgcgatgtcc accggcaaac aaccacgaat ttgtaatggt actaggcaaa   1440
ttctccgttt ggcggtgtgt gccggccaat tacacgtttt tgcggtgtcc tccgacaaaa   1500
tttgcctttt aaaacaatt ttataagaga agctccggag ataaaaggcc gtcaatgtta   1560
caagagtgaa gtcgtctact ccctccatcc caaaaaatgt aattctaagt atgagttgta   1620
ttattatttt tggacaaaag gagtatacca caagaatgat atcatcgtca tgcttagatc   1680 cttttttagta aagcttgagc ttctctaaaa gtagagaaat tagaaaaaaa tcacgttttt   1740
gtggtcttga tttctagcct ccacaaaatc tttggtttta catttttttgt ttgatttttgg   1800 tttcagaagt ccttatttat atgtgctagt ttggcagcac ttaaaatcgt tagagagagc   1860
ctaaacaaaa gccttttcaa aacgaccttg agccagattg gttgatggcc aaaatttgat   1920
tgtcaaaact taggcaagcc aagatttttag cagctatttg gtttggtacc aaaatttgcc   1980
aatgatctgt tcttttgcct tttcaaccgg tttatcagcc gtacttcagc ttattctctc   2040
tcacagaaca ctattgaatc agccgaaaag ccaccgcaga acaggaccag tatctcacaa   2100
atggcatgcc aaatatactc accgtcagtg agcccgttta acggcgtcga caagtctaac   2160
ggccaccaac cagcgaacca ccagcgtcaa gctagccaag cgaagcagac ggccgagacg   2220
ttgacacctt ggcgcgggca tctctctggc cccctctcga gagttccgct ccacctccac   2280
tggtggcggt ttccaagtcc gttccgcctc ctgctcctcc tcacacggca cgaaaccgtc   2340
acggcaccgg cagcacgggg gattcctttc ccaccgctcc ttcccttttcc cttcctcgcc   2400 cgccgtttta aatagccagc cccatcccca gcttctctcc ccgtacggcg atcatcctcc   2460
ctttctctac cttctcttct ctagactagg tcggcgatcc atggttaggg cctgctagtt   2520
ctgttcctgt ttttccgtgg ctgcgaggta caatagatct gatggcgtta tgatggttaa   2580
cttgtcatac tcctgcggtg tgcggtctat agtgctttta ggacatcaat ttgacctggc   2640
tcgttcgaga tcggcgatcc atggttagga ccctaggcgg tggagtcggg ttagatccgc   2700
gctgtttgtg ttagtagatg gatgcgacct ttacttcaga cacgttctga ttgttaactt   2760
gtcagcacct gggagtcctg ggatggttct agctggttcg cagatgagat cgatttcatg   2820
```

```
atctgctgta tcttgtttcg ttaggttcct tttaatctat ccgtggtatt atgctaacct    2880
atgatatggt tcgatcgtgc tagctacgtc ctgtgtcata attttagca tgccctttt     2940 tgtttggttt tgtctgattg ggctgtagat cagagtatac tgtttcaaac tacctactgg    3000
atatatttat taaatttgaa tctgtatgtg tgtcacatat atcttcataa ttaaaatgga    3060
tggaaagata tatggatagg tacatgtgtt gctgtgggtt ttactggtac tttgttagat    3120
atacatgctt agatacatga agcaacatga tgttacagtt caataattct tgtttaccta    3180
ataaacaaat aaggataggt gtatgttgct gtgggttttg ctggtacttt gttagatata    3240
tatgcttaga tatatgaagc aacatcctgc tacggtttaa taattattgt ttatatctaa    3300
tagacaagcc tgcttttaa ttattttgat atacttggat gatggcatac agcagctatg    3360
tgtggatttt taaatacca gcatcatgag catgcatgac cctgccttag tatgctgttt    3420
atttgcttga gacttctttt tttgttggta ctcaccttt gtagtttggt gactcttctg    3480
cag                                                                  3483
```

<210> SEQ ID NO 19
<211> LENGTH: 2536
<212> TYPE: DNA
<213> ORGANISM: Saccharum ravennae

<400> SEQUENCE: 19

```
gtggccagct tttgttctag ttcaacggcc ccggccttcc gggcacctaa taccctaatt      60
aatctattgc agctaacctc aaaagaaatg catttgcagt tgtctgtccc aatcaatcta     120
ctagcagact tacattatag atggaggaaa ttaaattcag cctttgacgt ggatgcaaca     180
actgcactgc acaggatacc atcttagccg ttgtgtcaaa gttgctttg ctaaacgttt     240 tgagaaaacc agctttgacc aacgcgagat gagcgcctta cgtttggcac aatgtaatgt     300
aatccggcac ggcaagttag actctgtagt gttagccggc ctctttacgt tttggcatagt    360 ttaattgaat ccggcatggc aagttagacc gtagtgtgag ccggccaacg caagttatta     420
tgacatatgt ataagagcaa gtgtattgtc acgtgatatt tatgttgaga tgaagaagag     480
aaaataaaca gcctgcaaat ttatagcgag tgatagatgg gcacaaggct tcctatttct     540
taaatcagac tttgtaagaa caaaaaaagg acttataaga gaatgggata aaccatatat     600
caatggtgta gtatgttagt atgcattaag atctgactat tatatgagtg agttgttaaa     660
ttcattttag gtgacatggc ccggttaaat tattagccat accctaacag ctctaaaaaa     720
gatatattcg ttgaggcact tttatgcaac cacatagtca acttgaatgc cgcttgagtg     780
cgttctcaag ttttttttct tgcaaattac gcttttttaa gaaagtataa tttggatcgt     840 gcgattttt ttctctaggt gtgcgtgact gtgtgagtaa caattttgga tctcagaaag     900
gtaataaaag aataatactg ctgcctactt tgaggattac aatatctttc tctaaaatgt     960
tttggtttgt tatttaaacc gtctttaagg ccaattgctc aagattcatt caacaattga    1020
aacgtctcac atgattaaat catataaggt tgctaaggtc ttgtttgaca aggtttttt    1080 tgtggaaatt tcatctaaat ttttgagtga aactatcaaa tactaattta aaaaaggcaa    1140
attttgctgg aggacactgc agaaacgtgt aattggccgg cacaaaccgc caaacggaga    1200
atttgcccag taccattata aattcatgat aaattcatgg ttgtttgcca gtggggctag    1260
ggttcctcgc gtatggtgcg gaatgtggtt tggttcgacc aactcgaact caatccgatc    1320
caaaggggca tcaatagtca ttttagaaag tttctctctc ccgagcagtg gaaatgatta    1380
```

-continued

```
ttctatttgg cgcgatgtcc accggcaaac aaccacgaat ttgtaatggt actaggcaaa    1440
ttctccgttt ggcggtgtgt gccggccaat tacacgtttt tgcggtgtcc tccgacaaaa    1500 tttgccttt  aaaaacaatt ttataagaga agctccggag ataaaaggcc gtcaatgtta    1560
caagagtgaa gtcgtctact ccctccatcc caaaaaatgt aattctaagt atgagttgta    1620
ttattatttt tggacaaaag gagtatacca caagaatgat atcatcgtca tgcttagatc    1680 cttttttagta aagcttgagc ttctctaaaa gtagagaaat tagaaaaaaa tcacgttttt    1740
gtggtcttga tttctagcct ccacaaaatc tttggtttta cattttttgt ttgatttgg    1800 tttcagaagt ccttatttat atgtgctagt tggcagcac ttaaaatcgt tagagagagc    1860
ctaaacaaaa gccttttcaa aacgaccttg agccagattg gttgatggcc aaaatttgat    1920
tgtcaaaact taggcaagcc aagatttttag cagctatttg gtttggtacc aaaatttgcc    1980
aatgatctgt tcttttgcct tttcaaccgg tttatcagcc gtacttcagc ttattctctc    2040
tcacagaaca ctattgaatc agccgaaaag ccaccgcaga acaggaccag tatctcacaa    2100
atggcatgcc aaatatactc accgtcagtg agcccgttta acggcgtcga caagtctaac    2160
ggccaccaac cagcgaacca ccagcgtcaa gctagccaag cgaagcagac ggccgagacg    2220
ttgacacctt ggcgcgggca tctctctggc ccctctcga gagttccgct ccacctccac     2280
tggtggcggt ttccaagtcc gttccgcctc ctgctcctcc tcacacggca cgaaaccgtc    2340
acggcaccgg cagcacgggg gattcctttc ccaccgctcc ttccctttcc cttcctcgcc    2400
cgccgtttta aatagccagc cccatcccca gcttctctcc ccaacctcag cttctctcgt    2460
tgttcggagc gcacacacaa cccgatcccc aatccccctcg tctctcctcg cgagcctcgt    2520
cgatccccgc ttcaag                                                     2536

<210> SEQ ID NO 20
<211> LENGTH: 94
<212> TYPE: DNA
<213> ORGANISM: Saccharum ravennae

<400> SEQUENCE: 20
aacctcagct tctctcgttg ttcggagcgc acacacaacc cgatccccaa tcccctcgtc     60
tctcctcgcg agcctcgtcg atcccccgctt caag                                 94

<210> SEQ ID NO 21
<211> LENGTH: 1041
<212> TYPE: DNA
<213> ORGANISM: Saccharum ravennae

<400> SEQUENCE: 21
gtacggcgat catcctccct ttctctacct tctcttctct agactaggtc ggcgatccat      60
ggttagggcc tgctagttct gttcctgttt ttccgtggct gcgaggtaca atagatctga    120
tggcgttatg atggttaact tgtcatactc ctgcggtgtg cggtctatag tgcttttagg    180
acatcaattt gacctggctc gttcgagatc ggcgatccat ggttaggacc ctaggcggtg    240
gagtcgggtt agatccgcgc tgtttgtgtt agtagatgga tgcgaccttt acttcagaca    300
cgttctgatt gttaacttgt cagcacctgg gagtcctggg atggttctag ctggttcgca    360
gatgagatcg atttcatgat ctgctgtatc ttgtttcgtt aggttccttt taatctatcc    420
gtggtattat gctaacctat gatatggttc gatcgtgcta gctacgtcct gtgtcataat    480
ttttagcatg cccttttttg tttggttttg tctgattggg ctgtagatca gagtatactg    540
tttcaaacta cctactggat atatttatta aatttgaatc tgtatgtgtg tcacatatat    600
```

```
cttcataatt aaaatggatg gaaagatata tggataggta catgtgttgc tgtgggtttt      660
actggtactt tgttagatat acatgcttag atacatgaag caacatgatg ttacagttca      720
ataattcttg tttacctaat aaacaaataa ggataggtgt atgttgctgt gggttttgct      780
ggtactttgt tagatatata tgcttagata tatgaagcaa catcctgcta cggtttaata      840
attattgttt atatctaata gacaagcctg cttttttaatt attttgatat acttggatga     900
tggcatacag cagctatgtg tggattttta aatacccagc atcatgagca tgcatgaccc      960
tgccttagta tgctgtttat ttgcttgaga cttcttttttt tgttggtact cacctttttgt  1020 agtttggtga ctcttctgca g                                               1041
```

<210> SEQ ID NO 22
<211> LENGTH: 3152
<212> TYPE: DNA
<213> ORGANISM: Saccharum ravennae

<400> SEQUENCE: 22

```
gtataagagc aagtgtattg tcacgtgata tttatgttga gatgaagaag agaaaataaa       60
cagcctgcaa atttatagcg agtgatagat gggcacaagg cttcctatttt cttaaatcag    120 actttgtaag aacaaaaaaa ggacttataa gagaatggga taaaccatat atcaatggtg      180
tagtatgtta gtatgcatta agatctgact attatatgag tgagttgtta aattcatttt      240
aggtgacatg gcccggttaa attattagcc ataccctaac agctctaaaa aagatatatt      300
cgttgaggca ctttttatgca accacatagt caacttgaat gccgcttgag tgcgttctca     360 agttttttttt cttgcaaatt acgctttttt aagaaagtat aatttggatc gtgcgatttt     420
ttttctctag gtgtgcgtga ctgtgtgagt aacaattttg gatctcagaa aggtaataaa      480
agaataatac tgctgcctac tttgaggatt acaatatctt tctctaaaat gttttggttt      540
gttatttaaa ccgtctttaa ggccaattgc tcaagattca ttcaacaatt gaaacgtctc      600
acatgattaa atcatataag gttgctaagg tcttgtttga caaggttttt tttgtggaaa      660
tttcatctaa atttttgagt gaaactatca aatactaatt taaaaaaggc aaattttgct      720
ggaggacact gcagaaacgt gtaattggcc ggcacaaacc gccaaacgga gaatttgccc      780
agtaccatta taaattcatg ataaattcat ggttgtttgc cagtggggct agggttcctc      840
gcgtatggtc cggaatgtgg tttggttcga ccaactcgaa ctcaatccga tccaaagggg      900
catcaatagt catttttagaa agtttctctc tcccgagcag tggaaatgat tattctatttt    960 ggcgcgatgt ccaccggcaa acaaccacga atttgtaatg gtactaggca aattctccgt    1020
ttggcggtgt gtgccggcca attacacgtt tttgcggtgt cctccgacaa aatttgcctt    1080
ttaaaaacaa ttttataaga gaagctccgg agataaaagg ccgtcaatgt tacaagagtg    1140
aagtcgtcta ctccctccat cccaaaaaat gtaattctaa gtatgagttg tattattatt    1200
tttggacaaa aggagtatac cacaagaatg atatcatcgt catgcttaga tccttttttag   1260 taaagcttga gcttctctaa aagtagagaa attagaaaaa aatcacgttt ttgtggtctt    1320
gatttctagc ctccacaaaa tctttggttt tacatttttt gtttgatttt ggtttcagaa    1380 gtccttatttt atatgtgcta gtttggcagc acttaaaatc gttagagaga gcctaaacaa    1440
aagccttttc aaaacgacct tgagccagat tggttgatgg ccaaaatttg attgtcaaaa    1500
cttaggcaag ccaagatttt agcagctatt tggtttggta ccaaaatttg ccaatgatct    1560 gttctttttgc cttttcaacc ggtttatcag ccgtacttca gcttattctc tctcacagaa    1620
```

```
cactattgaa tcagccgaaa agccaccgca gaacaggacc agtatctcac aaatggcatg    1680
ccaaatatac tcaccgtcag tgagcccgtt taacggcgtc gacaagtcta acggccacca    1740
accagcgaac caccagcgtc aagctagcca agcgaagcag acggccgaga cgttgacacc    1800
ttggcgcggg catctctctg ccccctctc gagagttccg ctccacctcc actggtggcg     1860
gtttccaagt ccgttccgcc tcctgctcct cctcacacgg cacgaaaccg tcacggcacc    1920
ggcagcacgg gggattcctt tcccaccgct ccttcccttt ccttcctcg cccgccgttt     1980 taaatagcca gccccatccc cagcttctct ccccaacctc agcttctctc gttgttcgga    2040
gcgcacacac aacccgatcc ccaatcccct cgtctctcct cgcgagcctc gtcgatcccc    2100
gcttcaaggt acggcgatca tcctcccttt ctctaccttc tcttctctag actaggtcgg    2160
cgatccatgg ttagggcctg ctagttctgt tcctgttttt ccgtggctgc gaggtacaat    2220
agatctgatg gcgttatgat ggttaacttg tcatactcct gcggtgtgcg gtctatagtg    2280
cttttaggac atcaatttga cctggctcgt tcgagatcgg cgatccatgg ttaggaccct    2340
aggcggtgga gtcgggttag atccgcgctg tttgtgttag tagatggatg cgacctttac    2400
ttcagacacg ttctgattgt taacttgtca gcacctggga gtcctgggat ggttctagct    2460
ggttcgcaga tgagatcgat ttcatgatct gctgtatctt gtttcgttag gttccttta     2520 atctatccgt ggtattatgc taacctatga tatggttcga tcgtgctagc tacgtcctgt    2580
gtcataattt ttagcatgcc cttttttgtt tggttttgtc tgattgggct gtagatcaga    2640
gtatactgtt tcaaactacc tactggatat atttattaaa tttgaatctg tatgtgtgtc    2700
acatatatct tcataattaa aatggatgga aagatatatg gataggtaca tgtgttgctg    2760
tgggttttac tggtactttg ttagatatac atgcttagat acatgaagca acatgatgtt    2820
acagttcaat aattcttgtt tacctaataa acaaataagg ataggtgtat gttgctgtgg    2880
gttttgctgg tactttgtta gatatatatg cttagatata tgaagcaaca tcctgctacg    2940
gtttaataat tattgtttat atctaataga caagcctgct ttttaattat tttgatatac    3000
ttggatgatg gcatacagca gctatgtgtg gatttttaaa tacccagcat catgagcatg    3060
catgaccctg ccttagtatg ctgtttattt gcttgagact tcttttttg ttggtactca     3120 ccttttgtag tttggtgact cttctgcagg tg                                  3152
```

<210> SEQ ID NO 23  
<211> LENGTH: 2014  
<212> TYPE: DNA  
<213> ORGANISM: Saccharum ravennae

<400> SEQUENCE: 23

```
gtataagagc aagtgtattg tcacgtgata tttatgttga gatgaagaag agaaaataaa     60
cagcctgcaa atttatagcg agtgatagat gggcacaagg cttcctattt cttaaatcag    120
actttgtaag aacaaaaaaa ggacttataa gagaatggga taaaccatat atcaatggtg    180
tagtatgtta gtatgcatta agatctgact attatatgag tgagttgtta aattcatttt    240
aggtgacatg gcccggttaa attattagcc ataccctaac agctctaaaa aagatatatt    300
cgttgaggca ctttttatgca accacatagt caacttgaat gccgcttgag tgcgttctca    360
agtttttttt cttgcaaatt acgctttttt aagaaagtat aatttggatc gtgcgatttt    420
ttttctctag gtgtgcgtga ctgtgtgagt aacaattttg gatctcagaa aggtaataaa    480
agaataatac tgctgcctac tttgaggatt acaaatatctt tctctaaaat gttttggttt    540
gttatttaaa ccgtctttaa ggccaattgc tcaagattca ttcaacaatt gaaacgtctc    600
```

```
acatgattaa atcatataag gttgctaagg tcttgtttga caaggttttt tttgtggaaa      660
tttcatctaa atttttgagt gaaactatca aatactaatt taaaaaaggc aaattttgct      720
ggaggacact gcagaaacgt gtaattggcc ggcacaaacc gccaaacgga gaatttgccc      780
agtaccatta taaattcatg ataaattcat ggttgtttgc cagtggggct agggttcctc      840
gcgtatggtg cggaatgtgg tttggttcga ccaactcgaa ctcaatccga tccaaagggg      900
catcaatagt cattttagaa agtttctctc tcccgagcag tggaaatgat tattctattt      960
ggcgcgatgt ccaccggcaa acaaccacga atttgtaatg gtactaggca aattctccgt     1020
ttggcggtgt gtgccggcca attacacgtt tttgcggtgt cctccgacaa aatttgcctt     1080
ttaaaaacaa ttttataaga gaagctccgg agataaaagg ccgtcaatgt tacaagagtg     1140
aagtcgtcta ctccctccat cccaaaaaat gtaattctaa gtatgagttg tattattatt     1200
tttggacaaa aggagtatac cacaagaatg atatcatcgt catgcttaga tcctttttag     1260
taaagcttga gctctctaa aagtagagaa attagaaaaa aatcacgttt ttgtggtctt      1320
gatttctagc ctccacaaaa tctttggttt tacatttttt gtttgatttt ggtttcagaa     1380
gtccttattt atatgtgcta gtttggcagc acttaaaatc gttagagaga gcctaaacaa     1440 aagcctttc aaaacgacct tgagccagat tggttgatgg ccaaaatttg attgtcaaaa      1500
cttaggcaag ccaagatttt agcagctatt tggtttggta ccaaaatttg ccaatgatct     1560
gttcttttgc cttttcaacc ggtttatcag ccgtacttca gcttattctc tctcacagaa     1620
cactattgaa tcagccgaaa agccaccgca gaacaggacc agtatctcac aaatggcatg     1680
ccaaatatac tcaccgtcag tgagcccgtt taacggcgtc gacaagtcta acggccacca     1740
accagcgaac caccagcgtc aagctagcca agcgaagcag acggccgaga cgttgacacc     1800
ttggcgcggg catctctctg gccccctctc gagagttccg ctccacctcc actggtggcg     1860
gtttccaagt ccgttccgcc tcctgctcct cctcacacgg cacgaaaccg tcacggcacc     1920
ggcagcacgg gggattcctt tcccaccgct ccttcccttt ccttcctcg cccgccgttt      1980 taaatagcca gccccatccc cagcttctct cccc                                 2014
```

<210> SEQ ID NO 24
<211> LENGTH: 1044
<212> TYPE: DNA
<213> ORGANISM: Saccharum ravennae

<400> SEQUENCE: 24

```
gtacggcgat catcctccct ttctctacct tctcttctct agactaggtc ggcgatccat       60
ggttagggcc tgctagttct gttcctgttt ttccgtggct gcgaggtaca atagatctga      120
tggcgttatg atggttaact tgtcatactc ctgcggtgtg cggtctatag tgcttttagg      180
acatcaattt gacctggctc gttcgagatc ggcgatccat ggttaggacc ctaggcggtg      240
gagtcgggtt agatccgcgc tgtttgtgtt agtagatgga tgcgaccttt acttcagaca      300
cgttctgatt gttaacttgt cagcacctgg gagtcctggg atggttctag ctggttcgca      360
gatgagatcg atttcatgat ctgctgtatc ttgtttcgtt aggttccttt taatctatcc      420
gtggtattat gctaacctat gatatggttc gatcgtgcta gctacgtcct gtgtcataat      480
ttttagcatg ccctttttg tttggttttg tctgattggg ctgtagatca gagtatactg       540
tttcaaacta cctactggat atatttatta aatttgaatc tgtatgtgtg tcacatatat      600
cttcataatt aaaatggatg gaaagatata tggataggta catgtgttgc tgtgggtttt      660
```

-continued

| | |
|---|---|
| actggtactt tgttagatat acatgcttag atacatgaag caacatgatg ttacagttca | 720 |
| ataattcttg tttacctaat aaacaaataa ggataggtgt atgttgctgt gggttttgct | 780 |
| ggtactttgt tagatatata tgcttagata tatgaagcaa catcctgcta cggtttaata | 840 |
| attattgttt atatctaata gacaagcctg cttttttaatt attttgatat acttggatga | 900 |
| tggcatacag cagctatgtg tggattttta aatacccagc atcatgagca tgcatgaccc | 960 |
| tgccttagta tgctgtttat ttgcttgaga cttcttttt tgttggtact cacctttgt | 1020 |
| agtttggtga ctcttctgca ggtg | 1044 |

<210> SEQ ID NO 25
<211> LENGTH: 2663
<212> TYPE: DNA
<213> ORGANISM: Saccharum ravennae

<400> SEQUENCE: 25

| | |
|---|---|
| ctgctgccta ctttgaggat tacaatatct ttctctaaaa tgttttggtt tgttatttaa | 60 |
| accgtcttta aggccaattg ctcaagattc attcaacaat tgaaacgtct cacatgatta | 120 |
| aatcatataa ggttgctaag gtcttgtttg acaaggtttt ttttgtggaa atttcatcta | 180 |
| aattttttgag tgaaactatc aaatactaat ttaaaaaagg caaattttgc tggaggacac | 240 |
| tgcagaaacg tgtaattggc cggcacaaac cgccaacgg agaatttgcc cagtaccatt | 300 |
| ataaattcat gataaattca tggttgtttg ccagtggggc tagggttcct cgcgtatggt | 360 |
| gcggaatgtg gtttggttcg accaactcga actcaatccg atccaaaggg gcatcaatag | 420 |
| tcattttaga aagtttctct ctcccgagca gtggaaatga ttattctatt tggcgcgatg | 480 |
| tccaccggca aacaaccacg aatttgtaat ggtactaggc aaattctccg tttggcggtg | 540 |
| tgtgccggcc aattacacgt ttttgcggtg tcctccgaca aaatttgcct tttaaaaaca | 600 |
| attttataag agaagctccg gagataaaag gccgtcaatg ttacaagagt gaagtcgtct | 660 |
| actccctcca tcccaaaaaa tgtaattcta agtatgagtt gtattattat ttttggacaa | 720 |
| aaggagtata ccacaagaat gatatcatcg tcatgcttag atccttttta gtaaagcttg | 780 |
| agcttctcta aaagtagaga aattagaaaa aaatcacgtt tttgtggtct tgatttctag | 840 |
| cctccacaaa atctttggtt ttacatttt tgtttgattt tggtttcaga agtccttatt | 900 |
| tatatgtgct agtttggcag cacttaaaat cgttagagag agcctaaaca aaagcctttt | 960 |
| caaaacgacc ttgagccaga ttggttgatg gccaaaattt gattgtcaaa acttaggcaa | 1020 |
| gccaagattt tagcagctat ttggtttggt accaaaattt gccaatgatc tgttcttttg | 1080 |
| cctttttcaac cggtttatca gccgtacttc agcttattct ctctcacaga acactattga | 1140 |
| atcagccgaa aagccaccgc agaacaggac cagtatctca caaatggcat gccaaatata | 1200 |
| ctcaccgtca gtgagcccgt ttaacggcgt cgacaagtct aacggccacc aaccagcgaa | 1260 |
| ccaccagcgt caagctagcc aagcgaagca gacggccgag acgttgacac cttggcgcgg | 1320 |
| gcatctctct ggcccctct cgagagttcc gctccacctc cactggtggc ggtttccaag | 1380 |
| tccgttccgc ctcctgctcc tcctcacacg gcacgaaacc gtcacggcac cggcagcacg | 1440 |
| ggggattcct ttcccaccgc tccttccctt tcccttcctc gcccgccgtt ttaaatagcc | 1500 |
| agccccatcc ccagcttctc tccccaacct cagcttctct cgttgttcgg agcgcacaca | 1560 |
| caacccgatc cccaatcccc tcgtctctcc tcgcgagccc cgtcgatccc cgcttcaagg | 1620 |
| tacggcgatc atcctccctt tctctacctt ctcttctcta gactaggtcg gcgatccatg | 1680 |
| gttagggcct gctagttctg ttcctgtttt tccgtggctg cgaggtacaa tagatctgat | 1740 |

```
ggcgttatga tggttaactt gtcatactcc tgcggtgtgc ggtctatagt gcttttagga    1800
catcaatttg acctggctcg ttcgagatcg gcgatccatg gttaggaccc taggcggtgg    1860
agtcgggtta gatccgcgct gtttgtgtta gtagatggat gcgacccttta cttcagacac    1920 gttctgattg ttaacttgtc agcacctggg agtcctggga tggttctagc tggttcgcag    1980
atgagatcga tttcatgatc tgctgtatct tgtttcgtta ggttcctttt aatctatccg    2040
tggtattatg ctaacctatg atatggttcg atcgtgctag ctacgtcctg tgtcataatt    2100
tttagcatgc cctttttttgt ttggttttgt ctgattgggc tgtagatcag agtatactgt    2160
ttcaaactac ctactggata tatttattaa atttgaatct gtatgtgtgt cacatatatc    2220
ttcataatta aaatggatgg aaagatatat ggataggtac atgtgttgct gtgggtttta    2280
ctggtacttt gttagatata catgcttaga tacatgaagc aacatgatgt tacagttcaa    2340
taattcttgt ttacctaata aacaaataag gataggtgta tgttgctgtg ggttttgctg    2400
gtactttgtt agatatatat gcttagatat atgaagcaac atcctgctac ggtttaataa    2460
ttattgttta tatctaatag acaagcctgc ttttttaatta ttttgatata cttggatgat    2520
ggcatacagc agctatgtgt ggatttttaa atacccagca tcatgagcat gcatgacccct   2580 gccttagtat gctgtttatt tgcttgagac ttcttttttt gttggtactc acctttttgta   2640 gtttggtgac tcttctgcag gtg                                             2663

<210> SEQ ID NO 26
<211> LENGTH: 1525
<212> TYPE: DNA
<213> ORGANISM: Saccharum ravennae

<400> SEQUENCE: 26
ctgctgccta ctttgaggat tacaatatct ttctctaaaa tgttttggtt tgttatttaa      60
accgtcttta aggccaattg ctcaagattc attcaacaat tgaaacgtct cacatgatta    120
aatcatataa ggttgctaag gtcttgtttg acaaggtttt ttttgtggaa atttcatcta    180
aatttttgag tgaaactatc aaatactaat ttaaaaaagg caaatttgc tggaggacac     240 tgcagaaacg tgtaattggc cggcacaaac cgccaaacgg agaatttgcc cagtaccatt    300
ataaattcat gataaaattca tggttgtttg ccagtgggc tagggttcct cgcgtatggt    360
gcggaatgtg gtttggttcg accaactcga actcaatccg atccaaaggg gcatcaatag    420
tcattttaga aagtttctct ctcccgagca gtggaaatga ttattctatt ggcgcgatg    480 tccaccggca aacaaccacg aatttgtaat ggtactaggc aaattctccg tttggcggtg    540
tgtgccggcc aattacacgt ttttgcggtg tcctccgaca aaatttgcct tttaaaaaca    600
attttataag agaagctccg gagataaaag gccgtcaatg ttacaagagt gaagtcgtct    660
actccctcca tcccaaaaaa tgtaattcta agtatgagtt gtattattat ttttggacaa    720
aaggagtata ccacaagaat gatatcatcg tcatgcttag atccttttta gtaaagcttg    780
agcttctcta aagtagaga aattagaaaaa aaatcacgtt tttgtggtct tgatttctag    840
cctccacaaa atctttggtt ttacattttt tgtttgattt tggtttcaga agtccttatt    900
tatatgtgct agtttggcag cacttaaaat cgttagagag agcctaaaca aaagcctttt    960
caaaacgacc ttgagccaga ttggttgatg gccaaaattt gattgtcaaa acttaggcaa   1020
gccaagattt tagcagctat ttggtttggt accaaaattt gccaatgatc tgttcttttg   1080
ccttttcaac cggtttatca gccgtacttc agcttattct ctctcacaga acactattga   1140
```

| | |
|---|---|
| atcagccgaa aagccaccgc agaacaggac cagtatctca caaatggcat gccaaatata | 1200 |
| ctcaccgtca gtgagcccgt ttaacggcgt cgacaagtct aacggccacc aaccagcgaa | 1260 |
| ccaccagcgt caagctagcc aagcgaagca gacggccgag acgttgacac cttggcgcgg | 1320 |
| gcatctctct ggcccctct cgagagttcc gctccacctc cactggtggc ggtttccaag | 1380 |
| tccgttccgc ctcctgctcc tcctcacacg gcacgaaacc gtcacggcac cggcagcacg | 1440 |
| ggggattcct ttcccaccgc tccttccctt tcccttcctc gcccgccgtt ttaaatagcc | 1500 |
| agccccatcc ccagcttctc tcccc | 1525 |

<210> SEQ ID NO 27
<211> LENGTH: 2182
<212> TYPE: DNA
<213> ORGANISM: Saccharum ravennae

<400> SEQUENCE: 27

| | |
|---|---|
| ccaccggcaa acaaccacga atttgtaatg gtactaggca aattctccgt ttggcggtgt | 60 |
| gtgccggcca attacacgtt tttgcggtgt cctccgacaa atttgcctt ttaaaaacaa | 120 |
| ttttataaga gaagctccgg agataaaagg ccgtcaatgt tacaagagtg aagtcgtcta | 180 |
| ctccctccat cccaaaaaat gtaattctaa gtatgagttg tattattatt tttggacaaa | 240 |
| aggagtatac cacaagaatg atatcatcgt catgcttaga tccttttag taaagcttga | 300 |
| gcttctctaa aagtagagaa attagaaaaa atcacgtttt ttgtggtctt gatttctagc | 360 |
| ctccacaaaa tctttggttt tacatttttt gtttgatttt ggtttcagaa gtccttattt | 420 |
| atatgtgcta gtttggcagc acttaaaatc gttagagaga gcctaaacaa aagccttttc | 480 |
| aaaacgacct tgagccagat tggttgatgg ccaaaatttg attgtcaaaa cttaggcaag | 540 |
| ccaagatttt agcagctatt tggttttggta ccaaaatttg ccaatgatct gttcttttgc | 600 |
| cttttcaacc ggtttatcag ccgtacttca gcttattctc tctcacagaa cactattgaa | 660 |
| tcagccgaaa agccaccgca gaacaggacc agtatctcac aaatggcatg ccaaatatac | 720 |
| tcaccgtcag tgagcccgtt taacggcgtc gacaagtcta acggccacca accagcgaac | 780 |
| caccagcgtc aagctagcca agcgaagcag acggccgaga cgttgacacc ttggcgcggg | 840 |
| catctctctg gcccctctc gagagttccg ctccacctcc actggtggcg gtttccaagt | 900 |
| ccgttccgcc tcctgctcct cctcacacg cacgaaaccg tcacggcacc ggcagcacgg | 960 |
| gggattcctt tcccaccgct ccttccctt ccctcctcg cccgccgttt taaatagcca | 1020 |
| gccccatccc cagcttctct ccccaacctc agcttctctc gttgttcgga gcgcacacac | 1080 |
| aacccgatcc ccaatcccct cgtctctcct cgcgagcctc gtcgatcccc gcttcaaggt | 1140 |
| acggcgatca tcctcccttt ctctaccttc tcttctctag actaggtcgg cgatccatgg | 1200 |
| ttagggcctg ctagttctgt tcctgttttt ccgtggctgc gaggtacaat agatctgatg | 1260 |
| gcgttatgat ggttaacttg tcatactcct gcggtgtgcg gtctatagtg cttttaggac | 1320 |
| atcaatttga cctggctcgt tcgagatcgg cgatccatgg ttaggaccct aggcggtgga | 1380 |
| gtcgggttag atccgcgctg tttgtgttag tagatggatg cgacctttac ttcagacacg | 1440 |
| ttctgattgt taacttgtca gcacctggga gtcctgggat ggttctagct ggttcgcaga | 1500 |
| tgagatcgat ttcatgatct gctgtatctt gtttcgttag gttccttta atctatccgt | 1560 |
| ggtattatgc taacctatga tatggttcga tcgtgctagc tacgtcctgt gtcataattt | 1620 |
| ttagcatgcc cttttttgtt tggttttgtc tgattgggct gtagatcaga gtatactgtt | 1680 |
| tcaaactacc tactggatat atttattaaa tttgaatctg tatgtgtgtc acatatatct | 1740 |

```
tcataattaa aatggatgga aagatatatg gataggtaca tgtgttgctg tgggttttac    1800
tggtactttg ttagatatac atgcttagat acatgaagca acatgatgtt acagttcaat    1860
aattcttgtt tacctaataa acaaataagg ataggtgtat gttgctgtgg gttttgctgg    1920
tactttgtta gatatatatg cttagatata tgaagcaaca tcctgctacg gtttaataat    1980
tattgtttat atctaataga caagcctgct ttttaattat tttgatatac ttggatgatg    2040
gcatacagca gctatgtgtg gatttttaaa tacccagcat catgagcatg catgaccctg    2100
ccttagtatg ctgtttattt gcttgagact tcttttttg ttggtactca ccttttgtag    2160
tttggtgact cttctgcagg tg                                              2182

<210> SEQ ID NO 28
<211> LENGTH: 1044
<212> TYPE: DNA
<213> ORGANISM: Saccharum ravennae

<400> SEQUENCE: 28
ccaccggcaa acaaccacga atttgtaatg gtactaggca aattctccgt ttggcggtgt     60
gtgccggcca attacacgtt tttgcggtgt cctccgacaa aatttgcctt ttaaaaacaa    120
ttttataaga gaagctccgg agataaaagg ccgtcaatgt acaagagtg aagtcgtcta    180 ctccctccat cccaaaaaat gtaattctaa gtatgagttg tattattatt tttgacaaa    240 aggagtatac cacaagaatg atatcatcgt catgcttaga tccttttag taaagcttga    300 gcttctctaa aagtagagaa attagaaaaa aatcacgttt ttgtggtctt gatttctagc    360
ctccacaaaa tctttggttt tacattttt gtttgatttt ggtttcagaa gtccttattt    420
atatgtgcta gttggcagc acttaaaatc gttagagaga gcctaaacaa aagccttttc    480
aaaacgacct tgagccagat tggttgatgg ccaaaatttg attgtcaaaa cttaggcaag    540
ccaagatttt agcagctatt tggttttggta ccaaaatttg ccaatgatct gttcttttgc    600
cttttcaacc ggtttatcag ccgtacttca gcttattctc tctcacagaa cactattgaa    660
tcagccgaaa agccaccgca gaacaggacc agtatctcac aaatggcatg ccaaatatac    720
tcaccgtcag tgagcccgtt taacggcgtc gacaagtcta acggccacca accagcgaac    780
caccagcgtc aagctagcca agcgaagcag acggccgaga cgttgacacc ttggcgcggg    840
catctctctg gcccctctc gagagttccg ctccacctcc actggtggcg gtttccaagt    900
ccgttccgcc tcctgctcct cctcacacgg cacgaaaccg tcacggcacc ggcagcacgg    960
gggattcctt tccaccgct ccttccctt cccttcctcg cccgccgttt taaatagcca   1020
gccccatccc cagcttctct cccc                                          1044

<210> SEQ ID NO 29
<211> LENGTH: 1934
<212> TYPE: DNA
<213> ORGANISM: Saccharum ravennae

<400> SEQUENCE: 29
accacaagaa tgatatcatc gtcatgctta gatccttttt agtaaagctt gagcttctct     60
aaaagtagag aaattagaaa aaaatcacgt ttttgtggtc ttgatttcta gcctccacaa    120
aatctttggt tttacatttt ttgtttgatt ttggtttcag aagtccttat ttatatgtgc    180
tagtttggca gcacttaaaa tcgttagaga gagcctaaac aaaagccttt tcaaaacgac    240
cttgagccag attggttgat ggccaaaatt tgattgtcaa aacttaggca agccaagatt    300
```

```
ttagcagcta tttggtttgg taccaaaatt tgccaatgat ctgttctttt gccttttcaa      360
ccggtttatc agccgtactt cagcttattc tctctcacag aacactattg aatcagccga      420
aaagccaccg cagaacagga ccagtatctc acaaatggca tgccaaatat actcaccgtc      480
agtgagcccg tttaacggcg tcgacaagtc taacggccac caaccagcga accaccagcg      540
tcaagctagc caagcgaagc agacggccga gacgttgaca ccttggcgcg ggcatctctc      600
tggccccctc tcgagagttc cgctccacct ccactggtgg cggtttccaa gtccgttccg      660
cctcctgctc ctcctcacac ggcacgaaac cgtcacggca ccggcagcac ggggggattcc     720
tttcccaccg ctccttccct ttcccttcct cgcccgccgt tttaaatagc cagccccatc      780
cccagcttct ctccccaacc tcagcttctc tcgttgttcg gagcgcacac acaacccgat      840
ccccaatccc ctcgtctctc ctcgcgagcc tcgtcgatcc ccgcttcaag gtacggcgat      900
catcctccct ttctctacct tctcttctct agactaggtc ggcgatccat ggttagggcc      960
tgctagttct gttcctgttt ttccgtggct gcgaggtaca atagatctga tggcgttatg     1020
atggttaact tgtcatactc ctgcggtgtg cggtctatag tgcttttagg acatcaattt     1080
gacctggctc gttcgagatc ggcgatccat ggttaggacc ctaggcggtg gagtcgggtt     1140
agatccgcgc tgtttgtgtt agtagatgga tcgacctttt acttcagaca cgttctgatt     1200
gttaacttgt cagcacctgg gagtcctggg atggttctag ctggttcgca gatgagatcg     1260
atttcatgat ctgctgtatc ttgtttcgtt aggttccttt taatctatcc gtggtattat     1320
gctaacctat gatatggttc gatcgtgcta gctacgtcct gtgtcataat ttttagcatg     1380
ccctttttttg tttggttttg tctgattggg ctgtagatca gagtatactg tttcaaacta     1440
cctactggat atatttatta aatttgaatc tgtatgtgtg tcacatatat cttcataatt     1500
aaaatggatg gaaagatata tggataggta catgtgttgc tgtgggtttt actggtactt     1560
tgttagatat acatgcttag atacatgaag caacatgatg ttacagttca ataattcttg     1620
tttacctaat aaacaaataa ggataggtgt atgttgctgt gggttttgct ggtactttgt     1680
tagatatata tgcttagata tatgaagcaa catcctgcta cggtttaata attattgttt     1740
atatctaata gacaagcctg cttttttaatt attttgatat acttggatga tggcatacag     1800
cagctatgtg tggattttta aatacccagc atcatgagca tgcatgaccc tgccttagta     1860
tgctgtttat ttgcttgaga cttcttttttt tgttggtact caccttttgt agtttggtga     1920
ctcttctgca ggtg                                                       1934
```

<210> SEQ ID NO 30
<211> LENGTH: 796
<212> TYPE: DNA
<213> ORGANISM: Saccharum ravennae

<400> SEQUENCE: 30

```
accacaagaa tgatatcatc gtcatgctta gatccttttt agtaaagctt gagcttctct       60
aaaagtagag aaattagaaa aaaatcacgt ttttgtggtc ttgatttcta gcctccacaa      120
aatctttggt tttacatttt ttgtttgatt ttggtttcag aagtccttat ttatatgtgc      180
tagtttggca gcacttaaaa tcgttagaga gagcctaaac aaaagccttt tcaaaacgac      240
cttgagccag attggttgat ggccaaaatt tgattgtcaa aacttaggca agccaagatt      300
ttagcagcta tttggtttgg taccaaaatt tgccaatgat ctgttctttt gccttttcaa      360
ccggtttatc agccgtactt cagcttattc tctctcacag aacactattg aatcagccga      420
aaagccaccg cagaacagga ccagtatctc acaaatggca tgccaaatat actcaccgtc      480
```

```
agtgagcccg tttaacggcg tcgacaagtc taacggccac caaccagcga accaccagcg    540
tcaagctagc caagcgaagc agacggccga gacgttgaca ccttggcgcg ggcatctctc    600
tggccccctc tcgagagttc cgctccacct ccactggtgg cggtttccaa gtccgttccg    660
cctcctgctc ctcctcacac ggcacgaaac cgtcacggca ccggcagcac ggggattcc     720 tttcccaccg ctccttccct ttcccttcct cgcccgccgt tttaaatagc cagccccatc    780
cccagcttct ctcccc                                                    796

<210> SEQ ID NO 31
<211> LENGTH: 1649
<212> TYPE: DNA
<213> ORGANISM: Saccharum ravennae

<400> SEQUENCE: 31
aggcaagcca agattttagc agctatttgg tttggtacca aaatttgcca atgatctgtt    60
cttttgcctt ttcaaccggt ttatcagccg tacttcagct tattctctct cacagaacac    120
tattgaatca gccgaaaagc caccgcagaa caggaccagt atctcacaaa tggcatgcca    180
aatatactca ccgtcagtga gcccgtttaa cggcgtcgac aagtctaacg ccaccaacc     240 agcgaaccac cagcgtcaag ctagccaagc gaagcagacg ccgagacgt tgacaccttg     300 gcgcgggcat ctctctggcc ccctctcgag agttccgctc cacctccact ggtggcggtt    360
tccaagtccg ttccgcctcc tgctcctcct cacacggcac gaaaccgtca cggcaccggc    420
agcacggggg attcctttcc caccgctcct tccctttccc ttcctcgccc gccgttttaa    480
atagccagcc ccatccccag cttctctccc caaccctcagc ttctctcgtt gttcggagcg    540
cacacacaac ccgatcccca atccctcgt ctctcctcgc gagcctcgtc gatcccgct     600 tcaaggtacg gcgatcatcc tccctttctc taccttctct tctctagact aggtcggcga    660
tccatggtta gggcctgcta gttctgttcc tgttttccg tggctgcgag gtacaataga     720
tctgatggcg ttatgatggt taacttgtca tactcctgcg gtgtgcggtc tatagtgctt    780
ttaggacatc aatttgacct ggctcgttcg agatcggcga tccatggtta ggaccctagg    840
cggtggagtc gggttagatc cgcgctgttt gtgttagtag atggatgcga cctttacttc    900
agacacgttc tgattgttaa cttgtcagca cctgggagtc ctgggatggt tctagctggt    960
tcgcagatga gatcgatttc atgatctgct gtatcttgtt tcgttaggtt cctttaatc    1020 tatccgtggt attatgctaa cctatgatat ggttcgatcg tgctagctac gtcctgtgtc    1080 ataatttta gcatgccctt ttttgtttgg ttttgtctga ttgggctgta gatcagagta    1140
tactgtttca aactacctac tggatatatt tattaaattt gaatctgtat gtgtgtcaca    1200
tatatcttca taattaaaat ggatggaaag atatatggat aggtacatgt gttgctgtgg    1260
gttttactgg tactttgtta gatatacatg cttagataca tgaagcaaca tgatgttaca    1320
gttcaataat tcttgtttac ctaataaaca aataaggata ggtgtatgtt gctgtgggtt    1380
ttgctggtac tttgttagat atatatgctt agatatatga agcaacatcc tgctacggtt    1440
taataattat tgtttatatc taatagacaa gcctgctttt taattatttt gatatacttg    1500
gatgatggca tacagcagct atgtgtggat ttttaaatac ccagcatcat gagcatgcat    1560
gaccctgcct tagtatgctg tttatttgct tgagacttct ttttttgttg gtactcacct    1620
tttgtagttt ggtgactctt ctgcaggtg                                     1649

<210> SEQ ID NO 32
```

```
<211> LENGTH: 511
<212> TYPE: DNA
<213> ORGANISM: Saccharum ravennae

<400> SEQUENCE: 32
aggcaagcca agattttagc agctatttgg tttggtacca aaatttgcca atgatctgtt      60
cttttgcctt ttcaaccggt ttatcagccg tacttcagct tattctctct cacagaacac     120
tattgaatca gccgaaaagc caccgcagaa caggaccagt atctcacaaa tggcatgcca     180
aatatactca ccgtcagtga gcccgtttaa cggcgtcgac aagtctaacg gccaccaacc     240
agcgaaccac cagcgtcaag ctagccaagc gaagcagacg gccgagacgt tgacaccttg     300
gcgcgggcat ctctctggcc ccctctcgag agttccgctc cacctccact ggtggcggtt     360
tccaagtccg ttccgcctcc tgctcctcct cacacggcac gaaaccgtca cggcaccggc     420
agcacggggg attcctttcc caccgctcct tcccttttccc ttcctcgccc gccgttttaa    480
atagccagcc ccatccccag cttctctccc c                                   511

<210> SEQ ID NO 33
<211> LENGTH: 2631
<212> TYPE: DNA
<213> ORGANISM: Setaria viridis

<400> SEQUENCE: 33
actgccgcga cacgcctcac tggcgggagg gctccgagcg ctctctcccc ggcggccggc      60
ggagcagcga tctggattgg agagaataga ggaaagagag ggaaaaggag agagatagcg     120
caaagagctg aaaagataag gttgtgcggg ctgtggtgat tagaggacca ctaatccctc     180
catctcctaa tgacgcggtg cccaagacca gtgccgcggc acaccagcgt ctaagtgaac     240
ttccgctaac cttccggtca ttgcgcctga aagatgtcat gtggcgaggc cccctctca     300
gtagattgcc aactgcctac cgtgccactc ttccatgcat gattgctccc gtctatcccg     360
tttctcacaa cagatagaca acagtaagca tcactaaagc aagcatgtgt agaaccttaa     420
aaaaaggctt atactaccag tatactatca accagcatgc cgttttttgaa gtatccagga    480
ttagaagctt ctactgcgct tttatattat agctgtggac ctgtggtaac ctttctcttt     540
tggcgcttgc ttaatctcgg ccgtgctggt ccatgcttag gcactaggca gagatagagc     600
cgggggtgaa tggggctaaa gctcagctgc tcgaggggcc gtgggctggt ttccactagc     660
ctacagctgt gccacgtgcg gccgcgcaag ccgaagcaag cacgctgagc cgttggacag     720
cttgtcataa tgccattacg tggattacag gtaactggcc ctgtaactac tcgttcggcc     780
atcatcaaac gacgacgtcc gctaggcgac gacacgggta atgcacgcag ccacccaggc     840
gcgcgcgcta gcggagcacg gtcaggtgac acgggcgtcg tgacgcttcc gagttgaagg     900
ggttaacgcc agaaacagtg tttggccagg gtatgaacat aacaaaaaat attcacacga     960
aagaatggaa gtatggagct gctactgtgt aaatgccaag caggaaactc acgcccgcta    1020
acatccaacg gccaacagct cgacgtgccg gtcagcagag acatcggaac actggtgatt    1080
ggtggagccg gcagtatgcg ccccagcacg gccgaggtgg tggtggcccg tggccctgct    1140
gtctgcgcgc tcgggacaa cttgaaactg ggccaccgcc tcgtcgcaac tcgcaacccg     1200
ttggcggaag aaaggaatgg ctcgtagggg cccgggtaga atccaagaat gttgcgctgg    1260
gcttcgattc acataacatg ggcctgaagc tctaaaacga cggccgtc accgggcgat     1320
ggaaagagac cggatcctcc tcgtgaattc tggaaggcca cacgagagcg acccaccacc    1380
gacgcggagg agtcgtgcgt ggtccaacac ggccggcggg ctgggctgcg accttaacca    1440
```

```
gcaaggcacg ccacgacccg cctcgccctc gaggcataaa taccctccca tcccgttgcc    1500
gcaagactca gatcagattc cgatcccag ttcttcccca atcaccttgt ggtctctcgt    1560
gtcgcggttc ccagggacgc ctccggctcg tcgctcgaca gcgatctccg ccccagcaag    1620
gtatagattc agttccttgc tccgatccca atctggttga gatgttgctc cgatgcgact    1680
tgattatgtc atatatctgc ggtttgcacc gatctgaagc ctagggtttc tcgagcgacc    1740
cagttgtttg caatttgcga tttgctcgtt tgttgcgcat cgtagtttat gtttggagta    1800
atcgaggatt tgtatgcggc gtcggcgcta cctgcttaat cacgccatgt gacgcggtta    1860
cttgcagagg ctgggttagt gggttctgtt atgtcgtgat ctaagaatct agattaggct    1920
cagtcgttct tgctgtcgac tagtttgttt tgatatccat gtagtacaag ttacttaaaa    1980
tttaggtcca atatattttg catgcttttg gcctgttatt cttgccaaca agttgtcctg    2040
gtaaaaagta gatgtgaaag tcacgtattg ggacaaattg atggttaagt gctatagttc    2100
tatagttctg tgatacatct atctgatttt ttttggtcta ttggtgccta acttatctga    2160
aaatcatgga acatgaggct agtttgatca tggtttagtt cattgtgatt aataatgtat    2220
gatttagtag ctattttggt gatcgtgtca ttttatttgt gaatggaatc attgtatgta    2280
aatgaagcta gttcagggt tatgatgtag ctggctttgt attctaaagg ctgctattat    2340
tcatccatcg atttcaccta tatgtaatcc agagctttcg atgtgaaatt tgtctgatcc    2400
ttcactagga aggacagaac attgttaata ttttggcaca tctgtcttat tctcatcctt    2460
tgtttgaaca tgttagcctg ttcaaacaga tactgttgta atgtcctagt tatataggta    2520
catatgtgtt ctctattgag tttatggact tttgtgtgtg aagttatatt tcattttgct    2580
caaaactcat gtttgcaagc tttctgacat tattctattg ttctgaaaca g             2631
```

<210> SEQ ID NO 34
<211> LENGTH: 1493
<212> TYPE: DNA
<213> ORGANISM: Setaria viridis
<400> SEQUENCE: 34

```
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc cccctctca    300 gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgttttgaa gtatccagga    480 ttagaagctt ctactgcgct tttatattat agctgtggac ctgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
```

```
ggttaacgcc agaaacagtg tttggccagg gtatgaacat aacaaaaaat attcacacga      960
aagaatggaa gtatggagct gctactgtgt aaatgccaag caggaaactc acgcccgcta     1020
acatccaacg gccaacagct cgacgtgccg gtcagcagag acatcggaac actggtgatt     1080
ggtggagccg gcagtatgcg ccccagcacg gccgaggtgg tggtggcccg tggccctgct     1140
gtctgcgcgg ctcgggacaa cttgaaactg gccaccgcc tcgtcgcaac tcgcaacccg      1200
ttggcggaag aaaggaatgg ctcgtagggg cccgggtaga atccaagaat gttgcgctgg     1260
gcttcgattc acataacatg ggcctgaagc tctaaaacga cggcccggtc accgggcgat     1320
ggaaagagac cggatcctcc tcgtgaattc tggaaggcca cacgagagcg acccaccacc     1380
gacgcggagg agtcgtgcgt ggtccaacac ggccggcggg ctgggctgcg accttaacca     1440
gcaaggcacg ccacgacccg cctcgccctc gaggcataaa taccctccca tcc            1493

<210> SEQ ID NO 35
<211> LENGTH: 127
<212> TYPE: DNA
<213> ORGANISM: Setaria viridis

<400> SEQUENCE: 35
cgttgccgca agactcagat cagattccga tccccagttc ttccccaatc accttgtggt       60
ctctcgtgtc gcggttccca gggacgcctc cggctcgtcg ctcgacagcg atctccgccc     120
cagcaag                                                              127

<210> SEQ ID NO 36
<211> LENGTH: 1011
<212> TYPE: DNA
<213> ORGANISM: Setaria viridis

<400> SEQUENCE: 36
gtatagattc agttccttgc tccgatccca atctggttga gatgttgctc cgatgcgact       60
tgattatgtc atatatctgc ggtttgcacc gatctgaagc ctagggtttc tcgagcgacc     120
cagttgtttg caatttgcga tttgctcgtt tgttgcgcat cgtagtttat gtttggagta     180
atcgaggatt tgtatgcggc gtcggcgcta cctgcttaat cacgccatgt gacgcggtta     240
cttgcagagg ctgggttagt gggttctgtt atgtcgtgat ctaagaatct agattaggct     300
cagtcgttct tgctgtcgac tagtttgttt tgatatccat gtagtacaag ttacttaaaa     360
tttaggtcca atatattttg catgcttttg gcctgttatt cttgccaaca agttgtcctg     420
gtaaaaagta gatgtgaaag tcacgtattg ggacaaattg atggttaagt gctatagttc     480
tatagttctg tgatacatct atctgatttt ttttggtcta ttggtgccta acttatctga     540
aaatcatgga acatgaggct agtttgatca tggtttagtt cattgtgatt aataatgtat     600
gatttagtag ctattttggt gatcgtgtca ttttatttgt gaatggaatc attgtatgta     660
aatgaagcta gttcagggt tatgatgtag ctggctttgt attctaaagg ctgctattat     720
tcatccatcg atttcaccta tatgtaatcc agagcttttcg atgtgaaatt tgtctgatcc     780
ttcactagga aggacagaac attgttaata ttttggcaca tctgtcttat tctcatcctt     840
tgtttgaaca tgttagcctg ttcaaacaga tactgttgta atgtcctagt tatataggta     900
catatgtgtt ctctattgag tttatggact tttgtgtgtg aagttatatt tcattttgct     960
caaaactcat gtttgcaagc tttctgacat tattctattg ttctgaaaca g             1011

<210> SEQ ID NO 37
<211> LENGTH: 2173
```

<212> TYPE: DNA
<213> ORGANISM: Setaria viridis

<400> SEQUENCE: 37

```
gccgtttttg aagtatccag gattagaagc ttctactgcg cttttatatt atagctgtgg      60
acctgtggta acctttctct tttggcgctt gcttaatctc ggccgtgctg gtccatgctt     120
aggcactagg cagagataga gccggggtg aatgggcta aagctcagct gctcgagggg      180
ccgtgggctg gtttccacta gcctacagct gtgccacgtg cggccgcgca agccgaagca     240
agcacgctga gccgttggac agcttgtcat aatgccatta cgtggattac aggtaactgg     300
ccctgtaact actcgttcgg ccatcatcaa acgacgacgt ccgctaggcg acgacacggg     360
taatgcacgc agccacccag gcgcgcgcgc tagcggagca cggtcaggtg acacgggcgt     420
cgtgacgctt ccgagttgaa gggggttaacg ccagaaacag tgtttggcca gggtatgaac    480
ataacaaaaa atattcacac gaaagaatgg aagtatggag ctgctactgt gtaaatgcca     540
agcaggaaac tcacgcccgc taacatccaa cggccaacag ctcgacgtgc cggtcagcag     600
agacatcgga acactggtga ttggtggagc cggcagtatg cgccccagca cggccgaggt     660
ggtggtggcc cgtggccctg ctgtctgcgc ggctcgggac aacttgaaac tgggccaccg     720
cctcgtcgca actcgcaacc cgttggcgga agaaaggaat ggctcgtagg ggcccgggta     780
gaatccaaga atgttgcgct gggcttcgat tcacataaca tgggcctgaa gctctaaaac     840
gacggcccgg tcaccgggcg atggaaagag accggatcct cctcgtgaat tctggaaggc     900
cacacgagag cgacccacca ccgacgcgga ggagtcgtgc gtggtccaac acggccggcg     960
ggctgggctg cgaccttaac cagcaaggca cgccacgacc cgcctcgccc tcgaggcata    1020
aatacccctcc catcccgttg ccgcaagact cagatcagat tccgatcccc agttcttccc    1080
caatcacctt gtggtctctc gtgtcgcggt tcccagggac gcctccggct cgtcgctcga    1140
cagcgatctc cgccccagca aggtatagat tcagttcctt gctccgatcc caatctggtt    1200
gagatgttgc tccgatgcga cttgattatg tcatatatct gcggtttgca ccgatctgaa    1260
gcctagggtt tctcgagcga cccagttgtt tgcaatttgc gatttgctcg tttgttgcgc    1320
atcgtagttt atgtttggag taatcgagga tttgtatgcg gcgtcggcgc tacctgctta    1380
atcacgccat gtgacgcggt tacttgcaga ggctgggtta gtgggttctg ttatgtcgtg    1440
atctaagaat ctagattagg ctcagtcgtt cttgctgtcg actagtttgt tttgatatcc    1500
atgtagtaca agttacttaa aatttaggtc caatatattt tgcatgcttt tggcctgtta    1560
ttcttgccaa caagttgtcc tggtaaaaag tagatgtgaa agtcacgtat tgggacaaat    1620
tgatggttaa gtgctatagt tctatagttc tgtgatacat ctatctgatt ttttttggtc    1680
tattggtgcc taacttatct gaaaatcatg gaacatgagg ctagtttgat catggtttag    1740
ttcattgtga ttaataatgt atgatttagt agctattttg gtgatcgtgt catttttattt    1800
gtgaatggaa tcattgtatg taaatgaagc tagttcaggg gttatgatgt agctggcttt    1860
gtattctaaa ggctgctatt attcatccat cgatttcacc tatatgtaat ccagagcttt    1920
cgatgtgaaa tttgtctgat ccttcactag gaaggacaga acattgttaa tattttggca    1980
catctgtctt attctcatcc tttgtttgaa catgttagcc tgttcaaaca gatactgttg    2040
taatgtccta gttatatagg tacatatgtg ttctctattg agtttatgga cttttgtgtg    2100
tgaagttata tttcattttg ctcaaaactc atgtttgcaa gctttctgac attattctat    2160
tgttctgaaa cag                                                       2173
```

<210> SEQ ID NO 38
<211> LENGTH: 1035
<212> TYPE: DNA
<213> ORGANISM: Setaria viridis

<400> SEQUENCE: 38
gccgtttttg aagtatccag gattagaagc ttctactgcg cttttatatt atagctgtgg 60
acctgtggta acctttctct tttggcgctt gcttaatctc ggccgtgctg gtccatgctt 120
aggcactagg cagagataga gccgggggtg aatggggcta aagctcagct gctcgagggg 180
ccgtgggctg gtttccacta gcctacagct gtgccacgtg cggccgcgca agccgaagca 240
agcacgctga gccgttggac agcttgtcat aatgccatta cgtggattac aggtaactgg 300
ccctgtaact actcgttcgg ccatcatcaa acgacgacgt ccgctaggcg acgacacggg 360
taatgcacgc agccacccag gcgcgcgcgc tagcggagca cggtcaggtg acacgggcgt 420
cgtgacgctt ccgagttgaa ggggttaacg ccagaaacag tgtttggcca gggtatgaac 480
ataacaaaaa atattcacac gaaagaatgg aagtatggag ctgctactgt gtaaatgcca 540
agcaggaaac tcacgcccgc taacatccaa cggccaacag ctcgacgtgc cggtcagcag 600
agacatcgga acactggtga ttggtggagc cggcagtatg cgccccagca cggccgaggt 660
ggtggtggcc cgtggccctg ctgtctgcgc ggctcgggac aacttgaaac tgggccaccg 720
cctcgtcgca actcgcaacc cgttggcgga agaaaggaat ggctcgtagg ggcccgggta 780
gaatccaaga atgttgcgct gggcttcgat tcacataaca tgggcctgaa gctctaaaac 840
gacggcccgg tcaccgggcg atggaaagag accggatcct cctcgtgaat tctggaaggc 900
cacacgagag cgacccacca ccgacgcgga ggagtcgtgc gtggtccaac acggccggcg 960
ggctgggctg cgaccttaac cagcaaggca cgccacgacc cgcctcgccc tcgaggcata 1020
aataccctcc catcc 1035

<210> SEQ ID NO 39
<211> LENGTH: 1819
<212> TYPE: DNA
<213> ORGANISM: Setaria viridis

<400> SEQUENCE: 39
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840

```
ctggttgaga tgttgctccg atgcgacttg attatgtcat atatctgcgg tttgcaccga    900
tctgaagcct agggtttctc gagcgaccca gttgtttgca atttgcgatt tgctcgtttg    960
ttgcgcatcg tagtttatgt ttggagtaat cgaggatttg tatgcggcgt cggcgctacc   1020
tgcttaatca cgccatgtga cgcggttact tgcagaggct gggttagtgg gttctgttat   1080
gtcgtgatct aagaatctag attaggctca gtcgttcttg ctgtcgacta gtttgttttg   1140
atatccatgt agtacaagtt acttaaaatt taggtccaat atattttgca tgcttttggc   1200
ctgttattct tgccaacaag ttgtcctggt aaaagtaga tgtgaaagtc acgtattggg    1260
acaaattgat ggtaagtgc tatagttcta tagttctgtg atacatctat ctgattttt    1320 ttggtctatt ggtgcctaac ttatctgaaa atcatggaac atgaggctag tttgatcatg   1380
gtttagttca ttgtgattaa taatgtatga tttagtagct attttggtga tcgtgtcatt   1440
ttatttgtga atggaatcat tgtatgtaaa tgaagctagt tcaggggtta tgatgtagct   1500
ggctttgtat tctaaaggct gctattattc atccatcgat ttcacctata tgtaatccag   1560
agctttcgat gtgaaatttg tctgatcctt cactaggaag acagaacat tgttaatatt    1620 ttggcacatc tgtcttattc tcatcctttg tttgaacatg ttagcctgtt caaacagata   1680
ctgttgtaat gtcctagtta tataggtaca tatgtgttct ctattgagtt tatggacttt   1740
tgtgtgtgaa gttatatttc attttgctca aaactcatgt ttgcaagctt tctgacatta   1800
ttctattgtt ctgaaacag                                                1819

<210> SEQ ID NO 40
<211> LENGTH: 681
<212> TYPE: DNA
<213> ORGANISM: Setaria viridis

<400> SEQUENCE: 40
cacgggtaat gcacgcagcc acccaggcgc gcgcgctagc ggagcacggt caggtgacac     60
gggcgtcgtg acgcttccga gttgaagggg ttaacgccag aaacagtgtt tggccagggt    120
atgaacataa caaaaaatat tcacacgaaa gaatggaagt atggagctgc tactgtgtaa    180
atgccaagca ggaaactcac gcccgctaac atccaacggc caacagctcg acgtgccggt    240
cagcagagac atcggaacac tggtgattgg tggagccggc agtatgcgcc ccagcacggc    300
cgaggtggtg gtgcccgtg gccctgctgt ctgcgcggct cgggacaact tgaaactggg     360
ccaccgcctc gtcgcaactc gcaacccgtt ggcggaagaa aggaatggct cgtaggggcc    420
cgggtagaat ccaagaatgt tgcgctgggc ttcgattcac ataacatggg cctgaagctc    480
taaaacgacg gcccggtcac cgggcgatgg aaagagaccg gatcctcctt gtgaattctg    540
gaaggccaca cgagagcgac ccaccaccga cgcggaggag tcgtgcgtgg tccaacacgg    600
ccggcgggct gggctgcgac cttaaccagc aaggcacgcc acgacccgcc tcgccctcga    660
ggcataaata ccctcccatc c                                              681

<210> SEQ ID NO 41
<211> LENGTH: 1922
<212> TYPE: DNA
<213> ORGANISM: Zea mays subsp. Mexicana

<400> SEQUENCE: 41
gtcgtgcccc tctctagaga taatgagcat tgcatgtcta agttataaaa aattaccaca     60 tattttttt tgtcacactt gtgtttgaag tgcagtttat ctatctctat acatatattt    120
```

```
aaacttcact atatgaataa tatagtctat agtattaaaa taatatcaat gttttagatg      180
attatataac tgaactgcta gacatggtct aaaggacaac cgagtatttt gacaacatga      240
ctctacagtt ttatctttt agtgtgcatg tgttctttt acttttgcaa atagcttcac       300
ctatataata cttcatccat tttattagta catccattta ctaaattttt agtacatcta     360
ttttattcta ttttagcctc taaattaaga aaacttaaac tctattttag tttttattt      420 aataatttag ataaaaata gaataaaata aagtgactaa aaataacta aatacctttt       480 aagaaataaa aaaactaagg aaccattttt cttgttccga gtagataatg acagcctgtt    540
caacgccgtc gacgagtcta acggacacca accagcgaac cagcagcgtc gcgtcgggcc    600
aagcgaagca gacggcacgg catctctgta gctgcctctg acccctctc gagagttccg     660 ctccaccgtt ggacttgctc cgctgtcggc atccagaaat tgcgtggcgg agcggcagac    720
gtgagccggc acggcaggcg gcctcctctc acggcaccgg cagctacggg ggattccttt    780
cccaccgctc cttcgctttc ccttcctcgc ccgccgtaat aaatagaccc cctccacacc    840
ctctttcccc aacctcgtgt tcgttcggag cgcgcacaca caaccagaa tctcccccaa     900 atccacccgt cggcacctcc gcttcaaggt acgccgctca tcctcctccc ccccctctct    960
ctaccttctc tagatcggcg tttcggtcca tggttagggc ccggtagttc tacttctgtt   1020
catgtttgtg ttagatccgt gtttgtgtta gatccgtgct gctagatttc gtacacggat    1080
gcgacctgta catcagacat gttctgattg ctaacttgcc agtgtttctc tttggggaat    1140
cctgggatgg ctctagccgt tccgcagacg ggatcgattt catgaatttt ttttgtttcg    1200
ttgcataggt tttggtttgc ccttttcctt tatttcaata tatgccgtgc acttgtttgt    1260
cgggtcatct tttcatgttt ttttttggctt ggttgtgatg atgtggtctg gttgggcggt   1320
cgttctagat cggagtagaa tactgtttca aactacctgg tggatttatt aaaggatctg   1380
tatgtatgtg ccatacatct tcatagttac gagtttaaga tgatggatgg aaatatcgat   1440
ctaggatagg tatacatgtt gatgcgggtt ttactgatgc atatacagag atgctttttt   1500
ttcgcttggt tgtgatgatg tggtctggtc gggcggtcgt tctagatcgg agtagaatac   1560
tgtttcaaac tacctggtgg atttattaat tttggatctg tatgtgtgtc atacatcttc    1620
atagttacga gtttaagatc gatggaaata tcgatctagg ataggtatac atgttgatgt   1680 gggtttact gatgcatata catggcatat gcagcatcta ttcatatgct ctaaccttga    1740
gtacctatct attataataa acaagtatgt tttataatta ttttgatctt gatatacttg    1800
gatgatggca tgcagcag ctatatgtgg attttttttag ccctgccttc atacgctatt    1860
tatttgcttg gtactgtttc ttttgtcgat gctcaccctg ttgtttggtg atacttctgc    1920
ag                                                                    1922

<210> SEQ ID NO 42
<211> LENGTH: 850
<212> TYPE: DNA
<213> ORGANISM: Zea mays subsp. Mexicana

<400> SEQUENCE: 42
gtcgtgcccc tctctagaga taatgagcat tgcatgtcta agttataaaa aattaccaca     60 tattttttt tgtcacactt gtgtttgaag tgcagtttat ctatctctat acatatattt    120
aaacttcact atatgaataa tatagtctat agtattaaaa taatatcaat gttttagatg    180
attatataac tgaactgcta gacatggtct aaaggacaac cgagtatttt gacaacatga    240
ctctacagtt ttatctttt agtgtgcatg tgttctttt acttttgcaa atagcttcac      300
```

```
ctatataata cttcatccat tttattagta catccattta ctaaattttt agtacatcta      360
ttttattcta ttttagcctc taaattaaga aaacttaaac tctattttag tttttttattt    420 aataatttag atataaaata gaataaaata aagtgactaa aaaataacta aatacctttt      480
aagaaataaa aaaactaagg aaccattttt cttgttccga gtagataatg acagcctgtt     540
caacgccgtc gacgagtcta acggacacca accagcgaac cagcagcgtc gcgtcgggcc    600
aagcgaagca gacggcacgg catctctgta gctgcctctg gacccctctc gagagttccg    660
ctccaccgtt ggacttgctc cgctgtcggc atccagaaat tgcgtggcgg agcggcagac    720
gtgagccggc acggcaggcg gcctcctctc acggcaccgg cagctacggg ggattccttt    780
cccaccgctc cttcgctttc ccttcctcgc ccgccgtaat aaatagaccc cctccacacc    840
ctctttcccc                                                           850

<210> SEQ ID NO 43
<211> LENGTH: 78
<212> TYPE: DNA
<213> ORGANISM: Zea mays subsp. Mexicana

<400> SEQUENCE: 43
aacctcgtgt tcgttcggag cgcgcacaca cacaaccaga tctcccccaa atccacccgt      60
cggcacctcc gcttcaag                                                   78

<210> SEQ ID NO 44
<211> LENGTH: 994
<212> TYPE: DNA
<213> ORGANISM: Zea mays subsp. Mexicana

<400> SEQUENCE: 44
gtacgccgct catcctcctc cccccctct ctctaccttc tctagatcgg cgtttcggtc       60
catggttagg gcccggtagt tctacttctg ttcatgtttg tgttagatcc gtgtttgtgt    120
tagatccgtg ctgctagatt tcgtacacgg atgcgacctg tacatcagac atgttctgat    180
tgctaacttg ccagtgtttc tctttgggga atcctgggat ggctctagcc gttccgcaga    240
cgggatcgat ttcatgaatt ttttttgttt cgttgcatag ggtttggttt gcccttttcc    300
tttatttcaa tatatgccgt gcacttgttt gtcgggtcat cttttcatgt ttttttttggc    360 ttggttgtga tgatgtggtc tggttgggcg gtcgttctag atcggagtag aatactgtttt    420 caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgtttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900 ggatttttt agccctgcct tcatacgcta ttatttgct tggtactgtt tcttttgtcg    960
atgctcaccc tgttgtttgg tgatacttct gcag                                994

<210> SEQ ID NO 45
<211> LENGTH: 1971
<212> TYPE: DNA
```

<213> ORGANISM: Zea mays subsp. Mexicana

<400> SEQUENCE: 45

```
gtcgtgcccc tctctagaga taaagagcat tgcatgtcta agttataaaa aattaccaca     60
tattttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240
tacagtttta tctttttagt gtgcatgtgt tctccttttt tttttgcaaa tagcttcacc    300
tatataatac ttcatccatt ttattagtac atccatttag ggtttagggt taatggtttt    360
tatagactaa ttttttagt acatctattt tattctattt tagcctctaa attaagaaaa    420
ctaaaactct attttagttt ttttatttaa taatttagat ataaaataga ataaaataaa    480
gtgactaaaa attaaacaaa tacccttttaa gaaattaaaa aaactaagga aacattttc    540
ttgtttcgag tagataatgc cagcctgtta acgccgtcg acgagtctaa cggacaccaa    600
ccagcgaacc agcagcgtcg cgtcgggcca agcgaagcag acggcacggc atctctgtcg    660
ctgcctctgg accctctcg agagttccgc tccaccgttg acttgctcc gctgtcggca    720
tccagaaatt gcgtggcgga gcggcagacg tgagccggca cggcaggcgg cctcctcctc    780
ctctcacggc accggcagct acggggatt cctttcccac cgctccttcg ctttcccttc    840
ctcgcccgcc gtaataaata gacacccct ccacaccttc tttccccaac ctcgtgttgt    900
tcggagcgca cacacacaca accagatctc ccccaaatcc accgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctctttgggg aatcctggga tggctctagc cgttccgcag   1200
acgggatcga tttcatgatt ttttttgttt cgttgcatag ggtttggttt gcccttttcc   1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc ttttgttcg cttggttgtg atgatgtggt   1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga ttttttagc cctgccttca tacgctattt atttgcttgg   1920
tactgtttct tttgtcgatg ctcaccctgt tgtttggtga tacttctgca g           1971
```

<210> SEQ ID NO 46
<211> LENGTH: 887
<212> TYPE: DNA
<213> ORGANISM: Zea mays subsp. Mexicana

<400> SEQUENCE: 46

```
gtcgtgcccc tctctagaga taaagagcat tgcatgtcta agttataaaa aattaccaca     60
```

```
tattttttt   gtcacacttg   tttgaagtgc   agtttatcta   tctttataca   tatatttaaa    120
ctttactcta  cgaataatat   aatctatagt   actacaataa   tatcagtgtt   ttagagaatc    180
atataaatga  acagttagac   atggtctaaa   ggacaattga   gtattttgac   aacaggactc    240
tacagtttta  tcttttagt    gtgcatgtgt   tctccttttt   ttttgcaaa    tagcttcacc    300 tatataatac  ttcatccatt   ttattagtac   atccatttag   gtttagggt    taatggtttt    360 tatagactaa  ttttttagt    acatctattt   tattctattt   tagcctctaa   attaagaaaa    420
ctaaaactct  attttagttt   ttttatttaa   taatttagat   ataaaataga   ataaaataaa    480
gtgactaaaa  attaaacaaa   tacccttaa    gaaattaaaa   aaactaagga   aacattttc     540 ttgtttcgag  tagataatgc   cagcctgtta   aacgccgtcg   acgagtctaa   cggacaccaa    600
ccagcgaacc  agcagcgtcg   cgtcgggcca   agcgaagcag   acggcacggc   atctctgtcg    660
ctgcctctgg  acccctctcg   agagttccgc   tccaccgttg   gacttgctcc   gctgtcggca    720
tccagaaatt  gcgtggcgga   gcggcagacg   tgagccggca   cggcaggcgg   cctcctcctc    780
ctctcacggc  accggcagct   acggggattt   cctttcccac   cgctccttcg   ctttcccttc    840
ctcgcccgcc  gtaataaata   gacaccccct   ccacaccttc   tttcccc                   887

<210> SEQ ID NO 47
<211> LENGTH: 77
<212> TYPE: DNA
<213> ORGANISM: Zea mays subsp. Mexicana

<400> SEQUENCE: 47
aacctcgtgt  tgttcggagc   gcacacacac   acaaccagat   ctcccccaaa   tccacccgtc    60
ggcacctccg  cttcaag                                                          77

<210> SEQ ID NO 48
<211> LENGTH: 1007
<212> TYPE: DNA
<213> ORGANISM: Zea mays subsp. Mexicana

<400> SEQUENCE: 48
gtacgccgct  catcctcccc   ccccctctc    taccttctct   agatcggcgt   tccggtccat    60
ggttagggcc  cggtagttct   acttctgttc   atgtttgtgt   tagatccgtg   tttgtgttag    120
atccgtgctg  ctagcgttcg   tacacggatg   cgacctgtac   gtcagacacg   ttctgattgc    180
taacttgcca  gtgtttctct   tggggaatc    ctgggatggc   tctagccgtt   ccgcagacgg    240
gatcgatttc  atgattttt    ttgtttcgtt   gcatagggtt   tggtttgccc   ttttccttta    300
tttcaatata  tgccgtgcac   ttgtttgtcg   ggtcatcttt   tcatgctttt   ttttgtcttg    360
gttgtgatga  tgtggtctgg   ttgggcggtc   gttctagatc   ggagaagaat   tctgtttcaa    420
actacctggt  ggatttatta   attttggatc   tgtatgtgtg   tgccatacat   attcatagtt    480
acgaattgaa  gatgatggat   ggaaatatcg   atctaggata   ggtatacatg   ttgatgcggg    540
ttttactgat  gcatatacag   agatgctttt   tgttcgcttg   gttgtgatga   tgtggtctgg    600
ttgggcggtc  gttcattcgt   tctagatcgg   agtagaatac   tgtttcaaac   tacctggtgt    660
atttattaat  tttggaactg   tatgtgtgtg   tcatacatct   tcatagttac   gagtttaaga    720
tggatggaaa  tatcgatcta   ggataggtat   acatgttgat   gtgggtttta   ctgatgcata    780
tacatgatgg  catatgcagc   atctattcat   atgctctaac   cttgagtacc   tatctattat    840
aataaacaag  tatgttttat   aattattttg   atcttgatat   acttggatga   tggcatatgc    900
```

| | |
|---|---|
| agcagctata tgtggatttt tttagccctg ccttcatacg ctatttattt gcttggtact | 960 |
| gtttcttttg tcgatgctca ccctgttgtt tggtgatact tctgcag | 1007 |

<210> SEQ ID NO 49
<211> LENGTH: 2005
<212> TYPE: DNA
<213> ORGANISM: Zea mays subsp. Mexicana

<400> SEQUENCE: 49

| | |
|---|---|
| gtcgtgcccc tctctagaga taaagagcat tgcatgtcta aagtataaaa aattaccaca | 60 |
| tatttttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatctttt agtgtgcatg tgatctctct gttttttttg caaatagctt gacctatata | 300 |
| atacttcatc cattttatta gtacatccat ttaggattta gggttgatgg tttctataga | 360 |
| ctaattttta gtacatccat tttattcttt ttagtctcta aattttttaa aactaaaact | 420 |
| ctattttagt tttttattta ataatttaga tataaaatga aataaaataa attgactaca | 480 |
| aataaaacaa atacccttta agaaataaaa aaactaagca aacattttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| accccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt cctttcccac cgctccttcg cttcccttc ctcgcccgcc | 840 |
| gtaataaata gacacccct ccacccctc ttcccaac ctcgtgttcg ttcggagcgc | 900 |
| acacacgc aaccagatct cccccaaatc cagccgtcgg cacctccgct tcaaggtacg | 960 |
| ccgctcatcc tccccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggttttact gatgcatata cagagatgct ttttttctcg cttggttgtg atgatatggt | 1320 |
| ctggttgggc ggtcgttcta gatcggagta gaatactgtt tcaaactacc tggtggatttt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt taagatgat | 1500 |
| ggatggaaat atcgatctag ataggtata catgttgatg cgggttttac tgatgcatat | 1560 |
| acagagatgc ttttttttcgc ttggttgtga tgatgtggtc tggttgggcg gtcgttctag | 1620 |
| atcggagtag aatactgttt caaactacct ggtggattta ttaattttgt atctttatgt | 1680 |
| gtgtgccata catcttcata gttacgagtt taagatgatg gatggaaata ttgatctagg | 1740 |
| ataggtatac atgttgatgt gggttttact gatgcatata catgatggca tatgcggcat | 1800 |
| ctattcatat gctctaacct tgagtaccta tctattataa taaacaagta tgttttataa | 1860 |
| ttattttgat cttgatatac ttggatgatg gcatatgcag cagctatatg tggattttt | 1920 |
| agccctgcct tcatacgcta tttatttgct tggtactgtt tcttttgtcc gatgctcacc | 1980 |
| ctgttgttgg gtgatacttc tgcag | 2005 |

<210> SEQ ID NO 50
<211> LENGTH: 877
<212> TYPE: DNA
<213> ORGANISM: Zea mays subsp. Mexicana

<400> SEQUENCE: 50

```
gtcgtgcccc tctctagaga taaagagcat tgcatgtcta aagtataaaa aattaccaca       60
tattttttg tcacacttat ttgaagtgta gtttatctat ctctatacat atatttaaac      120
ttcactctac aaataatata gtctataata ctaaataat attagtgttt tagaggatca      180
tataaataaa ctgctagaca tggtctaaag gataattgaa tattttgaca atctacagtt     240
ttatctttt agtgtgcatg tgatctctct gttttttttg caaatagctt gacctatata     300
atacttcatc cattttatta gtacatccat ttaggattta gggttgatgg tttctataga    360
ctaatttta gtacatccat tttattcttt ttagtctcta aattttttaa aactaaaact      420
ctattttagt tttttattta ataatttaga tataaaatga aataaaataa attgactaca    480
aataaaacaa atacccttta agaaataaaa aaactaagca acattttc ttgtttcgag       540
tagataatga caggctgttc aacgccgtcg acgagtctaa cggacaccaa ccagcgaacc    600
agcagcgtcg cgtcgggcca agcgaagcag acggcacggc atctctgtag ctgcctctgg    660
acccctctcg agagttccgc tccaccgttg gacttgctcc gctgtcggca tccagaaatt   720
gcgtggcgga gcggcagacg tgaggcggca cggcaggcgg cctcttcctc ctctcacggc   780
accggcagct acggggatt cctttcccac cgctccttcg ctttcccttc ctcgcccgcc    840
gtaataaata gacacccct ccacaccctc tttcccc                              877
```

<210> SEQ ID NO 51
<211> LENGTH: 78
<212> TYPE: DNA
<213> ORGANISM: Zea mays subsp. Mexicana

<400> SEQUENCE: 51

```
aacctcgtgt tcgttcggag cgcacacaca cgcaaccaga tctcccccaa atccagccgt       60
cggcacctcc gcttcaag                                                     78
```

<210> SEQ ID NO 52
<211> LENGTH: 1050
<212> TYPE: DNA
<213> ORGANISM: Zea mays subsp. Mexicana

<400> SEQUENCE: 52

```
gtacgccgct catcctcccc cccccctct ctctaccttc tctagatcgg cgatccggtc       60
catggttagg gcccggtagt tctacttctg ttcatgtttg tgttagagca aacatgttca     120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct   480
ggtggattta ttaaaggatc tgtatgtatg tgcctacatc ttcatagtta cgagtttaag   540
atgatggatg gaaatatcga tctaggatag gtatacatgt tgatgcgggt tttactgatg    600
```

```
catatacaga gatgcttttt ttcgcttggt tgtgatgatg tggtctggtt gggcggtcgt        660
tctagatcgg agtagaatac tgtttcaaac tacctggtgg atttattaat tttgtatctt        720
tatgtgtgtg ccatacatct tcatagttac gagtttaaga tgatggatgg aaatatttgat       780 ctaggatagg tatacatgtt gatgtgggtt ttactgatgc atatacatga tggcatatgc        840
ggcatctatt catatgctct aaccttgagt acctatctat tataataaac aagtatgttt        900
tataattatt ttgatcttga tatacttgga tgatggcata tgcagcagct atatgtggat        960
tttttagccc tgccttcata cgctatttat ttgcttggta ctgtttcttt tgtccgatgc       1020
tcaccctgtt gttgggtgat acttctgcag                                        1050

<210> SEQ ID NO 53
<211> LENGTH: 2005
<212> TYPE: DNA
<213> ORGANISM: Zea mays subsp. Mexicana

<400> SEQUENCE: 53
gtcgtgcccc tctctagaga taaagagcat tgcatgtcta aagtataaaa aattaccaca         60
tatttttttg tcacacttat ttgaagtgta gtttatctat ctctatacat atatttaaac        120
ttcactctac aaataatata gtctataata ctaaaataat attagtgttt tagaggatca        180
tataaataaa ctgctagaca tggtctaaag gataattgaa tattttgaca atctacagtt        240
ttatcttttt agtgtgcatg tgatctctct gtttttttttg caaatagctt gacctatata       300
atacttcatc cattttatta gtacatccat ttaggattta gggttgatgg tttctataga        360
ctaattttta gtacatccat tttattcttt ttagtctcta aattttttaa aactaaaact        420
ctattttagt ttttttattta ataatttaga tataaaatga aataaaataa attgactaca       480
aataaaacaa atacccttta agaaatagaa aaactaagca aacattttc ttgtttcgag         540 tagataatga caggctgttc aacgccgtcg acgagtctaa cggacaccaa ccagcgaacc        600
agcagcgtcg cgtcgggcca agcgaagcag acggcacggc atctctgtag ctgcctctgg        660 accctctcg agagttccgc tccaccgttg gacttgctcc gctgtcggca tccagaaatt         720
gcgtggcgga gcggcagacg tgaggcggca cggcaggcgg cctcttcctc ctctcacggc        780
accggcagct acgggggatt cctttcccac cgctccttcg cttttccttc ctcgcccgcc        840
gtaataaata gacaccccct ccacaccctc tttcccaac ctcgtgttcg ttcggagcgc         900
acacacacgc aaccagatct cccccaaatc cagccgtcgg cacctccgct tcaaggtacg        960
ccgctcatcc tcccccccc cctctctcta ccttctctag atcggcgatc cggtccatgg       1020
ttagggcccg gtagttctac ttctgttcat gtttgtgtta gagcaaacat gttcatgttc       1080
atgtttgtga tgatgtggtc tggttgggcg gtcgttctag atcggagtag gatactgttt      1140
caagctacct ggtggattta ttaatttttgt atctgtatgt gtgtgccata catcttcata      1200
gttacgagtt taagatgatg gatggaaata tcgatctagg ataggtatac atgttgatgc      1260
gggttttact gatgcatata cagagatgct tttttctcg cttggttgtg atgatatggt       1320
ctggttgggc ggtcgttcta gatcggagta gaatactgtt tcaaactacc tggtggatttt      1380 attaaaggat aaagggtcgt tctagatcgg agtagaatac tgtttcaaac tacctggtgg      1440
atttattaaa ggatctgtat gtatgtgcct acatcttcat agttacgagt ttaagatgat      1500
ggatggaaat atcgatctag gataggtata catgttgatg cgggttttac tgatgcatat      1560
acagagatgc ttttttcgc ttggttgtga tgatgtggtc tggttgggcg gtcgttctag      1620
atcggagtag aatactgttt caaactacct ggtggattta ttaattttgt atctttatgt      1680
```

```
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggattttt    1920 agccctgcct tcatacgcta tttatttgct tggtactgtt tcttttgtcc gatgctcacc   1980
ctgttgtttg gtgatacttc tgcag                                         2005

<210> SEQ ID NO 54
<211> LENGTH: 1050
<212> TYPE: DNA
<213> ORGANISM: Zea mays subsp. Mexicana

<400> SEQUENCE: 54
gtacgccgct catcctcccc ccccccctct ctctaccttc tctagatcgg cgatccggtc     60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480 ggtggatttta ttaaaggatc tgtatgtatg tgcctacatc ttcatagtta cgagtttaag    540
atgatggatg gaaatatcga tctaggatag gtatacatgt tgatgcgggt tttactgatg    600
catatacaga gatgcttttt ttcgcttggt tgtgatgatg tggtctggtt gggcggtcgt    660
tctagatcgg agtagaatac tgtttcaaac tacctggtgg atttattaat tttgtatctt    720
tatgtgtgtg ccatacatct tcatagttac gagtttaaga tgatggatgg aaatattgat    780
ctaggatagg tatacatgtt gatgtgggtt ttactgatgc atatacatga tggcatatgc    840
ggcatctatt catatgctct aaccttgagt acctatctat tataataaac aagtatgttt    900
tataattatt ttgatcttga tatacttgga tgatggcata tgcagcagct atatgtggat    960
tttttagccc tgccttcata cgctattat ttgcttggta ctgttctttt tgtccgatgc   1020
tcaccctgtt gtttggtgat acttctgcag                                   1050

<210> SEQ ID NO 55
<211> LENGTH: 1632
<212> TYPE: DNA
<213> ORGANISM: Sorghum bicolor

<400> SEQUENCE: 55
ccaagtccaa atgtcaattc ccttgaagat gatctatttt tatcttttgc attttgttat     60
ggaagtttgc aaatagcaac aaatgctaag tcaatttgcc aaagtctttg gagatgctct    120
tagtctataa ttgaacaata tttgtaaaat acaaaaaaaa atagtactat ttttatttta    180
aaaaattttt ggaagtaaac aaggccgagg atggggaaac ggaagtccaa cacgtcgttt    240
tctaagttgg gctcaaaagc ccatcacgga actgacctgc tatgggtcgg aggagagcgc    300
gtccagatgg ttccagaggc tggtggtggt gggccaaacg cggaactccg ccaccgccac    360
ggcctcgtgc gcaagcgcag cgcgttgccg tgagccgtga cgtaaccctc cgttgcccac    420
```

```
gataaaagct ccaccccga ccccggcccc ccgatttccc ctacggacca gtctccccc      480 gatcgcaatc gcgaattcgt cgcaccatcg gcacgcagac gaacgaagca aggctctccc    540
catcggctcg tcaaggtatg cgttccctag atttgttccc ttcctctctc ggtttgtcta    600
tatatatgca tgtatggtcg attcccgatc tcgtcgattc tcggtttcgc cttccgtacg    660
aagattcgtt tagattgttc atatgttctg ttgtgttacc agattgatcg gatcaacttg    720
atccagttat cttcgctcct ccgattagat ccgtttctat ttcagtatat atatactagt    780
atagtatcta gggttcacac tgttgaccga ctggttactt ggaattgatc cgtgctgagt    840
tcagttgttg ccgtccataa aggcccgtgc tattgtctgt tctgaaacga atcctgtag     900 atttcttagg gttagtgttc aattcatcaa aaggttgatt agtgaattat caaatttgag    960
agggttaaat cattctcatc atgttgtctc gaatgtaatc ccaaagatat tatagactgt    1020
gtttcgattt gatggattga tttgtgtatc atctaaatca acaaggctaa gtcatcagtt    1080
catagaatca tgtttaggtt tccgttcaat agactagttt tatcaatata taaaattata    1140
agaagggtag ggtaaatcac gttgcctcaa atgccatcct gtatggtttg gtttcaattc    1200
aattagtttg gttgattagg gtatgctctg gattaagatg gttaaatctt ccctagcatc    1260
ttccctgcct atccttactt gatccgtttc ggatatgttg gaagtacagc gagcttattt    1320
catgttgata gtgacccctt tcagattata ctattgaata ttgtatgttt gccacttctg    1380
tatgttgaat tatcctgcta aattagcaat ggaattagca tattggcaat ggtatgcat    1440 ggacctaatc aggacggatg tggttatgtt agtttcaatt cattgtcaat tcattgttca    1500
cctgcgttag atatatatga tgattttttac gtgtagttca tagttcttga gttttggatc   1560
tttcttatct gatatatgct ttcctgtgcc tgtgctttat tgtgtcttac catgcgattt    1620
ttgtctatgc ag                                                         1632

<210> SEQ ID NO 56
<211> LENGTH: 401
<212> TYPE: DNA
<213> ORGANISM: Sorghum bicolor

<400> SEQUENCE: 56
ccaagtccaa atgtcaattc ccttgaagat gatctatttt tatcttttgc attttgttat     60
ggaagtttgc aaatagcaac aaatgctaag tcaatttgcc aaagtctttg gagatgctct    120
tagtctataa ttgaacaata tttgtaaaat acaaaaaaaa atagtactat tttttatttta   180 aaaaatttt ggaagtaaac aaggccgagg atggggaaac ggaagtccaa cacgtcgttt     240
tctaagttgg gctcaaaagc ccatcacgga actgacctgc tatgggtcgg aggagagcgc    300
gtccagatgg ttccagaggc tggtggtggt gggccaaacg cggaactccg ccaccgccac    360
ggcctcgtgc gcaagcgcag cgcgttgccg tgagccgtga c                        401

<210> SEQ ID NO 57
<211> LENGTH: 154
<212> TYPE: DNA
<213> ORGANISM: Sorghum bicolor

<400> SEQUENCE: 57
gtaaccctcc gttgcccacg ataaaagctc caccccgac cccggccccc cgatttcccc     60
tacggaccag tctcccccg atcgcaatcg cgaattcgtc gcaccatcgg cacgcagacg    120
aacgaagcaa ggctctcccc atcggctcgt caag                                 154
```

<210> SEQ ID NO 58
<211> LENGTH: 1077
<212> TYPE: DNA
<213> ORGANISM: Sorghum bicolor

<400> SEQUENCE: 58

| | | | | | |
|---|---|---|---|---|---|
| gtatgcgttc | cctagatttg | ttcccttcct | ctctcggttt | gtctatatat | atgcatgtat | 60 |
| ggtcgattcc | cgatctcgtc | gattctcggt | ttcgccttcc | gtacgaagat | tcgtttagat | 120 |
| tgttcatatg | ttctgttgtg | ttaccagatt | gatcggatca | acttgatcca | gttatcttcg | 180 |
| ctcctccgat | tagatccgtt | tctatttcag | tatatatata | ctagtatagt | atctagggtt | 240 |
| cacactgttg | accgactggt | tacttggaat | tgatccgtgc | tgagttcagt | tgttgccgtc | 300 |
| cataaaggcc | cgtgctattg | tctgttctga | aacgaaatcc | tgtagatttc | ttagggttag | 360 |
| tgttcaattc | atcaaaaggt | tgattagtga | attatcaaat | ttgagagggt | taaatcattc | 420 |
| tcatcatgtt | gtctcgaatg | taatcccaaa | gatattatag | actgtgtttc | gatttgatgg | 480 |
| attgatttgt | gtatcatcta | aatcaacaag | gctaagtcat | cagttcatag | aatcatgttt | 540 |
| aggtttccgt | tcaatagact | agttttatca | atatataaaa | ttataagaag | ggtagggtaa | 600 |
| atcacgttgc | ctcaaatgcc | atcctgtatg | gtttggtttc | aattcaatta | gtttggttga | 660 |
| ttagggtatg | ctctggatta | agatggttaa | atcttcccta | gcatcttccc | tgcctatcct | 720 |
| tacttgatcc | gtttcggata | tgttggaagt | acagcgagct | tatttcatgt | tgatagtgac | 780 |
| ccctttcaga | ttatactatt | gaatattgta | tgtttgccac | ttctgtatgt | tgaattatcc | 840 |
| tgctaaatta | gcaatggaat | tagcatattg | gcaattggta | tgcatggacc | taatcaggac | 900 |
| ggatgtggtt | atgttagttt | caattcattg | tcaattcatt | gttcacctgc | gttagatata | 960 |
| tatgatgatt | tttacgtgta | gttcatagtt | cttgagtttt | ggatcttct | tatctgatat | 1020 |
| atgctttcct | gtgcctgtgc | tttattgtgt | cttaccatgc | gattttgtc | tatgcag | 1077 |

<210> SEQ ID NO 59
<211> LENGTH: 2000
<212> TYPE: DNA
<213> ORGANISM: Sorghum bicolor

<400> SEQUENCE: 59

| | | | | | |
|---|---|---|---|---|---|
| cactagctgc | gcatgataaa | gccacaagcc | aaaattaatt | attatgggtg | agaataaata | 60 |
| cgtaccagca | ccggccatag | aaaaagtaca | ttattaaagg | tctaatttgg | aaacagtctg | 120 |
| aaaacgacgt | gcgctgcaga | ggtaaatgta | atttttcggca | ctaaaaccat | tatcaactaa | 180 |
| ttcattcaat | aacagttatt | tagaaaatgt | atagctcgct | ctaaaaaaac | agtttagaaa | 240 |
| aacagtcaaa | ataattcgac | caacaaacag | ttaataaggt | tcattaaata | tataatgcac | 300 |
| ggtgctattt | gatcttttaa | aggaaaaaga | ggaaatagtcg | tgggcgccag | gcgggaattg | 360 |
| gggcgcggga | gtctgccgga | cgacgcgttc | cgtccgaacg | gccggacccg | acgaggcccc | 420 |
| cccgccgccc | cacgtcgcag | aaccgtccgt | gggtggtaat | ctggccgggt | acaccagccg | 480 |
| tccccttggg | cggcctcaca | gcactgggct | cacacgtgag | ttttgttctg | ggcttcggat | 540 |
| cgcaccatat | gggcctcggc | atcagaaaga | cggggcccgt | ctgggataga | agagacagga | 600 |
| acctcctcgt | ggattccaga | agccagccac | gagcgaccac | cgacgcggag | gatactcgtc | 660 |
| gtccaagtcc | aacacggcgg | gcgggcgggc | ggacgcgtgg | gctgggctaa | ctgcctaacc | 720 |
| ttaacctcca | aggcacgcca | aggcccgctt | ctcccacccg | acataaatat | cccccccatcc | 780 |
| aggcaaggcg | cagagcctca | gaccagattc | cgatcaatca | cccataagct | cccccccaaat | 840 |

```
ctgttcctcg tctccgtct cgcggtttcc tacttccctc ggacgcctcc ggcaagtcgc      900
tcgaccgcgc gattccgccc gctcaaggta tcaactcggt tcaccactcc aatctacgtc      960
tgatttagat gttacttcca tctatgtcta atttagatgt tactccgatg cgattggatt     1020
atgtttatgc ggtttgcact gctctggaaa ctggaatcta gggtttcgag tgatttgatc     1080
gatcgcgatc tgtgatttcg ttgcgccttg tgtatgcttg gagtgatcta ggcttgtata     1140
tgcggcatcg cgatctgacg cggttgcttt gtagaggctg ggggtctagg ctgtgatttt     1200
agaatcaaat aaagctgttc cttaccgtag atgtttccta catgttctgt ccagtactcc     1260
agtgctatat tcacattgtt tgaggcttga gttttgtcga tcagtggtca tgagaaaaat     1320
atatctcatg attttagagg cacctattgg gaaaggtaga tggttccgtt ttacatgttt     1380
tatagacctt gtggcatggc tcctttgttc tatgggtgct ttattttcct gaataacagt     1440
aatgcgagac tggtctatgg gtgctttgac cagtaatgcg agactagtta tttgatcatg     1500
gtgcagttcc tagtgattac gaacaacaat ttggtagctc agttcattca gcattggttt     1560
ctacgatcct tatcatttta cttctgaatg aatttattta tttaagatat tacagtgcaa     1620
taaactgctg tataatatca gtaacaaact gctattacta gtaaatgcct agattcataa     1680
taattcatta ttctacttga aaatgatctt aggcctttt atgcggtcct acgcatcctt      1740
ccacaggact tgctgtttgt ttgttttttg taatccctcg ctgggacgca gaatggttca     1800
tctgtgctaa taatttttt gcatatataa gtttatagtt ctcattattc atgtggctat      1860
ggtagcctgt aaaatctatt gtaataacat attagtcagc catacatctg ttccaacttg     1920
ctcaattgca aatcatatct ccacttaaag cacatgtttg caagctttct gacaagtttc     1980
tttgtgtttg attgaaacag                                                 2000

<210> SEQ ID NO 60
<211> LENGTH: 791
<212> TYPE: DNA
<213> ORGANISM: Sorghum bicolor

<400> SEQUENCE: 60
cactagctgc gcatgataaa gccacaagcc aaaattaatt attatgggtg agaataaata       60
cgtaccagca ccggccatag aaaaagtaca ttattaaagg tctaatttgg aaacagtctg      120
aaaacgacgt gcgctgcaga ggtaaatgta attttcggca ctaaaaccat tatcaactaa      180
ttcattcaat aacagttatt tagaaaatgt atagctcgct ctaaaaaaac agtttagaaa      240
aacagtcaaa ataattcgac caacaaacag ttaataaggt tcattaaata tataatgcac      300
ggtgctattt gatcttttaa aggaaaaaga ggaatagtcg tgggcgccag gcgggaattg      360
gggcgcggga gtctgccgga cgacgcgttc cgtccgaacg gccggacccg acgaggcccc      420
cccgccgccc cacgtcgcag aaccgtccgt gggtggtaat ctggccgggt acaccagccg      480
tccccttggg cggcctcaca gcactgggct cacacgtgag ttttgttctg ggcttcggat      540
cgcaccatat gggcctcggc atcagaaaga cggggcccgt ctgggataga agagacagga      600
acctcctcgt ggattccaga agccagccac gagcgaccac cgacgcggag gatactcgtc      660
gtccaagtcc aacacggcgg gcgggcgggc ggacgcgtgg gctgggctaa ctgcctaacc      720
ttaacctcca aggcacgcca aggcccgctt ctcccacccg acataaatat ccccccatcc      780
aggcaaggcg c                                                          791

<210> SEQ ID NO 61
<211> LENGTH: 136
```

```
<212> TYPE: DNA
<213> ORGANISM: Sorghum bicolor

<400> SEQUENCE: 61
agagcctcag accagattcc gatcaatcac ccataagctc cccccaaatc tgttcctcgt        60
ctcccgtctc gcggtttcct acttccctcg gacgcctccg gcaagtcgct cgaccgcgcg      120
attccgcccg ctcaag                                                      136

<210> SEQ ID NO 62
<211> LENGTH: 1073
<212> TYPE: DNA
<213> ORGANISM: Sorghum bicolor

<400> SEQUENCE: 62
gtatcaactc ggttcaccac tccaatctac gtctgattta gatgttactt ccatctatgt        60
ctaatttaga tgttactccg atgcgattgg attatgttta tgcggtttgc actgctctgg      120
aaactggaat ctagggtttc gagtgatttg atcgatcgcg atctgtgatt tcgttgcgcc      180
ttgtgtatgc ttggagtgat ctaggcttgt atatgcggca tcgcgatctg acgcggttgc      240
tttgtagagg ctggggtct  aggctgtgat tttagaatca aataaagctg ttccttaccg      300
tagatgtttc ctacatgttc tgtccagtac tccagtgcta tattcacatt gtttgaggct      360
tgagttttgt cgatcagtgg tcatgagaaa aatatatctc atgattttag aggcacctat      420
tgggaaaggt agatggttcc gttttacatg ttttatagac cttgtggcat ggctcctttg      480
ttctatgggt gctttatttt cctgaataac agtaatgcga gactggtcta tgggtgcttt      540
gaccagtaat gcgagactag ttatttgatc atggtgcagt tcctagtgat tacgaacaac      600
aatttggtag ctcagttcat tcagcattgg tttctacgat ccttatcatt ttacttctga      660
atgaatttat ttatttaaga tattacagtg caataaactg ctgtataata tcagtaacaa      720
actgctatta ctagtaaatg cctagattca taataattca ttattctact tgaaaatgat      780
cttaggcctt tttatgcggt cctacgcatc cttccacagg acttgctgtt tgtttgtttt      840
ttgtaatccc tcgctgggac gcagaatggt tcatctgtgc taataatttt tttgcatata      900
taagtttata gttctcatta ttcatgtggc tatggtagcc tgtaaaatct attgtaataa      960
catattagtc agccatacat ctgttccaac ttgctcaatt gcaaatcata tctccactta     1020
aagcacatgt ttgcaagctt tctgacaagt ttctttgtgt ttgattgaaa cag            1073

<210> SEQ ID NO 63
<211> LENGTH: 2064
<212> TYPE: DNA
<213> ORGANISM: Sorghum bicolor

<400> SEQUENCE: 63
cattaaaagt cattatgtgc atgcgtcgta actaacatgg atatgttgct gcactatctc        60
ctcgcactag ctgcgcatga taaagccaca agccaaaatt aattattatg ggtgagaata      120
aatacgtacc agcaccggcc atagaaaaag tacattatta aaggtctaat ttggaaacag      180
tctgaaaacg acgtgcgctg cagaggtaaa tgtaattttc ggcactaaaa ccattatcaa      240
ctaattcatt caataacagt tatttagaaa atgtatagct cgctctaaaa aaacagttta      300
gaaaaacagt caaaataatt cgaccaacaa acagttaata aggttcatta aatatataat      360
gcacggtgct atttgatctt ttaaaggaaa agaggaata  gtcgtgggcg ccaggcggga      420
attggggcgc gggagtctgc cggacgacgc gttccgtccg aacggccgga cccgacgagg      480
```

```
cccccccgcc gccccacgtc gcagaaccgt ccgtgggtgg taatctggcc gggtacacca    540
gccgtcccct tgggcggcct cacagcactg ggctcacacg tgagttttgt tctgggcttc    600
ggatcgcacc atatgggcct cggcatcaga aagacggggc ccgtctggga tagaagagac    660
aggaacctcc tcgtggattc cagaagccag ccacgagcga ccaccgacgc ggaggatact    720
cgtcgtccaa gtccaacacg gcgggcgggc gggcggacgc gtgggctggg ctaactgcct    780
aaccttaacc tccaaggcac gccaaggccc gcttctccca cccgacataa atatcccccc    840
atccaggcaa ggcgcagagc tcagaccag  attccgatca atcacccata agctccccc     900
aaatctgttc ctcgtctccc gtctcgcggt ttcctacttc cctcggacgc ctccggcaag    960
tcgctcgacc gcgcgattcc gcccgctcaa ggtatcaact cggttcacca ctccaatcta   1020
cgtctgattt agatgttact tccatctatg tctaatttag atgttactcc gatgcgattg   1080
gattatgttt atgcggtttg cactgctctg gaaactggaa tctagggttt cgagtgattt   1140
gatcgatcgc gatctgtgat ttcgttgcgc cttgtgtatg cttggagtga tctaggcttg   1200
tatatgcggc atcgcgatct gacgcggttg ctttgtagag gctggggtc  taggctgtga   1260
ttttagaatc aaataaagct gttccttacc gtagatgttt cctacatgtt ctgtccagta   1320
ctccagtgct atattcacat tgtttgaggc ttgagttttg tcgatcagtg gtcatgagaa   1380
aaatatatct catgatttta gaggcaccta ttgggaaagg tagatggttc cgttttacat   1440
gtttataga  ccttgtggca tggctccttt gttctatggg tgctttattt tcctgaataa   1500
cagtaatgcg agactggtct atgggtgctt tgaccagtaa tgcgagacta gttatttgat   1560
catggtgcag ttcctagtga ttacgaacaa caatttggta gctcagttca ttcagcattg   1620
gtttctacga tccttatcat tttacttctg aatgaattta tttatttaag atattacagt   1680
gcaataaact gctgtataat atcagtaaca aactgctatt actagtaaat gcctagattc   1740
ataataattc attattctac ttgaaaatga tcttaggcct ttttatgcgg tcctacgcat   1800
ccttccacag gacttgctgt ttgtttgttt tttgtaatcc ctcgctggga cgcagaatgg   1860
ttcatctgtg ctaataattt ttttgcatat ataagtttat agttctcatt attcatgtgg   1920
ctatggtagc ctgtaaaatc tattgtaata acatattagt cagccataca tctgttccaa   1980
cttgctcaat tgcaaatcat atctccactt aaagcacatg tttgcaagct ttctgacaag   2040
tttctttgtg tttgattgaa acag                                          2064

<210> SEQ ID NO 64
<211> LENGTH: 855
<212> TYPE: DNA
<213> ORGANISM: Sorghum bicolor

<400> SEQUENCE: 64
cattaaaagt cattatgtgc atgcgtcgta actaacatgg atatgttgct gcactatctc     60
ctcgcactag ctgcgcatga taaagccaca agccaaaatt aattattatg ggtgagaata    120
aatacgtacc agcaccggcc atagaaaaag tacattatta aaggtctaat ttggaaacag    180
tctgaaaacg acgtgcgctg cagaggtaaa tgtaattttc ggcactaaaa ccattatcaa    240
ctaattcatt caataacagt tatttagaaa atgtatagct cgctctaaaa aaacagttta    300
gaaaaacagt caaaataatt cgaccaacaa acagttaata aggttcatta aatatataat    360
gcacggtgct atttgatctt ttaaaggaaa aagaggaata gtcgtgggcg ccaggcggga    420
attgggcgc  gggagtctgc cggacgacgc gttccgtccg aacggccgga cccgacgagg    480
cccccccgcc gccccacgtc gcagaaccgt ccgtgggtgg taatctggcc gggtacacca    540
```

```
gccgtccct   tgggcggcct   cacagcactg   ggctcacacg   tgagttttgt   tctgggcttc      600
ggatcgcacc   atatgggcct   cggcatcaga   aagacggggc   ccgtctggga   tagaagagac      660
aggaacctcc   tcgtggattc   cagaagccag   ccacgagcga   ccaccgacgc   ggaggatact      720
cgtcgtccaa   gtccaacacg   gcgggcgggc   gggcggacgc   gtgggctggg   ctaactgcct      780
aaccttaacc   tccaaggcac   gccaaggccc   gcttctccca   cccgacataa   atatccccc       840 atccaggcaa   ggcgc                                                               855

<210> SEQ ID NO 65
<211> LENGTH: 2000
<212> TYPE: DNA
<213> ORGANISM: Sorghum bicolor

<400> SEQUENCE: 65
agaagtaaaa   aaaagttcg    tttcagaatc   ataaaggtaa   gttaaaaaaa   gaccatacaa       60
aaaagaggta   tttaatgata   aactataatc   cagaatttgt   taggatagta   tataagaata      120
agaccttgtt   tagtttcaaa   aaaatttgca   aaattttcca   gattcctcgt   cacatcaaat      180
ctttagaggt   atgcatggag   tattaaatat   agacaagacc   taaataagaa   acatgaaat       240 gttcacgaaa   aaaatcaagc   caatgcatga   tcgaagcaaa   cggtatagta   acggtgttaa      300
cctgatccat   tgatctttgt   aatctttaac   ggccacctac   cgcgggcagc   aaacggcgtc      360
cccctcctcg   atatctccgc   ggcggcctct   ggcttttcc    gcggaattgc   gcggtgggga      420
cggattccac   gagaccgcaa   cgcaaccgcc   tctcgccgct   gggccccaca   ccgctcggtg      480
ccgtagcccg   tagcctcacg   ggattctttc   tccctcctcc   cccgtgtata   aattggcttc      540
atcccctccc   tgcctcatcc   atccaaatcc   cactccccaa   tcccatcccg   tcggagaaat      600
tcatcgaagc   gaagcgaagc   gaatcctccc   gatcctctca   aggtacgcga   gttttcgaat      660
cccctccaga   cccctcgtat   gctttccctg   ttcgttttcg   tcgtagcgtt   tgattaggta      720
tgctttccct   gttcgtgttc   gtcgtagggt   tcgattaggt   cgtgtgaggc   catggcctgc      780
tgtgataaat   ttatttgttg   ttatatcgga   tctgtagtcg   atttgggggt   cgtggtgtag      840
atccgcgggc   tgtgatgaag   ttatttggtg   tgattgtgct   cgcgtgattc   tgcgcgttga      900
gctcgagtag   atctgatggt   tggacgaccg   attggttcgt   tggctggctg   cgctaaggtt      960
gggctgggct   catgttgcgt   tcgctgttgc   gcgtgattcc   gcggatggac   ttgcgcttga     1020
ttgccgccag   atcacgttac   gattatgtga   tttcgtttgg   aacttttag    atttgtagct     1080 tctgcttatt   atatgacaga   tgcgcctact   gctcatatgc   ctgtggtaaa   taatggatgg     1140
ctgtgggtca   aactagttga   ttgtcgagtc   atgtatcata   tacaggtgta   tagacttgcg     1200
tctaattgtt   tgcatgttgc   agttatatga   tttgttttag   attgtttgtt   ccactcatct     1260
aggctgtaaa   agggacacta   cttattagct   tgttgtttaa   tcttttttatt  agtagattat     1320 attggtaatg   ttttactaat   tattattatg   ttatatgtga   cttctgctca   tgcctgatta     1380
taatcataga   tcactgtagt   tgattgttga   atcatgtgtc   aaatacccgt   atacataaca     1440
ctacacattt   gcttagttgt   ttccttaact   catgcaaatt   gaacaccatg   tatgatttgc     1500
atggtgctgt   aatgttaaat   actacagtcc   tgttggtact   tgtttagtaa   gaatctgctt     1560
catacaacta   tatgctatgc   ctgatgataa   tcatatatct   ttgtgtaatt   aataattagt     1620
tgactgttga   ataatgtatc   gagtacatac   catggcacaa   ttgcttagtc   acttccttaa     1680
ccatgcatat   tgaactgacc   ccttcatgtt   ctgctgaatt   gttctattct   gattagacca     1740
```

```
tacatcatgt attgcaatct ttatttgcaa ttgtaatgta atggttcggt tctcaaatgt    1800
taaatgctat agttgtgcta ctttctaatg ttaaatgcta tagctgtgct acttgtaaga    1860
tctgcttcat agtttagtta aattaggatg atgagctttg atgctgtaac tttgtttgat    1920
tatgttcata gttgatcagt ttttgttaga ctcacagtaa cttatggtct cactcttctt    1980
ctggtctttg atgtttgcag                                                2000

<210> SEQ ID NO 66
<211> LENGTH: 565
<212> TYPE: DNA
<213> ORGANISM: Sorghum bicolor

<400> SEQUENCE: 66
agaagtaaaa aaaagttcg tttcagaatc ataaaggtaa gttaaaaaaa gaccatacaa      60
aaaagaggta tttaatgata aactataatc cagaatttgt taggatagta tataagaata    120
agaccttgtt tagtttcaaa aaaatttgca aaattttcca gattcctcgt cacatcaaat    180
ctttagaggt atgcatggag tattaaatat agacaagacc taaataagaa acatgaaat    240 gttcacgaaa aaaatcaagc caatgcatga tcgaagcaaa cggtatagta acggtgttaa    300
cctgatccat tgatctttgt aatctttaac ggccacctac cgcgggcagc aaacggcgtc    360
cccctcctcg atatctccgc ggcggcctct ggcttttttcc gcggaattgc gcggtgggga    420
cggattccac gagaccgcaa cgcaaccgcc tctcgccgct gggccccaca ccgctcggtg    480
ccgtagcccg tagcctcacg ggattctttc tccctcctcc cccgtgtata aattggcttc    540
atcccctccc tgcctcatcc atcca                                          565

<210> SEQ ID NO 67
<211> LENGTH: 77
<212> TYPE: DNA
<213> ORGANISM: Sorghum bicolor

<400> SEQUENCE: 67
aatcccactc cccaatccca tcccgtcgga gaaattcatc gaagcgaagc gaagcgaatc     60
ctcccgatcc tctcaag                                                   77

<210> SEQ ID NO 68
<211> LENGTH: 1358
<212> TYPE: DNA
<213> ORGANISM: Sorghum bicolor

<400> SEQUENCE: 68
gtacgcgagt tttcgaatcc cctccagacc cctcgtatgc tttccctgtt cgttttcgtc     60
gtagcgtttg attaggtatg ctttccctgt tcgtgttcgt cgtagggttc gattaggtcg    120
tgtgaggcca tggcctgctg tgataaattt atttgttgtt atatcggatc tgtagtcgat    180 ttggggggtcg tggtgtagat ccgcgggctg tgatgaagtt atttggtgtg attgtgctcg    240
cgtgattctg cgcgttgagc tcgagtagat ctgatggttg gacgaccgat tggttcgttg    300
gctggctgcg ctaaggttgg gctgggctca tgttgcgttc gctgttgcgc gtgattccgc    360
ggatggactt gcgcttgatt gccgccagat cacgttacga ttatgtgatt tcgtttggaa    420 cttttttagat ttgtagcttc tgcttattat atgacagatg cgcctactgc tcatatgcct    480
gtggtaaata atggatggct gtgggtcaaa ctagttgatt gtcgagtcat gtatcatata    540
caggtgtata gacttgcgtc taattgtttg catgttgcag ttatatgatt tgttttagat    600
tgtttgttcc actcatctag gctgtaaaag ggacactact tattagcttg ttgtttaatc    660
```

```
tttttattag tagattatat tggtaatgtt ttactaatta ttattatgtt atatgtgact      720
tctgctcatg cctgattata atcatagatc actgtagttg attgttgaat catgtgtcaa      780
atacccgtat acataacact acacatttgc ttagttgttt ccttaactca tgcaaattga      840
acaccatgta tgatttgcat ggtgctgtaa tgttaaatac tacagtcctg ttggtacttg      900
tttagtaaga atctgcttca tacaactata tgctatgcct gatgataatc atatatcttt      960
gtgtaattaa taattagttg actgttgaat aatgtatcga gtacatacca tggcacaatt     1020
gcttagtcac ttccttaacc atgcatattg aactgacccc ttcatgttct gctgaattgt     1080
tctattctga ttagaccata catcatgtat tgcaatcttt atttgcaatt gtaatgtaat     1140
ggttcggttc tcaaatgtta aatgctatag ttgtgctact ttctaatgtt aaatgctata     1200
gctgtgctac ttgtaagatc tgcttcatag tttagttaaa ttaggatgat gagctttgat     1260
gctgtaactt tgtttgatta tgttcatagt tgatcagttt ttgttagact cacagtaact     1320
tatggtctca ctcttcttct ggtctttgat gtttgcag                              1358
```

<210> SEQ ID NO 69
<211> LENGTH: 2622
<212> TYPE: DNA
<213> ORGANISM: Setaria italica

<400> SEQUENCE: 69

```
actgccgcga cacgcctcac tggcgggagg gctccgagcg ctctctcccc ggcggccggc       60
ggagcagcga tctggattgg agagaataga ggaaagagag ggaaaaggag agagatagcg      120
caaagagctg aaaagataag gttgtgcggg ctgtggtgat tagaggacca ctaatccctc      180
catctcctaa tgacgcggtg cccaagacca gtgccgcggc acaccagcgt ctaagtgaac      240
ttccgctaac cttccggtca ttgcgcctga aagatgtcat gtggcgaggc cccctctca      300 gtagattgcc aactgcctac cgtgccactc ttccatgcat gattgctccc gtctatcccg      360
tttctcacaa cagatagaca acagtaagca tcactaaagc aagcatgtgt agaaccttaa      420
aaaaaggctt atactaccag tatactatca accagcatgc cgtttttgaa gtatccagga      480
ttagaagctt ctactgcgct tttatattat agctgtggac ctgtggtaac cttttctcttt     540 tggcgcttgc ttaatctcgg ccgtgctggt ccatgcttag gcactaggca gagatagagc      600 cggggggtgaa tggggctaaa gctcagctgc tcgaggggcc gtgggctggt ttccactagc     660
ctacagctgt gccacgtgcg gccgcgcaag ccgaagcaag cacgctgagc cgttggacag      720
cttgtcataa tgccattacg tggattacac gtaactggcc ctgtaactac tcgttcggcc      780
atcatcaaac gacgacgtcc gctaggcgac gacacgggta atgcacgcag ccacccaggc      840
gcgcgcgcta gcggagcacg gtcaggtgac acgggcgtcg tgacgcttcc gagttgaagg      900
ggttaacgcc agaaacagtg tttggccagg gtatgaacat aacaaaaaat attcacacga      960
aagaatggaa gtatggagct gctactgtgt aaatgccaag caggaaactc acgcccgcta     1020
acatccaacg gccaacagct cgacgtgccg gtcagcagag catcggaaca ctggtgattg     1080
gtggagccgg cagtatgcgc cccagcacgg ccgaggtggt ggtggcccgt ggccctgctg     1140
tctgcgcggc tcgggacaac ttgaaactgg gccaccgcct cgtcgcaact cgcaacccgt     1200
tggcggaaga aggaatggcc tcgtaggggc ccgggtagaa tcgaagaatg ttgcgctggg     1260
cttcgattca cataacatgg gcctgaagct ctaaaacgac ggcccggtcg ccgcgcgatg     1320
gaaagagacc ggatcctcct cgtgaattct ggaaggccac acgagagcga cccaccaccg     1380
```

-continued

```
acgcggagga gtcgtgcgtg gtccaacacg gccggcgggc tgggctgcga ccttaaccag    1440
caaggcacgc cacgacccgc cccgccctcg aggcataaat accctcccat cccgttgccg    1500
caagactcag atcagattcc gatccccagt tcttccccaa tcaccttgtg gtctctcgtg    1560
tcgcggttcc cagggacgcc tccggctcgt cgctcgacag cgatctccgc cccagcaagg    1620
tatagattca gttccttgct ccgatcccaa tctggttgag atgttgctcc gatgcgactt    1680
gattatgtca tatatctgcg gtttgcaccg atctgaagcc tagggtttct cgagcgaccc    1740
agttatttgc aatttgcgat ttgctcgttt gttgcgcagc gtagtttatg tttggagtaa    1800
tcgaggattt gtatgcggcg tcggcgctac ctgcttaatc acgccatgtg acgcggttac    1860
ttgcagaggc tgggttctgt tatgtcgtga tctaagaatc tagattaggc tcagtcgttc    1920
ttgctgtcga ctagtttgtt ttgatatcca tgtagtacaa gttacttaaa atttaggtcc    1980
aatatatttt gcatgctttt ggcctgttat tcttgccaac aagttgtcct ggtaaaaagt    2040
agatgtgaaa gtcacgtatt gggacaaatt gatggtttag tgctatagtt ctatagttct    2100
gtgatacatc tatctgattt ttttttggtct attggtgcct aacttatctg aaaatcatgg    2160
aacatgaggc tagtttgatc atggtttagt tcattgtgat taataatgta tgatttagta    2220
gctattttgg tgatcgtgtc attttatttg tgaatgaat cattgtatgt aaatgaagct    2280
agttcagggg ttacgatgta gctggctttg tattctaaag gctgctatta ttcatccatc    2340
gatttcacct atatgtaatc cagagctttt gatgtgaaat ttgtctgatc cttcactagg    2400
aaggacagaa cattgttaat attttggcac atctgtctta ttctcatcct ttgtttgaac    2460
atgttagcct gttcaaacag atactgttgt aatgtcctag ttatataggt acatatgtgt    2520
tctctattga gtttatggac ttttgtgtgt gaagttatat ttcattttgc tcaaaactca    2580
tgtttgcaag ctttctgaca ttattctatt gttctgaaac ag                       2622
```

<210> SEQ ID NO 70
<211> LENGTH: 1492
<212> TYPE: DNA
<213> ORGANISM: Setaria italica

<400> SEQUENCE: 70

```
actgccgcga cacgcctcac tggcgggagg gctccgagcg ctctctcccc ggcggccggc      60
ggagcagcga tctggattgg agagaataga ggaaagagag ggaaaaggag agagatagcg     120
caaagagctg aaaagataag gttgtgcggg ctgtggtgat tagaggacca ctaatccctc     180
catctcctaa tgacgcggtg cccaagacca gtgccgcggc acaccagcgt ctaagtgaac     240
ttccgctaac cttccggtca ttgcgcctga aagatgtcat gtggcgaggc cccctctca     300 gtagattgcc aactgcctac cgtgccactc ttccatgcat gattgctccc gtctatcccg     360
tttctcacaa cagatagaca acagtaagca tcactaaagc aagcatgtgt agaaccttaa     420
aaaaaggctt atactaccag tatactatca accagcatgc cgttttttgaa gtatccagga    480 ttagaagctt ctactgcgct tttatattat agctgtggac ctgtggtaac cttctctttt     540
tggcgcttgc ttaatctcgg ccgtgctggt ccatgcttag gcactaggca gagatagagc     600
cgggggtgaa tgggctaaa gctcagctgc tcgaggggcc gtgggctggt ttccactagc      660
ctacagctgt gccacgtgcg gccgcgcaag ccgaagcaag cacgctgagc cgttggacag     720
cttgtcataa tgccattacg tggattacac gtaactggcc ctgtaactac tcgttcggcc     780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
```

```
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaacccgt   1200
tggcggaaga aggaatggc tcgtagggc cgggtagaa tcgaagaatg ttgcgctggg      1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cc           1492
```

<210> SEQ ID NO 71
<211> LENGTH: 127
<212> TYPE: DNA
<213> ORGANISM: Setaria italica

<400> SEQUENCE: 71

```
cgttgccgca agactcagat cagattccga tccccagttc ttccccaatc accttgtggt     60
ctctcgtgtc gcggttccca gggacgcctc cggctcgtcg ctcgacagcg atctccgccc    120
cagcaag                                                              127
```

<210> SEQ ID NO 72
<211> LENGTH: 1003
<212> TYPE: DNA
<213> ORGANISM: Setaria italica

<400> SEQUENCE: 72

```
gtatagattc agttccttgc tccgatccca atctggttga gatgttgctc cgatgcgact     60
tgattatgtc atatatctgc ggtttgcacc gatctgaagc ctagggtttc tcgagcgacc    120
cagttatttg caatttgcga tttgctcgtt tgttgcgcag cgtagtttat gtttggagta    180
atcgaggatt tgtatgcggc gtcggcgcta cctgcttaat cacgccatgt gacgcggtta    240
cttgcagagg ctgggttctg ttatgtcgtg atctaagaat ctagattagg ctcagtcgtt    300
cttgctgtcg actagtttgt tttgatatcc atgtagtaca agttacttaa aatttaggtc    360
caatatattt tgcatgcttt tggcctgtta ttcttgccaa caagttgtcc tggtaaaaag    420
tagatgtgaa agtcacgtat tgggacaaat tgatggttta gtgctatagt tctatagttc    480
tgtgatacat ctatctgatt tttttggtc tattggtgcc taacttatct gaaaatcatg     540
gaacatgagg ctagtttgat catggtttag ttcattgtga ttaataatgt atgatttagt    600
agctattttg gtgatcgtgt cattttattt gtgaatggaa tcattgtatg taaatgaagc    660
tagttcaggg gttacgatgt agctggcttt gtattctaaa ggctgctatt attcatccat    720
cgatttcacc tatatgtaat ccagagcttt tgatgtgaaa tttgtctgat ccttcactag    780
gaaggacaga acattgttaa tatttggca catctgtctt attctcatcc tttgtttgaa     840
catgttagcc tgttcaaaca gatactgttg taatgtccta gttatatagg tacatatgtg    900
ttctctattg agtttatgga cttttgtgtg tgaagttata tttcatttg ctcaaaactc     960
atgtttgcaa gctttctgac attattctat tgttctgaaa cag                     1003
```

<210> SEQ ID NO 73

<211> LENGTH: 2622
<212> TYPE: DNA
<213> ORGANISM: Setaria italica

<400> SEQUENCE: 73

```
actgccgcga cacgcctcac tggcgggagg gctccgagcg ctctctcccc ggcggccggc    60
ggagcagcga tctggattgg agagaataga ggaaagagag ggaaaaggag agagatagcg   120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga aagatgtcat gtggcgaggc cccctctca   300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgttttgaa gtatccagga   480
ttagaagctt ctactgcgct tttatattat agctgtggac ccgtggtaac ctttctcttt   540
tggcgcttgc ttaatctcgg ccgtgctggt ccatgcttag cactaggca gagatagagc   600
cgggggtgaa tggggctaaa gctcagctgc tcgagggcc gtgggctggt ttccactagc   660
ctacagctgt gccacgtgcg gccgcgcaag ccgaagcaag cacgctgagc cgttggacag   720
cttgtcataa tgccattacg tggattacac gtaactggcc ctgtaactac tcgttcggcc   780
atcatcaaac gacgacgtcc gctaggcgac gacacgggta atgcacgcag ccacccaggc   840
gcgcgcgcta gcggagcacg gtcaggtgac acgggcgtcg tgacgcttcc gagttgaagg   900
ggttaacgcc agaaacagtg tttggccagg gtatgaacat aacaaaaaat attcacacga   960
aagaatggaa gtatggagct gctactgtgt aaatgccaag caggaaactc acgcccgcta  1020
acatccaacg gccaacagct cgacgtgccg gtcagcagag catcggaaca ctggtgattg  1080
gtggagccgg cagtatgcgc cccagcacgg ccgaggtggt ggtggcccgt ggccctgctg  1140
tctgcgcggc tcgggacaac ttgaaactgg gccaccgcct cgtcgcaact cgcaacccgt  1200
tggcggaaga aaggaatggc tcgtaggggc ccgggtagaa tcgaagaatg ttgcgctggg  1260
cttcgattca cataacatgg gcctgaagct ctaaaacgac ggcccggtcg ccgcgcgatg  1320
gaaagagacc ggatcctcct cgtgaattct ggaaggccac acgagagcga cccaccaccg  1380
acgcggagga gtcgtgcgtg gtccaacacg gccggcgggc tgggctgcga ccttaaccag  1440
caaggcacgc cacgacccgc cccgccctcg aggcataaat accctcccat cccgttgccg  1500
caagactcag atcagattcc gatcccagt tcttccccaa tccttgtg gtctctcgtg  1560
tcgcggttcc cagggacgcc tccggctcgt cgctcgacag cgatctccgc cccagcaagg  1620
tatagattca gttccttgct ccgatcccaa tctggttgag atgttgctcc gatgcgactt  1680
gattatgtca tatatctgcg gtttgcaccg atctgaagcc tagggtttct cgagcgaccc  1740
agttatttgc aatttgcgat ttgctcgttt gttgcgcagc gtagtttatg tttggagtaa  1800
tcgaggattt gtatgcggcg tcggcgctac ctgcttaatc acgccatgtg acgcggttac  1860
ttgcagaggc tgggttctgt tatgtcgtga tctaagaatc tagattaggc tcagtcgttc  1920
ttgctgtcga ctagtttgtt ttgatatcca tgtagtacaa gttacttaaa atttaggtcc  1980
aatatatttt gcatgctttt ggcctgttat tcttgccaac aagttgtcct ggtaaaaagt  2040
agatgtgaaa gtcacgtatt gggacaaatt gatggtttag tgctatagtt ctatagttct  2100
gtgatacatc tatctgattt tttttggtct attggtgcct aacttatctg aaaatcatgg  2160
aacatgaggc tagtttgatc atggtttagt tcattgtgat taataatgta tgatttagta  2220
```

```
gctatttttgg tgatcgtgtc attttatttg tgaatggaat cattgtatgt aaatgaagct    2280
agttcagggg ttacgatgta gctggctttg tattctaaag gctgctatta ttcatccatc    2340
gatttcacct atatgtaatc cagagctttt gatgtgaaat ttgtctgatc cttcactagg    2400
aaggacagaa cattgttaat attttggcac atctgtctta ttctcatcct ttgtttgaac    2460
atgttagcct gttcaaacag atactgttgt aatgtcctag ttatataggt acatatgtgt    2520
tctctattga gttatggac ttttgtgtgt gaagttatat ttcattttgc tcaaaactca    2580
tgtttgcaag ctttctgaca ttattctatt gttctgaaac ag                       2622

<210> SEQ ID NO 74
<211> LENGTH: 1492
<212> TYPE: DNA
<213> ORGANISM: Setaria italica

<400> SEQUENCE: 74
actgccgcga cacgcctcac tggcgggagg gctccgagcg ctctctcccc ggcggccggc      60
ggagcagcga tctggattgg agagaataga ggaaagagag ggaaaaggag agagatagcg     120
caaagagctg aaaagataag gttgtgcggg ctgtggtgat tagaggacca ctaatccctc     180
catctcctaa tgacgcggtg cccaagacca gtgccgcggc acaccagcgt ctaagtgaac     240
ttccgctaac cttccggtca ttgcgcctga aagatgtcat gtggcgaggc cccctctca     300 gtagattgcc aactgcctac cgtgccactc ttccatgcat gattgctccc gtctatcccg     360
tttctcacaa cagatagaca acagtaagca tcactaaagc aagcatgtgt agaaccttaa     420
aaaaaggctt atactaccag tatactatca accagcatgc cgttttttgaa gtatccagga     480 ttagaagctt ctactgcgct tttatattat agctgtggac ccgtggtaac ctttctcttt     540
tggcgcttgc ttaatctcgg ccgtgctggt ccatgcttag gcactaggca gagatagagc     600
cgggggtgaa tggggctaaa gctcagctgc tcgaggggcc gtgggctggt ttccactagc     660
ctacagctgt gccacgtgcg gccgcgcaag ccgaagcaag cacgctgagc cgttggacag     720
cttgtcataa tgccattacg tggattacac gtaactggcc ctgtaactac tcgttcggcc     780
atcatcaaac gacgacgtcc gctaggcgac gacacgggta atgcacgcag ccacccaggc     840
gcgcgcgcta gcggagcacg gtcaggtgac acgggcgtcg tgacgcttcc gagttgaagg     900
ggttaacgcc agaaacagtg tttggccagg gtatgaacat aacaaaaaat attcacacga     960
aagaatggaa gtatggagct gctactgtgt aaatgccaag caggaaactc acgcccgcta    1020
acatccaacg gccaacagct cgacgtgccg gtcagcagag catcggaaca ctggtgattg    1080
gtggagccgg cagtatgcgc cccagcacgg ccgaggtggt ggtggcccgt ggccctgctg    1140
tctgcgcggc tcgggacaac ttgaaactgg gccaccgcct cgtcgcaact cgcaacccgt    1200
tggcggaaga aaggaatggc tcgtaggggc ccgggtagaa tcgaagaatg ttgcgctggg    1260
cttcgattca cataacatgg gcctgaagct ctaaaacgac ggcccggtcg ccgcgcgatg    1320
gaaagagacc ggatcctcct cgtgaattct ggaaggccac acgagagcga cccaccaccg    1380
acgcggagga gtcgtgcgtg gtccaacacg gccggcgggc tgggctgcga ccttaaccag    1440
caaggcacgc cacgacccgc cccgcccctcg aggcataaat accctcccat cc            1492

<210> SEQ ID NO 75
<211> LENGTH: 2164
<212> TYPE: DNA
<213> ORGANISM: Setaria italica
```

<400> SEQUENCE: 75

```
gccgttttg aagtatccag gattagaagc ttctactgcg cttttatatt atagctgtgg      60
acctgtggta acctttctct tttggcgctt gcttaatctc ggccgtgctg gtccatgctt    120
aggcactagg cagagataga gccggggtg aatggggcta aagctcagct gctcgagggg    180
ccgtgggctg gtttccacta gcctacagct gtgccacgtg cggccgcgca agccgaagca    240
agcacgctga gccgttggac agcttgtcat aatgccatta cgtggattac acgtaactgg    300
ccctgtaact actcgttcgg ccatcatcaa acgacgacgt ccgctaggcg acgacacggg    360
taatgcacgc agccacccag gcgcgcgcgc tagcggagca cggtcaggtg acacgggcgt    420
cgtgacgctt ccgagttgaa ggggttaacg ccagaaacag tgtttggcca gggtatgaac    480
ataacaaaaa atattcacac gaaagaatgg aagtatggag ctgctactgt gtaaatgcca    540
agcaggaaac tcacgcccgc taacatccaa cggccaacag ctcgacgtgc cggtcagcag    600
agcatcggaa cactggtgat tggtggagcc ggcagtatgc gccccagcac ggccgaggtg    660
gtggtggccc gtggccctgc tgtctgcgcg gctcgggaca acttgaaact gggccaccgc    720
ctcgtcgcaa ctcgcaaccc gttggcggaa gaaaggaatg gctcgtaggg gcccgggtag    780
aatcgaagaa tgttgcgctg ggcttcgatt cacataacat gggcctgaag ctctaaaacg    840
acggcccggt cgccgcgcga tggaaagaga ccggatcctc ctcgtgaatt ctggaaggcc    900
acacgagagc gacccaccac cgacgcggag gagtcgtgcg tggtccaaca cggccggcgg    960
gctgggctgc gaccttaacc agcaaggcac gccacgaccc gccccgccct cgaggcataa   1020
ataccctccc atcccgttgc cgcaagactc agatcagatt ccgatcccca gttcttcccc   1080
aatcaccttg tggtctctcg tgtcgcggtt cccaggacg cctccggctc gtcgctcgac    1140
agcgatctcc gccccagcaa ggtatagatt cagttccttg ctccgatccc aatctggttg   1200
agatgttgct ccgatgcgac ttgattatgt catatatctg cggtttgcac cgatctgaag   1260
cctaggttt ctcgagcgac ccagttattt gcaatttgcg atttgctcgt ttgttgcgca    1320
gcgtagttta tgtttggagt aatcgaggat ttgtatgcgg cgtcggcgct acctgcttaa   1380
tcacgccatg tgacgcggtt acttgcagag gctgggttct gttatgtcgt gatctaagaa   1440
tctagattag gctcagtcgt tcttgctgtc gactagtttg ttttgatatc catgtagtac    1500
aagttactta aaatttaggt ccaatatatt ttgcatgctt ttggcctgtt attcttgcca   1560
acaagttgtc ctggtaaaaa gtagatgtga aagtcacgta ttgggacaaa ttgatggttt   1620
agtgctatag ttctatagtt ctgtgataca tctatctgat tttttttggt ctattggtgc   1680
ctaacttatc tgaaaatcat ggaacatgag gctagtttga tcatggttta gttcattgtg   1740
attaataatg tatgatttag tagctatttt ggtgatcgtg tcattttatt tgtgaatgga   1800
atcattgtat gtaaatgaag ctagttcagg ggttacgatg tagctggctt tgtattctaa   1860
aggctgctat tattcatcca tcgatttcac ctatatgtaa tccagagctt ttgatgtgaa   1920
atttgtctga tccttcacta ggaaggacag aacattgtta atattttggc acatctgtct   1980
tattctcatc ctttgtttga acatgttagc ctgttcaaac agatactgtt gtaatgtcct   2040
agttatatag gtacatatgt gttctctatt gagtttatgg acttttgtgt gtgaagttat   2100
atttcatttt gctcaaaact catgtttgca agctttctga cattattcta ttgttctgaa   2160
acag                                                                2164
```

<210> SEQ ID NO 76
<211> LENGTH: 1034

```
<212> TYPE: DNA
<213> ORGANISM: Setaria italica

<400> SEQUENCE: 76
gccgtttttg aagtatccag gattagaagc ttctactgcg cttttatatt atagctgtgg    60
acctgtggta acctttctct tttggcgctt gcttaatctc ggccgtgctg gtccatgctt   120
aggcactagg cagagataga gccggggtg aatggggcta aagctcagct gctcgagggg    180
ccgtgggctg gtttccacta gcctacagct gtgccacgtg cggccgcgca agccaagca    240 agcacgctga gccgttggac agcttgtcat aatgccatta cgtggattac acgtaactgg   300
ccctgtaact actcgttcgg ccatcatcaa acgacgacgt ccgctaggcg acgacacggg   360
taatgcacgc agccacccag gcgcgcgcgc tagcggagca cggtcaggtg acacgggcgt   420
cgtgacgctt ccgagttgaa gggttaacg ccagaaacag tgtttggcca gggtatgaac    480
ataacaaaaa atattcacac gaaagaatgg aagtatggag ctgctactgt gtaaatgcca   540
agcaggaaac tcacgcccgc taacatccaa cggccaacag ctcgacgtgc cggtcagcag   600
agcatcggaa cactggtgat tggtggagcc ggcagtatgc gccccagcac ggccgaggtg   660
gtggtggccc gtgccctgc tgtctgcgcg gctcgggaca acttgaaact gggccaccgc    720
ctcgtcgcaa ctcgcaaccc gttggcggaa gaaaggaatg gctcgtaggg gcccgggtag   780
aatcgaagaa tgttgcgctg ggcttcgatt cacataacat gggcctgaag ctctaaaacg   840
acggcccggt cgccgcgcga tggaaagaga ccggatcctc ctcgtgaatt ctggaaggcc   900
acacgagagc gacccaccac cgacgcggag gagtcgtgcg tggtccaaca cggccggcgg   960
gctgggctgc gaccttaacc agcaaggcac gccacgaccc gccccgccct cgaggcataa  1020 atacctccc atcc                                                    1034

<210> SEQ ID NO 77
<211> LENGTH: 1810
<212> TYPE: DNA
<213> ORGANISM: Setaria italica

<400> SEQUENCE: 77
cacgggtaat gcacgcagcc acccaggcgc gcgcgctagc ggagcacggt caggtgacac    60
gggcgtcgtg acgcttccga gttgaagggg ttaacgccag aaacagtgtt tggccagggt   120
atgaacataa caaaaatat tcacacgaaa gaatggaagt atggagctgc tactgtgtaa    180
atgccaagca ggaaactcac gcccgctaac atccaacggc caacagctcg acgtgccggt   240
cagcagagca tcggaacact ggtgattggt ggagccggca gtatgcgccc cagcacggcc   300
gaggtggtgg tggcccgtgg ccctgctgtc tgcgcggctc gggacaactt gaaactgggc   360
caccgcctcg tcgcaactcg caacccgttg gcggaagaaa ggaatggctc gtaggggccc   420
gggtagaatc gaagaatgtt gcgctgggct tcgattcaca taacatgggc ctgaagctct   480
aaaacgacgg cccggtcgcc gcgcgatgga aagagaccgg atcctcctcg tgaattctgg   540
aaggccacac gagagcgacc caccaccgac gcggaggagt cgtgcgtggt ccaacacggc   600
cggcgggctg gctgcgacc ttaaccagca aggcacgcca cgacccgccc cgccctcgag    660
gcataaatac cctcccatcc cgttgccgca agactcagat cagattccga tccccagttc   720
ttccccaatc accttgtggt ctctcgtgtc gcggttccca gggacgcctc cggctcgtcg   780
ctcgacagcg atccgccc cagcaaggta tagattcagt tccttgctcc gatcccaatc    840
tggttgagat gttgctccga tgcgacttga ttatgtcata tatctgcggt ttgcaccgat   900
```

```
ctgaagccta gggtttctcg agcgacccag ttatttgcaa tttgcgattt gctcgtttgt    960
tgcgcagcgt agtttatgtt tggagtaatc gaggatttgt atgcggcgtc ggcgctacct   1020
gcttaatcac gccatgtgac gcggttactt gcagaggctg ggttctgtta tgtcgtgatc   1080
taagaatcta gattaggctc agtcgttctt gctgtcgact agtttgtttt gatatccatg   1140
tagtacaagt tacttaaaat ttaggtccaa tatattttgc atgcttttgg cctgttattc   1200
ttgccaacaa gttgtcctgg taaaaagtag atgtgaaagt cacgtattgg gacaaattga   1260
tggtttagtg ctatagttct atagttctgt gatacatcta tctgattttt tttggtctat   1320
tggtgcctaa cttatctgaa aatcatggaa catgaggcta gtttgatcat ggtttagttc   1380
attgtgatta ataatgtatg atttagtagc tattttggtg atcgtgtcat tttatttgtg   1440
aatggaatca ttgtatgtaa atgaagctag ttcaggggtt acgatgtagc tggctttgta   1500
ttctaaaggc tgctattatt catccatcga tttcacctat atgtaatcca gagcttttga   1560
tgtgaaattt gtctgatcct tcactaggaa ggacagaaca ttgttaatat tttggcacat   1620
ctgtcttatt ctcatccttt gtttgaacat gttagcctgt tcaaacagat actgttgtaa   1680
tgtcctagtt ataggtac atatgtgttc tctattgagt ttatggactt ttgtgtgtga   1740
agttatattt cattttgctc aaaactcatg tttgcaagct ttctgacatt attctattgt   1800
tctgaaacag                                                          1810

<210> SEQ ID NO 78
<211> LENGTH: 680
<212> TYPE: DNA
<213> ORGANISM: Setaria italica

<400> SEQUENCE: 78
cacgggtaat gcacgcagcc acccaggcgc gcgcgctagc ggagcacggt caggtgacac     60
gggcgtcgtg acgcttccga gttgaagggg ttaacgccag aaacagtgtt tggccagggt    120
atgaacataa caaaaaatat tcacacgaaa gaatggaagt atggagctgc tactgtgtaa    180
atgccaagca ggaaactcac gcccgctaac atccaacggc caacagctcg acgtgccggt    240
cagcagagca tcggaacact ggtgattggt ggagccggca gtatgcgccc cagcacggcc    300
gaggtggtgg tggcccgtgg ccctgctgtc tgcgcggctc gggacaactt gaaactgggc    360
caccgcctcg tcgcaactcg caacccgttg gcggaagaaa ggaatggctc gtaggggccc    420
gggtagaatc gaagaatgtt gcgctgggct tcgattcaca taacatgggc ctgaagctct    480
aaaacgacgg cccggtcgcc gcgcgatgga aagagaccgg atcctcctcg tgaattctgg    540
aaggccacac gagagcgacc caccaccgac gcggaggagt cgtgcgtggt ccaacacggc    600
cggcgggctg ggctgcgacc ttaaccagca aggcacgcca cgacccgccc cgcccctcgag   660
gcataaatac cctcccatcc                                                680

<210> SEQ ID NO 79
<211> LENGTH: 1940
<212> TYPE: DNA
<213> ORGANISM: Coix lacryma-jobi

<400> SEQUENCE: 79
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
tagggggggcg gtactcgcac cgtggttgtt tcctgttatg taatatcgga tgggggagca    240
```

```
gtcggctagg ttggtcccat cggtactggt cgtccctag tgcgctagat gcgcgatgtt    300
tgtcctcaaa aactcttttc ttcttaataa caatcatacg caaatttttt gcgtattcga    360 gaaaaaaga agattctatc tgttttttt ttgaaatggc tccaatttat aggaggagcc     420
cgtttaacgg cgtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccctcc agcttccttc gccacatcct      840
ctcatcatct tctctcgtgt agcacgcgca gcccgatccc caatcccctc tcctcgcgag    900
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaatttta ggaagactgt tccaaaccat ctgctggatt tattaaattt    1440
ggatctggat gtgtcacata caccttcata attaaaatgg atggaaatat ctcttatctt   1500
ttagatatgg ataggcattt atatgatgct gtgagtttta ctagtacttt cttagaatat   1560 atgtacttt ttagacggaa tattgatatg tatacatgtg tagatacatg aagcaacatg    1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg cttttttaatt tatcttgata   1800 tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag                                               1940

<210> SEQ ID NO 80
<211> LENGTH: 837
<212> TYPE: DNA
<213> ORGANISM: Coix lacryma-jobi

<400> SEQUENCE: 80
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca    180 tagggggggcg gtactcgcac cgtggttgtt tcctgttatg taatatcgga tgggggagca    240
gtcggctagg ttggtcccat cggtactggt cgtccctag tgcgctagat gcgcgatgtt    300
tgtcctcaaa aactcttttc ttcttaataa caatcatacg caaatttttt gcgtattcga    360
```

```
gaaaaaaaga agattctatc tgttttttt ttgaaatggc tccaatttat aggaggagcc    420
cgtttaacgg cgtcgacaaa tctaacggac accaaccagc gaatgagcga acccaccagc    480
gccaagctag ccaagcgaag cagacggccg agacgctgac acccttgcct tggcgcggca    540
tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccccctccc agcttccttc gccacat      837
```

<210> SEQ ID NO 81
<211> LENGTH: 86
<212> TYPE: DNA
<213> ORGANISM: Coix lacryma-jobi

<400> SEQUENCE: 81

```
cctctcatca tcttctctcg tgtagcacgc gcagcccgat ccccaatccc ctctcctcgc    60
gagcctcgtc gatccctcgc ttcaag                                         86
```

<210> SEQ ID NO 82
<211> LENGTH: 1017
<212> TYPE: DNA
<213> ORGANISM: Coix lacryma-jobi

<400> SEQUENCE: 82

```
gtatggctat cgtccttcct ctctctctct ttaccttatc tagatcggcg atccatggtt    60
agggcctgct agttctccgt tcgtgtttgt cgatggctgt gaggcacaat agatccgtcg   120
gcgttatgat ggttagcctg tcatgctctt gcgatctgtg gttcctttag gaaaggcatt   180
aatttaatcc ctgatggttc gagatcggtg atccatggtt agtaccctaa gctgtggagt   240
cgggtttaga tccgcgctgt tcgtaggcga tctgttctga ttgttaactt gtcagtacct   300
gcgaatcctc ggtggttcta gctggttcgg agatcagatc gattccatta tctgctatac   360
atcttgtttc gttgcctagg ctccgtttaa tctatccatc gtatgatgtt agcctttgat   420
atgattcgat cgtgctagct atgtcctgtg gacttaattg tcaggtccta atttttagga   480
agactgttcc aaaccatctg ctggatttat taaatttgga tctggatgtg tcacatacac   540
cttcataatt aaaatggatg gaaatatctc ttatctttta gatatggata ggcatttata   600
tgatgctgtg agttttacta gtactttctt agaatatatg tacttttta gacggaatat   660
tgatatgtat acatgtgtag atacatgaag caacatgctg ctgtagtcta ataattcctg   720
ttcatctaat aatcaagtat gtatatgttc tgtgtgtttt attggtattt gattagatat   780
atacatgctt agatacatac atgaagcagc atgctgctac agtttaatca ttattgttta   840
tccaataaac aaacatgctt tttaatttat cttgatatgc ttggatgacg gaatatgcag   900
agattttaag tacccagcat catgagcatg catgaccctg cgttagtatg ctgtttattt   960
gcttgagact ctttcttttg tagatactca ccctgtttc tggtgatcct actgcag     1017
```

<210> SEQ ID NO 83
<211> LENGTH: 1845
<212> TYPE: DNA
<213> ORGANISM: Coix lacryma-jobi

<400> SEQUENCE: 83

```
ctatctgttt tcttttgcc ctgaaagagt gaagtcatca tcatatttac catggcgcgc    60
```

```
gtaggagcgc ttcgtcgaag acccataggg gggcggtact cgcaccgtgg ttgtttcctg      120
ttatgtaata tcggatgggg gagcagtcgg ctaggttggt cccatcggta ctggtcgtcc      180
cctagtgcgc tagatgcgcg atgtttgtcc tcaaaaactc ttttcttctt aataacaatc     240
atacgcaaat ttttgcgta ttcgagaaaa aagaagatt ctatctgttt tttttttgaa       300
atggctccaa tttataggag gagcccgttt aacggcgtcg acaaatctaa cggacaccaa     360
ccagcgaatg agcgaaccca ccagcgccaa gctagccaag cgaagcagac ggccgagacg     420
ctgacaccct tgccttggcg cggcatctcc gtcgctggct cgctggctct ggccccttcg     480
cgagagttcc ggtccacctc cacctgtgtc ggtttccaac tccgttccgc cttcgcgtgg     540
gacttgttcc gttcatccgt tggcggcatc cggaaattgc gtggcgtaga gcacggggcc     600
ctcctctcac acggcacgga accgtcacga gctcacggca ccggcagcac ggcggggatt     660
ccttccccac caccgctcct tccctttccc ttcctcgccc gccatcataa atagccaccc     720
ctcccagctt cctttcgccac atcctctcat catcttctct cgtgtagcac gcgcagcccg   780
atccccaatc ccctctcctc gcgagcctcg tcgatccctc gcttcaaggt atggctatcg     840
tccttcctct ctctctcttt accttatcta gatcggcgat ccatggttag ggcctgctag     900
ttctccgttc gtgtttgtcg atggctgtga ggcacaatag atccgtcggc gttatgatgg     960
ttagcctgtc atgctcttgc gatctgtggt tcctttagga aaggcattaa tttaatccct    1020
gatggttcga gatcggtgat ccatggttag taccctaagc tgtggagtcg ggtttagatc   1080
cgcgctgttc gtaggcgatc tgttctgatt gttaacttgt cagtacctgc gaatcctcgg    1140
tggttctagc tggttcggag atcagatcga ttccattatc tgctatacat cttgtttcgt   1200
tgcctaggct ccgtttaatc tatccatcgt atgatgttag cctttgatat gattcgatcg    1260
tgctagctat gtcctgtgga cttaattgtc aggtcctaat ttttaggaag actgttccaa    1320
accatctgct ggatttatta aatttggatc tggatgtgtc acatacacct tcataattaa    1380
aatggatgga aatatctctt atctttttaga tatggatagg catttatatg atgctgtgag   1440
ttttactagt acttcttag aatatatgta ctttttaga cggaatattg atatgtatac      1500
atgtgtagat acatgaagca acatgctgct gtagtctaat aattcctgtt catctaataa    1560
tcaagtatgt atatgttctg tgtgttttat tggtatttga ttagatatat acatgcttag    1620
atacatacat gaagcagcat gctgctacag tttaatcatt attgtttatc caataaacaa    1680
acatgctttt taatttatct tgatatgctt ggatgacgga atatgcagag atttaagta    1740 cccagcatca tgagcatgca tgaccctgcg ttagtatgct gtttatttgc ttgagactct    1800
ttcttttgta gatactcacc ctgtttctg gtgatcctac tgcag                      1845
```

<210> SEQ ID NO 84
<211> LENGTH: 742
<212> TYPE: DNA
<213> ORGANISM: Coix lacryma-jobi

<400> SEQUENCE: 84

```
ctatctgttt tcttttgcc ctgaaagagt gaagtcatca tcatatttac catggcgcgc       60
gtaggagcgc ttcgtcgaag acccataggg gggcggtact cgcaccgtgg ttgtttcctg     120
ttatgtaata tcggatgggg gagcagtcgg ctaggttggt cccatcggta ctggtcgtcc     180
cctagtgcgc tagatgcgcg atgtttgtcc tcaaaaactc ttttcttctt aataacaatc    240
atacgcaaat ttttgcgta ttcgagaaaa aagaagatt ctatctgttt tttttttgaa      300
```

```
atggctccaa tttataggag gagcccgttt aacggcgtcg acaaatctaa cggacaccaa      360
ccagcgaatg agcgaaccca ccagcgccaa gctagccaag cgaagcagac ggccgagacg      420
ctgacaccct tgccttggcg cggcatctcc gtcgctggct cgctggctct ggccccttcg      480
cgagagttcc ggtccacctc cacctgtgtc ggtttccaac tccgttccgc cttcgcgtgg      540
gacttgttcc gttcatccgt tggcggcatc cggaaattgc gtggcgtaga gcacggggcc      600
ctcctctcac acggcacgga accgtcacga gctcacggca ccggcagcac ggcggggatt      660
ccttccccac caccgctcct ccctttccc ttcctcgccc gccatcataa atagccaccc       720
ctcccagctt ccttcgccac at                                               742
```

`<210>` SEQ ID NO 85
`<211>` LENGTH: 1504
`<212>` TYPE: DNA
`<213>` ORGANISM: Coix lacryma-jobi

`<400>` SEQUENCE: 85

```
caaatctaac ggacaccaac cagcgaatga gcgaacccac cagcgccaag ctagccaagc       60
gaagcagacg gccgagacgc tgacaccctt gccttggcgc ggcatctccg tcgctggctc      120
gctggctctg gccccttcgc gagagttccg gtccacctcc acctgtgtcg gtttccaact      180
ccgttccgcc ttcgcgtggg acttgttccg ttcatccgtt ggcggcatcc ggaaattgcg      240
tggcgtagag cacggggccc tcctctcaca cggcacggaa ccgtcacgag ctcacggcac      300
cggcagcacg gcggggattc cttccccacc accgctcctt cctttccct tcctcgcccg      360 ccatcataaa tagccacccc tcccagcttc cttcgccaca tcctctcatc atcttctctc      420
gtgtagcacg cgcagcccga tccccaatcc cctctcctcg cgagcctcgt cgatccctcg      480
cttcaaggta tggctatcgt ccttcctctc tctctcttta ccttatctag atcggcgatc      540
catggttagg gcctgctagt tctccgttcg tgtttgtcga tggctgtgag gcacaataga      600
tccgtcggcg ttatgatggt tagcctgtca tgctcttgcg atctgtggtt cctttaggaa      660
aggcattaat ttaatccctg atggttcgag atcggtgatc catggttagt accctaagct      720
gtggagtcgg gttagatcc gcgctgttcg taggcgatct gttctgattg ttaacttgtc       780
agtacctgcg aatcctcggt ggttctagct ggttcggaga tcagatcgat tccattatct      840
gctatacatc ttgtttcgtt gcctaggctc cgtttaatct atccatcgta tgatgttagc      900
ctttgatatg attcgatcgt gctagctatg tcctgtggac ttaattgtca ggtcctaatt      960
tttaggaaga ctgttccaaa ccatctgctg gatttattaa atttggatct ggatgtgtca     1020
catacacctt cataattaaa atggatggaa atatctctta tcttttagat atggataggc     1080
atttatatga tgctgtgagt tttactagta cttttcttaga atatatgtac ttttttagac     1140
ggaatattga tatgtataca tgtgtagata catgaagcaa catgctgctg tagtctaata     1200
attcctgttc atctaataat caagtatgta tatgttctgt gtgttttatt ggtatttgat     1260
tagatatata catgcttaga tacatacatg aagcagcatg ctgctacagt ttaatcatta     1320
ttgtttatcc aataaacaaa catgcttttt aatttatctt gatatgcttg gatgacggaa     1380
tatgcagaga tttaagtac ccagcatcat gagcatgcat gaccctgcgt tagtatgctg      1440
tttatttgct tgagactctt tcttttgtag atactcaccc tgttttctgg tgatcctact     1500
gcag                                                                  1504
```

`<210>` SEQ ID NO 86
`<211>` LENGTH: 401

```
<212> TYPE: DNA
<213> ORGANISM: Coix lacryma-jobi

<400> SEQUENCE: 86
caaatctaac ggacaccaac cagcgaatga gcgaacccac cagcgccaag ctagccaagc      60
gaagcagacg gccgagacgc tgacacccct tgccttggcg ccgcatctccg tcgctggctc    120
gctggctctg gcccttcgc gagagttccg gtccacctcc acctgtgtcg gtttccaact     180
ccgttccgcc ttcgcgtggg acttgttccg ttcatccgtt ggcggcatcc ggaaattgcg    240
tggcgtagag cacggggccc tcctctcaca cggcacggaa ccgtcacgag ctcacggcac    300
cggcagcacg gcggggattc cttccccacc accgctcctt ccctttccct tcctcgcccg    360
ccatcataaa tagccacccc tcccagcttc cttcgccaca t                         401

<210> SEQ ID NO 87
<211> LENGTH: 1157
<212> TYPE: DNA
<213> ORGANISM: Coix lacryma-jobi

<400> SEQUENCE: 87
ccttcctcgc ccgccatcat aaatagccac ccctcccagc ttccttcgcc acatcctctc      60
atcatcttct ctcgtgtagc acgcgcagcc cgatccccaa tccctctcc tcgcgagcct     120
cgtcgatccc tcgcttcaag gtatggctat cgtccttcct ctctctctct ttaccttatc    180
tagatcggcg atccatggtt agggcctgct agttctccgt tcgtgtttgt cgatggctgt    240
gaggcacaat agatccgtcg gcgttatgat ggttagcctg tcatgctctt gcgatctgtg    300
gttcctttag gaaaggcatt aatttaatcc ctgatggttc gagatcggtg atccatggtt    360
agtaccctaa gctgtggagt cgggtttaga tccgcgctgt tcgtaggcga tctgttctga    420
ttgttaactt gtcagtacct gcgaatcctc ggtggttcta gctggttcgg agatcagatc    480
gattccatta tctgctatac atcttgtttc gttgccagg ctccgtttaa tctatccatc     540
gtatgatgtt agcctttgat atgattcgat cgtgctagct atgtcctgtg gacttaattg    600
tcaggtccta attttaggaa agactgttcc aaaccatctg ctggatttat taaatttgga    660
tctggatgtg tcacatacac cttcataatt aaaatggatg gaaatatctc ttatctttta    720
gatatggata ggcatttata tgatgctgtg agttttacta gtactttctt agaatatatg    780
tactttttta gacggaatat tgatatgtat acatgtgtag atacatgaag caacatgctg    840
ctgtagtcta ataattcctg ttcatctaat aatcaagtat gtatatgttc tgtgtgtttt    900
attggtattt gattagatat atacatgctt agatacatac atgaagcagc atgctgctac    960
agtttaatca ttattgttta tccaataaac aaacatgctt tttaatttat cttgatatgc   1020
ttggatgacg gaatatgcag agattttaag tacccagcat catgagcatg catgaccctg   1080
cgttagtatg ctgtttattt gcttgagact cttctttttg tagatactca ccctgttttc   1140
tggtgatcct actgcag                                                  1157

<210> SEQ ID NO 88
<211> LENGTH: 54
<212> TYPE: DNA
<213> ORGANISM: Coix lacryma-jobi

<400> SEQUENCE: 88
ccttcctcgc ccgccatcat aaatagccac ccctcccagc ttccttcgcc acat            54

<210> SEQ ID NO 89
```

```
<211> LENGTH: 798
<212> TYPE: DNA
<213> ORGANISM: Coix lacryma-jobi

<400> SEQUENCE: 89
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180
taggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactcttttc ttcttaataa caatcatacg caaatttttt gcgtattcga     360
gaaaaaaga agattctatc tgtttttttt ttgaaatggc tccaatttat aggaggagcc      420
cgtttaacgg cgtcgacaaa tctaacggac accaaccagc gaatgagcga acccaccagc     480
gccaagctag ccaagcgaag cagacggccg agacgctgac accttgcct tggcgcggca      540
tctccgtcgc tggctcgctg gctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggcctcct ctcacacggc acggaaccgt      720
cacgagctca cggcaccggc agcacggcgg ggattccttc cccaccaccg ctccttccct     780
ttcccttcct cgcccgcc                                                    798

<210> SEQ ID NO 90
<211> LENGTH: 3393
<212> TYPE: DNA
<213> ORGANISM: Coix lacryma-jobi

<400> SEQUENCE: 90
ggttctatac aacaccacac actgtgtgag tgtgtgacca gtggccaact tttgttcagt      60
tcaacgatcc tggcctttcc gggcacccaa tacactaatt aatctattgc agctaacctc     120
aaaagaaatg catttgcagt tgtctgtcct aatcaatcta ctagcagact cacattattg     180
atgtaggaaa taaaattcag cctgtgacgt ggatgcaaca actgcactgc acaggatacc     240
atcttagccg ttgtgtcaca atttgctttg ctaatgtttt gagaaaccca gctttgacaa     300
acgtaagatc gatgagggcc ttacgtttgg cacaatatgt attgtaatcc ggcacggcaa     360
gttagactcg gtagtgttta gccggcatct ttatgtttgg cacaatttaa tttaattcgg     420
catggtaggt tagactgcag cgtgagccgg tcattgcaag ttattatgac atgttagagc     480
atctccaaca agttggaaaa atgacttgg tatatcatgg tatatcatga gttttagcaa      540
cttattaatt catttgacaa gtaaaaaaaa gatccctctt caacaatttg ctattccaac     600
tcgctaaaat aaaaaaaaat taggctcacc taggccgatc tgcgttgccg cgggagagga     660
gggtaaaaga ttttgcgcta ggagaggtgg aggaacaggg cgcgggagcc ggccacggtg     720
aaatcacggg atagcaacct cacccgcgcg cgcaaattta cgcgtgtggc atggaggaat     780
agaaagttgg aaaagatagc aagttcattt agggagttgt tggagaagaa tatttgtgct     840
tttaccaaat ttataagaat agcaagtgag aatagagagt tgttggagat gctcaacaaa     900
tatacacaat aaagtggtat aataagcggc aagttattat gacatatata agagcaagta     960
tacaataagg tgaactgtta tatcgatcga tttttttttg agcacatatc gatcgaattt    1020
attgtaagat agaaaagaga agatataaaa acttatagtg atgaacaata ataatataaa    1080
gattattttt aaactatgaa aacaataacc gaactactcg ctctcttcta attagtaaag    1140
```

```
taaaggcttc tcattgtata tatataaaaa aattcgttct gatttcttat attcaagacg    1200
gggagagtgc tgagtgctaa cttactagtc tacgagagaa gcttcaaatc aaacagtgta    1260
ctatagggct tacacaattt ttctgaggga agcgattgtc tgaaatgaac taaaaggctg    1320
agagctggaa aaagtagctt attctgattc tgtgaagtga ttctccatgc tgattttaaa    1380
agtttatgat aaaaaatcaa agagaataac tttcagccac agaatcactt ctctcagaga    1440
atcaacttat atggagaatc agaatcagat ggagctctac caaactggcc ctaggcatta    1500
acctaccatg gatcacatcg taaaaaaaaa accctaccat ggatcctatc tgttttcttt    1560
ttgccctgaa agagtgaagt catcatcata tttaccatgg cgcgcgtagg agcgcttcgt    1620
cgaagaccca taggggggcg gtactcgcac cgtggttgtt tcctgttatg taatatcgga    1680
tgggggagca gtcggctagg ttggtcccat cggtactggt cgtcccctag tgcgctagat    1740
gcgcgatgtt tgtcctcaaa aactctttc ttcttaataa caatcatacg caaatttttt    1800
gcgtattcga gaaaaaaaga agattctatc tgttttttt ttgaaatggc tccaatttat    1860
aggaggagcc cgtttaacgg cgtcgacaaa tctaacggac accaaccagc gaatgagcga    1920
acccaccagc gccaagctag ccaagcgaag cagacggccg agacgctgac acccttgcct    1980
tggcgcggca tctccgtcgc tggctcgctg gctctggccc cttcgcgaga gttccggtcc    2040
acctccacct gtgtcggttt ccaactccgt tccgccttcg cgtgggactt gttccgttca    2100
tccgttggcg gcatccggaa attgcgtggc gtagagcacg gggccctcct ctcacacggc    2160
acggaaccgt cacgagctca cggcaccggc agcacggcgg ggattccttc cccaccaccg    2220
ctccttccct ttcccttcct cgcccgccat cataaatagc caccctccc agcttccttc    2280 gccacatcct ctcatcatct tctctcgtgt agcacgcgca gcccgatccc caatcccctc    2340
tcctcgcgag cctcgtcgat ccctcgcttc aaggtatggc tatcgtcctt cctctctctc    2400
tctttacctt atctagatcg gcgatccatg gttagggcct gctagttctc cgttcgtgtt    2460
tgtcgatggc tgtgaggcac aatagatccg tcggcgttat gatggttagc ctgtcatgct    2520
cttgcgatct gtggttcctt taggaaaggc attaatttaa tccctgatgg ttcgagatcg    2580
gtgatccatg gttagtaccc taagctgtgg agtcgggttt agatccgcgc tgttcgtagg    2640
cgatctgttc tgattgttaa cttgtcagta cctgcgaatc ctcggtggtt ctagctggtt    2700
cggagatcag atcgattcca ttatctgcta tacatcttgt ttcgttgcct aggctccgtt    2760
taatctatcc atcgtatgat gttagccttt gatatgattc gatcgtgcta gctatgtcct    2820
gtggacttaa ttgtcaggtc ctaatttta ggaagactgt tccaaaccat ctgctggatt    2880
tattaaattt ggatctggat gtgtcacata caccttcata attaaaatgg atggaaatat    2940
ctcttatctt ttagatatgg ataggcattt atatgatgct gtgagtttta ctagtacttt    3000
cttagaatat atgtactttt ttagacggaa tattgatatg tatacatgtg tagatacatg    3060
aagcaacatg ctgctgtagt ctaataattc ctgttcatct aataatcaag tatgtatatg    3120
ttctgtgtgt tttattggta tttgattaga tatatacatg cttagataca tacatgaagc    3180
agcatgctgc tacagtttaa tcattattgt ttatccaata aacaaacatg cttttttaatt    3240 tatcttgata tgcttggatg acggaatatg cagagatttt aagtacccag catcatgagc    3300
atgcatgacc ctgcgttagt atgctgttta tttgcttgag actctttctt ttgtagatac    3360
tcaccctgtt ttctggtgat cctactgcag gtg                                 3393
```

<210> SEQ ID NO 91

```
<211> LENGTH: 2287
<212> TYPE: DNA
<213> ORGANISM: Coix lacryma-jobi

<400> SEQUENCE: 91
ggttctatac aacaccacac actgtgtgag tgtgtgacca gtggccaact tttgttcagt      60
tcaacgatcc tggcctttcc gggcacccaa tacactaatt aatctattgc agctaacctc     120
aaaagaaatg catttgcagt tgtctgtcct aatcaatcta ctagcagact cacattattg     180
atgtaggaaa taaaattcag cctgtgacgt ggatgcaaca actgcactgc acaggatacc     240
atcttagccg ttgtgtcaca atttgctttg ctaatgtttt gagaaaccca gctttgacaa     300
acgtaagatc gatgagggcc ttacgtttgg cacaatatgt attgtaatcc ggcacggcaa     360
gttagactcg gtagtgttta gccggcatct ttatgtttgg cacaatttaa tttaattcgg     420
catggtaggt tagactgcag cgtgagccgg tcattgcaag ttattatgac atgttagagc     480
atctccaaca agttggaaaa aatgacttgg tatatcatgg tatatcatga gttttagcaa     540
cttattaatt catttgacaa gtaaaaaaaa gatccctctt caacaatttg ctattccaac     600
tcgctaaaat aaaaaaaaat taggctcacc taggccgatc tgcgttgccg cgggagagga     660
gggtaaaaga ttttgcgcta ggagaggtgg aggaacaggg cgcgggagcc ggccacggtg     720
aaatcacggg atagcaacct cacccgcgcg cgcaaattta cgcgtgtggc atggaggaat     780
agaaagttgg aaaagatagc aagttcattt agggagttgt tggagaagaa tatttgtgct     840
tttaccaaat ttataagaat agcaagtgag aatagagagt tgttggagat gctcaacaaa     900
tatacacaat aaagtggtat aataagcggc aagttattat gacatatata agagcaagta     960
tacaataagg tgaactgtta tatcgatcga tttttttttg agcacatatc gatcgaattt    1020
attgtaagat agaaaagaga agatataaaa acttatagtg atgaacaata ataatataaa    1080 gattatttt aaactatgaa acaataacc gaactactcg ctctcttcta attagtaaag    1140
taaaggcttc tcattgtata tatataaaaa aattcgttct gatttcttat attcaagacg    1200
gggagagtgc tgagtgctaa cttactagtc tacgagagaa gcttcaaatc aaacagtgta    1260
ctatagggct tacacaattt ttctgaggga agcgattgtc tgaaatgaac taaaaggctg    1320
agagctggaa aaagtagctt attctgattc tgtgaagtga ttctccatgc tgattttaaa    1380
agtttatgat aaaaaatcaa agagaataac tttcagccac agaatcactt ctctcagaga    1440
atcaacttat atggagaatc agaatcagat ggagctctac caaactggcc ctaggcatta    1500
acctaccatg gatcacatcg taaaaaaaaa accctaccat ggatcctatc tgttttcttt    1560 ttgcccctgaa agagtgaagt catcatcata tttaccatgg cgcgcgtagg agcgcttcgt    1620
cgaagaccca taggggggcg gtactcgcac cgtggttgtt tcctgttatg taatatcgga    1680
tgggggagca gtcggctagg ttggtcccat cggtactggt cgtccctag tgcgctagat    1740 gcgcgatgtt tgtcctcaaa aactctttc ttcttaataa caatcatacg caaatttttt    1800
gcgtattcga gaaaaaaga agattctatc tgttttttt ttgaaatggc tccaatttat    1860
aggaggagcc cgtttaacgg cgtcgacaaa tctaacggac accaaccagc gaatgagcga    1920
acccaccagc gccaagctag ccaagcgaag cagacggccg agacgctgac acccttgcct    1980
tggcgcggca tctccgtcgc tggctcgctg gctctggccc cttcgcgaga gttccggtcc    2040
acctccacct gtgtcggttt ccaactccgt tccgccttcg cgtgggactt gttccgttca    2100
tccgttggcg gcatccggaa attgcgtggc gtagagcacg gggccctcct ctcacacggc    2160
acggaaccgt cacgagctca cggcaccggc agcacggcgg ggattccttc cccaccaccg    2220
```

| | |
|---|---|
| ctccttccct ttcccttcct cgcccgccat cataaatagc cacccctccc agcttccttc | 2280 |
| gccacat | 2287 |

<210> SEQ ID NO 92
<211> LENGTH: 1020
<212> TYPE: DNA
<213> ORGANISM: Coix lacryma-jobi

<400> SEQUENCE: 92

| | |
|---|---|
| gtatggctat cgtccttcct ctctctctct ttaccttatc tagatcggcg atccatggtt | 60 |
| agggcctgct agttctccgt tcgtgtttgt cgatggctgt gaggcacaat agatccgtcg | 120 |
| gcgttatgat ggttagcctg tcatgctctt gcgatctgtg gttcctttag gaaaggcatt | 180 |
| aatttaatcc ctgatggttc gagatcggtg atccatggtt agtaccctaa gctgtggagt | 240 |
| cgggtttaga tccgcgctgt tcgtaggcga tctgttctga ttgttaactt gtcagtacct | 300 |
| gcgaatcctc ggtggttcta gctggttcgg agatcagatc gattccatta tctgctatac | 360 |
| atcttgtttc gttgcctagg ctccgtttaa tctatccatc gtatgatgtt agcctttgat | 420 |
| atgattcgat cgtgctagct atgtcctgtg gacttaattg tcaggtccta attttaagga | 480 |
| agactgttcc aaaccatctg ctggatttat taaatttgga tctggatgtg tcacatacac | 540 |
| cttcataatt aaaatggatg gaaatatctc ttatctttta gatatggata ggcatttata | 600 |
| tgatgctgtg agttttacta gtacttcctt agaatatatg tactttttta gacggaatat | 660 |
| tgatatgtat acatgtgtag atacatgaag caacatgctg ctgtagtcta ataattcctg | 720 |
| ttcatctaat aatcaagtat gtatatgttc tgtgtgtttt attggtattt gattagatat | 780 |
| atacatgctt agatacatac atgaagcagc atgctgctac agtttaatca ttattgttta | 840 |
| tccaataaac aaacatgctt tttaatttat cttgatatgc ttggatgacg gaatatgcag | 900 |
| agattttaag tacccagcat catgagcatg catgaccctg cgttagtatg ctgtttattt | 960 |
| gcttgagact ctttcttttg tagatactca ccctgttttc tggtgatcct actgcaggtg | 1020 |

<210> SEQ ID NO 93
<211> LENGTH: 3393
<212> TYPE: DNA
<213> ORGANISM: Coix lacryma-jobi

<400> SEQUENCE: 93

| | |
|---|---|
| ggttctatac aacaccacac actgtgtgag tgtgtgacca gtggccaact tttgttcagt | 60 |
| tcaacgatcc tggcctttcc gggcacccaa tacactaatt aatctattgc agctaacctc | 120 |
| aaaagaaatg catttgcagt tgtctgtcct aatcaatcta ctagcagact cacattattg | 180 |
| atgtaggaaa taaaattcag cctgtgacgt ggatgcaaca actgcactgc acaggatacc | 240 |
| atcttagccg ttgtgtcaca atttgctttg ctaatgtttt gagaaaccca gctttgacaa | 300 |
| acgtaagatc gatgagggcc ttacgtttgg cacaatatgt attgtaatcc ggcacggcaa | 360 |
| gttagactcg gtagtgttta gccggcatct ttatgtttgg cacaatttaa tttaattcgg | 420 |
| catggtaggt tagactgcag cgtgagccgg tcattgcaag ttattatgac atgttagagc | 480 |
| atctccaaca agttggaaaa aatgacttgg tatatcatgg tatatcatga gttttagcaa | 540 |
| cttattaatt catttgacaa gtaaaaaaaa gatccctctt caacaatttg ctattccaac | 600 |
| tcgctaaaat aaaaaaaaat taggctcacc taggccgatc tgcgttgccg cgggagagga | 660 |
| gggtaaaaga ttttgcgcta ggagaggtgg aggaacaggg cgcgggagcc ggccacggtg | 720 |

```
aaatcacggg atagcaacct cacccgcgcg cgcaaattta cgcgtgtggc atggaggaat    780
agaaagttgg aaaagatagc aagttcattt agggagttgt tggagaagaa tatttgtgct    840
tttaccaaat ttataagaat agcaagtgag aatagagagt tgttggagat gctcaacaaa    900
tatacacaat aaagtggtat aataagcggc aagttattat gacatatata agagcaagta    960
tacaataagg tgaactgtta tatcgatcga ttttttttg agcacatatc gatcgaattt     1020
attgtaagat agaaaagaga agatataaaa acttatagtg atgaacaata ataatataaa    1080
gattattttt aaactatgaa aacaataacc gaactactcg ctctcttcta attagtaaag    1140
taaaggcttc tcattgtata tatataaaaa aattcgttct gatttcttat attcaagacg    1200
gggagagtgc tgagtgctaa cttactagtc tacgagagaa gcttcaaatc aaacagtgta    1260
ctatagggct tacacaattt ttctgaggga acgattgtc tgaaatgaac taaaaggctg     1320
agagctggaa aaagtagctt attctgattc tgtgaagtga ttctccatgc tgattttaaa    1380
agtttatgat aaaaaatcaa agagaataac tttcagccac agaatcactt ctctcagaga    1440
atcaacttat atggagaatc agaatcagat ggagctctac caaactggcc ctaggcatta    1500
acctaccatg gatcacatcg taaaaaaaaa accctaccat ggatcctatc tgttttcttt    1560
ttgccctgaa agagtgaagt catcatcata tttaccatgg cgcgcgtagg agcgcttcgt    1620
cgaagaccca tagggggcg gtactcgcac cgtggttgtt tcctgttatg taatatcgga     1680
tgggggagca gtcggctagg ttggtccat cggtactggt cgtcccctag tgcgctagat     1740
gcgcgatgtt tgtcctcaaa aactcttttc ttcttaataa caatcatacg caaatttttt    1800
gcgtattcga gaaaaaaga agattctatc tgttttttt ttgaaatggc tccaattat      1860 aggaggagcc cgtttaacgg cgtcgacaaa tctaacggac accaaccagc gaatgagcga    1920
acccaccagc gccaagctag ccaagcgaag cagacggccg agacgctgac acccttgcct    1980
tggcgcggca tctccgtcgc tggctcgctg gctctggccc cttcgcgaga gttccggtcc    2040
acctccacct gtgtcggttt ccaactccgt tccgccttcg cgtgggactt gttccgttca    2100
tccgttggcg gcatccggaa attgcgtggc gtagagcacg gggccctcct ctcacacggc    2160
acggaaccgt cacgagctca cggcaccggc agcacggcgg ggattccttc cccaccaccg    2220
ctccttccct ttcccttcct cgcccgccat cataaatagc caccccctccc agcttccttc   2280 gccacatcct ctcatcatct tctctcgtgt agcacgcgca gcccgatccc caatcccctc    2340
tcctcgcgag cctcgtcgat ccctcgcttc aaggtatggc tatcgtcctt cctctctctc    2400
tctttacctt atctagatcg gcgatccatg gttagggcct gctagttctc cgttcgtgtt    2460
tgtcgatggc tgtgaggcac aatagatccg tcggcgttat gatggttagc ctgtcatgct    2520
cttgcgatct gtggttcctt taggaaaggc attaatttaa tccctgatgg ttcgagatcg    2580
gtgatccatg gttagtaccc taagctgtgg agtcgggttt agatccgcgc tgttcgtagg    2640
cgatctgttc tgattgttaa cttgtcagta cctgcgaatc tcggtggtt ctagctggtt     2700 cggagatcag atcgattcca ttatctgcta tacatcttgt ttcgttgcct aggctccgtt    2760
taatctatcc atcgtatgat gttagccttt gatatgattc gatcgtgcta gctatgtcct    2820
gtggacttaa ttgtcaggtc ctaattttta ggaagactgt tccaaaccat ctgctggatt    2880
tattaaattt ggatctggat gtgtcacata caccttcata attaaaatgg atggaaatat    2940
ctcttatctt ttagatatgg ataggcattt atatgatgct gtgagtttta ctagtacttt    3000
cttagaatat atgtactttt ttagacggaa tattgatatg tatacatgtg tagatacatg    3060
aagcaacatg ctgctgtagt ctaataattc ctgttcatct aataatcaag tatgtatatg    3120
```

```
ttctgtgtgt tttattggta tttgattaga tatatacatg cttagataca tacatgaagc   3180
agcatgctgc tacagtttaa tcattattgt ttatccaata acaaacatg cttttttaatt   3240 tatcttgata tgcttggatg acggaatatg cagagatttt aagtacccag catcatgagc   3300
atgcatgacc ctgcgttagt atgctgttta tttgcttgag actctttctt ttgtagatac   3360
tcaccctgtt ttctggtgat cctactgcag gtc                                3393
```

<210> SEQ ID NO 94
<211> LENGTH: 1020
<212> TYPE: DNA
<213> ORGANISM: Coix lacryma-jobi

<400> SEQUENCE: 94

```
gtatggctat cgtccttcct ctctctctct ttaccttatc tagatcggcg atccatggtt     60
agggcctgct agttctccgt cgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta attttttagga   480 agactgttcc aaaccatctg ctggatttat taaatttgga tctggatgtg tcacatacac    540
cttcataatt aaaatggatg gaaatatctc ttatctttta gatatggata ggcatttata    600
tgatgctgtg agttttacta gtactttctt agaatatatg tacttttta gacggaatat     660 tgatatgtat acatgtgtag atacatgaag caacatgctg ctgtagtcta ataattcctg    720
ttcatctaat aatcaagtat gtatatgttc tgtgtgtttt attggtattt gattagatat    780
atacatgctt agatacatac atgaagcagc atgctgctac agtttaatca ttattgttta    840
tccaataaac aaacatgctt tttaatttat cttgatatgc ttggatgacg gaatatgcag    900
agattttaag tacccagcat catgagcatg catgaccctg cgttagtatg ctgtttattt    960
gcttgagact ctttcttttg tagatactca ccctgttttc tggtgatcct actgcaggtc   1020
```

<210> SEQ ID NO 95
<211> LENGTH: 2166
<212> TYPE: DNA
<213> ORGANISM: Coix lacryma-jobi

<400> SEQUENCE: 95

```
gtctacgaga gaagcttcaa atcaaacagt gtactatagg gcttacacaa ttttctgag     60 ggaagcgatt gtctgaaatg aactaaaagg ctgagagctg gaaaagtag cttattctga    120 ttctgtgaag tgattctcca tgctgatttt aaaagtttat gataaaaaat caagagaat     180 aactttcagc cacagaatca cttctctcag agaatcaact tatatggaga atcagaatca    240
gatggagctc taccaaactg gccctaggca ttaacctacc atggatcaca tcgtaaaaaa    300
aaaaccctac catggatcct atctgttttc ttttgccct gaaagagtga agtcatcatc     360
atatttacca tggcgcgcgt aggagcgctt cgtcgaagac ccataggggg gcggtactcg    420
caccgtggtt gttcctgtt atgtaatatc ggatgggga gcagtcggct aggttggtcc     480
catcggtact ggtcgtcccc tagtgcgcta gatgcgcgat gtttgtcctc aaaaactctt    540
```

```
ttcttcttaa taacaatcat acgcaaattt tttgcgtatt cgagaaaaaa agaagattct    600
atctgttttt tttttgaaat ggctccaatt tataggagga gcccgtttaa cggcgtcgac    660
aaatctaacg gacaccaacc agcgaatgag cgaacccacc agcgccaagc tagccaagcg    720
aagcagacgg ccgagacgct gacacccttg ccttggcgcg gcatctccgt cgctggctcg    780
ctggctctgg ccccttcgcg agagttccgg tccacctcca cctgtgtcgg tttccaactc    840
cgttccgcct tcgcgtggga cttgttccgt tcatccgttg gcggcatccg gaaattgcgt    900
ggcgtagagc acggggccct cctctcacac ggcacggaac cgtcacgagc tcacggcacc    960
ggcagcacgg cggggattcc ttccccacca ccgctccttc cctttccctt cctcgccccgc   1020 catcataaat agccacccct cccagcttcc ttcgccacat cctctcatca tcttctctcg   1080
tgtagcacgc gcagcccgat ccccaatccc ctctcctcgc gagcctcgtc gatccctcgc   1140
ttcaaggtat ggctatcgtc cttcctctct ctctctttac cttatctaga tcggcgatcc   1200
atggttaggg cctgctagtt ctccgttcgt gtttgtcgat ggctgtgagg cacaatagat   1260
ccgtcggcgt tatgatggtt agcctgtcat gctcttgcga tctgtggttc ctttaggaaa   1320
ggcattaatt taatccctga tggttcgaga tcggtgatcc atggttagta ccctaagctg   1380
tggagtcggg tttagatccg cgctgttcgt aggcgatctg ttctgattgt taacttgtca   1440
gtacctgcga atcctcggtg gttctagctg gttcggagat cagatcgatt ccattatctg   1500
ctatacatct tgtttcgttg cctaggctcc gtttaatcta tccatcgtat gatgttagcc   1560
tttgatatga ttcgatcgtg ctagctatgt cctgtggact taattgtcag gtcctaattt   1620
ttaggaagac tgttccaaac catctgctgg atttattaaa tttggatctg gatgtgtcac   1680
atacaccttc ataattaaaa tggatggaaa tatctcttat cttttagata tggataggca   1740
tttatatgat gctgtgagtt ttactagtac tttcttagaa tatatgtact tttttagacg   1800
gaatattgat atgtatacat gtgtagatac atgaagcaac atgctgctgt agtctaataa   1860
ttcctgttca tctaataatc aagtatgtat atgttctgtg tgttttattg gtatttgatt   1920
agatatatac atgcttagat acatacatga agcagcatgc tgctacagtt taatcattat   1980
tgtttatcca ataaacaaac atgctttta atttatcttg atatgcttgg atgacgaat    2040 atgcagagat tttaagtacc cagcatcatg agcatgcatg accctgcgtt agtatgctgt   2100
ttatttgctt gagactcttt cttttgtaga tactcaccct gttttctggt gatcctactg   2160
caggtg                                                              2166
```

<210> SEQ ID NO 96
<211> LENGTH: 1060
<212> TYPE: DNA
<213> ORGANISM: Coix lacryma-jobi

<400> SEQUENCE: 96

```
gtctacgaga gaagcttcaa atcaaacagt gtactatagg gcttacacaa tttttctgag     60
ggaagcgatt gtctgaaatg aactaaaagg ctgagagctg gaaaaagtag cttattctga    120
ttctgtgaag tgattctcca tgctgatttt aaaagtttat gataaaaaat caaagagaat    180
aactttcagc cacagaatca cttctctcag agaatcaact tatatggaga atcagaatca    240
gatggagctc taccaaactg gccctaggca ttaacctacc atggatcaca tcgtaaaaaa    300
aaaaccctac catggatcct atctgttttc ttttgccct gaaagagtga agtcatcatc     360
atatttacca tggcgcgcgt aggagcgctt cgtcgaagac ccatagggg gcggtactcg     420 caccgtggtt gtttcctgtt atgtaatatc ggatggggga gcagtcggct aggttggtcc    480
```

```
catcggtact ggtcgtcccc tagtgcgcta gatgcgcgat gtttgtcctc aaaaactctt    540
ttcttcttaa taacaatcat acgcaaattt tttgcgtatt cgagaaaaaa agaagattct    600
atctgttttt tttttgaaat ggctccaatt tataggagga gcccgtttaa cggcgtcgac    660
aaatctaacg dacaccaacc agcgaatgag cgaacccacc agcgccaagc tagccaagcg    720
aagcagacgg ccgagacgct gacacccttg ccttggcgcg gcatctccgt cgctggctcg    780
ctggctctgg cccttcgcg agagttccgg tccacctcca cctgtgtcgg tttccaactc     840
cgttccgcct tcgcgtggga cttgttccgt tcatccgttg gcggcatccg gaaattgcgt    900
ggcgtagagc acggggccct cctctcacac ggcacggaac cgtcacgagc tcacggcacc    960
ggcagcacgg cggggattcc ttccccacca ccgctccttc cctttccctt cctcgcccgc   1020
catcataaat agccacccct cccagcttcc ttcgccacat                         1060
```

<210> SEQ ID NO 97
<211> LENGTH: 2166
<212> TYPE: DNA
<213> ORGANISM: Coix lacryma-jobi
<400> SEQUENCE: 97

```
gtctacgaga gaagcttcaa atcaaacagt gtactatagg gcttacacaa ttttctgag    60 ggaagcgatt gtctgaaatg aactaaaagg ctgagagctg gaaaaagtag cttattctga   120
ttctgtgaag tgattctcca tgctgatttt aaaagtttat gataaaaaat caaagagaat   180
aactttcagc cacagaatca cttctctcag agaatcaact tatatggaga atcagaatca   240
gatggagctc taccaaactg gccctaggca ttaacctacc atggatcaca tcgtaaaaaa   300
aaaaccctac catggatcct atctgttttc ttttgccct gaaagagtga agtcatcatc    360
atatttacca tggcgcgcgt aggagcgctt cgtcgaagac ccatagggg gcggtactcg    420 caccgtggtt gtttcctgtt atgtaatatc ggatggggga gcagtcggct aggttggtcc   480
catcggtact ggtcgtcccc tagtgcgcta gatgcgcgat gtttgtcctc aaaaactctt    540
ttcttcttaa taacaatcat acgcaaattt tttgcgtatt cgagaaaaaa agaagattct    600
atctgttttt tttttgaaat ggctccaatt tataggagga gcccgtttaa cggcgtcgac    660
aaatctaacg gacaccaacc agcgaatgag cgaacccacc agcgccaagc tagccaagcg    720
aagcagacgg ccgagacgct gacacccttg ccttggcgcg gcatctccgt cgctggctcg    780
ctggctctgg cccttcgcg agagttccgg tccacctcca cctgtgtcgg tttccaactc     840
cgttccgcct tcgcgtggga cttgttccgt tcatccgttg gcggcatccg gaaattgcgt    900
ggcgtagagc acggggccct cctctcacac ggcacggaac cgtcacgagc tcacggcacc    960
ggcagcacgg cggggattcc ttccccacca ccgctccttc cctttccctt cctcgcccgc   1020
catcataaat agccacccct cccagcttcc ttcgccacat cctctcatca tcttctctcg   1080
tgtagcacgc gcagcccgat ccccaatccc ctctcctcgc gagcctcgtc gatccctcgc   1140
ttcaaggtat ggctatcgtc cttcctctct ctctctttac cttatctaga tcggcgatcc   1200
atggttaggg cctgctagtt ctccgttcgt gtttgtcgat ggctgtgagg cacaatagat   1260
ccgtcggcgt tatgatggtt agcctgtcat gctcttgcga tctgtggttc ctttaggaaa   1320
ggcattaatt taatccctga tggttcgaga tcggtgatcc atggttagta ccctaagctg   1380
tggagtcggg tttagatccg cgctgttcgt aggcgatctg ttctgattgt taacttgtca   1440
gtacctgcga atcctcggtg gttctagctg gttcggagat cagatcgatt ccattatctg   1500
```

-continued

| | |
|---|---|
| ctatacatct tgtttcgttg cctaggctcc gtttaatcta tccatcgtat gatgttagcc | 1560 |
| tttgatatga ttcgatcgtg ctagctatgt cctgtggact taattgtcag gtcctaattt | 1620 |
| ttaggaagac tgttccaaac catctgctgg atttattaaa tttggatctg gatgtgtcac | 1680 |
| atacaccttc ataattaaaa tggatggaaa tatctcttat cttttagata tggataggca | 1740 |
| tttatatgat gctgtgagtt ttactagtac tttcttagaa tatatgtact tttttagacg | 1800 |
| gaatattgat atgtatacat gtgtagatac atgaagcaac atgctgctgt agtctaataa | 1860 |
| ttcctgttca tctaataatc aagtatgtat atgttctgtg tgttttattg gtatttgatt | 1920 |
| agatatatac atgcttagat acatacatga agcagcatgc tgctacagtt taatcattat | 1980 |
| tgtttatcca ataaacaaac atgcttttta atttatcttg atatgcttgg atgacggaat | 2040 |
| atgcagagat tttaagtacc cagcatcatg agcatgcatg accctgcgtt agtatgctgt | 2100 |
| ttatttgctt gagactcttt cttttgtaga tactcaccct gttttctggt gatcctactg | 2160 |
| caggtc | 2166 |

<210> SEQ ID NO 98
<211> LENGTH: 1943
<212> TYPE: DNA
<213> ORGANISM: Coix lacryma-jobi

<400> SEQUENCE: 98

| | |
|---|---|
| agcagactcg cattatcgat ggagctctac caaactggcc ctaggcatta acctaccatg | 60 |
| gatcacatcg taaaaaaaaa accctaccat ggatcctatc tgttttcttt ttgccctgaa | 120 |
| agagtgaagt catcatcata tttaccatgg cgcgcgtagg agcgcttcgt cgaagaccca | 180 |
| taggggggcg gtactcgcac cgtggttgtt tcctgttatg taatatcgga tgggggagca | 240 |
| gtcggctagg ttggtcccat cggtactggt cgtcccctag tgcgctagat gcgcgatgtt | 300 |
| tgtcctcaaa aactctttc ttcttaataa caatcatacg caaatttttt gcgtattcga | 360 |
| gaaaaaaga agattctatc tgttttttt ttgaaatggc tccaattat aggaggagcc | 420 |
| cgtttaacgg cgtcgacaaa tctaacggac accaaccagc gaatgagcga acccaccagc | 480 |
| gccaagctag ccaagcgaag cagacggccg agacgctgac accccttgcct ggcgcggca | 540 |
| tctccgtcgc tggctcgctg gctctggccc cttcgcgaga gttccggtcc acctccacct | 600 |
| gtgtcggttt ccaactccgt tccgccttcg cgtgggactt gttccgttca tccgttggcg | 660 |
| gcatccggaa attgcgtggc gtagagcacg gggccctcct ctcacacggc acggaaccgt | 720 |
| cacgagctca cggcaccggc agcacggcgg ggattccttc cccaccaccg ctccttccct | 780 |
| ttcccttcct cgcccgccat cataaatagc cacccctccc agcttccttc gccacatcct | 840 |
| ctcatcatct tctctcgtgt agcacgcgca gcccgatccc caatccctc tcctcgcgag | 900 |
| cctcgtcgat ccctcgcttc aaggtatggc tatcgtcctt cctctctctc tctttacctt | 960 |
| atctagatcg gcgatccatg gttagggcct gctagttctc cgttcgtgtt tgtcgatggc | 1020 |
| tgtgaggcac aatagatccg tcggcgttat gatggttagc ctgtcatgct cttgcgatct | 1080 |
| gtggttcctt taggaaaggc attaatttaa tccctgatgg ttcgagatcg gtgatccatg | 1140 |
| gttagtaccc taagctgtgg agtcgggttt agatccgcgc tgttcgtagg cgatctgttc | 1200 |
| tgattgttaa cttgtcagta cctgcgaatc ctcggtggtt ctagctggtt cggagatcag | 1260 |
| atcgattcca ttatctgcta tacatcttgt ttcgttgcct aggctccgtt taatctatcc | 1320 |
| atcgtatgat gttagccttt gatatgattc gatcgtgcta gctatgtcct gtggacttaa | 1380 |
| ttgtcaggtc ctaattttta ggaagactgt tccaaccat ctgctggatt tattaaattt | 1440 |

```
ggatctggat gtgtcacata caccttcata attaaaatgg atggaaatat ctcttatctt    1500
ttagatatgg ataggcattt atatgatgct gtgagtttta ctagtacttt cttagaatat    1560
atgtactttt ttagacggaa tattgatatg tatacatgtg tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttttaatt tatcttgata    1800 tgcttggatg acggaatatg cagagatttt aagtacccag catcatgagc atgcatgacc    1860
ctgcgttagt atgctgttta tttgcttgag actctttctt ttgtagatac tcaccctgtt    1920
ttctggtgat cctactgcag gtc                                             1943
```

<210> SEQ ID NO 99
<211> LENGTH: 1943
<212> TYPE: DNA
<213> ORGANISM: Coix lacryma-jobi

<400> SEQUENCE: 99

```
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180 tagggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactcttttc ttcttaataa caatcatacg caaattttttt gcgtattcga     360 gaaaaaaga agattctatc tgttttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac accccttgcct tggcgcggca     540 tctccgtcgc tggctcgctg gctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggcctcct ctcacacggc acggaaccgt     720
cacgagctca cggcaccggc agcacggcgg ggattccttc cccaccaccg ctccttccct     780 tcccttcct cgcccgccat cataaatagc caccctccc agcttccttc gccacatcct     840
ctcatcatct tctctcgtgt agcacgcgca gcccgatccc caatcccctc tcctcgcgag     900
cctcgtcgat ccctcgcttc aaggtatggc tatcgtccttt cctctctctc tctttacctt     960
atctagatcg gcgatccatg gttagggcct gctagttctc cgttcgtgtt tgtcgatggc    1020
tgtgaggcac aatagatccg tcggcgttat gatggttagc ctgtcatgct cttgcgatct    1080
gtggttcctt taggaaaggc attaatttaa tccctgatgg ttcgagatcg gtgatccatg    1140
gttagtaccc taagctgtgg agtcgggttt agatccgcgc tgttcgtagg cgatctgttc    1200
tgattgttaa cttgtcagta cctgcgaatc ctcggtggtt ctagctggtt cggagatcag    1260
atcgattcca ttatctgcta tacatcttgt ttcgttgcct aggctccgtt taatctatcc    1320
atcgtatgat gttagccttt gatatgattc gatcgtgcta gctatgtcct gtggacttaa    1380
ttgtcaggtc ctaattttta ggaagactgt tccaaaccat ctgctggatt tattaaattt    1440
ggatctggat gtgtcacata caccttcata attaaaatgg atggaaatat ctcttatctt    1500
ttagatatgg ataggcattt atatgatgct gtgagtttta ctagtacttt cttagaatat    1560
```

| atgtactttt ttagacggaa tattgatatg tatacatgtg tagatacatg aagcaacatg | 1620 |
| ctgctgtagt ctaataattc ctgttcatct aataatcaag tatgtatatg ttctgtgtgt | 1680 |
| tttattggta tttgattaga tatatacatg cttagataca tacatgaagc agcatgctgc | 1740 |
| tacagtttaa tcattattgt ttatccaata aacaaacatg cttttttaatt tatcttgata | 1800 |
| tgcttggatg acggaatatg cagagatttt aagtacccag catcatgagc atgcatgacc | 1860 |
| ctgcgttagt atgctgttta tttgcttgag actctttctt ttgtagatac tcaccctgtt | 1920 |
| ttctggtgat cctactgcag gtg | 1943 |

<210> SEQ ID NO 100
<211> LENGTH: 1943
<212> TYPE: DNA
<213> ORGANISM: Coix lacryma-jobi

<400> SEQUENCE: 100

| agcagactcg cattatcgat ggagctctac caaactggcc ctaggcatta acctaccatg | 60 |
| gatcacatcg taaaaaaaaa accctaccat ggatcctatc tgttttctttt ttgccctgaa | 120 |
| agagtgaagt catcatcata tttaccatgg cgcgcgtagg agcgcttcgt cgaagaccca | 180 |
| tagggggggcg gtactcgcac cgtggttgtt tcctgttatg taatatcgga tgggggagca | 240 |
| gtcggctagg ttggtcccat cggtactggt cgtcccctag tgcgctagat gcgcgatgtt | 300 |
| tgtcctcaaa aactcttttc ttcttaataa caatcatacg caaatttttt gcgtattcga | 360 |
| gaaaaaaga agattctatc tgtttttttt ttgaaatggc tccaatttat aggaggagcc | 420 |
| cgtttaacgg cgtcgacaaa tctaacggac accaaccagc gaatgagcga acccaccagc | 480 |
| gccaagctag ccaagcgaag cagacggccg agacgctgac acccttgcct ggcgcggca | 540 |
| tctccgtcgc tggctcgctg gctctggccc cttcgcgaga gttccggtcc acctccacct | 600 |
| gtgtcggttt ccaactccgt tccgccttcg cgtgggactt gttccgttca tccgttggcg | 660 |
| gcatccggaa attgcgtggc gtagagcacg gggccctcct ctcacacggc acggaaccgt | 720 |
| cacgagctca cggcaccggc agcacggcgg ggattccttc cccaccaccg ctccttccct | 780 |
| ttcccttcct cgcccgccat cataaatagc caccccctccc agcttccttc gccacatcct | 840 |
| ctcatcatct tctctcgtgt agcacgcgca gcccgatccc caatcccctc tcctcgcgag | 900 |
| cctcgtcgat ccctcgcttc aaggtatggc tatcgtcctt cctctctctc tctttacctt | 960 |
| atctagatcg gcgatccatg gttagggcct gctagttctc cgttcgtgtt tgtcgatggc | 1020 |
| tgtgaggcac aatagatccg tcggcgttat gatggttagc ctgtcatgct cttgcgatct | 1080 |
| gtggttcctt taggaaaggc attaatttaa tccctgatgg ttcgagatcg gtgatccatg | 1140 |
| gttagtaccc taagctgtgg agtcgggttt agatccgcgc tgttcgtagg cgatctgttc | 1200 |
| tgattgttaa cttgtcagta cctgcgaatc ctcggtggtt ctagctggtt cggagatcag | 1260 |
| atcgattcca ttatctgcta tacatcttgt ttcgttgcct aggctccgtt taatctatcc | 1320 |
| atcgtatgat gttagccttt gatatgattc gatcgtgcta gctatgtcct gtggacttaa | 1380 |
| ttgtcaggtc ctaattttta ggaagactgt tccaaaccat ctgctggatt tattaaattt | 1440 |
| ggatctggat gtgtcacata caccttcata attaaaatgg atggaaatat ctcttatctt | 1500 |
| ttagatatgg ataggcattt atatgatgct gtgagtttta ctagtacttt cttagaatat | 1560 |
| atgtactttt ttagacggaa tattgatatg tatacatgtg tagatacatg aagcaacatg | 1620 |
| ctgctgtagt ctaataattc ctgttcatct aataatcaag tatgtatatg ttctgtgtgt | 1680 |
| tttattggta tttgattaga tatatacatg cttagataca tacatgaagc agcatgctgc | 1740 |

```
tacagtttaa tcattattgt ttatccaata aacaaacatg cttttttaatt tatcttgata    1800 tgcttggatg acggaatatg cagagatttt aagtacccag catcatgagc atgcatgacc    1860
ctgcgttagt atgctgttta tttgcttgag actctttctt ttgtagatac tcaccctgtt    1920
ttctggtgat cctactgcag gcg                                            1943

<210> SEQ ID NO 101
<211> LENGTH: 1020
<212> TYPE: DNA
<213> ORGANISM: Coix lacryma-jobi

<400> SEQUENCE: 101
gtatggctat cgtccttcct ctctctctct ttaccttatc tagatcggcg atccatggtt      60
agggcctgct agttctccgt tcgtgtttgt cgatggctgt gaggcacaat agatccgtcg     120
gcgttatgat ggttagcctg tcatgctctt gcgatctgtg gttcctttag gaaaggcatt     180
aatttaatcc ctgatggttc gagatcggtg atccatggtt agtaccctaa gctgtggagt     240
cgggtttaga tccgcgctgt tcgtaggcga tctgttctga ttgttaactt gtcagtacct     300
gcgaatcctc ggtggttcta gctggttcgg agatcagatc gattccatta tctgctatac     360
atcttgtttc gttgcctagg ctccgtttaa tctatccatc gtatgatgtt agcctttgat     420
atgattcgat cgtgctagct atgtcctgtg gacttaattg tcaggtccta attttttagga     480 agactgttcc aaaccatctg ctggatttat aaatttgga tctggatgtg tcacatacac     540
cttcataatt aaaatggatg gaaatatctc ttatcttta gatatggata ggcatttata     600
tgatgctgtg agttttacta gtactttctt agaatatatg tactttttta gacggaatat     660
tgatatgtat acatgtgtag atacatgaag caacatgctg ctgtagtcta ataattcctg     720
ttcatctaat aatcaagtat gtatatgttc tgtgtgtttt attggtattt gattagatat     780
atacatgctt agatacatac atgaagcagc atgctgctac agtttaatca ttattgttta     840
tccaataaac aaacatgctt tttaatttat cttgatatgc ttggatgacg gaatatgcag     900
agattttaag tacccagcat catgagcatg catgaccctg cgttagtatg ctgttttattt    960 gcttgagact ctttcttttg tagatactca ccctgttttc tggtgatcct actgcaggcg    1020

<210> SEQ ID NO 102
<211> LENGTH: 1943
<212> TYPE: DNA
<213> ORGANISM: Coix lacryma-jobi

<400> SEQUENCE: 102
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180 tagggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactctttttc ttcttaataa caatcatacg caaattttttt gcgtattcga     360 gaaaaaaaga agattctatc tgtttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac acccttgcct ggcgcggca      540 tctccgtcgc tggctcgctg gctctggccc cttcgcgaga gttccggtcc acctccacct     600
```

```
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccccctccc agcttccttc gccacatcct    840
ctcatcatct tctctcgtgt agcacgcgca gcccgatccc caatcccctc tcctcgcgag    900
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaattttta ggaagactgt tccaaaccat ctgctggatt tattaaattt   1440
ggatctggat gtgtcacata caccttcata attaaaatgg atgaaatat ctcttatctt     1500 ttagatatgg ataggcattt atatgatgct gtgagttta ctagtactt cttagaatat      1560 atgtactttt ttagacggaa tattgatatg tatacatgtg tagatacatg aagcaacatg   1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg ctttttaatt tatcttgata   1800
tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag gac                                            1943
```

<210> SEQ ID NO 103
<211> LENGTH: 1020
<212> TYPE: DNA
<213> ORGANISM: Coix lacryma-jobi

<400> SEQUENCE: 103

```
gtatggctat cgtccttcct ctctctctct ttaccttatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta atttttagga    480
agactgttcc aaaccatctg ctggatttat taaatttgga tctggatgtg tcacatacac    540
cttcataatt aaaatggatg aaatatctc ttatctttta gatatggata ggcatttata    600
tgatgctgtg agttttacta gtactttctt agaatatatg tactttttta gacggaatat   660
tgatatgtat acatgtgtag acatgaag caacatgctg ctgtagtcta ataattcctg    720
ttcatctaat aatcaagtat gtatatgttc tgtgtgtttt attggtattt gattagatat   780
```

```
atacatgctt agatacatac atgaagcagc atgctgctac agtttaatca ttattgttta     840
tccaataaac aaacatgctt tttaatttat cttgatatgc ttggatgacg aaatatgcag     900
agattttaag tacccagcat catgagcatg catgaccctg cgttagtatg ctgtttattt     960
gcttgagact ctttcttttg tagatactca ccctgttttc tggtgatcct actgcaggac    1020

<210> SEQ ID NO 104
<211> LENGTH: 1943
<212> TYPE: DNA
<213> ORGANISM: Coix lacryma-jobi

<400> SEQUENCE: 104
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180
taggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactcttttc ttcttaataa caatcatacg caaattttt gcgtattcga      360 gaaaaaaga gattctatc tgttttttt ttgaaatggc tccaatttat aggaggagcc       420
cgtttaacgg cgtcgacaaa tctaacggac accaaccagc gaatgagcga acccaccagc     480
gccaagctag ccaagcgaag cagacggccg agacgctgac acccttgcct ggcgcggca      540 tctccgtcgc tggctcgctg gctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggccctcct ctcacacggc acggaaccgt     720
cacgagctca cggcaccggc agcacggcgg ggattccttc cccaccaccg ctccttccct     780 ttccccttcct cgcccgccat cataaatagc caccccctccc agcttccttc gccacatcct    840
ctcatcatct tctctcgtgt agcacgcgca gcccgatccc caatcccctc tcctcgcgag     900
cctcgtcgat ccctcgcttc aaggtatggc tatcgtcctt cctctctctc tctttacctt     960
atctagatcg gcgatccatg gttagggcct gctagttctc cgttcgtgtt tgtcgatggc    1020
tgtgaggcac aatagatccg tcggcgttat gatggttagc ctgtcatgct cttgcgatct    1080
gtggttcctt taggaaaggc attaatttaa tccctgatgg ttcgagatcg gtgatccatg    1140
gttagtaccc taagctgtgg agtcgggttt agatccgcgc tgttcgtagg cgatctgttc    1200
tgattgttaa cttgtcagta cctgcgaatc ctcggtggtt ctagctggtt cggagatcag    1260
atcgattcca ttatctgcta tacatcttgt ttcgttgcct aggctccgtt taatctatcc    1320
atcgtatgat gttagccttt gatatgattc gatcgtgcta gctatgtcct gtggacttaa    1380
ttgtcaggtc ctaatttta ggaagactgt tccaaaccat ctgctggatt tattaaattt    1440
ggatctggat gtgtcacata cccttcata attaaaatgg atgaaatat ctcttatctt     1500 ttagatatgg ataggcattt atatgatgct gtgagtttta ctagtacttt cttagaatat    1560
atgtactttt ttagacggaa tattgatatg tatacatgtg tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttttaatt tatcttgata    1800 tgcttggatg acggaatatg cagagatttt aagtacccag catcatgagc atgcatgacc    1860
```

```
ctgcgttagt atgctgttta tttgcttgag actctttctt ttgtagatac tcaccctgtt    1920
ttctggtgat cctactgcag acc                                            1943

<210> SEQ ID NO 105
<211> LENGTH: 1020
<212> TYPE: DNA
<213> ORGANISM: Coix lacryma-jobi

<400> SEQUENCE: 105
gtatggctat cgtccttcct ctctctctct ttaccttatc tagatcggcg atccatggtt      60
agggcctgct agttctccgt tcgtgtttgt cgatggctgt gaggcacaat agatccgtcg     120
gcgttatgat ggttagcctg tcatgctctt gcgatctgtg gttcctttag gaaaggcatt     180
aatttaatcc ctgatggttc gagatcggtg atccatggtt agtaccctaa gctgtggagt     240
cgggtttaga tccgcgctgt tcgtaggcga tctgttctga ttgttaactt gtcagtacct     300
gcgaatcctc ggtggttcta gctggttcgg agatcagatc gattccatta tctgctatac     360
atcttgtttc gttgcctagg ctccgtttaa tctatccatc gtatgatgtt agcctttgat     420
atgattcgat cgtgctagct atgtcctgtg gacttaattg tcaggtccta atttttagga     480
agactgttcc aaaccatctg ctggatttat taaatttgga tctggatgtg tcacatacac     540
cttcataatt aaaatggatg aaatatctc ttatctttta gatatggata ggcatttata      600
tgatgctgtg agttttacta gtactttctt agaatatatg tactttttta gacggaatat     660
tgatatgtat acatgtgtag atacatgaag caacatgctg ctgtagtcta ataattcctg     720
ttcatctaat aatcaagtat gtatatgttc tgtgtgtttt attggtattt gattagatat     780
atacatgctt agatacatac atgaagcagc atgctgctac agtttaatca ttattgttta     840
tccaataaac aaacatgctt tttaatttat cttgatatgc ttggatgacg gaatatgcag     900
agattttaag tacccagcat catgagcatg catgaccctg cgttagtatg ctgtttattt     960
gcttgagact ctttcttttg tagatactca ccctgttttc tggtgatcct actgcagacc    1020

<210> SEQ ID NO 106
<211> LENGTH: 1943
<212> TYPE: DNA
<213> ORGANISM: Coix lacryma-jobi

<400> SEQUENCE: 106
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180
taggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactcttttc ttcttaataa caatcatacg caaattttt gcgtattcga       360 gaaaaaaga agattctatc tgttttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac acccttgcct tggcgcggca     540
tctccgtcgc tggctcgctg ctctggccc cttcgcgaga gttccggtcc acctccacct      600
gtgtcggttt ccaactccgt tccgccttcg cgtgggactt gttccgttca tccgttggcg     660
gcatccggaa attgcgtggc gtagagcacg gggcctcct ctcacacggc acggaaccgt      720
cacgagctca cggcaccggc agcacggcgg ggattccttc cccaccaccg ctccttccct     780
```

```
ttcccttcct cgcccgccat cataaatagc caccccctccc agcttccttc gccacatcct      840
ctcatcatct tctctcgtgt agcacgcgca gcccgatccc caatcccctc tcctcgcgag      900
cctcgtcgat ccctcgcttc aaggtatggc tatcgtcctt cctctctctc tctttacctt      960
atctagatcg gcgatccatg gttagggcct gctagttctc cgttcgtgtt tgtcgatggc     1020
tgtgaggcac aatagatccg tcggcgttat gatggttagc ctgtcatgct cttgcgatct     1080
gtggttcctt taggaaaggc attaatttaa tccctgatgg ttcgagatcg gtgatccatg     1140
gttagtaccc taagctgtgg agtcgggttt agatccgcgc tgttcgtagg cgatctgttc     1200
tgattgttaa cttgtcagta cctgcgaatc ctcggtggtt ctagctggtt cggagatcag     1260
atcgattcca ttatctgcta tacatcttgt ttcgttgcct aggctccgtt taatctatcc     1320
atcgtatgat gttagccttt gatatgattc gatcgtgcta gctatgtcct gtggacttaa     1380
ttgtcaggtc ctaattttta ggaagactgt tccaaaccat ctgctggatt tattaaattt     1440
ggatctggat gtgtcacata caccttcata attaaaatgg atggaaatat ctcttatctt     1500
ttagatatgg ataggcattt atatgatgct gtgagtttta ctagtacttt cttagaatat     1560
atgtactttt ttagacggaa tattgatatg tatacatgtg tagatacatg aagcaacatg     1620
ctgctgtagt ctaataattc ctgttcatct aataatcaag tatgtatatg ttctgtgtgt     1680
tttattggta tttgattaga tatatacatg cttagataca tacatgaagc agcatgctgc     1740
tacagtttaa tcattattgt ttatccaata acaaacatg cttttttaatt tatcttgata     1800 tgcttggatg acggaaatg cagagattt aagtacccag catcatgagc atgcatgacc     1860
ctgcgttagt atgctgttta tttgcttgag actctttctt ttgtagatac tcaccctgtt     1920
ttctggtgat cctactgcag ggg                                             1943

<210> SEQ ID NO 107
<211> LENGTH: 1020
<212> TYPE: DNA
<213> ORGANISM: Coix lacryma-jobi

<400> SEQUENCE: 107
gtatggctat cgtccttcct ctctctctct ttaccttatc tagatcggcg atccatggtt       60
agggcctgct agttctccgt tcgtgtttgt cgatggctgt gaggcacaat agatccgtcg      120
gcgttatgat ggttagcctg tcatgctctt gcgatctgtg gttcctttag gaaaggcatt      180
aatttaatcc ctgatggttc gagatcggtg atccatggtt agtaccctaa gctgtggagt      240
cgggtttaga tccgcgctgt tcgtaggcga tctgttctga ttgttaactt gtcagtacct      300
gcgaatcctc ggtggttcta gctggttcgg agatcagatc gattccatta tctgctatac      360
atcttgtttc gttgcctagg ctccgtttaa tctatccatc gtatgatgtt agcctttgat      420
atgattcgat cgtgctagct atgtcctgtg gacttaattg tcaggtccta attttttagga     480 agactgttcc aaaccatctg ctggatttat taaatttgga tctggatgtg tcacatacac     540
cttcataatt aaaatggatg gaaatatctc ttatctttta gatatggata ggcatttata     600
tgatgctgtg agttttacta gtacttcctt agaatatatg tactttttta gacggaatat     660
tgatatgtat acatgtgtag atacatgaag caacatgctg ctgtagtcta ataattcctg     720
ttcatctaat aatcaagtat gtatatgttc tgtgtgtttt attggtattt gattagatat     780
atacatgctt agatacatac atgaagcagc atgctgctac agtttaatca ttattgttta     840
tccaataaac aaacatgctt tttaatttat cttgatatgc ttggatgacg gaatatgcag     900
```

```
agattttaag tacccagcat catgagcatg catgaccctg cgttagtatg ctgtttattt    960
gcttgagact ctttcttttg tagatactca ccctgttttc tggtgatcct actgcagggg   1020
```

<210> SEQ ID NO 108
<211> LENGTH: 1943
<212> TYPE: DNA
<213> ORGANISM: Coix lacryma-jobi

<400> SEQUENCE: 108

```
agcagactcg cattatcgat ggagctctac caaactggcc ctaggcatta acctaccatg     60
gatcacatcg taaaaaaaaa accctaccat ggatcctatc tgttttcttt ttgccctgaa    120
agagtgaagt catcatcata tttaccatgg cgcgcgtagg agcgcttcgt cgaagaccca    180
taggggggcg gtactcgcac cgtggttgtt cctgttatg taatatcgga tgggggagca    240
gtcggctagg ttggtcccat cggtactggt cgtcccctag tgcgctagat gcgcgatgtt    300
tgtcctcaaa aactcttttc ttcttaataa caatcatacg caaattttt gcgtattcga     360 gaaaaaaga agattctatc tgtttttttt ttgaaatggc tccaatttat aggaggagcc     420
cgtttaacgg cgtcgacaaa tctaacggac accaaccagc gaatgagcga acccaccagc    480
gccaagctag ccaagcgaag cagacggccg agacgctgac acccttgcct ggcgcggca     540 tctccgtcgc tggctcgctg gctctggccc cttcgcgaga gttccggtcc acctccacct    600
gtgtcggttt ccaactccgt tccgccttcg cgtgggactt gttccgttca tccgttggcg    660
gcatccggaa attgcgtggc gtagagcacg gggccctcct ctcacacggc acggaaccgt    720
cacgagctca cggcaccggc agcacggcgg ggattccttc cccaccaccg ctccttccct    780
ttcccttcct cgcccgccat cataaatagc caccccctccc agcttccttc gccacatcct    840
ctcatcatct tctctcgtgt agcacgcgca gcccgatccc caatccccctc tcctcgcgag    900 cctcgtcgat ccctcgcttc aaggtatggc tatcgtcctt cctctctctc tctttaccttt    960 atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa    1380
ttgtcaggtc ctaattttta ggaagactgt tccaaaccat ctgctggatt tattaaattt    1440
ggatctggat gtgtcacata caccttcata attaaaatgg atggaaatat ctcttatctt    1500
ttagatatgg ataggcattt atatgatgct gtgagtttta ctagtacttt cttagaatat    1560
atgtactttt ttagacggaa tattgatatg tatacatgtg tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttttaatt tatcttgata   1800 tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag ggt                                            1943
```

<210> SEQ ID NO 109
<211> LENGTH: 1020
<212> TYPE: DNA
<213> ORGANISM: Coix lacryma-jobi

<400> SEQUENCE: 109

```
gtatggctat cgtccttcct ctctctctct ttaccttatc tagatcggcg atccatggtt      60
agggcctgct agttctccgt tcgtgtttgt cgatggctgt gaggcacaat agatccgtcg     120
gcgttatgat ggttagcctg tcatgctctt gcgatctgtg gttcctttag gaaaggcatt     180
aatttaatcc ctgatggttc gagatcggtg atccatggtt agtaccctaa gctgtggagt     240
cgggtttaga tccgcgctgt tcgtaggcga tctgttctga ttgttaactt gtcagtacct     300
gcgaatcctc ggtggttcta gctggttcgg agatcagatc gattccatta tctgctatac     360
atcttgtttc gttgcctagg ctccgtttaa tctatccatc gtatgatgtt agcctttgat     420
atgattcgat cgtgctagct atgtcctgtg gacttaattg tcaggtccta atttttagga     480
agactgttcc aaaccatctg ctggatttat taaatttgga tctggatgtg tcacatacac     540
cttcataatt aaaatggatg gaaatatctc ttatctttta gatatggata ggcatttata     600
tgatgctgtg agttttacta gtactttctt agaatatatg tacttttta gacggaatat      660
tgatatgtat acatgtgtag atacatgaag caacatgctg ctgtagtcta ataattcctg     720
ttcatctaat aatcaagtat gtatatgttc tgtgtgtttt attggtattt gattagatat     780
atacatgctt agatacatac atgaagcagc atgctgctac agtttaatca ttattgttta     840
tccaataaac aaacatgctt tttaatttat cttgatatgc ttggatgacg gaatatgcag     900
agattttaag tacccagcat catgagcatg catgaccctg cgttagtatg ctgtttattt     960
gcttgagact ctttcttttg tagatactca ccctgttttc tggtgatcct actgcagggt    1020
```

<210> SEQ ID NO 110
<211> LENGTH: 1943
<212> TYPE: DNA
<213> ORGANISM: Coix lacryma-jobi

<400> SEQUENCE: 110

```
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180
taggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactcttttc ttcttaataa caatcatacg caaatttttt gcgtattcga     360
gaaaaaaga agattctatc tgttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac acccttgcct ggcgcggca      540
tctccgtcgc tggctcgctg ctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggccctcct ctcacacggc acggaaccgt     720
cacgagctca cggcaccggc agcacggcgg ggattccttc cccaccaccg ctccttccct     780
ttcccttcct cgcccgccat cataaatagc caccccctccc agcttccttc gccacatcct    840
ctcatcatct tctctcgtgt agcacgcgca gcccgatccc caatcccctc tcctcgcgag     900
```

```
cctcgtcgat ccctcgcttc aaggtatggc tatcgtcctt cctctctctc tctttacctt    960
atctagatcg gcgatccatg gttagggcct gctagttctc cgttcgtgtt tgtcgatggc   1020
tgtgaggcac aatagatccg tcggcgttat gatggttagc ctgtcatgct cttgcgatct   1080
gtggttcctt taggaaaggc attaatttaa tccctgatgg ttcgagatcg gtgatccatg   1140
gttagtaccc taagctgtgg agtcgggttt agatccgcgc tgttcgtagg cgatctgttc   1200
tgattgttaa cttgtcagta cctgcgaatc ctcggtggtt ctagctggtt cggagatcag   1260
atcgattcca ttatctgcta tacatcttgt ttcgttgcct aggctccgtt taatctatcc   1320
atcgtatgat gttagccttt gatatgattc gatcgtgcta gctatgtcct gtggacttaa   1380
ttgtcaggtc ctaattttta ggaagactgt tccaaaccat ctgctggatt tattaaattt   1440
ggatctggat gtgtcacata ccttcata attaaaatgg atggaaatat ctcttatctt    1500
ttagatatgg ataggcattt atgatgctgt gagttttta ctagtacttt cttagaatat    1560
atgtactttt ttagacggaa tattgatatg tatacatgtg tagatacatg aagcaacatg   1620
ctgctgtagt ctaataattc ctgttcatct aataatcaag tatgtatatg ttctgtgtgt   1680
tttattggta tttgattaga tatatacatg cttagataca tacatgaagc agcatgctgc   1740
tacagtttaa tcattattgt ttatccaata aacaaacatg cttttttaatt tatcttgata  1800
tgcttggatg acggaatatg cagagatttt aagtacccag catcatgagc atgcatgacc   1860
ctgcgttagt atgctgttta tttgcttgag actctttctt ttgtagatac tcaccctgtt   1920
ttctggtgat cctactgcag cgt                                           1943

<210> SEQ ID NO 111
<211> LENGTH: 1020
<212> TYPE: DNA
<213> ORGANISM: Coix lacryma-jobi

<400> SEQUENCE: 111
gtatggctat cgtccttcct ctctctctct ttaccttatc tagatcggcg atccatggtt     60
agggcctgct agttctccgt tcgtgtttgt cgatggctgt gaggcacaat agatccgtcg    120
gcgttatgat ggttagcctg tcatgctctt gcgatctgtg gttcctttag gaaaggcatt    180
aatttaatcc ctgatggttc gagatcggtg atccatggtt agtaccctaa gctgtggagt    240
cgggtttaga tccgcgctgt tcgtaggcga tctgttctga ttgttaactt gtcagtacct    300
gcgaatcctc ggtggttcta gctggttcgg agatcagatc gattccatta tctgctatac    360
atcttgtttc gttgcctagg ctccgtttaa tctatccatc gtatgatgtt agcctttgat    420
atgattcgat cgtgctagct atgtcctgtg gacttaattg tcaggtccta attttaggaa    480
agactgttcc aaaccatctg ctggatttat aaatttgga tctggatgtg tcacatacac    540
cttcataatt aaaatggatg gaaatatctc ttatctttta gatatggata ggcatttata    600
tgatgctgtg agttttacta gtacttcctt agaatatatg tacttttta gacggaatat    660
tgatatgtat acatgtgtag atacatgaag caacatgctg ctgtagtcta ataattcctg    720
ttcatctaat aatcaagtat gtatatgttc tgtgtgtttt attggtattt gattagatat    780
atacatgctt agatacatac atgaagcagc atgctgctac agtttaatca ttattgttta    840
tccaataaac aaacatgctt tttaatttat cttgatatgc ttggatgacg gaatatgcag    900
agattttaag tacccagcat catgagcatg catgaccctg cgttagtatg ctgtttattt    960
gcttgagact ctttcttttg tagatactca ccctgttttc tggtgatcct actgcagcgt   1020
```

-continued

<210> SEQ ID NO 112
<211> LENGTH: 1943
<212> TYPE: DNA
<213> ORGANISM: Coix lacryma-jobi

<400> SEQUENCE: 112

```
agcagactcg cattatcgat ggagctctac caaactggcc ctaggcatta acctaccatg      60
gatcacatcg taaaaaaaaa accctaccat ggatcctatc tgttttcttt ttgccctgaa     120
agagtgaagt catcatcata tttaccatgg cgcgcgtagg agcgcttcgt cgaagaccca     180
taggggggcg gtactcgcac cgtggttgtt tcctgttatg taatatcgga tgggggagca     240
gtcggctagg ttggtcccat cggtactggt cgtcccctag tgcgctagat gcgcgatgtt     300
tgtcctcaaa aactctttc ttcttaataa caatcatacg caattttttt gcgtattcga     360
gaaaaaaga agattctatc tgtttttttt ttgaaatggc tccaatttat aggaggagcc     420
cgtttaacgg cgtcgacaaa tctaacggac accaaccagc gaatgagcga acccaccagc     480
gccaagctag ccaagcgaag cagacggccg agacgctgac acccttgcct ggcgcggca     540
tctccgtcgc tggctcgctg gctctggccc cttcgcgaga gttccggtcc acctccacct     600
gtgtcggttt ccaactccgt tccgccttcg cgtgggactt gttccgttca tccgttggcg     660
gcatccggaa attgcgtggc gtagagcacg gggccctcct ctcacacggc acggaaccgt     720
cacgagctca cggcaccggc agcacggcgg ggattccttc cccaccaccg ctccttccct     780
ttcccttcct cgcccgccat cataaatagc cacccctccc agcttccttc gccacatcct     840
ctcatcatct tctctcgtgt agcacgcgca gcccgatccc caatcccctc tcctcgcgag     900
cctcgtcgat ccctcgcttc aaggtatggc tatcgtcctt cctctctctc tctttacctt     960
atctagatcg gcgatccatg gttagggcct gctagttctc cgttcgtgtt tgtcgatggc    1020
tgtgaggcac aatagatccg tcggcgttat gatggttagc ctgtcatgct cttgcgatct    1080
gtggttcctt taggaaaggc attaatttaa tccctgatgg ttcgagatcg gtgatccatg    1140
gttagtaccc taagctgtgg agtcgggttt agatccgcgc tgttcgtagg cgatctgttc    1200
tgattgttaa cttgtcagta cctgcgaatc ctcggtggtt ctagctggtt cggagatcag    1260
atcgattcca ttatctgcta tacatcttgt ttcgttgcct aggctccgtt taatctatcc    1320
atcgtatgat gttagccttt gatatgattc gatcgtgcta gctatgtcct gtggacttaa    1380
ttgtcaggtc ctaattttta ggaagactgt tccaaaccat ctgctggatt tattaaattt    1440
ggatctggat gtgtcacata caccttcata attaaaatgg atggaaatat ctcttatctt    1500
ttagatatgg ataggcattt atatgatgct gtgagtttta ctagtacttt cttagaatat    1560
atgtactttt ttagacggaa tattgatatg tatacatgtg tagatacatg aagcaacatg    1620
ctgctgtagt ctaataattc ctgttcatct aataatcaag tatgtatatg ttctgtgtgt    1680
tttattggta tttgattaga tatatacatg cttagataca tacatgaagc agcatgctgc    1740
tacagtttaa tcattattgt ttatccaata aacaaacatg cttttaatt tatcttgata    1800
tgcttggatg acggaatatg cagagatttt aagtacccag catcatgagc atgcatgacc    1860
ctgcgttagt atgctgtta tttgcttgag actctttctt ttgtagatac tcaccctgtt    1920
ttctggtgat cctactgcag tgt                                             1943
```

<210> SEQ ID NO 113
<211> LENGTH: 1020
<212> TYPE: DNA
<213> ORGANISM: Coix lacryma-jobi

<400> SEQUENCE: 113

```
gtatggctat cgtccttcct ctctctctct ttaccttatc tagatcggcg atccatggtt    60
agggcctgct agttctccgt tcgtgtttgt cgatggctgt gaggcacaat agatccgtcg   120
gcgttatgat ggttagcctg tcatgctctt gcgatctgtg gttcctttag gaaaggcatt   180
aatttaatcc ctgatggttc gagatcggtg atccatggtt agtaccctaa gctgtggagt   240
cgggtttaga tccgcgctgt tcgtaggcga tctgttctga ttgttaactt gtcagtacct   300
gcgaatcctc ggtggttcta gctggttcgg agatcagatc gattccatta tctgctatac   360
atcttgtttc gttgcctagg ctccgtttaa tctatccatc gtatgatgtt agcctttgat   420
atgattcgat cgtgctagct atgtcctgtg gacttaattg tcaggtccta atttttagga   480
agactgttcc aaaccatctg ctggatttat taaatttgga tctggatgtg tcacatacac   540
cttcataatt aaaatggatg gaaatatctc ttatctttta gatatggata ggcatttata   600
tgatgctgtg agttttacta gtactttctt agaatatatg tacttttta gacggaatat    660
tgatatgtat acatgtgtag atacatgaag caacatgctg ctgtagtcta ataattcctg   720
ttcatctaat aatcaagtat gtatatgttc tgtgtgtttt attggtattt gattagatat   780
atacatgctt agatacatac atgaagcagc atgctgctac agtttaatca ttattgttta   840
tccaataaac aaacatgctt tttaatttat cttgatatgc ttggatgacg aatatgcag   900
agattttaag tacccagcat catgagcatg catgaccctg cgttagtatg ctgtttattt   960
gcttgagact ctttcttttg tagatactca ccctgttttc tggtgatcct actgcagtgt  1020
```

<210> SEQ ID NO 114
<211> LENGTH: 1848
<212> TYPE: DNA
<213> ORGANISM: Coix lacryma-jobi

<400> SEQUENCE: 114

```
ctatctgttt tcttttttgcc ctgaaagagt gaagtcatca tcatatttac catggcgcgc    60
gtaggagcgc ttcgtcgaag acccataggg gggcggtact cgcaccgtgg ttgtttcctg   120
ttatgtaata tcggatgggg gagcagtcgg ctaggttggt cccatcggta ctggtcgtcc   180
cctagtgcgc tagatgcgcg atgtttgtcc tcaaaaactc tttctcttctt aataacaatc   240
atacgcaaat ttttgcgta ttcgagaaaa aagaagatt ctatctgttt ttttttttgaa    300
atggctccaa tttataggag gagcccgttt aacggcgtcg acaaatctaa cggacaccaa   360
ccagcgaatg agcgaaccca ccagcgccaa gctagccaag cgaagcagac ggccgagacg   420
ctgacaccct tgccttggcg cggcatctcc gtcgctggct cgctggctct ggccccttcg   480
cgagagttcc ggtccacctc cacctgtgtc ggtttccaac tccgttccgc cttcgcgtgg   540
gacttgttcc gttcatccgt tggcggcatc cggaaattgc gtggcgtaga gcacgggggcc   600
ctcctctcac acggcacgga accgtcacga gctcacggca ccggcagcac ggcggggatt   660
ccttccccac caccgctcct tcccctttccc ttcctcgccc gccatcataa atagccaccc   720
ctcccagctt ccttcgccac atcctctcat catcttctct cgtgtagcac gcgcagcccg   780
atccccaatc ccctctcctc gcgagcctcg tcgatccctc gcttcaaggt atggctatcg   840
tccttcctct ctctctcttt accttatcta gatcggcgat ccatggttag gcctgctag    900
ttctccgttc gtgttttgtcg atggctgtga ggcacaatag atccgtcggc gttatgatgg   960
ttagcctgtc atgctcttgc gatctgtggt tcctttagga aaggcattaa tttaatccct  1020
gatggttcga gatcggtgat ccatggttag taccctaagc tgtggagtcg ggtttagatc  1080
```

```
cgcgctgttc gtaggcgatc tgttctgatt gttaacttgt cagtacctgc gaatcctcgg    1140
tggttctagc tggttcggag atcagatcga ttccattatc tgctatacat cttgtttcgt    1200
tgcctaggct ccgtttaatc tatccatcgt atgatgttag cctttgatat gattcgatcg    1260
tgctagctat gtcctgtgga cttaattgtc aggtcctaat ttttaggaag actgttccaa    1320
accatctgct ggatttatta aatttggatc tggatgtgtc acatacacct tcataattaa    1380
aatgatggaa atatctctt atcttttaga tatggatagg catttatatg atgctgtgag    1440
ttttactagt actttcttag aatatatgta cttttttaga cggaatattg atatgtatac    1500
atgtgtagat acatgaagca acatgctgct gtagtctaat aattcctgtt catctaataa    1560
tcaagtatgt atatgttctg tgtgttttat tggtatttga ttagatatat acatgcttag    1620
atacatacat gaagcagcat gctgctacag tttaatcatt attgtttatc caataaacaa    1680
acatgctttt taatttatct tgatatgctt ggatgacgga atatgcagag attttaagta    1740
cccagcatca tgagcatgca tgaccctgcg ttagtatgct gtttatttgc ttgagactct    1800
ttcttttgta gatactcacc ctgttttctg gtgatcctac tgcaggtc                 1848

<210> SEQ ID NO 115
<211> LENGTH: 1507
<212> TYPE: DNA
<213> ORGANISM: Coix lacryma-jobi

<400> SEQUENCE: 115
caaatctaac ggacaccaac cagcgaatga gcgaacccac cagcgccaag ctagccaagc      60
gaagcagacg gccgagacgc tgacaccctt gccttggcgc ggcatctccg tcgctggctc     120
gctggctctg gcccttcgc gagagttccg gtccacctcc acctgtgtcg gtttccaact     180
ccgttccgcc ttcgcgtggg acttgttccg ttcatccgtt ggcggcatcc ggaaattgcg     240
tggcgtagag cacggggccc tcctctcaca cggcacggaa ccgtcacgag ctcacggcac     300
cggcagcacg gcggggattc cttccccacc accgctcctt cccttccct tcctcgcccg     360 ccatcataaa tagccacccc tcccagcttc cttcgccaca tcctctcatc atcttctctc     420
gtgtagcacg cgcagcccga tccccaatcc cctctcctcg cgagcctcgt cgatccctcg     480
cttcaaggta tggctatcgt ccttcctctc tctctcttta ccttatctag atcggcgatc     540
catggttagg gcctgctagt tctccgttcg tgtttgtcga tggctgtgag gcacaataga     600
tccgtcggcg ttatgatggt tagcctgtca tgctcttgcg atctgtggtt cctttaggaa     660
aggcattaat ttaatccctg atggttcgag atcggtgatc catggttagt accctaagct     720
gtggagtcgg gtttagatcc gcgctgttcg taggcgatct gttctgattg ttaacttgtc     780
agtacctgcg aatcctcggt ggttctagct ggttcggaga tcagatcgat tccattatct     840
gctatacatc ttgtttcgtt gcctaggctc cgtttaatct atccatcgta tgatgttagc     900
ctttgatatg attcgatcgt gctagctatg tcctgtggac ttaattgtca ggtcctaatt     960
tttaggaaga ctgttccaaa ccatctgctg gatttattaa atttggatct ggatgtgtca    1020
catacccttt cataattaaa atggatggaa atatctctta tcttttagat atggataggc    1080
atttatatga tgctgtgagt tttactagta ctttcttaga atatatgtac tttttttagac    1140 ggaatattga tatgtataca tgtgtagata catgaagcaa catgctgctg tagtctaata    1200
attcctgttc atctaataat caagtatgta tatgttctgt gtgttttatt ggtatttgat    1260
tagatatata catgcttaga tacatacatg aagcagcatg ctgctacagt ttaatcatta    1320
```

| | |
|---|---|
| ttgtttatcc aataaacaaa catgcttttt aatttatctt gatatgcttg gatgacggaa | 1380 |
| tatgcagaga ttttaagtac ccagcatcat gagcatgcat gaccctgcgt tagtatgctg | 1440 |
| tttatttgct tgagactctt tcttttgtag atactcaccc tgttttctgg tgatcctact | 1500 |
| gcaggtc | 1507 |

<210> SEQ ID NO 116
<211> LENGTH: 1160
<212> TYPE: DNA
<213> ORGANISM: Coix lacryma-jobi

<400> SEQUENCE: 116

| | |
|---|---|
| ccttcctcgc ccgccatcat aaatagccac ccctcccagc ttccttcgcc acatcctctc | 60 |
| atcatcttct ctcgtgtagc acgcgcagcc cgatccccaa tccctctcc tcgcgagcct | 120 |
| cgtcgatccc tcgcttcaag gtatggctat cgtccttcct ctctctctct ttaccttatc | 180 |
| tagatcggcg atccatggtt agggcctgct agttctccgt tcgtgtttgt cgatggctgt | 240 |
| gaggcacaat agatccgtcg gcgttatgat ggttagcctg tcatgctctt gcgatctgtg | 300 |
| gttcctttag gaaaggcatt aatttaatcc ctgatggttc gagatcggtg atccatggtt | 360 |
| agtaccctaa gctgtggagt cgggtttaga tccgcgctgt tcgtaggcga tctgttctga | 420 |
| ttgttaactt gtcagtacct gcgaatcctc ggtggttcta gctggttcgg agatcagatc | 480 |
| gattccatta tctgctatac atcttgtttc gttgcctagg ctccgtttaa tctatccatc | 540 |
| gtatgatgtt agcctttgat atgattcgat cgtgctagct atgtcctgtg gacttaattg | 600 |
| tcaggtccta atttttagga agactgttcc aaaccatctg ctggatttat taaatttgga | 660 |
| tctggatgtg tcacatacac cttcataatt aaaatggatg gaaatatctc ttatctttta | 720 |
| gatatggata ggcattttata tgatgctgtg agttttacta gtactttctt agaatatatg | 780 |
| tacttttta gacggaatat tgatatgtat acatgtgtag atacatgaag caacatgctg | 840 |
| ctgtagtcta ataattcctg ttcatctaat aatcaagtat gtatatgttc tgtgtgtttt | 900 |
| attggtattt gattagatat atacatgctt agatacatac atgaagcagc atgctgctac | 960 |
| agtttaatca ttattgttta tccaataaac aaacatgctt tttaatttat cttgatatgc | 1020 |
| ttggatgacg gaatatgcag agattttaag tacccagcat catgagcatg catgaccctg | 1080 |
| cgttagtatg ctgtttattt gcttgagact ctttctttg tagatactca ccctgttttc | 1140 |
| tggtgatcct actgcaggtc | 1160 |

<210> SEQ ID NO 117
<211> LENGTH: 2625
<212> TYPE: DNA
<213> ORGANISM: Setaria italica

<400> SEQUENCE: 117

| | |
|---|---|
| actgccgcga cacgcctcac tggcgggagg gctccgagcg ctctctcccc ggcggccggc | 60 |
| ggagcagcga tctggattgg agagaataga ggaaagagag ggaaaaggag agagatagcg | 120 |
| caaagagctg aaaagataag gttgtgcggg ctgtggtgat tagaggacca ctaatccctc | 180 |
| catctcctaa tgacgcggtg cccaagacca gtgccgcggc acaccagcgt ctaagtgaac | 240 |
| ttccgctaac cttccggtca ttgcgcctga agatgtcat gtggcgaggc cccctctca | 300 |
| gtagattgcc aactgcctac cgtgccactc ttccatgcat gattgctccc gtctatcccg | 360 |
| tttctcacaa cagatagaca acagtaagca tcactaaagc aagcatgtgt agaaccttaa | 420 |
| aaaaaggctt atactaccag tatactatca accagcatgc cgttttttgaa gtatccagga | 480 |

```
ttagaagctt ctactgcgct tttatattat agctgtggac ctgtggtaac ctttctcttt      540
tggcgcttgc ttaatctcgg ccgtgctggt ccatgcttag gcactaggca gagatagagc      600
cgggggtgaa tggggctaaa gctcagctgc tcgaggggcc gtgggctggt ttccactagc      660
ctacagctgt gccacgtgcg gccgcgcaag ccgaagcaag cacgctgagc cgttggacag      720
cttgtcataa tgccattacg tggattacac gtaactggcc ctgtaactac tcgttcggcc      780
atcatcaaac gacgacgtcc gctaggcgac gacacgggta atgcacgcag ccacccaggc      840
gcgcgcgcta gcggagcacg gtcaggtgac acgggcgtcg tgacgcttcc gagttgaagg      900
ggttaacgcc agaaacagtg tttggccagg gtatgaacat aacaaaaaat attcacacga      960
aagaatggaa gtatggagct gctactgtgt aaatgccaag caggaaactc acgcccgcta     1020
acatccaacg gccaacagct cgacgtgccg gtcagcagag catcggaaca ctggtgattg     1080
gtggagccgg cagtatgcgc cccagcacgg ccgaggtggt ggtggcccgt ggccctgctg     1140
tctgcgcggc tcgggacaac ttgaaactgg gccaccgcct cgtcgaact cgcaacccgt     1200
tggcggaaga aaggaatggc tcgtaggggc ccgggtagaa tcgaagaatg ttgcgctggg     1260
cttcgattca cataacatgg gcctgaagct ctaaaacgac ggcccggtcg ccgcgcgatg     1320
gaaagagacc ggatcctcct cgtgaattct ggaaggccac acgagagcga cccaccaccg     1380
acgcggagga gtcgtgcgtg gtccaacacg gccggcgggc tgggctgcga ccttaaccag     1440
caaggcacgc cacgacccgc cccgccctcg aggcataaat accctcccat cccgttgccg     1500
caagactcag atcagattcc gatccccagt tcttccccaa tcaccttgtg gtctctcgtg     1560
tcgcggttcc cagggacgcc tccggctcgt cgctcgacag cgatctccgc cccagcaagg     1620
tatagattca gttccttgct ccgatcccaa tctggttgag atgttgctcc gatgcgactt     1680
gattatgtca tatatctgcg gtttgcaccg atctgaagcc tagggtttct cgagcgaccc     1740
agttatttgc aatttgcgat ttgctcgttt gttgcgcagc gtagtttatg tttggagtaa     1800
tcgaggattt gtatgcggcg tcggcgctac ctgcttaatc acgccatgtg acgcggttac     1860
ttgcagaggc tgggttctgt tatgtcgtga tctaagaatc tagattaggc tcagtcgttc     1920
ttgctgtcga ctagtttgtt ttgatatcca tgtagtacaa gttacttaaa atttaggtcc     1980
aatatatttt gcatgctttt ggcctgttat tcttgccaac aagttgtcct ggtaaaaagt     2040
agatgtgaaa gtcacgtatt gggacaaatt gatggtttag tgctatagtt ctatagttct     2100
gtgatacatc tatctgattt tttttggtct attggtgcct aacttatctg aaaatcatgg     2160
aacatgaggc tagtttgatc atggtttagt tcattgtgat taataatgta tgatttagta     2220
gctatttgg tgatcgtgtc attttatttg tgaatggaat cattgtatgt aaatgaagct      2280
agttcagggg ttacgatgta gctggctttg tattctaaag gctgctatta ttcatccatc     2340
gatttcacct atatgtaatc cagagctttt gatgtgaaat ttgtctgatc cttcactagg     2400
aaggacagaa cattgttaat attttggcac atctgtctta ttctcatcct ttgtttgaac     2460
atgttagcct gttcaaacag atactgttgt aatgtcctag ttatataggt acatatgtgt     2520
tctctattga gtttatggac ttttgtgtgt gaagttatat ttcattttgc tcaaaactca     2580
tgtttgcaag ctttctgaca ttattctatt gttctgaaac aggtg                    2625
```

<210> SEQ ID NO 118
<211> LENGTH: 1006
<212> TYPE: DNA
<213> ORGANISM: Setaria italica

<400> SEQUENCE: 118

```
gtatagattc agttccttgc tccgatccca atctggttga gatgttgctc cgatgcgact    60
tgattatgtc atatatctgc ggtttgcacc gatctgaagc ctagggtttc tcgagcgacc   120
cagttatttg caatttgcga tttgctcgtt tgttgcgcag cgtagtttat gtttggagta   180
atcgaggatt tgtatgcggc gtcggcgcta cctgcttaat cacgccatgt gacgcggtta   240
cttgcagagg ctgggttctg ttatgtcgtg atctaagaat ctagattagg ctcagtcgtt   300
cttgctgtcg actagtttgt tttgatatcc atgtagtaca agttacttaa aatttaggtc   360
caatatattt tgcatgcttt tggcctgtta ttcttgccaa caagttgtcc tggtaaaaag   420
tagatgtgaa agtcacgtat tgggacaaat tgatggttta gtgctatagt tctatagttc   480
tgtgatacat ctatctgatt ttttttggtc tattggtgcc taacttatct gaaaatcatg   540
gaacatgagg ctagtttgat catggtttag ttcattgtga ttaataatgt atgatttagt   600
agctattttg gtgatcgtgt cattttattt gtgaatggaa tcattgtatg taaatgaagc   660
tagttcaggg gttacgatgt agctggcttt gtattctaaa ggctgctatt attcatccat   720
cgatttcacc tatatgtaat ccagagcttt tgatgtgaaa tttgtctgat ccttcactag   780
gaaggacaga acattgttaa tattttggca catctgtctt attctcatcc tttgtttgaa   840
catgttagcc tgttcaaaca gatactgttg taatgtccta gttatatagg tacatatgtg   900
ttctctattg agtttatgga cttttgtgtg tgaagttata tttcattttg ctcaaaactc   960
atgtttgcaa gctttctgac attattctat tgttctgaaa caggtg                1006
```

<210> SEQ ID NO 119
<211> LENGTH: 2625
<212> TYPE: DNA
<213> ORGANISM: Setaria italica

<400> SEQUENCE: 119

```
actgccgcga cacgcctcac tggcgggagg gctccgagcg ctctctcccc ggcggccggc    60
ggagcagcga tctggattgg agagaataga ggaaagagag ggaaaaggag agagatagcg   120
caaagagctg aaaagataag gttgtgcggg ctgtggtgat tagaggacca ctaatccctc   180
catctcctaa tgacgcggtg cccaagacca gtgccgcggc acaccagcgt ctaagtgaac   240
ttccgctaac cttccggtca ttgcgcctga aagatgtcat gtggcgaggc cccctctca   300
gtagattgcc aactgcctac cgtgccactc ttccatgcat gattgctccc gtctatcccg   360
tttctcacaa cagatagaca acagtaagca tcactaaagc aagcatgtgt agaaccttaa   420
aaaaaggctt atactaccag tatactatca accagcatgc cgttttgaa gtatccagga   480
ttagaagctt ctactgcgct tttatattat agctgtggac ccgtggtaac ctttctcttt   540
tggcgcttgc ttaatctcgg ccgtgctggt ccatgcttag gcactaggca gagatagagc   600
cggggtgaa tggggctaaa gctcagctgc tcgaggggcc gtgggctggt ttccactagc   660
ctacagctgt gccacgtgcg gccgcgcaag ccgaagcaag cacgctgagc cgttggacag   720
cttgtcataa tgccattacg tggattacac gtaactggcc ctgtaactac tcgttcggcc   780
atcatcaaac gacgacgtcc gctaggcgac gacgggta atgcacgcag ccacccaggc   840
gcgcgcgcta gcggagcacg gtcaggtgac acgggcgtcg tgacgcttcc gagttgaagg   900
ggttaacgcc agaaacagtg tttggccagg gtatgaacat aacaaaaaat attcacacga   960
agaatggaa gtatggagct gctactgtgt aaatgccaag caggaaactc acgcccgcta  1020
acatccaacg gccaacagct cgacgtgccg gtcagcagag catcggaaca ctggtgattg  1080
```

```
gtggagccgg cagtatgcgc cccagcacgg ccgaggtggt ggtggcccgt ggccctgctg      1140
tctgcgcggc tcgggacaac ttgaaactgg gccaccgcct cgtcgcaact cgcaacccgt      1200
tggcggaaga aaggaatggc tcgtaggggc ccgggtagaa tcgaagaatg ttgcgctggg      1260
cttcgattca cataacatgg gcctgaagct ctaaaacgac ggcccggtcg ccgcgcgatg      1320
gaaagagacc ggatcctcct cgtgaattct ggaaggccac acgagagcga cccaccaccg      1380
acgcggagga gtcgtgcgtg gtccaacacg gccggcgggc tgggctgcga ccttaaccag      1440
caaggcacgc cacgacccgc cccgccctcg aggcataaat accctcccat cccgttgccg      1500
caagactcag atcagattcc gatccccagt tcttccccaa tcaccttgtg gtctctcgtg      1560
tcgcggttcc cagggacgcc tccggctcgt cgctcgacag cgatctccgc cccagcaagg      1620
tatagattca gttccttgct ccgatcccaa tctggttgag atgttgctcc gatgcgactt      1680
gattatgtca tatatctgcg gtttgcaccg atctgaagcc tagggtttct cgagcgaccc      1740
agttatttgc aatttgcgat ttgctcgttt gttgcgcagc gtagtttatg tttggagtaa      1800
tcgaggattt gtatgcggcg tcggcgctac ctgcttaatc acgccatgtg acgcggttac      1860
ttgcagaggc tgggttctgt tatgtcgtga tctaagaatc tagattaggc tcagtcgttc      1920
ttgctgtcga ctagtttgtt ttgatatcca tgtagtacaa gttacttaaa atttaggtcc      1980
aatatatttt gcatgctttt ggcctgttat tcttgccaac aagttgtcct ggtaaaaagt      2040
agatgtgaaa gtcacgtatt gggacaaatt gatggtttag tgctatagtt ctatagttct      2100
gtgatacatc tatctgattt tttttggtct attggtgcct aacttatctg aaaatcatgg      2160
aacatgaggc tagtttgatc atggtttagt tcattgtgat aataatgta tgatttagta      2220 gctattttgg tgatcgtgtc attttatttg tgaatggaat cattgtatgt aaatgaagct      2280
agttcagggg ttacgatgta gctggctttg tattctaaag gctgctatta ttcatccatc      2340
gatttcacct atatgtaatc cagagctttt gatgtgaaat ttgtctgatc cttcactagg      2400
aaggacagaa cattgttaat attttggcac atctgtctta ttctcatcct ttgtttgaac      2460
atgttagcct gttcaaacag atactgttgt aatgtcctag ttatataggt acatatgtgt      2520
tctctattga gtttatggac ttttgtgtgt gaagttatat ttcattttgc tcaaaactca      2580
tgtttgcaag ctttctgaca ttattctatt gttctgaaac agggt                     2625
```

<210> SEQ ID NO 120
<211> LENGTH: 1006
<212> TYPE: DNA
<213> ORGANISM: Setaria italica

<400> SEQUENCE: 120

```
gtatagattc agttccttgc tccgatccca atctggttga gatgttgctc cgatgcgact       60
tgattatgtc atatatctgc ggtttgcacc gatctgaagc ctagggtttc tcgagcgacc      120
cagttatttg caatttgcga tttgctcgtt tgttgcgcag cgtagtttat gtttggagta      180
atcgaggatt tgtatgcggc gtcggcgcta cctgcttaat cacgccatgt gacgcggtta      240
cttgcagagg ctgggttctg ttatgtcgtg atctaagaat ctagattagg ctcagtcgtt      300
cttgctgtcg actagtttgt tttgatatcc atgtagtaca agttacttaa atttaggtc      360 caatatattt tgcatgcttt tggcctgtta ttcttgccaa caagttgtcc tggtaaaaag      420
tagatgtgaa agtcacgtat tgggacaaat tgatggttta gtgctatagt tctatagttc      480
tgtgatacat ctatctgatt tttttggtc tattggtgcc taacttatct gaaaatcatg      540
```

```
gaacatgagg ctagtttgat catggtttag ttcattgtga ttaataatgt atgatttagt    600
agctattttg gtgatcgtgt cattttattt gtgaatggaa tcattgtatg taaatgaagc    660
tagttcaggg gttacgatgt agctggcttt gtattctaaa ggctgctatt attcatccat    720
cgatttcacc tatatgtaat ccagagcttt tgatgtgaaa tttgtctgat ccttcactag    780
gaaggacaga acattgttaa tattttggca catctgtctt attctcatcc tttgtttgaa    840
catgttagcc tgttcaaaca gatactgttg taatgtccta gttatatagg tacatatgtg    900
ttctctattg agtttatgga cttttgtgtg tgaagttata tttcattttg ctcaaaactc    960
atgtttgcaa gctttctgac attattctat tgttctgaaa cagggt                  1006

<210> SEQ ID NO 121
<211> LENGTH: 2625
<212> TYPE: DNA
<213> ORGANISM: Setaria italica

<400> SEQUENCE: 121
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga aagatgtcat gtggcgaggc ccccctctca    300
gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgttttttgaa gtatccagga    480 ttagaagctt ctactgcgct tttatattat agctgtggac ccgtggtaac ctttctcttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattcacg gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaacccgt   1200
tggcggaaga aaggaatggc tcgtagggc cggtagaa tcgaagaatg ttgcgctggg    1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgccctcg aggcataaat accctcccat cccgttgccg   1500
caagactcag atcagattcc gatcccagt tcttccccaa tcaccttgtg gtctctcgtg    1560
tcgcggttcc cagggacgcc tccggctcgt cgctcgacag cgatccgcgc cccagcaagg   1620
tatagattca gttccttgct ccgatcccaa tctggttgag atgttgctcc gatgcgactt   1680
```

```
gattatgtca tatatctgcg gtttgcaccg atctgaagcc tagggtttct cgagcgaccc    1740
agttatttgc aatttgcgat ttgctcgttt gttgcgcagc gtagtttatg tttggagtaa    1800
tcgaggattt gtatgcggcg tcggcgctac ctgcttaatc acgccatgtg acgcggttac    1860
ttgcagaggc tgggttctgt tatgtcgtga tctaagaatc tagattaggc tcagtcgttc    1920
ttgctgtcga ctagtttgtt ttgatatcca tgtagtacaa gttacttaaa atttaggtcc    1980
aatatatttt gcatgctttt ggcctgttat tcttgccaac aagttgtcct ggtaaaaagt    2040
agatgtgaaa gtcacgtatt gggacaaatt gatggtttag tgctatagtt ctatagttct    2100
gtgatacatc tatctgattt ttttttggtct attggtgcct aacttatctg aaaatcatgg   2160
aacatgaggc tagtttgatc atggtttagt tcattgtgat taataatgta tgatttagta    2220
gctattttgg tgatcgtgtc attttatttg tgaatggaat cattgtatgt aaatgaagct    2280
agttcagggg ttacgatgta gctggctttg tattctaaag gctgctatta ttcatccatc    2340
gatttcacct atatgtaatc cagagctttt gatgtgaaat ttgtctgatc cttcactagg    2400
aaggacagaa cattgttaat attttggcac atctgtctta ttctcatcct ttgtttgaac    2460
atgttagcct gttcaaacag atactgttgt aatgtcctag ttataggt acatatgtgt      2520 tctctattga gtttatggac ttttgtgtgt gaagttatat ttcattttgc tcaaaactca    2580
tgtttgcaag ctttctgaca ttattctatt gttctgaaac agacc                   2625

<210> SEQ ID NO 122
<211> LENGTH: 1006
<212> TYPE: DNA
<213> ORGANISM: Setaria italica

<400> SEQUENCE: 122
gtatagattc agttccttgc tccgatccca atctggttga gatgttgctc cgatgcgact     60
tgattatgtc atatatctgc ggtttgcacc gatctgaagc ctagggtttc tcgagcgacc    120
cagttatttg caatttgcga tttgctcgtt tgttgcgcag cgtagtttat gtttggagta    180
atcgaggatt tgtatgcggc gtcggcgcta cctgcttaat cacgccatgt gacgcggtta    240
cttgcagagg ctgggttctg ttatgtcgtg atctaagaat ctagattagg ctcagtcgtt    300
cttgctgtcg actagtttgt tttgatatcc atgtagtaca agttacttaa aatttaggtc    360
caatatattt tgcatgcttt tggcctgtta ttcttgccaa caagttgtcc tggtaaaaag    420
tagatgtgaa agtcacgtat tgggacaaat tgatggttta gtgctatagt tctatagttc    480
tgtgatacat ctatctgatt ttttttggtc tattggtgcc taacttatct gaaaatcatg    540
gaacatgagg ctagtttgat catggtttag ttcattgtga ttaataatgt atgatttagt    600
agctattttg gtgatcgtgt catttt attt gtgaatggaa tcattgtatg taatgaagc    660 tagttcaggg gttacgatgt agctggcttt gtattctaaa ggctgctatt attcatccat    720
cgatttcacc tatatgtaat ccagagcttt tgatgtgaaa tttgtctgat ccttcactag    780
gaaggacaga acattgttaa tattttggca catctgtctt attctcatcc tttgtttgaa    840
catgttagcc tgttcaaaca gatactgttg taatgtccta gttataggta catatgtg     900 ttctctattg agtttatgga cttttgtgtg tgaagttata tttcattttg ctcaaaactc    960
atgtttgcaa gctttctgac attattctat tgttctgaaa cagacc                  1006

<210> SEQ ID NO 123
<211> LENGTH: 2167
<212> TYPE: DNA
```

<213> ORGANISM: Setaria italica

<400> SEQUENCE: 123

```
gccgtttttg aagtatccag gattagaagc ttctactgcg cttttatatt atagctgtgg      60
acctgtggta acctttctct tttggcgctt gcttaatctc ggccgtgctg gtccatgctt     120
aggcactagg cagagataga gccggggtg aatggggcta aagctcagct gctcgagggg     180
ccgtgggctg gtttccacta gcctacagct gtgccacgtg cggccgcgca agccgaagca     240
agcacgctga gccgttggac agcttgtcat aatgccatta cgtggattac acgtaactgg     300
ccctgtaact actcgttcgg ccatcatcaa cgacgacgt ccgctaggcg acgacacggg     360
taatgcacgc agccacccag gcgcgcgcgc tagcggagca cggtcaggtg acacgggcgt     420
cgtgacgctt ccgagttgaa ggggttaacg ccagaaacag tgtttggcca gggtatgaac     480
ataacaaaaa atattcacac gaaagaatgg aagtatggag ctgctactgt gtaaatgcca     540
agcaggaaac tcacgcccgc taacatccaa cggccaacag ctcgacgtgc cggtcagcag     600
agcatcggaa cactggtgat tggtggagcc ggcagtatgc gccccagcac ggccgaggtg     660
gtggtggccc gtggcctgc tgtctgcgcg gctcgggaca acttgaaact gggccaccgc     720
ctcgtcgcaa ctcgcaaccc gttggcgaa gaaaggaatg gctcgtaggg gcccgggtag     780
aatcgaagaa tgttgcgctg ggcttcgatt cacataacat gggcctgaag ctctaaaacg     840
acggcccggt cgccgcgcga tggaaagaga ccggatcctc ctcgtgaatt ctggaaggcc     900
acacgagagc gacccaccac cgacgcggag gagtcgtgcg tggtccaaca cggccggcgg     960
gctgggctgc gaccttaacc agcaaggcac gccacgaccc gccccgccct cgaggcataa    1020
ataccctccc atcccgttgc cgcaagactc agatcagatt ccgatcccca gttcttcccc    1080
aatcaccttg tggtctctcg tgtcgcggtt cccaggacg cctccggctc gtcgctcgac    1140
agcgatctcc gccccagcaa ggtatagatt cagttccttg ctccgatccc aatctggttg    1200
agatgttgct ccgatgcgac ttgattatgt catatatctg cggtttgcac cgatctgaag    1260
cctagggttt ctcgagcgac ccagttattt gcaatttgcg atttgctcgt tgttgcgca    1320
gcgtagttta tgtttggagt aatcgaggat ttgtatgcgg cgtcggcgct acctgcttaa    1380
tcacgccatg tgacgcggtt acttgcagag gctgggttct gttatgtcgt gatctaagaa    1440
tctagattag gctcagtcgt tcttgctgtc gactagtttg ttttgatatc catgtagtac    1500
aagttactta aaatttaggt ccaatatatt ttgcatgctt ttggcctgtt attcttgcca    1560
acaagttgtc ctggtaaaaa gtagatgtga aagtcacgta ttgggacaaa ttgatggttt    1620
agtgctatag ttctatagtt ctgtgataca tctatctgat ttttttggt ctattggtgc    1680
ctaacttatc tgaaaatcat ggaacatgag gctagtttga tcatggttta gttcattgtg    1740
attaataatg tatgatttag tagctatttt ggtgatcgtg tcattttatt tgtgaatgga    1800
atcattgtat gtaaatgaag ctagttcagg ggttacgatg tagctggctt tgtattctaa    1860
aggctgctat tattcatcca tcgatttcac ctatatgtaa tccagagctt ttgatgtgaa    1920
atttgtctga tccttcacta ggaaggacag aacattgtta atattttggc acatctgtct    1980
tattctcatc ctttgtttga acatgttagc ctgttcaaac agatactgtt gtaatgtcct    2040
agttatatag gtacatatgt gttctctatt gagtttatgg acttttgtgt gtgaagttat    2100
atttcatttt gctcaaaact catgtttgca agctttctga cattattcta ttgttctgaa    2160
acaggtg                                                             2167
```

<210> SEQ ID NO 124
<211> LENGTH: 1813
<212> TYPE: DNA
<213> ORGANISM: Setaria italica

<400> SEQUENCE: 124

| | | | | | |
|---|---|---|---|---|---|
| cacgggtaat | gcacgcagcc | acccaggcgc | gcgcgctagc | ggagcacggt | caggtgacac | 60 |
| gggcgtcgtg | acgcttccga | gttgaagggg | ttaacgccag | aaacagtgtt | tggccagggt | 120 |
| atgaacataa | caaaaaatat | tcacacgaaa | gaatggaagt | atggagctgc | tactgtgtaa | 180 |
| atgccaagca | ggaaactcac | gcccgctaac | atccaacggc | caacagctcg | acgtgccggt | 240 |
| cagcagagca | tcggaacact | ggtgattggt | ggagccggca | gtatgcgccc | cagcacggcc | 300 |
| gaggtggtgg | tggcccgtgg | ccctgctgtc | tgcgcggctc | gggacaactt | gaaactgggc | 360 |
| caccgcctcg | tcgcaactcg | caacccgttg | cggaagaaa | ggaatggctc | gtaggggccc | 420 |
| gggtagaatc | gaagaatgtt | gcgctgggct | tcgattcaca | taacatgggc | ctgaagctct | 480 |
| aaaacgacgg | cccggtcgcc | gcgcgatgga | aagagaccgg | atcctcctcg | tgaattctgg | 540 |
| aaggccacac | gagagcgacc | caccaccgac | gcggaggagt | cgtgcgtggt | ccaacacggc | 600 |
| cggcgggctg | ggctgcgacc | ttaaccagca | aggcacgcca | cgacccgccc | cgccctcgag | 660 |
| gcataaatac | cctcccatcc | cgttgccgca | agactcagat | cagattccga | tccccagttc | 720 |
| ttccccaatc | accttgtggt | ctctcgtgtc | gcggttccca | gggacgcctc | cggctcgtcg | 780 |
| ctcgacagcg | atctccgccc | cagcaaggta | tagattcagt | tccttgctcc | gatcccaatc | 840 |
| tggttgagat | gttgctccga | tgcgacttga | ttatgtcata | tatctgcggt | ttgcaccgat | 900 |
| ctgaagccta | gggtttctcg | agcgacccag | ttatttgcaa | tttgcgattt | gctcgtttgt | 960 |
| tgcgcagcgt | agtttatgtt | tggagtaatc | gaggatttgt | atgcggcgtc | ggcgctacct | 1020 |
| gcttaatcac | gccatgtgac | gcggttactt | gcagaggctg | ggttctgtta | tgtcgtgatc | 1080 |
| taagaatcta | gattaggctc | agtcgttctt | gctgtcgact | agtttgtttt | gatatccatg | 1140 |
| tagtacaagt | tacttaaaat | ttaggtccaa | tatattttgc | atgcttttgg | cctgttattc | 1200 |
| ttgccaacaa | gttgtcctgg | taaaaagtag | atgtgaaagt | cacgtattgg | gacaaattga | 1260 |
| tggtttagtg | ctatagttct | atagttctgt | gatacatcta | tctgattttt | tttggtctat | 1320 |
| tggtgcctaa | cttatctgaa | aatcatggaa | catgaggcta | gtttgatcat | ggtttagttc | 1380 |
| attgtgatta | ataatgtatg | atttagtagc | tattttggtg | atcgtgtcat | tttatttgtg | 1440 |
| aatggaatca | ttgtatgtaa | atgaagctag | ttcaggggtt | acgatgtagc | tggctttgta | 1500 |
| ttctaaaggc | tgctattatt | catccatcga | tttcacctat | atgtaatcca | gagctttga | 1560 |
| tgtgaaattt | gtctgatcct | tcactaggaa | ggacagaaca | ttgttaatat | tttggcacat | 1620 |
| ctgtcttatt | ctcatccttt | gtttgaacat | gttagcctgt | tcaaacagat | actgttgtaa | 1680 |
| tgtcctagtt | atataggtac | atatgtgttc | tctattgagt | ttatggactt | ttgtgtgtga | 1740 |
| agttatattt | cattttgctc | aaaactcatg | tttgcaagct | ttctgacatt | attctattgt | 1800 |
| tctgaaacag | gtg | | | | | 1813 |

<210> SEQ ID NO 125
<211> LENGTH: 1813
<212> TYPE: DNA
<213> ORGANISM: Setaria italica

<400> SEQUENCE: 125

| | | | | | |
|---|---|---|---|---|---|
| cacgggtaat | gcacgcagcc | acccaggcgc | gcgcgctagc | ggagcacggt | caggtgacac | 60 |

```
gggcgtcgtg acgcttccga gttgaagggg ttaacgccag aaacagtgtt tggccagggt      120
atgaacataa caaaaaatat tcacacgaaa gaatggaagt atggagctgc tactgtgtaa      180
atgccaagca ggaaactcac gcccgctaac atccaacggc aacagctcg acgtgccggt       240 cagcagagca tcggaacact ggtgattggt ggagccggca gtatgcgccc cagcacggcc      300
gaggtggtgg tggcccgtgg ccctgctgtc tgcgcggctc gggacaactt gaaactgggc      360
caccgcctcg tcgcaactcg caacccgttg gcggaagaaa ggaatggctc gtaggggccc      420
gggtagaatc gaagaatgtt gcgctgggct tcgattcaca taacatgggc ctgaagctct      480
aaaacgacgg cccggtcgcc gcgcgatgga aagagaccgg atcctcctcg tgaattctgg      540
aaggccacac gagagcgacc caccaccgac gcggaggagt cgtgcgtggt ccaacacggc      600
cggcgggctg ggctgcgacc ttaaccagca aggcacgcca cgacccgccc cgccctcgag      660
gcataaatac cctcccatcc cgttgccgca agactcagat cagattccga tccccagttc      720
ttccccaatc accttgtggt ctctcgtgtc gcggttccca gggacgcctc cggctcgtcg      780
ctcgacagcg atccgcccc cagcaaggta tagattcagt tccttgctcc gatcccaatc      840
tggttgagat gttgctccga tgcgacttga ttatgtcata tatctgcggt ttgcaccgat      900
ctgaagccta gggtttctcg agcgacccag ttatttgcaa tttgcgattt gctcgtttgt      960
tgcgcagcgt agtttatgtt tggagtaatc gaggatttgt atgcggcgtc ggcgctacct     1020
gcttaatcac gccatgtgac gcggttactt gcagaggctg ggttctgtta tgtcgtgatc     1080
taagaatcta gattaggctc agtcgttctt gctgtcgact agtttgtttt gatatccatg     1140
tagtacaagt tacttaaaat ttaggtccaa tatattttgc atgcttttgg cctgttattc     1200
ttgccaacaa gttgtcctgg taaaaagtag atgtgaaagt cacgtattgg gacaaattga     1260
tggtttagtg ctatagttct atagttctgt gatacatcta tctgattttt tttggtctat     1320
tggtgcctaa cttatctgaa aatcatggaa catgaggcta gtttgatcat ggtttagttc     1380
attgtgatta ataatgtatg atttagtagc tattttggtg atcgtgtcat tttatttgtg     1440
aatggaatca ttgtatgtaa atgaagctag ttcaggggtt acgatgtagc tggctttgta     1500
ttctaaaggc tgctattatt catccatcga tttcacctat atgtaatcca gagcttttga     1560
tgtgaaattt gtctgatcct tcactaggaa ggacagaaca ttgttaatat tttggcacat     1620
ctgtcttatt ctcatccttt gtttgaacat gttagcctgt tcaaacagat actgttgtaa     1680
tgtcctagtt atataggtac atatgtgttc tctattgagt ttatggactt tgtgtgtga      1740 agttatattt cattttgctc aaaactcatg tttgcaagct ttctgacatt attctattgt     1800
tctgaaacag ggt                                                       1813
```

<210> SEQ ID NO 126
<211> LENGTH: 1813
<212> TYPE: DNA
<213> ORGANISM: Setaria italica

<400> SEQUENCE: 126

```
cacgggtaat gcacgcagcc acccaggcgc gcgcgctagc ggagcacggt caggtgacac       60
gggcgtcgtg acgcttccga gttgaagggg ttaacgccag aaacagtgtt tggccagggt      120
atgaacataa caaaaaatat tcacacgaaa gaatggaagt atggagctgc tactgtgtaa      180
atgccaagca ggaaactcac gcccgctaac atccaacggc aacagctcg acgtgccggt       240 cagcagagca tcggaacact ggtgattggt ggagccggca gtatgcgccc cagcacggcc      300
gaggtggtgg tggcccgtgg ccctgctgtc tgcgcggctc gggacaactt gaaactgggc      360
```

```
caccgcctcg tcgcaactcg caacccgttg gcggaagaaa ggaatggctc gtaggggccc      420
gggtagaatc gaagaatgtt gcgctgggct tcgattcaca taacatgggc ctgaagctct      480
aaaacgacgg cccggtcgcc gcgcgatgga aagagaccgg atcctcctcg tgaattctgg      540
aaggccacac gagagcgacc caccaccgac gcggaggagt cgtgcgtggt ccaacacggc      600
cggcgggctg ggctgcgacc ttaaccagca aggcacgcca cgacccgccc cgccctcgag      660 gcataaaatac cctcccatcc cgttgccgca agactcagat cagattccga tccccagttc      720
ttccccaatc accttgtggt ctctcgtgtc gcggttccca gggacgcctc cggctcgtcg      780
ctcgacagcg atccgccc cagcaaggta tagattcagt tccttgctcc gatcccaatc       840
tggttgagat gttgctccga tgcgacttga ttatgtcata tatctgcggt ttgcaccgat      900
ctgaagccta gggtttctcg agcgacccag ttatttgcaa tttgcgattt gctcgtttgt      960
tgcgcagcgt agtttatgtt tggagtaatc gaggatttgt atgcggcgtc ggcgctacct     1020
gcttaatcac gccatgtgac gcggttactg cagaggctg ggttctgtta tgtcgtgatc     1080
taagaatcta gattaggctc agtcgttctt gctgtcgact agtttgtttt gatatccatg     1140
tagtacaagt tacttaaaat ttaggtccaa tatattttgc atgcttttgg cctgttattc     1200
ttgccaacaa gttgtcctgg taaaaagtag atgtgaaagt cacgtattgg gacaaattga     1260
tggtttagtg ctatagttct atagttctgt gatacatcta tctgattttt tttggtctat     1320
tggtgcctaa cttatctgaa aatcatggaa catgaggcta gtttgatcat ggtttagttc     1380
attgtgatta ataatgtatg atttagtagc tattttggtg atcgtgtcat tttatttgtg     1440
aatggaatca ttgtatgtaa atgaagctag ttcaggggtt acgatgtagc tggctttgta     1500
ttctaaaggc tgctattatt catccatcga tttcacctat atgtaatcca gagcttttga     1560
tgtgaaattt gtctgatcct tcactaggaa ggacagaaca ttgttaatat tttggcacat     1620
ctgtcttatt ctcatccttt gtttgaacat gttagcctgt tcaaacagat actgttgtaa     1680
tgtcctagtt ataggtac atatgtgttc tctattgagt ttatggactt ttgtgtgtga      1740
agttatattt cattttgctc aaaactcatg tttgcaagct ttctgacatt attctattgt     1800
tctgaaacag ggc                                                       1813
```

<210> SEQ ID NO 127
<211> LENGTH: 1006
<212> TYPE: DNA
<213> ORGANISM: Setaria italica

<400> SEQUENCE: 127

```
gtatagattc agttccttgc tccgatccca atctggttga gatgttgctc cgatgcgact       60
tgattatgtc atatatctgc ggtttgcacc gatctgaagc ctagggtttc tcgagcgacc      120
cagttatttg caatttgcga tttgctcgtt tgttgcgcag cgtagtttat gtttggagta      180
atcgaggatt tgtatgcggc gtcggcgcta cctgcttaat cacgccatgt gacgcggtta      240
cttgcagagg ctgggttctg ttatgtcgtg atctaagaat ctagattagg ctcagtcgtt      300
cttgctgtcg actagtttgt tttgatatcc atgtagtaca agttacttaa aatttaggtc      360
caatatattt tgcatgcttt tggcctgtta ttcttgccaa caagttgtcc tggtaaaaag      420
tagatgtgaa agtcacgtat tgggacaaat tgatggttta gtgctatagt tctatagttc      480
tgtgatacat ctatctgatt ttttttggtc tattggtgcc taacttatct gaaaatcatg      540
gaacatgagg ctagtttgat catggtttag ttcattgtga ttaataatgt atgatttagt      600
```

```
agctattttg gtgatcgtgt cattttatttt gtgaatggaa tcattgtatg taaatgaagc    660
tagttcaggg gttacgatgt agctggcttt gtattctaaa ggctgctatt attcatccat    720
cgatttcacc tatatgtaat ccagagcttt tgatgtgaaa tttgtctgat ccttcactag    780
gaaggacaga acattgttaa tattttggca catctgtctt attctcatcc tttgtttgaa    840
catgttagcc tgttcaaaca gatactgttg taatgtccta gttatatagg tacatatgtg    900
ttctctattg agtttatgga cttttgtgtg tgaagttata tttcattttg ctcaaaactc    960
atgtttgcaa gctttctgac attattctat tgttctgaaa cagggc                  1006
```

```
<210> SEQ ID NO 128
<211> LENGTH: 2634
<212> TYPE: DNA
<213> ORGANISM: Setaria viridis
<400> SEQUENCE: 128
actgccgcga cacgcctcac tggcgggagg gctccgagcg ctctctcccc ggcggccggc     60
ggagcagcga tctggattgg agagaataga ggaaagagag ggaaaaggag agagatagcg    120
caaagagctg aaaagataag gttgtgcggg ctgtggtgat tagaggacca ctaatccctc    180
catctcctaa tgacgcggtg cccaagacca gtgccgcggc acaccagcgt ctaagtgaac    240
ttccgctaac cttccggtca ttgcgcctga agatgtcat gtggcgaggc cccctctca    300 gtagattgcc aactgcctac cgtgccactc ttccatgcat gattgctccc gtctatcccg    360
tttctcacaa cagatagaca acagtaagca tcactaaagc aagcatgtgt agaaccttaa    420
aaaaaggctt atactaccag tatactatca accagcatgc cgttttttgaa gtatccagga    480 ttagaagctt ctactgcgct tttatattat agctgtggac ctgtggtaac cttctctttt    540
tggcgcttgc ttaatctcgg ccgtgctggt ccatgcttag gcactaggca gagatagagc    600
cgggggtgaa tggggctaaa gctcagctgc tcgaggggcc gtgggctggt ttccactagc    660
ctacagctgt gccacgtgcg gccgcgcaag ccgaagcaag cacgctgagc cgttggacag    720
cttgtcataa tgccattacg tggattacag gtaactggcc ctgtaactac tcgttcggcc    780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg    900
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag acatcggaac actggtgatt   1080
ggtggagccg gcagtatgcg ccccagcacg gccgaggtgg tggtggcccg tggccctgct   1140
gtctgcgcgg ctcgggacaa cttgaaactg ggccaccgcc tcgtcgcaac tcgcaaccccg   1200 ttggcggaag aaaggaatgg ctcgtagggg cccgggtaga atccaagaat gttgcgctgg   1260
gcttcgattc acataacatg ggcctgaagc tctaaaacga cggcccggtc accgggcgat   1320
ggaaagagac cggatcctcc tcgtgaattc tggaaggcca cacgagagcg acccaccacc   1380
gacgcggagg agtcgtgcgt ggtccaacac ggccggcggg ctgggctgcg accttaacca   1440
gcaaggcacg ccacgacccg cctcgccctc gaggcataaa taccctccca tcccgttgcc   1500
gcaagactca gatcagattc cgatcccag ttcttcccca atcaccttgt ggtctctcgt   1560
gtcgcggttc ccaggacgc ctccggctcg tcgctcgaca gcgatctccg ccccagcaag   1620
gtatagattc agttccttgc tccgatccca atctggttga gatgttgctc cgatgcgact   1680
tgattatgtc atatatctgc ggtttgcacc gatctgaagc ctagggtttc tcgagcgacc   1740
```

```
cagttgtttg caatttgcga tttgctcgtt tgttgcgcat cgtagtttat gtttggagta   1800
atcgaggatt tgtatgcggc gtcggcgcta cctgcttaat cacgccatgt gacgcggtta   1860
cttgcagagg ctgggttagt gggttctgtt atgtcgtgat ctaagaatct agattaggct   1920
cagtcgttct tgctgtcgac tagtttgttt tgatatccat gtagtacaag ttacttaaaa   1980
tttaggtcca atatattttg catgcttttg gcctgttatt cttgccaaca agttgtcctg   2040
gtaaaaagta gatgtgaaag tcacgtattg gacaaattg atggttaagt gctatagttc    2100
tatagttctg tgatacatct atctgatttt ttttggtcta ttggtgccta acttatctga   2160
aaatcatgga acatgaggct agtttgatca tggtttagtt cattgtgatt aataatgtat   2220
gatttagtag ctattttggt gatcgtgtca ttttatttgt gaatggaatc attgtatgta   2280
aatgaagcta gttcagggg tatgatgtag ctggctttgt attctaaagg ctgctattat    2340
tcatccatcg atttcaccta tatgtaatcc agagctttcg atgtgaaatt tgtctgatcc   2400
ttcactagga aggacagaac attgttaata ttttggcaca tctgtcttat tctcatcctt   2460
tgtttgaaca tgttagcctg ttcaaacaga tactgttgta atgtcctagt tatataggta   2520
catatgtgtt ctctattgag tttatggact tttgtgtgtg aagttatatt tcattttgct   2580
caaaactcat gtttgcaagc tttctgacat tattctattg ttctgaaaca ggtg          2634
```

<210> SEQ ID NO 129
<211> LENGTH: 1014
<212> TYPE: DNA
<213> ORGANISM: Setaria viridis

<400> SEQUENCE: 129

```
gtatagattc agttccttgc tccgatccca atctggttga gatgttgctc cgatgcgact    60
tgattatgtc atatatctgc ggtttgcacc gatctgaagc ctagggtttc tcgagcgacc   120
cagttgtttg caatttgcga tttgctcgtt tgttgcgcat cgtagtttat gtttggagta   180
atcgaggatt tgtatgcggc gtcggcgcta cctgcttaat cacgccatgt gacgcggtta   240
cttgcagagg ctgggttagt gggttctgtt atgtcgtgat ctaagaatct agattaggct   300
cagtcgttct tgctgtcgac tagtttgttt tgatatccat gtagtacaag ttacttaaaa   360
tttaggtcca atatattttg catgcttttg gcctgttatt cttgccaaca agttgtcctg   420
gtaaaaagta gatgtgaaag tcacgtattg gacaaattg atggttaagt gctatagttc    480
tatagttctg tgatacatct atctgatttt ttttggtcta ttggtgccta acttatctga   540
aaatcatgga acatgaggct agtttgatca tggtttagtt cattgtgatt aataatgtat   600
gatttagtag ctattttggt gatcgtgtca ttttatttgt gaatggaatc attgtatgta   660
aatgaagcta gttcagggg tatgatgtag ctggctttgt attctaaagg ctgctattat    720
tcatccatcg atttcaccta tatgtaatcc agagctttcg atgtgaaatt tgtctgatcc   780
ttcactagga aggacagaac attgttaata ttttggcaca tctgtcttat tctcatcctt   840
tgtttgaaca tgttagcctg ttcaaacaga tactgttgta atgtcctagt tatataggta   900
catatgtgtt ctctattgag tttatggact tttgtgtgtg aagttatatt tcattttgct   960
caaaactcat gtttgcaagc tttctgacat tattctattg ttctgaaaca ggtg         1014
```

<210> SEQ ID NO 130
<211> LENGTH: 2634
<212> TYPE: DNA
<213> ORGANISM: Setaria viridis

```
<400> SEQUENCE: 130
actgccgcga cacgcctcac tggcgggagg gctccgagcg ctctctcccc ggcggccggc      60
ggagcagcga tctggattgg agagaataga ggaaagagag ggaaaaggag agagatagcg     120
caaagagctg aaaagataag gttgtgcggg ctgtggtgat tagaggacca ctaatccctc     180
catctcctaa tgacgcggtg cccaagacca gtgccgcggc acaccagcgt ctaagtgaac     240
ttccgctaac cttccggtca ttgcgcctga aagatgtcat gtggcgaggc cccctctca      300
gtagattgcc aactgcctac cgtgccactc ttccatgcat gattgctccc gtctatcccg     360
tttctcacaa cagatagaca acagtaagca tcactaaagc aagcatgtgt agaaccttaa     420
aaaaaggctt atactaccag tatactatca accagcatgc cgttttttgaa gtatccagga    480
ttagaagctt ctactgcgct tttatattat agctgtggac ctgtggtaac ctttctcttt     540
tggcgcttgc ttaatctcgg ccgtgctggt ccatgcttag gcactaggca gagatagagc     600
cgggggtgaa tggggctaaa gctcagctgc tcgaggggcc gtgggctggt ttccactagc     660
ctacagctgt gccacgtgcg gccgcgcaag ccgaagcaag cacgctgagc cgttggacag     720
cttgtcataa tgccattacg tggattacag gtaactggcc ctgtaactac tcgttcggcc     780
atcatcaaac gacgacgtcc gctaggcgac gacacgggta atgcacgcag ccacccaggc     840
gcgcgcgcta gcggagcacg gtcaggtgac acgggcgtcg tgacgcttcc gagttgaagg     900
ggttaacgcc agaaacagtg tttggccagg gtatgaacat aacaaaaaat attcacacga     960
aagaatggaa gtatggagct gctactgtgt aaatgccaag caggaaactc acgcccgcta    1020
acatccaacg gccaacagct cgacgtgccg gtcagcagag catcggaac actggtgatt    1080
ggtggagccg gcagtatgcg ccccagcacg gccgaggtgg tggtggcccg tggccctgct    1140
gtctgcgcg ctcgggacaa cttgaaactg gccaccgcc tcgtcgcaac tcgcaacccg      1200
ttggcggaag aaaggaatgg ctcgtagggg cccgggtaga atccaagaat gttgcgctgg    1260
gcttcgattc acataacatg ggcctgaagc tctaaaacga cggcccggtc accgggcgat    1320
ggaaagagac cggatcctcc tcgtgaattc tggaaggcca cacgagagcg acccaccacc    1380
gacgcggagg agtcgtgcgt ggtccaacac ggccggcggg ctgggctgcg accttaacca    1440
gcaaggcacg ccacgacccg cctcgccctc gaggcataaa taccctccca tcccgttgcc    1500
gcaagactca gatcagattc cgatccccag ttcttcccca atcaccttgt ggtctctcgt    1560
gtcgcggttc ccagggacgc ctccggctcg tcgctcgaca gcgatctccg ccccagcaag    1620
gtatagattc agttccttgc tccgatccca atctggttga gatgttgctc cgatgcgact    1680
tgattatgtc atatatctgc ggtttgcacc gatctgaagc ctagggtttc tcgagcgacc    1740
cagttgtttg caatttgcga tttgctcgtt tgttgcgcat cgtagtttat gtttggagta    1800
atcgaggatt tgtatgcggc gtcggcgcta cctgcttaat cacgccatgt gacgcggtta    1860
cttgcagagg ctgggttagt gggttctgtt atgtcgtgat ctaagaatct agattaggct    1920
cagtcgttct tgctgtcgac tagtttgttt tgatatccat gtagtacaag ttacttaaaa    1980
tttaggtcca atatattttg catgcttttg gcctgttatt cttgccaaca gttgtcctg     2040
gtaaaaagta gatgtgaaag tcacgtattg gacaaattg atggttaagt gctatagttc     2100
tatagttctg tgatacatct atctgatttt ttttggtcta ttggtgccta acttatctga    2160
aaatcatgga acatgaggct agtttgatca tggtttagtt cattgtgatt aataatgtat    2220
gatttagtag ctattttggt gatcgtgtca tttttatttgt gaatggaatc attgtatgta    2280
aatgaagcta gttcaggggt tatgatgtag ctggctttgt attctaaagg ctgctattat    2340
```

```
tcatccatcg atttcaccta tatgtaatcc agagctttcg atgtgaaatt tgtctgatcc    2400
ttcactagga aggacagaac attgttaata ttttggcaca tctgtcttat tctcatcctt    2460
tgtttgaaca tgttagcctg ttcaaacaga tactgttgta atgtcctagt tatataggta    2520
catatgtgtt ctctattgag tttatggact tttgtgtgtg aagttatatt tcattttgct    2580
caaaactcat gtttgcaagc tttctgacat tattctattg ttctgaaaca gggt          2634
```

<210> SEQ ID NO 131
<211> LENGTH: 1014
<212> TYPE: DNA
<213> ORGANISM: Setaria viridis

<400> SEQUENCE: 131

```
gtatagattc agttccttgc tccgatccca atctggttga gatgttgctc cgatgcgact      60
tgattatgtc atatatctgc ggtttgcacc gatctgaagc ctagggtttc tcgagcgacc     120
cagttgtttg caatttgcga tttgctcgtt tgttgcgcat cgtagtttat gtttggagta     180
atcgaggatt tgtatgcggc gtcggcgcta cctgcttaat cacgccatgt gacgcggtta     240
cttgcagagg ctgggttagt gggttctgtt atgtcgtgat ctaagaatct agattaggct     300
cagtcgttct tgctgtcgac tagtttgttt tgatatccat gtagtacaag ttacttaaaa     360
tttaggtcca atatattttg catgcttttg gcctgttatt cttgccaaca agttgtcctg     420
gtaaaaagta gatgtgaaag tcacgtattg ggacaaattg atggttaagt gctatagttc     480
tatagttctg tgatacatct atctgatttt ttttggtcta ttggtgccta acttatctga     540
aaatcatgga acatgaggct agtttgatca tggtttagtt cattgtgatt aataatgtat     600
gatttagtag ctattttggt gatcgtgtca ttttatttgt gaatggaatc attgtatgta     660
aatgaagcta gttcaggggt tatgatgtag ctggctttgt attctaaagg ctgctattat     720
tcatccatcg atttcaccta tatgtaatcc agagctttcg atgtgaaatt tgtctgatcc     780
ttcactagga aggacagaac attgttaata ttttggcaca tctgtcttat tctcatcctt     840
tgtttgaaca tgttagcctg ttcaaacaga tactgttgta atgtcctagt tatataggta     900
catatgtgtt ctctattgag tttatggact tttgtgtgtg aagttatatt tcattttgct     960
caaaactcat gtttgcaagc tttctgacat tattctattg ttctgaaaca gggt          1014
```

<210> SEQ ID NO 132
<211> LENGTH: 2176
<212> TYPE: DNA
<213> ORGANISM: Setaria viridis

<400> SEQUENCE: 132

```
gccgttttg aagtatccag gattagaagc ttctactgcg cttttatatt atagctgtgg       60
acctgtggta acctttctct tttggcgctt gcttaatctc ggccgtgctg gtccatgctt     120
aggcactagg cagagataga gccggggtg aatgggcta aagctcagct gctcgagggg      180
ccgtgggctg gtttccacta gcctacagct gtgccacgtg cggccgcgca agccgaagca     240
agcacgctga gccgttggac agcttgtcat aatgccatta cgtggattac aggtaactgg     300
ccctgtaact actcgttcgg ccatcatcaa acgacgacgt ccgctaggcg acgacacggg     360
taatgcacgc agccacccag gcgcgcgcgc tagcggagca cggtcaggtg acacgggcgt     420
cgtgacgctt ccgagttgaa gggggttaacg ccagaaacag tgtttggcca gggtatgaac    480
ataacaaaaa atattcacac gaaagaatgg aagtatggag ctgctactgt gtaaatgcca     540
```

```
agcaggaaac tcacgcccgc taacatccaa cggccaacag ctcgacgtgc cggtcagcag      600
agacatcgga acactggtga ttggtggagc cggcagtatg cgccccagca cggccgaggt      660
ggtggtggcc cgtggccctg ctgtctgcgc ggctcgggac aacttgaaac tgggccaccg      720
cctcgtcgca actcgcaacc cgttggcgga agaaaggaat ggctcgtagg gcccgggta      780 gaatccaaga atgttgcgct gggcttcgat tcacataaca tgggcctgaa gctctaaaac      840 gacgcccgg tcaccgggcg atggaaagag accggatcct cctcgtgaat tctggaaggc      900
cacacgagag cgacccacca ccgacgcgga ggagtcgtgc gtggtccaac acggccggcg      960
ggctgggctg cgaccttaac cagcaaggca cgccacgacc cgcctcgccc tcgaggcata     1020 aatacccctcc catcccgttg ccgcaagact cagatcagat tccgatcccc agttcttccc     1080
caatcacctt gtggtctctc gtgtcgcggt tcccagggac gcctccggct cgtcgctcga     1140
cagcgatctc cgccccagca aggtatagat tcagttcctt gctccgatcc caatctggtt     1200
gagatgttgc tccgatgcga cttgattatg tcatatatct gcggtttgca ccgatctgaa     1260
gcctagggtt tctcgagcga cccagttgtt tgcaatttgc gatttgctcg tttgttgcgc     1320
atcgtagttt atgtttggag taatcgagga tttgtatgcg cgtcggcgc tacctgctta     1380 atcacgccat gtgacgcggt tacttgcaga ggctgggtta gtgggttctg ttatgtcgtg     1440
atctaagaat ctagattagg ctcagtcgtt cttgctgtcg actagtttgt tttgatatcc     1500
atgtagtaca agttacttaa aatttaggtc caatatattt gcatgctttt ggcctgtta     1560 ttcttgccaa caagttgtcc tggtaaaaag tagatgtgaa agtcacgtat tgggacaaat     1620
tgatggttaa gtgctatagt tctatagttc tgtgatacat ctatctgatt ttttttggtc     1680
tattggtgcc taacttatct gaaaatcatg gaacatgagg ctagtttgat catggtttag     1740
ttcattgtga ttaataatgt atgatttagt agctattttg gtgatcgtgt cattttattt     1800
gtgaatggaa tcattgtatg taaatgaagc tagttcaggg gttatgatgt agctggcttt     1860
gtattctaaa ggctgctatt attcatccat cgatttcacc tatatgtaat ccagagcttt     1920
cgatgtgaaa tttgtctgat ccttcactag gaaggacaga acattgttaa tattttggca     1980
catctgtctt attctcatcc tttgtttgaa catgttagcc tgttcaaaca gatactgttg     2040
taatgtccta gttatatagg tacatatgtg ttctctattg agtttatgga cttttgtgtg     2100
tgaagttata tttcattttg ctcaaaactc atgtttgcaa gctttctgac attattctat     2160
tgttctgaaa caggtg                                                     2176

<210> SEQ ID NO 133
<211> LENGTH: 1822
<212> TYPE: DNA
<213> ORGANISM: Setaria viridis

<400> SEQUENCE: 133
cacgggtaat gcacgcagcc acccaggcgc gcgcgctagc ggagcacggt caggtgacac       60
gggcgtcgtg acgcttccga gttgaagggg ttaacgccag aaacagtgtt tggccagggt      120
atgaacataa caaaaaatat tcacacgaaa gaatggaagt atggagctgc tactgtgtaa      180
atgccaagca ggaaactcac gcccgctaac atccaacggc aacagctcg acgtgccggt       240 cagcagagac atcggaacac tggtgattgg tggagccggc agtatgcgcc ccagcacggc      300
cgaggtggtg gtggcccgtg gccctgctgt ctgcgcggct cgggacaact tgaaactggg      360
ccaccgcctc gtcgcaactc gcaacccgtt ggcggaagaa aggaatggct cgtagggcc      420 cgggtagaat ccaagaatgt tgcgctgggc ttcgattcac ataacatggg cctgaagctc      480
```
taaaacgacg gcccggtcac cgggcgatgg aaagagaccg gatcctcctt gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720
cttccccaat caccttgtgg tctctcgtgt cgcggttccc agggacgcct ccggctcgtc 780
gctcgacagc gatctccgcc ccagcaaggt atagattcag ttccttgctc cgatcccaat 840
ctggttgaga tgttgctccg atgcgacttg attatgtcat atatctgcgg tttgcaccga 900
tctgaagcct agggtttctc gagcgaccca gttgtttgca atttgcgatt tgctcgtttg 960
ttgcgcatcg tagtttatgt ttggagtaat cgaggatttg tatgcggcgt cggcgctacc 1020
tgcttaatca cgccatgtga cgcggttact tgcagaggct gggttagtgg gttctgttat 1080
gtcgtgatct aagaatctag attaggctca gtcgttcttg ctgtcgacta gtttgttttg 1140
atatccatgt agtacaagtt acttaaaatt taggtccaat atattttgca tgcttttggc 1200
ctgttattct tgccaacaag ttgtcctggt aaaaagtaga tgtgaaagtc acgtattggg 1260
acaaattgat ggttaagtgc tatagttcta tagttctgtg atacatctat ctgatttttt 1320
ttggtctatt ggtgcctaac ttatctgaaa atcatggaac atgaggctag tttgatcatg 1380
gtttagttca ttgtgattaa taatgtatga tttagtagct attttggtga tcgtgtcatt 1440
ttatttgtga atggaatcat tgtatgtaaa tgaagctagt tcaggggtta tgatgtagct 1500
ggctttgtat tctaaaggct gctattattc atccatcgat ttcacctata tgtaatccag 1560
agctttcgat gtgaaatttg tctgatcctt cactaggaag gacagaacat tgttaatatt 1620
ttggcacatc tgtcttattc tcatcctttg tttgaacatg ttagcctgtt caaacagata 1680
ctgttgtaat gtcctagtta tataggtaca tatgtgttct ctattgagtt tatggacttt 1740
tgtgtgtgaa gttatatttc attttgctca aaactcatgt ttgcaagctt tctgacatta 1800
ttctattgtt ctgaaacagg tg 1822

<210> SEQ ID NO 134
<211> LENGTH: 1822
<212> TYPE: DNA
<213> ORGANISM: Setaria viridis

<400> SEQUENCE: 134
cacgggtaat gcacgcagcc acccaggcgc gcgcgctagc ggagcacggt caggtgacac 60
gggcgtcgtg acgcttccga gttgaagggg ttaacgccag aaacagtgtt tggccagggt 120
atgaacataa caaaaaatat tcacacgaaa gaatggaagt atggagctgc tactgtgtaa 180
atgccaagca ggaaactcac gcccgctaac atccaacggc caacagctcg acgtgccggt 240
cagcagagac atcggaacac tggtgattgg tggagccggc agtatgcgcc ccagcacggc 300
cgaggtggtg gtggcccgtg gccctgctgt ctgcgcggct cgggacaact tgaaactggg 360
ccaccgcctc gtcgcaactc gcaacccgtt ggcggaagaa aggaatggct cgtaggggcc 420
cgggtagaat ccaagaatgt tgcgctgggc ttcgattcac ataacatggg cctgaagctc 480
taaaacgacg gcccggtcac cgggcgatgg aaagagaccg gatcctcctc gtgaattctg 540
gaaggccaca cgagagcgac ccaccaccga cgcggaggag tcgtgcgtgg tccaacacgg 600
ccggcgggct gggctgcgac cttaaccagc aaggcacgcc acgacccgcc tcgccctcga 660
ggcataaata ccctcccatc ccgttgccgc aagactcaga tcagattccg atccccagtt 720

```
cttccccaat caccttgtgg tctctcgtgt cgcggttccc agggacgcct ccggctcgtc      780
gctcgacagc gatctccgcc ccagcaaggt atagattcag ttccttgctc cgatcccaat      840
ctggttgaga tgttgctccg atgcgacttg attatgtcat atatctgcgg tttgcaccga      900
tctgaagcct agggtttctc gagcgaccca gttgtttgca atttgcgatt tgctcgtttg      960
ttgcgcatcg tagtttatgt ttggagtaat cgaggatttg tatgcggcgt cggcgctacc     1020
tgcttaatca cgccatgtga cgcggttact tgcagaggct gggttagtgg gttctgttat     1080
gtcgtgatct aagaatctag attaggctca gtcgttcttg ctgtcgacta gtttgttttg     1140
atatccatgt agtacaagtt acttaaaatt taggtccaat atattttgca tgcttttggc     1200
ctgttattct tgccaacaag ttgtcctggt aaaaagtaga tgtgaaagtc acgtattggg     1260
acaaattgat ggttaagtgc tatagttcta tagttctgtg atacatctat ctgattttt      1320 ttggtctatt ggtgcctaac ttatctgaaa atcatggaac atgaggctag tttgatcatg     1380
gtttagttca ttgtgattaa taatgtatga tttagtagct attttggtga tcgtgtcatt     1440
ttatttgtga atggaatcat tgtatgtaaa tgaagctagt tcaggggtta tgatgtagct     1500
ggctttgtat tctaaaggct gctattattc atccatcgat ttcacctata tgtaatccag     1560
agctttcgat gtgaaatttg tctgatcctt cactaggaag gacagaacat tgttaatatt     1620
ttggcacatc tgtcttattc tcatcctttg tttgaacatg ttagcctgtt caaacagata     1680
ctgttgtaat gtcctagtta tataggtaca tatgtgttct ctattgagtt tatggacttt     1740
tgtgtgtgaa gttatatttc attttgctca aaactcatgt ttgcaagctt tctgacatta     1800
ttctattgtt ctgaaacagg tg                                              1822

<210> SEQ ID NO 135
<211> LENGTH: 681
<212> TYPE: DNA
<213> ORGANISM: Setaria viridis

<400> SEQUENCE: 135
cacgggtaat gcacgcagcc acccaggcgc gcgcgctagc ggagcacggt caggtgacac       60
gggcgtcgtg acgcttccga gttgaagggg ttaacgccag aaacagtgtt tggccagggt      120
atgaacataa caaaaaatat tcacacgaaa gaatggaagt atggagctgc tactgtgtaa      180
atgccaagca ggaaactcac gcccgctaac atccaacggc caacagctcg acgtgccggt      240
cagcagagac atcggaacac tggtgattgg tggagccggc agtatgcgcc ccagcacggc      300
cgaggtggtg gtgccccgtg gccctgctgt ctgcgcggct cgggacaact tgaaactggg      360
ccaccgcctc gtcgcaactc gcaacccgtt ggcggaagaa aggaatggct cgtaggggcc      420
cgggtagaat ccaagaatgt tgcgctgggc ttcgattcac ataacatggg cctgaagctc      480
taaaacgacg gcccggtcac cgggcgatgg aaagagaccg gatcctcctc gtgaattctg      540
gaaggccaca cgagagcgac ccaccaccga cgcggaggag tcgtgcgtgg tccaacacgg      600
ccggcgggct gggctgcgac cttaaccagc aaggcacgcc acgacccgcc tcgccctcga      660
ggcataaata ccctcccatc c                                               681

<210> SEQ ID NO 136
<211> LENGTH: 1822
<212> TYPE: DNA
<213> ORGANISM: Setaria viridis

<400> SEQUENCE: 136
cacgggtaat gcacgcagcc acccaggcgc gcgcgctagc ggagcacggt caggtgacac       60
```

```
gggcgtcgtg acgcttccga gttgaagggg ttaacgccag aaacagtgtt tggccagggt      120
atgaacataa caaaaaatat tcacacgaaa gaatggaagt atggagctgc tactgtgtaa      180
atgccaagca ggaaactcac gcccgctaac atccaacggc caacagctcg acgtgccggt      240
cagcagagac atcggaacac tggtgattgg tggagccggc agtatgcgcc ccagcacggc      300
cgaggtggtg gtggcccgtg gccctgctgt ctgcgcggct cgggacaact tgaaactggg      360
ccaccgcctc gtcgcaactc gcaacccgtt ggcggaagaa aggaatggct cgtaggggcc      420
cgggtagaat ccaagaatgt tgcgctgggc ttcgattcac ataacatggg cctgaagctc      480
taaaacgacg gcccggtcac cgggcgatgg aaagagaccg gatcctcctt gtgaattctg      540
gaaggccaca cgagagcgac ccaccaccga cgcggaggag tcgtgcgtgg tccaacacgg      600
ccggcgggct gggctgcgac cttaaccagc aaggcacgcc acgacccgcc tcgccctcga      660
ggcataaata ccctcccatc ccgttgccgc aagactcaga tcagattccg atccccagtt      720
cttccccaat caccttgtgg tctctcgtgt cgcggttccc agggacgcct ccggctcgtc      780
gctcgacagc gatctccgcc ccagcaaggt atagattcag ttccttgctc cgatcccaat      840
ctggttgaga tgttgctccg atgcgacttg attatgtcat atatctgcgg tttgcaccga      900
tctgaagcct agggtttctc gagcgaccca gttgtttgca atttgcgatt gctcgtttg      960 ttgcgcatcg tagtttatgt ttggagtaat cgaggatttg tatgcggcgt cggcgctacc     1020
tgcttaatca cgccatgtga cgcggttact tgcagaggct gggttagtgg gttctgttat     1080
gtcgtgatct aagaatctag attaggctca gtcgttcttg ctgtcgacta gtttgttttg     1140
atatccatgt agtacaagtt acttaaaatt taggtccaat atattttgca tgcttttggc     1200
ctgttattct tgccaacaag ttgtcctggt aaaaagtaga tgtgaaagtc acgtattggg     1260
acaaattgat ggttaagtgc tatagttcta tagttctgtg atacatctat ctgatttttt     1320
ttggtctatt ggtgcctaac ttatctgaaa atcatggaac atgaggctag tttgatcatg     1380
gtttagttca ttgtgattaa taatgtatga tttagtagct attttggtga tcgtgtcatt     1440
ttatttgtga atggaatcat tgtatgtaaa tgaagctagt tcaggggtta tgatgtagct     1500
ggctttgtat tctaaaggct gctattattc atccatcgat ttcacctata tgtaatccag     1560
agctttcgat gtgaaatttg tctgatcctt cactaggaag gacagaacat tgttaatatt     1620
ttggcacatc tgtcttattc tcatcctttg tttgaacatg ttagcctgtt caaacagata     1680
ctgttgtaat gtcctagtta tataggtaca tatgtgttct ctattgagtt tatggacttt     1740
tgtgtgtgaa gttatatttc attttgctca aaactcatgt ttgcaagctt tctgacatta     1800
ttctattgtt ctgaaacagg gt                                              1822
```

<210> SEQ ID NO 137
<211> LENGTH: 1925
<212> TYPE: DNA
<213> ORGANISM: Zea mays subsp. Mexicana

<400> SEQUENCE: 137

```
gtcgtgcccc tctctagaga taatgagcat tgcatgtcta agttataaaa aattaccaca       60
tatttttttt tgtcacactt tgtgtttgaag tgcagtttat ctatctctat acatatattt     120
aaacttcact atatgaataa tatagtctat agtattaaaa taatatcaat gtttagatg      180 attatataac tgaactgcta gacatggtct aaaggacaac cgagtatttt gacaacatga     240
ctctacagtt ttatcttttt agtgtgcatg tgttcttttt acttttgcaa atagcttcac     300
```

```
ctatataata cttcatccat tttattagta catccattta ctaaatttttt agtacatcta      360
ttttattcta ttttagcctc taaattaaga aaacttaaac tctattttag ttttttattt      420
aataatttag atataaaata gaataaaata aagtgactaa aaataacta aataccttt        480
aagaaataaa aaaactaagg aaccatttt cttgttccga gtagataatg acagcctgtt      540
caacgccgtc gacgagtcta acggacacca accagcgaac cagcagcgtc gcgtcgggcc     600
aagcgaagca gacggcacgg catctctgta gctgcctctg gaccctctc gagagttccg      660
ctccaccgtt ggacttgctc cgctgtcggc atccagaaat tgcgtggcgg agcggcagac     720
gtgagccggc acggcaggcg gcctcctctc acggcaccgg cagctacggg ggattccttt     780
cccaccgctc cttcgctttc ccttcctcgc ccgccgtaat aaatagaccc cctccacacc     840
ctctttcccc aacctcgtgt tcgttcggag cgcgcacaca cacaaccaga tctcccccaa     900
atccacccgt cggcacctcc gcttcaaggt acgccgctca tcctcctccc cccctctct     960
ctaccttctc tagatcggcg tttcggtcca tggttagggc ccggtagttc tacttctgtt    1020
catgtttgtg ttagatccgt gtttgtgtta gatccgtgct gctagatttc gtacacggat    1080
gcgacctgta catcagacat gttctgattg ctaacttgcc agtgtttctc tttggggaat    1140
cctgggatgg ctctagccgt tccgcagacg ggatcgattt catgaatttt ttttgtttcg    1200
ttgcataggg tttggtttgc ccttttcctt tatttcaata tatgccgtgc acttgtttgt    1260
cgggtcatct tttcatgttt ttttttggctt ggttgtgatg atgtggtctg gttgggcggt    1320
cgttctagat cggagtagaa tactgtttca aactacctgg tggatttatt aaaggatctg    1380
tatgtatgtg ccatacatct tcatagttac gagtttaaga tgatggatgg aaatatcgat    1440
ctaggatagg tatacatgtt gatgcgggtt ttactgatgc atatacagag atgctttttt    1500
ttcgcttggt tgtgatgatg tggtctggtc gggcggtcgt tctagatcgg agtagaatac    1560
tgtttcaaac tacctggtgg atttattaat tttggatctg tatgtgtgtc atacatcttc    1620
atagttacga gtttaagatc gatggaaata tcgatctagg ataggtatac atgttgatgt    1680
gggttttact gatgcatata catggcatat gcagcatcta ttcatatgct ctaaccttga    1740
gtacctatct attataataa acaagtatgt tttataatta ttttgatctt gatatacttg    1800
gatgatggca tatgcagcag ctatatgtgg attttttttag ccctgccttc atacgctatt    1860
tatttgcttg gtactgtttc tttttgtcgat gctcaccctg ttgtttggtg atacttctgc    1920
aggtc                                                                 1925

<210> SEQ ID NO 138
<211> LENGTH: 997
<212> TYPE: DNA
<213> ORGANISM: Zea mays subsp. Mexicana

<400> SEQUENCE: 138
gtacgccgct catcctcctc ccccccctct ctctaccttc tctagatcgg cgtttcggtc       60
catggttagg gcccggtagt tctacttctg ttcatgtttg tgttagatcc gtgtttgtgt     120
tagatccgtg ctgctagatt tcgtacacgg atgcgacctg tacatcagac atgttctgat     180
tgctaacttg ccagtgtttc tctttgggga atcctgggat ggctctagcc gttccgcaga     240
cgggatcgat ttcatgaatt ttttttgttt cgttgcatag ggtttggttt gcccttttcc     300
tttatttcaa tatatgccgt gcacttgttt gtcgggtcat cttttcatgt ttttttttggc     360
ttggttgtga tgatgtggtc tggttgggcg gtcgttctag atcggagtag aatactgttt     420
caaactacct ggtggattta ttaaaggatc tgtatgtatg tgccatacat cttcatagtt     480
```

```
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgtttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900
ggattttttt agccctgcct tcatacgcta tttatttgct tggtactgtt tcttttgtcg    960
atgctcaccc tgttgtttgg tgatacttct gcaggtc                            997
```

```
<210> SEQ ID NO 139
<211> LENGTH: 1925
<212> TYPE: DNA
<213> ORGANISM: Zea mays subsp. Mexicana

<400> SEQUENCE: 139
gtcgtgcccc tctctagaga taatgagcat tgcatgtcta agttataaaa aattaccaca     60 tattttttt tgtcacactt gtgtttgaag tgcagtttat ctatctctat acatatattt    120
aaacttcact atatgaataa tatagtctat agtattaaaa taatatcaat gttttagatg    180
attatataac tgaactgcta gacatggtct aaaggacaac cgagtatttt gacaacatga    240
ctctacagtt ttatctttt agtgtgcatg tgttcttttt acttttgcaa atagcttcac    300
ctatataata cttcatccat tttattagta catccattta ctaaattttt agtacatcta    360
ttttattcta ttttagcctc taaattaaga aaacttaaac tctattttag ttttttattt    420
aataatttag atataaaata gaataaaata aagtgactaa aaaataacta aataccttt     480 aagaaataaa aaaactaagg aaccattttt cttgttccga gtagataatg acagcctgtt    540
caacgccgtc gacgagtcta acggacacca accagcgaac cagcagcgtc gcgtcgggcc    600
aagcgaagca gacggcacgg catctctgta gctgcctctg gaccctctc gagagttccg    660 ctccaccgtt ggacttgctc cgctgtcggc atccagaaat tgcgtggcgg agcggcagac    720
gtgagccggc acggcaggcg gcctcctctc acggcaccgg cagctacggg ggattccttt    780
cccaccgctc cttcgcttt ccttcctcgc ccgccgtaat aaatagaccc cctccacacc    840
ctctttcccc aacctcgtgt tcgttcggag cgcgcacaca cacaaccaga tctcccccaa    900 atccaccgt cggcacctcc gcttcaaggt acgccgctca tcctcctccc ccccctctct    960
ctaccttctc tagatcggcg tttcggtcca tggttagggc ccggtagttc tacttctgtt   1020
catgtttgtg ttagatccgt gtttgtgtta gatccgtgct gctagatttc gtacacggat   1080
gcgacctgta catcagacat gttctgattg ctaacttgcc agtgtttctc tttggggaat   1140
cctgggatgg ctctagccgt tccgcagacg ggatcgattt catgaatttt ttttgtttcg   1200
ttgcataggg tttggtttgc ccttttcctt tatttcaata tatgccgtgc acttgtttgt   1260
cgggtcatct tttcatgttt tttttggctt ggttgtgatg atgtggtctg gttgggcggt   1320
cgttctagat cggagtagaa tactgtttca aactacctgg tggatttatt aaaggatctg   1380
tatgtatgtg ccatacatct tcatagttac gagtttaaga tgatggatgg aaatatcgat   1440
ctaggatagg tatacatgtt gatgcgggtt ttactgatgc atatacagag atgcttttt   1500 ttcgcttggt tgtgatgatg tggtctggtc gggcggtcgt tctagatcgg agtagaatac   1560
```

```
tgtttcaaac tacctggtgg atttattaat tttggatctg tatgtgtgtc atacatcttc   1620
atagttacga gtttaagatc gatggaaata tcgatctagg ataggtatac atgttgatgt   1680
gggttttact gatgcatata catggcatat gcagcatcta ttcatatgct ctaaccttga   1740
gtacctatct attataataa acaagtatgt tttataatta ttttgatctt gatatacttg   1800
gatgatggca tatgcagcag ctatatgtgg attttttag  ccctgccttc atacgctatt   1860
tatttgcttg gtactgtttc ttttgtcgat gctcaccctg ttgtttggtg atacttctgc   1920
agggt                                                                1925

<210> SEQ ID NO 140
<211> LENGTH: 997
<212> TYPE: DNA
<213> ORGANISM: Zea mays subsp. Mexicana

<400> SEQUENCE: 140
gtacgccgct catcctcctc ccccccctct ctctaccttc tctagatcgg cgtttcggtc     60
catggttagg gcccggtagt tctacttctg ttcatgtttg tgttagatcc gtgtttgtgt    120
tagatccgtg ctgctagatt tcgtacacgg atgcgacctg tacatcagac atgttctgat    180
tgctaacttg ccagtgtttc tctttgggga atcctgggat ggctctagcc gttccgcaga    240
cgggatcgat ttcatgaatt ttttttgttt cgttgcatag ggtttggttt gcccttttcc    300
tttatttcaa tatatgccgt gcacttgttt gtcgggtcat cttttcatgt ttttttggc     360 ttggttgtga tgatgtggtc tggttgggcg gtcgttctag atcggagtag aatactgttt    420
caaactacct ggtggattta ttaaaggatc tgtatgtatg tgccatacat cttcatagtt    480
acgagtttaa gatgatggat ggaaatatcg atctaggata ggtatacatg ttgatgcggg    540
ttttactgat gcatatacag agatgctttt ttttcgcttg gttgtgatga tgtggtctgg    600
tcgggcggtc gttctagatc ggagtagaat actgtttcaa actacctggt ggatttatta    660
attttggatc tgtatgtgtg tcatacatct tcatagttac gagtttaaga tcgatggaaa    720
tatcgatcta ggataggtat acatgttgat gtgggtttta ctgatgcata tacatggcat    780
atgcagcatc tattcatatg ctctaacctt gagtacctat ctattataat aaacaagtat    840
gttttataat tattttgatc ttgatatact tggatgatgg catatgcagc agctatatgt    900
ggattttttt agccctgcct tcatacgcta tttatttgct tggtactgtt tcttttgtcg    960
atgctcaccc tgttgtttgg tgatacttct gcagggt                             997

<210> SEQ ID NO 141
<211> LENGTH: 1974
<212> TYPE: DNA
<213> ORGANISM: Zea mays subsp. Mexicana

<400> SEQUENCE: 141
gtcgtgcccc tctctagaga taaagagcat tgcatgtcta agttataaaa aattaccaca     60
tatttttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240
tacagtttta tcttttttagt gtgcatgtgt tctccttttt ttttgcaaa  tagcttcacc    300 tatataatac ttcatccatt ttattagtac atccatttag ggtttagggt taatggtttt    360
tatagactaa tttttttagt acatctattt tattctattt tagcctctaa attaagaaaa    420
ctaaaactct attttagttt ttttattta a taatttagat ataaaataga ataaaataaa    480
```

```
gtgactaaaa attaaacaaa taccctttaa gaaattaaaa aaactaagga aacattttc    540
ttgtttcgag tagataatgc cagcctgtta acgccgtcg acgagtctaa cggacaccaa    600
ccagcgaacc agcagcgtcg cgtcgggcca agcgaagcag acggcacggc atctctgtcg   660
ctgcctctgg accctctcg agagttccgc tccaccgttg acttgctcc gctgtcggca     720
tccagaaatt gcgtggcgga gcggcagacg tgagccggca cggcaggcgg cctcctcctc   780
ctctcacggc accggcagct acgggggatt ccttcccac cgctccttcg ctttcccttc    840
ctcgcccgcc gtaataaata gacacccct ccacaccttc tttccccaac ctcgtgttgt    900
tcggagcgca cacacacaca accagatctc ccccaaatcc accgtcggc acctccgctt    960
caaggtacgc cgctcatcct cccccccccc tctctacctt ctctagatcg gcgttccggt   1020
ccatggttag ggcccggtag ttctacttct gttcatgttt tgttagatc cgtgtttgtg    1080
ttagatccgt gctgctagcg ttcgtacacg gatgcgacct gtacgtcaga cacgttctga   1140
ttgctaactt gccagtgttt ctcttgggg aatcctggga tggctctagc cgttccgcag    1200
acgggatcga tttcatgatt ttttttgttt cgttgcatag ggtttggttt gccctttcc    1260
tttatttcaa tatatgccgt gcacttgttt gtcgggtcat cttttcatgc ttttttttgt   1320
cttggttgtg atgatgtggt ctggttgggc ggtcgttcta gatcggagaa gaattctgtt   1380
tcaaactacc tggtggattt attaattttg gatctgtatg tgtgtgccat acatattcat   1440
agttacgaat tgaagatgat ggatggaaat atcgatctag gataggtata catgttgatg   1500
cgggttttac tgatgcatat acagagatgc ttttgttcg cttggttgtg atgatgtggt    1560
ctggttgggc ggtcgttcat tcgttctaga tcggagtaga atactgtttc aaactacctg   1620
gtgtatttat taattttgga actgtatgtg tgtgtcatac atcttcatag ttacgagttt   1680
aagatggatg gaaatatcga tctaggatag gtatacatgt tgatgtgggt tttactgatg   1740
catatacatg atggcatatg cagcatctat tcatatgctc taaccttgag tacctatcta   1800
ttataataaa caagtatgtt ttataattat tttgatcttg atatacttgg atgatggcat   1860
atgcagcagc tatatgtgga ttttttagc cctgccttca tacgctattt atttgcttgg    1920
tactgtttct tttgtcgatg ctcaccctgt tgtttggtga tacttctgca ggtc          1974

<210> SEQ ID NO 142
<211> LENGTH: 1010
<212> TYPE: DNA
<213> ORGANISM: Zea mays subsp. Mexicana

<400> SEQUENCE: 142
gtacgccgct catcctcccc cccccctctc taccttctct agatcggcgt tccggtccat    60
ggttagggcc cggtagttct acttctgttc atgtttgtgt tagatccgtg tttgtgttag   120
atccgtgctg ctagcgttcg tacacggatg cgacctgtac gtcagacacg ttctgattgc   180
taacttgcca gtgtttctct tggggaatc ctgggatggc tctagccgtt ccgcagacgg    240
gatcgatttc atgattttt tgtttcgtt gcatagggtt tggtttgccc ttttccttta    300
tttcaatata tgccgtgcac ttgtttgtcg ggtcatcttt tcatgctttt ttttgtcttg   360
gttgtgatga tgtggtctgg ttgggcggtc gttctagatc ggagaagaat tctgtttcaa   420
actacctggt ggatttatta attttggatc tgtatgtgtg tgccatacat attcatagtt   480
acgaattgaa gatgatggat ggaaatatcg atctaggata ggtatacatg ttgatgcggg   540
ttttactgat gcatatacag agatgctttt tgttcgcttg gttgtgatga tgtggtctgg   600
```

```
ttgggcggtc gttcattcgt tctagatcgg agtagaatac tgtttcaaac tacctggtgt    660
atttattaat tttggaactg tatgtgtgtg tcatacatct tcatagttac gagtttaaga    720
tggatggaaa tatcgatcta ggataggtat acatgttgat gtgggtttta ctgatgcata    780
tacatgatgg catatgcagc atctattcat atgctctaac cttgagtacc tatctattat    840
aataaacaag tatgttttat aattattttg atcttgatat acttggatga tggcatatgc    900
agcagctata tgtggatttt tttagccctg ccttcatacg ctatttattt gcttggtact    960 gtttctttg tcgatgctca ccctgttgtt tggtgatact tctgcaggtc                1010
```

<210> SEQ ID NO 143
<211> LENGTH: 1974
<212> TYPE: DNA
<213> ORGANISM: Zea mays subsp. Mexicana

<400> SEQUENCE: 143

```
gtcgtgcccc tctctagaga taaagagcat tgcatgtcta agttataaaa aattaccaca     60
tatttttttt gtcacacttg tttgaagtgc agtttatcta tctttataca tatatttaaa    120
ctttactcta cgaataatat aatctatagt actacaataa tatcagtgtt ttagagaatc    180
atataaatga acagttagac atggtctaaa ggacaattga gtattttgac aacaggactc    240 tacagttta tcttttagt gtgcatgtgt tctccttttt tttttgcaaa tagcttcacc       300
tatataatac ttcatccatt ttattagtac atccatttag ggtttagggt taatggtttt    360
tatagactaa tttttttagt acatctattt tattctattt tagcctctaa attaagaaaa    420
ctaaaactct attttagttt ttttatttaa taatttgat ataaaataga ataaaataaa     480
gtgactaaaa attaaacaaa tacccttta gaaattaaaa aaactaagga aacattttc      540 ttgtttcgag tagataatgc cagcctgtta acgccgtcg acgagtctaa cggacaccaa     600
ccagcgaacc agcagcgtcg cgtcgggcca agcgaagcag acggcacggc atctctgtcg    660
ctgcctctgg accctctcg agagttccgc tccaccgttg gacttgctcc gctgtcggca    720
tccagaaatt gcgtggcgga gcggcagacg tgagccggca cggcaggcgg cctcctcctc    780
ctctcacggc accggcagct acggggggatt cctttcccac cgctccttcg ctttcccttc    840
ctcgcccgcc gtaataaata gacaccccct ccacaccttc tttccccaac ctcgtgttgt    900
tcggagcgca cacacacaca accagatctc ccccaaatcc acccgtcggc acctccgctt    960
caaggtacgc cgctcatcct cccccccccc tctctacctt ctctagatcg gcgttccggt   1020
ccatggttag ggcccggtag ttctacttct gttcatgttt gtgttagatc cgtgtttgtg   1080
ttagatccgt gctgctagcg ttcgtacacg gatgcgacct gtacgtcaga cacgttctga   1140
ttgctaactt gccagtgttt ctcttggg aatcctggga tggctctagc cgttccgcag     1200
acgggatcga tttcatgatt ttttttgttt cgttgcatag ggtttggttt gccctttcc    1260 tttattcaa tatatgccgt gcacttgttt gtcgggtcat ctttcatgc tttttttgt     1320 cttggttgtg atgatgtggt ctggttgggc ggtcgttcat tcgttctaga tcggagaa gaattctgtt   1380 tcaaactacc tggtggattt attaattttg gatctgtatg tgtgtgccat acatattcat    1440
agttacgaat tgaagatgat ggatggaaat atcgatctag gataggtata catgttgatg   1500
cgggttttac tgatgcatat acagagatgc ttttgttcg cttggttgtg atgatgtggt    1560
ctggttgggc ggtcgttcat tcgttctaga tcggagtaga atactgtttc aaactacctg   1620
gtgtatttat taatttggaa actgtatgtg tgtgtcatac atcttcatag ttacgagttt   1680
aagatggatg gaaatatcga tctaggatag gtatacatgt tgatgtgggt tttactgatg   1740
```

| catatacatg atggcatatg cagcatctat tcatatgctc taaccttgag tacctatcta | 1800 |
| ttataataaa caagtatgtt ttataattat tttgatcttg atatacttgg atgatggcat | 1860 |
| atgcagcagc tatatgtgga ttttttttagc cctgccttca tacgctattt atttgcttgg | 1920 |
| tactgtttct tttgtcgatg ctcaccctgt tgtttggtga tacttctgca gggt | 1974 |

<210> SEQ ID NO 144
<211> LENGTH: 1010
<212> TYPE: DNA
<213> ORGANISM: Zea mays subsp. Mexicana

<400> SEQUENCE: 144

| gtacgccgct catcctcccc cccccctctc taccttctct agatcggcgt tccggtccat | 60 |
| ggttagggcc cggtagttct acttctgttc atgtttgtgt tagatccgtg tttgtgttag | 120 |
| atccgtgctg ctagcgttcg tacacggatg cgacctgtac gtcagacacg ttctgattgc | 180 |
| taacttgcca gtgtttctct ttggggaatc ctgggatggc tctagccgtt ccgcagacgg | 240 |
| gatcgatttc atgatttttt ttgtttcgtt gcatagggtt tggtttgccc ttttcctttca | 300 |
| tttcaatata tgccgtgcac ttgtttgtcg ggtcatcttt tcatgctttt ttttgtcttg | 360 |
| gttgtgatga tgtggtctgg ttgggcggtc gttctagatc ggagaagaat tctgtttcaa | 420 |
| actacctggt ggatttatta attttggatc tgtatgtgtg tgccatacat attcatagtt | 480 |
| acgaattgaa gatgatggat ggaaatatcg atctaggata ggtatacatg ttgatgcggg | 540 |
| ttttactgat gcatatacag agatgctttt tgttcgcttg gttgtgatga tgtggtctgg | 600 |
| ttgggcggtc gttcattcgt tctagatcgg agtagaatac tgtttcaaac tacctggtgt | 660 |
| atttattaat tttggaactg tatgtgtgtg tcatacatct tcatagttac gagtttaaga | 720 |
| tggatggaaa tatcgatcta ggataggtat acatgttgat gtgggttttta ctgatgcata | 780 |
| tacatgatgg catatgcagc atcattcat atgctctaac cttgagtacc tatctattat | 840 |
| aataaacaag tatgttttat aattattttg atcttgatat acttggatga tggcatatgc | 900 |
| agcagctata tgtggatttt tttagccctg ccttcatacg ctatttattt gcttggtact | 960 |
| gtttcttttg tcgatgctca ccctgttgtt tggtgatact tctgcagggt | 1010 |

<210> SEQ ID NO 145
<211> LENGTH: 2008
<212> TYPE: DNA
<213> ORGANISM: Zea mays subsp. Mexicana

<400> SEQUENCE: 145

| gtcgtgcccc tctctagaga taaagagcat tgcatgtcta aagtataaaa aattaccaca | 60 |
| tatttttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gttttttttg caaatagctt gacctatata | 300 |
| atacttcatc cattttatta gtacatccat ttaggattta gggttgatgg tttctataga | 360 |
| ctaatttta gtacatccat tttattcttt ttagtctcta aatttttttaa aactaaaact | 420 |
| ctatttagt tttttattta ataatttaga tataaaatga aataaaataa attgactaca | 480 |
| aataaaacaa atacccttta agaaatataaa aaactaagca aacatttttc ttgtttcgag | 540 |
| tagataatga caggctgttc aacgccgtcg acgagtctaa cggacaccaa ccagcgaacc | 600 |

```
agcagcgtcg cgtcgggcca agcgaagcag acggcacggc atctctgtag ctgcctctgg    660
acccctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acgggggatt cctttcccac cgctccttcg cttccccttc ctcgcccgcc    840
gtaataaata gacacccct ccacaccctc tttccccaac ctcgtgttcg ttcggagcgc     900
acacacacgc aaccagatct cccccaaatc cagccgtcgg cacctccgct tcaaggtacg    960
ccgctcatcc tcccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt   1140
caagctacct ggtggattta ttaattttgt atctgtatgt gtgtgccata catcttcata    1200
gttacgagtt taagatgatg gatggaaata tcgatctagg ataggtatac atgttgatgc   1260
gggttttact gatgcatata cagagatgct tttttctcg cttggttgtg atgatatggt    1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc tttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggatttttt   1920
agccctgcct tcatacgcta tttatttgct tggtactgtt tcttttgtcc gatgctcacc   1980
ctgttgttgg gtgatacttc tgcaggtc                                      2008

<210> SEQ ID NO 146
<211> LENGTH: 1053
<212> TYPE: DNA
<213> ORGANISM: Zea mays subsp. Mexicana

<400> SEQUENCE: 146
gtacgccgct catcctcccc ccccccctct ctctaccttc tctagatcgg cgatccggtc     60
catggttagg gcccggtagt tctacttctg ttcatgtttg tgttagagca aacatgttca    120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgcttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt ttactgatg     600 catatacaga gatgctttt ttcgcttggt tgtgatgatg tggtctggtt gggcggtcgt     660
tctagatcgg agtagaatac tgtttcaaac tacctggtgg atttattaat tttgtatctt    720
```

| | |
|---|---|
| tatgtgtgtg ccatacatct tcatagttac gagtttaaga tgatggatgg aaatattgat | 780 |
| ctaggatagg tatacatgtt gatgtgggtt ttactgatgc atatacatga tggcatatgc | 840 |
| ggcatctatt catatgctct aaccttgagt acctatctat tataataaac aagtatgttt | 900 |
| tataattatt ttgatcttga tatacttgga tgatggcata tgcagcagct atatgtggat | 960 |
| tttttagccc tgccttcata cgctatttat ttgcttggta ctgtttcttt tgtccgatgc | 1020 |
| tcaccctgtt gttgggtgat acttctgcag gtc | 1053 |

<210> SEQ ID NO 147
<211> LENGTH: 2008
<212> TYPE: DNA
<213> ORGANISM: Zea mays subsp. Mexicana

<400> SEQUENCE: 147

| | |
|---|---|
| gtcgtgcccc tctctagaga taaagagcat tgcatgtcta aagtataaaa aattaccaca | 60 |
| tatttttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gttttttttg caaatagctt gacctatata | 300 |
| atacttcatc cattttatta gtacatccat ttaggattta gggttgatgg tttctataga | 360 |
| ctaattttta gtacatccat tttattcttt ttagtctcta aattttttaa aactaaaact | 420 |
| ctattttagt tttttattta ataatttaga tataaaatga aataaaataa attgactaca | 480 |
| aataaaacaa atacccttta agaaataaaa aaactaagca aacatttttc ttgtttcgag | 540 |
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| acccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt ccttcccac cgctccttcg cttcccttc ctcgcccgcc | 840 |
| gtaataaata gacaccccct ccacaccctc tttcccaac ctcgtgttcg ttcggagcgc | 900 |
| acacacacgc aaccagatct ccccccaaatc cagccgtcgg cacctccgct tcaaggtacg | 960 |
| ccgctcatcc tccccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggttttact gatgcatata cagagatgct tttttctcg cttggttgtg atgatatggt | 1320 |
| ctggttgggc ggtcgttcta gatcggagta gaatactgtt tcaaactacc tggtggattt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt ttaagatgat | 1500 |
| ggatggaaat atcgatctag gataggtata catgttgatg cgggttttac tgatgcatat | 1560 |
| acagagatgc tttttttcgc ttggttgtga tgatgtggtc tggttgggcg gtcgttctag | 1620 |
| atcggagtag aatactgttt caaactacct ggtggattta ttaattttgt atctttatgt | 1680 |
| gtgtgccata catcttcata gttacgagtt taagatgatg gatggaaata ttgatctagg | 1740 |

| | |
|---|---|
| ataggtatac atgttgatgt gggttttact gatgcatata catgatggca tatgcggcat | 1800 |
| ctattcatat gctctaacct tgagtaccta tctattataa taaacaagta tgttttataa | 1860 |
| ttattttgat cttgatatac ttggatgatg gcatatgcag cagctatatg tggattttt | 1920 |
| agccctgcct tcatacgcta tttatttgct tggtactgtt tcttttgtcc gatgctcacc | 1980 |
| ctgttgtttg gtgatacttc tgcaggtc | 2008 |

<210> SEQ ID NO 148
<211> LENGTH: 1053
<212> TYPE: DNA
<213> ORGANISM: Zea mays subsp. Mexicana

<400> SEQUENCE: 148

| | |
|---|---|
| gtacgccgct catcctcccc ccccccctct ctctaccttc tctagatcgg cgatccggtc | 60 |
| catggttagg gcccggtagt tctacttctg ttcatgtttg tgttagagca acatgttca | 120 |
| tgttcatgtt tgtgatgatg tggtctggtt gggcggtcgt tctagatcgg agtaggatac | 180 |
| tgtttcaagc tacctggtgg atttattaat tttgtatctg tatgtgtgtg ccatacatct | 240 |
| tcatagttac gagtttaaga tgatggatgg aaatatcgat ctaggatagg tatacatgtt | 300 |
| gatgcgggtt ttactgatgc atatacagag atgcttttt tctcgcttgg ttgtgatgat | 360 |
| atggtctggt tgggcggtcg ttctagatcg gagtagaata ctgtttcaaa ctacctggtg | 420 |
| gatttattaa aggataaagg gtcgttctag atcggagtag aatactgttt caaactacct | 480 |
| ggtggattta ttaaaggatc tgtatgtatg tgcctacatc ttcatagtta cgagtttaag | 540 |
| atgatggatg gaaatatcga tctaggatag gtatacatgt tgatgcgggt tttactgatg | 600 |
| catatacaga gatgcttttt ttcgcttggt tgtgatgatg tggtctggtt gggcggtcgt | 660 |
| tctagatcgg agtagaatac tgtttcaaac tacctggtgg atttattaat tttgtatctt | 720 |
| tatgtgtgtg ccatacatct tcatagttac gagtttaaga tgatggatgg aaatattgat | 780 |
| ctaggatagg tatacatgtt gatgtgggtt ttactgatgc atatacatga tggcatatgc | 840 |
| ggcatctatt catatgctct aaccttgagt acctatctat tataaataaac aagtatgttt | 900 |
| tataattatt ttgatcttga tacttggga tgatggcata tgcagcagct atatgtggat | 960 |
| tttttagccc tgccttcata cgctatttat ttgcttggta ctgtttcttt tgtccgatgc | 1020 |
| tcaccctgtt gtttggtgat acttctgcag gtc | 1053 |

<210> SEQ ID NO 149
<211> LENGTH: 2008
<212> TYPE: DNA
<213> ORGANISM: Zea mays subsp. Mexicana

<400> SEQUENCE: 149

| | |
|---|---|
| gtcgtgcccc tctctagaga taaagagcat tgcatgtcta aagtataaaa aattaccaca | 60 |
| tattttttg tcacacttat ttgaagtgta gtttatctat ctctatacat atatttaaac | 120 |
| ttcactctac aaataatata gtctataata ctaaaataat attagtgttt tagaggatca | 180 |
| tataaataaa ctgctagaca tggtctaaag gataattgaa tattttgaca atctacagtt | 240 |
| ttatcttttt agtgtgcatg tgatctctct gtttttttg caaatagctt gacctatata | 300 |
| atacttcatc catttttatta gtacatccat ttaggattta gggttgatgg tttctataga | 360 |
| ctaattttta gtacatccat tttattcttt ttagtctcta atttttttaa aactaaaact | 420 |
| ctattttagt tttttattta ataatttaga tataaaatga aataaaataa attgactaca | 480 |
| aataaaacaa ataccctta agaaataaaa aaactaagca aacattttc ttgtttcgag | 540 |

```
tagataatga caggctgttc aacgccgtcg acgagtctaa cggacaccaa ccagcgaacc      600
agcagcgtcg cgtcgggcca agcgaagcag acggcacggc atctctgtag ctgcctctgg      660 accccctctcg agagttccgc tccaccgttg gacttgctcc gctgtcggca tccagaaatt     720
gcgtggcgga gcggcagacg tgaggcggca cggcaggcgg cctcttcctc ctctcacggc      780
accggcagct acgggggatt ccttttcccac cgctccttcg ctttcccttc ctcgcccgcc    840
gtaataaata gacaccccct ccacaccctc tttccccaac ctcgtgttcg ttcggagcgc     900
acacacacgc aaccagatct cccccaaatc cagccgtcgg cacctccgct tcaaggtacg     960
ccgctcatcc tccccccccc cctctctcta ccttctctag atcggcgatc cggtccatgg    1020
ttagggcccg gtagttctac ttctgttcat gtttgtgtta gagcaaacat gttcatgttc    1080
atgtttgtga tgatgtggtc tggttgggcg gtcgttctag atcggagtag gatactgttt    1140
caagctacct ggtggattta ttaattttgt atctgtatgt gtgtgccata catcttcata    1200
gttacgagtt taagatgatg gatggaaata tcgatctagg ataggtatac atgttgatgc    1260
gggttttact gatgcatata cagagatgct tttttctcg cttggttgtg atgatatggt      1320
ctggttgggc ggtcgttcta gatcggagta gaatactgtt tcaaactacc tggtggattt    1380
attaaaggat aaagggtcgt tctagatcgg agtagaatac tgtttcaaac tacctggtgg    1440
atttattaaa ggatctgtat gtatgtgcct acatcttcat agttacgagt taagatgat     1500 ggatggaaat atcgatctag gataggtata catgttgatg cgggttttac tgatgcatat    1560
acagagatgc tttttttcgc ttggttgtga tgatgtggtc tggttgggcg gtcgttctag    1620
atcggagtag aatactgttt caaactacct ggtggattta ttaattttgt atctttatgt    1680
gtgtgccata catcttcata gttacgagtt taagatgatg gatggaaata ttgatctagg    1740
ataggtatac atgttgatgt gggttttact gatgcatata catgatggca tatgcggcat    1800
ctattcatat gctctaacct tgagtaccta tctattataa taacaagta tgttttataa     1860 ttattttgat cttgatatac ttggatgatg gcatatgcag cagctatatg tggatttttt    1920
agccctgcct tcatacgcta tttatttgct tggtactgtt tcttttgtcc gatgctcacc    1980
ctgttgttgg gtgatacttc tgcagggt                                       2008

<210> SEQ ID NO 150
<211> LENGTH: 1053
<212> TYPE: DNA
<213> ORGANISM: Zea mays subsp. Mexicana

<400> SEQUENCE: 150
gtacgccgct catcctcccc cccccctct ctctaccttc tctagatcgg cgatccggtc       60
catggttagg gcccggtagt tctacttctg ttcatgtttg tgttagagca aacatgttca     120
tgttcatgtt tgtgatgatg tggtctggtt gggcggtcgt tctagatcgg agtaggatac    180
tgtttcaagc tacctggtgg atttattaat tttgtatctg tatgtgtgtg ccatacatct    240
tcatagttac gagtttaaga tgatggatgg aaatatcgat ctaggatagg tatacatgtt    300
gatgcgggtt ttactgatgc atatacagag atgctttttt tctcgcttgg ttgtgatgat    360
atggtctggt tgggcggtcg ttctagatcg gagtagaata ctgtttcaaa ctacctggtg    420
gatttattaa aggataaagg gtcgttctag atcggagtag aatactgttt caaactacct    480
ggtggattta ttaaaggatc tgtatgtatg tgcctacatc ttcatagtta cgagtttaag    540
atgatggatg gaaatatcga tctaggatag gtatacatgt tgatgcgggt tttactgatg    600
```

```
catatacaga gatgcttttt ttcgcttggt tgtgatgatg tggtctggtt gggcggtcgt      660
tctagatcgg agtagaatac tgtttcaaac tacctggtgg atttattaat tttgtatctt      720
tatgtgtgtg ccatacatct tcatagttac gagtttaaga tgatggatgg aaatatttgat    780 ctaggatagg tatacatgtt gatgtgggtt ttactgatgc atacatgca tggcatatgc      840 ggcatctatt catatgctct aaccttgagt acctatctat taataaaac aagtatgttt      900 tataattatt ttgatcttga tatacttgga tgatggcata tgcagcagct atatgtggat     960
tttttagccc tgccttcata cgctatttat ttgcttggta ctgtttcttt tgtccgatgc    1020
tcaccctgtt gttgggtgat acttctgcag ggt                                 1053

<210> SEQ ID NO 151
<211> LENGTH: 1635
<212> TYPE: DNA
<213> ORGANISM: Sorghum bicolor

<400> SEQUENCE: 151
ccaagtccaa atgtcaattc ccttgaagat gatctatttt tatcttttgc attttgttat      60
ggaagtttgc aaatagcaac aaatgctaag tcaatttgcc aaagtctttg gagatgctct     120
tagtctataa ttgaacaata tttgtaaaat acaaaaaaaa atagtactat ttttatttta     180 aaaaatttt ggaagtaaac aaggccgagg atggggaaac ggaagtccaa cacgtcgttt      240
tctaagttgg gctcaaaagc ccatcacgga actgacctgc tatgggtcgg aggagagcgc    300
gtccagatgg ttccagaggc tggtggtggt gggccaaacg cggaactccg ccaccgccac    360
ggcctcgtgc gcaagcgcag cgcgttgccg tgagccgtga cgtaacccte cgttgcccac    420 gataaaagct ccaccccga ccccggcccc ccgatttccc ctacggacca gtctccccc      480 gatcgcaatc gcgaattcgt cgcaccatcg gcacgcagac gaacgaagca aggctctccc    540
catcggctcg tcaaggtatg cgttccctag atttgttccc ttcctctctc ggtttgtcta    600
tatatatgca tgtatggtcg attcccgatc tcgtcgattc tcggtttcgc cttccgtacg    660
aagattcgtt tagattgttc atatgttctg ttgtgttacc agattgatcg gatcaacttg    720
atccagttat cttcgctcct ccgattagat ccgtttctat ttcagtatat atatactagt    780
atagtatcta gggttcacac tgttgaccga ctggttactt ggaattgatc cgtgctgagt    840
tcagttgttg ccgtccataa aggcccgtgc tattgtctgt tctgaaacga atcctgtag     900 atttcttagg gttagtgttc aattcatcaa aaggttgatt agtgaattat caaatttgag    960
agggttaaat cattctcatc atgttgtctc gaatgtaatc ccaaagatat tatagactgt   1020
gtttcgattt gatggattga tttgtgtatc atctaaatca acaaggctaa gtcatcagtt   1080
catagaatca tgtttaggtt tccgttcaat agactagttt tatcaatata taaaattata   1140
agaagggtag ggtaaatcac gttgcctcaa atgccatcct gtatggtttg gtttcaattc   1200
aattagtttg gttgattagg gtatgctctg gattaagatg gttaaatctt ccctagcatc   1260
ttccctgcct atccttactt gatccgtttc ggatatgttg gaagtacagc gagcttattt   1320
catgttgata gtgacccctt tcagattata ctattgaata ttgtatgttt gccacttctg   1380
tatgttgaat tatcctgcta aattagcaat ggaattagca tattggcaat ggtatgcat    1440 ggacctaatc aggacggatg tggttatgtt agtttcaatt cattgtcaat tcattgttca   1500
cctgcgttag atatatatga tgattttac gtgtagttca tagttcttga gttttggatc   1560
tttcttatct gatatatgct ttcctgtgcc tgtgctttat tgtgtcttac catgcgattt   1620
ttgtctatgc aggtc                                                     1635
```

<210> SEQ ID NO 152
<211> LENGTH: 1080
<212> TYPE: DNA
<213> ORGANISM: Sorghum bicolor

<400> SEQUENCE: 152

```
gtatgcgttc cctagatttg ttcccttcct ctctcggttt gtctatatat atgcatgtat      60
ggtcgattcc cgatctcgtc gattctcggt ttcgccttcc gtacgaagat tcgtttagat     120
tgttcatatg ttctgttgtg ttaccagatt gatcggatca acttgatcca gttatcttcg     180
ctcctccgat tagatccgtt tctatttcag tatatatata ctagtatagt atctagggtt     240
cacactgttg accgactggt tacttggaat tgatccgtgc tgagttcagt tgttgccgtc     300
cataaaggcc cgtgctattg tctgttctga aacgaaatcc tgtagatttc ttagggttag     360
tgttcaattc atcaaaaggt tgattagtga attatcaaat ttgagagggt taaatcattc     420
tcatcatgtt gtctcgaatg taatcccaaa gatattatag actgtgtttc gatttgatgg     480
attgatttgt gtatcatcta aatcaacaag gctaagtcat cagttcatag aatcatgttt     540
aggtttccgt tcaatagact agttttatca atatatataaa ttataagaag ggtagggtaa     600
atcacgttgc ctcaaatgcc atcctgtatg gtttggtttc aattcaatta gtttggttga     660
ttagggtatg ctctggatta agatggttaa atcttcccta gcatcttccc tgcctatcct     720
tacttgatcc gtttcggata tgttggaagt acagcgagct tatttcatgt tgatagtgac     780
cccttttcaga ttatactatt gaatattgta tgtttgccac ttctgtatgt tgaattatcc     840
tgctaaatta gcaatggaat tagcatattg gcaattggta tgcatggacc taatcaggac     900
ggatgtggtt atgttagttt caattcattg tcaattcatt gttcacctgc gttagatata     960
tatgatgatt tttacgtgta gttcatagtt cttgagtttt ggatctttct tatctgatat    1020
atgctttcct gtgcctgtgc tttattgtgt cttaccatgc gatttttgtc tatgcaggtc    1080
```

<210> SEQ ID NO 153
<211> LENGTH: 2067
<212> TYPE: DNA
<213> ORGANISM: Sorghum bicolor

<400> SEQUENCE: 153

```
cattaaaagt cattatgtgc atgcgtcgta actaacatgg atatgttgct gcactatctc      60
ctcgcactag ctgcgcatga taaagccaca agccaaaatt aattattatg ggtgagaata     120
aatacgtacc agcaccggcc atagaaaaag tacattatta aaggtctaat ttggaaacag     180
tctgaaaacg acgtgcgctg cagaggtaaa tgtaattttc ggcactaaaa ccattatcaa     240
ctaattcatt caataacagt tatttagaaa atgtatagct cgctctaaaa aaacagttta     300
gaaaaacagt caaaataatt cgaccaacaa acagttaata aggttcatta aatatataat     360
gcacggtgct atttgatctt ttaaaggaaa agaggaata gtcgtgggcg ccaggcggga     420
attgggcgc gggagtctgc cggacgacgc gttccgtccg aacggccgga cccgacgagg     480
cccccccgcc gccccacgtc gcagaaccgt ccgtgggtgg taatctggcc gggtacacca     540
gccgtcccct tgggcggcct cacagcactg gctcacacg tgagttttgt tctgggcttc     600
ggatcgcacc atatgggcct cggcatcaga aagacggggc ccgtctggga tagaagagac     660
aggaaccctcc tcgtggattc cagaagccag ccacgagcga ccaccgacgc ggaggatact     720
cgtcgtccaa gtccaacacg gcgggcgggc gggcggacgc gtgggctggg ctaactgcct     780
```

| | |
|---|---|
| aaccttaacc tccaaggcac gccaaggccc gcttctccca cccgacataa atatccccccc | 840 |
| atccaggcaa ggcgcagagc ctcagaccag attccgatca atcacccata agctccccccc | 900 |
| aaatctgttc ctcgtctccc gtctcgcggt ttcctacttc cctcggacgc ctccggcaag | 960 |
| tcgctcgacc gcgcgattcc gcccgctcaa ggtatcaact cggttcacca ctccaatcta | 1020 |
| cgtctgattt agatgttact tccatctatg tctaatttag atgttactcc gatgcgattg | 1080 |
| gattatgttt atgcggtttg cactgctctg gaaactggaa tctagggttt cgagtgattt | 1140 |
| gatcgatcgc gatctgtgat ttcgttgcgc cttgtgtatg cttggagtga tctaggcttg | 1200 |
| tatatgcggc atcgcgatct gacgcggttg cttttgtagag gctgggggtc taggctgtga | 1260 |
| ttttagaatc aaataaagct gttccttacc gtagatgttt cctacatgtt ctgtccagta | 1320 |
| ctccagtgct atattcacat tgtttgaggc ttgagttttg tcgatcagtg gtcatgagaa | 1380 |
| aaatatatct catgatttta gaggcaccta ttgggaaagg tagatggttc cgttttacat | 1440 |
| gttttataga ccttgtggca tggctccttt gttctatggg tgctttatttt tcctgaataa | 1500 |
| cagtaatgcg agactggtct atgggtgctt tgaccagtaa tgcgagacta gttatttgat | 1560 |
| catggtgcag ttcctagtga ttacgaacaa caatttggta gctcagttca ttcagcattg | 1620 |
| gtttctacga tccttatcat tttacttctg aatgaattta tttatttaag atattacagt | 1680 |
| gcaataaaact gctgtataat atcagtaaca aactgctatt actagtaaat gcctagattc | 1740 |
| ataataattc attattctac ttgaaaatga tcttaggcct ttttatgcgg tcctacgcat | 1800 |
| ccttccacag gacttgctgt tgtttgttt tttgtaatcc ctcgctggga cgcagaatgg | 1860 |
| ttcatctgtg ctaataattt tttttgcatat ataagtttat agttctcatt attcatgtgg | 1920 |
| ctatggtagc ctgtaaaatc tattgtaata acatattagt cagccataca tctgttccaa | 1980 |
| cttgctcaat tgcaaatcat atctccactt aaagcacatg tttgcaagct ttctgacaag | 2040 |
| tttctttgtg tttgattgaa acaggtg | 2067 |

<210> SEQ ID NO 154
<211> LENGTH: 1076
<212> TYPE: DNA
<213> ORGANISM: Sorghum bicolor

<400> SEQUENCE: 154

| | |
|---|---|
| gtatcaactc ggttcaccac tccaatctac gtctgattta gatgttactt ccatctatgt | 60 |
| ctaatttaga tgttactccg atgcgattgg attatgttta tgcggtttgc actgctctgg | 120 |
| aaactggaat ctagggtttc gagtgatttg atcgatcgcg atctgtgatt tcgttgcgcc | 180 |
| ttgtgtatgc ttggagtgat ctaggcttgt atatgcggca tcgcgatctg acgcggttgc | 240 |
| tttgtagagg ctgggggtct aggctgtgat tttagaatca aataaagctg ttccttaccg | 300 |
| tagatgtttc ctacatgttc tgtccagtac tccagtgcta tattcacatt gtttgaggct | 360 |
| tgagttttgt cgatcagtgg tcatgagaaa aatatatctc atgattttag aggcacctat | 420 |
| tgggaaaggt agatggttcc gttttacatg ttttatagac cttgtggcat ggctcctttg | 480 |
| ttctatgggt gctttatttt cctgaataac agtaatgcga gactggtcta tgggtgcttt | 540 |
| gaccagtaat gcgagactag ttatttgatc atggtgcagt tcctagtgat tacgaacaac | 600 |
| aatttggtag ctcagttcat tcagcattgg tttctacgat ccttatcatt ttacttctga | 660 |
| atgaatttat ttatttaaga tattacagtg caataaactg ctgtataata tcagtaacaa | 720 |
| actgctatta ctagtaaatg cctagattca taataattca ttattctact tgaaaatgat | 780 |
| cttaggcctt tttatgcggt cctacgcatc cttccacagg acttgctgtt tgtttgtttt | 840 |

| | |
|---|---|
| ttgtaatccc tcgctgggac gcagaatggt tcatctgtgc taataatttt tttgcatata | 900 |
| taagtttata gttctcatta ttcatgtggc tatggtagcc tgtaaaatct attgtaataa | 960 |
| catattagtc agccatacat ctgttccaac ttgctcaatt gcaaatcata tctccactta | 1020 |
| aagcacatgt ttgcaagctt tctgacaagt ttctttgtgt ttgattgaaa caggtg | 1076 |

<210> SEQ ID NO 155
<211> LENGTH: 2067
<212> TYPE: DNA
<213> ORGANISM: Sorghum bicolor

<400> SEQUENCE: 155

| | |
|---|---|
| cattaaaagt cattatgtgc atgcgtcgta actaacatgg atatgttgct gcactatctc | 60 |
| ctcgcactag ctgcgcatga taaagccaca agccaaaatt aattattatg ggtgagaata | 120 |
| aatacgtacc agcaccggcc atagaaaaag tacattatta aaggtctaat ttggaaacag | 180 |
| tctgaaaacg acgtgcgctg cagaggtaaa tgtaattttc ggcactaaaa ccattatcaa | 240 |
| ctaattcatt caataacagt tatttagaaa atgtatagct cgctctaaaa aaacagttta | 300 |
| gaaaaacagt caaaataatt cgaccaacaa acagttaata aggttcatta aatatataat | 360 |
| gcacggtgct atttgatctt ttaaaggaaa agaggaata gtcgtgggcg ccaggcggga | 420 |
| attggggcgc gggagtctgc cggacgacgc gttccgtccg aacggccgga cccgacgagg | 480 |
| ccccccccgcc gccccacgtc gcagaaccgt ccgtgggtgg taatctggcc gggtacacca | 540 |
| gccgtcccct tgggcggcct cacagcactg ggctcacacg tgagttttgt tctgggcttc | 600 |
| ggatcgcacc atatgggcct cggcatcaga aagacggggc ccgtctggga tagaagagac | 660 |
| aggaacctcc tcgtggattc cagaagccag ccacgagcga ccaccgacgc ggaggatact | 720 |
| cgtcgtccaa gtccaacacg gcgggcgggc gggcggacgc gtgggctggg ctaactgcct | 780 |
| aaccttaacc tccaaggcac gccaaggccc gcttctccca cccgacataa atatccccc | 840 |
| atccaggcaa ggcgcagagc ctcagaccag attccgatca atcacccata agctcccccc | 900 |
| aaatctgttc ctcgtctccc gtctcgcggt ttcctacttc cctcggacgc ctccggcaag | 960 |
| tcgctcgacc gcgcgattcc gcccgctcaa ggtatcaact cggttcacca ctccaatcta | 1020 |
| cgtctgattt agatgttact tccatctatg tctaatttag atgttactcc gatgcgattg | 1080 |
| gattatgttt atgcggtttg cactgctctg gaaactggaa tctagggttt cgagtgattt | 1140 |
| gatcgatcgc gatctgtgat ttcgttgcgc cttgtgtatg cttggagtga tctaggcttg | 1200 |
| tatatgcgga atcgcgatct gacgcggttg cttttgtagag gctgggggtc taggctgtga | 1260 |
| ttttagaatc aaataaagct gttccttacc gtagatgttt cctacatgtt ctgtccagta | 1320 |
| ctccagtgct atattcacat tgtttgaggc ttgagttttg tcgatcagtg gtcatgagaa | 1380 |
| aaatatatct catgattta gaggcaccta ttgggaaagg tagatggttc cgttttacat | 1440 |
| gttttataga ccttgtggca tggctccttt gttctatggg tgctttattt tcctgaataa | 1500 |
| cagtaatgcg agactggtct atgggtgctt tgaccagtaa tgcgagacta gttatttgat | 1560 |
| catggtgcag ttcctagtga ttacgaacaa caatttggta gctcagttca ttcagcattg | 1620 |
| gtttctacga tccttatcat tttacttctg aatgaattta tttatttaag atattacagt | 1680 |
| gcaataaact gctgtataat atcagtaaca aactgctatt actagtaaat gcctagattc | 1740 |
| ataataattc attattctac ttgaaaatga tcttaggcct ttttatgcgg tcctacgcat | 1800 |
| ccttccacag gacttgctgt ttgtttgttt tttgtaatcc ctcgctggga cgcagaatgg | 1860 |

```
ttcatctgtg ctaataattt ttttgcatat ataagtttat agttctcatt attcatgtgg      1920
ctatggtagc ctgtaaaatc tattgtaata acatattagt cagccataca tctgttccaa      1980
cttgctcaat tgcaaatcat atctccactt aaagcacatg tttgcaagct ttctgacaag      2040
tttctttgtg tttgattgaa acagggt                                          2067

<210> SEQ ID NO 156
<211> LENGTH: 1076
<212> TYPE: DNA
<213> ORGANISM: Sorghum bicolor

<400> SEQUENCE: 156
gtatcaactc ggttcaccac tccaatctac gtctgattta gatgttactt ccatctatgt        60
ctaatttaga tgttactccg atgcgattgg attatgttta tgcggtttgc actgctctgg       120
aaactggaat ctagggtttc gagtgatttg atcgatcgcg atctgtgatt tcgttgcgcc       180
ttgtgtatgc ttggagtgat ctaggcttgt atatgcggca tcgcgatctg acgcggttgc       240
tttgtagagg ctgggggtct aggctgtgat tttagaatca aataaagctg ttccttaccg       300
tagatgtttc ctacatgttc tgtccagtac tccagtgcta tattcacatt gtttgaggct       360
tgagttttgt cgatcagtgg tcatgagaaa aatatatctc atgattttag aggcacctat       420
tgggaaaggt agatggttcc gttttacatg ttttatagac cttgtggcat ggctcctttg       480
ttctatgggt gctttatttt cctgaataac agtaatgcga gactggtcta tgggtgcttt       540
gaccagtaat gcgagactag ttatttgatc atggtgcagt tcctagtgat tacgaacaac       600
aatttggtag ctcagttcat tcagcattgg tttctacgat ccttatcatt ttacttctga       660
atgaatttat ttatttaaga tattacagtg caataaactg ctgtataata tcagtaacaa       720
actgctatta ctagtaaatg cctagattca taataattca ttattctact tgaaaatgat       780
cttaggcctt tttatgcggt cctacgcatc cttccacagg acttgctgtt tgtttgtttt       840
ttgtaatccc tcgctgggac gcagaatggt tcatctgtgc taataatttt tttgcatata       900
taagtttata gttctcatta ttcatgtggc tatggtagcc tgtaaaatct attgtaataa       960
catattagtc agccatacat ctgttccaac ttgctcaatt gcaaatcata tctccactta      1020
aagcacatgt ttgcaagctt tctgacaagt ttctttgtgt ttgattgaaa cagggt          1076

<210> SEQ ID NO 157
<211> LENGTH: 2003
<212> TYPE: DNA
<213> ORGANISM: Sorghum bicolor

<400> SEQUENCE: 157
agaagtaaaa aaaagttcg ttcagaatc ataaaggtaa gttaaaaaaa gaccatacaa          60 aaagaggta tttaatgata aactataatc cagaatttgt taggatagta tataagaata       120
agaccttgtt tagtttcaaa aaaatttgca aaatttccca gattcctcgt cacatcaaat       180
ctttagaggt atgcatggag tattaaatat agacaagacc taaataagaa acatgaaat       240 gttcacgaaa aaatcaagc caatgcatga tcgaagcaaa cggtatagta acggtgttaa       300
cctgatccat tgatctttgt aatctttaac ggccacctac cgcgggcagc aaacggcgtc       360
cccctcctcg atatctccgc ggcggcctct ggcttttttcc gcggaattgc gcggtgggga       420
cggattccac gagaccgcaa cgcaaccgcc tctgccgct gggccccaca ccgctcggtg       480
ccgtagcccg tagcctcacg ggattctttc tccctcctcc cccgtgtata aattggcttc       540
atcccctccc tgcctcatcc atccaaatcc cactcccaa tcccatcccg tcggagaaat        600
```

```
tcatcgaagc gaagcgaagc gaatcctccc gatcctctca aggtacgcga gttttcgaat      660
cccctccaga cccctcgtat gctttccctg ttcgttttcg tcgtagcgtt tgattaggta      720
tgctttccct gttcgtgttc gtcgtagggt tcgattaggt cgtgtgaggc catggcctgc      780
tgtgataaat ttatttgttg ttatatcgga tctgtagtcg atttggggt cgtggtgtag      840 atccgcgggc tgtgatgaag ttatttggtg tgattgtgct cgcgtgattc tgcgcgttga      900
gctcgagtag atctgatggt tggacgaccg attggttcgt tggctggctg cgctaaggtt      960
gggctgggct catgttgcgt tcgctgttgc gcgtgattcc gcggatggac ttgcgcttga     1020
ttgccgccag atcacgttac gattatgtga tttcgtttgg aacttttag atttgtagct      1080 tctgcttatt atatgacaga tgcgcctact gctcatatgc ctgtggtaaa taatggatgg     1140
ctgtgggtca aactagttga ttgtcgagtc atgtatcata tacaggtgta tagacttgcg     1200
tctaattgtt tgcatgttgc agttatatga tttgttttag attgtttgtt ccactcatct     1260
aggctgtaaa agggacacta cttattagct tgttgtttaa tcttttatt agtagattat      1320 attggtaatg ttttactaat tattattatg ttatatgtga cttctgctca tgcctgatta     1380
taatcataga tcactgtagt tgattgttga atcatgtgtc aaatacccgt atacataaca     1440
ctacacattt gcttagttgt ttccttaact catgcaaatt gaacaccatg tatgatttgc     1500
atggtgctgt aatgttaaat actacagtcc tgttggtact tgtttagtaa gaatctgctt     1560
catacaacta tatgctatgc ctgatgataa tcatatatct ttgtgtaatt aataattagt     1620
tgactgttga ataatgtatc gagtacatac catggcacaa ttgcttagtc acttccttaa     1680
ccatgcatat tgaactgacc ccttcatgtt ctgctgaatt gttctattct gattagacca     1740
tacatcatgt attgcaatct ttatttgcaa ttgtaatgta atggttcggt tctcaaatgt     1800
taaatgctat agttgtgcta ctttctaatg ttaaatgcta tagctgtgct acttgtaaga     1860
tctgcttcat agtttagtta aattaggatg atgagctttg atgctgtaac tttgtttgat     1920
tatgttcata gttgatcagt ttttgttaga ctcacagtaa cttatggtct cactcttctt     1980
ctggtctttg atgtttgcag cgg                                              2003
```

<210> SEQ ID NO 158
<211> LENGTH: 1361
<212> TYPE: DNA
<213> ORGANISM: Sorghum bicolor

<400> SEQUENCE: 158

```
gtacgcgagt tttcgaatcc cctccagacc cctcgtatgc tttccctgtt cgttttcgtc       60
gtagcgtttg attaggtatg ctttccctgt tcgtgttcgt cgtagggttc gattaggtcg      120
tgtgaggcca tggcctgctg tgataaattt atttgttgtt atatcggatc tgtagtcgat      180 tgggggtcg tggtgtagat ccgcgggctg tgatgaagtt atttggtgtg attgtgctcg      240
cgtgattctg cgcgttgagc tcgagtagat ctgatggttg gacgaccgat tggttcgttg      300
gctggctgcg ctaaggttgg gctgggctca tgttgcgttc gctgttgcgc gtgattccgc      360
ggatggactt gcgcttgatt gccgccagat cacgttacga ttatgtgatt tcgtttggaa      420 cttttagat ttgtagcttc tgcttattat atgacagatg cgcctactgc tcatatgcct       480
gtggtaaata atggatggct gtgggtcaaa ctagttgatt gtcgagtcat gtatcatata     540
caggtgtata gacttgcgtc taattgtttg catgttgcag ttatatgatt tgttttagat     600
tgtttgttcc actcatctag gctgtaaaag ggacactact tattagcttg ttgtttaatc     660
```

```
tttttattag tagattatat tggtaatgtt ttactaatta ttattatgtt atatgtgact      720
tctgctcatg cctgattata atcatagatc actgtagttg attgttgaat catgtgtcaa      780
atacccgtat acataacact acacatttgc ttagttgttt ccttaactca tgcaaattga      840
acaccatgta tgatttgcat ggtgctgtaa tgttaaatac tacagtcctg ttggtacttg      900
tttagtaaga atctgcttca tacaactata tgctatgcct gatgataatc atatatcttt      960
gtgtaattaa taattagttg actgttgaat aatgtatcga gtacatacca tggcacaatt     1020
gcttagtcac ttccttaacc atgcatattg aactgacccc ttcatgttct gctgaattgt     1080
tctattctga ttagaccata catcatgtat tgcaatcttt atttgcaatt gtaatgtaat     1140
ggttcggttc tcaaatgtta aatgctatag ttgtgctact ttctaatgtt aaatgctata     1200
gctgtgctac ttgtaagatc tgcttcatag tttagttaaa ttaggatgat gagctttgat     1260
gctgtaactt tgtttgatta tgttcatagt tgatcagttt ttgttagact cacagtaact     1320
tatggtctca ctcttcttct ggtctttgat gtttgcagcg g                          1361
```

<210> SEQ ID NO 159
<211> LENGTH: 1812
<212> TYPE: DNA
<213> ORGANISM: Artificial sequence
<220> FEATURE:
<221> NAME/KEY: misc_feature
<222> LOCATION: (1)..(1812)
<223> OTHER INFORMATION: Codon redesigned coding sequence.

<400> SEQUENCE: 159

```
atggtccgtc ctgtagaaac cccaacccgt gaaatcaaaa aactcgacgg cctgtgggca       60
ttcagtctgg atcgcgaaaa ctgtggaatt gatcagcgtt ggtgggaaag cgcgttacaa      120
gaaagccggg caattgctgt gccaggcagt tttaacgatc agttcgccga tgcagatatt      180
cgtaattatg cgggcaacgt ctggtatcag cgcgaagtct ttataccgaa aggttgggca      240
ggccagcgta tcgtgctgcg tttcgatgcg gtcactcatt acggcaaagt gtgggtcaat      300
aatcaggaag tgatggagca tcagggcggc tatacgccat tgaagccga tgtcacgccg      360 tatgttattg ccgggaaaag tgtacgtatc accgtttgtg tgaacaacga actgaactgg      420
cagactatcc cgccgggaat ggtgattacc gacgaaaacg gcaagaaaaa gcagtcttac      480
ttccatgatt tctttaacta tgccggaatc catcgcagcg taatgctcta caccacgccg      540
aacacctggg tggacgatat caccgtggtg acgcatgtcg cgcaagactg taaccacgcg      600
tctgttgact ggcaggtggt ggccaatggt gatgtcagcg ttgaactgcg tgatgcggat      660
caacaggtgg ttgcaactgg acaaggcact agcgggactt gcaagtggt gaatccgcac      720 ctctggcaac cggtgaagg ttatctctat gaactgtgcg tcacagccaa agccagaca      780 gagtgtgata tctacccgct tcgcgtcggc atccggtcag tggcagtgaa gggcgaacag      840
ttcctgatta ccacaaaacc gttctacttt actggctttg gtcgtcatga agatgcggac      900
ttgcgtggca aaggattcga taacgtgctg atggtgcacg accacgcatt aatggactgg      960
attggggcca actcctaccg tacctcgcat taccccttacg ctgaagagat gctcgactgg     1020
gcagatgaac atggcatcgt ggtgattgat gaaactgctg ctgtcggctt taacctctct     1080
ttaggcattg gtttcgaagc gggcaacaag ccgaaagaac tgtacagcga agaggcagtc     1140 aacgggaaa ctcagcaagc gcacttacag gcgattaaag agctgatagc gcgtgacaaa     1200
aaccacccaa gcgtggtgat gtggagtatt gccaacgaac cggatacccg tccgcaaggt     1260
gcacgggaat atttcgcgcc actggcggaa gcaacgcgta aactcgaccc gacgcgtccg     1320
```

```
atcacctgcg tcaatgtaat gttctgcgac gctcacaccg ataccatcag cgatctcttt    1380
gatgtgctgt gcctgaaccg ttattacgga tggtatgtcc aaagcggcga tttggaaacg    1440
gcagagaagg tactggaaaa agaacttctg gcctggcagg agaaactgca tcagccgatt    1500
atcatcaccg aatacggcgt ggatacgtta gccgggctgc actcaatgta caccgacatg    1560
tggagtgaag agtatcagtg tgcatggctg gatatgtatc accgcgtctt tgatcgcgtc    1620
agcgccgtcg tcggtgaaca ggtatggaat ttcgccgatt ttgcgacctc gcaaggcata    1680
ttgcgcgttg gcggtaacaa gaaagggatc ttcactcgcg accgcaaacc gaagtcggcg    1740
gcttttctgc tgcaaaaacg ctggactggc atgaacttcg gtgaaaaacc gcagcaggga    1800
ggcaaacaat ga                                                        1812
```

<210> SEQ ID NO 160
<211> LENGTH: 2001
<212> TYPE: DNA
<213> ORGANISM: Artificial sequence
<220> FEATURE:
<221> NAME/KEY: misc_feature
<222> LOCATION: (1)..(2001)
<223> OTHER INFORMATION: Codon redesigned coding sequence.

<400> SEQUENCE: 160

```
atggtccgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat tgaagccga tgtcacgccg     360 tatgttattg ccgggaaaag tgtacgtaag tttctgcttc tacctttgat atatatataa     420
taattatcat taattagtag taatataata tttcaaatat tttttcaaa ataaaagaat      480 gtagtatata gcaattgctt ttctgtagtt tataagtgtg tatattttaa tttataactt     540
ttctaatata tgaccaaaat ttgttgatgt gcaggtatca ccgtttgtgt gaacaacgaa     600
ctgaactggc agactatccc gccgggaatg gtgattaccg acgaaaacgg caagaaaaag     660
cagtcttact tccatgattt ctttaactat gccggaatcc atcgcagcgt aatgctctac     720
accacgccga cacctgggt ggacgatatc accgtggtga cgcatgtcgc gcaagactgt     780
aaccacgcgt ctgttgactg gcaggtggtg gccaatggtg atgtcagcgt tgaactgcgt     840
gatgcggatc aacaggtggt tgcaactgga caaggcacta gcgggacttt gcaagtggtg     900
aatccgcacc tctggcaacc gggtgaaggt tatctctatg aactgtgcgt cacagccaaa     960
agccagacag agtgtgatat ctacccgctt cgcgtcggca tccggtcagt ggcagtgaag    1020
ggcgaacagt tcctgattaa ccacaaaccg ttctactttta ctggctttgg tcgtcatgaa    1080
gatgcggact tgcgtggcaa aggattcgat aacgtgctga tggtgcacga ccacgcatta    1140
atggactgga ttggggccaa ctcctaccgt acctcgcatt accttacgc tgaagagatg    1200 ctcgactggg cagatgaaca tggcatcgtg gtgattgatg aaactgctgc tgtcggcttt    1260
aacctctctt taggcattgg tttcgaagcg ggcaacaagc gaaagaact gtacagcgaa    1320 gaggcagtca acggggaaac tcagcaagcg cacttacagg cgattaaaga gctgatagcg    1380
cgtgacaaaa accaccccaag cgtggtgatg tggagtattg ccaacgaacc ggataccgt    1440
```

```
ccgcaaggtg cacgggaata tttcgcgcca ctggcggaag caacgcgtaa actcgacccg   1500
acgcgtccga tcacctgcgt caatgtaatg ttctgcgacg ctcacaccga taccatcagc   1560
gatctctttg atgtgctgtg cctgaaccgt tattacggat ggtatgtcca aagcggcgat   1620
ttggaaacgg cagagaaggt actggaaaaa gaacttctgg cctggcagga gaaactgcat   1680
cagccgatta tcatcaccga atacggcgtg gatacgttag ccgggctgca ctcaatgtac   1740
accgacatgt ggagtgaaga gtatcagtgt gcatggctgg atatgtatca ccgcgtctttt  1800 gatcgcgtca gcgccgtcgt cggtgaacag gtatggaatt cgccgatttt gcgacctcg    1860 caaggcatat tgcgcgttgg cggtaacaag aaagggatct tcactcgcga ccgcaaaccg   1920
aagtcggcgg cttttctgct gcaaaaacgc tggactggca tgaacttcgg tgaaaaaccg   1980
cagcagggag gcaaacaatg a                                             2001

<210> SEQ ID NO 161
<211> LENGTH: 253
<212> TYPE: DNA
<213> ORGANISM: Agrobacterium tumefaciens

<400> SEQUENCE: 161
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggttttatg attagagtcc cgcaattata catttaatac     180
gcgatagaaa acaaaatata gcgcgcaaac taggataaat tatcgcgcgc ggtgtcatct    240
atgttactag atc                                                      253

<210> SEQ ID NO 162
<211> LENGTH: 210
<212> TYPE: DNA
<213> ORGANISM: Triticum aestivum

<400> SEQUENCE: 162
ctgcatgcgt ttggacgtat gctcattcag gttggagcca atttggttga tgtgtgtgcg     60
agttcttgcg agtctgatga gacatctctg tattgtgttt cttccccag tgttttctgt     120 acttgtgtaa tcggctaatc gccaacagat tcggcgatga ataaatgaga ataaaattgt    180
tctgattttg agtgcaaaaa aaaaggaatt                                     210

<210> SEQ ID NO 163
<211> LENGTH: 1204
<212> TYPE: DNA
<213> ORGANISM: Artificial sequence
<220> FEATURE:
<221> NAME/KEY: misc_feature
<222> LOCATION: (1)..(1204)
<223> OTHER INFORMATION: Chimeric transcriptional regulatory expression
      element group.

<400> SEQUENCE: 163
ggtccgattg agacttttca acaaagggta atatccggaa acctcctcgg attccattgc     60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg gaaaagaag acgttccaac cacgtcttca    240
aagcaagtgg attgatgtga tggtccgatt gagacttttc aacaaagggt aatatccgga    300
aacctcctcg gattccattg cccagctatc tgtcacttta ttgtgaagat agtggaaaag    360
```

```
gaaggtggct cctacaaatg ccatcattgc gataaaggaa aggccatcgt tgaagatgcc    420
tctgccgaca gtggtcccaa agatggaccc ccacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gacccttcct ctatataagg aagttcattt    600
catttggaga ggacacgctg acaagctgac tctagcagat cctctagaac catcttccac    660
acactcaagc cacactattg gagaaacacac agggacaaca caccataaga tccaagggag    720
gcctccgccg ccgccggtaa ccaccccgcc cctctcctct ttctttctcc gttttttttt    780
ccgtctcggt ctcgatcttt ggccttggta gtttgggtgg cgagaggcg gcttcgtgcg      840 cgcccagatc ggtgcgcggg aggggcggga tctcgcggct ggggctctcg ccggcgtgga    900
tccggcccgg atctcgcggg gaatgggcgct ctcggatgta gatctgcgat ccgccgttgt    960
tgggggagat gatgggggggt ttaaaatttc cgccgtgcta acaagatca ggaagagggg    1020 aaaagggcac tatggtttat attttatat atttctgctg cttcgtcagg cttagatgtg     1080
ctagatcttt ctttcttctt tttgtgggta gaatttgaat ccctcagcat tgttcatcgg    1140 tagttttttct tttcatgatt tgtgacaaat gcagcctcgt gcggagcttt tttgtaggta    1200
gaag                                                                  1204
```

<210> SEQ ID NO 164
<211> LENGTH: 1399
<212> TYPE: DNA
<213> ORGANISM: Oryza sativa

<400> SEQUENCE: 164

```
tcgaggtcat tcatatgctt gagaagagag tcgggatagt ccaaaataaa acaaaggtaa     60
gattacctgg tcaaaagtga aaacatcagt taaaggtgg tataaagtaa aatatccggta    120 ataaaaggtg gcccaaagtg aaatttactc ttttctacta ttataaaaat tgaggatgtt    180
tttgtcggta ctttgatacg tcatttttgt atgaattggt ttttaagttt attcgctttt    240
ggaaatgcat atctgtattt gagtcgggtt ttaagttcgt ttgcttttgt aaatacagag    300
ggatttgtat aagaaatatc tttagaaaaa cccatatgct aatttgacat aattttttgag    360 aaaaatatat attcaggcga attctcacaa tgaacaataa taagattaaa atagcttttcc    420 cccgttgcag cgcatgggta ttttttctag taaaaataaa agataaactt agactcaaaa    480
catttacaaa acaacccct aaagttccta agcccaaag tgctatccac gatccatagc      540
aagcccagcc caacccaacc caacccaacc caccccagtc cagccaactg gacaatagtc    600 tccacaccccc cccactatca ccgtgagttg tccgcacgca ccgcacgtct cgcagccaaa    660
aaaaaaaaga aagaaaaaaa agaaaaagaa aaaacagcag gtgggtccgg gtcgtggggg    720
ccggaaacgc gaggaggatc gcgagccagc gacgaggccg gccctccctc cgcttccaaa    780
gaaacgcccc ccatcgccac tatatacata ccccccccctc tcctcccatc cccccaaccc    840
taccaccacc accaccacca cctccacctc ctcccccctc gctgccggac gacgagctcc    900 tccccctcc cctccgccg ccgccgcgcc ggtaaccacc ccgcccctct cctctttctt       960
tctccgtttt ttttccgtc tcggtctcga tctttggcct tggtagtttg ggtgggcgag    1020
aggcggcttc gtgcgcgccc agatcggtgc gcgggagggg cgggatctcg cggctggggc    1080 tctcgcggg gtggatccgg cccggatctc gcgggaatg gggctctcgg atgtagatct    1140
gcgatccgcc gttgttgggg gagatgatgg ggggttaaa atttccgccg tgctaaacaa    1200
gatcaggaag agggggaaaag ggcactatgg tttatatttt tatatatttc tgctgcttcg    1260
```

```
tcaggcttag atgtgctaga tctttctttc ttcttttttgt gggtagaatt tgaatccctc    1320
agcattgttc atcggtagtt tttcttttca tgatttgtga caaatgcagc ctcgtgcgga    1380
gcttttttgt aggtagaag                                                 1399

<210> SEQ ID NO 165
<211> LENGTH: 2181
<212> TYPE: DNA
<213> ORGANISM: Oryza sativa

<400> SEQUENCE: 165
gacaacaaca tgcttctcat caacatggag ggaagaggga gggagaaagt gtcgcctggt      60
cacctccatt gtcacactag ccactggcca gctctcccac accaccaatg ccaggggcga    120
gctttagcac agccaccgct tcacctccac caccgcacta ccctagcttc gcccaacagc    180
caccgtcaac gcctcctctc cgtcaacata agagagagag agaagaggag agtagccatg    240
tggggaggag gaatagtaca tggggcctac cgtttggcaa gttattttgg gttgccaagt    300
taggccaata aggggaggga tttggccatc cggttggaaa ggttattggg gtagtatctt    360
tttactagaa ttgtcaaaaa aaaatagttt gagagccatt tggagaggat gttgcctgtt    420
agaggtgctc ttaggacatc aaattccata aaaacatcag aaaaattctc tcgatgaaga    480
tttataacca ctaaaactgc cctcaattcg aagggagttc aaaacaatta aaatcatgtt    540
cgaattgagt ttcaatttca cttttaacccc tttgaaatct caatggtaaa acatcaaccc    600
gtcaggtagc atggttcttt ttattccttt caaaaagagt taattacaaa cagaatcaaa    660
actaacagtt aggcccaagg cccatccgag caaacaatag atcatgggcc aggcctgcca    720
ccaccctccc cctcctggct cccgctcttg aatttcaaaa tccaaaaata tcggcacgac    780
tggccgccga cggagcgggc ggaaaatgac ggaacaaccc ctcgaattct accccaacta    840
cgcccaccaa cccacacgcc actgacaatc cggtcccacc cttgtgggcc cacctacaag    900
cgagacgtca gtcgctcgca gcaaccagtg ggcccacctc ccagtgagcg gcgggtagat    960
ctggactctt acccacccac actaaacaaa acggcatgaa tattttgcac taaaaccctc   1020
agaaaaattc cgatattcca aaccagtaca gttcctgacc gttggaggag ccaaagtgga   1080
gcggagtgta aaattgggaa acttaatcga ggggttaaa cgcaaaaacg ccgaggcgcc    1140
tcccgctcta tagaaagggg aggagtggga ggtggaaacc ctaccacacc gcagagaaag   1200
gcgtcttcgt actcgcctct ctccgcgccc tcctccgccg ccgctcgccg ccgttcgtct   1260
ccgccgccac cggctagcca tccaggtaaa acaaacaaaa acggatctga tgcttccatt   1320
cctccgtttc tcgtagtagc gcgcttcgat ctgtgggtgg atctgggtga tcctggggtg   1380
tggttcgttc tgtttgatag atctgtcggt ggatctggcc ttctgtggtt gtcgatgtcc   1440
ggatctgcgt tttgatcagt ggtagttcgt ggatctggcg aaatgttttg gatctggcag   1500
tgagacgcta agaatcggga aatgatgcaa tattaggggg gtttcggatg gggatccact   1560
gaattagtct gtctccctgc tgataatctg ttccttttg gtagatctgg ttagtgtatg    1620
tttgtttcgg atagatctga tcaatgcttg tttgttttt caaattttct acctaggttg    1680
tataggaatg gcatgcggat ctggttggat tgccatgatc cgtgctgaaa tgccccttttg   1740 gttgatggat cttgatattt tactgctgtt cacctagatt tgtactcccg tttatactta   1800
atttgttgct tattatgaat agatctgtaa cttaggcaca tgtatggacg gagtatgtgg   1860
atctgtagta tgtacattgc tgcgagctaa gaactatttc agagcaagca cagaaaaaaa   1920
```

| | |
|---|---|
| tatttagaca gattgggcaa ctatttgatg gtctttggta tcatgctttg tagtgctcgt | 1980 |
| ttctgcgtag taatcttttg atctgatctg aagataggtg ctattatatt cttaaaggtc | 2040 |
| attagaacgc tatctgaaag gctgtattat gtggattggt tcacctgtga ctccctgttc | 2100 |
| gtcttgtctt gataaatcct gtgataaaaa aaattcttaa ggcgtaattt gttgaaatct | 2160 |
| tgttttgtcc tatgcagcct g | 2181 |

```
<210> SEQ ID NO 166
<211> LENGTH: 1653
<212> TYPE: DNA
<213> ORGANISM: Artificial sequence
<220> FEATURE:
<221> NAME/KEY: misc_feature
<222> LOCATION: (1)..(1653)
<223> OTHER INFORMATION: Codon redesigned coding sequence.

<400> SEQUENCE: 166
```

| | |
|---|---|
| atggaagacg ccaaaaacat aaagaaaggc ccggcgccat tctatcctct agaggatgga | 60 |
| accgctggag agcaactgca taaggctatg aagagatacg ccctggttcc tggaacaatt | 120 |
| gcttttacag atgcacatat cgaggtgaac atcacgtacg cggaatactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgaacatt | 360 |
| tcgcagccta ccgtagtgtt tgtttccaaa aagggggttgc aaaaaatttt gaacgtgcaa | 420 |
| aaaaaattac caataatcca gaaaattatt atcatggatt ctaaaacgga ttaccaggga | 480 |
| tttcagtcga tgtacacgtt cgtcacatct catctacctc ccggttttaa tgaatacgat | 540 |
| tttgtaccag agtcctttga tcgtgacaaa acaattgcac tgataatgaa ttcctctgga | 600 |
| tctactgggt tacctaaggg tgtggccctt ccgcatagaa ctgcctgcgt cagattctcg | 660 |
| catgccagag atcctatttt tggcaatcaa atcattccgg atactgcgat tttaagtgtt | 720 |
| gttccattcc atcacggttt tggaatgttt actacactcg gatatttgat atgtggattt | 780 |
| cgagtcgtct taatgtatag atttgaagaa gagctgtttt tacgatccct tcaggattac | 840 |
| aaaattcaaa gtgcgttgct agtaccaacc ctatttcat tcttcgccaa aagcactctg | 900 |
| attgacaaat acgatttatc taatttacac gaaattgctt ctgggggcgc acctctttcg | 960 |
| aaagaagtcg gggaagcggt tgcaaaacgc ttccatcttc cagggatacg acaaggatat | 1020 |
| gggctcactg agactacatc agctattctg attacacccg agggggatga taaaccgggc | 1080 |
| gcggtcggta agttgttcc atttttttgaa gcgaaggttg tggatctgga taccgggaaa | 1140 |
| acgctgggcg ttaatcagag aggcgaatta tgtgtcagag acctatgat tatgtccggt | 1200 |
| tatgtaaaca atccggaagc gaccaacgcc ttgattgaca aggatggatg ctacattct | 1260 |
| ggagacatag cttactggga cgaagacgaa cacttcttca gttgaccg cttgaagtct | 1320 |
| ttaattaaat acaaaggata tcaggtggcc cccgctgaat tggaatcgat attgttacaa | 1380 |
| caccccaaca tcttcgacgc gggcgtggca ggtcttcccg acgatgacgc cggtgaactt | 1440 |
| cccgccgccg ttgttgtttt ggagcacgga aagacgatga cggaaaaaga tcgtggat | 1500 |
| tacgtcgcca gtcaagtaac aaccgcgaaa aagttgcgcg gaggagttgt gtttgtggac | 1560 |
| gaagtaccga aaggtcttac cggaaaactc gacgcaagaa aaatcagaga gatcctcata | 1620 |
| aaggccaaga agggcggaaa gtccaaattg taa | 1653 |

<210> SEQ ID NO 167
<211> LENGTH: 936
<212> TYPE: DNA
<213> ORGANISM: Artificial sequence
<220> FEATURE:
<221> NAME/KEY: misc_feature
<222> LOCATION: (1)..(936)
<223> OTHER INFORMATION: Codon redesigned coding sequence.

<400> SEQUENCE: 167

| | |
|---|---|
| atggcttcca aggtgtacga ccccgagcaa cgcaaacgca tgatcactgg gcctcagtgg | 60 |
| tgggctcgct gcaagcaaat gaacgtgctg gactccttca tcaactacta tgattccgag | 120 |
| aagcacgccg agaacgccgt gattttctg catggtaacg ctgcctccag ctacctgtgg | 180 |
| aggcacgtcg tgcctcacat cgagcccgtg gctagatgca tcatccctga tctgatcgga | 240 |
| atgggtaagt ccggcaagag cgggaatggc tcatatcgcc tcctggatca ctacaagtac | 300 |
| ctcaccgctt ggttcgagct gctgaacctt ccaaagaaaa tcatctttgt gggccacgac | 360 |
| tgggggggctt gtctggcctt tcactactcc tacgagcacc aagacaagat caaggccatc | 420 |
| gtccatgctg agagtgtcgt ggacgtgatc gagtcctggg acgagtggcc tgacatcgag | 480 |
| gaggatatcg ccctgatcaa gagcgaagag ggcgagaaaa tggtgcttga gaataacttc | 540 |
| ttcgtcgaga ccatgctccc aagcaagatc atgcggaaac tggagcctga ggagttcgct | 600 |
| gcctacctgg agccattcaa ggagaagggc gaggttagac ggcctaccct ctcctggcct | 660 |
| cgcgagatcc ctctcgttaa gggaggcaag cccgacgtcg tccagattgt ccgcaactac | 720 |
| aacgcctacc ttcgggccag cgacgatctg cctaagatgt tcatcgagtc cgaccctggg | 780 |
| ttctttttcca acgctattgt cgagggagct aagaagttcc ctaacaccga gttcgtgaag | 840 |
| gtgaagggcc tccacttcag ccaggaggac gctccagatg aaatgggtaa gtacatcaag | 900 |
| agcttcgtgg agcgcgtgct gaagaacgag cagtaa | 936 |

<210> SEQ ID NO 168
<211> LENGTH: 675
<212> TYPE: DNA
<213> ORGANISM: Artificial sequence
<220> FEATURE:
<221> NAME/KEY: misc_feature
<222> LOCATION: (1)..(675)
<223> OTHER INFORMATION: Chimeric transcriptional regulatory expression element group.

<400> SEQUENCE: 168

| | |
|---|---|
| ggtccgatgt gagactttc aacaaagggt aatatccgga aacctcctcg gattccattg | 60 |
| cccagctatc tgtcacttta ttgtgaagat agtggaaaag gaaggtggct cctacaaatg | 120 |
| ccatcattgc gataaaggaa aggccatcgt gaagatgcc tctgccgaca gtggtcccaa | 180 |
| agatggaccc ccacccacga ggagcatcgt ggaaaaagaa gacgttccaa ccacgtcttc | 240 |
| aaagcaagtg gattgatgtg atggtccgat gtgagacttt tcaacaaagg gtaatatccg | 300 |
| gaaacctcct cggattccat tgcccagcta tctgtcactt tattgtgaag atagtggaaa | 360 |
| aggaaggtgg ctcctacaaa tgccatcatt gcgataaagg aaaggccatc gttgaagatg | 420 |
| cctctgccga cagtggtccc aaagatggac cccacccac gaggagcatc gtggaaaaag | 480 |
| aagacgttcc aaccacgtct tcaaagcaag tggattgatg tgatatctcc actgacgtaa | 540 |
| gggatgacgc acaatcccac tatccttcgc aagacccttc ctctatataa ggaagttcat | 600 |
| ttcatttgga gaggaaccat cttccacaca ctcaagccac actattggag aacacacagg | 660 |
| gacaacacac cataa | 675 |

<210> SEQ ID NO 169
<211> LENGTH: 622
<212> TYPE: DNA
<213> ORGANISM: Cauliflower mosaic virus

<400> SEQUENCE: 169

| | |
|---|---|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg aaaaagaag acgttccaac cacgtcttca | 240 |
| aagcaagtgg attgatgtga tggtccgatt gagacttttc aacaaagggt aatatccgga | 300 |
| aacctcctcg gattccattg cccagctatc tgtcacttta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaaagaa | 480 |
| gacgttccaa ccacgtcttc aaagcaagtg gattgatgtg atatctccac tgacgtaagg | 540 |
| gatgacgcac aatcccacta tctagacgca agacccttcc tctatataag gaagttcatt | 600 |
| tcatttggag aggacacgct ga | 622 |

<210> SEQ ID NO 170
<211> LENGTH: 1446
<212> TYPE: DNA
<213> ORGANISM: Artificial sequence
<220> FEATURE:
<221> NAME/KEY: misc_feature
<222> LOCATION: (1)..(1446)
<223> OTHER INFORMATION: Chimeric transcriptional regulatory expression
      element group.

<400> SEQUENCE: 170

| | |
|---|---|
| ggtccgattg agacttttca acaaagggta atatccggaa acctcctcgg attccattgc | 60 |
| ccagctatct gtcactttat tgtgaagata gtggaaaagg aaggtggctc ctacaaatgc | 120 |
| catcattgcg ataaaggaaa ggccatcgtt gaagatgcct ctgccgacag tggtcccaaa | 180 |
| gatggacccc cacccacgag gagcatcgtg aaaaagaag acgttccaac cacgtcttca | 240 |
| aagcaagtgg attgatgtga tggtccgatt gagacttttc aacaaagggt aatatccgga | 300 |
| aacctcctcg gattccattg cccagctatc tgtcacttta ttgtgaagat agtggaaaag | 360 |
| gaaggtggct cctacaaatg ccatcattgc gataaaggaa aggccatcgt tgaagatgcc | 420 |
| tctgccgaca gtggtcccaa agatggaccc ccacccacga ggagcatcgt ggaaaaagaa | 480 |
| gacgttccaa ccacgtcttc aaagcaagtg gattgatgtg atatctccac tgacgtaagg | 540 |
| gatgacgcac aatcccacta tccttcgcaa gaccccttcct ctatataagg aagttcattt | 600 |
| catttggaga ggacacgctg acaagctgac tctagcagat ctaccgtctt cggtacgcgc | 660 |
| tcactccgcc ctctgccttt gttactgcca cgtttctctg aatgctctct tgtgtggtga | 720 |
| ttgctgagag tggtttagct ggatctagaa ttacactctg aaatcgtgtt ctgcctgtgc | 780 |
| tgattacttg ccgtccttg tagcagcaaa atatagggac atggtagtac gaaacgaaga | 840 |
| tagaacctac acagcaatac gagaaatgtg taatttggtg cttagcggta tttatttaag | 900 |
| cacatgttgg tgttataggg cacttggatt cagaagtttg ctgttaattt aggcacaggc | 960 |
| ttcatactac atgggtcaat agtataggga ttcatattat aggcgatact ataataattt | 1020 |
| gttcgtctgc agagcttatt atttgccaaa attagatatt cctattctgt ttttgtttgt | 1080 |

```
gtgctgttaa attgttaacg cctgaaggaa taaatataaa tgacgaaatt ttgatgttta      1140
tctctgctcc tttattgtga ccataagtca agatcagatg cacttgtttt aaatattgtt      1200
gtctgaagaa ataagtactg acagtatttt gatgcattga tctgcttgtt tgttgtaaca      1260
aaatttaaaa ataaagagtt tccttttgt tgctctcctt acctcctgat ggtatctagt       1320
atctaccaac tgacactata ttgcttctct ttacatacgt atcttgctcg atgccttctc      1380
cctagtgttg accagtgtta ctcacatagt ctttgctcat ttcattgtaa tgcagatacc      1440
aagcgg                                                                  1446

<210> SEQ ID NO 171
<211> LENGTH: 1165
<212> TYPE: DNA
<213> ORGANISM: Artificial sequence
<220> FEATURE:
<221> NAME/KEY: misc_feature
<222> LOCATION: (1)..(1165)
<223> OTHER INFORMATION: Chimeric transcriptional regulatory expression
      element group.

<400> SEQUENCE: 171
ggtccgatgt gagactttc aacaaagggt aatatccgga aacctcctcg gattccattg        60
cccagctatc tgtcacttta ttgtgaagat agtggaaaag gaaggtggct cctacaaatg      120
ccatcattgc gataaaggaa aggccatcgt tgaagatgcc tctgccgaca gtggtcccaa      180
agatggaccc ccacccacga ggagcatcgt ggaaaaagaa gacgttccaa ccacgtcttc      240 aaaagcaagtg gattgatgtg atggtccgat gtgagacttt tcaacaaagg gtaatatccg    300
gaaacctcct cggattccat tgcccagcta tctgtcactt tattgtgaag atagtggaaa    360
aggaaggtgg ctcctacaaa tgccatcatt gcgataaagg aaaggccatc gttgaagatg    420
cctctgccga cagtggtccc aaagatggac cccacccac gaggagcatc gtggaaaaag      480
aagacgttcc aaccacgtct tcaaagcaag tggattgatg tgatatctcc actgacgtaa    540
gggatgacgc acaatcccac tatccttcgc aagacccttc ctctatataa ggaagttcat    600
ttcatttgga gaggacacgc tgacaagctg actctagcag atcctctaga accatcttcc    660
acacactcaa gccacactat tggagaacac acagggacaa cacaccataa gatccaaggg    720
aggcctccgc cgccgccggt aaccaccccg cccctctcct cttctttct ccgtttttt      780 ttccgtctcg gtctcgatct ttggccttgg tagtttgggt gggcgagagg cggcttcgtg    840
cgcgcccaga tcggtgcgcg ggaggggcgg gatctcgcgg ggaatggggc tctcggatgt    900
agatctgcga tccgccgttg ttgggggaga tgatggggg tttaaaattt gcgccgtgct      960
aaacaagatc aggaagaggg gaaaagggca ctatggttta tatttttata tatttctgct    1020
gcttcgtcag gcttagatgt gctagatctt tctttcttct ttttgtgggt agaatttgaa    1080
tccctcagca ttgttcatcg gtagttttc ttttcatgat ttgtgacaaa tgcagcctcg     1140
tgcggagctt ttttgtaggt agaag                                            1165

<210> SEQ ID NO 172
<211> LENGTH: 1751
<212> TYPE: DNA
<213> ORGANISM: Artificial sequence
<220> FEATURE:
<221> NAME/KEY: misc_feature
<222> LOCATION: (1)..(1751)
<223> OTHER INFORMATION: Chimeric transcriptional regulatory expression
      element group.
```

<400> SEQUENCE: 172

```
tcgaggtcat tcatatgctt gagaagagag tcgggatagt ccaaaataaa acaaaggtaa        60
gattacctgg tcaaaagtga aaacatcagt taaaaggtgg tataaagtaa aatatcggta       120
ataaaaggtg gcccaaagtg aaatttactc ttttctacta ttataaaaat tgaggatgtt       180
tttgtcggta ctttgatacg tcattttttgt atgaattggt ttttaagttt attcgctttt      240
ggaaatgcat atctgtattt gagtcgggtt ttaagttcgt ttgcttttgt aaatacagag       300
ggatttgtat aagaaatatc tttagaaaaa cccatatgct aatttgacat aattttttgag      360
aaaaatatat attcaggcga attagcttag gcctcatcgt tgaagatgcc tctgccgaca       420
gtggtcccaa agatggaccc ccacccacga ggagcatcgt ggaaaaagaa gacgttccaa       480
ccacgtcttc aaagcaagtg gattgatgtg atatctccac tgacgtaagg gatgacgcac       540
aatcccacta tccttcgagg cctcatcgtt gaagatgcct ctgccgacag tggtcccaaa       600
gatggacccc cacccacgag gagcatcgtg gaaaaagaag acgttccaac cacgtcttca       660
aagcaagtgg attgatgtga tatctccact gacgtaaggg atgacgcaca atcccactat       720
ccttcgaagc taattctcac aatgaacaat aataagatta aaatagcttt ccccgttgc        780
agcgcatggg tattttttct agtaaaaata aaagataaac ttagactcaa aacatttaca       840
aaacaacccc ctaaagttcc taaagcccaa agtgctatcc acgatccata gcaagcccag       900
cccaacccaa cccaacccaa cccaccccag tccagccaac tggacaatag tctccacacc       960
cccccactat caccgtgagt tgtccgcacg caccgcacgt ctcgcagcca aaaaaaaaa       1020
gaaagaaaaa aagaaaaaag aaaaaacagc aggtgggtcc gggtcgtggg ggccggaaac      1080
gcgaggagga tcgcgagcca gcgacgaggc cggccctccc tccgcttcca agaaacgcc       1140
ccccatcgcc actatataca tacccccccc tctcctccca tccccccaac cctaccacca      1200
ccaccaccac cacctccacc tcctcccccc tcgctgccgg acgacgagct cctccccct       1260
cccctccgc cgccgccgcg ccggtaacca ccccgcccct ctcctctttc tttctccgtt       1320
ttttttccg tctcggtctc gatctttggc cttggtagtt tgggtgggcg agaggcggct       1380
tcgtgcgcgc ccagatcggt gcgcgggagg ggcgggatct cgcggctggg gctctcgccg      1440
gcgtggatcc ggcccggatc tcgcggggaa tgggctctc ggatgtagat ctgcgatccg      1500
ccgttgttgg gggagatgat gggggtttta aaatttccgc cgtgctaaac aagatcagga      1560
agagggaaa agggcactat ggtttatatt tttatatatt tctgctgctt cgtcaggctt      1620
agatgtgcta gatctttctt tcttctttt gtgggtagaa tttgaatccc tcagcattgt      1680
tcatcggtag ttttttcttt catgatttgt gacaaatgca gcctcgtgcg gagctttttt     1740
gtaggtagaa g                                                           1751
```

<210> SEQ ID NO 173
<211> LENGTH: 1101
<212> TYPE: DNA
<213> ORGANISM: Artificial sequence
<220> FEATURE:
<221> NAME/KEY: misc_feature
<222> LOCATION: (1)..(1101)
<223> OTHER INFORMATION: Chimeric transcriptional regulatory expression element group.

<400> SEQUENCE: 173

```
ggtccgattg agacttttca acaaagggta atatccggaa acctcctcgg attccattgc        60
ccagctatct gtcactttat tgtgaagata gtggaaaagg aaggtggctc ctacaaatgc       120
```

```
catcattgcg ataaaggaaa ggccatcgtt gaagatgcct ctgccgacag tggtcccaaa      180
gatggacccc cacccacgag gagcatcgtg gaaaaagaag acgttccaac cacgtcttca      240
aagcaagtgg attgatgtga tggtccgatt gagacttttc aacaaagggt aatatccgga      300
aacctcctcg gattccattg cccagctatc tgtcacttta ttgtgaagat agtggaaaag      360
gaaggtggct cctacaaatg ccatcattgc gataaaggaa aggccatcgt tgaagatgcc      420
tctgccgaca gtggtcccaa agatggaccc cacccacgag gagcatcgt ggaaaaagaa       480 gacgttccaa ccacgtcttc aaagcaagtg gattgatgtg atatctccac tgacgtaagg      540
gatgacgcac aatcccacta tccttcgcaa gaccccttcct ctatataagg aagttcattt     600
catttggaga ggacacgctg accgccgccg ccggtaacca ccccgcccct ctcctctttc      660
tttctccgtt ttttttttccg tctcggtctc gatctttggc cttggtagtt tgggtgggcg     720
agaggcggct tcgtgcgcgc ccagatcggt gcgcgggagg ggcgggatct cgcggctggg      780
gctctcgccg gcgtggatcc ggcccggatc tcgcggggaa tggggctctc ggatgtagat      840
ctgcgatccg ccgttgttgg gggagatgat gggggggttta aaatttccgc cgtgctaaac    900
aagatcagga agaggggaaa agggcactat ggtttatatt tttatatatt tctgctgctt      960
cgtcaggctt agatgtgcta gatctttctt tcttctttt gtgggtagaa tttgaatccc      1020
tcagcattgt tcatcggtag ttttttcttt catgatttgt gacaaatgca gcctcgtgcg     1080
gagctttttt gtaggtagaa g                                                1101

<210> SEQ ID NO 174
<211> LENGTH: 200
<212> TYPE: DNA
<213> ORGANISM: Cauliflower mosaic virus

<400> SEQUENCE: 174
aaatcaccag tctctctcta caaatctatc tctctctatt tttctccaga ataatgtgtg     60
agtagttccc agataaggga attagggttc ttatagggtt tcgctcatgt gttgagcata     120
taagaaaccc ttagtatgta tttgtatttg taaaatactt ctatcaataa aatttctaat     180
tcctaaaacc aaaatccagt                                                   200

<210> SEQ ID NO 175
<211> LENGTH: 300
<212> TYPE: DNA
<213> ORGANISM: Oryza sativa

<400> SEQUENCE: 175
attaatcgat cctccgatcc cttaattacc ataccattac accatgcatc aatatccata     60
tatatataaa ccctttcgca cgtacttata ctatgttttg tcatacatat atatgtgtcg     120
aacgatcgat ctatcactga tatgatatga ttgatccatc agcctgatct ctgtatcttg     180
ttatttgtat accgtcaaat aaaagttttct tccacttgtg ttaataatta gctactctca     240
tctcatgaac cctatatata actagtttaa tttgctgtca attgaacatg atgatcgatg      300

<210> SEQ ID NO 176
<211> LENGTH: 623
<212> TYPE: DNA
<213> ORGANISM: Cauliflower mosaic virus

<400> SEQUENCE: 176
ggtccgatgt gagactttc aacaaagggt aatatccgga aacctcctcg gattccattg       60
cccagctatc tgtcacttta ttgtgaagat agtggaaaag gaaggtggct cctacaaatg     120
```

```
ccatcattgc gataaaggaa aggccatcgt tgaagatgcc tctgccgaca gtggtcccaa      180
agatggaccc ccaccacga ggagcatcgt ggaaaaagaa gacgttccaa ccacgtcttc      240
aaagcaagtg gattgatgtg atggtccgat gtgagacttt tcaacaaagg gtaatatccg      300
gaaacctcct cggattccat tgcccagcta tctgtcactt tattgtgaag atagtggaaa      360
aggaaggtgg ctcctacaaa tgccatcatt gcgataaagg aaaggccatc gttgaagatg      420
cctctgccga cagtggtccc aaagatggac ccccacccac gaggagcatc gtggaaaaag      480
aagacgttcc aaccacgtct tcaaagcaag tggattgatg tgatatctcc actgacgtaa      540
gggatgacgc acaatcccac tatccttcgc aagacccttc ctctatataa ggaagttcat      600
ttcatttgga gaggacacgc tga                                              623
```

<210> SEQ ID NO 177
<211> LENGTH: 8
<212> TYPE: DNA
<213> ORGANISM: Cauliflower mosaic virus

<400> SEQUENCE: 177

```
acacgctg                                                                8
```

<210> SEQ ID NO 178
<211> LENGTH: 804
<212> TYPE: DNA
<213> ORGANISM: Zea mays

<400> SEQUENCE: 178

```
accgtcttcg gtacgcgctc actccgccct ctgcctttgt tactgccacg tttctctgaa       60
tgctctcttg tgtggtgatt gctgagagtg gtttagctgg atctagaatt acactctgaa      120
atcgtgttct gcctgtgctg attacttgcc gtcctttgta gcagcaaaat atagggacat      180
ggtagtacga aacgaagata gaacctacac agcaatacga gaaatgtgta atttggtgct      240
tagcggtatt tatttaagca catgttggtg ttatagggca cttggattca gaagtttgct      300
gttaatttag gcacaggctt catactacat gggtcaatag tatagggatt catattatag      360
gcgatactat aataatttgt tcgtctgcag agcttattat ttgccaaaat tagatattcc      420
tattctgttt ttgtttgtgt gctgttaaat tgttaacgcc tgaaggaata aatataaatg      480
acgaaatttt gatgtttatc tctgctcctt tattgtgacc ataagtcaag atcagatgca      540
cttgttttaa atattgttgt ctgaagaaat aagtactgac agtattttga tgcattgatc      600
tgcttgtttt ttgtaacaaa atttaaaaat aaagagtttc cttttttgttg ctctccttac      660 ctcctgatgg tatctagtat ctaccaactg acactatatt gcttctcttt acatacgtat      720
cttgctcgat gccttctccc tagtgttgac cagtgttact cacatagtct ttgctcattt      780
cattgtaatg cagataccaa gcgg                                             804
```

<210> SEQ ID NO 179
<211> LENGTH: 1396
<212> TYPE: DNA
<213> ORGANISM: Oryza sativa

<400> SEQUENCE: 179

```
tcgaggtcat tcatatgctt gagaagagag tcgggatagt ccaaaataaa acaaaggtaa       60 gattaccctgg tcaaaagtga aaacatcagt taaaaggtgg tataaagtaa aatatcggta      120
ataaaaggtg gcccaaagtg aaatttactc ttttctacta ttataaaaat tgaggatgtt      180
```

```
tttgtcggta ctttgatacg tcattttttgt atgaattggt ttttaagttt attcgctttt      240
ggaaatgcat atctgtattt gagtcgggtt ttaagttcgt ttgcttttgt aaatacagag      300
ggatttgtat aagaaatatc tttagaaaaa cccatatgct aatttgacat aattttttgag     360
aaaaatatat attcaggcga attctcacaa tgaacaataa taagattaaa atagctttcc      420
cccgttgcag cgcatgggta ttttttctag taaaaataaa agataaactt agactcaaaa      480
catttacaaa aacaacccct aaagttccta aagcccaaag tgctatccac gatccatagc      540
aagcccagcc caacccaacc caacccagcc caccccagtc cagccaactg acaatagtc       600
tccacacccc cccactatca ccgtgagttg tccgcacgca ccgcacgtct cgcagccaaa      660
aaaaaaaga aagaaaaaaa agaaaagaa aaaacagcag gtgggtccgg gtcgtggggg       720
ccggaaacgc gaggaggatc gcgagccagc gacgaggccg gccctccctc cgcttccaaa      780
gaaacgcccc ccatcgccac tatatacata ccccccccctc tcctcccatc cccccaaccc    840
taccaccacc accaccacca cctccacctc ctcccccctc gctgccggac gacgagctcc      900
tccccctcc cctccgccg ccgccgcgcc ggtaaccacc ccgcccctct cctctttctt        960
tctccgtttt tttttccgtc tcggtctcga tctttggcct tggtagtttg ggtgggcgag      1020
aggcggcttc gtgccgccca gatcggtgcg cgggaggggc gggatctcgc ggctggctct     1080
cgcccccgtg gatccggccc ggatctcgcg gggaatgggg ctctcggatg tagatctgcg     1140
atccgccgtt gttggggccg atgatggggc ccttaaaatt tccgccgtgc taaacaagat      1200
caggaagagg ggaaaagggc actatggttt atattttttat atatttctgc tgcttcgtca    1260
ggcttagatg tgctagatct ttctttcttc tttttgtggg tagaatttaa tccctcagca     1320
ttgttcatcg gtagtttttc ttttcatgat tcgtgacaaa tgcagcctcg tgcggacgtt      1380
tttttgtagg tagaag                                                     1396

<210> SEQ ID NO 180
<211> LENGTH: 2625
<212> TYPE: DNA
<213> ORGANISM: Setaria italica

<400> SEQUENCE: 180
actgccgcga cacgcctcac tggcgggagg gctccgagcg ctctctcccc ggcggccggc       60
ggagcagcga tctggattgg agagaataga ggaaagagag ggaaaaggag agagatagcg      120
caaagagctg aaaagataag gttgtgcggg ctgtggtgat tagaggacca ctaatccctc      180
catctcctaa tgacgcggtg cccaagacca gtgccgcggc acaccagcgt ctaagtgaac      240
ttccgctaac cttccggtca ttgcgcctga aagatgtcat gtggcgaggc cccctctca     300
gtagattgcc aactgcctac cgtgccactc ttccatgcat gattgctccc gtctatcccg      360
tttctcacaa cagatagaca acagtaagca tcactaaagc aagcatgtgt agaaccttaa      420
aaaaaggctt atactaccag tatactatca accagcatgc cgttttttgaa gtatccagga    480
ttagaagctt ctactgcgct tttatattat agctgtggac ccgtggtaac ctttctcttt      540
tggcgcttgc ttaatctcgg ccgtgctggt ccatgcttag cactaggca gagatagagc       600
cggggggtgaa tggggctaaa gctcagctgc tcgaggggcc gtgggctggt ttccactagc    660
ctacagctgt gccacgtgcg gccgcgcaag ccgaagcaag cacgctgagc cgttggacag     720
cttgtcataa tgccattacg tggattacac gtaactggcc ctgtaactac tcgttcggcc     780
atcatcaaac gacgacgtcc gctaggcgac gacacgggta atgcacgcag ccacccaggc    840
gcgcgcgcta gcggagcacg gtcaggtgac acgggcgtcg tgacgcttcc gagttgaagg     900
```

```
ggttaacgcc agaaacagtg tttggccagg gtatgaacat aacaaaaaat attcacacga    960
aagaatggaa gtatggagct gctactgtgt aaatgccaag caggaaactc acgcccgcta   1020
acatccaacg gccaacagct cgacgtgccg gtcagcagag catcggaaca ctggtgattg   1080
gtggagccgg cagtatgcgc cccagcacgg ccgaggtggt ggtggcccgt ggccctgctg   1140
tctgcgcggc tcgggacaac ttgaaactgg gccaccgcct cgtcgcaact cgcaacccgt   1200
tggcggaaga aggaatggc tcgtaggggc cgggtagaa tcgaagaatg ttgcgctggg   1260
cttcgattca cataacatgg gcctgaagct ctaaaacgac ggcccggtcg ccgcgcgatg   1320
gaaagagacc ggatcctcct cgtgaattct ggaaggccac acgagagcga cccaccaccg   1380
acgcggagga gtcgtgcgtg gtccaacacg gccggcgggc tgggctgcga ccttaaccag   1440
caaggcacgc cacgacccgc cccgcccctcg aggcataaat accctcccat cccgttgccg   1500
caagactcag atcagattcc gatccccagt tcttccccaa tcaccttgtg gtctctcgtg   1560
tcgcggttcc cagggacgcc tccggctcgt cgctcgacag cgatctccgc cccagcaagg   1620
tatagattca gttccttgct ccgatcccaa tctggttgag atgttgctcc gatgcgactt   1680
gattatgtca tatatctgcg gtttgcaccg atctgaagcc tagggtttct cgagcgaccc   1740
agttatttgc aatttgcgat ttgctcgttt gttgcgcagc gtagtttatg tttggagtaa   1800
tcgaggattt gtatgcggcg tcggcgctac ctgcttaatc acgccatgtg acgcggttac   1860
ttgcagaggc tgggttctgt tatgtcgtga tctaagaatc tagattaggc tcagtcgttc   1920
ttgctgtcga ctagtttgtt ttgatatcca tgtagtacaa gttacttaaa atttaggtcc   1980
aatatatttt gcatgctttt ggcctgttat tcttgccaac aagttgtcct ggtaaaaagt   2040
agatgtgaaa gtcacgtatt gggacaaatt gatggtttag tgctatagtt ctatagttct   2100
gtgatacatc tatctgattt ttttggtct attggtgcct aacttatctg aaaatcatgg   2160
aacatgaggc tagtttgatc atggtttagt tcattgtgat taataatgta tgatttagta   2220
gctattttgg tgatcgtgtc attttatttg tgaatggaat cattgtatgt aaatgaagct   2280
agttcagggg ttacgatgta gctggctttg tattctaaag gctgctatta ttcatccatc   2340
gatttcacct atatgtaatc cagagctttt gatgtgaaat ttgtctgatc cttcactagg   2400
aaggacagaa cattgttaat attttggcac atctgtctta ttctcatcct ttgtttgaac   2460
atgttagcct gttcaaacag atactgttgt aatgtcctag ttatataggt acatatgtgt   2520
tctctattga gtttatggac ttttgtgtgt gaagttatat ttcattttgc tcaaaactca   2580
tgtttgcaag cttctctgaca ttattctatt gttctgaaac aggtg            2625
```

<210> SEQ ID NO 181
<211> LENGTH: 2008
<212> TYPE: DNA
<213> ORGANISM: Zea mays subsp. Mexicana

<400> SEQUENCE: 181

```
gtcgtgcccc tctctagaga taaagagcat tgcatgtcta aagtataaaa aattaccaca     60
tatttttttg tcacacttat ttgaagtgta gtttatctat ctctatacat atatttaaac    120
ttcactctac aaataatata gtctataata ctaaaataat attagtgttt tagaggatca    180
tataaataaa ctgctagaca tggtctaaag gataattgaa tattttgaca atctacagtt    240
ttatcttttt agtgtgcatg tgatctctct gttttttttg caaatagctt gacctatata    300
atacttcatc catttttatta gtacatccat ttaggattta gggttgatgg tttctataga    360
```

```
ctaatttta gtacatccat tttattcttt ttagtctcta aatttttaa aactaaaact      420
ctatttagt tttttatta ataattaga tataaaatga aataaaataa attgactaca      480
aataaaacaa atacccttta agaaataaaa aaactaagca aacattttc ttgtttcgag    540
tagataatga caggctgttc aacgccgtcg acgagtctaa cggacaccaa ccagcgaacc   600
agcagcgtcg cgtcgggcca agcgaagcag acggcacggc atctctgtag ctgcctctgg  660
acccctctcg agagttccgc tccaccgttg gacttgctcc gctgtcggca tccagaaatt  720
gcgtggcgga gcggcagacg tgaggcggca cggcaggcgg cctcttcctc ctctcacggc  780
accggcagct acgggggatt cctttcccac cgctccttcg cttttcccttc ctcgcccgcc  840
gtaataaata gacaccccct ccacaccctc tttccccaac ctcgtgttcg ttcggagcgc  900
acacacacgc aaccagatct cccccaaatc cagccgtcgg cacctccgct tcaaggtacg  960
ccgctcatcc tcccccccc cctctctcta ccttctctag atcggcgatc cggtccatgg  1020
ttagggcccg gtagttctac ttctgttcat gtttgtgtta gagcaaacat gttcatgttc  1080
atgtttgtga tgatgtggtc tggttgggcg gtcgttctag atcggagtag atactgtttt  1140
caagctacct ggtggattta ttaattttgt atctgtatgt gtgtgccata catcttcata  1200
gttacgagtt aagatgatg gatggaaata tcgatctagg ataggtatac atgttgatgc   1260
gggttttact gatgcatata cagagatgct ttttttctcg cttggttgtg atgatatggt  1320
ctggttgggc ggtcgttcta gatcggagta gaatactgtt tcaaactacc tggtggatt   1380
attaaaggat aaagggtcgt tctagatcgg agtagaatac tgtttcaaac tacctggtgg  1440
atttattaaa ggatctgtat gtatgtgcct acatcttcat agttacgagt ttaagatgat  1500
ggatggaaat atcgatctag gataggtata catgttgatg cgggttttac tgatgcatat  1560
acagagatgc ttttttttcgc ttggttgtga tgatgtggtc tggttgggcg gtcgttctag 1620
atcggagtag aatactgttt caaactacct ggtggattta ttaattttgt atctttatgt  1680
gtgtgccata catcttcata gttacgagtt aagatgatg gatggaaata ttgatctagg   1740
ataggtatac atgttgatgt gggttttact gatgcatata catgatggca tatgcggcat  1800
ctattcatat gctctaacct tgagtaccta tctattataa taaacaagta tgttttataa  1860
ttattttgat cttgatatac ttggatgatg gcatatgcag cagctatatg tggatttttt  1920
agccctgcct tcatacgcta ttatttgct tggtactgtt tcttttgtcc gatgctcacc   1980
ctgttgttgg gtgatacttc tgcagcgg                                     2008
```

<210> SEQ ID NO 182
<211> LENGTH: 1053
<212> TYPE: DNA
<213> ORGANISM: Zea mays subsp. Mexicana

<400> SEQUENCE: 182

```
gtacgccgct catcctcccc cccccctct ctctaccttc tctagatcgg cgatccggtc    60
catggttagg gcccggtagt tctacttctg ttcatgtttg tgttagagca aacatgttca  120
tgttcatgtt tgtgatgatg tggtctggtt gggcggtcgt tctagatcgg agtaggatac  180
tgtttcaagc tacctggtgg atttattaat tttgtatctg tatgtgtgtg ccatacatct  240
tcatagttac gagtttaaga tgatggatgg aaatatcgat ctaggatagg tatacatgtt  300
gatgcgggtt ttactgatgc atatacagag atgcttttttt tctcgcttgg ttgtgatgat  360
atggtctggt tgggcggtcg ttctagatcg gagtagaata ctgtttcaaa ctacctggtg  420
gatttattaa aggataaagg gtcgttctag atcggagtag aatactgttt caaactacct  480
```

```
ggtggattta ttaaaggatc tgtatgtatg tgcctacatc ttcatagtta cgagtttaag      540
atgatggatg gaaatatcga tctaggatag gtatacatgt tgatgcgggt tttactgatg      600
catatacaga gatgcttttt ttcgcttggt tgtgatgatg tggtctggtt gggcggtcgt      660
tctagatcgg agtagaatac tgtttcaaac tacctggtgg atttattaat tttgtatctt      720
tatgtgtgtg ccatacatct tcatagttac gagtttaaga tgatggatgg aaatattgat      780
ctaggatagg tatacatgtt gatgtgggtt ttactgatgc atatacatga tggcatatgc      840
ggcatctatt catatgctct aaccttgagt acctatctat tataataaac aagtatgttt      900
tataattatt ttgatcttga tacttggat  tgatggcata tgcagcagct atatgtggat      960
tttttagccc tgccttcata cgctatttat ttgcttggta ctgtttcttt tgtccgatgc     1020
tcaccctgtt gttgggtgat acttctgcag cgg                                 1053
```

<210> SEQ ID NO 183
<211> LENGTH: 2625
<212> TYPE: DNA
<213> ORGANISM: Setaria italica

<400> SEQUENCE: 183

```
actgccgcga cacgcctcac tggcgggagg gctccgagcg ctctctcccc ggcggccggc       60
ggagcagcga tctggattgg agagaataga ggaaagagag ggaaaaggag agagatagcg      120
caaagagctg aaaagataag gttgtgcggg ctgtggtgat tagaggacca ctaatccctc      180
catctcctaa tgacgcggtg cccaagacca gtgccgcggc acaccagcgt ctaagtgaac      240
ttccgctaac cttccggtca ttgcgcctga aagatgtcat gtggcgaggc cccctctca       300 gtagattgcc aactgcctac cgtgccactc ttccatgcat gattgctccc gtctatcccg      360
tttctcacaa cagatagaca acagtaagca tcactaaagc aagcatgtgt agaaccttaa      420
aaaaaggctt atactaccag tatactatca accagcatgc cgtttttgaa gtatccagga      480
ttagaagctt ctactgcgct tttatattat agctgtggac ccgtggtaac ctttctcttt      540
tggcgcttgc ttaatctcgg ccgtgctggt ccatgcttag cactaggca gagatagagc       600 cgggggtgaa tggggctaaa gctcagctgc tcgaggggcc gtgggctggt ttccactagc      660
ctacagctgt gccacgtgcg gccgcgcaag ccgaagcaag cacgctgagc cgttggacag      720
cttgtcataa tgccattacg tggattacac gtaactggcc ctgtaactac tcgttcggcc      780
atcatcaaac gacgacgtcc gctaggcgac gacacgggta atgcacgcag ccacccaggc      840
gcgcgcgcta gcggagcacg tcaggtgac acgggcgtcg tgacgcttcc gagttgaagg       900
ggttaacgcc agaaacagtg tttggccagg gtatgaacat aacaaaaaat attcacacga      960
aagaatggaa gtatggagct gctactgtgt aaatgccaag caggaaactc acgcccgcta     1020
acatccaacg gccaacagct cgacgtgccg gtcagcagag catcggaaca ctggtgattg     1080
gtggagccgg cagtatgcgc cccagcacgg ccgaggtggt ggtggcccgt ggccctgctg     1140
tctgcgcggc tcgggacaac ttgaaactgg gccaccgcct cgtcgcaact cgcaacccgt     1200
tggcggaaga aaggaatggc tcgtagggc  ccgggtagaa tcgaagaatg ttgcgctggg     1260
cttcgattca cataacatgg gcctgaagct ctaaaacgac ggcccggtcg ccgcgcgatg     1320
gaaagagacc ggatcctcct cgtgaattct ggaaggccac acgagagcga cccaccaccg     1380
acgcggagga gtcgtgcgtg gtccaacacg gccggcgggc tgggctgcga ccttaaccag     1440
caaggcacgc cacgacccgc cccgccctcg aggcataaat accctcccat cccgttgccg     1500
```

-continued

```
caagactcag atcagattcc gatccccagt tcttccccaa tcaccttgtg gtctctcgtg    1560
tcgcggttcc cagggacgcc tccggctcgt cgctcgacag cgatctccgc cccagcaagg    1620
tatagattca gttccttgct ccgatcccaa tctggttgag atgttgctcc gatgcgactt    1680
gattatgtca tatatctgcg gtttgcaccg atctgaagcc tagggtttct cgagcgaccc    1740
agttatttgc aatttgcgat ttgctcgttt gttgcgcagc gtagtttatg tttggagtaa    1800
tcgaggattt gtatgcggcg tcggcgctac ctgcttaatc acgccatgtg acgcggttac    1860
ttgcagaggc tgggttctgt tatgtcgtga tctaagaatc tagattaggc tcagtcgttc    1920
ttgctgtcga ctagtttgtt ttgatatcca tgtagtacaa gttacttaaa atttaggtcc    1980
aatatatttt gcatgctttt ggcctgttat tcttgccaac aagttgtcct ggtaaaaagt    2040
agatgtgaaa gtcacgtatt gggacaaatt gatggtttag tgctatagtt ctatagttct    2100
gtgatacatc tatctgattt tttttggtct attggtgcct aacttatctg aaaatcatgg    2160
aacatgaggc tagtttgatc atggtttagt tcattgtgat taataatgta tgatttagta    2220
gctattttgg tgatcgtgtc attttatttg tgaatgaaat cattgtatgt aaatgaagct    2280
agttcagggg ttacgatgta gctggctttg tattctaaag gctgctatta ttcatccatc    2340
gatttcacct atatgtaatc cagagctttt gatgtgaaat ttgtctgatc cttcactagg    2400
aaggacagaa cattgttaat attttggcac atctgtctta ttctcatcct ttgtttgaac    2460
atgttagcct gttcaaacag atactgttgt aatgtcctag ttatataggt acatatgtgt    2520
tctctattga gtttatggac ttttgtgtgt gaagttatat ttcattttgc tcaaaactca    2580
tgtttgcaag ctttctgaca ttattctatt gttctgaaac aggtg                    2625
```

US 9,771,595 B2

PLANT REGULATORY ELEMENTS AND USES THEREOF

REFERENCE TO RELATED APPLICATIONS

This application is a continuation of pending U.S. application Ser .No. 13/428,994, filed on Mar. 23, 2012, which claims the benefit of U.S provisional application No. 61/467,875 filed Mar. 25, 2011, each of which are herein incorporated by reference in their entirety.

INCORPORATION OF SEQUENCE LISTING

The sequence listing that is contained in the file named "MONS282US_seq.txt", which is 347 KB (as measured in Microsoft Windows®) and was created on Mar. 21, 2012, is filed herewith by electronic submission and is incorporated by reference herein.

FIELD OF THE INVENTION

The invention relates to the field of plant molecular biology and plant genetic engineering, and DNA molecules useful for modulating gene expression in plants.

BACKGROUND

Regulatory elements are genetic elements that regulate gene activity by modulating the transcription of an operably linked transcribable polynucleotide molecule. Such elements include promoters, leaders, introns, and 3' untranslated regions and are useful in the field of plant molecular biology and plant genetic engineering.

SUMMARY OF THE INVENTION

The present invention provides novel gene regulatory elements for use in plants. The present invention also provides DNA constructs comprising the regulatory elements. The present invention also provides transgenic plant cells, plants, and seeds comprising the regulatory elements. The sequences may be provided operably linked to a transcribable polynucleotide molecule. In one embodiment, the transcribable polynucleotide molecule may be heterologous with respect to a regulatory sequence provided herein. A regulatory element sequence provided by the invention thus may, in particular embodiments, be defined as operably linked to a heterologous transcribable polynucleotide molecule. The present invention also provides methods of making and using the regulatory elements, the DNA constructs comprising the regulatory elements, and the transgenic plant cells, plants, and seeds comprising the regulatory elements operably linked to a transcribable polynucleotide molecule.

Thus, in one aspect, the present invention provides a DNA molecule comprising a DNA sequence selected from the group consisting of: a) a sequence with at least about 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the DNA molecule comprises at least about 90 percent, at least about 95 percent, at least about 98 percent, or at least about 99 percent sequence identity to the DNA sequence of any of SEQ ID NOs: 1-158 and 180-183.

In certain embodiments of the DNA molecule, the DNA sequence comprises a regulatory element. In some embodiments the regulatory element comprises a promoter. In particular embodiments, the heterologous transcribable polynucleotide molecule comprises a gene of agronomic interest, such as a gene capable of providing herbicide resistance in plants, or a gene capable of providing plant pest resistance in plants.

The invention also provides a transgenic plant cell comprising a heterologous DNA construct provided by the invention, including a sequence of any of SEQ ID NOs: 1-158 and 180-183, or a fragment or variant thereof, wherein said sequence is operably linked to a heterologous transcribable polynucleotide molecule. In certain embodiments, the transgenic plant cell is a monocotyledonous plant cell. In other embodiments, the transgenic plant cell is a dicotyledonous plant cell.

Further provided by the invention is a transgenic plant, or part thereof, comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule. In specific embodiments, the transgenic plant may be a progeny plant of any generation that comprises the DNA molecule, relative to a starting transgenic plant comprising the DNA molecule. Still further provided is a transgenic seed comprising a DNA molecule according to the invention.

In yet another aspect, the invention provides a method of producing a commodity product comprising obtaining a transgenic plant or part thereof according to the invention and producing the commodity product therefrom. In one embodiment, a commodity product of the invention is protein concentrate, protein isolate, grain, starch, seeds, meal, flour, biomass, or seed oil. In another aspect, the invention provides a commodity produced using the above method. For instance, in one embodiment the invention provides a commodity product comprising a DNA molecule as provided herein, including a DNA sequence selected from the group consisting of: a) a sequence with at least 85 percent sequence identity to any of SEQ ID NOs: 1-158 and 180-183; b) a sequence comprising any of SEQ ID NOs: 1-158 and 180-183; and c) a fragment of any of SEQ ID NOs: 1-158 and 180-183, wherein the fragment has gene-regulatory activity; wherein the sequence is operably linked to a heterologous transcribable polynucleotide molecule.

In still yet another aspect, the invention provides a method of expressing a transcribable polynucleotide molecule that comprises obtaining a transgenic plant according to the invention, such as a plant comprising a DNA molecule as described herein, and cultivating plant, wherein a transcribable polynucleotide in the DNA molecule is expressed.

Throughout this specification and the claims, unless the context requires otherwise, the word "comprise" and its variations, such as "comprises" and "comprising," will be understood to imply the inclusion of a stated composition, step, and/or value, or group thereof, but not the exclusion of any other composition, step, and/or value, or group thereof.

BRIEF DESCRIPTION OF THE FIGURES

FIGS. 1a-1h depict alignment of promoter size variants corresponding to promoter elements isolated from the grass species *Andropogon gerardii*. In particular, FIGS. 1a-1h show alignment of the 2603 bp promoter sequence P-ANDge.Ubq1-1:1:11 (SEQ ID NO: 2), found in the transcriptional regulatory expression element group EXP-ANDge.Ubq1:1:9 (SEQ ID NO: 1), with promoter sequences derived via deletion analysis of P-ANDge.Ubq1-1:1:11. Deletion, for instance of the 5' end of P-ANDge.Ubq1-1:1:11, produced the promoter P-ANDge.Ubq1-1:1:9 (SEQ ID NO: 6), a 2114 bp sequence which is found within EXP-ANDge.Ubq1:1:7 (SEQ ID NO: 5). Other promoter sequences in FIG. 1 include P-ANDge.Ubq1-1:1:10 (SEQ ID NO: 9), a 1644 bp sequence comprised within EXP-ANDge.Ubq1:1:8 (SEQ ID NO: 8); P-ANDge.Ubq1-1:1:12 (SEQ ID NO: 11), a 1472 bp sequence comprised within EXP-ANDge.Ubq1:1:10 (SEQ ID NO: 10); P-ANDge.Ubq1-1:1:8 (SEQ ID NO: 13), a 1114 bp sequence comprised within EXP-ANDge.Ubq1:1:6 (SEQ ID NO: 12); P-ANDge.Ubq1-1:1:13 (SEQ ID NO: 15), a 771 bp sequence comprised within EXP-ANDge.Ubq1:1:11 (SEQ ID NO: 14); and P-ANDge.Ubq1-1:1:14 (SEQ ID NO: 17), a 482 bp sequence comprised within EXP-ANDge.Ubq1:1:12 (SEQ ID NO: 16).

FIGS. 2a-2g depict alignment of promoter variants isolated from the grass *Saccharum ravennae* (*Erianthus ravennae*). In particular, FIGS. 2a-2g show an alignment of the 2536 bp promoter sequence P-ERIra.Ubq1-1:1:10 (SEQ ID NO: 19) (found, for instance, within the transcriptional regulatory expression element group EXP-ERIra.Ubq1 (SEQ ID NO: 18)) with promoter sequences derived from deletion analysis of P-ERIra.Ubq1-1:1:10: a 2014 bp promoter sequence P-ERIra.Ubq1-1:1:9 (SEQ ID NO: 23); a 1525 bp promoter sequence P-ERIra.Ubq1-1:1:11 (SEQ ID NO: 26); a 1044 bp promoter sequence P-ERIra.Ubq1-1:1:8 (SEQ ID NO: 28); a 796 bp sequence P-ERIra.Ubq1-1:1:12 (SEQ ID NO: 30); and a 511 bp sequence P-ERIra.Ubq1-1:1:13 (SEQ ID NO: 32).

FIGS. 3a-3c depict alignment of promoter size variants corresponding to promoter elements isolated from the grass species *Setaria viridis*. In particular, FIGS. 3a-3c show an alignment of a 1493 bp promoter sequence, P-Sv.Ubq1-1:1:1 (SEQ ID NO: 34) with promoters derived from deletion analysis of the 5' end of P-Sv.Ubq1-1:1:1: a 1035 bp sized promoter P-Sv.Ubq1-1:1:2 (SEQ ID NO: 38); and a 681 bp promoter sequence P-Sv.Ubq1-1:1:3 (SEQ ID NO: 40).

FIGS. 4a-4e depict alignment of transcriptional regulatory expression element group variants derived from the grass *Zea mays* subsp. *mexicana*. In particular, FIGS. 4a-4e compare a 2005 bp transcriptional regulatory expression element group termed EXP-Zm.UbqM1:1:2 (SEQ ID NO: 49) with allelic variant EXP-Zm.UbqM1:1:5 (SEQ ID NO: 53), as well as with size variants EXP-Zm.UbqM1:1:1 (SEQ ID NO: 41), which is 1922 bps in length, and EXP-Zm.UbqM1:1:4 (SEQ ID NO: 45), which is 1971 bps in length.

FIGS. 5a-5b depict alignment of promoter size variants isolated from the grass *Sorghum bicolor*. In particular, FIGS. 5a-5b shows alignment of the 791 bp sized promoter element, P-Sb.Ubq6-1:1:2 (SEQ ID NO: 60) comprised within the transcriptional regulatory expression element group EXP-Sb.Ubq6 (SEQ ID NO: 59), with 855 bp promoter element P-Sb.Ubq6-1:1:1 (SEQ ID NO: 64) comprised within EXP-Sb.Ubq6:1:1 (SEQ ID NO: 63).

FIGS. 6a-6c depict alignment of promoter size variants corresponding to promoter elements isolated from the grass *Setaria italica*. In particular, FIGS. 6a-6c show an alignment of the 1492 bp promoter variant P-SETit.Ubq1-1:1:1 (SEQ ID NO: 70) with 1492 bp promoter variant P-SETit.Ubq1-1:1:4 (SEQ ID NO: 74), 1034 bp promoter element P-SETit.Ubq1-1:1:2 (SEQ ID NO: 76), and 680 bp promoter element P-SETit.Ubq1-1:1:3 (SEQ ID NO: 78).

FIGS. 7a-7b depict alignment of promoter size variants and an enhancer element corresponding to promoter elements isolated from the grass species *Coix lachryma-jobi*. In particular, FIGS. 7a and 7b show an alignment of the 837 bp promoter variant, P-Cl.Ubq1-1:1:1 (SEQ ID NO: 80) found within transcriptional regulatory expression element group EXP-Cl.Ubq1:1:1 (SEQ ID NO: 79), with an enhancer fragment derived from P-Cl.Ubq1-1:1:1, termed E-Cl.Ubq1:1:1 (SEQ ID NO: 89) that is 798 bp in length, as well as with three 5' end deletion variants of P-Cl.Ubq1-1:1:1: a 742 bp element P-Cl.Ubq1-1:1:4 (SEQ ID NO: 84); a 401 bp element P-Cl.Ubq1-1:1:3 (SEQ ID NO: 86); and a 54 bp minimal promoter element P-Cl.Ubq1-1:1:5 (SEQ ID NO: 88).

FIG. 8 depicts transgene cassette configurations of the present invention.

BRIEF DESCRIPTION OF THE SEQUENCES

SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183 are sequences of transcriptional regulatory expression element groups or EXP sequences comprising a promoter sequence operably linked 5' to a leader sequence which is operably linked 5' to an intron sequence.

SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 are promoter sequences.

SEQ ID NOS: 3, 20, 35, 43, 47, 51, 57, 61, 67, 71 and 81 are leader sequences.

SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are intron sequences.

SEQ ID NO: 89 is the sequence of an enhancer.

DETAILED DESCRIPTION OF THE INVENTION

The invention disclosed herein provides polynucleotide molecules having beneficial gene regulatory activity from plant species. The design, construction, and use of these polynucleotide molecules are provided by the invention. The nucleotide sequences of these polynucleotide molecules are provided among SEQ ID NOs: 1-158 and 180-183. These polynucleotide molecules are, for instance, capable of affecting the expression of an operably linked transcribable polynucleotide molecule in plant tissues, and therefore selectively regulating gene expression, or activity of an encoded gene product, in transgenic plants. The present invention also provides methods of modifying, producing, and using the same. The invention also provides compositions, transformed host cells, transgenic plants, and seeds containing the promoters and/or other disclosed nucleotide sequences, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e. a polymer of deoxyribonucleotide bases or a polynucleotide molecule, read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations §1.822, and set forth in the tables in WIPO Standard ST.25 (1998), Appendix 2, Tables 1 and 3.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

Any number of methods well known to those skilled in the art can be used to isolate and manipulate a DNA molecule, or fragment thereof, disclosed in the present invention. For example, PCR (polymerase chain reaction) technology can be used to amplify a particular starting DNA molecule and/or to produce variants of the original molecule. DNA molecules, or fragment thereof, can also be obtained by other techniques such as by directly synthesizing the fragment by chemical means, as is commonly practiced by using an automated oligonucleotide synthesizer.

As used herein, the term "sequence identity" refers to the extent to which two optimally aligned polynucleotide sequences or two optimally aligned polypeptide sequences are identical. An optimal sequence alignment is created by manually aligning two sequences, e.g. a reference sequence and another sequence, to maximize the number of nucleotide matches in the sequence alignment with appropriate internal nucleotide insertions, deletions, or gaps. As used herein, the term "reference sequence" refers to a sequence provided as the polynucleotide sequences of SEQ ID NOs: 1-158 and 180-183.

As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence. Thus, one embodiment of the invention is a DNA molecule comprising a sequence that when optimally aligned to a reference sequence, provided herein as SEQ ID NOs: 1-158 and 180-183, has at least about 85 percent identity, at least about 90 percent identity, at least about 95 percent identity, at least about 96 percent identity, at least about 97 percent identity, at least about 98 percent identity, or at least about 99 percent identity to the reference sequence. In particular embodiments such sequences may be defined as having gene-regulatory activity.

Regulatory Elements

A regulatory element is a DNA molecule having gene regulatory activity, i.e. one that has the ability to affect the transcription and/or translation of an operably linked transcribable polynucleotide molecule. The term "gene regulatory activity" thus refers to the ability to affect the expression pattern of an operably linked transcribable polynucleotide molecule by affecting the transcription and/or translation of that operably linked transcribable polynucleotide molecule. As used herein, a transcriptional regulatory expression element group or "EXP" sequence may be comprised of expression elements, such as enhancers, promoters, leaders and introns, operably linked. Thus a transcriptional regulatory expression element group may be comprised, for instance, of a promoter operably linked 5' to a leader sequence, which is in turn operably linked 5' to an intron sequence. The intron sequence may be comprised of a sequence beginning at the point of the first intron/exon splice junction of the native sequence and further may be comprised of a small leader fragment comprising the second intron/exon splice junction so as to provide for proper intron/exon processing to facilitate transcription and proper processing of the resulting transcript. Leaders and introns may positively affect transcription of an operably linked transcribable polynucleotide molecule as well as translation of the resulting transcribed RNA. The pre-processed RNA molecule comprises leaders and introns, which may affect the post-transcriptional processing of the transcribed RNA and/or the export of the transcribed RNA molecule from the cell nucleus into the cytoplasm. Following post-transcriptional processing of the transcribed RNA molecule, the leader sequence may be retained as part of the final messenger RNA and may positively affect the translation of the messenger RNA molecule.

Regulatory elements such as promoters, leaders, introns, and transcription termination regions (or 3' UTRs) are DNA molecules that have gene regulatory activity and play an integral part in the overall expression of genes in living cells. The term "regulatory element" refers to a DNA molecule having gene regulatory activity, i.e. one that has the ability to affect the transcription and/or translation of an operably linked transcribable polynucleotide molecule. Isolated regulatory elements, such as promoters and leaders that function in plants are therefore useful for modifying plant phenotypes through the methods of genetic engineering.

Regulatory elements may be characterized by their expression pattern effects (qualitatively and/or quantitatively), e.g. positive or negative effects and/or constitutive or other effects such as by their temporal, spatial, developmental, tissue, environmental, physiological, pathological, cell cycle, and/or chemically responsive expression pattern, and any combination thereof, as well as by quantitative or qualitative indications. A promoter is useful as a regulatory element for modulating the expression of an operably linked transcribable polynucleotide molecule.

As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a dsRNA, a tRNA, an rRNA, a miRNA, and the like.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a DNA molecule that is involved in recognition and binding of RNA polymerase II and other proteins (trans-acting transcription factors) to initiate transcription. A promoter may be initially isolated from the 5' untranslated region (5' UTR) of a genomic copy of a gene. Alternately, promoters may be synthetically produced or manipulated DNA molecules. Promoters may also be chimeric, that is a promoter produced through the fusion of two or more heterologous DNA molecules. Promoters useful in practicing the present invention include SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, or fragments or variants thereof. In specific embodiments of the invention, such molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent sequence for recognition and binding of the RNA polymerase II complex for initiation of transcription.

In one embodiment, fragments are provided of a promoter sequence disclosed herein. Promoter fragments may comprise promoter activity, as described above, and may be useful alone or in combination with other promoters and promoter fragments, such as in constructing chimeric promoters. In specific embodiments, fragments of a promoter are provided comprising at least about 50, 95, 150, 250, 500, 750, or at least about 1000 contiguous nucleotides, or longer, of a polynucleotide molecule having promoter activity disclosed herein.

Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135, such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue or cell specific effects on expression. Compositions derived from any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 comprised of 3' deletions in which the TATA box element or equivalent sequence thereof and downstream sequence is removed can be used, for example, to make enhancer elements. Further deletions can be made to remove any elements that have positive or negative; tissue specific; cell specific; or timing specific (such as, but not limited to, circadian rhythms) effects on expression. Any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and fragments or enhancers derived there from can be used to make chimeric transcriptional regulatory element compositions comprised of any of the promoters presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135 and the fragments or enhancers derived therefrom operably linked to other enhancers and promoters. The efficacy of the modifications, duplications or deletions described herein on the desired expression aspects of a particular transgene may be tested empirically in stable and transient plant assays, such as those described in the working examples herein, so as to validate the results, which may vary depending upon the changes made and the goal of the change in the starting molecule.

As used herein, the term "leader" refers to a DNA molecule isolated from the untranslated 5' region (5' UTR) of a genomic copy of a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable polynucleotide molecule. Leader molecules may be used with a heterologous promoter or with their native promoter. Promoter molecules of the present invention may thus be operably linked to their native leader or may be operably linked to a heterologous leader. Leaders useful in practicing the present invention include SEQ ID NOS: 3, 20, 35, 43, 47, 51, 57, 61, 67, 71 and 81 or fragments or variants thereof. In specific embodiments, such sequences may be provided defined as being capable of acting as a leader in a host cell, including, for example, a transgenic plant cell. In one embodiment such sequences are decoded as comprising leader activity.

The leader sequences (5' UTR) presented as SEQ ID NOS: 3, 20, 35, 43, 47, 51, 57, 61, 67, 71 and 81 may be comprised of regulatory elements or may adopt secondary structures that can have an effect on transcription or translation of a transgene. The leader sequences presented as SEQ ID NOS: 3, 20, 35, 43, 47, 51, 57, 61, 67, 71 and 81 can be used in accordance with the invention to make chimeric regulatory elements that affect transcription or translation of a transgene. In addition, the leader sequences presented as SEQ ID NOS: 3, 20, 35, 43, 47, 51, 57, 61, 67, 71 and 81 can be used to make chimeric leader sequences that affect transcription or translation of a transgene.

The introduction of a foreign gene into a new plant host does not always result in a high expression of the incoming gene. Furthermore, if dealing with complex traits, it is sometimes necessary to modulate several genes with spatially or temporarily different expression pattern. Introns can principally provide such modulation. However multiple use of the same intron in one plant has shown to exhibit disadvantages. In those cases it is necessary to have a collection of basic control elements for the construction of appropriate recombinant DNA elements. As the available collection of introns known in the art with expression enhancing properties is limited, alternatives are needed.

Compositions derived from any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be comprised of internal deletions or duplications of cis regulatory elements; and/or alterations of the 5' and 3' sequences comprising the intron/exon splice junctions can be used to improve expression or specificity of expression when operably linked to a promoter+leader or chimeric promoter+leader and coding sequence. Alterations of the 5' and 3' regions comprising the intron/exon splice junction can also be made to reduce the potential for introduction of false start and stop codons being produced in the resulting transcript after processing and splicing of the messenger RNA. The introns can be tested empirically as described in the working examples to determine the intron's effect on expression of a transgene.

In accordance with the invention a promoter or promoter fragment may be analyzed for the presence of known promoter elements, i.e. DNA sequence characteristics, such as a TATA-box and other known transcription factor binding site motifs. Identification of such known promoter elements may be used by one of skill in the art to design variants of the promoter having a similar expression pattern to the original promoter.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box or equivalent sequence. A promoter may naturally comprise one or more enhancer elements that affect the transcription of an operably linked polynucleotide sequence. An isolated enhancer element may also be fused to a promoter to produce a chimeric promoter cis-element, which confers an aspect of the overall modulation of gene expression. A promoter or promoter fragment may comprise one or more enhancer elements that effect the transcription of operably linked genes. Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e. deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed by the present invention.

In plants, the inclusion of some introns in gene constructs leads to increased mRNA and protein accumulation relative to constructs lacking the intron.

This effect has been termed "intron mediated enhancement" (IME) of gene expression (Mascarenhas et al., (1990) *Plant Mol. Biol.* 15:913-920). Introns known to stimulate expression in plants have been identified in maize genes (e.g. tubA1, Adh1, Sh1, Ubi1 (Jeon et al. (2000) *Plant Physiol.* 123:1005-1014; Callis et al. (1987) *Genes Dev.* 1:1183-1200; Vasil et al. (1989) *Plant Physiol.* 91:1575-1579; Christiansen et al. (1992) *Plant Mol. Biol.* 18:675-689) and in rice genes (e.g. salt, tpi: McElroy et al., *Plant Cell* 2:163-171 (1990); Xu et al., *Plant Physiol.* 106:459-467 (1994)). Similarly, introns from dicotyledonous plant genes like those from petunia (e.g. rbcS), potato (e.g. st-ls1) and from *Arabidopsis thaliana* (e.g. ubq3 and pat1) have been found to elevate gene expression rates (Dean et al. (1989) *Plant Cell* 1:201-208; Leon et al. (1991) *Plant Physiol.* 95:968-972; Norris et al. (1993) *Plant Mol Biol* 21:895-906; Rose and Last (1997) *Plant J.* 11:455-464). It has been shown that deletions or mutations within the splice sites of an intron reduce gene expression, indicating that splicing might be needed for IME (Mascarenhas et al. (1990) *Plant Mol Biol.* 15:913-920; Clancy and Hannah (2002) *Plant Physiol.* 130:918-929). However, that splicing per se is not required for a certain IME in dicotyledonous plants has been shown by point mutations within the splice sites of the pat1 gene from *A. thaliana* (Rose and Beliakoff (2000) *Plant Physiol.* 122:535-542).

Enhancement of gene expression by introns is not a general phenomenon because some intron insertions into recombinant expression cassettes fail to enhance expression (e.g. introns from dicot genes (rbcS gene from pea, phaseolin gene from bean and the stls-1 gene from *Solanum tuberosum*) and introns from maize genes (adh1 gene the ninth intron, hsp81 gene the first intron)) (Chee et al. (1986) *Gene* 41:47-57; Kuhlemeier et al. (1988) *Mol Gen Genet* 212:405-411; Mascarenhas et al. (1990) *Plant Mol. Biol.* 15:913-920; Sinibaldi and Mettler (1992) In W E Cohn, K Moldave, eds, Progress in *Nucleic Acid Research and Molecular Biology*, Vol 42. Academic Press, New York, pp 229-257; Vancanneyt et al. 1990 *Mol. Gen. Genet.* 220:245-250). Therefore, not each intron can be employed in order to manipulate the gene expression level of non-endogenous genes or endogenous genes in transgenic plants. What characteristics or specific sequence features must be present in an intron sequence in order to enhance the expression rate of a given gene is not known in the prior art and therefore from the prior art it is not possible to predict whether a given plant intron, when used heterologously, will cause enhancement of expression at the DNA level or at the transcript level (IME).

As used herein, the term "chimeric" refers to a single DNA molecule produced by fusing a first DNA molecule to a second DNA molecule, where neither first nor second DNA molecule would normally be found in that configuration, i.e. fused to the other. The chimeric DNA molecule is thus a new DNA molecule not otherwise normally found in nature. As used herein, the term "chimeric promoter" refers to a promoter produced through such manipulation of DNA molecules. A chimeric promoter may combine two or more DNA fragments; an example would be the fusion of a promoter to an enhancer element. Thus, the design, construction, and use of chimeric promoters according to the methods disclosed herein for modulating the expression of operably linked transcribable polynucleotide molecules are encompassed by the present invention.

As used herein, the term "variant" refers to a second DNA molecule that is in composition similar, but not identical to, a first DNA molecule and yet the second DNA molecule still maintains the general functionality, i.e. same or similar expression pattern, of the first DNA molecule. A variant may be a shorter or truncated version of the first DNA molecule and/or an altered version of the sequence of the first DNA molecule, such as one with different restriction enzyme sites and/or internal deletions, substitutions, and/or insertions. A "variant" can also encompass a regulatory element having a nucleotide sequence comprising a substitution, deletion and/or insertion of one or more nucleotides of a reference sequence, wherein the derivative regulatory element has more or less or equivalent transcriptional or translational activity than the corresponding parent regulatory molecule.

The regulatory element "variants" will also encompass variants arising from mutations that naturally occur in bacterial and plant cell transformation. In the present invention, a polynucleotide sequence provided as SEQ ID NOs: 1-158 and 180-183 may be used to create variants that are in composition similar, but not identical to, the polynucleotide sequence of the original regulatory element, while still maintaining the general functionality, i.e. same or similar expression pattern, of the original regulatory element. Production of such variants of the present invention is well within the ordinary skill of the art in light of the disclosure and is encompassed within the scope of the present invention. Chimeric regulatory element "variants" comprise the same constituent elements as a reference sequence but the constituent elements comprising the chimeric regulatory element may be operatively linked by various methods known in the art such as, restriction enzyme digestion and ligation, ligation independent cloning, modular assembly of PCR products during amplification, or direct chemical synthesis of the regulatory element as well as other methods known in the art. The resulting chimeric regulatory element "variant" can be comprised of the same, or variants of the same, constituent elements of the reference sequence but differ in the sequence or sequences that comprise the linking sequence or sequences which allow the constituent parts to be operatively linked. In the present invention, a polynucleotide sequence provided as SEQ ID NOs: 1-158 and 180-183 provide a reference sequence wherein the constituent elements that comprise the reference sequence may be joined by methods known in the art and may comprise substitutions, deletions and/or insertions of one or more nucleotides or mutations that naturally occur in bacterial and plant cell transformation.

Constructs

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" means any recombinant polynucleotide construct that may be used for the purpose of transformation, i.e. the introduction of heterologous DNA into a host cell. The term includes an expression cassette isolated from any of the aforementioned molecules.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

The constructs of the present invention may be provided, in one embodiment, as double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *A. tumefaciens* cells, permit the integration of the T-DNA into the genome of a plant cell (see, for example, U.S. Pat. No. 6,603,061). The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404; however, other strains known to those skilled in the art of plant transformation can function in the present invention.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see, for example, *Molecular Cloning: A Laboratory Manual*, 3$^{rd}$ edition Volumes 1, 2, and 3 (2000) J. Sambrook, D. W. Russell, and N. Irwin, Cold Spring Harbor Laboratory Press. Methods for making recombinant vectors particularly suited to plant transformation include, without limitation, those described in U.S. Pat. Nos. 4,971,908; 4,940,835; 4,769,061; and 4,757,011 in their entirety. These types of vectors have also been reviewed in the scientific literature (see, for example, Rodriguez, et al., *Vectors: A Survey of Molecular Cloning Vectors and Their Uses*, Butterworths, Boston, (1988) and Glick, et al., *Methods in Plant Molecular Biology and Biotechnology*, CRC Press, Boca Raton, Fla. (1993)). Typical vectors useful for expression of nucleic acids in higher plants are well known in the art and include vectors derived from the tumor-inducing (Ti) plasmid of *Agrobacterium tumefaciens* (Rogers, et al., *Methods in Enzymology* 153: 253-277 (1987)). Other recombinant vectors useful for plant transformation, including the pCaMVCN transfer control vector, have also been described in the scientific literature (see, for example, Fromm, et al., *Proc. Natl. Acad. Sci. USA* 82: 5824-5828 (1985)).

Various regulatory elements may be included in a construct including any of those provided herein. Any such regulatory elements may be provided in combination with other regulatory elements. Such combinations can be designed or modified to produce desirable regulatory features. In one embodiment, constructs of the present invention comprise at least one regulatory element operably linked to a transcribable polynucleotide molecule operably linked to a 3' UTR.

Constructs of the present invention may include any promoter or leader provided herein or known in the art. For example, a promoter of the present invention may be operably linked to a heterologous non-translated 5' leader such as one derived from a heat shock protein gene (see, for example, U.S. Pat. Nos. 5,659,122 and 5,362,865). Alternatively, a leader of the present invention may be operably linked to a heterologous promoter such as the Cauliflower Mosaic Virus 35S transcript promoter (see, U.S. Pat. No. 5,352,605).

As used herein, the term "intron" refers to a DNA molecule that may be isolated or identified from the genomic copy of a gene and may be defined generally as a region spliced out during mRNA processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable polynucleotide molecule. A DNA construct may comprise an intron, and the intron may or may not be heterologous with respect to the transcribable polynucleotide molecule sequence. Examples of introns in the art include the rice actin intron (U.S. Pat. No. 5,641,876) and the corn HSP70 intron (U.S. Pat. No. 5,859,347). Introns useful in practicing the present invention include SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182. Further, when modifying intron/exon boundary sequences, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified in this manner.

As used herein, the term "3' transcription termination molecule" or "3' UTR" refers to a DNA molecule that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et al., *Proc. Natl. Acad. Sci. USA*, 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806).

3' UTRs typically find beneficial use for the recombinant expression of specific genes. In animal systems, a machinery of 3' UTRs has been well defined (e.g. Zhao et al., *Microbiol Mol Biol Rev* 63:405-445 (1999); Proudfoot, *Nature* 322: 562-565 (1986); Kim et al., *Biotechnology Progress* 19:1620-1622 (2003); Yonaha and Proudfoot, *EMBO J.* 19:3770-3777 (2000); Cramer et al., *FEBS Letters* 498:179-182 (2001); Kuerstem and Goodwin, *Nature Reviews Genetics* 4:626-637 (2003)). Effective termination of RNA transcription is required to prevent unwanted transcription of trait-unrelated (downstream) sequences, which may interfere with trait performance. Arrangement of multiple gene expression cassettes in local proximity to one another (e.g. within one T-DNA) may cause suppression of gene expression of one or more genes in said construct in comparison to independent insertions (Padidam and Cao, *BioTechniques* 31:328-334 (2001). This may interfere with achieving adequate levels of expression, for instance in cases were strong gene expression from all cassettes is desired.

In plants, clearly defined polyadenylation signal sequences are not known. Hasegawa et al., *Plant J.* 33:1063-1072, (2003)) were not able to identify conserved polyadenylation signal sequences in both in vitro and in vivo systems in *Nicotiana sylvestris* and to determine the actual length of the primary (non-polyadenylated) transcript. A weak 3' UTR has the potential to generate read-through, which may affect the expression of the genes located in the neighboring expression cassettes (Padidam and Cao, *BioTechniques* 31:328-334 (2001)). Appropriate control of transcription termination can prevent read-through into sequences (e.g. other expression cassettes) localized downstream and can further allow efficient recycling of RNA polymerase, to improve gene expression. Efficient termination of transcription (release of RNA Polymerase II from the DNA) is pre-requisite for re-initiation of transcription and thereby directly affects the overall transcript level. Subsequent to transcription termination, the mature mRNA is released from the site of synthesis and template to the cytoplasm. Eukaryotic mRNAs are accumulated as poly(A) forms in vivo, so that it is difficult to detect transcriptional termination sites by conventional methods. However, prediction of functional and efficient 3' UTRs by bioinformatics methods is difficult in that there are no conserved sequences which would allow easy prediction of an effective 3' UTR.

From a practical standpoint, it is typically beneficial that a 3' UTR used in a transgene cassette possesses the following characteristics. The 3' UTR should be able to efficiently and effectively terminate transcription of the transgene and prevent read-through of the transcript into any neighboring DNA sequence which can be comprised of another transgene cassette as in the case of multiple cassettes residing in one T-DNA, or the neighboring chromosomal DNA into which the T-DNA has inserted. The 3' UTR should not cause a reduction in the transcriptional activity imparted by the promoter, leader and introns that are used to drive expression of the transgene. In plant biotechnology, the 3' UTR is often used for priming of amplification reactions of reverse transcribed RNA extracted from the transformed plant and used to (1) assess the transcriptional activity or expression of the transgene cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette.

3' UTRs useful in providing expression of a transgene in plants may be identified based upon the expression of expressed sequence tags (ESTs) in cDNA libraries made from messenger RNA isolated from seed, flower and other tissues derived from Big bluestem (*Andropogon gerardii*), Plume grass (*Saccharum ravennae* (*Erianthus ravennae*)), Green bristlegrass (*Setaria viridis*), Teosinte (*Zea mays* subsp. *mexicana*), Foxtail millet (*Setaria italica*), or Coix (*Coix lacryma-jobi*). Libraries of cDNA are made from tissues isolated from selected plant species using methods known to those skilled in the art from flower tissue, seed, leaf and root. The resulting cDNAs are sequenced using various sequencing methods known in the art. The resulting ESTs are assembled into clusters using bioinformatics software such as cic_ref$_{13}$ assemble_complete version 2.01.37139 (CLC bio USA, Cambridge, Mass. 02142). Transcript abundance of each cluster is determined by counting the number of cDNA reads for each cluster. The identified 3' UTRs may be comprised of sequence derived from cDNA sequence as well as sequence derived from genomic DNA. The cDNA sequence is used to design primers, which are then used with GenomeWalker™ (Clontech Laboratories, Inc, Mountain View, Calif.) libraries constructed following the manufacturer's protocol to clone the 3' region of the corresponding genomic DNA sequence to provide a longer termination sequence. Analysis of relative transcript abundance either by direct counts or normalized counts of observed sequence reads for each tissue library can be used to infer properties about patters of expression. For example, some 3' UTRs may be found in transcripts seen in higher abundance in root tissue as opposed to leaf. This is suggestive that the transcript is highly expressed in root and that the properties of root expression may be attributable to the transcriptional regulation of the promoter, the lead, the introns or the 3' UTR. Empirical testing of 3' UTRs identified by the properties of expression within specific organs, tissues or cell types can result in the identification of 3' UTRs that enhance expression in those specific organs, tissues or cell types.

Constructs and vectors may also include a transit peptide coding sequence that expresses a linked peptide that is useful for targeting of a protein product, particularly to a chloroplast, leucoplast, or other plastid organelle; mitochondria; peroxisome; vacuole; or an extracellular location. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (See, Klee et al., *Mol. Gen. Genet.* 210:437-442 (1987)) or the *Petunia hybrida* EPSPS CTP (CTP4) (See, della-Cioppa et al., *Proc. Nall. Acad. Sci. USA* 83:6873-6877 (1986)) has been show to target heterologous EPSPS protein sequences to chloroplasts in transgenic plants (See, U.S. Pat. Nos. 5,627,061; 5,633,435; and 5,312,910 and EP 0218571; EP 189707; EP 508909; and EP 924299).

Transcribable Polynucleotide Molecules

As used herein, the term "transcribable polynucleotide molecule" refers to any DNA molecule capable of being transcribed into a RNA molecule, including, but not limited to, those having protein coding sequences and those producing RNA molecules having sequences useful for gene suppression. A "transgene" refers to a transcribable polynucleotide molecule heterologous to a host cell at least with respect to its location in the genome and/or a transcribable polynucleotide molecule artificially incorporated into a host cell's genome in the current or any prior generation of the cell.

A promoter of the present invention may be operably linked to a transcribable polynucleotide molecule that is heterologous with respect to the promoter molecule. As used herein, the term "heterologous" refers to the combination of two or more polynucleotide molecules when such a combination is not normally found in nature. For example, the two molecules may be derived from different species and/or the two molecules may be derived from different genes, e.g. different genes from the same species or the same genes from different species. A promoter is thus heterologous with respect to an operably linked transcribable polynucleotide molecule if such a combination is not normally found in nature, i.e. that transcribable polynucleotide molecule is not naturally occurring operably linked in combination with that promoter molecule.

The transcribable polynucleotide molecule may generally be any DNA molecule for which expression of a RNA transcript is desired. Such expression of an RNA transcript may result in translation of the resulting mRNA molecule and thus protein expression. Alternatively, for example, a transcribable polynucleotide molecule may be designed to ultimately cause decreased expression of a specific gene or protein. In one embodiment, this may be accomplished by using a transcribable polynucleotide molecule that is oriented in the antisense direction. One of ordinary skill in the art is familiar with using such antisense technology. Briefly, as the antisense transcribable polynucleotide molecule is transcribed, the RNA product hybridizes to and sequesters a complimentary RNA molecule inside the cell. This duplex RNA molecule cannot be translated into a protein by the cell's translational machinery and is degraded in the cell. Any gene may be negatively regulated in this manner.

Thus, one embodiment of the invention is a regulatory element of the present invention, such as those provided as SEQ ID NOs: 1-158 and 180-183, operably linked to a transcribable polynucleotide molecule so as to modulate transcription of the transcribable polynucleotide molecule at a desired level or in a desired pattern when the construct is integrated in the genome of a plant cell. In one embodiment, the transcribable polynucleotide molecule comprises a protein-coding region of a gene, and the promoter affects the transcription of an RNA molecule that is translated and expressed as a protein product. In another embodiment, the transcribable polynucleotide molecule comprises an antisense region of a gene, and the promoter affects the transcription of an antisense RNA molecule, double stranded RNA or other similar inhibitory RNA molecule in order to inhibit expression of a specific RNA molecule of interest in a target host cell.

Genes of Agronomic Interest

Transcribable polynucleotide molecules may be genes of agronomic interest. As used herein, the term "gene of agronomic interest" refers to a transcribable polynucleotide molecule that when expressed in a particular plant tissue, cell, or cell type confers a desirable characteristic, such as associated with plant morphology, physiology, growth, development, yield, product, nutritional profile, disease or pest resistance, and/or environmental or chemical tolerance. Genes of agronomic interest include, but are not limited to, those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, a pesticidal protein, or any other agent such as an antisense or RNAi molecule targeting a particular gene for suppression. The product of a gene of agronomic interest may act within the plant in order to cause an effect upon the plant physiology or metabolism or may be act as a pesticidal agent in the diet of a pest that feeds on the plant.

In one embodiment of the invention, a promoter of the present invention is incorporated into a construct such that the promoter is operably linked to a transcribable polynucleotide molecule that is a gene of agronomic interest. The expression of the gene of agronomic interest is desirable in order to confer an agronomically beneficial trait. A beneficial agronomic trait may be, for example, but is not limited to, herbicide tolerance, insect control, modified yield, fungal disease resistance, virus resistance, nematode resistance, bacterial disease resistance, plant growth and development, starch production, modified oils production, high oil production, modified fatty acid content, high protein production, fruit ripening, enhanced animal and human nutrition, biopolymers, environmental stress resistance, pharmaceutical peptides and secretable peptides, improved processing traits, improved digestibility, enzyme production, flavor, nitrogen fixation, hybrid seed production, fiber production, and biofuel production. Examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463,175), increased yield (U.S. Pat. Nos. RE38,446; 6,716,474; 6,663,906; 6,476,295; 6,441,277; 6,423,828; 6,399,330; 6,372,211; 6,235,971; 6,222,098; and 5,716, 837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426, 447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. RE37,543; 6,228, 623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristic or phenotype by encoding a RNA molecule that causes the targeted modulation of gene expression of an endogenous gene, for example via antisense (see e.g. U.S. Pat. No. 5,107,065); inhibitory RNA ("RNAi", including modulation of gene expression via miRNA-, siRNA-, trans-acting siRNA-, and phased sRNA-mediated mechanisms, e.g. as described in published applications US 2006/0200878 and US 2008/0066206, and in U.S. patent application Ser. No. 11/974,469); or cosuppression-mediated mechanisms. The RNA could also be a catalytic RNA molecule (e.g. a ribozyme or a riboswitch; see e.g. US 2006/0200878) engineered to cleave a desired endogenous mRNA product. Thus, any transcribable polynucleotide molecule that encodes a transcribed RNA molecule that affects an agronomically important phenotype or morphology change of interest may be useful for the practice of the present invention. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829, and posttranscriptional gene suppression using a construct with a sense-oriented transcribable polynucleotide molecule to regulate gene expression in plants is disclosed in U.S. Pat. Nos. 5,283,184 and 5,231,020. Expression of a transcribable polynucleotide in a plant cell can also be used to suppress plant pests feeding on the plant cell, for example, compositions isolated from coleopteran pests (U.S. Patent Publication No. US20070124836) and compositions isolated from nematode pests (U.S. Patent Publication No. US20070250947). Plant pests include, but are not limited to arthropod pests, nematode pests, and fungal or microbial pests. Exemplary transcribable polynucleotide molecules for incorporation into constructs of the present invention include, for example, DNA molecules or genes from a species other than the target species or genes that originate with or are present in the same species, but are incorporated into recipient cells by genetic engineering methods rather than classical reproduction or breeding techniques. The type of polynucleotide molecule can include, but is not limited to, a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

Selectable Markers

As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding β-glucuronidase (GUS described in U.S. Pat. No. 5,599,670), green fluorescent protein and variants thereof (GFP described in U.S. Pat. Nos. 5,491,084 and 6,146,826), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: amino-methyl-phosphonic acid, glyphosate, glufosinate, sulfonylureas, imidazolinones, bromoxynil, dalapon, dicamba, cyclohexanedione, protoporphyrinogen oxidase inhibitors, and isoxasflutole herbicides. Transcribable polynucleotide molecules encoding proteins involved in herbicide tolerance are known in the art, and include, but are not limited to, a transcribable polynucleotide molecule encoding 5-enolpyruvylshikimate-3-phosphate synthase (EPSPS for glyphosate tolerance described in U.S.

Pat. Nos. 5,627,061; 5,633,435; 6,040,497; and 5,094,945); a transcribable polynucleotide molecule encoding a glyphosate oxidoreductase and a glyphosate-N-acetyl transferase (GOX described in U.S. Pat. No. 5,463,175; GAT described in U.S. Patent publication No. 20030083480, and dicamba monooxygenase U.S. Patent publication No. 20030135879); a transcribable polynucleotide molecule encoding bromoxynil nitrilase (Bxn for Bromoxynil tolerance described in U.S. Pat. No. 4,810,648); a transcribable polynucleotide molecule encoding phytoene desaturase (crtI) described in Misawa, et al., *Plant Journal* 4:833-840 (1993) and Misawa, et al., *Plant Journal* 6:481-489 (1994) for norflurazon tolerance; a transcribable polynucleotide molecule encoding acetohydroxyacid synthase (AHAS, aka ALS) described in Sathasiivan, et al., *Nucl. Acids Res.* 18:2188-2193 (1990) for tolerance to sulfonylurea herbicides; and the bar gene described in DeBlock, et al., *EMBO Journal* 6:2513-2519 (1987) for glufosinate and bialaphos tolerance. The promoter molecules of the present invention can express linked transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, aryloxyalkanoate dioxygenases, acetyl CoA carboxylase, glyphosate oxidoreductase, and glyphosate-N-acetyl transferase.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g. by ELISA), small active enzymes which are detectable in extracellular solution (e.g, alpha-amylase, beta-lactamase, phosphinothricin transferase), or proteins which are inserted or trapped in the cell wall (such as proteins which include a leader sequence such as that found in the expression unit of extension or tobacco pathogenesis related proteins also known as tobacco PR-S). Other possible selectable marker genes will be apparent to those of skill in the art and are encompassed by the present invention.

Cell Transformation

The invention is also directed to a method of producing transformed cells and plants which comprise a promoter operably linked to a transcribable polynucleotide molecule.

The term "transformation" refers to the introduction of nucleic acid into a recipient host. As used herein, the term "host" refers to bacteria, fungi, or plant, including any cells, tissue, organs, or progeny of the bacteria, fungi, or plant. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign polynucleotide molecule, such as a construct, has been introduced. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules.

There are many methods for introducing polynucleic acid molecules into plant cells. The method generally comprises the steps of selecting a suitable host cell, transforming the host cell with a recombinant vector, and obtaining the transformed host cell. Suitable methods include bacterial infection (e.g. *Agrobacterium*), binary bacterial artificial chromosome vectors, direct delivery of DNA (e.g. via PEG-mediated transformation, desiccation/inhibition-mediated DNA uptake, electroporation, agitation with silicon carbide fibers, and acceleration of DNA coated particles, etc. (reviewed in Potrykus, et al., *Ann. Rev. Plant Physiol. Plant Mol. Biol.* 42: 205 (1991)).

Technology for introduction of a DNA molecule into cells is well known to those of skill in the art. Methods and materials for transforming plant cells by introducing a plant DNA construct into a plant genome in the practice of this invention can include any of the well-known and demonstrated methods. Any transformation methods may be utilized to transform a host cell with one or more promoters and/or constructs of the present. Host cells may be any cell or organism such as a plant cell, algae cell, algae, fungal cell, fungi, bacterial cell, or insect cell. Preferred hosts and transformed cells include cells from: plants, *Aspergillus*, yeasts, insects, bacteria and algae.

Regenerated transgenic plants can be self-pollinated to provide homozygous transgenic plants. Alternatively, pollen obtained from the regenerated transgenic plants may be crossed with non-transgenic plants, preferably inbred lines of agronomically important species. Descriptions of breeding methods that are commonly used for different traits and crops can be found in one of several reference books, see, for example, Allard, *Principles of Plant Breeding*, John Wiley & Sons, NY, U. of CA, Davis, Calif., 50-98 (1960); Simmonds, *Principles of crop improvement*, Longman, Inc., NY, 369-399 (1979); Sneep and Hendriksen, Plant breeding perspectives, Wageningen (ed), Center for Agricultural Publishing and Documentation (1979); Fehr, *Soybeans: Improvement, Production and Uses*, 2nd Edition, Monograph, 16:249 (1987); Fehr, *Principles of variety development, Theory and Technique*, (Vol. 1) and *Crop* Species *Soybean* (Vol 2), Iowa State Univ., Macmillan Pub. Co., NY, 360-376 (1987). Conversely, pollen from non-transgenic plants may be used to pollinate the regenerated transgenic plants.

The transformed plants may be analyzed for the presence of the genes of interest and the expression level and/or profile conferred by the regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays. The expression of a transcribable polynucleotide molecule can be measured using TaqMan® (Applied Biosystems, Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used transgene expression.

The seeds of the plants of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include leaves, stems, roots, tubers, seeds, endosperm, ovule, and pollen. The invention also includes and provides transformed plant cells which comprise a nucleic acid molecule of the present invention.

The transgenic plant may pass along the transgenic polynucleotide molecule to its progeny. Progeny includes any regenerable plant part or seed comprising the transgene derived from an ancestor plant. The transgenic plant is preferably homozygous for the transformed polynucleotide molecule and transmits that sequence to all offspring as a result of sexual reproduction. Progeny may be grown from seeds produced by the transgenic plant. These additional plants may then be self-pollinated to generate a true breeding line of plants. The progeny from these plants are evaluated, among other things, for gene expression. The gene expression may be detected by several common methods such as western blotting, northern blotting, immunoprecipitation, and ELISA.

Commodity Products

The present invention provides a commodity product comprising DNA molecules according to the invention. As used herein, a "commodity product" refers to any composition or product which is comprised of material derived from a plant, seed, plant cell or plant part comprising a DNA molecule of the invention. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. Plants comprising a DNA molecule according to the invention can thus be used to manufacture any commodity product typically acquired from plants or parts thereof.

Having now generally described the invention, the same will be more readily understood through reference to the following examples which are provided by way of illustration, and are not intended to be limiting of the present invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Identification and Cloning of Regulatory Elements

Novel ubiquitin transcriptional regulatory elements, or transcriptional regulatory expression element group (EXP) sequences were identified and isolated from genomic DNA of the monocot species Big bluestem (*Andropogon gerardii*), Plume Grass (*Saccharum ravennae* (*Erianthus ravennae*)), Green bristlegrass (*Setaria viridis*), Teosinte (*Zea mays* subsp. *mexicana*), Foxtail millet (*Setaria italica*), and Coix (*Coix lacryma-jobi*).

Ubiquitin 1 transcript sequences were identified from each of the above species. The 5' untranslated region (5' UTR) of each of the Ubiquitin 1 transcripts was used to design primers to amplify the corresponding transcriptional regulatory elements for the identified Ubiquitin gene, which comprises a promoter, leader (5' UTR) and first intron operably linked. The primers were used with GenomeWalker™ (Clontech Laboratories, Inc, Mountain View, Calif.) libraries constructed following the manufacturer's protocol to clone the 5' region of the corresponding genomic DNA sequence. Ubiquitin transcriptional regulatory elements were also isolated from the monocot *Sorghum bicolor* using public sequences that are homologs to the Ubiquitin 4, 6 and 7 genes of *Zea mays*.

Using the identified sequences, a bioinformatic analysis was conducted to identify regulatory elements within the amplified DNA. Using the results of this analysis, regulatory elements were defined within the DNA sequences and primers designed to amplify the regulatory elements. The corresponding DNA molecule for each regulatory element was amplified using standard polymerase chain reaction conditions with primers containing unique restriction enzyme sites and genomic DNA isolated from *A. gerardii, S. ravennae, S. viridis, Z. mays* subsp. *mexicana, S. italica, C. lacryma-jobi*, and *S. bicolor*. The resulting DNA fragments were ligated into base plant expression vectors and sequenced. An analysis of the regulatory element TSS and intron/exon splice junctions was then done using transformed plant protoplasts. Briefly, the protoplasts were transformed with the plant expression vectors comprising the cloned DNA fragments operably linked to a heterologous transcribable polynucleotide molecule and the 5' RACE System for Rapid Amplification of cDNA Ends, Version 2.0 (Invitrogen, Carlsbad, Calif. 92008) was used to confirm the regulatory element TSS and intron/exon splice junctions by analyzing the sequence of the mRNA transcripts produced thereby.

Sequences of the identified transcriptional regulatory expression element groups ("EXP's") are provided herein as SEQ ID NOS: 1, 5, 8, 10, 12, 14, 16, 18, 22, 25, 27, 29, 31, 33, 37, 39, 41, 45, 49, 53, 55, 59, 63, 65, 69, 73, 75, 77, 79, 83, 85, 87, 90, 93, 95, 97, 98, 99, 100, 102, 104, 106, 108, 110, 112, 114, 115, 116, 117, 119, 121, 123, 124, 125, 126, 128, 130, 132, 133, 134, 136, 137, 139, 141, 143, 145, 147, 149, 151, 153, 155, 157, 180, 181 and 183, as listed in Table 1 below. Promoter sequences are provided herein as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. Leader sequences are provided herein as SEQ ID NOS: 3, 20, 35, 43, 47, 51, 57, 61, 67, 71 and 81. Intron sequences are provided herein as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182. An enhancer sequence is provided as SEQ ID NO: 89.

TABLE 1

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-ANDge.Ubq1:1:9 | 1 | 3741 | A. gerardii | EXP: P-ANDge.Ubq1-1:1:11 (SEQ ID NO: 2); L-ANDge.Ubq1-1:1:2 (SEQ ID NO: 3); I-ANDge.Ubq1-1:1:3 (SEQ ID NO: 4). | |
| P-ANDge.Ubq1-1:1:11 | 2 | 2603 | A. gerardii | promoter | |
| L-ANDge.Ubq1-1:1:2 | 3 | 99 | A. gerardii | leader | |
| I-ANDge.Ubq1-1:1:3 | 4 | 1039 | A. gerardii | intron | |
| EXP-ANDge.Ubq1:1:7 | 5 | 3255 | A. gerardii | EXP: P-ANDge.Ubq1-1:1:9 (SEQ ID NO: 6); L-ANDge.Ubq1-1:1:2 (SEQ ID NO: 3); I-ANDge.Ubq1-1:1:4 (SEQ ID NO: 7). | pMON136264, PCR0145892, pMON140896, PCR41 |
| P-ANDge.Ubq1-1:1:9 | 6 | 2114 | A. gerardii | promoter | |
| I-ANDge.Ubq1-1:1:4 | 7 | 1042 | A. gerardii | intron | |
| EXP-ANDge.Ubq1:1:8 | 8 | 2785 | A. gerardii | EXP: P-ANDge.Ubq1-1:1:10 (SEQ ID NO: 9); L-ANDge.Ubq1-1:1:2 (SEQ ID NO: 3); I-ANDge.Ubq1-1:1:4 (SEQ ID NO: 7). | pMON140917, PCR42 |
| P-ANDge.Ubq1-1:1:10 | 9 | 1644 | A. gerardii | promoter | |
| EXP-ANDge.Ubq1:1:10 | 10 | 2613 | A. gerardii | EXP: P-ANDge.Ubq1-1:1:12 (SEQ ID NO: 11); L-ANDge.Ubq1-1:1:2 (SEQ ID NO: 3); I-ANDge.Ubq1-1:1:4 (SEQ ID NO: 7). | PCR0145815, PCR43 |
| P-ANDge.Ubq1-1:1:12 | 11 | 1472 | A. gerardii | promoter | |
| EXP-ANDge.Ubq1:1:6 | 12 | 2255 | A. gerardii | EXP: P-ANDge.Ubq1-1:1:8 (SEQ ID NO: 13); L-ANDge.Ubq1-1:1:2 (SEQ ID NO: 3); I-ANDge.Ubq1-1:1:4 (SEQ ID NO: 7). | pMON136259, PCR0145893, pMON140898, PCR44 |
| P-ANDge.Ubq1-1:1:8 | 13 | 1114 | A. gerardii | promoter | |
| EXP-ANDge.Ubq1:1:11 | 14 | 1912 | A. gerardii | EXP: P-ANDge.Ubq1-1:1:13 (SEQ ID NO: 15); L-ANDge.Ubq1-1:1:2 (SEQ ID NO: 3); I-ANDge.Ubq1-1:1:4 (SEQ ID NO: 7). | PCR0145817, pMON140899, PCR45 |
| P-ANDge.Ubq1-1:1:13 | 15 | 771 | A. gerardii | promoter | |
| EXP-ANDge.Ubq1:1:12 | 16 | 1623 | A. gerardii | EXP: P-ANDge.Ubq1-1:1:14 (SEQ ID NO: 17); L-ANDge.Ubq1-1:1:2 (SEQ ID NO: 3); I-ANDge.Ubq1-1:1:4 (SEQ ID NO: 7). | PCR0145819, pMON140900, PCR46 |
| P-ANDge.Ubq1-1:1:14 | 17 | 482 | A. gerardii | promoter | |
| EXP-ERIra.Ubq1 | 18 | 3483 | E. ravennae | EXP: P-ERIra.Ubq1-1:1:10 (SEQ ID NO: 19); L-ERIra.Ubq1-1:1:2 (SEQ ID NO: 20); I-ERIra.Ubq1-1:1:1 (SEQ ID NO: 21). | |
| P-ERIra.Ubq1-1:1:10 | 19 | 2536 | E. ravennae | promoter | |
| L-ERIra.Ubq1-1:1:2 | 20 | 94 | E. ravennae | leader | |
| I-ERIra.Ubq1-1:1:1 | 21 | 1041 | E. ravennae | intron | |
| EXP-ERIra.Ubq1:1:9 | 22 | 3152 | E. ravennae | EXP: P-ERIra.Ubq1-1:1:9 (SEQ ID NO: 23); L-ERIra.Ubq1-1:1:2 (SEQ ID NO: 20); I-ERIra.Ubq1-1:1:2 (SEQ ID NO: 24). | pMON136263, PCR0145896, pMON140904, PCR50 |
| P-ERIra.Ubq1-1:1:9 | 23 | 2014 | E. ravennae | promoter | |
| I-ERIra.Ubq1-1:1:2 | 24 | 1044 | E. ravennae | intron | |
| EXP-ERIra.Ubq1:1:10 | 25 | 2663 | E. ravennae | EXP: P-ERIra.Ubq1-1:1:11 (SEQ ID NO: 26); L-ERIra.Ubq1-1:1:2 (SEQ ID NO: 20); I-ERIra.Ubq1-1:1:2 (SEQ ID NO: 24). | PCR0145820, pMON140905, PCR51 |
| P-ERIra.Ubq1-1:1:11 | 26 | 1525 | E. ravennae | promoter | |
| EXP-ERIra.Ubq1:1:8 | 27 | 2182 | E. ravennae | EXP: P-ERIra.Ubq1-1:1:8 (SEQ ID NO: 28); L-ERIra.Ubq1-1:1:2 (SEQ ID NO: 20); I-ERIra.Ubq1-1:1:2 (SEQ ID NO: 24). | pMON136258, PCR0145897, pMON140906, PCR52, pMON142864, pMON142862 |
| P-ERIra.Ubq1-1:1:8 | 28 | 1044 | E. ravennae | promoter | |
| EXP-ERIra.Ubq1:1:11 | 29 | 1934 | E. ravennae | EXP: P-ERIra.Ubq1-1:1:12 (SEQ ID NO: 30); L-ERIra.Ubq1-1:1:2 (SEQ ID NO: 20); I-ERIra.Ubq1-1:1:2 (SEQ ID NO: 24). | PCR0145821, pMON140907, PCR53 |
| P-ERIra.Ubq1-1:1:12 | 30 | 796 | E. ravennae | promoter | |
| EXP-ERIra.Ubq1:1:12 | 31 | 1649 | E. ravennae | EXP: P-ERIra.Ubq1-1:1:13 (SEQ ID NO: 32); L-ERIra.Ubq1-1:1:2 (SEQ ID NO: 20); I-ERIra.Ubq1-1:1:2 (SEQ ID NO: 24). | PCR0145822, pMON140908, PCR54 |
| P-ERIra.Ubq1-1:1:13 | 32 | 511 | E. ravennae | promoter | |
| EXP-Sv.Ubq1:1:2 | 33 | 2631 | S. viridis | EXP: P-Sv.Ubq1-1:1:1 (SEQ ID NO: 34); L-Sv.Ubq1-1:1:2 (SEQ ID NO: 35); I-Sv.Ubq1-1:1:1 (SEQ ID NO: 36). | pMON140878, PCR0145909, pMON129203, pMON131958 |
| P-Sv.Ubq1-1:1:1 | 34 | 1493 | S. viridis | promoter | |
| L-Sv.Ubq1-1:1:2 | 35 | 127 | S. viridis | leader | |
| I-Sv.Ubq1-1:1:1 | 36 | 1011 | S. viridis | intron | |
| EXP-Sv.Ubq1:1:3 | 37 | 2173 | S. viridis | EXP: P-Sv.Ubq1-1:1:2 (SQ ID NO: 38); L-Sv.Ubq1-1:1:2 (SEQ ID NO: 35); I-Sv.Ubq1-1:1:1 (SEQ ID NO: 36). | PCR0145929, pMON129204 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| P-Sv.Ubq1-1:1:2 | 38 | 1035 | S. viridis | promoter | |
| EXP-Sv.Ubq1:1:5 | 39 | 1819 | S. viridis | EXP: P-Sv.Ubq1-1:1:3 (SEQ ID NO: 40); L-Sv.Ubq1-1:1:2 (SEQ ID NO: 35); I-Sv.Ubq1-1:1:1 (SEQ ID NO: 36). | pMON129205, pMON131959 |
| P-Sv.Ubq1-1:1:3 | 40 | 681 | S. viridis | promoter | |
| EXP-Zm.UbqM1-1:1:1 (Allele-1) | 41 | 1922 | Z. mays subsp. mexicana | EXP: P-Zm.UbqM1-1:1:1 (SEQ ID NO: 42); L-Zm.UbqM1-1:1:5 (SEQ ID NO: 43); I-Zm.UbqM1-1:1:5 (SEQ ID NO: 44). | pMON140881, PCR0145914, pMON129210, pMON131961 |
| P-Zm.UbqM1-1:1:1 (Allele-1) | 42 | 850 | Z. mays subsp. mexicana | promoter | |
| L-Zm.UbqM1-1:1:1 (Allele-1) | 43 | 78 | Z. mays subsp. mexicana | leader | |
| I-Zm.UbqM1-1:1:5 (Allele-1) | 44 | 994 | Z. mays subsp. mexicana | intron | |
| EXP-Zm.UbqM1-1:1:4 (Allele-2) | 45 | 1971 | Z. mays subsp. mexicana | EXP: P-Zm.UbqM1-1:1:4 (SEQ ID NO: 46); L-Zm.UbqM1-1:1:5 (SEQ ID NO: 47); I-Zm.UbqM1-1:1:4 (SEQ ID NO: 48). | pMON140882, PCR0145915, pMON129212, pMON131963 |
| P-Zm.UbqM1-1:1:4 (Allele-2) | 46 | 887 | Z. mays subsp. mexicana | promoter | |
| L-Zm.UbqM1-1:1:5 (Allele-2) | 47 | 77 | Z. mays subsp. mexicana | leader | |
| I-Zm.UbqM1-1:1:4 (Allele-2) | 48 | 1007 | Z. mays subsp. mexicana | intron | |
| EXP-Zm.UbqM1:1:2 (Allele-3) | 49 | 2005 | Z. mays subsp. mexicana | EXP: P-Zm.UbqM1-1:1:5 (SEQ ID NO: 50); L-Zm.UbqM1-1:1:4 (SEQ ID NO: 51); I-Zm.UbqM1-1:1:11 (SEQ ID NO: 52). | PCR0145916, pMON129211, pMON131962, pMON132047 |
| P-Zm.UbqM1-1:1:5 (Allele-3) | 50 | 877 | Z. mays subsp. mexicana | promoter | |
| L-Zm.UbqM1-1:1:4 (Allele-3) | 51 | 78 | Z. mays subsp. mexicana | leader | |
| I-Zm.UbqM1-1:1:11 (Allele-3) | 52 | 1050 | Z. mays subsp. mexicana | intron | |
| EXP-Zm.UbqM1-1:1:5 (Allele-3) | 53 | 2005 | Z. mays subsp. mexicana | EXP: P-Zm.UbqM1-1:1:5 (SEQ ID NO: 50); L-Zm.UbqM1-1:1:4 (SEQ ID NO: 51); I-Zm.UbqM1-1:1:12 (SEQ ID NO: 54). | |
| I-Zm.UbqM1-1:1:12 (Allele-3) | 54 | 1050 | Z. mays subsp. mexicana | intron | |
| EXP-Sb.Ubq4:1:1 | 55 | 1632 | S. bicolor | EXP: P-Sb.Ubq4-1:1:1 (SEQ ID NO: 56); L-Sb.Ubq4-1:1:1 (SEQ ID NO: 57); I-Sb.Ubq4-1:1:1 (SEQ ID NO: 58). | pMON140886, PCR0145921, pMON129219, pMON132932 |
| P-Sb.Ubq4-1:1:1 | 56 | 401 | S. bicolor | promoter | |
| L-Sb.Ubq4-1:1:1 | 57 | 154 | S. bicolor | leader | |
| I-Sb.Ubq4-1:1:1 | 58 | 1077 | S. bicolor | intron | |
| EXP-Sb.Ubq6 | 59 | 2000 | S. bicolor | EXP: P-Sb.Ubq6-1:1:2 (SEQ ID NO: 60); L-Sb.Ubq6-1:1:1 (SEQ ID NO: 61); I-Sb.Ubq6-1:1:1 (SEQ ID NO: 62). | |
| P-Sb.Ubq6-1:1:2 | 60 | 791 | S. bicolor | promoter | |
| L-Sb.Ubq6-1:1:1 | 61 | 136 | S. bicolor | leader | |
| I-Sb.Ubq6-1:1:1 | 62 | 1073 | S. bicolor | intron | |
| EXP-Sb.Ubq6:1:1 | 63 | 2064 | S. bicolor | EXP: P-Sb.Ubq6-1:1:1 (SEQ ID NO: 64); L-Sb.Ubq6-1:1:1 (SEQ ID NO: 61); I-Sb.Ubq6-1:1:1 (SEQ ID NO: 62). | pMON140887, PCR0145920, pMON129218 |
| P-Sb.Ubq6-1:1:1 | 64 | 855 | S. bicolor | promoter | |
| EXP-Sb.Ubq7:1:1 | 65 | 2000 | S. bicolor | EXP: P-Sb.Ubq7-1:1:1 (SEQ ID NO: 66); L-Sb.Ubq7-1:1:1 (SEQ ID NO: 67); I-Sb.Ubq7-1:1:1 (SEQ ID NO: 68). | pMON132974 |
| P-Sb.Ubq7-1:1:1 | 66 | 565 | S. bicolor | promoter | |
| L-Sb.Ubq7-1:1:1 | 67 | 77 | S. bicolor | leader | |
| I-Sb.Ubq7-1:1:1 | 68 | 1358 | S. bicolor | intron | |
| EXP-SETit.Ubq1:1:1 | 69 | 2622 | S. italica | EXP: P-SETit.Ubq1-1:1:1 (SEQ ID NO: 70); L-SETit.Ubq1-1:1:1 (SEQ ID NO: 71); I-SETit.Ubq1-1:1:1 (SEQ ID NO: 72). | pMON140877, PCR0145900, pMON129200 |
| P-SETit.Ubq1-1:1:1 | 70 | 1492 | S. italica | promoter | |
| L-SETit.Ubq1-1:1:1 | 71 | 127 | S. italica | leader | |
| I-SETit.Ubq1-1:1:1 | 72 | 1003 | S. italica | intron | |
| EXP-SETit.Ubq1:1:4 | 73 | 2622 | S. italica | EXP: P-SETit.Ubq1-1:1:4 (SEQ ID NO: 74); L-SETit.Ubq1-1:1:1 (SEQ ID NO: 71); I-SETit.Ubq1-1:1:1 (SEQ ID NO: 72). | pMON132037 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| P-SETit.Ubq1-1:1:4 | 74 | 1492 | S. italica | promoter | |
| EXP-SETit.Ubq1:1:2 | 75 | 2164 | S. italica | EXP: P-SETit.Ubq1-1:1:2 (SEQ ID NO: 76); L-SETit.Ubq1-1:1:1 (SEQ ID NO: 71); I-SETit.Ubq1-1:1:1 (SEQ ID NO: 72). | |
| P-SETit.Ubq1-1:1:2 | 76 | 1034 | S. italica | promoter | |
| EXP-SETit.Ubq1:1:3 | 77 | 1810 | S. italica | EXP: P-SETit.Ubq1-1:1:3 (SEQ ID NO: 78); L-SETit.Ubq1-1:1:1 (SEQ ID NO: 71); I-SETit.Ubq1-1:1:1 (SEQ ID NO: 72). | PCR0145905, pMON129202, pMON131957 |
| P-SETit.Ubq1-1:1:3 | 78 | 680 | S. italica | promoter | |
| EXP-Cl.Ubq1:1:1 | 79 | 1940 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:1 (SEQ ID NO: 82). | pMON140889, PCR0145922, pMON140913, PCR19, pMON129221, pMON146795, pMON146796, pMON146797, pMON146798, pMON146799, pMON132047, pMON146800, pMON146801, pMON146802 |
| P-Cl.Ubq1-1:1:1 | 80 | 837 | C. lacryma-jobi | promoter | |
| L-Cl.Ubq1-1:1:1 | 81 | 86 | C. lacryma-jobi | leader | |
| I-Cl.Ubq1-1:1:1 | 82 | 1017 | C. lacryma-jobi | intron | |
| EXP-Cl.Ubq1:1:3 | 83 | 1845 | C. lacryma-jobi | EXP: P-Cl.Ubq1-1:1:4 (SEQ ID NO: 84); L-Cl.Ubq1-1:1:1 (SEQ ID NO: 81); I-Cl.Ubq1-1:1:1 (SEQ ID NO: 82). | PCR0145945, pMON140914, PCR20 |
| P-Cl.Ubq1-1:1:4 | 84 | 742 | C. lacryma-jobi | promoter | |
| EXP-Cl.Ubq1:1:4 | 85 | 1504 | C. lacryma-jobi | EXP: P-Cl.Ubq1-1:1:3 (SEQ ID NO: 86); L-Cl.Ubq1-1:1:1 (SEQ ID NO: 81); I-Cl.Ubq1-1:1:1 (SEQ ID NO: 82). | PCR0145946, pMON140915, PCR21 |
| P-Cl.Ubq1-1:1:3 | 86 | 401 | C. lacryma-jobi | promoter | |
| EXP-Cl.Ubq1:1:5 | 87 | 1157 | C. lacryma-jobi | EXP: P-Cl.Ubq1-1:1:5 (SEQ ID NO: 88); L-Cl.Ubq1-1:1:1 (SEQ ID NO: 81); I-Cl.Ubq1-1:1:1 (SEQ ID NO: 82). | PCR0145947, pMON140916, PCR22 |
| P-Cl.Ubq1-1:1:5 | 88 | 54 | C. lacryma-jobi | promoter | |
| E-Cl.Ubq1-1:1:1 | 89 | 798 | C. lacryma-jobi | enhancer | |
| EXP-Cl.Ubq1:1:12 | 90 | 3393 | C. lacryma-jobi | EXP: P-Cl.Ubq1-1:1:9 (SEQ ID NO: 91); L-Cl.Ubq1-1:1:1 (SEQ ID NO: 81); I-Cl.Ubq1-1:1:7 (SEQ ID NO: 92) | pMON142729 |
| P-Cl.Ubq1-1:1:9 | 91 | 2287 | C. lacryma-jobi | Promoter | |
| I-Cl.Ubq1-1:1:7 | 92 | 1020 | C. lacryma-jobi | Intron | |
| EXP-Cl.Ubq1:1:16 | 93 | 3393 | C. lacryma-jobi | EXP: P-Cl.Ubq1-1:1:9 (SEQ ID NO: 91); L-Cl.Ubq1-1:1:1 (SEQ ID NO: 81); I-Cl.Ubq1-1:1:6 (SEQ ID NO: 94) | pMON146750, pMON142748 |
| I-Cl.Ubq1-1:1:6 | 94 | 1020 | C. lacryma-jobi | Intron | |
| EXP-Cl.Ubq1:1:11 | 95 | 2166 | C. lacryma-jobi | EXP: P-Cl.Ubq1-1:1:10 (SEQ ID NO: 96); L-Cl.Ubq1-1:1:1 (SEQ ID NO: 81); I-Cl.Ubq1-1:1:7 (SEQ ID NO: 92) | pMON142730 |
| P-Cl.Ubq1-1:1:10 | 96 | 1060 | C. lacryma-jobi | Promoter | |
| EXP-Cl.Ubq1:1:17 | 97 | 2166 | C. lacryma-jobi | EXP: P-Cl.Ubq1-1:1:10 (SEQ ID NO: 96); L-Cl.Ubq1-1:1:1 (SEQ ID NO: 81); I-Cl.Ubq1-1:1:6 (SEQ ID NO: 94) | pMON146751, pMON142749 |
| EXP-Cl.Ubq1:1:10 | 98 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:6 (SEQ ID NO: 94) | pMON140889, PCR0145922, pMON140913, PCR19, pMON129221 |
| EXP-Cl.Ubq1:1:18 | 99 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:7 (SEQ ID NO: 92) | pMON146795 |
| EXP-Cl.Ubq1:1:19 | 100 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:8 (SEQ ID NO: 101) | pMON146796 |
| I-Cl.Ubq1-1:1:8 | 101 | 1020 | C. lacryma-jobi | Intron | |
| EXP-Cl.Ubq1:1:20 | 102 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:9 (SEQ ID NO: 103) | pMON146797 |
| I-Cl.Ubq1-1:1:9 | 103 | 1020 | C. lacryma-jobi | Intron | |
| EXP-Cl.Ubq1:1:21 | 104 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:10 (SEQ ID NO: 105) | pMON146798 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| I-Cl.Ubq1-1:1:10 | 105 | 1020 | C. lacryma-jobi | Intron | |
| EXP-Cl.Ubq1:1:22 | 106 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:11 (SEQ ID NO: 107) | pMON146799 |
| I-Cl.Ubq1-1:1:11 | 107 | 1020 | C. lacryma-jobi | Intron | |
| EXP-Cl.Ubq1:1:23 | 108 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:12 (SEQ ID NO: 109) | pMON132047, pMON146800 |
| I-Cl.Ubq1-1:1:12 | 109 | 1020 | C. lacryma-jobi | Intron | |
| EXP-Cl.Ubq1:1:24 | 110 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:13 (SEQ ID NO: 111) | pMON146801 |
| I-Cl.Ubq1-1:1:13 | 111 | 1020 | C. lacryma-jobi | Intron | |
| EXP-Cl.Ubq1:1:25 | 112 | 1943 | C. lacryma-jobi | EXP: P-Cl.Ubq1-1:1:1 (SEQ ID NO: 80); L-Cl.Ubq1-1:1:1 (SEQ ID NO: 81); I-Cl.Ubq1-1:1:14 (SEQ ID NO: 113) | pMON146802 |
| I-Cl.Ubq1-1:1:14 | 113 | 1020 | C. lacryma-jobi | Intron | |
| EXP-Cl.Ubq1:1:13 | 114 | 1848 | C. lacryma-jobi | EXP: P-Cl.Ubq1-1:1:4 (SEQ ID NO: 84); L-Cl.Ubq1-1:1:1 (SEQ ID NO: 81); I-Cl.Ubq1-1:1:6 (SEQ ID NO: 94) | PCR0145945, pMON140914, PCR20 |
| EXP-Cl.Ubq1:1:14 | 115 | 1507 | C. lacryma-jobi | EXP: P-Cl.Ubq1-1:1:3 (SEQ ID NO: 86); L-Cl.Ubq1-1:1:1 (SEQ ID NO: 81); I-Cl.Ubq1-1:1:6 (SEQ ID NO: 94) | PCR0145946, pMON140915, PCR21 |
| EXP-Cl.Ubq1:1:15 | 116 | 1160 | C. lacryma-jobi | EXP: P-Cl.Ubq1-1:1:5 (SEQ ID NO: 88); L-Cl.Ubq1-1:1:1 (SEQ ID NO: 81); I-Cl.Ubq1-1:1:6 (SEQ ID NO: 94) | PCR0145947, pMON140916, PCR22 |
| EXP-SETit.Ubq1:1:5 | 117 | 2625 | S. italica | EXP: P-SETit.Ubq1-1:1:1 (SEQ ID NO: 70); L-SETit.Ubq1-1:1:1 (SEQ ID NO: 71); I-SETit.Ubq1-1:1:2 (SEQ ID NO: 118) | pMON140877, PCR0145900, pMON129200 |
| I-SETit.Ubq1-1:1:2 | 118 | 1006 | S. italica | Intron | |
| EXP-SETit.Ubq1:1:10 | 119 | 2625 | S. italica | EXP: P-SETit.Ubq1-1:1:4 (SEQ ID NO: 64); L-SETit.Ubq1-1:1:1 (SEQ ID NO: 71); I-SETit.Ubq1-1:1:3 (SEQ ID NO: 120) | pMON132037 |
| I-SETit.Ubq1-1:1:3 | 120 | 1006 | S. italica | Intron | |
| EXP-SETit.Ubq1:1:12 | 121 | 2625 | S. italica | EXP: P-SETit.Ubq1-1:1:4 (SEQ ID NO: 64); L-SETit.Ubq1-1:1:1 (SEQ ID NO: 71); I-SETit.Ubq1-1:1:4 (SEQ ID NO: 122) | |
| I-SETit.Ubq1-1:1:4 | 122 | 1006 | S. italica | Intron | |
| EXP-SETit.Ubq1:1:7 | 123 | 2167 | S. italica | EXP: P-SETit.Ubq1-1:1:2 (SEQ ID NO: 71); L-SETit.Ubq1-1:1:1 (SEQ ID NO: 71); I-SETit.Ubq1-1:1:2 (SEQ ID NO: 118) | PCR0145928, pMON129201 |
| EXP-SETit.Ubq1:1:6 | 124 | 1813 | S. italica | EXP: P-SETit.Ubq1-1:1:3 (SEQ ID NO: 73); L-SETit.Ubq1-1:1:1 (SEQ ID NO: 71); I-SETit.Ubq1-1:1:2 (SEQ ID NO: 118) | PCR0145905, pMON129202 |
| EXP-SETit.Ubq1:1:11 | 125 | 1813 | S. italica | EXP: P-SETit.Ubq1-1:1:3 (SEQ ID NO: 73); L-SETit.Ubq1-1:1:1 (SEQ ID NO: 71); I-SETit.Ubq1-1:1:3 (SEQ ID NO: 120) | pMON131957 |
| EXP-SETit.Ubq1:1:13 | 126 | 1813 | S. italica | EXP: P-SETit.Ubq1-1:1:3 (SEQ ID NO: 73); L-SETit.Ubq1-1:1:1 (SEQ ID NO: 71); I-SETit.Ubq1-1:1:5 (SEQ ID NO: 127) | |
| I-SETit.Ubq1-1:1:5 | 127 | 1006 | S. italica | Intron | |
| EXP-Sv.Ubq1:1:7 | 128 | 2634 | S. viridis | EXP: P-Sv.Ubq1-1:1:1 (SEQ ID NO: 34); L-Sv.Ubq1-1:1:2 (SEQ ID NO: 35); I-Sv.Ubq1-1:1:2 (SEQ ID NO: 129) | pMON140878, PCR0145909, pMON129203 |
| I-Sv.Ubq1-1:1:2 | 129 | 1014 | S. viridis | Intron | |
| EXP-Sv.Ubq1:1:11 | 130 | 2634 | S. viridis | EXP: P-Sv.Ubq1-1:1:1 (SEQ ID NO: 34); L-Sv.Ubq1-1:1:2 (SEQ ID NO: 35); I-Sv.Ubq1-1:1:3 (SEQ ID NO: 131) | pMON131958 |
| I-Sv.Ubq1-1:1:3 | 131 | 1014 | S. viridis | Intron | |
| EXP-Sv.Ubq1:1:8 | 132 | 2176 | S. viridis | EXP: P-Sv.Ubq1-1:1:2 (SEQ ID NO: 38); L-Sv.Ubq1-1:1:2 (SEQ ID NO: 35); I-Sv.Ubq1-1:1:2 (SEQ ID NO: 129) | PCR0145929, pMON129204 |
| EXP-Sv.Ubq1:1:9 | 133 | 1822 | S. viridis | EXP: P-Sv.Ubq1-1:1:3 (SEQ ID NO: 40); L-Sv.Ubq1-1:1:2 (SEQ ID NO: 35); I-Sv.Ubq1-1:1:2 (SEQ ID NO: 129) | pMON129205 |
| EXP-Sv.Ubq1:1:10 | 134 | 1822 | S. viridis | EXP: P-Sv.Ubq1-1:1:4 (SEQ ID NO: 135); L-Sv.Ubq1-1:1:2 (SEQ ID NO: 35); I-Sv.Ubq1-1:1:2 (SEQ ID NO: 129) | PCR0145911 |
| P-Sv.Ubq1-1:1:4 | 135 | 681 | S. viridis | Promoter | |
| EXP-Sv.Ubq1:1:12 | 136 | 1822 | S. viridis | EXP: P-Sv.Ubq1-1:1:3 (SEQ ID NO: 40); L-Sv.Ubq1-1:1:2 (SEQ ID NO: 35); I-Sv.Ubq1-1:1:3 (SEQ ID NO: 131) | pMON131959 |

TABLE 1-continued

Transcriptional regulatory expression element groups ("EXP's"), promoters, enhancers, leaders and introns isolated from various grass species.

| Annotation | SEQ ID NO: | Size (bp) | Source Genus/species | Description and/or regulatory elements of EXP linked in 5' → 3' direction (SEQ ID NOs): | Plasmid Construct(s) and Amplicons comprising EXP |
|---|---|---|---|---|---|
| EXP-Zm.UbqM1:1:6 (Allele-1) | 137 | 1925 | Z. mays subsp. Mexicana | EXP: P-Zm.UbqM1-1:1:1 (SEQ ID NO: 42); L-Zm.UbqM1-1:1:1 (SEQ ID NO: 43); I-Zm.UbqM1-1:1:13 (SEQ ID NO: 138) | pMON140881, PCR0145914, pMON129210 |
| I-Zm.UbqM1-1:1:13 (Allele-1) | 138 | 997 | Z. mays subsp. Mexicana | Intron | |
| EXP-Zm.UbqM1:1:10 (Allele-1) | 139 | 1925 | Z. mays subsp. Mexicana | EXP: P-Zm.UbqM1-1:1:1 (SEQ ID NO: 42); L-Zm.UbqM1-1:1:1 (SEQ ID NO: 43); I-Zm.UbqM1-1:1:17 (SEQ ID NO: 140) | pMON131961 |
| I-Zm.UbqM1-1:1:17 (Allele-1) | 140 | 997 | Z. mays subsp. Mexicana | Intron | |
| EXP-Zm.UbqM1:1:7 (Allele-2) | 141 | 1974 | Z. mays subsp. Mexicana | EXP: P-Zm.UbqM1-1:1:4 (SEQ ID NO: 46); L-Zm.UbqM1-1:1:5 (SEQ ID NO: 47); I-Zm.UbqM1-1:1:14 (SEQ ID NO: 142) | pMON140882, PCR0145915, pMON129212 |
| I-Zm.UbqM1-1:1:14 (Allele-2) | 142 | 1010 | Z. mays subsp. Mexicana | Intron | |
| EXP-Zm.UbqM1:1:12 (Allele-2) | 143 | 1974 | Z. mays subsp. Mexicana | EXP: P-Zm.UbqM1-1:1:4 (SEQ ID NO: 46); L-Zm.UbqM1-1:1:5 (SEQ ID NO: 47); I-Zm.UbqM1-1:1:19 (SEQ ID NO: 144) | pMON131963 |
| I-Zm.UbqM1-1:1:19 (Allele-2) | 144 | 1010 | Z. mays subsp. Mexicana | Intron | |
| EXP-Zm.UbqM1:1:8 (Allele-3) | 145 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:15 (SEQ ID NO: 146) | PCR0145916, pMON129211 |
| I-Zm.UbqM1-1:1:15 (Allele-3) | 146 | 1053 | Z. mays subsp. Mexicana | Intron | |
| EXP-Zm.UbqM1:1:9 (Allele-3) | 147 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:16 (SEQ ID NO: 148) | |
| I-Zm.UbqM1-1:1:16 (Allele-3) | 148 | 1053 | Z. mays subsp. Mexicana | Intron | |
| EXP-Zm.UbqM1:1:11 (Allele-3) | 149 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:18 (SEQ ID NO: 150) | pMON131962, pMON132047 |
| I-Zm.UbqM1-1:1:18 (Allele-3) | 150 | 1053 | Z. mays subsp. Mexicana | Intron | |
| EXP-Sb.Ubq4:1:2 | 151 | 1635 | S. bicolor | EXP: P-Sb.Ubq4-1:1:1 (SEQ ID NO: 56); L-Sb.Ubq4-1:1:1 (SEQ ID NO: 57); I-Sb.Ubq4-1:1:2 (SEQ ID NO: 152) | pMON140886, PCR0145921, pMON129219, pMON132932 |
| I-Sb.Ubq4-1:1:2 | 152 | 1080 | S. bicolor | Intron | |
| EXP-Sb.Ubq6:1:2 | 153 | 2067 | S. bicolor | EXP: P-Sb.Ubq6-1:1:1 (SEQ ID NO: 64); L-Sb.Ubq6-1:1:1 (SEQ ID NO: 57); I-Sb.Ubq6-1:1:2 (SEQ ID NO: 154) | pMON140887, PCR0145920, pMON129218, pMON132931 |
| I-Sb.Ubq6-1:1:2 | 154 | 1076 | S. bicolor | Intron | |
| EXP-Sb.Ubq6:1:3 | 155 | 2067 | S. bicolor | EXP: P-Sb.Ubq6-1:1:1 (SEQ ID NO: 64); L-Sb.Ubq6-1:1:1 (SEQ ID NO: 57); I-Sb.Ubq6-1:1:3 (SEQ ID NO: 1569) | pMON132931 |
| I-Sb.Ubq6-1:1:3 | 156 | 1076 | S. bicolor | Intron | |
| EXP-Sb.Ubq7:1:2 | 157 | 2003 | S. bicolor | EXP: P-Sb.Ubq7-1:1:1 (SEQ ID NO: 66); L-Sb.Ubq7-1:1:1 (SEQ ID NO: 67); I-Sb.Ubq7-1:1:A (SEQ ID NO: 158) | pMON132974 |
| I-Sb.Ubq7-1:1:2 | 158 | 1361 | S. bicolor | Intron | |
| EXP-SETit.Ubq1:1:E | 180 | 2625 | S. italica | EXP: P-SETit.Ubq1-1:1:4 (SEQ ID NO: 64); L-SETit.Ubq1-1:1:1 (SEQ ID NO: 71); I-SETit.Ubq1-1:1:5 (SEQ ID NO: 127) | |
| EXP-Zm.UbqM1:1:13 (Allele-3) | 181 | 2008 | Z. mays subsp. Mexicana | EXP: P-Zm.UbqM1-1:1:5 (SEQ ID NO: 50); L-Zm.UbqM1-1:1:4 (SEQ ID NO: 51); I-Zm.UbqM1-1:1:20 (SEQ ID NO: 182) | |
| I-Zm.UbqM1-1:1:20 (Allele-3) | 182 | 1053 | Z. mays subsp. Mexicana | Intron | |
| EXP-SETit.Ubq1:1:9 | 183 | 2625 | S. italica | EXP: P-SETit.Ubq1-1:1:4 (SEQ ID NO: 64); L-SETit.Ubq1-1:1:1 (SEQ ID NO: 71); I-SETit.Ubq1-1:1:2 (SEQ ID NO: 118) | |

As shown in Table 1, for example, the transcriptional regulatory EXP sequence designated EXP-ANDge.Ubq1:1:9 (SEQ ID NO: 1), with components isolated from *A. gerardii*, comprises a promoter element, P-ANDge.Ubq1-1:1:11 (SEQ ID NO: 2), operably linked 5' to a leader element, L-ANDge.Ubq1-1:1:2 (SEQ ID NO: 3), operably linked 5' to an intron element, I-ANDge.Ubq1-1:1:3 (SEQ ID NO: 4). Other EXP's are linked similarly, as outlined in Table 1.

As shown in Table 1, the sequence listing and FIGS. 1-7, variants of promoter sequences from the species *A. gerardii*, *E. ravennae*, *Z. mays* subsp. *mexicana*, *S. bicolor*, *C. lacryma-jobi*, *S. italica*, and *S. viridis* were engineered which comprise shorter promoter fragments of, for instance, P-ANDge.Ubq1-1:1:11 (SEQ ID NO:2), P-ERIra.Ubq1-1:1:10 (SEQ ID NO:19) or other respective promoters from other species, and for instance resulting in P-ANDge.Ubq1-1:1:9 (SEQ ID NO: 6), P-ERIra.Ubq1-1:1:9 (SEQ ID NO: 23), P-Cl.Ubq1-1:1:10 (SEQ ID NO: 96), P-SETit.Ubq1-1:1:2 (SEQ ID NO: 76) and P-Sv.Ubq1-1:1:2 (SEQ ID NO: 38), as well as other promoter fragments. P-SETit.Ubq1-1:1:4 (SEQ ID NO: 74) comprises a single nucleotide change relative to P-SETit.Ubq1-1:1:1 (SEQ ID NO: 70). Likewise, P-Sv.Ubq1-1:1:3 (SEQ ID NO: 40) comprises a single nucleotide change relative to P-Sv.Ubq1-1:1:4 (SEQ ID NO: 135).

In some instances, variants of specific introns were created by altering the last 3' nucleotides of each respective intron following the sequence 5'-AG-3' of the 3' intron splice junction. These intron variants are shown in Table 2 below.

TABLE 2

3' end sequence of intron variants.

| Annotation | SEQ ID NO: | Intron 3' end nucleotides immediately following 3' splice site AG |
|---|---|---|
| I-Cl.Ubq1-1:1:7 | 92 | GTG |
| I-Cl.Ubq1-1:1:6 | 94 | GTC |
| I-Cl.Ubq1-1:1:8 | 101 | GCG |
| I-Cl.Ubq1-1:1:9 | 103 | GAC |
| I-Cl.Ubq1-1:1:10 | 105 | ACC |
| I-Cl.Ubq1-1:1:11 | 107 | GGG |
| I-Cl.Ubq1-1:1:12 | 109 | GGT |
| I-Cl.Ubq1-1:1:13 | 111 | CGT |
| I-Cl.Ubq1-1:1:14 | 113 | TGT |
| I-SETit.Ubq1-1:1:2 | 118 | GTG |
| I-SETit.Ubq1-1:1:3 | 120 | GGT |
| I-SETit.Ubq1-1:1:4 | 122 | ACC |
| I-SETit.Ubq1-1:1:5 | 127 | GGC |
| I-Sv.Ubq1-1:1:2 | 129 | GTG |
| I-Sv.Ubq1-1:1:3 | 131 | GGT |
| I-Zm.UbqM1-1:1:13 (Allele-1) | 138 | GTC |
| I-Zm.UbqM1-1:1:17 (Allele-1) | 140 | GGT |
| I-Zm.UbqM1-1:1:14 (Allele-2) | 142 | GTC |
| I-Zm.UbqM1-1:1:19 (Allele-2) | 144 | GGT |
| I-Zm.UbqM1-1:1:15 (Allele-3) | 146 | GTC |
| I-Zm.UbqM1-1:1:18 (Allele-3) | 148 | GGT |
| I-Sb.Ubq6-1:1:2 | 154 | GTG |
| I-Sb.Ubq6-1:1:3 | 156 | GGT |
| I-Zm.UbqM1-1:1:20 (Allele-3) | 182 | CGG |

Also listed in Table 1 are three allelic variants isolated using the same primer sets designed for amplification of genomic DNA from *Z. mays* subsp. *mexicana*. Allelic variants of the EXP sequences are comprised of sequence that shares some identity within various regions of other sequences, but insertions, deletions and nucleotide mismatches may also be apparent within each promoter, leader and/or intron of each of the EXP sequences. The EXP sequence designated EXP-Zm.UbqM1:1:1 (SEQ ID NO: 41) represents a first allele (Allele-1) of the *Z. mays* subsp. *mexicana* Ubq1 gene transcriptional regulatory expression element group. The EXP sequences designated EXP-Zm.UbqM1:1:6 (SEQ ID NO: 137) and EXP-Zm.UbqM1:1:10 (SEQ ID NO: 139) represent a first allele (Allele-1), with the only difference between the two EXPs occurring in the last 3' nucleotides of each respective intron following the sequence 5'-AG-3' of the 3' intron splice junction. The EXP sequence designated EXP-Zm.UbqM1:1:4 (SEQ ID NO: 45) represents a second allele (Allele-2) of the *Z. mays* subsp. *mexicana* Ubq1 gene transcriptional regulatory expression element group. The EXP sequences designated EXP-Zm.UbqM1:1:7 (SEQ ID NO: 141) and EXP-Zm.UbqM1:1:12 (SEQ ID NO: 143) represent a second allele (Allele-2), with the only difference between the two EXPs occurring in the last 3' nucleotides of each respective intron following the sequence 5'-AG-3' of the 3' intron splice junction. The EXP sequences EXP-Zm.UbqM1:1:2 (SEQ ID NO: 49) and EXP-Zm.UbqM1:1:5 (SEQ ID NO: 53) represents a third allel (Allele-3) of the *Z. mays* subsp. *mexicana* Ubq1 gene transcriptional regulatory expression element group and comprise a single nucleotide difference at position 1034 within their respective introns (G for I-Zm.UbqM1-1:1:11, SEQ ID NO: 52 and T for I-Zm.UbqM1-1:1:12, SEQ ID NO: 54). The EXP sequences designated EXP-Zm.UbqM1:1:8 (SEQ ID NO: 145), EXP-Zm.UbqM1:1:9 (SEQ ID NO: 147), EXP-Zm.UbqM1:1:11 (SEQ ID NO: 149) and EXP-Zm.UbqM1:1:13 (SEQ ID NO: 181) also represent a third allele (Allele-3). The intron of EXP-Zm.UbqM1:1:9, I-Zm.UbqM1-1:1:16 (SEQ ID NO: 148) comprises a thymine residue at position 1034, while the introns of EXP-Zm.UbqM1:1:8, EXP-Zm.UbqM1:1:11 and EXP-Zm.UbqM1:1:13 (I-Zm.UbqM1-1:1:15, SEQ ID NO: 146; I-Zm.UbqM1-1:1:18, SEQ ID NO: 11 and; I-Zm.UbqM1-1:1:20, SEQ ID NO: 182) each comprise a guanine residue at position 1034. In addition, the last 3, 3' end nucleotides of EXP-Zm.UbqM1:1:8 (SEQ ID NO: 145) and EXP-Zm.UbqM1:1:9 (SEQ ID NO: 147) differ from those of EXP-Zm.UbqM1:1:11 (SEQ ID NO: 149) and EXP-Zm.UbqM1:1:13 (SEQ ID NO: 181).

Example 2

Analysis of Regulatory Elements Driving GUS in Corn Protoplasts

Corn leaf protoplasts were transformed with plant expression vectors containing an EXP sequence driving expression of the β-glucuronidase (GUS) transgene and compared to GUS expression in leaf protoplasts in which expression of GUS is driven by known constitutive promoters.

Expression of a transgene driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was compared with expression from known constitutive promoters. The foregoing EXP sequences were cloned into plant expression vectors as shown in Table 3 below to yield vectors in which an EXP sequence is operably linked 5' to a β-glucuronidase (GUS) reporter that contained a processable intron (referred to as GUS-2, SEQ ID NO: 160) derived from the potato light-inducible tissue-specific ST-LS1 gene (GenBank Accession: X04753) or a contiguous GUS coding sequence (GUS-1, SEQ ID NOS: 159), which was operably linked 5' to a 3' UTR derived from the *A. tumefaciens* Nopaline synthase gene (T-AGRtu.nos-1:1:13, SEQ ID NO: 161) or the wheat Hsp17 gene (T-Ta.Hsp17-1:1:1, SEQ ID NO: 162).

TABLE 3

GUS plant expression plasmid construct and corresponding EXP sequence, GUS coding sequence and 3' UTR used for transformation of corn leaf protoplasts. "SEQ ID NO:" refers to given EXP sequence.

| Plasmid | EXP sequence | SEQ ID NO: | GUS | 3' UTR |
|---|---|---|---|---|
| pMON19469 | EXP-CaMV.35S-enh + Zm.DnaK:1:1 | 170 | GUS-1 | T-AGRtu.nos-1:1:13 |
| pMON65328 | EXP-CaMV.35S-enh + Ta.Lhcb1 + Os.Act1:1:1 | 163 | GUS-2 | T-Ta.Hsp17-1:1:1 |
| pMON25455 | EXP-Os.Act1:1:9 | 179 | GUS-1 | T-AGRtu.nos-1:1:13 |
| pMON122605 | EXP-Os.TubA-3:1:1 | 165 | GUS-1 | T-AGRtu.nos-1:1:13 |
| pMON136264 | EXP-ANDge.Ubq1:1:7 | 5 | GUS-1 | T-AGRtu.nos-1:1:13 |
| pMON136259 | EXP-ANDge.Ubq1:1:6 | 12 | GUS-1 | T-AGRtu.nos-1:1:13 |
| pMON136263 | EXP-ERIra.Ubq1:1:9 | 22 | GUS-1 | T-AGRtu.nos-1:1:13 |
| pMON136258 | EXP-ERIra.Ubq1:1:8 | 27 | GUS-1 | T-AGRtu.nos-1:1:13 |

Control plasmids (pMON19469, pMON65328, pMON25455 and pMON122605) used for comparison were constructed as described above and contain a known EXP sequence: EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), EXP-Os.Act1:1:9 (SEQ ID NO: 179), or EXP-Os.TubA-3:1:1 (SEQ ID NO: 165), respectively, operably linked 5' to a GUS coding sequence and 3' UTR. Three additional controls were provided to assess background GUS and luciferase expression: a no DNA control, an empty vector which is not designed for transgene expression, and an expression vector used to express green fluorescent protein (GFP).

Two plasmids, for use in co-transformation and normalization of data, were also constructed using methods known in the art. Each plasmid contained a specific luciferase coding sequence that was driven by a constitutive EXP sequence. The plant vector pMON19437 comprises a transgene cassette with a constitutive promoter operably linked 5' to an intron, (EXP-CaMV.35S-enh+Zm.DnaK:1:1, SEQ ID NO: 170), operably linked 5' to a firefly (*Photinus pyralis*) luciferase coding sequence (LUCIFERASE:1:3, SEQ ID NO: 166), operably linked 5' to a 3' UTR from the *Agrobacterium tumefaciens* nopaline synthase gene (T-AGRtu.nos-1:1:13, SEQ ID NO: 161). The plant vector pMON63934 comprises a transgene cassette with a constitutive EXP sequence (EXP-CaMV.35S-enh-Lhcb1, SEQ ID NO: 168), operably linked 5' to a sea pansy (*Renilla reniformis*) luciferase coding sequence (CR-Ren.hRenilla Lucife-0:0:1, SEQ ID NO: 167), operably linked 5' to a 3' UTR from the *Agrobacterium tumefaciens* nopaline synthase gene (T-AGRtu.nos-1:1:13, SEQ ID NO: 161).

Corn leaf protoplasts were transformed using a PEG-based transformation method, as is well known in the art. Protoplast cells were transformed with pMON19437 plasmid DNA, pMON63934 plasmid DNA, and an equimolar quantity of one of the plasmids presented in Table 3 and incubated overnight in total darkness. Measurements of both GUS and luciferase were conducted by placing aliquots of a lysed preparation of cells transformed as above into two different small-well trays. One tray was used for GUS measurements, and a second tray was used to perform a dual luciferase assay using the dual luciferase reporter assay system (Promega Corp., Madison, Wis.; see for example, Promega Notes Magazine, No: 57, 1996, p. 02). One or two transformations for each EXP sequence were performed and the mean expression values for each EXP sequence determined from several samples from each transformation experiment. Sample measurements were made using four replicates of each EXP sequence construct transformation, or alternatively, three replicates of each EXP sequence construct per one of two transformation experiments. The mean GUS and luciferase expression levels are provided in Table 4. In this table, the firefly luciferase values (e.g. from expression of pMON19437) are provided in the column labeled "FLuc" and the *Renilla* luciferase values are provided as in the column labeled "RLuc."

TABLE 4

Mean GUS and Luciferase activity in transformed corn leaf protoplast cells.

| Plasmid | EXP sequence | SEQ ID NO: | Gus | RLuc | FLuc |
|---|---|---|---|---|---|
| pMON19469 | EXP-CaMV.35S-enh + Zm.DnaK:1:1 | 170 | 789147 | 298899 | 36568 |
| pMON65328 | EXP-CaMV.35S-enh + Ta.Lhcb1 + Os.Act1:1:1 | 163 | 508327 | 158227 | 17193 |
| pMON25455 | EXP-Os.Act1:1:9 | 179 | 460579 | 183955 | 53813 |
| pMON122605 | EXP-Os.TubA-3:1:1 | 165 | 25082 | 25821 | 21004 |
| pMON136264 | EXP-ANDge.Ubq1:1:7 | 5 | 926083 | 101213 | 23704 |
| pMON136259 | EXP-ANDge.Ubq1:1:6 | 12 | 845274 | 193153 | 51479 |
| pMON136263 | EXP-ERIra.Ubq1:1:9 | 22 | 901985 | 132765 | 41313 |
| pMON136258 | EXP-ERIra.Ubq1:1:8 | 27 | 1011447 | 210635 | 66803 |

To compare the relative activity of each EXP sequence, GUS values were expressed as a ratio of GUS to luciferase activity and normalized with respect to the expression levels observed for the EXP sequence EXP-Os.TubA-3:1:1 (SEQ ID NO: 165). Table 5 below shows the GUS/RLuc ratios of expression normalized with respect to EXP-Os.TubA-3:1:1 expression in corn protoplasts.

As can be seen in Table 5, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was 4.51 to 9.42 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

TABLE 5

GUS/RLuc fold expression as relative to EXP-Os.TubA-3:1:1 expression in corn leaf protoplast cells.

| Plasmid | EXP sequence | SEQ ID NO: | Gus/RLuc | Gus/RLuc Normalized with respect to EXP-Os.TubA-3:1:1 |
|---|---|---|---|---|
| pMON19469 | EXP-CaMV.35S-enh + Zm.DnaK:1:1 | 170 | 2.640000 | 2.72 |
| pMON65328 | EXP-CaMV.35S-enh + Ta.Lhcb1 + Os.Act1:1:1 | 163 | 3.210000 | 3.31 |
| pMON25455 | EXP-Os.Act1:1:9 | 179 | 2.500000 | 2.57 |
| pMON122605 | EXP-Os.TubA-3:1:1 | 165 | 0.971000 | 1.00 |
| pMON136264 | EXP-ANDge.Ubq1:1:7 | 5 | 9.150000 | 9.42 |
| pMON136259 | EXP-ANDge.Ubq1:1:6 | 12 | 4.380000 | 4.51 |
| pMON136263 | EXP-ERIra.Ubq1:1:9 | 22 | 6.790000 | 6.99 |
| pMON136258 | EXP-ERIra.Ubq1:1:8 | 27 | 4.800000 | 4.94 |

Table 6 below show GUS/FLuc ratios of expression normalized with respect to EXP-Os.TubA-3:1:1 expression in corn protoplasts.

TABLE 6

GUS/FLuc fold expression as relative to EXP-Os.TubA-3:1:1 expression in corn leaf protoplast cells.

| Plasmid | EXP sequence | SEQ ID NO: | Gus/FLuc | Normalized with respect to EXP-Os.TubA-3:1:1 |
|---|---|---|---|---|
| pMON19469 | EXP-CaMV.35S-enh + Zm.DnaK:1:1 | 170 | 21.600000 | 18.15 |
| pMON65328 | EXP-CaMV.35S-enh + Ta.Lhcb1 + Os.Act1:1:1 | 163 | 29.600000 | 24.87 |
| pMON25455 | EXP-Os.Act1:1:9 | 179 | 8.560000 | 7.19 |
| pMON122605 | EXP-Os.TubA-3:1:1 | 165 | 1.190000 | 1.00 |
| pMON136264 | EXP-ANDge.Ubq1:1:7 | 5 | 39.100000 | 32.86 |
| pMON136259 | EXP-ANDge.Ubq1:1:6 | 12 | 16.400000 | 13.78 |
| pMON136263 | EXP-ERIra.Ubq1:1:9 | 22 | 21.800000 | 18.32 |
| pMON136258 | EXP-ERIra.Ubq1:1:8 | 27 | 15.100000 | 12.69 |

As can be seen in Table 6, GUS expression, driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) demonstrated the same general trend when expressed as ratio of GUS/FLuc values and is normalized with respect to EXP-Os.TubA-3:1:1 (SEQ ID NO: 165). Expression was 12.69 to 32.86 fold higher than GUS expression driven by EXP-Os.TubA-3:1:1 (SEQ ID NO: 165). GUS expression driven by EXP-ANDge.Ubq1:1:7 (SEQ ID NO: 5), EXP-ANDge.Ubq1:1:6 (SEQ ID NO: 12), EXP-ERIra.Ubq1:1:9 (SEQ ID NO: 22) or EXP-ERIra.Ubq1:1:8 (SEQ ID NO: 27) was also higher in certain comparisons than that of EXP-CaMV.35S-enh+Zm.DnaK:1:1 (SEQ ID NO: 170), EXP-CaMV.35S-enh+Ta.Lhcb1+Os.Act1:1:1 (SEQ ID NO: 163), or EXP-Os.Act1:1:9 (SEQ ID NO: 179).

Example 3

Analysis of Regulatory Elements Driving GUS in Corn Protoplasts Using GUS Transgene Cassette Amplicons Corn leaf protoplasts were transformed with DNA amplicons derived from plant expression vectors containing an EXP sequence, driving expression of the β-glucuronidase (GUS) transgene, and compared to leaf protoplast in which expression of GUS is driven by known constitutive promoters in a series of experiments presented below.

In a first set of experiments, corn protoplast cells, derived from leaf tissue were transformed as above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP- Zm.UbqM1:1:7 (SEQ ID NO: 141), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) with that of known constitutive promoters. Each EXP sequence comprising the amplification template from which the transgene cassette amplicon is produced was cloned using methods known in the art into a plant expression vector shown in Table 7 below under the heading of "Amplicon Template." The resulting plant expression vectors comprise a transgene cassette comprised of a EXP sequence, operably linked 5' to a coding sequence for β-glucuronidase (GUS) that either contains a processable intron ("GUS-2" as discussed in Example 2 above), or a contiguous GUS coding sequence ("GUS-1", as discussed above), operably linked 5' to a 3' UTR T-AGRtu.nos-1:1:13 or T-Ta.Hsp17-1:1:1, as also noted above. Amplicons were produced using methods known to those skilled in the art using the plasmid construct templates presented in Table 7 below. Briefly, a 5' oligonucleotide primer was designed to anneal to the promoter sequence and a 3' oligonucleotide primer, which anneals at the 3' end of the 3' UTR was used for amplification of each transgene cassette. Successive 5' deletions were introduced into the promoter sequences comprising the transgene cassettes, giving rise to different EXP sequences, by the use of different oligonucleotide primers which were designed to anneal at different positions within the promoter sequence comprising each amplicon template.

Plasmid constructs listed as amplicon templates in Table 7 served as templates for amplification of transgene expression cassettes comprising the listed EXP sequences of Table 7. Control plasmids used to generate GUS transgene amplicons for comparison were constructed as previously described with known constitutive EXP sequences described in Example 2. Negative controls for determination of GUS and luciferase background, a no DNA control, and a control sample in which the two luciferase plasmids are used in transformation along with a plasmid DNA that does not express a coding sequence were also used. Plasmids pMON19437 and pMON63934, as discussed in Example 2, were also employed for co-transformation and normalization of data.

Corn leaf protoplasts were transformed using a PEG-based transformation method as described in Example 2, above. Table 8 below shows the average GUS and luciferase expression values determined for each transgene cassette.

TABLE 8

Mean GUS and Luciferase activity in transformed corn leaf protoplast cells.

| EXP sequence | SEQ ID NO: | GUS | RLuc | FLuc |
|---|---|---|---|---|
| EXP-Os.Act1:1:9 | 179 | 1540.3 | 105416.8 | 2671.8 |
| P-CAMV.35S-ENH-1:1:102/L-CAMV.35S-1:1:2 | 169 | 10426.3 | 344088.6 | 8604.1 |
| EXP-CaMV.35S-enh + Ta.Lhcb 1 + Os.Act1:1:1 | 163 | 12530.8 | 137722.6 | 3067.1 |

TABLE 7

GUS plant expression amplicons and corresponding plasmid construct amplicon templates, EXP sequence, GUS coding sequence and 3' UTR used for transformation of corn leaf protoplasts.

| Amplicon ID | Amplicon Template | EXP sequence | SEQ ID NO: | Coding Sequence | 3' UTR |
|---|---|---|---|---|---|
| PCR0145942 | pMON25455 | EXP-Os.Act1:1:9 | 179 | GUS-1 | T-AGRtu.nos-1:1:13 |
| PCR0145941 | pMON33449 | P-CAMV.35S-ENH-1:1:102/L-CAMV.35S-1:1:2 | 169 | GUS-1 | T-AGRtu.nos-1:1:13 |
| PCR0145943 | pMON65328 | EXP-CaMV.35S-enh + Ta.Lhcb1 + Os.Act1:1:1 | 163 | GUS-2 | T-Ta.Hsp17-1:1:1 |
| PCR0145944 | pMON81552 | EXP-CaMV.35S-enh + Zm.DnaK:1:1 | 170 | GUS-1 | T-AGRtu.nos-1:1:13 |
| PCR0145892 | pMON136264 | EXP-ANDge.Ubq1:1:7 | 5 | GUS-1 | T-AGRtu.nos-1:1:13 |
| PCR0145815 | pMON136264 | EXP-ANDge.Ubq1:1:10 | 10 | GUS-1 | T-AGRtu.nos-1:1:13 |
| PCR0145893 | pMON136259 | EXP-ANDge.Ubq1:1:6 | 12 | GUS-1 | T-AGRtu.nos-1:1:13 |
| PCR0145817 | pMON136264 | EXP-ANDge.Ubq1:1:11 | 14 | GUS-1 | T-AGRtu.nos-1:1:13 |
| PCR0145819 | pMON136264 | EXP-ANDge.Ubq1:1:12 | 16 | GUS-1 | T-AGRtu.nos-1:1:13 |
| PCR0145896 | pMON136263 | EXP-ERIra.Ubq1:1:9 | 22 | GUS-1 | T-AGRtu.nos-1:1:13 |
| PCR0145820 | pMON136263 | EXP-ERIra.Ubq1:1:10 | 25 | GUS-1 | T-AGRtu.nos-1:1:13 |
| PCR0145897 | pMON136258 | EXP-ERIra.Ubq1:1:8 | 27 | GUS-1 | T-AGRtu.nos-1:1:13 |
| PCR0145821 | pMON136263 | EXP-ERIra.Ubq1:1:11 | 29 | GUS-1 | T-AGRtu.nos-1:1:13 |
| PCR0145822 | pMON136263 | EXP-ERIra.Ubq1:1:12 | 31 | GUS-1 | T-AGRtu.nos-1:1:13 |
| PCR0145900 | pMON140877 | EXP-SETit.Ubq1:1:5 | 117 | GUS-1 | T-AGRtu.nos-1:1:13 |
| PCR0145928 | pMON140877 | EXP-SETit.Ubq1:1:7 | 123 | GUS-1 | T-AGRtu.nos-1:1:13 |
| PCR0145905 | pMON140877 | EXP-SETit.Ubq1:1:6 | 124 | GUS-1 | T-AGRtu.nos-1:1:13 |
| PCR0145909 | pMON140878 | EXP-Sv.Ubq1:1:7 | 128 | GUS-1 | T-AGRtu.nos-1:1:13 |
| PCR0145929 | pMON140878 | EXP-Sv.Ubq1:1:8 | 132 | GUS-1 | T-AGRtu.nos-1:1:13 |
| PCR0145911 | pMON140878 | EXP-Sv.Ubq1:1:10 | 134 | GUS-1 | T-AGRtu.nos-1:1:13 |
| PCR0145914 | pMON140881 | EXP-Zm.UbqM1:1:6 | 137 | GUS-1 | T-AGRtu.nos-1:1:13 |
| PCR0145915 | pMON140882 | EXP-Zm.UbqM1:1:7 | 141 | GUS-1 | T-AGRtu.nos-1:1:13 |
| PCR0145921 | pMON140886 | EXP-Sb.Ubq4:1:2 | 151 | GUS-1 | T-AGRtu.nos-1:1:13 |
| PCR0145920 | pMON140887 | EXP-Sb.Ubq6:1:2 | 153 | GUS-1 | T-AGRtu.nos-1:1:13 |
| PCR0145922 | pMON140889 | EXP-Cl.Ubq1:1:10 | 98 | GUS-1 | T-AGRtu.nos-1:1:13 |

TABLE 8-continued

Mean GUS and Luciferase activity in transformed corn leaf protoplast cells.

| EXP sequence | SEQ ID NO: | GUS | RLuc | FLuc |
|---|---|---|---|---|
| EXP-CaMV.35S-enh + Zm.DnaK:1:1 | 170 | 61036.1 | 208125.3 | 5787.6 |
| EXP-ANDge.Ubq1:1:7 | 5 | 59447.4 | 84667.6 | 2578.4 |
| EXP-ANDge.Ubq1:1:10 | 10 | 40123.3 | 76753.8 | 2419.8 |
| EXP-ANDge.Ubq1:1:6 | 12 | 42621.0 | 121751.3 | 3974.8 |
| EXP-ANDge.Ubq1:1:11 | 14 | 44358.5 | 87105.8 | 2687.1 |
| EXP-ANDge.Ubq1:1:12 | 16 | 48219.0 | 107762.1 | 3279.6 |
| EXP-ERIra.Ubq1:1:9 | 22 | 31253.0 | 171684.1 | 6476.1 |
| EXP-ERIra.Ubq1:1:10 | 25 | 7905.8 | 21235.6 | 462.4 |
| EXP-ERIra.Ubq1:1:8 | 27 | 39935.8 | 173766.6 | 5320.3 |
| EXP-ERIra.Ubq1:1:11 | 29 | 34141.3 | 111626.8 | 3377.6 |
| EXP-ERIra.Ubq1:1:12 | 31 | 11540.3 | 42362.1 | 1045.3 |
| EXP-SETit.Ubq1:1:5 | 117 | 20496.5 | 88695.8 | 2358.8 |
| EXP-SETit.Ubq1:1:7 | 123 | 75728.5 | 185223.8 | 4723.1 |
| EXP-SETit.Ubq1:1:6 | 124 | 44148.3 | 161216.3 | 4962.1 |
| EXP-Sv.Ubq1:1:7 | 128 | 15043.8 | 74670.6 | 1888.3 |
| EXP-Sv.Ubq1:1:8 | 132 | 31997.8 | 113787.1 | 3219.8 |
| EXP-Sv.Ubq1:1:10 | 134 | 38952.8 | 220208.6 | 7011.3 |
| EXP-Zm.UbqM1:1:6 | 137 | 30528.3 | 90113.1 | 2453.6 |
| EXP-Zm.UbqM1:1:7 | 141 | 34986.3 | 105724.7 | 2553.8 |
| EXP-Sb.Ubq4:1:2 | 151 | 9982.3 | 72593.8 | 2171.6 |
| EXP-Sb.Ubq6:1:2 | 153 | 33689.0 | 114709.6 | 3879.6 |
| EXP-Cl.Ubq1:1:10 | 98 | 50622.3 | 107084.3 | 2621.3 |

To compare the relative activity of each EXP sequence GUS values were expressed as a ratio of GUS to luciferase activity and normalized with respect to the expression levels observed for EXP-Os.Act1:1:1 and EXP-CaMV.35S-enh+Ta.Lhcb1+Os.Act1:1:1. Table 9 below shows the GUS/RLuc ratios of expression normalized with respect to EXP-Os.Act1:1:1 and EXP-CaMV.35S-enh+Ta.Lhcb1+Os.Act1:1:1 driven expression in corn protoplasts. Table 10 below shows the GUS/FLuc ratios of expression normalized with respect to EXP-Os.Act1:1:1 and EXP-CaMV.35S-enh+Ta.Lhcb1+Os.Act1:1:1 driven expression in corn protoplasts.

TABLE 9

GUS/RLuc and GUS/FLuc ratios of expression normalized with respect to EXP-CaMV.35S-enh + Ta.Lhcb1 + Os.Act1:1:1 (SEQ ID NO: 163) in corn protoplasts.

| EXP sequence | SEQ ID NO: | GUS/RLuc Relative to EXP-CaMV.35S-enh + Ta.Lhcb1 + Os.Act1:1:1 | GUS/FLuc Relative to EXP-CaMV.35S-enh + Ta.Lhcb1 + Os.Act1:1:1 |
|---|---|---|---|
| EXP-Os.Act1:1:9 | 179 | 0.16 | 0.14 |
| P-CAMV.35S-ENH-1:1:102/L-CAMV.35S-1:1:2 | 169 | 0.33 | 0.30 |
| EXP-CaMV.35S-enh + Ta.Lhcb1 + Os.Act1:1:1 | 163 | 1.00 | 1.00 |
| EXP-CaMV.35S-enh + Zm.DnaK:1:1 | 170 | 3.22 | 2.58 |
| EXP-ANDge.Ubq1:1:7 | 5 | 7.72 | 5.64 |
| EXP-ANDge.Ubq1:1:10 | 10 | 5.75 | 4.06 |
| EXP-ANDge.Ubq1:1:6 | 12 | 3.85 | 2.62 |
| EXP-ANDge.Ubq1:1:11 | 14 | 5.60 | 4.04 |
| EXP-ANDge.Ubq1:1:12 | 16 | 4.92 | 3.60 |
| EXP-ERIra.Ubq1:1:9 | 22 | 2.00 | 1.18 |
| EXP-ERIra.Ubq1:1:10 | 25 | 4.09 | 4.18 |
| EXP-ERIra.Ubq1:1:8 | 27 | 2.53 | 1.84 |
| EXP-ERIra.Ubq1:1:11 | 29 | 3.36 | 2.47 |
| EXP-ERIra.Ubq1:1:12 | 31 | 2.99 | 2.70 |
| EXP-SETit.Ubq1:1:5 | 117 | 2.54 | 2.13 |
| EXP-SETit.Ubq1:1:7 | 123 | 4.49 | 3.92 |
| EXP-SETit.Ubq1:1:6 | 124 | 3.01 | 2.18 |
| EXP-Sv.Ubq1:1:7 | 128 | 2.21 | 1.95 |
| EXP-Sv.Ubq1:1:8 | 132 | 3.09 | 2.43 |
| EXP-Sv.Ubq1:1:10 | 134 | 1.94 | 1.36 |
| EXP-Zm.UbqM1:1:6 | 137 | 3.72 | 3.05 |
| EXP-Zm.UbqM1:1:7 | 141 | 3.64 | 3.35 |
| EXP-Sb.Ubq4:1:2 | 151 | 1.51 | 1.13 |
| EXP-Sb.Ubq6:1:2 | 153 | 3.23 | 2.13 |
| EXP-Cl.Ubq1:1:10 | 98 | 5.20 | 4.73 |

TABLE 10

GUS/RLuc and GUS/FLuc ratios of expression normalized with respect to EXP-Os.Act1:1:9 (SEQ ID NO: 179) in corn leaf protoplasts.

| EXP sequence | SEQ ID NO: | GUS/RLuc Relative to EXP-Os.Act1:1:9 | GUS/FLuc Relative to EXP-Os.Act1:1:9 |
|---|---|---|---|
| EXP-Os.Act1:1:9 | 179 | 1.00 | 1.00 |
| P-CAMV.35S-ENH-1:1:102/L-CAMV.35S-1:1:2 | 169 | 2.07 | 2.10 |
| EXP-CaMV.35S-enh + Ta.Lhcb1 + Os.Act1:1:1 | 163 | 6.23 | 7.09 |
| EXP-CaMV.35S-enh + Zm.DnaK:1:1 | 170 | 20.07 | 18.29 |
| EXP-ANDge.Ubq1:1:7 | 5 | 48.05 | 39.99 |
| EXP-ANDge.Ubq1:1:10 | 10 | 35.78 | 28.76 |
| EXP-ANDge.Ubq1:1:6 | 12 | 23.96 | 18.60 |
| EXP-ANDge.Ubq1:1:11 | 14 | 34.85 | 28.64 |
| EXP-ANDge.Ubq1:1:12 | 16 | 30.62 | 25.50 |
| EXP-ERIra.Ubq1:1:9 | 22 | 12.46 | 8.37 |
| EXP-ERIra.Ubq1:1:10 | 25 | 25.48 | 29.66 |
| EXP-ERIra.Ubq1:1:8 | 27 | 15.73 | 13.02 |
| EXP-ERIra.Ubq1:1:11 | 29 | 20.93 | 17.53 |
| EXP-ERIra.Ubq1:1:12 | 31 | 18.64 | 19.15 |
| EXP-SETit.Ubq1:1:5 | 117 | 15.82 | 15.07 |
| EXP-SETit.Ubq1:1:7 | 123 | 27.98 | 27.81 |
| EXP-SETit.Ubq1:1:6 | 124 | 18.74 | 15.43 |
| EXP-Sv.Ubq1:1:7 | 128 | 13.79 | 13.82 |
| EXP-Sv.Ubq1:1:8 | 132 | 19.25 | 17.24 |
| EXP-Sv.Ubq1:1:10 | 134 | 12.11 | 9.64 |
| EXP-Zm.UbqM1:1:6 | 137 | 23.19 | 21.58 |
| EXP-Zm.UbqM1:1:7 | 141 | 22.65 | 23.76 |
| EXP-Sb.Ubq4:1:2 | 151 | 9.41 | 7.97 |
| EXP-Sb.Ubq6:1:2 | 153 | 20.10 | 15.06 |
| EXP-Cl.Ubq1:1:10 | 98 | 32.35 | 33.50 |

As can be seen in Tables 9 and 10, nearly all of the EXP sequences were capable of driving GUS transgene expression in corn cells. Average GUS expression was higher for EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:

1:10 (SEQ ID NO: 134), EXP-Zm.UbqM1:1:6 (SEQ ID NO: 137), EXP-Zm.UbqM1:1:7 (SEQ ID NO: 141), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) when compared to GUS expression driven by EXP-Os.Act1:1:1 or EXP-CaMV.35S-enh+Ta.Lhcb1+Os.Act1:1:1.

In a second set of experiments, a GUS cassette amplicon comprising the EXP sequence EXP-Zm.UbqM1:1:8 (SEQ ID NO: 145) was compared to the control amplicons, PCR0145942 (EXP-Os.Act1:1:9, SEQ ID NO: 179) and PCR0145944 (EXP-CaMV.35S-enh+Zm.DnaK:1:1, SEQ ID NO: 170) with respect to GUS expression. GUS expression driven by the EXP sequence EXP-Zm.UbqM1:1:8 was higher than that of the two controls. Table 11 below shows the mean GUS and luciferase values determined for each amplicon. Table 12 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 11

Mean GUS and Luciferase activity in transformed corn leaf protoplast cells.

| Amplicon | EXP sequence | SEQ ID NO: | GUS | RLuc | FLuc |
|---|---|---|---|---|---|
| PCR0145942 | EXP-Os.Act1:1:9 | 179 | 1512.25 | 190461 | 11333.8 |
| PCR0145944 | EXP-CaMV.35S-enh + Zm.DnaK:1:1 | 170 | 41176.5 | 330837 | 13885.8 |
| PCR0145916 | EXP-Zm.UbqM1:1:8 | 145 | 79581.5 | 330756 | 15262.5 |

TABLE 12

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.06 | 0.04 |
| EXP-CaMV.35S-enh + Zm.DnaK:1:1 | 170 | 15.68 | 22.22 | 1.00 | 1.00 |
| EXP-Zm.UbqM1:1:8 | 145 | 30.30 | 39.08 | 1.93 | 1.76 |

In a third set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK:1:1 (SEQ ID NO: 170). Table 13 below shows the mean GUS and luciferase values determined for each amplicon. Table 14 below shows the GUS/RLuc ratios of expression normalized with respect to EXP-Os.Act1:1:9 and EXP-CaMV.35S-enh+Zm.DnaK:1:1 driven expression in corn protoplasts.

TABLE 13

Mean GUS and Luciferase activity in transformed corn leaf protoplast cells.

| Amplicon ID | EXP sequence | SEQ ID NO: | GUS | RLuc |
|---|---|---|---|---|
| PCR0145942 | EXP-Os.Act1:1:9 | 179 | 9445.25 | 929755 |
| PCR0145944 | EXP-CaMV.35S-enh + Zm.DnaK:1:1 | 170 | 78591.25 | 445127 |
| PCR0146628 | EXP-ANDge.Ubq1:1:8 | 8 | 192056.75 | 972642 |
| PCR0145922 | EXP-Cl.Ubq1:1:10 | 98 | 175295.25 | 395563 |
| PCR0145945 | EXP-Cl.Ubq1:1:13 | 114 | 173674.5 | 402966 |
| PCR0145946 | EXP-Cl.Ubq1:1:14 | 115 | 185987.5 | 390052 |
| PCR0145947 | EXP-Cl.Ubq1:1:15 | 116 | 9435 | 320749 |

TABLE 14

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh + Zm.DnaK:1:1 | 170 | 17.38 | 1.00 |
| EXP-ANDge.Ubq1:1:8 | 8 | 19.44 | 1.12 |
| EXP-Cl.Ubq1:1:10 | 98 | 43.62 | 2.51 |
| EXP-Cl.Ubq1:1:13 | 114 | 42.43 | 2.44 |
| EXP-Cl.Ubq1:1:14 | 115 | 46.94 | 2.70 |
| EXP-Cl.Ubq1:1:15 | 116 | 2.90 | 0.17 |

As can be seen in Table 14 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+Zm.DnaK:1:1 (SEQ ID NO: 170) but higher than the control, EXP-Os.Act1:1:9 (SEQ ID NO: 179).

In a fourth set of experiments, amplicon GUS transgene cassettes were made as described above and assayed for expression driven by the EXP sequences, EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-Os.Act1:1:9 (SEQ ID NO: 179) and EXP-CaMV.35S-enh+Zm.DnaK:1:1 (SEQ ID NO: 170). Table 15 below shows the mean GUS and luciferase values determined for each amplicon. Table 16 below shows the GUS/RLuc and GUS/FLuc ratios of expression normalized with respect to EXP-Os.Act1:1:9 and EXP-CaMV.35S-enh+Zm.DnaK:1:1 driven expression in corn protoplasts.

TABLE 15

Mean GUS and Luciferase activity in transformed corn leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 5333.5 | 171941.75 | 77817.88 |
| PCR0145944 | EXP-CaMV.35S-enh + Zm.DnaK:1:1 | 170 | 88517 | 177260.25 | 54207.38 |
| PCR0145922 | EXP-Cl.Ubq1:1:10 | 98 | 130125.75 | 194216 | 32055 |
| pMON146750 | EXP-Cl.Ubq1:1:16 | 93 | 134101.75 | 182317.5 | 32434.5 |
| pMON146751 | EXP-Cl.Ubq1:1:17 | 97 | 107122.5 | 151783.25 | 51354.38 |

TABLE 16

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in corn leaf protoplasts.

| Amplicon ID | EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|---|
| PCR0145942 | EXP-Os.Act1:1:9 | 179 | 1.00 | 1.00 | 0.06 | 0.04 |
| PCR0145944 | EXP-CaMV.35S-enh + Zm.DnaK:1:1 | 170 | 16.10 | 23.83 | 1.00 | 1.00 |
| PCR0145922 | EXP-Cl.Ubq1:1:10 | 98 | 21.60 | 59.23 | 1.34 | 2.49 |
| pMON146750 | EXP-Cl.Ubq1:1:16 | 93 | 23.71 | 60.32 | 1.47 | 2.53 |
| pMON146751 | EXP-Cl.Ubq1:1:17 | 97 | 22.75 | 30.43 | 1.41 | 1.28 |

As can be seen in Table 16, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fifth set of experiments, amplicon GUS transgene cassettes were made as described above assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+Os.Act1:1:1 (SEQ ID NO: 163). Table 17 below shows the mean GUS and luciferase values determined for each amplicon. Table 18 below shows the GUS/RLuc ratios of expression normalized with respect to EXP-Os.Act1:1:9 and EXP-CaMV.35S-enh+Ta.Lhcb1+Os.Act1:1:1 driven expression in corn protoplasts.

TABLE 17

Mean GUS and Luciferase activity in transformed corn leaf protoplast cells.

| Template | Amplicon | EXP sequence | SEQ ID NO: | GUS | RLuc |
|---|---|---|---|---|---|
| pMON65328 | PCR0145943 | EXP-CaMV.35S-enh + Ta.Lhcb1 + Os.Act1:1:1 | 163 | 70352.00 | 79028.75 |

TABLE 17-continued

Mean GUS and Luciferase activity in transformed corn leaf protoplast cells.

| Template | Amplicon | EXP sequence | SEQ ID NO: | GUS | RLuc |
|---|---|---|---|---|---|
| pMON25455 | PCR0145942 | EXP-Os.Act1:1:9 | 179 | 33155.25 | 92337.00 |
| pMON131962 | pMON131962 | EXP-Zm.UbqM1:1:11 | 149 | 18814.75 | 33663.00 |
| pMON132047 | pMON132047 | EXP-Cl.Ubq1:1:23 | 108 | 15387.50 | 40995.50 |

TABLE 18

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in corn leaf protoplasts.

| Amplicon | EXP sequence | SEQ ID NO: | GUS/RLuc relative to EXP-Os.Act1:1:9 | GUS/RLuc relative to EXP-CaMV.35S-enh + Ta.Lhcb1 + Os.Act1:1:1 |
|---|---|---|---|---|
| PCR0145943 | EXP-CaMV.35S-enh + Ta.Lhcb1 + Os.Act1:1:1 | 163 | 2.48 | 1.00 |
| PCR0145942 | EXP-Os.Act1:1:9 | 179 | 1.00 | 0.40 |
| pMON131962 | EXP-Zm.UbqM1:1:11 | 149 | 1.56 | 0.63 |
| pMON132047 | EXP-Cl.Ubq1:1:23 | 108 | 1.05 | 0.42 |

As can be seen in Table 18 above, the EXP sequences, EXP-Zm.UbqM1:1:11 (SEQ ID NO: 149) and EXP-Cl.Ubq1:1:23 (SEQ ID NO: 108) were able to drive GUS expression in corn leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

The efficacy of regulatory elements driving GUS expression from amplicons can be similarly studied in sugarcane leaf protoplasts. For instance, sugarcane protoplasts may be transformed with DNA amplicons derived from plant expression vectors containing an EXP sequence, driving expression of the β-glucuronidase (GUS) transgene, and compared to leaf protoplast in which expression of GUS is driven by known constitutive promoters. Likewise, regulatory elements driving CP4 expression from amplicons in corn or wheat protoplasts may be similarly studied.

Example 4

Analysis of Regulatory Elements Driving GUS in Wheat Protoplasts Using GUS Transgene Cassette Amplicons Wheat leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Wheat protoplast cells derived from leaf tissue were transformed using methods known in the art with amplicons produced from amplification of GUS transgene cassettes comprising plant expression vectors to compare expression of a transgene (GUS) driven by the EXP sequences listed in Tables 10-11 with that of known constitutive promoters with methodology as described in a previous example (Example 3), using the same GUS cassette amplicons as that used for assay in Corn in Example 3 above. Control GUS cassette amplicons and Luciferase plasmids used for wheat protoplast transformation were also the same as those presented in the previous example and provided in Table 7 above in Example 3. Likewise, negative controls were used for the determination of GUS and luciferase background, as described above. Wheat leaf protoplasts were transformed using a PEG-based transformation method, as described in Example 3 above. Table 19 lists mean GUS and LUC activity seen in transformed wheat leaf protoplast cells, and Table 20 shows normalized GUS/RLuc ratios of expression in wheat protoplasts.

TABLE 19

Mean GUS and Luciferase activity in transformed wheat leaf protoplast cells.

| EXP sequence | SEQ ID NO: | GUS | RLuc | GUS/RLuc |
|---|---|---|---|---|
| EXP-Os.Act1:1:9 | 179 | 2976.33 | 53334.8 | 0.0558047 |
| P-CAMV.35S-ENH-1:1:102/L-CAMV.35S-1:1:2 | 169 | 1431.33 | 55996.1 | 0.0255612 |
| EXP-CaMV.35S-enh + Ta.Lhcb1 + Os.Act1:1:1 | 163 | 29299.3 | 50717.4 | 0.5776973 |
| EXP-CaMV.35S-enh + Zm.DnaK:1:1 | 170 | 34294.3 | 63307.9 | 0.5417066 |
| EXP-ANDge.Ubq1:1:7 | 5 | 68444.3 | 60329.1 | 1.1345158 |
| EXP-ANDge.Ubq1:1:10 | 10 | 60606.3 | 60659.4 | 0.9991245 |
| EXP-ANDge.Ubq1:1:6 | 12 | 33386.3 | 56712.1 | 0.5886984 |
| EXP-ANDge.Ubq1:1:11 | 14 | 43237.3 | 48263.4 | 0.8958609 |
| EXP-ANDge.Ubq1:1:12 | 16 | 51712.7 | 64702.8 | 0.7992341 |
| EXP-ERIra.Ubq1:1:9 | 22 | 20998.3 | 60273.4 | 0.3483845 |
| EXP-ERIra.Ubq1:1:10 | 25 | 17268.3 | 25465.4 | 0.6781084 |
| EXP-ERIra.Ubq1:1:8 | 27 | 34635.7 | 59467.1 | 0.5824341 |
| EXP-ERIra.Ubq1:1:11 | 29 | 28979 | 56153.8 | 0.516065 |
| EXP-ERIra.Ubq1:1:12 | 31 | 41409.7 | 55152.4 | 0.7508221 |
| EXP-SETit.Ubq1:1:5 | 117 | 39427.7 | 57463.1 | 0.6861388 |
| EXP-SETit.Ubq1:1:7 | 123 | 108091 | 49330.4 | 2.191169 |
| EXP-SETit.Ubq1:1:6 | 124 | 58703 | 46110.1 | 1.2731047 |
| EXP-Sv.Ubq1:1:7 | 128 | 29330 | 43367.1 | 0.676319 |
| EXP-Sv.Ubq1:1:8 | 132 | 53359 | 40076.4 | 1.3314306 |
| EXP-Sv.Ubq1:1:10 | 134 | 49122.7 | 53180.8 | 0.9236922 |
| EXP-Zm.UbqM1:1:6 | 137 | 37268 | 54088.1 | 0.6890239 |
| EXP-Zm.UbqM1:1:7 | 141 | 51408 | 47297.4 | 1.0869087 |
| EXP-Sb.Ubq4:1:2 | 151 | 35660.3 | 62591.7 | 0.5697347 |
| EXP-Sb.Ubq6:1:2 | 153 | 27543 | 57826.4 | 0.4763046 |
| EXP-Cl.Ubq1:1:10 | 98 | 54493.3 | 41964.1 | 1.2985699 |

TABLE 20

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in wheat leaf protoplasts.

| EXP sequence | SEQ ID NO: | GUS/RLuc Relative to EXP-Os.Act1:1:9 | GUS/RLuc Relative to EXP-CaMV.35S-enh + Ta.Lhcb1 + Os.Act1:1:1 |
|---|---|---|---|
| EXP-Os.Act1:1:9 | 179 | 1.00 | 0.10 |
| P-CAMV.35S-ENH-1:1:102/L-CAMV.35S-1:1:2 | 169 | 0.46 | 0.04 |
| EXP-CaMV.35S-enh + Ta.Lhcb1 + Os.Act1:1:1 | 163 | 10.35 | 1.00 |
| EXP-CaMV.35S-enh + Zm.DnaK:1:1 | 170 | 9.71 | 0.94 |
| EXP-ANDge.Ubq1:1:7 | 5 | 20.33 | 1.96 |
| EXP-ANDge.Ubq1:1:10 | 10 | 17.90 | 1.73 |
| EXP-ANDge.Ubq1:1:6 | 12 | 10.55 | 1.02 |
| EXP-ANDge.Ubq1:1:11 | 14 | 16.05 | 1.55 |
| EXP-ANDge.Ubq1:1:12 | 16 | 14.32 | 1.38 |
| EXP-ERIra.Ubq1:1:9 | 22 | 6.24 | 0.60 |
| EXP-ERIra.Ubq1:1:10 | 25 | 12.15 | 1.17 |
| EXP-ERIra.Ubq1:1:8 | 27 | 10.44 | 1.01 |
| EXP-ERIra.Ubq1:1:11 | 29 | 9.25 | 0.89 |
| EXP-ERIra.Ubq1:1:12 | 31 | 13.45 | 1.30 |
| EXP-SETit.Ubq1:1:5 | 117 | 12.30 | 1.19 |
| EXP-SETit.Ubq1:1:7 | 123 | 39.26 | 3.79 |
| EXP-SETit.Ubq1:1:6 | 124 | 22.81 | 2.20 |
| EXP-Sv.Ubq1:1:7 | 128 | 12.12 | 1.17 |
| EXP-Sv.Ubq1:1:8 | 132 | 23.86 | 2.30 |
| EXP-Sv.Ubq1:1:10 | 134 | 16.55 | 1.60 |
| EXP-Zm.UbqM1:1:6 | 137 | 12.35 | 1.19 |
| EXP-Zm.UbqM1:1:7 | 141 | 19.48 | 1.88 |
| EXP-Sb.Ubq4:1:2 | 151 | 10.21 | 0.99 |
| EXP-Sb.Ubq6:1:2 | 153 | 8.54 | 0.82 |
| EXP-Cl.Ubq1:1:10 | 98 | 23.27 | 2.25 |

As can be seen in Table 20 above, nearly all of the EXP sequences were capable of driving GUS transgene expression in wheat cells. GUS transgene expression driven by EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbqM1:1:7 (SEQ ID NO: 141), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) was much higher than GUS expression driven by EXP-Os.Act1:1:9. GUS expression of the amplicons in wheat leaf protoplast cells relative to EXP-CaMV.35S-enh+Ta.Lhcb1+Os.Act1:1:1 was slightly different from the expression observed in corn protoplast cells. Each of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sv.Ubq1:1:7 (SEQ ID NO: 128), EXP-Sv.Ubq1:1:8 (SEQ ID NO: 132), EXP-Sv.Ubq1:1:10 (SEQ ID NO: 134), EXP-Zm.UbqM1:1:6 (SEQ ID NO: 137), EXP-Zm.UbqM1:1:7 (SEQ ID NO: 141) and EXP-Cl.Ubq1:1:10 (SEQ ID NO: 98) demonstrated higher levels of GUS expression relative to EXP-CaMV.35S-enh+Ta.Lhcb1+Os.Act1:1:1. The EXP sequences EXP-ERIra.Ubq1:1:9 (SEQ ID NO: 22), EXP-ERIra.Ubq1:1:11 (SEQ ID NO: 29), EXP-Sb.Ubq4:1:2 (SEQ ID NO: 151) and EXP-Sb.Ubq6:1:2 (SEQ ID NO: 153) demonstrated lower levels of GUS expression relative to EXP-CaMV.35S-enh+Ta.Lhcb1+Os.Act1:1:1.

In a second set of experiments, amplicon GUS transgene cassettes were made as described above and assayed for expression driven by the EXP sequences, EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116). The amplicons were comprised of an EXP sequence operably linked to the GUS-1 coding sequence which was operably linked to the T-AGRtu.nos-1:1:13 3' UTR. Expression was compared to the controls EXP-Os.Act1:1:9 (SEQ ID NO: 179) and EXP-CaMV.35S-enh+Zm.DnaK: 1:1 (SEQ ID NO: 170). Table 21 below shows the mean GUS and luciferase values determined for each amplicon. Table 22 below shows the GUS/RLuc ratios of expression normalized with respect to EXP-Os.Act1:1:9 and EXP-CaMV.35S-enh+Zm.DnaK:1:1 driven expression in corn protoplasts.

TABLE 21

Mean GUS and Luciferase activity in transformed wheat leaf protoplast cells.

| Amplicon ID | EXP sequence | SEQ ID NO: | GUS | RLuc |
|---|---|---|---|---|
| PCR0145942 | EXP-Os.Act1:1:9 | 179 | 1234 | 176970.5 |
| PCR0145944 | EXP-CaMV.35S-enh + Zm.DnaK:1:1 | 170 | 12883.5 | 119439 |
| PCR0146628 | EXP-ANDge.Ubq1:1:8 | 8 | 38353.3 | 171535.3 |
| PCR0145922 | EXP-Cl.Ubq1:1:10 | 98 | 34938 | 154245.8 |
| PCR0145945 | EXP-Cl.Ubq1:1:13 | 114 | 32121 | 122220.8 |
| PCR0145946 | EXP-Cl.Ubq1:1:14 | 115 | 56814 | 143318.3 |
| PCR0145947 | EXP-Cl.Ubq1:1:15 | 116 | 1890.5 | 167178.5 |

TABLE 22

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in wheat leaf protoplasts.

| EXP sequence | SEQ ID NO: | GUS/RLuc relative to EXP-Os.Act1:1:9 | GUS/RLuc relative to EXP-CaMV.35S-enh + Zm.DnaK:1:1 |
|---|---|---|---|
| EXP-Os.Act1:1:9 | 179 | 1.00 | 0.06 |
| EXP-CaMV.35S-enh + Zm.DnaK:1:1 | 170 | 15.47 | 1.00 |
| EXP-ANDge.Ubq1:1:8 | 8 | 32.07 | 2.07 |
| EXP-Cl.Ubq1:1:10 | 98 | 32.48 | 2.10 |
| EXP-Cl.Ubq1:1:13 | 114 | 37.69 | 2.44 |
| EXP-Cl.Ubq1:1:14 | 115 | 56.85 | 3.68 |
| EXP-Cl.Ubq1:1:15 | 116 | 1.62 | 0.10 |

As can be seen in Table 22 above, the EXP sequences EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) are capable of driving transgene expression. Expression driven by EXP-ANDge.Ubq1:1:8 (SEQ ID NO: 8), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) was higher than that of both controls. Expression driven by EXP-Cl.Ubq1:1:15 (SEQ ID NO: 116) was lower than EXP-CaMV.35S-enh+

Zm.DnaK:1:1 (SEQ ID NO: 170) but higher than the control, EXP-Os.Act1:1:9 (SEQ ID NO: 179).

In a third set of experiments, amplicon GUS transgene cassettes were made as described above to assay expression driven by the EXP sequences, EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97). Expression was compared to the controls EXP-Os.Act1:1:9 (SEQ ID NO: 179) and EXP-CaMV.35S-enh+Zm.DnaK: 1:1 (SEQ ID NO: 170). Table 23 below shows the mean GUS and luciferase values determined for each amplicon. Table 24 below shows the GUS/RLuc and GUS/FLuc ratios of expression normalized with respect to EXP-Os.Act1:1:9 and EXP-CaMV.35S-enh+ Zm.DnaK:1:1 driven expression in corn protoplasts.

TABLE 23

Mean GUS and Luciferase activity in transformed wheat leaf protoplast cells.

| Amplicon ID | EXP sequence | SEQ ID NO: | GUS | RLuc | FLuc |
|---|---|---|---|---|---|
| PCR0145942 | EXP-Os.Act1:1:9 | 179 | 478 | 46584.5 | 2709.75 |
| PCR0145944 | EXP-CaMV.35S-enh + Zm.DnaK:1:1 | 170 | 8178.5 | 43490.8 | 2927.25 |
| PCR0145922 | EXP-Cl.Ubq1:1:10 | 98 | 22068.3 | 47662.3 | 1289 |
| pMON146750 | EXP-Cl.Ubq1:1:16 | 93 | 34205 | 45064.5 | 1379.63 |
| pMON146751 | EXP-Cl.Ubq1:1:17 | 97 | 31758 | 45739.3 | 2820.75 |

TABLE 24

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in wheat leaf protoplasts.

| Amplicon ID | EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|---|
| PCR0145942 | EXP-Os.Act1:1:9 | 179 | 1.00 | 1.00 | 0.05 | 0.06 |
| PCR0145944 | EXP-CaMV.35S-enh + Zm.DnaK:1:1 | 170 | 18.33 | 15.84 | 1.00 | 1.00 |
| PCR0145922 | EXP-Cl.Ubq1:1:10 | 98 | 45.12 | 97.05 | 2.46 | 6.13 |
| pMON146750 | EXP-Cl.Ubq1:1:16 | 93 | 73.97 | 140.55 | 4.04 | 8.87 |
| pMON146751 | EXP-Cl.Ubq1:1:17 | 97 | 67.67 | 63.82 | 3.69 | 4.03 |

As can be seen in Table 24 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive transgene expression. Expression driven by each of the EXP sequences was higher than that of both controls.

In a fourth set of experiments, amplicon GUS transgene cassettes were made as described above to assay expression driven by the EXP sequences, EXP-Zm.UbqM1:1:11 (SEQ ID NO: 149) and EXP-Cl.Ubq1:1:23 (SEQ ID NO: 108). Expression was compared to the controls EXP-Os.Act1:1:9 (SEQ ID NO: 179) and EXP-CaMV.35S-enh+Ta.Lhcb1+ Os.Act1:1:1 (SEQ ID NO: 163). Table 25 below shows the mean GUS and luciferase values determined for each amplicon. Table 26 below shows the GUS/RLuc ratios of expression normalized with respect to EXP-Os.Act1:1:9 and EXP-CaMV.35S-enh+Ta.Lhcb1+Os.Act1:1:1 driven expression in corn protoplasts.

TABLE 25

Mean GUS and Luciferase activity in transformed wheat leaf protoplast cells.

| Template | Amplicon ID | EXP sequence | SEQ ID NO: | GUS | RLuc |
|---|---|---|---|---|---|
| pMON65328 | PCR0145943 | EXP-CaMV.35S-enh + Ta.Lhcb1 + Os.Act1:1:1 | 163 | 67459.13 | 11682.00 |
| pMON25455 | PCR0145942 | EXP-Os.Act1:1:9 | 179 | 56618.33 | 16654.83 |
| pMON131962 | pMON131962 | EXP-Zm.UbqM1:1:11 | 149 | 53862.13 | 10313.75 |
| pMON132047 | pMON132047 | EXP-Cl.Ubq1:1:23 | 108 | 38869.38 | 12279.00 |

TABLE 26

GUS/RLuc ratios of expression normalized with respect to EXP-Os.Act1:1:9 (SEQ ID NO: 179) and EXP-CaMV.35S-enh + Ta.Lhcb1 + Os.Act1:1:1 (SEQ ID NO: 163) in wheat leaf protoplasts.

| Amplicon ID | EXP sequence | SEQ ID NO: | GUS/RLuc relative to EXP-Os.Act1:1:9 | GUS/RLuc relative to EXP-CaMV.35S-enh + Ta.Lhcb1 + Os.Act1:1:1 |
|---|---|---|---|---|
| PCR0145943 | EXP-CaMV.35S-enh + Ta.Lhcb1 + Os.Act1:1:1 | 163 | 1.70 | 1.00 |
| PCR0145942 | EXP-Os.Act1:1:9 | 179 | 1.00 | 0.59 |
| pMON131962 | EXP-Zm.UbqM1:1:11 | 149 | 1.54 | 0.90 |
| pMON132047 | EXP-Cl.Ubq1:1:23 | 108 | 0.93 | 0.55 |

As can be seen in Table 26 above, the EXP sequences, EXP-Zm.UbqM1:1:11 (SEQ ID NO: 149) and EXP-Cl.Ubq1:1:23 (SEQ ID NO: 108) were able to drive GUS expression in wheat leaf protoplasts. Expression was similar to that of the control, EXP-Os.Act1:1:9 (SEQ ID NO: 179) and lower than that of EXP-CaMV.35S-enh+Ta.Lhcb1+Os.Act1:1:1 (SEQ ID NO: 163).

Example 5

Analysis of Regulatory Elements Driving GUS in Sugarcane Protoplasts Using GUS Transgene Cassette Amplicons Sugarcane leaf protoplasts were transformed with DNA amplicons derived from plant expression vectors containing an EXP sequence, driving expression of the β-glucuronidase (GUS) transgene, and compared to leaf protoplast in which expression of GUS was driven by known constitutive promoters.

Sugarcane protoplast cells derived from leaf tissue were transformed using a PEG-based transformation method, as described in Example 3 above with amplicons produced from amplification of GUS transgene cassettes comprising plant expression vectors to compare expression of a transgene (GUS) driven by one of EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) and presented in Table 27 below, with that of known constitutive promoters.

TABLE 27

GUS plant expression amplicons and corresponding plasmid construct amplicon template and EXP sequence.

| Amplicon ID | Amplicon Template | EXP sequence | SEQ ID NO: |
|---|---|---|---|
| PCR0145942 | pMON25455 | EXP-Os.Act1:1:9 | 179 |
| PCR0145944 | pMON81552 | EXP-CaMV.35S-enh + Zm.DnaK:1:1 | 170 |
| PCR0145892 | pMON136264 | EXP-ANDge.Ubq1:1:7 | 5 |
| PCR0145815 | pMON136264 | EXP-ANDge.Ubq1:1:10 | 10 |
| PCR0145893 | pMON136259 | EXP-ANDge.Ubq1:1:6 | 12 |
| PCR0145817 | pMON136264 | EXP-ANDge.Ubq1:1:11 | 14 |
| PCR0145819 | pMON136264 | EXP-ANDge.Ubq1:1:12 | 16 |
| PCR0145896 | pMON136263 | EXP-ERIra.Ubq1:1:9 | 22 |
| PCR0145820 | pMON136263 | EXP-ERIra.Ubq1:1:10 | 25 |
| PCR0145897 | pMON136258 | EXP-ERIra.Ubq1:1:8 | 27 |
| PCR0145821 | pMON136263 | EXP-ERIra.Ubq1:1:11 | 29 |
| PCR0145822 | pMON136263 | EXP-ERIra.Ubq1:1:12 | 31 |
| PCR0145922 | pMON140889 | EXP-Cl.Ubq1:1:10 | 98 |
| PCR0145945 | pMON140889 | EXP-Cl.Ubq1:1:13 | 114 |
| PCR0145946 | pMON140889 | EXP-Cl.Ubq1:1:14 | 115 |
| PCR0145947 | pMON140889 | EXP-Cl.Ubq1:1:15 | 116 |

Control GUS cassette amplicons and Luciferase plasmids used for sugarcane protoplast transformation were also the same as those presented in Examples 2 through 4 and provided in Table 7 above in Example 3. Likewise, negative controls were used for the determination of GUS and luciferase background, as described above. Table 28 lists mean GUS and Luc activity seen in transformed sugarcane leaf protoplast cells, and Table 29 shows normalized GUS/RLuc ratios of expression in sugarcane leaf protoplasts.

TABLE 28

Mean GUS and Luciferase activity in transformed wheat leaf protoplast cells.

| EXP sequence | SEQ ID NO: | GUS | RLuc | FLuc |
|---|---|---|---|---|
| EXP-Os.Act1:1:9 | 179 | 6667.5 | 3024.5 | 1129.25 |
| EXP-CaMV.35S-enh + Zm.DnaK:1:1 | 170 | 14872.8 | 5171 | 2019.5 |
| EXP-ANDge.Ubq1:1:7 | 5 | 15225 | 4618.25 | 1775.75 |
| EXP-ANDge.Ubq1:1:10 | 10 | 17275.3 | 4333 | 1678 |
| EXP-ANDge.Ubq1:1:6 | 12 | 17236 | 5633.25 | 2240 |
| EXP-ANDge.Ubq1:1:11 | 14 | 22487.8 | 6898.25 | 2878 |
| EXP-ANDge.Ubq1:1:12 | 16 | 22145.3 | 6240.25 | 2676.5 |
| EXP-ERIra.Ubq1:1:9 | 22 | 16796.5 | 7759.75 | 3179 |
| EXP-ERIra.Ubq1:1:10 | 25 | 16267.5 | 5632.75 | 2436.75 |
| EXP-ERIra.Ubq1:1:8 | 27 | 25351 | 9019.5 | 4313.5 |
| EXP-ERIra.Ubq1:1:11 | 29 | 16652.3 | 3672.25 | 1534 |
| EXP-ERIra.Ubq1:1:12 | 31 | 12654.5 | 3256.75 | 1261.5 |
| EXP-Cl.Ubq1:1:10 | 98 | 22383.8 | 7097.5 | 3109.25 |
| EXP-Cl.Ubq1:1:13 | 114 | 14532.3 | 2786.5 | 1198.25 |

TABLE 28-continued

Mean GUS and Luciferase activity in transformed wheat leaf protoplast cells.

| EXP sequence | SEQ ID NO: | GUS | RLuc | FLuc |
|---|---|---|---|---|
| EXP-Cl.Ubq1:1:14 | 115 | 19244.5 | 3455.25 | 1475 |
| EXP-Cl.Ubq1:1:15 | 116 | 6676.5 | 3870.25 | 1497.75 |

TABLE 29

GUS/RLuc and GUS/FLuc ratios of expression normalized with respect to EXP-Os.Act1:1:9 (SEQ ID NO: 179) and EXP-CaMV.35S-enh + Zm.DnaK:1:1 (SEQ ID NO: 170) in sugarcane leaf protoplasts.

| EXP sequence | SEQ ID NO: | GUS/RLuc relative to EXP-Os.Act1:1:9 | GUS/FLuc relative to EXP-Os.Act1:1:9 | GUS/RLuc relative to EXP-CaMV.35S-enh + Zm.DnaK:1:1 | GUS/FLuc relative to EXP-CaMV.35S-enh + Zm.DnaK:1:1 |
|---|---|---|---|---|---|
| EXP-Os.Act1:1:9 | 179 | 1.00 | 1.00 | 0.77 | 0.80 |
| EXP-CaMV.35S-enh + Zm.DnaK:1:1 | 170 | 1.30 | 1.25 | 1.00 | 1.00 |
| EXP-ANDge.Ubq1:1:7 | 5 | 1.50 | 1.45 | 1.15 | 1.16 |
| EXP-ANDge.Ubq1:1:10 | 10 | 1.81 | 1.74 | 1.39 | 1.40 |
| EXP-ANDge.Ubq1:1:6 | 12 | 1.39 | 1.30 | 1.06 | 1.04 |
| EXP-ANDge.Ubq1:1:11 | 14 | 1.48 | 1.32 | 1.13 | 1.06 |
| EXP-ANDge.Ubq1:1:12 | 16 | 1.61 | 1.40 | 1.23 | 1.12 |
| EXP-ERIra.Ubq1:1:9 | 22 | 0.98 | 0.89 | 0.75 | 0.72 |
| EXP-ERIra.Ubq1:1:10 | 25 | 1.31 | 1.13 | 1.00 | 0.91 |
| EXP-ERIra.Ubq1:1:8 | 27 | 1.27 | 1.00 | 0.98 | 0.80 |
| EXP-ERIra.Ubq1:1:11 | 29 | 2.06 | 1.84 | 1.58 | 1.47 |
| EXP-ERIra.Ubq1:1:12 | 31 | 1.76 | 1.70 | 1.35 | 1.36 |
| EXP-Cl.Ubq1:1:10 | 98 | 1.43 | 1.22 | 1.10 | 0.98 |
| EXP-Cl.Ubq1:1:13 | 114 | 2.37 | 2.05 | 1.81 | 1.65 |
| EXP-Cl.Ubq1:1:14 | 115 | 2.53 | 2.21 | 1.94 | 1.77 |
| EXP-Cl.Ubq1:1:15 | 116 | 0.78 | 0.75 | 0.60 | 0.61 |

As can be seen in Table 29 above, the EXP sequences EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were all capable of driving transgene expression in sugarcane protoplasts. The EXP sequences, EXP-ANDge.Ubq1:1:7 (SEQ ID NO: 5), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:10 (SEQ ID NO: 25), EXP-ERIra.Ubq1:1:8 (SEQ ID NO: 27), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) expressed GUS higher than EXP-CaMV.35S-enh+Zm.DnaK:1:1 (SEQ ID NO: 170) in this experiment.

Example 6

Analysis of Regulatory Elements Driving CP4 in Corn Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151) and EXP-Sb.Ubq6:1:2 (SEQ ID NO: 153) in driving expression of glyphosate tolerance gene CP4 in corn protoplasts. These EXP sequences were cloned into plant binary transformation plasmid constructs using methods known in the art. The resulting plant expression vectors contained a right border region from *A. tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from *A. tumefaciens* (B-AGRtu.left border). The resulting plasmid constructs were used to transform corn leaf protoplasts cells using methods known in the art.

Plasmid constructs listed in Table 30, with EXP sequences as defined in Table 1, were utilized. Three control plasmids (pMON30098, pMON42410, and pMON30167), with known constitutive regulatory elements driving either CP4 or GFP, were constructed and used to compare the relative CP4 expression levels driven by these EXP sequences with CP4 expression driven by known constitutive expression elements. Two other plasmids (pMON19437 and pMON63934) were also used as described above to evaluate transformation efficiency and viability. Each plasmid contains a specific luciferase coding sequence driven by a constitutive EXP sequence.

Corn leaf protoplasts were transformed using a PEG-based transformation method, as described in Example 2 above. Measurements of both CP4 and luciferase were conducted similarly to Example 2 above. The average levels of CP4 protein expression expressed as part per million (ppm) is shown in Table 30 below.

TABLE 30

Average CP4 protein expression in corn leaf protoplasts.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON42410 | EXP-CaMV.35S-enh + Ta.Lhcb1 + Os.Act1:1:1 | 163 | 34.1 | 15.6 |
| pMON30167 | EXP-Os.Act1:1:1 | 164 | 40.4 | 11.6 |
| pMON129203 | EXP-Sv.Ubq1:1:7 | 128 | 45.2 | 6.2 |
| pMON129204 | EXP-Sv.Ubq1:1:8 | 132 | 101.9 | 13.8 |
| pMON129205 | EXP-Sv.Ubq1:1:9 | 133 | 71.1 | 8.7 |
| pMON129210 | EXP-Zm.UbqM1:1:6 | 137 | 137.1 | 14.8 |
| pMON129211 | EXP-Zm.UbqM1:1:8 | 145 | 136.5 | 12.3 |
| pMON129212 | EXP-Zm.UbqM1:1:7 | 141 | 170.2 | 18.1 |
| pMON129200 | EXP-SETit.Ubq1:1:5 | 117 | 44.3 | 9.5 |
| pMON129201 | EXP-SETit.Ubq1:1:7 | 123 | 105.1 | 8.4 |
| pMON129202 | EXP-SETit.Ubq1:1:6 | 124 | 124.9 | 33.7 |
| pMON129219 | EXP-Sb.Ubq4:1:2 | 151 | 14.3 | 1 |
| pMON129218 | EXP-Sb.Ubq6:1:2 | 153 | 75.7 | 8.9 |

As can be seen in Table 30, EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124) and EXP-Sb.Ubq6:1:2 (SEQ ID NO: 153) drove expression of the CP4 transgene at levels close to or higher than CP4 expression levels driven by EXP-CaMV.35S-enh+Ta.Lhcb1+Os.Act1:1:1 and EXP-Os.Act1:1:1. The EXP sequence, EXP-Sb.Ubq4:1:2 (SEQ ID NO: 151) demonstrated the ability to drive expression of CP4, but the level of expression was lower than that of the constitutive controls.

Similar data to that above may also be obtained from plants stably transformed with plasmid constructs described above, for instance, plants of progeny generation(s) $R_0$, $R_1$ or $F_1$ or later. Likewise, expression from other plasmid constructs may be studied. For instance, pMON141619, comprises the EXP sequence EXP-ANDge.Ubq1:1:8, while pMON142862 is comprised of the EXP sequence EXP-ERIra.Ubq1:1:8. These and other constructs may be analyzed in this manner.

Example 7

Analysis of Regulatory Elements Driving CP4 in Corn Protoplasts using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in corn protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from A. tumefaciens. The resulting amplicons were used to transform corn leaf protoplasts cells.

Corn leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 31 and 32 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed corn leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 31 below.

TABLE 31

Average CP4 protein expression in corn leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.0 | 0.0 |
| pMON30098 | | GFP (negative control) | | 0.0 | 0.0 |
| pMON19469 | PCR24 | EXP-CaMV.35S-enh + Zm.DnaK:1:1 | 170 | 605.5 | 27.6 |
| pMON30167 | PCR25 | EXP-Os.Act1:1:1 | 164 | 50.6 | 14.2 |
| pMON140896 | PCR41 | EXP-ANDge.Ubq1:1:7 | 5 | 459.0 | 60.9 |
| pMON140917 | PCR42 | EXP-ANDge.Ubq1:1:8 | 8 | 258.2 | 38.4 |
| pMON140897 | PCR43 | EXP-ANDge.Ubq1:1:10 | 10 | 324.8 | 21.6 |

TABLE 31-continued

Average CP4 protein expression in corn leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON140898 | PCR44 | EXP-ANDge.Ubq1:1:6 | 12 | 394.9 | 66.4 |
| pMON140899 | PCR45 | EXP-ANDge.Ubq1:1:11 | 14 | 508.7 | 89.6 |
| pMON140900 | PCR46 | EXP-ANDge.Ubq1:1:12 | 16 | 329.3 | 14.5 |
| pMON140904 | PCR50 | EXP-ERIra.Ubq1:1:9 | 22 | 148.6 | 24.4 |
| pMON140905 | PCR51 | EXP-ERIra.Ubq1:1:10 | 25 | 215.8 | 22.6 |
| pMON140906 | PCR52 | EXP-ERIra.Ubq1:1:8 | 27 | 376.6 | 44.1 |
| pMON140907 | PCR53 | EXP-ERIra.Ubq1:1:11 | 29 | 459.9 | 104.7 |
| pMON140908 | PCR54 | EXP-ERIra.Ubq1:1:12 | 31 | 221.6 | 15.9 |
| pMON140913 | PCR19 | EXP-Cl.Ubq1:1:10 | 98 | 287.8 | 50.9 |
| pMON140914 | PCR20 | EXP-Cl.Ubq1:1:13 | 114 | 585.8 | 47.9 |
| pMON140915 | PCR21 | EXP-Cl.Ubq1:1:14 | 115 | 557.5 | 76.6 |
| pMON140916 | PCR22 | EXP-Cl.Ubq1:1:15 | 116 | 33.2 | 9.5 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were lower than that of EXP-CaMV.35S-enh+Zm.DnaK:1:1 (SEQ ID NO: 170).

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed corn leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 32

Average CP4 protein expression in corn leaf protoplasts.

| Amplicon Template | Amplicon ID | EXP sequence | SEQ ID NO: | Maize Leaf CP4 mg/total protein Avg | Maize Leaf CP4 mg/total protein StdDev |
|---|---|---|---|---|---|
| pMON30167 | PCR25 | EXP-Os.Act1:1:1 | 164 | 12.2 | 1.69 |
| pMON140913 | PCR19 | EXP-Cl.Ubq1:1:10 | 98 | 307.5 | 24.21 |
| pMON142748 | pMON142748 | EXP-Cl.Ubq1:1:16 | 93 | 245.95 | 30.14 |
| pMON142749 | pMON142749 | EXP-Cl.Ubq1:1:17 | 97 | 302.85 | 25.32 |

As can be seen in Table 32 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 8

Analysis of Regulatory Elements Driving CP4 in Wheat Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151) and EXP-Sb.Ubq6:1:2 (SEQ ID NO: 153) to drive CP4 expression in wheat leaf protoplasts. These EXP sequences were cloned into plant binary transformation plasmid constructs using methods known in the art, and as described in Examples 2 and 5 above.

Three control plasmids (pMON30098, pMON42410, as previously described, and pMON43647 comprising a right border region from *Agrobacterium tumefaciens* with EXP-Os.Act1+CaMV.35S.2xA1-B3+Os.Act1:1:1 (SEQ ID NO: 138) operably linked 5' to a plastid targeted glyphosate tolerance coding sequence (CP4, U.S. RE39247), operably linked 5' to T-AGRtu.nos-1:1:13, and a left border region (B-AGRtu.left border) with known constitutive regulatory elements driving either CP4 or GFP were constructed as outlined in Example 5.

Wheat leaf protoplasts were transformed using a PEG-based transformation method as described in the previous examples with the exception that $1.5 \times 10^5$ protoplast cells per assay were used. Assays of luciferase and CP4 transgene expression were performed as described in Example 6 above. The mean CP4 expression levels determined by CP4 ELISA are presented in Table 34 below.

TABLE 34

Mean CP4 Protein Expression in Wheat Leaf Protoplast Cells.

| Plasmid | EXP sequence | SEQ ID NO: | CP4 Average ppm | CP4 STDEV ppm |
|---|---|---|---|---|
| No DNA | No DNA | | 0 | 0 |
| pMON30098 | GFP | | 0 | 0 |
| pMON43647 | EXP-Os.Act1 + CaMV.35S.2xA1-B3 + Os.Act1:1:1 | 172 | 656.2 | 124.5 |
| pMON42410 | EXP-CaMV.35S-enh + Ta.Lhcb1 + Os.Act1::1:1 | 163 | 438.3 | 78.9 |
| pMON30167 | EXP-Os.Act1:1:1 | 164 | 583 | 107.4 |
| pMON129203 | EXP-Sv.Ubq1:1:7 | 128 | 156.9 | 25.1 |
| pMON129204 | EXP-Sv.Ubq1:1:8 | 132 | 39.5 | 7 |
| pMON129205 | EXP-Sv.Ubq1:1:9 | 133 | 154.5 | 56.5 |
| pMON129210 | EXP-Zm.UbqM1:1:6 | 137 | 1500 | 0 |
| pMON129211 | EXP-Zm.UbqM1:1:8 | 145 | 199.7 | 64.9 |
| pMON129212 | EXP-Zm.UbqM1:1:7 | 141 | 234.6 | 66.9 |
| pMON129200 | EXP-SETit.Ubq1:1:5 | 117 | 725.7 | 149.7 |
| pMON129201 | EXP-SETit.Ubq1:1:7 | 123 | 64.9 | 14.5 |
| pMON129202 | EXP-SETit.Ubq1:1:6 | 124 | 122.9 | 48.7 |
| pMON129219 | EXP-Sb.Ubq4:1:2 | 151 | 113.1 | 32.8 |

The total amount of CP4 expression in wheat protoplasts driven by the EXP sequences and the known constitutive EXP sequence EXP-CaMV.35S-enh+Ta.Lhcb1+Os.Act1:1:1 demonstrated different levels of CP4 expression in wheat protoplasts when compared to corn protoplasts.

Several EXP sequences drove CP4 expression at lower levels in wheat protoplasts than the known constitutive EXP sequences EXP-Os.Act1+CaMV.35S.2xA1-B3+Os.Act1:1:1 and EXP-CaMV.35S-enh+Ta.Lhcb1+Os.Act1:1:1. Two EXP sequences, EXP-Zm.UbqM1:1:6 (SEQ ID NO: 137), and EXP-SETit.Ubq1:1:5 (SEQ ID NO: 117), provide higher levels of CP4 expression in wheat protoplasts than the known constitutive, EXP sequences in this assay. EXP-Zm.UbqM1:1:2 drove expression of CP4 at the highest level, with expression levels being 2.2 to 3.4 fold higher than EXP-Os.Act1+CaMV.35S.2xA1-B3+Os.Act1:1:1 and EXP-CaMV.35S-enh+Ta.Lhcb1+Os.Act1:1:1, respectively. All EXP sequences assayed demonstrated the capacity to drive expression of CP4 in wheat cells.

Example 9

Analysis of Regulatory Elements Driving CP4 in Wheat Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115), EXP-Cl.Ubq1:1:15 (SEQ ID NO: 116), EXP-Cl.Ubq1:1:16 (SEQ ID NO: 93) and EXP-Cl.Ubq1:1:17 (SEQ ID NO: 97) in driving expression of glyphosate tolerance gene CP4 in wheat protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate tolerant EPSPS coding sequence (CP4, U.S. RE39247), operably linked 5' to the T-AGRtu.nos-1:1:13 3' UTR and a left border region from A. tumefaciens. The resulting amplicons were used to transform corn leaf protoplasts cells.

Wheat leaf protoplasts were transformed using a PEG-based transformation method, as described in Example 2 above. Measurements of both CP4 were conducted using an ELISA-based assay. The average levels of CP4 protein expression expressed as part per million (ppm) is shown in Tables 35 and 36 below.

In a first series of experiments, expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Tables 35 below.

TABLE 35

Average CP4 protein expression in wheat leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| | | no DNA | | 0.00 | 0.00 |
| pMON30098 | | GFP (negative control) | | 0.00 | 0.00 |
| pMON19469 | PCR24 | EXP-CaMV.35S-enh + Zm.DnaK:1:1 | 170 | 76.11 | 18.65 |
| pMON30167 | PCR25 | EXP-Os.Act1:1:1 | 164 | 3.83 | 0.73 |
| pMON140896 | PCR41 | EXP-ANDge.Ubq1:1:7 | 5 | 103.46 | 16.31 |
| pMON140917 | PCR42 | EXP-ANDge.Ubq1:1:8 | 8 | 61.48 | 1.99 |
| pMON140897 | PCR43 | EXP-ANDge.Ubq1:1:10 | 10 | 62.65 | 4.58 |
| pMON140898 | PCR44 | EXP-ANDge.Ubq1:1:6 | 12 | 48.74 | 3.09 |
| pMON140899 | PCR45 | EXP-ANDge.Ubq1:1:11 | 14 | 54.91 | 3.50 |

TABLE 35-continued

Average CP4 protein expression in wheat leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON140900 | PCR46 | EXP-ANDge.Ubq1:1:12 | 16 | 42.81 | 5.97 |
| pMON140904 | PCR50 | EXP-ERIra.Ubq1:1:9 | 22 | 31.26 | 1.69 |
| pMON140905 | PCR51 | EXP-ERIra.Ubq1:1:10 | 25 | 49.82 | 5.96 |
| pMON140906 | PCR52 | EXP-ERIra.Ubq1:1:8 | 27 | 37.43 | 4.52 |
| pMON140907 | PCR53 | EXP-ERIra.Ubq1:1:11 | 29 | 27.17 | 0.96 |
| pMON140908 | PCR54 | EXP-ERIra.Ubq1:1:12 | 31 | 17.41 | 4.13 |
| pMON140913 | PCR19 | EXP-Cl.Ubq1:1:10 | 98 | 66.66 | 13.45 |
| pMON140914 | PCR20 | EXP-Cl.Ubq1:1:13 | 114 | 79.42 | 10.74 |
| pMON140915 | PCR21 | EXP-Cl.Ubq1:1:14 | 115 | 75.53 | 9.32 |
| pMON140916 | PCR22 | EXP-Cl.Ubq1:1:15 | 116 | 0.00 | 0.00 |

As can be seen in Table 31 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were able to drive CP4 expression. All of the EXP sequences with the exception of one EXP-Cl.Ubq1:1:15 (SEQ ID NO: 116) drove CP4 expression levels at a much higher level than the constitutive control, EXP-Os.Act1:1:1 (SEQ ID NO: 164). Expression levels were around the same level or lower than that of EXP-CaMV.35S-enh+Zm.DnaK:1:1 (SEQ ID NO: 170) for most of the EXP sequences.

In a second series of experiments, expression of CP4 driven by amplicons comprised of the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were assayed in transformed wheat leaf protoplasts and compared to CP4 expression levels driven by the constitutive control, EXP-Os.Act1:1:1 (SEQ ID NO: 164). The average levels of CP4 protein expression expressed as part per million (ppm) is shown in Tables 32 below.

TABLE 36

Average CP4 protein expression in wheat leaf protoplasts.

| Amplicon Template | Amplicon ID | EXP sequence | SEQ ID NO: | Maize Leaf CP4 mg/total protein Avg | Maize Leaf CP4 mg/total protein StdDev |
|---|---|---|---|---|---|
| pMON30167 | PCR25 | EXP-Os.Act1:1:1 | 164 | 15.84 | 2.12 |
| pMON140913 | PCR19 | EXP-Cl.Ubq1:1:10 | 98 | 736.32 | 79.56 |
| pMON142748 | pMON142748 | EXP-Cl.Ubq1:1:16 | 93 | 593.72 | 80.22 |
| pMON142749 | pMON142749 | EXP-Cl.Ubq1:1:17 | 97 | 763.95 | 86.94 |

As can be seen in Table 36 above, the EXP sequences EXP-Cl.Ubq1:1:10 (SEQ ID NO: 98), EXP-Cl.Ubq1:1:16 (SEQ ID NO: 93) and EXP-Cl.Ubq1:1:17 (SEQ ID NO: 97) were able to drive CP4 expression. Expression levels driven by all three EXP sequences were higher than that of the constitutive control, EXP-Os.Act1:1:1 (SEQ ID NO: 164).

Example 10

Analysis of Regulatory Elements Driving CP4 in Sugarcane Protoplasts

This example illustrates the ability of EXP-Sv.Ubq1:1:7 (SEQ ID NO: 128), EXP-Sv.Ubq1:1:8 (SEQ ID NO: 132), EXP-Sv.Ubq1:1:9 (SEQ ID NO: 133), EXP-Zm.UbqM1:1:6 (SEQ ID NO: 137), EXP-Zm.UbqM1:1:8 (SEQ ID NO: 145), EXP-Zm.UbqM1:1:7 (SEQ ID NO: 141), EXP-SETit.Ubq1:1:5 (SEQ ID NO: 117), EXP-SETit.Ubq1:1:7 (SEQ ID NO: 123), EXP-SETit.Ubq1:1:6 (SEQ ID NO: 124), EXP-Sb.Ubq4:1:2 (SEQ ID NO: 151), EXP-Sb.Ubq6:1:2 (SEQ ID NO: 153) and EXP-Cl.Ubq1:1:10 (SEQ ID NO: 98) in driving expression of CP4 in sugar cane leaf protoplasts. The EXP sequences were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 (SEQ ID NO: 127) or T-CaMV.35S-1:1:1 (SEQ ID NO: 140) 3' UTR and a left border region from *A. tumefaciens* (B-AGRtu.left border). The resulting plasmid constructs were used to transform sugarcane leaf protoplasts cells using PEG transformation method.

Plasmid constructs pMON129203, pMON12904, pMON12905, pMON129210, pMON129211, pMON129212, pMON129200, pMON129201, pMON129202, pMON129219, and pMON129218 are as described in Table 12 above.

Three control plasmids (pMON30167 described above; pMON130803 also comprising EXP-Os.Act1:1:1 (SEQ ID NO: 164); and pMON132804 comprising EXP-P-CaMV.35S-enh-1:1:13/L-CaMV.35S-1:1:2/I-Os.Act1-1:1:19 (SEQ ID NO: 139), with known constitutive regulatory elements driving CP4 were constructed and used to compare the relative CP4 expression levels driven by the ubiquitin EXP sequences listed in Table 37 below.

Sugarcane leaf protoplasts were transformed using a PEG-based transformation method. The mean CP4 expression levels determined by CP4 ELISA are presented in Table 37 below.

the glyphosate tolerance gene CP4 in sugarcane protoplasts. These EXP sequences were cloned into plant binary transformation plasmid constructs. The resulting plant expression vectors were used as amplification templates to produce a transgene cassette amplicon comprised of an ubiquitin EXP sequence operably linked 5' to a plastid targeted glyphosate

TABLE 37

Mean CP4 Protein Expression in Sugarcane Leaf Protoplast Cells.

| | | | Experiment 1 | | Experiment 2 | |
|---|---|---|---|---|---|---|
| Plasmid Construct | EXP sequence | SEQ ID NO: | CP4 Average ppm | CP4 STDEV ppm | CP4 Average ppm | CP4 STDEV ppm |
| pMON132804 | EXP-P-CaMV.35S-enh-1:1:13/L-CaMV.35S-1:1:2/I-Os.Act1-1:1:19 | 173 | 557.97 | 194.05 | 283.63 | 95.8 |
| pMON30167 | EXP-Os.Act1:1:1 | 164 | 57.15 | 20.99 | 18.36 | 5.41 |
| pMON130803 | EXP-Os.Act1:1:1 | 164 | 34.26 | 1.61 | 16.57 | 3.71 |
| pMON129203 | EXP-Sv.Ubq1:1:7 | 128 | 89.2 | 32.46 | 56.86 | 9.55 |
| pMON129204 | EXP-Sv.Ubq1:1:8 | 132 | 87.2 | 45.87 | 98.46 | 12.93 |
| pMON129205 | EXP-Sv.Ubq1:1:9 | 133 | 263.57 | 70.14 | 72.53 | 9.25 |
| pMON129210 | EXP-Zm.UbqM1:1:6 | 137 | 353.08 | 29.16 | 199.31 | 41.7 |
| pMON129211 | EXP-Zm.UbqM1:1:8 | 145 | 748.18 | 15.1 | 411.24 | 17.12 |
| pMON129212 | EXP-Zm.UbqM1:1:7 | 141 | 454.88 | 75.77 | 215.06 | 23.22 |
| pMON129200 | EXP-SETit.Ubq1:1:5 | 117 | 150.74 | 63.21 | 91.71 | 41.35 |
| pMON129201 | EXP-SETit.Ubq1:1:7 | 123 | 119.57 | 58.1 | 102.72 | 31.12 |
| pMON129202 | EXP-SETit.Ubq1:1:6 | 124 | 43.79 | 25.77 | 97.63 | 46.07 |
| pMON129219 | EXP-Sb.Ubq4:1:2 | 151 | 95.63 | 38.69 | | |
| pMON129218 | EXP-Sb.Ubq6:1:2 | 153 | 343.34 | 119.2 | 179.75 | 51.16 |
| pMON129221 | EXP-Cl.Ubq1:1:10 | 98 | 374.8 | 205.28 | 258.93 | 38.03 |

As can be seen in Table 37 above, the EXP sequences demonstrated the ability to drive expression CP4 expression in sugarcane protoplasts. The levels of expression were similar to or greater than that of CP4 expression driven by EXP-Os.Act1:1:1 (SEQ ID NO: 164). One EXP sequence, EXP-Zm.UbqM1:1:8 (SEQ ID NO: 145), demonstrated higher levels of expression when compared to EXP-P-CaMV.35S-enh-1:1:13/L-CaMV.35S-1:1:2/I-Os.Act1-1:1:19 (SEQ ID NO: 139) in sugarcane protoplasts.

Example 11

Analysis of Regulatory Elements Driving CP4 in Sugarcane Protoplasts Using CP4 Transgene Cassette Amplicons This example illustrates the ability of EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) in driving expression of tolerant EPSPS coding sequence (CP4, U.S. RE39247), operably linked 5' to the T-AGRtu.nos-1:1:13 3' UTR and a left border region from A. tumefaciens. The resulting amplicons were used to transform sugarcane leaf protoplasts cells.

Sugarcane leaf protoplasts were transformed using a PEG-based transformation method, as described in Example 2 above. Measurements of both CP4 were conducted using an ELISA-based assay.

Expression of CP4 driven by amplicons comprised of the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114), EXP-Cl.Ubq1:1:14 (SEQ ID NO: 115) and EXP-Cl.Ubq1:1:15 (SEQ ID NO: 116) were assayed in transformed wheat leaf protoplasts and compared to CP4 expression levels driven by the constitutive controls, EXP-CaMV.35S-enh+Zm.DnaK:1:1 (SEQ ID NO: 170) and EXP-Os.Act1:1:1 (SEQ ID NO: 164). The average levels of CP4 protein expression expressed as part per million (ppm) is shown in Table 38 below.

TABLE 38

Average CP4 protein expression in sugarcane leaf protoplasts.

| Amplicon Template | Amplicon ID | EXP sequence | SEQ ID NO: | CP4 ng/mg total protein Average | CP4 ng/mg total protein STDEV |
|---|---|---|---|---|---|
| pMON19469 | PCR24 | EXP-CaMV.35S-enh + Zm.DnaK:1:1 | 170 | 99.6 | 7.2 |
| pMON30167 | PCR25 | EXP-Os.Act1:1:1 | 164 | 0.0 | 0.0 |
| pMON140896 | PCR41 | EXP-ANDge.Ubq1:1:7 | 5 | 21.9 | 3.3 |
| pMON140917 | PCR42 | EXP-ANDge.Ubq1:1:8 | 8 | 15.4 | 1.9 |
| pMON140897 | PCR43 | EXP-ANDge.Ubq1:1:10 | 10 | 20.7 | 2.2 |
| pMON140898 | PCR44 | EXP-ANDge.Ubq1:1:6 | 12 | 21.8 | 2.8 |
| pMON140899 | PCR45 | EXP-ANDge.Ubq1:1:11 | 14 | 36.9 | 7.2 |
| pMON140900 | PCR46 | EXP-ANDge.Ubq1:1:12 | 16 | 51.7 | 5.6 |
| pMON140904 | PCR50 | EXP-ERIra.Ubq1:1:9 | 22 | 10.3 | 1.1 |
| pMON140905 | PCR51 | EXP-ERIra.Ubq1:1:10 | 25 | 25.3 | 4.7 |
| pMON140906 | PCR52 | EXP-ERIra.Ubq1:1:8 | 27 | 29.9 | 4.6 |
| pMON140907 | PCR53 | EXP-ERIra.Ubq1:1:11 | 29 | 44.0 | 7.1 |
| pMON140908 | PCR54 | EXP-ERIra.Ubq1:1:12 | 31 | 37.0 | 5.4 |
| pMON140913 | PCR19 | EXP-Cl.Ubq1:1:10 | 98 | 19.2 | 1.3 |
| pMON140914 | PCR20 | EXP-Cl.Ubq1:1:13 | 114 | 20.5 | 2.1 |
| pMON140915 | PCR21 | EXP-Cl.Ubq1:1:14 | 115 | 23.2 | 1.6 |
| pMON140916 | PCR22 | EXP-Cl.Ubq1:1:15 | 116 | 0.0 | 0.0 |

As can be seen in Table 38 above, the EXP sequences EXP-ANDge.Ubq1:1:7 (SEQ ID NO: 5), EXP-ANDge.Ubq1:1:8 (SEQ ID NO: 8), EXP-ANDge.Ubq1:1:10 (SEQ ID NO: 10), EXP-ANDge.Ubq1:1:6 (SEQ ID NO: 12), EXP-ANDge.Ubq1:1:11 (SEQ ID NO: 14), EXP-ANDge.Ubq1:1:12 (SEQ ID NO: 16), EXP-ERIra.Ubq1:1:9 (SEQ ID NO: 22), EXP-ERIra.Ubq1:1:10 (SEQ ID NO: 25), EXP-ERIra.Ubq1:1:8 (SEQ ID NO: 27), EXP-ERIra.Ubq1:1:11 (SEQ ID NO: 29), EXP-ERIra.Ubq1:1:12 (SEQ ID NO: 31), EXP-Cl.Ubq1:1:10 (SEQ ID NO: 98), EXP-Cl.Ubq1:1:13 (SEQ ID NO: 114) and EXP-Cl.Ubq1:1:14 (SEQ ID NO: 115) were able to drive CP4 expression. EXP-Cl.Ubq1:1:15 (SEQ ID NO: 116) did not appear to express CP4 expression in this assay.

Example 12

Analysis of Regulatory Elements Driving GUS in Transgenic Corn

Corn plants were transformed with plant expression vectors containing a EXP sequences driving expression of the β-glucuronidase (GUS) transgene, and the resulting plants were analyzed for GUS protein expression. The ubiquitin EXP sequences were cloned into plant binary transformation plasmid constructs using methods known in the art.

The resulting plant expression vectors contain a right border region from A. tumefaciens, a first transgene cassette to assay the EXP sequence operably linked to a coding sequence for β-glucuronidase (GUS) that possesses the processable intron GUS-2, described above, operably linked 5' to the 3' UTR from the rice lipid transfer protein gene (T-Os.LTP-1:1:1, SEQ ID NO: 141); a second transgene selection cassette used for selection of transformed plant cells that confers resistance to the herbicide glyphosate (driven by the rice Actin 1 promoter), and a left border region from A. tumefaciens. The resulting plasmids were used to transform corn plants. Table 39 lists the plasmid designations, the EXP sequences and the SEQ ID NOs, which are also described in Table 1.

TABLE 39

Binary plant transformation plasmids and the associated EXP sequences.

| Plasmid Construct | EXP sequence | SEQ ID NO: | Data |
|---|---|---|---|
| pMON142865 | EXP-ANDge.Ubq1:1:8 | 8 | $R_0$ and $R_1$ |
| pMON142864 | EXP-ERIra.Ubq1:1:8 | 27 | $R_0$ and $R_1$ |
| pMON142729 | EXP-Cl.Ubq1:1:12 | 90 | $R_0$ |
| pMON142730 | EXP-Cl.Ubq1:1:11 | 95 | $R_0$ |
| pMON132047 | EXP-Cl.Ubq1:1:23 | 108 | $R_0$ |
| pMON132037 | EXP-SETit.Ubq1:1:10 | 119 | $R_0$ and $F_1$ |
| pMON131957 | EXP-SETit.Ubq1:1:11 | 125 | $F_1$ |
| pMON131958 | EXP-Sv.Ubq1:1:11 | 130 | $R_0$ and $F_1$ |
| pMON131959 | EXP-Sv.Ubq1:1:12 | 136 | $R_0$ |
| pMON131961 | EXP-Zm.UbqM1:1:10 | 139 | $R_0$ |
| pMON131963 | EXP-Zm.UbqM1:1:12 | 143 | $R_0$ |
| pMON131962 | EXP-Zm.UbqM1:1:11 | 149 | $R_0$ |
| pMON132932 | EXP-Sb.Ubq4:1:2 | 151 | $R_0$ |
| pMON132931 | EXP-Sb.Ubq6:1:3 | 155 | $R_0$ |
| pMON132974 | EXP-Sb.Ubq7:1:2 | 157 | $R_0$ and $F_1$ |

Plants were transformed using Agrobacterium-mediated transformations, for instance as described in U.S. Patent Application Publication 20090138985.

Histochemical GUS analysis was used for qualitative expression analysis of transformed plants. Whole tissue sections were incubated with GUS staining solution X-Gluc (5-bromo-4-chloro-3-indolyl-b-glucuronide) (1 milligram/milliliter) for an appropriate length of time, rinsed, and visually inspected for blue coloration. GUS activity was qualitatively determined by direct visual inspection or inspection under a microscope using selected plant organs and tissues. The $R_0$ plants are inspected for expression in the roots and leaves as well as the anther, silk and developing seed and embryo 21 days after pollination (21 DAP).

For quantitative analysis, total protein was extracted from selected tissues of transformed corn plants. One microgram of total protein was used with the fluorogenic substrate 4-methyleumbelliferyl-β-D-glucuronide (MUG) in a total reaction volume of 50 microliters. The reaction product, 4-methlyumbelliferone (4-MU), is maximally fluorescent at high pH, where the hydroxyl group is ionized. Addition of a basic solution of sodium carbonate simultaneously stops the assay and adjusts the pH for quantifying the fluorescent product. Fluorescence was measured with excitation at 365 nm, emission at 445 nm using a Fluoromax-3 (Horiba; Kyoto, Japan) with Micromax Reader, with slit width set at excitation 2 nm and emission 3 nm.

The average $R_0$ GUS expression observed for each transformation is presented in Tables 40 and 41 below. The $R_0$ GUS assay performed on transformants transformed with pMON131957 (EXP-SETit.Ubq1:1:11, SEQ ID NO:125) did not pass quality standards. These transformants were assayed at F1 generation and are presented further below in this example.

TABLE 40

Average $R_0$ GUS expression in root and leaf tissue.

| EXP sequence | SEQ ID NO: | V3 Root | V4 Root | V7 Root | VT Root | V3 Leaf | V4 Leaf | V7 Leaf | VT Leaf |
|---|---|---|---|---|---|---|---|---|---|
| EXP-ANDge.Ubq1:1:8 | 8 | nd | 255 | 199 | 70 | nd | 638 | 168 | 130 |
| EXP-ERIra.Ubq1:1:8 | 27 | nd | 477 | 246 | 62 | nd | 888 | 305 | 242 |
| EXP-Cl.Ubq1:1:12 | 90 | nd | 27 | 147 | 52 | nd | 75 | 189 | 199 |
| EXP-Cl.Ubq1:1:11 | 95 | nd | 28 | 77 | 50 | nd | 101 | 177 | 223 |
| EXP-Cl.Ubq1:1:23 | 108 | 0 | nd | 75 | 34 | 201 | nd | 194 | 200 |
| EXP-SETit.Ubq1:1:10 | 119 | 0 | nd | 29 | 57 | 58 | nd | 37 | 46 |
| EXP-Sv.Ubq1:1:11 | 130 | nd | nd | nd | 9 | 20 | nd | 55 | 29 |
| EXP-Sv.Ubq1:1:12 | 136 | 63 | nd | 0 | 28 | 184 | nd | 27 | 16 |
| EXP-Zm.UbqM1:1:10 | 139 | 0 | nd | 237 | 18 | 221 | nd | 272 | 272 |
| EXP-Zm.UbqM1:1:12 | 143 | 0 | nd | 21 | 43 | 234 | nd | 231 | 196 |
| EXP-Zm.UbqM1:1:11 | 149 | 124 | nd | 103 | 112 | 311 | nd | 369 | 297 |
| EXP-Sb.Ubq4:1:2 | 151 | 125 | nd | 0 | 95 | 233 | nd | 150 | 88 |
| EXP-Sb.Ubq6:1:3 | 155 | 154 | nd | 13 | 128 | 53 | nd | 39 | 55 |
| EXP-Sb.Ubq7:1:2 | 157 | 37 | nd | 22 | 18 | 165 | nd | 89 | 177 |

TABLE 41

Average $R_0$ GUS expression in corn reproductive organs (anther, silk) and developing seed (embryo and endosperm).

| EXP sequence | SEQ ID NO: | VT Anther | VT/R1 Silk | 21 DAP Embryo | 21 DAP Endosperm |
|---|---|---|---|---|---|
| EXP-ANDge.Ubq1:1:8 | 8 | 247 | 256 | 24 | 54 |
| EXP-ERIra.Ubq1:1:8 | 27 | 246 | 237 | 36 | 61 |
| EXP-Cl.Ubq1:1:12 | 90 | 420 | 121 | 26 | 220 |
| EXP-Cl.Ubq1:1:11 | 95 | 326 | 227 | 41 | 221 |
| EXP-Cl.Ubq1:1:23 | 108 | 598 | 416 | 212 | 234 |
| EXP-SETit.Ubq1:1:10 | 119 | 132 | 85 | 50 | 63 |
| EXP-Sv.Ubq1:1:11 | 130 | 217 | 3 | 45 | 92 |
| EXP-Sv.Ubq1:1:12 | 136 | 120 | 21 | 49 | 112 |
| EXP-Zm.UbqM1:1:10 | 139 | 261 | 506 | 403 | 376 |
| EXP-Zm.UbqM1:1:12 | 143 | 775 | 362 | 253 | 247 |
| EXP-Zm.UbqM1:1:11 | 149 | 551 | 452 | 234 | 302 |
| EXP-Sb.Ubq4:1:2 | 151 | 213 | 0 | 25 | 79 |
| EXP-Sb.Ubq6:1:3 | 155 | 295 | 87 | 51 | 61 |
| EXP-Sb.Ubq7:1:2 | 157 | 423 | 229 | 274 | 90 |

In $R_0$ corn plants, GUS expression levels in the leaf and root differed amongst the ubiquitin EXP sequences. While all of the EXP sequences demonstrated the ability to drive GUS transgene expression in stably transformed plants, each EXP sequence demonstrated a unique pattern of expression relative to the others. For example, high levels of GUS expression were observed in early stages of root development (V4 and V7) for EXP-ANDge.Ubq1:1:8 (SEQ ID NO: 8) and EXP-ERIra.Ubq1:1:8 (SEQ ID NO: 27) and declined by VT stage. Root expression driven by EXP-Zm.UbqM1: 1:10 (SEQ ID NO: 139) demonstrated no expression at V3 but was high at V7 and then dropped by VT stage. Root expression driven by EXP-Zm.UbqM1:1:11 (SEQ ID NO: 149) was maintained to a similar level throughout development from stages V3, V7 through VT. Root expression was observed to increase from early development (V3/V4) to V7 stage and then drop from V7 to V8 stage in plants transformed with EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108). GUS expression levels showed dramatic differences in leaf tissue as well. The highest levels of leaf expression were conferred in early development (V3/V4) with EXP-ANDge.Ubq1:1:8 (SEQ ID NO: 8) and EXP-ERIra.Ubq1:1:8 (SEQ ID NO: 27) which decline at V7 through VT stage. GUS expression is retained from V3 through VT stage using EXP-Zm.UbqM1:1:10 (SEQ ID NO: 139), EXP-Zm.UbqM1:1:11 (SEQ ID NO: 149), EXP-Zm.UbqM1:1:12 (SEQ ID NO: 143) and EXP-Cl.Ubq1:1:23 (SEQ ID NO: 108); and to a lower extent using EXP-SETit.Ubq1:1:10 (SEQ ID NO: 119) and EXP-Sb.Ubq6:1:3 (SEQ ID NO: 155). Expression in the leaf increased from V3 to V7 to VT stage using EXP-Cl.Ubq1:1:12 (SEQ ID NO: 90), EXP-Cl.Ubq1:1:11 (SEQ ID NO: 95) and EXP-Cl.Ubq1:1:23 (SEQ ID NO: 108) while expression declined from V3 to VT stage using EXP-Sv.Ubq1:1:12 (SEQ ID NO: 136) and EXP-Sb.Ubq4:1:2 (SEQ ID NO: 151).

Likewise, with respect to reproductive tissue (anther and silk) and developing seed (21DAP embryo and endosperm) different patterns of expression were observed unique to each EXP sequence. For example, High levels of expression were observed in anther and silk as well as the developing seed using EXP-Zm.UbqM1:1:10 (SEQ ID NO: 139), EXP-Zm.UbqM1:1:11 (SEQ ID NO: 149), EXP-Zm.UbqM1:1:12 (SEQ ID NO: 143) and EXP-Cl.Ubq1:1:23 (SEQ ID NO: 108). Expression was high in the anther and silk but low in the developing seed using EXP-ANDge.Ubq1:1:8 (SEQ ID NO: 8) and EXP-ERIra.Ubq1:1:8 (SEQ ID NO: 27). Expression driven by EXP-Sb.Ubq7:1:2 (SEQ ID NO: 157) was high in reproductive tissue and high in the developing embryo but was lower in the developing endosperm. The EXP sequence, EXP-Sb.Ubq4:1:2 (SEQ ID NO: 151) only demonstrated expression in the anther but not in the silk and expressed much lower in the developing seed. EXP-Sv.Ubq1:1:11 (SEQ ID NO: 130) demonstrated a similar pattern as EXP-Sb.Ubq4:1:2 (SEQ ID NO: 151) with respect to reproductive tissue and developing seed, but whereas EXP-Sb.Ubq4:1:2 (SEQ ID NO: 151) showed expression in root and leaf tissues, EXP-Sv.Ubq1:1:11 (SEQ ID NO: 130) expressed much lower in these same tissues.

R₀ generation transformants, selected for single copy insertions were crossed with a non-transgenic LH244 line (resulting in $F_1$) or were self-pollinated (resulting in $R_1$) in order to produce an $F_1$ or $R_1$ population of seeds. In either case, heterozygous $F_1$ or $R_1$ plants were selected for study. GUS expression levels were measured in selected tissues over the course of development as previously described. The $F_1$ or $R_1$ tissues used for this study included: imbibed seed embryo, imbibed seed endosperm, root and coleoptide at 4 days after germination (DAG); leaf and root at V3 stage; root and mature leaf at V8 stage; root, mature leaves, VT stage (at tasseling, prior to reproduction) anther, pollen, leaf and senescing leaf; R1 cob, silk, root and internode; kernel 12 days after pollination (DAP) and; embryo and endosperm 21 and 38 DAP. Selected tissue samples were also analyzed for $F_1$ plants exposed to conditions of drought and cold stress for transformants comprising pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubq7:1:2, SEQ ID NO: 157). V3 root and leaf tissue was sampled after cold and drought exposure.

Drought stress was induced in $F_1$, V3 plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubq7:1:2, SEQ ID NO: 157) by withholding watering for 4 days allowing the water content to be reduced by at least 50% of the original water content of the fully watered plant. The drought protocol was comprised essentially of the following steps. V3 stage plants were deprived of water. As a corn plant experiences drought, the shape of the leaf will change from the usual healthy and unfolded appearance to a leaf demonstrating folding at the mid-rib vascular bundle and appearing V-shaped when viewed from the leaf tip to the stem. This change in morphology usually began to occur by about 2 days after the cessation of watering and was shown in earlier experiments to be associated with water loss of around 50% as measured by weight of pots prior to cessation of watering and weight of pots when the leaf curl morphology was observed in un-watered plants. Plants were considered to be under drought conditions, when the leaves showed wilting as evidenced by an inward curling (V-shape) of the leaf. This level of stress is considered to be a form of sub-lethal stress. Once each plant demonstrated drought induction as defined above, the plant was destroyed to acquire both root and leaf samples.

In addition to drought, $F_1$ V3 stage plants transformed with pMON132037 (EXP-SETit.Ubq1:1:10, SEQ ID NO: 119), pMON131957 (EXP-SETit.Ubq1:1:11, SEQ ID NO: 125), pMON131958 (EXP-Sv.Ubq1:1:11, SEQ ID NO: 130) and pMON132974 (EXP-Sb.Ubq7:1:2, SEQ ID NO: 157) were also exposed to conditions of cold to determine if the regulatory elements demonstrated cold-induced expression of GUS. Whole plants were assayed for induction of GUS expression under cold stress at V3 stage. V3 stage corn plants were exposed to a temperature of 12° C. in a growth chamber for 24 hours. Plants in the growth chamber were grown under a white light fluence of 800 micro moles per meter squared per second with a light cycle of ten hours of white light and fourteen hours of darkness. After cold exposure, leaf and root tissues were sampled for quantitative GUS expression.

GUS expression was measured as described above. The average $F_1$ GUS expression determined for each tissue sample is presented in Tables 42 and 43 below.

TABLE 42

Average $F_1$ GUS expression in plants transformed with pMON142864 and pMON142865.

| Organ | pMON142864 | pMON142865 |
|---|---|---|
| V3 Leaf | 86 | 74 |
| V3 Root | 41 | 52 |
| V8 Leaf | 109 | 123 |
| V8 Root | 241 | 252 |
| VT Flower, anthers | 168 | 208 |
| VT Leaf | 158 | 104 |
| R1 Cob | 171 | 224 |
| R1 silk | 314 | 274 |
| R1 Root | 721 | 308 |
| R1 internode | 428 | 364 |
| R2 Seed-12DAP | 109 | 72 |
| R3 Seed-21DAP-Embryo | 45 | 32 |
| R3 Seed-21DAP-Endosperm | 175 | 196 |
| R5 Seed-38DAP-Embryo | 163 | 58 |
| R5 Seed-38DAP-Endosperm | 90 | 69 |

TABLE 43

Average $F_1$ GUS expression in plants transformed with pMON132037, pMON131957, pMON131958 and pMON132974.

| Organ | pMON132037 | pMON131957 | pMON131958 | pMON132974 |
|---|---|---|---|---|
| Imbibed Seed Embryo | 536 | 285 | 288 | 1190 |
| Imbibed Seed Endosperm | 95 | 71 | 73 | 316 |
| Coleoptile-4 DAG | 218 | 60 | 143 | 136 |
| Root-4 DAG | 74 | 33 | 101 | 48 |
| V3 Leaf | 104 | 120 | 66 | 52 |
| V3 Root | 74 | 71 | 81 | 194 |
| V3 Leaf-cold | 73 | 15 | 72 | N/A |
| V3 Root-cold | 113 | 44 | 89 | 49 |
| V3 Leaf-drought | 97 | 344 | 103 | 157 |
| V3 Root-drought | 205 | 153 | 129 | 236 |
| V8 Leaf | 185 | 142 | 77 | 282 |
| V8 Root | 33 | 16 | 61 | 28 |
| VT Flower-anthers | 968 | 625 | 619 | 888 |

TABLE 43-continued

Average F₁ GUS expression in plants transformed with
pMON132037, pMON131957, pMON131958 and pMON132974.

| Organ | pMON132037 | pMON131957 | pMON131958 | pMON132974 |
|---|---|---|---|---|
| VT Leaf | 138 | 89 | 132 | 268 |
| VT Leaf-senescing | 121 | 100 | 156 | 345 |
| VT Pollen | 610 | 1119 | 332 | 4249 |
| R1 Cob | 291 | 70 | 168 | 127 |
| R1 silk | 164 | 124 | 167 | 101 |
| R1 Root | 36 | 39 | 39 | 21 |
| R1 internode | 255 | 89 | 232 | 141 |
| R2 Seed-12DAP | 138 | 170 | 165 | 169 |
| R3 Seed-21 DAP-Embryo | 94 | 97 | 489 | 389 |
| R3 Seed-21 DAP-Endosperm | 57 | 118 | 52 | 217 |
| R5 Seed-38 DAP-Embryo | 600 | 147 | 377 | 527 |
| R5 Seed-38 DAP-Endosperm | 58 | 36 | 57 | 106 |

In F₁ corn plants, GUS expression levels in the various tissues sampled differed amongst the ubiquitin EXP sequences. While all of the EXP sequences demonstrated the ability to drive GUS transgene expression in stably transformed F₁ corn plants, each EXP sequence demonstrated a unique pattern of expression relative to the others. For example, R1 root expression is about twice that for EXP-ERIra.Ubq1:1:8 (SEQ ID NO: 27) than EXP-ANDge.Ubq1:1:8 (SEQ ID NO: 8). GUS expression in the developing seed embryo at 38 DAP is almost three fold higher for EXP-ERIra.Ubq1:1:8 (SEQ ID NO: 27) than EXP-ANDge.Ubq1:1:8 (SEQ ID NO: 8). In contrast leaf and root expression at V3 and V8 stage is about the same for EXP-ERIra.Ubq1:1:8 (SEQ ID NO: 27) than EXP-ANDge.Ubq1:1:8 (SEQ ID NO: 8).

The F₁ GUS expression in imbided seeds (embryo and endosperm tissues) was much higher in plants transformed with EXP-Sb.Ubq7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Drought caused an increase in V3 root expression in plants transformed with EXP-SETit.Ubq1:1:10 (SEQ ID NO: 119), EXP-SETit.Ubq1:1:11 (SEQ ID NO: 125), EXP-Sv.Ubq1:1:11 (SEQ ID NO: 130) and EXP-Sb.Ubq7:1:2 (SEQ ID NO: 157), but only increased leaf expression in plants transformed with EXP-SETit.Ubq1:1:11 (SEQ ID NO: 125), EXP-Sv.Ubq1:1:11 (SEQ ID NO: 130) and EXP-Sb.Ubq7:1:2 (SEQ ID NO: 157). The drought enhanced V3 expression was greatest using EXP-SETit.Ubq1:1:11 (SEQ ID NO: 125). Pollen expression was also much higher in plants transformed with EXP-Sb.Ubq7:1:2 (SEQ ID NO: 157) than in those transformed with EXP-SETit.Ubq1:1:10 (SEQ ID NO: 119), EXP-SETit.Ubq1:1:11 (SEQ ID NO: 125) and EXP-Sv.Ubq1:1:11 (SEQ ID NO: 130). Expression in the R1 internode was greatest with EXP-SETit.Ubq1:1:10 (SEQ ID NO: 119) and EXP-Sv.Ubq1:1:11 (SEQ ID NO: 130) and least in plants transformed with EXP-SETit.Ubq1:1:11 (SEQ ID NO: 125).

Each EXP sequence demonstrated the ability to drive transgene expression in stably transformed corn plants. However, each EXP sequence had a pattern of expression for each tissue that was unique and offers an opportunity to select the EXP sequence which will best provide expression of a specific transgene depending upon the tissue expression strategy needed to achieve the desired results. This example demonstrates EXP sequences isolated from homologous genes do not necessarily behave equivalently in the transformed plant and that expression can only be determined through empirical investigation of the properties for each EXP sequence and cannot be predicted based upon the gene homology from which the promoter was derived.

Example 13

Analysis of Regulatory Elements Driving CP4 in Transgenic Corn

Corn plants were transformed with plant expression vectors containing EXP sequences driving expression of the CP4 transgene, and the resulting plants were analyzed for CP4 protein expression.

The EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:7 (SEQ ID NO: 141) were cloned into plant binary transformation plasmid constructs. The resulting vectors contained a right border region from *Agrobacterium tumefaciens*, an ubiquitin EXP sequence operably linked 5' to a plastid targeted glyphosate tolerant EPSPS coding sequence (CP4, U.S. RE39247), operably linked 5' to the T-AGRtu.nos-1:1:13 (SEQ ID NO: 127) 3' UTR and a left border region from *A. tumefaciens*. Table 44 below shows the plasmid constructs used to transform corn and the corresponding EXP sequences.

TABLE 44

CP4 plasmid constructs and corresponding
EXP sequences used to transform corn.

| Plasmid Construct | EXP sequence | SEQ ID NO: | Data |
|---|---|---|---|
| pMON141619 | EXP-ANDge.Ubq1:1:8 | 8 | R₀ and F₁ |
| pMON142862 | EXP-ERIra.Ubq1:1:8 | 27 | R₀ and F₁ |
| pMON129221 | EXP-Cl.Ubq1:1:10 | 98 | R₀ and F₁ |
| pMON129205 | EXP-Sv.Ubq1:1:9 | 133 | R₀ and F₁ |
| pMON129212 | EXP-Zm.UbqM1:1:7 | 141 | R₀ |

The resulting plasmids were used to transform corn plants. Transformed plants were selected for one or two copies of the inserted T-DNA and grown in the greenhouse. Selected tissues were sampled from the R₀ transformed plants at specific stages of development and CP4 protein levels were measured in those tissues using an CP4 ELISA assay. The average CP4 expression observed for each transformation is presented in Tables 45 and 46 below and graphically in FIG. 7.

TABLE 45

Average leaf and root CP4 expression in $R_0$ transformed corn plants.

| EXP sequence | SEQ ID NO: | V4 Leaf | V7 Leaf | VT Leaf | V4 Root | V7 Root | VT Root |
|---|---|---|---|---|---|---|---|
| EXP-ANDge.Ubq1:1:8 | 8 | 20.90 | 18.53 | 25.49 | 11.50 | 26.54 | 17.20 |
| EXP-ERIra.Ubq1:1:8 | 27 | 19.92 | 16.60 | 25.58 | 9.92 | 26.31 | 13.33 |
| EXP-Cl.Ubq1:1:10 | 98 | 10.70 | 12.49 | 17.42 | 7.56 | 13.95 | 6.68 |
| EXP-Sv.Ubq1:1:9 | 133 | 3.72 | 4.34 | 4.48 | 2.90 | 6.99 | 2.78 |
| EXP-Zm.UbqM1:1:7 | 141 | 13.42 | 21.89 | 38.78 | 9.56 | 16.69 | 11.15 |

TABLE 46

Average CP4 expression in reproductive tissue and developing seed in $R_0$ transformed corn plants.

| EXP sequence | SEQ ID NO: | VT Tassel | R1 Silk | R3 Embryo | R3 Endosperm |
|---|---|---|---|---|---|
| EXP-ANDge.Ubq1:1:8 | 8 | 24.14 | 5.55 | 7.29 | 4.91 |
| EXP-ERIra.Ubq1:1:8 | 27 | 19.20 | 10.27 | 12.60 | 4.70 |
| EXP-Cl.Ubq1:1:10 | 98 | 18.70 | 16.21 | 8.26 | 8.82 |
| EXP-Sv.Ubq1:1:9 | 133 | 7.10 | 4.72 | 3.13 | 1.74 |
| EXP-Zm.UbqM1:1:7 | 141 | 67.25 | 11.21 | 7.85 | 10.69 |

As can be seen in Tables 45 and 46, each of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:7 (SEQ ID NO: 141) was able to drive CP4 expression in all tissues sampled from the R₀ transformed plants. Higher expression of CP4 in the root and leaf of transformants comprising EXP-ANDge.Ubq1:1:8 (SEQ ID NO: 8) and EXP-ERIra.Ubq1:1:8 (SEQ ID NO: 27) driving CP4 than EXP-Cl.Ubq1:1:10 (SEQ ID NO: 98) driving CP4 may be related to the level of vegetative tolerance to glyphosate application as observed for these populations of transformants (see Example 14 below).

Each EXP sequence exhibited a unique expression pattern with respect to the level of expression for each tissue sampled. For example, while CP4 expression in leaf, root and tassel were similar for the EXP sequences, EXP-ANDge.Ubq1:1:8 (SEQ ID NO: 8) and EXP-ERIra.Ubq1:1:8 (SEQ ID NO: 27), expression in silk using EXP-ANDge.Ubq1:1:8 (SEQ ID NO: 8) was half that of expression driven by ERIra.Ubq1:1:8 (SEQ ID NO: 21). This might be advantageous for expression of transgenes in which constitutive expression is desired but less expression in silk tissue would be preferred. The EXP sequences demonstrate unique patterns of CP4 constitutive expression in R₀ transformed corn plants.

The R₀ transformed corn plants were crossed with a non-transgenic LH244 variety to produce F₁ seed. The resulting F₁ generation seed was analyzed for segregation of the transgene cassette and plants heterozygous for the CP4 cassette were selected for analysis of CP4 expression. Seed was grown in the greenhouse and two groups of plants were produced, one group was sprayed with glyphosate while the other was left unsprayed. Expression of CP4 was analyzed in selected tissues using a standard ELISA based assay. The average CP4 expression is shown in Tables 47 and 48 below.

TABLE 47

Average CP4 expression in $F_1$ transformed corn plants.

| Organ | pMON141619 | pMON142862 | pMON129221 |
|---|---|---|---|
| V4 Leaf | 11.50 | 13.51 | 7.68 |
| V4 Root | 12.48 | 12.60 | 10.29 |
| V7 Leaf | 16.59 | 20.21 | 12.01 |
| V7 Root | 11.00 | 13.62 | 8.15 |
| VT Leaf | 39.88 | 44.85 | 29.42 |
| VT Root | 17.43 | 21.83 | 13.43 |
| VT Flower, anthers | 52.74 | 55.72 | 53.62 |
| R1 Silk | 16.01 | 23.81 | 14.42 |
| R3 Seed-21 DAP-Embryo | 33.29 | 57.96 | 51.64 |
| R3 Seed-21 DAP-Endosperm | 2.99 | 3.20 | 6.44 |

As can be seen in Table 47 above, CP4 expression in leaf and root was higher in F₁ transformants transformed with pMON141619 (EXP-ANDge.Ubq1:1:8, SEQ ID NO: 5) and pMON142862 (EXP-ERIra.Ubq1:1:8, SEQ ID NO: 27) than in those transformed with pMON129221 (EXP-Cl.Ubq1:1:10, SEQ ID NO: 98). Expression in the anther tissue was similar for all three EXP sequences while expression in the silk was highest using EXP-ERIra.Ubq1:1:8 (SEQ ID NO: 27). Expression in the developing embryo (21 DAP) was highest in transformants comprising EXP-ERIra.Ubq1:1:8 (SEQ ID NO: 27) and EXP-Cl.Ubq1:1:10 (SEQ ID NO: 98) driving CP4. Expression in the developing endosperm was higher in transformants comprising EXP-Cl.Ubq1:1:10 (SEQ ID NO: 98) driving CP4.

TABLE 48

Average CP4 expression in $F_1$ transformed corn plants.

| Organ | pMON129205 |
|---|---|
| V4 Leaf | 1.73 |
| V4 Root | 2.44 |
| V7 Leaf | 2.84 |
| V7 Root | 1.51 |
| VT Leaf | 3.29 |
| VT Root | 2.63 |
| VT Flower, anthers | 7.52 |
| R1 Silk | 1.99 |
| R3 Seed-21 DAP-Embryo | 3.40 |
| R3 Seed-21 DAP-Endosperm | 1.79 |

As can be seen in Tables 47-48 above, CP4 expression was lower in all tissues of F₁ transformants transformed with pMON129205 (EXP-Sv.Ubq1:1:9, SEQ ID NO: 133) than those transformed with pMON141619 (EXP-ANDge.Ubq1:1:8, SEQ ID NO: 8), pMON142862 (EXP-ERIra.Ubq1:1:8, SEQ ID NO: 27) and pMON129221 (EXP-Cl.Ubq1:1:10, SEQ ID NO: 98).

The unique patterns of expression conferred by each of the EXP sequences assayed provide an opportunity to produce a transgenic plant in which expression can be fine-tuned to make small adjustments in transgene expression for optimal performance or effectiveness. In addition, empirical testing of these EXP sequences driving different transgene expression may produce results in which one particular EXP sequence is most suitable for expression of a specific transgene or class of transgenes while another EXP sequence is found to be best for a different transgene or class of transgenes.

Example 14

Analysis of Vegetative Glyphosate Tolerance in R₀ Transgenic Corn Plants

Corn plants were transformed with plant expression vectors containing EXP sequences driving expression of the CP4 transgene, and the resulting plants were assessed for vegetative and reproductive tolerance to glyphosate application.

$F_1$ transformed corn plants described in Example 13 above transformed with pMON141619, pMON142862, pMON129221, pMON129205 and pMON129212 and comprised of the EXP sequences EXP-ANDge.Ubq1:1:8 (SEQ ID NO: 8), EXP-ERIra.Ubq1:1:8 (SEQ ID NO: 27), EXP-Cl.Ubq1:1:10 (SEQ ID NO: 98), EXP-Sv.Ubq1:1:9 (SEQ ID NO: 133) and EXP-Zm.UbqM1:1:7 (SEQ ID NO: 141), respectively driving CP4 were assessed for both vegetative and reproductive tolerance when sprayed with glyphosate. Ten $F_1$ plants for each event were divided into two groups, the first group consisting of five plants that received glyphosate spray and V4 and V8 stage of development; and a second group of five plants that were left unsprayed (i.e. control). Glyphosate was applied by broadcast foliar spray application using Roundup WeatherMax® at an application rate of 1.5 a.e./acre (a.e. acid equivalent). After seven to ten days, the leaves of each plant were assessed for damage. Vegetative tolerance (Veg Tol in Table 49) was assessed comparing the unsprayed and sprayed plants for each event and a damage rating scale was used to provide a final rating for vegetative tolerance (T=tolerant, NT=not tolerant). In addition seed set was assayed for all of the plants in each event. Seed set measures between control plants and sprayed plants was compared and an assignment of reproductive tolerance (Repro Tol in Table 49) was given for each event based upon the percent seed set of sprayed plants relative to the controls (T=tolerant, NT=not tolerant). Table 49 below shows the vegetative and reproductive tolerance ratings for each event sprayed at V4 and V8 stage. The letter "T" denotes tolerant and "NT" denotes not tolerant.

TABLE 49

Leaf damage ratings of individual transformed corn events at V4 and V8 stage.

| Plasmid Construct | EXP sequence | SEQ ID NO: | Event | Veg Tol V4 | Veg Tol V8 | Repro Tol |
|---|---|---|---|---|---|---|
| pMON141619 | EXP-ANDge.Ubq1:1:8 | 8 | Event 1 | T | T | NT |
| | | | Event 2 | T | T | T |
| | | | Event 3 | T | T | NT |
| | | | Event 4 | T | T | NT |
| | | | Event 5 | T | T | T |
| | | | Event 6 | T | T | NT |
| | | | Event 7 | T | T | T |
| | | | Event 8 | T | T | T |
| | | | Event 9 | T | T | NT |
| pMON142862 | EXP-ERIra.Ubq1:1:8 | 27 | Event 1 | T | T | T |
| | | | Event 2 | T | T | NT |
| | | | Event 3 | T | T | T |
| | | | Event 4 | T | T | T |
| | | | Event 5 | T | T | NT |
| | | | Event 6 | T | T | T |
| | | | Event 7 | T | T | NT |
| | | | Event 8 | T | T | T |
| | | | Event 9 | T | T | T |
| pMON129221 | EXP-Cl.Ubq1:1:10 | 98 | Event 1 | T | T | NT |
| | | | Event 2 | T | T | NT |
| | | | Event 3 | NT | NT | T |
| | | | Event 4 | NT | NT | T |
| | | | Event 5 | T | T | NT |
| | | | Event 6 | NT | NT | T |
| | | | Event 7 | T | T | T |
| pMON129205 | EXP-Sv.Ubq1:1:9 | 133 | Event 1 | NT | NT | |
| | | | Event 2 | NT | NT | NT |
| | | | Event 3 | T | T | NT |
| | | | Event 4 | NT | NT | |
| | | | Event 5 | NT | NT | NT |
| | | | Event 6 | NT | NT | NT |
| | | | Event 7 | NT | NT | NT |
| pMON129212 | EXP-Zm.UbqM1:1:7 | 141 | Event 1 | T | T | |
| | | | Event 2 | T | T | |
| | | | Event 3 | T | T | |
| | | | Event 4 | T | T | |
| | | | Event 5 | T | T | |
| | | | Event 6 | T | T | |
| | | | Event 7 | T | T | |
| | | | Event 8 | T | T | |
| | | | Event 9 | T | T | |
| | | | Event 10 | T | T | |

From Table 49 above, all transformed events assayed comprising CP4 transgene cassettes comprising the EXP sequences EXP-ANDge.Ubq1:1:8 (SEQ ID NO: 8), EXP-ERIra.Ubq1:1:8 (SEQ ID NO: 27) and EXP-Zm.UbqM1:1:7 (SEQ ID NO: 141) demonstrated full vegetative tolerance based upon damage ratings that did not exceed a score of ten. Four events of nine comprising EXP-ANDge.Ubq1:1:8 (SEQ ID NO: 8) and six events of nine comprising EXP-ERIra.Ubq1:1:8 (SEQ ID NO: 27) were both vegetatively and reproductively tolerant to glyphosate application. In contrast, events comprising EXP-Cl.Ubq1:1:10 (SEQ ID NO: 98) were either vegetatively tolerant or reproductively tolerant but not both. Only one event comprising EXP-Sv.Ubq1:1:9 (SEQ ID NO: 133) demonstrated vegetative tolerance and none of the events tested were reproductive tolerant. All events comprising EXP-Zm.UbqM1:1:7 (SEQ ID NO: 141) demonstrated vegetative tolerance but and assessment of reproductive tolerance is still in progress.

Example 15

Analysis of Expression Using Different 3' End Intron/Exon Splice Junction Sequences Corn and Wheat leaf protoplast cells were transformed with plant expression constructs comprising EXP sequences driving GUS expression that comprise the same promoter and leader but have different 3' end nucleotides following the intron/exon splice junction sequence, 5'-AG-3' to see if expression is affected by the slight change in sequence. Expression was also compared to that of two constitutive control plasmids.

Plant expression constructs are built comprising a GUS expression cassette. The resulting vectors are comprised of the *Coix lacryma-jobi* ubiquitin promoter, P-Cl.Ubq1-1:1:1 (SEQ ID NO: 80) operably linked 5' to the leader sequence, L-Cl.Ubq1-1:1:1 (SEQ ID NO: 81), operably linked 5' to an intron element shown in Table 50 below which each comprise different nucleotides at the very 3' end just after the intron/exon splice junction 5'-AG-3' sequence, operably linked 5' to a GUS coding sequence which is operably linked 5' to T-AGRtu.nos-1:1:13 (SEQ ID NO: 127) 3' UTR. Table 50 below shows the plant expression constructs and the corresponding 3' end sequence.

TABLE 50

Plant expression constructs, introns and 3' end sequence following the intron/exon splice junction sequence 5'-AG-3'.

| Plasmid construct | EXP sequence | SEQ ID NO: | Intron Variant | Intron 3' end nucleotides immediately following 3' splice site AG |
|---|---|---|---|---|
| pMON140889 | EXP-Cl.Ubq1:1:10 | 98 | I-Cl.Ubq1-1:1:6 (SEQ ID NO: 94) | GTC |
| pMON146795 | EXP-Cl.Ubq1:1:18 | 99 | I-Cl.Ubq1-1:1:7 (SEQ ID NO: 92) | GTG |
| pMON146796 | EXP-Cl.Ubq1:1:19 | 100 | I-Cl.Ubq1-1:1:8 (SEQ ID NO: 101) | GCG |
| pMON146797 | EXP-Cl.Ubq1:1:20 | 102 | I-Cl.Ubq1-1:1:9 (SEQ ID NO: 103) | GAC |
| pMON146798 | EXP-Cl.Ubq1:1:21 | 104 | I-Cl.Ubq1-1:1:10 (SEQ ID NO: 105) | ACC |
| pMON146799 | EXP-Cl.Ubq1:1:22 | 106 | I-Cl.Ubq1-1:1:11 (SEQ ID NO: 107) | GGG |
| pMON146800 | EXP-Cl.Ubq1:1:23 | 108 | I-Cl.Ubq1-1:1:12 (SEQ ID NO: 109) | GGT |
| pMON146801 | EXP-Cl.Ubq1:1:24 | 110 | I-Cl.Ubq1-1:1:13 (SEQ ID NO: 111) | CGT |
| pMON146802 | EXP-Cl.Ubq1:1:25 | 112 | I-Cl.Ubq1-1:1:14 (SEQ ID NO: 113) | TGT |
| pMON25455 | EXP-Os.Act1:1:9 | 179 | | Constitutive Control |
| pMON65328 | EXP-CaMV.35S-enh + Ta.Lhcb1 + Os.Act1:1:1 | 163 | | Constitutive Control |

Corn and Wheat protoplasts were transformed as previously described and assayed for GUS and luciferase expression. Table 51 below shows the average GUS and RLuc values for both corn and wheat protoplast expression.

TABLE 51

Average GUS and RLuc values for corn and wheat protoplast cells.

| | Intron 3' end nucleotides immed. following 3' splice site AG | Corn | | | Wheat | | |
|---|---|---|---|---|---|---|---|
| EXP sequence | | Average GUS | Average RLuc | GUS/RLuc | Ave. GUS | Ave. RLuc | GUS/RLuc |
| EXP-Cl.Ubq1:1:10 | GTC | 140343.0 | 93870.75 | 1.50 | 40906.25 | 17381.75 | 2.35 |
| EXP-Cl.Ubq1:1:18 | GTG | 143106.25 | 60565.25 | 2.36 | 56709.00 | 17898.75 | 3.17 |
| EXP-Cl.Ubq1:1:19 | GCG | 136326.83 | 88589.75 | 1.54 | 43211.00 | 17352.50 | 2.49 |
| EXP-Cl.Ubq1:1:20 | GAC | 138110.83 | 104751.42 | 1.32 | 31711.50 | 17953.75 | 1.77 |
| EXP-Cl.Ubq1:1:21 | ACC | 137906.75 | 72519.50 | 1.90 | 54164.17 | 17772.83 | 3.05 |
| EXP-Cl.Ubq1:1:22 | GGG | 137306.83 | 92643.42 | 1.48 | 55198.25 | 14476.75 | 3.81 |
| EXP-Cl.Ubq1:1:23 | GGT | 144085.50 | 64351.25 | 2.24 | 43008.83 | 13911.50 | 3.09 |
| EXP-Cl.Ubq1:1:24 | CGT | 142061.5 | 65884.00 | 2.16 | 51210.50 | 15041.00 | 3.40 |
| EXP-Cl.Ubq1:1:25 | TGT | 140353.00 | 61249.50 | 2.29 | 49577.75 | 15348.25 | 3.23 |
| EXP-Os.Act1:1:9 | Constitutive Control | 37665.25 | 65835.50 | 0.57 | 10830.25 | 17716.50 | 0.61 |
| EXP-CaMV.35S-enh + Ta.Lhcb1 + Os.Act1:1:1 | Constitutive Control | 49833.75 | 41268.75 | 1.21 | 15598.83 | 14877.50 | 1.05 |

The GUS/RLuc values for each *Coix lacryma-jobi* ubiquitin EXP sequence from Table 46 above were used to normalize the expression relative to the two constitutive controls EXP-Os.Act1:1:9 (SEQ ID NO: 179) and EXP-CaMV.35S-enh+Ta.Lhcb1+Os.Act1:1:1 (SEQ ID NO: 163) and are presented in Table 52 below.

TABLE 52

Normalized expression values of the *Coix lacryma-jobi* ubiquitin EXP sequences relative to EXP-Os.Act1:1:9 (SEQ ID NO: 179) and EXP-CaMV.35S-enh + Ta.Lhcb1 + Os.Act1:1:1 (SEQ ID NO: 163).

| | | Corn | | Wheat | |
|---|---|---|---|---|---|
| EXP sequence | Intron 3' end nucleotides immediately following 3' splice site AG | GUS/RLuc Normalized with respect to EXP-Os.Act1:1:9 | GUS/RLuc Normalized with respect to EXP-CaMV.35S-enh + Ta.Lhcb1 + Os.Act1:1:1 | GUS/Rluc Normalized with respect to EXP-Os.Act1:1:9 | GUS/Rluc Normalized with respect to EXP-CaMV.35S-enh + Ta.Lhcb1 + Os.Act1:1:1 |
| EXP-Cl.Ubq1:1:10 | GTC | 2.61 | 1.24 | 3.85 | 2.24 |
| EXP-Cl.Ubq1:1:18 | GTG | 4.13 | 1.96 | 5.18 | 3.02 |
| EXP-Cl.Ubq1:1:19 | GCG | 2.69 | 1.27 | 4.07 | 2.38 |
| EXP-Cl.Ubq1:1:20 | GAC | 2.30 | 1.09 | 2.89 | 1.68 |
| EXP-Cl.Ubq1:1:21 | ACC | 3.32 | 1.57 | 4.99 | 2.91 |
| EXP-Cl.Ubq1:1:22 | GGG | 2.59 | 1.23 | 6.24 | 3.64 |
| EXP-Cl.Ubq1:1:23 | GGT | 3.91 | 1.85 | 5.06 | 2.95 |
| EXP-Cl.Ubq1:1:24 | CGT | 3.77 | 1.79 | 5.57 | 3.25 |
| EXP-Cl.Ubq1:1:25 | TGT | 4.01 | 1.90 | 5.28 | 3.08 |
| EXP-Os.Act1:1:9 | Constitutive Control | 1.00 | 0.47 | 1.00 | 0.58 |
| EXP-CaMV.35S-enh + Ta.Lhcb1 + Os.Act1:1:1 | Constitutive Control | 2.11 | 1.00 | 1.72 | 1.00 |

As is shown in Table 52 above, each of the *Coix lacryma-jobi* ubiquitin EXP sequences provided expression that was greater than either constitutive control in both corn and wheat. Expression in corn protoplasts was relatively similar for all of the *Coix* ubiquitin EXP sequences. Expression in wheat was a little more variable. The use of different 3' end nucleotides following the intron/exon splice junction sequence, 5'-AG-3' did not appear to dramatically affect expression of GUS with the exception of GUS driven by EXP-Cl.Ubq1:1:20 (SEQ ID NO: 102). EXP-Cl.Ubq1:1:20 comprises the 3' end nucleotide sequences, 5'-GAC-3' following the intron/exon splice junction 5'-AG-3' sequence and caused expression to drop slightly relative to the other *Coix* ubiquitin EXP sequences. Assessment of the resulting spliced messenger RNA showed that approximately 10% of the mRNA expressed using EXP-Cl.Ubq1:1:20 (SEQ ID NO: 102) to drive GUS expression was improperly spliced. The mRNA resulting from GUS expression using the other *Coix* ubiquitin EXP sequences appeared to process properly. This experiment provides evidence that any of the 3' end nucleotides for any of the intron variants presented in Table 2 of Example 1 with the exception of the 3' end sequence 5'-GAC-3' which is found associated only with the intron element, I-Cl.Ubq1-1:1:9 (SEQ ID NO: 103) should be suitable for use in transgene expression cassettes without significant loss of activity and processing.

Example 16

Enhancers Derived from the Regulatory Elements

Enhancers are derived from the promoter elements provided herein, such as those presented as SEQ ID NOS: 2, 6, 9, 11, 13, 15, 17, 19, 23, 26, 28, 30, 32, 34, 38, 40, 42, 46, 50, 56, 60, 64, 66, 70, 74, 76, 78, 80, 84, 86, 88, 91, 96 and 135. The enhancer element may be comprised of one or more cis regulatory elements that, when operably linked 5' or 3' to a promoter element, or operably linked 5' or 3' to additional enhancer elements that are operably linked to a promoter, can enhance or modulate expression of a transgene, or provide expression of a transgene in a specific cell type or plant organ or at a particular time point in development or circadian rhythm. Enhancers are made by removing the TATA box or functionally similar elements and any downstream sequence from the promoters that allow transcription to be initiated from the promoters provided herein as described above, including fragments thereof, in which the TATA box or functionally similar elements and sequence downstream of the TATA box are removed. The enhancer element, E-Cl.Ubq1-1:1:1 (SEQ ID NO: 89) which is derived from the promoter element, P-Cl.Ubq1-1:1:1 is provided herein to demonstrate enhancers derived from a promoter element.

Enhancer elements may be derived from the promoter elements provided herein and cloned using methods known in the art to be operably linked 5' or 3' to a promoter element, or operably linked 5' or 3' to additional enhancer elements that are operably linked to a promoter. Alternatively, enhancer elements are cloned, using methods known in the art, to be operably linked to one or more copies of the enhancer element which are operably linked 5' or 3' to a promoter element, or operably linked 5' or 3' to additional enhancer elements that are operably linked to a promoter. Enhancer elements can also be cloned to be operably linked 5' or 3' to a promoter element derived from a different genus organism, or operably linked 5' or 3' to additional enhancer elements derived from other genus organisms or the same genus organism that are operably linked to a promoter derived from either the same or different genus organism, resulting in a chimeric regulatory element. A GUS expression plant transformation vector is constructed using methods known in the art similar to the constructs described in the previous examples in which the resulting plant expression vectors contain a right border region from *A. tumefaciens*, a first transgene cassette to test the regulatory or a chimeric regulatory element comprised of, a regulatory or chimeric regulatory element, operably linked to an intron derived from the HSP70 heat shock protein of *Z. mays* (I-Zm.DnaK-1:1:1 SEQ ID NO: 144) or any of the introns presented herein or any other intron, operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu-.nos-1:1:13, SEQ ID NO: 161) or the 3' UTR from the rice lipid transfer protein gene (T-Os.LTP-1:1:1, SEQ ID NO: 175); a second transgene selection cassette used for selection of transformed plant cells that confers resistance to the herbicide glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by other *Agrobacterium*-mediated or particle bombardment methods known in the art. Alternatively, protoplast cells derived from corn or other genus plants are transformed using methods known in the art to perform transient assays GUS expression driven by the regulatory element comprising one or more enhancers is evaluated in stable or transient plant assays to determine the effects of the enhancer element on expression of a transgene. Modifications to one or more enhancer elements or duplication of one or more enhancer elements is performed based upon empirical experimentation and the resulting gene expression regulation that is observed using each regulatory element composition. Altering the relative positions of one or more enhancers in the resulting regulatory or chimeric regulatory element may affect the transcriptional activity or specificity of the regulatory or chimeric regulatory element and is determined empirically to identify the best enhancers for the desired transgene expression profile within the corn plant or other genus plant.

Example 17

Analysis of Intron Enhancement of GUS Activity Using Plant Derived Protoplasts

An intron is selected based upon experimentation and comparison with an intronless expression vector control to empirically select an intron and configuration within the vector T-DNA element arrangement for optimal expression of a transgene. For example, in the expression of an herbicide resistance gene, such as CP4 which confers tolerance to glyphosate, it is desirable to have transgene expression within the reproductive tissues as well as the vegetative tissues, to prevent the loss of yield when applying the herbicide. An intron in this instance would be selected upon its ability when operably linked to a constitutive promoter, to enhance expression of the herbicide resistance conferring transgene, particularly within the reproductive cells and tissues of the transgenic plant and thus providing both vegetative and reproductive tolerance to the transgenic plant, when sprayed with the herbicide. In most ubiquitin genes, the 5' UTR is comprised of a leader, which has an intron sequence embedded within it. The expression elements derived from such genes are therefore assayed using the entire 5' UTR comprising the promoter, leader, and intron. To achieve different expression profiles or to modulate the level of transgene expression, the intron from such an expression element may be removed or substituted with a heterologous intron.

Introns presented herein as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are identified using genomic DNA contigs in comparison to expressed sequence tag clusters or cDNA contigs to identify exon and intron sequences within the genomic DNA. In addition, 5' UTR or leader sequences are also used to define the intron/exon splice junction of one or more introns under conditions when the gene sequence encodes a leader sequence that is interrupted by one or more introns. Introns are cloned using methods known in the art into a plant transformation vector to be operably linked 3' to a transcriptional regulatory element and leader fragment and operably linked 5' to either a second leader fragment or to coding sequences, for instance as depicted in the two transgene cassettes presented in FIG. 1.

Thus, for instance, a first possible transgene cassette (Transgene Cassette Configuration 1 in FIG. 8) is comprised of a promoter or chimeric promoter element [A], operably linked 5' to a leader element [B], operably linked 5' to a test intron element [C], operably linked to a coding region [D], which is operably linked to a 3' UTR element [E]. Alternatively, a second possible transgene cassette (Transgene Cassette Configuration 2 in FIG. 8) is comprised of a promoter or chimeric promoter element [F], operably linked 5' to a first leader element or first leader element fragment [G], operably linked 5' to a test intron element [H], operably linked 5' to a second leader element or first leader element second fragment [I], operably linked to a coding region [J], which is operably linked to a 3' UTR element [K]. Further, a third possible transgene cassette (Transgene Cassette Configuration 3 in FIG. 8) is comprised of a promoter or chimeric promoter element [L], operably linked 5' to a leader element [M], operably linked 5' to a first fragment of the coding sequence element [N], operably linked 5' to an intron element [O] element, operably linked 5' to a second fragment of the coding sequence element [P], which is operably linked to a 3' UTR element [Q]. Transgene Cassette Configuration 3 is designed to allow splicing of the intron in such a manner as to produce a complete open reading frame without a frame shift between the first and second fragment of the coding sequence.

The first 6 nucleotides on the 5' end and the last 6 nucleotides on the 3' end of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 represent nucleotides before and after the intron/exon splice junction, respectively. These short 6 nucleotide sequences, for example, can be modified by having additional sequence appended (i.e. native or artificial) to facilitate cloning of the intron into a plant transformation vector, so long as the first and second nucleotides from the 5' end (GT) and the fourth and fifth nucleotide from the 3' end (AG) of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 are preserved, thus preserving the intron/exon splice junction of the intron. As discussed above, it may be preferable to avoid using the nucleotide sequence AT or the nucleotide A just prior to the 5' end of the splice site (GT) and the nucleotide G or the nucleotide sequence TG, respectively just after 3' end of the splice site (AG) to eliminate the potential of unwanted start codons from being formed during processing of the messenger RNA into the final transcript. The sequence around the 5' or 3' end splice junction sites of the intron can thus be modified.

The introns are assayed for an enhancement effect through the ability to enhance expression in transient assay or stable plant assay. For transient assay of intron enhancement, a base plant vector is constructed using methods known in the art. The intron is cloned into a base plant vector which comprises an expression cassette comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177), operably linked 5' to a test intron element (e.g. one of SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182), operably linked to a coding sequence for β-glucuronidase (GUS) that either possesses a processable intron (GUS-2, SEQ ID NO: 160) or no intron (GUS-1, SEQ ID NO: 159), operably linked to the Nopaline synthase 3' UTR from *A. tumefaciens* (T-AGRtu.nos-1:1:13, SEQ ID NO: 161). Protoplast cells derived from corn or other genus plant tissue are transformed with the base plant vector and luciferase control vectors as described previously in Example 2 above and assayed for activity. To compare the relative ability of the intron to enhance expression, GUS values are expressed as a ratio of GUS to luciferase activity and compared with those levels imparted by a construct comprising the constitutive promoter operably linked to a known intron standard such as that as the intron derived from the HSP70 heat shock protein of *Zea mays*, I-Zm.D-naK-1:1:1 (SEQ ID NO: 178) as well as a construct comprising the constitutive promoter but without an intron operably linked to the promoter.

For stable plant assay of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182, a GUS expression plant transformation vector is constructed similar to the constructs described in the previous examples in which the resulting plant expression vectors contains a right border region from *A. tumefaciens*, a first transgene cassette to test the intron comprised of a constitutive promoter such as the Cauliflower mosaic virus promoter, P-CaMV.35S-enh-1:1:9 (SEQ ID NO: 176), operably linked 5' to a leader element, L-CaMV.35S-1:1:15 (SEQ ID NO: 177), operably linked 5' to a test intron element provided herein, operably linked to a coding sequence for β-glucuronidase (GUS) that either possesses a processable intron (GUS-2, SEQ ID NO: 160) or no intron (GUS-1, SEQ ID NO: 158), operably linked to the Nopaline synthase 3' UTR from *A. tumefaciens* (T-AGRtu.nos-1:1:13, SEQ ID NO: 161); a second transgene selection cassette used for selection of transformed plant cells that confers resistance to glyphosate (driven by the rice Actin 1 promoter), or alternatively, the antibiotic kanamycin (driven by the rice Actin 1 promoter) and a left border region from *A. tumefaciens*. The resulting plasmids are used to transform corn plants or other genus plants by the methods described above or by *Agrobacterium*-mediated methods known in the art. Single-copy or low copy number transformants are selected for comparison to single-copy or low copy number transformed plants, transformed with a plant transformation vector identical to the test vector but without the test intron to determine if the test intron provides an intron mediated enhancement effect.

Any of the introns presented as SEQ ID NOS: 4, 7, 21, 24, 36, 44, 48, 52, 54, 58, 62, 68, 72, 82, 92, 94, 101, 103, 105, 107, 109, 111, 113, 118, 120, 122, 127, 129, 131, 138, 140, 142, 144, 146, 148, 150, 152, 154, 156, 158 and 182 can be modified in a number of ways, such as deleting fragments within the intron sequence, which may reduce expression or duplication of fragments with the intron that may enhance expression. In addition, sequences within the intron that may affect the specificity of expression to either particular cells types or tissues and organs can be duplicated or altered or deleted to affect expression and patterns of expression of the transgene. In addition, the introns provided herein can be modified to remove any potential start codons (ATG) that may cause unintentional transcripts from being expressed from improperly spliced introns as different, longer or truncated proteins. Once the intron has been empirically tested, or it has been altered based upon experimentation, the intron is used to enhance expression of a transgene in stably transformed plants that can be of any genus monocot or dicot plant, so long as the intron provides enhancement of the transgene. The intron can also be used to enhance expression in other organisms, such as algae, fungi or animal cells, so long as the intron provides enhancement or attenuation or specificity of expression of the transgene to which it is operably linked.

\* \* \*

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A DNA molecule comprising a DNA sequence selected from the group consisting of:
   a) a sequence with at least 95 percent sequence identity to SEQ ID NO: 8 and having promoter activity;
   b) a sequence comprising SEQ ID NO: 8; and
   c) a fragment of SEQ ID NO: 8 comprising SEQ ID NO: 17,
   wherein said DNA sequence is operably linked to a heterologous transcribable polynucleotide molecule.

2. The DNA molecule of claim 1, wherein the heterologous transcribable polynucleotide molecule comprises a gene of agronomic interest.

3. The DNA molecule of claim 2, wherein the gene of agronomic interest confers herbicide tolerance in plants.

4. The DNA molecule of claim 2, wherein the gene of agronomic interest confers pest resistance in plants.

5. A transgenic plant cell comprising a heterologous DNA molecule comprising a sequence selected from the group consisting of:
   a) a sequence with at least 95 percent sequence identity to SEQ ID NO: 8 and having promoter activity;
   b) a sequence comprising SEQ ID NO: 8; and
   c) a fragment of SEQ ID NO: 8 comprising SEQ ID NO: 17,
   wherein said DNA sequence is operably linked to a heterologous transcribable polynucleotide molecule.

6. The transgenic plant cell of claim 5, wherein said transgenic plant cell is a monocotyledonous plant cell.

7. The transgenic plant cell of claim 5, wherein said transgenic plant cell is a dicotyledonous plant cell.

8. A transgenic plant, or part thereof, comprising the DNA molecule of claim 1.

9. A progeny plant of the transgenic plant of claim 8, or a part thereof, wherein the progeny plant or part thereof comprises said DNA molecule.

10. A transgenic seed, wherein the seed comprises the DNA molecule of claim 1.

11. A method of producing a commodity product comprising obtaining the transgenic plant or part thereof according to claim 8 and producing the commodity product therefrom.

12. The method of claim 11, wherein the commodity product is protein concentrate, protein isolate, grain, starch, seeds, meal, flour, biomass, or seed oil.

13. A commodity product comprising the DNA molecule of claim 1.

14. The commodity product of claim 13, wherein the commodity product is protein concentrate, protein isolate, grain, starch, seeds, meal, flour, biomass, or seed oil.

15. A method of expressing a transcribable polynucleotide molecule comprising obtaining the transgenic plant according to claim 8 and cultivating plant, wherein the transcribable polynucleotide is expressed.

* * * * *